US011104661B1

(12) United States Patent
Bursavich et al.

(10) Patent No.: US 11,104,661 B1
(45) Date of Patent: Aug. 31, 2021

(54) INHIBITING HUMAN INTEGRIN (α-4) (β-7)

(71) Applicant: Morphic Therapeutic, Inc., Waltham, MA (US)

(72) Inventors: Matthew G. Bursavich, Needham, MA (US); Dan Cui, Cambridge, MA (US); James E. Dowling, Lexington, MA (US); Kristopher N. Hahn, Medford, MA (US); Bryce A. Harrison, Framingham, MA (US); Fu-Yang Lin, Sudbury, MA (US); Blaise S. Lippa, Newton, MA (US); Bruce N. Rogers, Belmont, MA (US); Dawn M. Troast, Bedford, MA (US); Cheng Zhong, Belmont, MA (US); Kyle D. Konze, Brooklyn, NY (US); Aleksey I. Gerasyuto, Flemington, NJ (US); Byungchan Kim, West New York, NJ (US); Salma Rafi, Lexington, MA (US); Tyler Day, New York, NY (US); Eugene Hickey, Danbury, CT (US); Evelyne Houang, Queens, NY (US); Robert Zahler, Pennington, NJ (US)

(73) Assignee: Morphic Therapeutic, Inc., Waltham, MA (US)

( * ) Notice: Subject to any disclaimer, the term of this patent is extended or adjusted under 35 U.S.C. 154(b) by 0 days.

(21) Appl. No.: 17/072,797

(22) Filed: Oct. 16, 2020

Related U.S. Application Data

(60) Provisional application No. 62/916,062, filed on Oct. 16, 2019.

(51) Int. Cl.
   *C07D 401/06* (2006.01)
   *C07D 213/64* (2006.01)

(52) U.S. Cl.
   CPC ......... *C07D 401/06* (2013.01); *C07D 213/64* (2013.01)

(58) Field of Classification Search
   CPC ............................ C07D 401/06; C07D 213/64
   See application file for complete search history.

(56) References Cited

U.S. PATENT DOCUMENTS

| | | | |
|---|---|---|---|
| 5,721,366 A | 2/1998 | Abood et al. |
| 5,981,492 A | 11/1999 | Zoller et al. |
| 6,294,562 B1 | 9/2001 | Stilz et al. |
| 6,645,939 B1 | 11/2003 | Durette et al. |
| 6,723,711 B2 | 4/2004 | Biediger et al. |
| 6,972,296 B2 | 12/2005 | Biediger et al. |
| 7,807,167 B2 | 10/2010 | Taylor et al. |
| 7,972,775 B2 | 7/2011 | Rubin et al. |
| 9,493,567 B2 | 11/2016 | Lieberburg |
| 9,873,742 B2 | 1/2018 | Keir et al. |
| 10,233,245 B2 | 3/2019 | Lieberburg |
| 10,246,451 B2 | 4/2019 | Biediger et al. |
| 10,273,542 B2 | 4/2019 | Hackney et al. |
| 10,494,367 B2 | 12/2019 | Biediger et al. |
| 10,759,756 B2 | 9/2020 | Bursavich et al. |
| 2003/0199692 A1 | 10/2003 | Biediger et al. |
| 2004/0009169 A1 | 1/2004 | Taylor et al. |
| 2004/0010023 A1 | 1/2004 | Stahle et al. |
| 2007/0025989 A1 | 2/2007 | Taylor et al. |
| 2011/0064729 A1 | 3/2011 | Taylor et al. |
| 2014/0120084 A1 | 5/2014 | Anand et al. |
| 2015/0152182 A1 | 6/2015 | Taylor et al. |
| 2017/0306026 A1 | 10/2017 | Taylor et al. |
| 2018/0086833 A1 | 3/2018 | Hassanali et al. |
| 2020/0148773 A1 | 5/2020 | Taylor et al. |
| 2020/0385352 A1 | 12/2020 | Bursavich et al. |

FOREIGN PATENT DOCUMENTS

| | | |
|---|---|---|
| EP | 1213288 A1 | 6/2002 |
| WO | WO-98/16524 A1 | 4/1998 |
| WO | WO-98/16547 A1 | 4/1998 |
| WO | WO-99/36393 A1 | 7/1999 |
| WO | WO-2000/068188 A1 | 11/2000 |
| WO | WO-01/21584 A1 | 3/2001 |
| WO | WO-2002/16328 A1 | 2/2002 |
| WO | WO-2003/040173 A1 | 5/2003 |
| WO | WO-03/072040 A2 | 9/2003 |
| WO | WO-2006/026759 A2 | 3/2006 |
| WO | WO-2006/126529 A1 | 11/2006 |
| WO | WO-2006/126637 A1 | 11/2006 |
| WO | WO-2006/131200 A1 | 12/2006 |
| WO | WO-2010/091411 A1 | 8/2010 |
| WO | WO-2012/135589 A1 | 10/2012 |
| WO | WO-2016/011940 A1 | 1/2016 |
| WO | WO-2016/138207 A1 | 9/2016 |
| WO | WO-2019/200202 A1 | 10/2019 |
| WO | WO-2020/092375 A1 | 5/2020 |
| WO | WO-2020/092383 A1 | 5/2020 |
| WO | WO-2020/092394 A1 | 5/2020 |
| WO | WO-2020/092401 A1 | 5/2020 |
| WO | WO-2021/076890 A1 | 4/2021 |
| WO | WO-2021/076902 A1 | 4/2021 |

OTHER PUBLICATIONS

International Search Report and Written Opinion for International Application No. PCT/US2020/055986 dated Feb. 9, 2021.
International Search Report and Written Opinion for International Application No. PCT/US2020/056001 dated Dec. 8, 2020.
Kapp et al., "Integrin modulators: a patent review," Expert Opinion on Therapeutic Patents, 23(10): 1273-1295 (2013).
Pubchem, SID 245847741, Modify Date: Jun. 25, 2015 [retrieved on Jan. 15, 2021]. Retrieved from the Internet <URL:https://pubchem.ncbi.nlm.nih.gov/substance/245847741>.
"Athena Neurosciences Antibody Shows Progress in MS Model," Dow Jones News Service Nov. 14, 1994.
Bjorkesten et al., "Surrogate markers and clinical indices, alone or combined, as indicators for endoscopic remission in anti-TNF-treated luminal Crohn's disease," Scandinavian Journal of Gastroenterology, 47(5): 528-537 (2012).

(Continued)

*Primary Examiner* — Patricia L Morris
(74) *Attorney, Agent, or Firm* — Foley Hoag LLP; Dana M. Gordon; Lawrence P. Tardibono

(57) ABSTRACT

Disclosed are small molecule antagonists of human $\alpha_4\beta_7$ integrin, and methods of using them to treat a number of diseases and conditions.

24 Claims, 44 Drawing Sheets

(56) References Cited

OTHER PUBLICATIONS

Ferrante et al., "Validation of Endoscopic Activity Scores in Patients With Crohn's Disease Based on a Post Hoc Analysis of Data From SONIC," Gastroenterology, 145: 978-986 (2013).
Invitation to Pay Additional Fees for International Application No. PCT/US2020/055986 dated Dec. 8, 2020.
Kent et al., "A monoclonal antibody to ?4?integrin reverses the MR?detectable signs of experimental allergic encephalomyelitis in the Guinea pig," JMRI, 5(5): 535-540 (1995).
Moskovotz et al., "Defining and Validating Cut-Off's for the Simple Endoscopic Score for Crohn's Disease," Gastroenterology, 132:S1097 (2007).
PubChem CID 10162717, "(3S)-3-[2-(3-Benzyl-5-methyl-2-oxopyridin-1-yl)hexanoylamino]-3-(3-fluorophenyl)propanoic acid," Created Oct. 25, 2006.
Tubridy et al., "The effect of anti-?4 integrin antibody on brain lesion activity in MS," Neurology, 53(3): 466-472 (1999).
ClinicalTrials.gov, "Study of MORF 057 to Evaluate Single and Multi Ascending Doses in Healthy Volunteers," Identifier: NCT04580745, Publication date: Oct. 8, 2020.
Form 2 "VLA-4 Antagonists," The Patents Act 1970 (39 of 1970 & The Patent Rule, 2003), Ranbaxy Laboratories Limited 1-19 (2005).
International Search Report and Written Opinion for International Application No. PCT/US2019/27141 dated Aug. 16, 2019 (Our reference MTX-00525).
Sattigeri et al., "Synthesis and biological evaluation of ureido derivatives as VLA-4 antagonists," Ind J Chem 45B:2534-2541 (2006).
Sircar et al., "Synthesis and SAR of N-Benzoyl-I-Biphenylalanine Derivatives: Discovery of TR-14035, A Dual a4β7/a4β1 Integrin Antagonist," Bioorganic & Medicinal Chemistry, 10(6): 2051-2066 (2002).
Stilz et al., "Discovery of an Orally Active Non-Peptide Fibrinogen Receptor Antagonist," J Med Chem 39:2118-2122 (1996).
Wong et al., "Morphic presents positive preclinical data supporting MORF-057 as an oral inhibitor of the α4β7 integrin and potential treatment for inflammatory bowel disease," Morphic Therapeutic, Feb. 14, 2020.
Wong et al., "Morphic therapeutic presents positive preclinical data supporting development of MORF-057 in inflammatory bowel disease at digestive disease week 2020," Morphic Therapeutic, Jun. 29, 2020.
Wong et al., "Preclinical characterization of an oral small molecule inhibitor targeting the integrin A4B7 for the treatment of inflammatory bowel diseases (IBD)," May 20, 2020.
Written Opinion for International Application No. PCT/US2019/058573 dated May 7, 2020.
Li et al., "α4β7 integrin inhibitors: a patent review," Expert Opinion on Therapeutic Patents, 28(12): 903-917 (2018).
Arndt et al., "Peptide derived non-peptidic α4β7-integrin antagonists," Peptides 2002: 4 pages (2002).
Gottschling et al., "Combinatorial and Rational Strategies to Develop Nonpeptidic α4β7-Integrin Antagonists from Cyclic Peptides," Angew. Chem. Int. Ed., 41(16): 3007-3011 (2002).
Mangada et al., "Translational Biomarkers For Selective, Oral, Small Molecule a4β7 Inhibitor MORF-057," Morphic Therapeutic, UEG Week 2020 Abstract Submission: 2 pages (2020).

| Compounds | a4b7.FP.Mn.CP.Ecto (IC$_{50}$) [nM] | a4b7.LBA.Mn.CP.8866M AdCAM (IC$_{50}$) [nM] |
|---|---|---|
|  | B | B |
|  | A | A |
|  | B | |

| Compounds | a4b7.FP.Mn.CP.Ecto (IC$_{50}$) [nM] | a4b7.LBA.Mn.CP.8866M AdCAM (IC$_{50}$) [nM] |
|---|---|---|
|  | B | |
|  | C | |
|  | B | |

INHIBITING HUMAN INTEGRIN (α-4) (β-7)

RELATED APPLICATION

This application claims the benefit of priority to U.S. Provisional Patent Application No. 62/916,062, filed Oct. 16, 2019.

TECHNICAL FIELD

Disclosed are novel compounds and related methods useful for the inhibition of the $\alpha_4\beta_7$ integrin. The compounds and methods disclosed herein are applicable to the development of medicaments for the treatment of $\alpha_4\beta_7$ integrin-mediated conditions, such as inflammatory bowel disease (IBD), ulcerative colitis (UC), and Crohn's disease (CD).

BACKGROUND

Integrins are noncovalently associated α/β heterodimeric cell surface receptors involved in numerous cellular processes. Differential expression of integrins can regulate a cell's adhesive properties, allowing different leukocyte populations to be recruited to specific organs in response to different inflammatory signals. The α4 integrins, including $\alpha_4\beta_7$, play a role in lymphocyte migration throughout the gastrointestinal tract. They are expressed on most leukocytes, including B and T lymphocytes, where they mediate cell adhesion via selective binding to its primary ligand, mucosal addressin cell adhesion molecule (MAdCAM). Memory T lymphocytes expressing the $\alpha_4\beta_7$ integrin preferentially migrate into the gastrointestinal tract via firm adhesion to mucosal vascular addressin cell adhesion molecule 1 (MAdCAM-1).

Inhibitors of specific integrin-ligand interactions have been used for the treatment of various diseases. For example, monoclonal antibodies displaying high binding affinity for $\alpha_4\beta_7$ have displayed therapeutic benefits for gastrointestinal auto-inflammatory/autoimmune diseases, such as Crohn's disease, and ulcerative colitis. However, these therapies also have certain undesirable properties for the patient. A monoclonal antibody $\alpha_4\beta_7$ integrin inhibitor is administered by parenteral administration, has a long half-life with inability to rapidly modify exposures, and a reduced activity due to anti-drug antibody formation. Monoclonal antibody therapies can be challenging to manufacture in comparison to small molecule therapies. In addition, some therapies that inhibit $\alpha_4\beta_7$ have also interfered with $\alpha_4\beta_1$ integrin-ligand interactions, thereby resulting in dangerous side effects to the patient. Activity at $\alpha_4\beta_1$ integrin is implicated in emergence of progressive multifocal leukoencephalopathy (PML), a life-threatening and progressive brain infection, in immunosuppressed patients.

There remains a medical need for an effective and safe oral $\alpha_4\beta_7$ integrin inhibitor as an important addition to the therapeutic armamentarium for $\alpha_4\beta_7$ integrin-mediated conditions, such as inflammatory bowel disease (IBD), ulcerative colitis (UC) and Crohn's disease (CD).

SUMMARY

In certain embodiments, the invention relates to compounds of Formula (I):

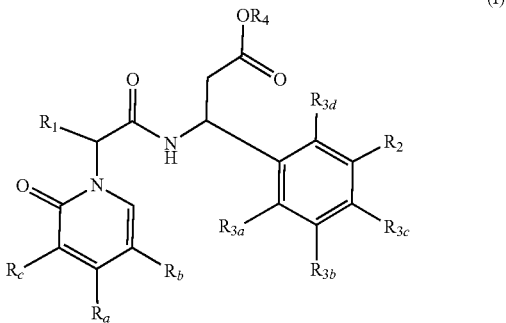

(I)

wherein $R_a$, $R_b$, and $R_c$ are independently selected from the group consisting of H, Me, halide, $CF_3$, $C(H)F_2$, $C(F)H_2$, —CN, —$OCF_3$, substituted or unsubstituted ($C_1$-$C_5$)-alkyl, substituted or unsubstituted ($C_1$-$C_5$)-alkoxy, —$CH_2CF_3$, and substituted or unsubstituted —($C_1$-$C_5$)alkylene-N—($R_x$)($R_y$); provided that at least one of $R_a$, $R_b$, and $R_c$ is —($C_1$-$C_5$) alkylene-N—($R_x$)($R_y$);

$R_x$ and $R_y$ are independently selected from the group consisting of H and substituted or unsubstituted ($C_1$-$C_6$)-alkyl; or $R_x$ and $R_y$ taken together with the N to which they are attached form a 4-6 membered ring;

$R_1$ is substituted or unsubstituted ($C_1$-$C_6$)-alkyl, substituted or unsubstituted ($C_1$-$C_4$)-alkylene-($C_3$-$C_6$)-cycloalkyl, or substituted or unsubstituted ($C_1$-$C_4$)-alkylene-($C_1$-$C_4$)-alkoxy;

$R_2$ is

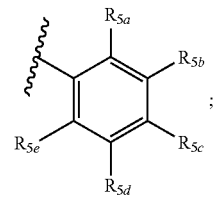

;

$R_{3a}$ and $R_{3b}$ are independently selected from the group consisting of H, substituted or unsubstituted ($C_1$-$C_5$)-alkyl, substituted or unsubstituted ($C_3$-$C_6$)-cycloalkyl, substituted or unsubstituted 3-6 membered heterocycloalkyl, —OH, —CN, halide, $CF_3$, $C(H)F_2$, $C(F)H_2$, —($C_1$-$C_4$)-alkoxy, —$OCF_3$, and substituted or unsubstituted ($C_1$-$C_4$)-alkylene-($C_1$-$C_4$)-alkoxy; provided that $R_{3a}$ and $R_{3b}$ are not both H;

$R_{3c}$ is selected from the group consisting of H, substituted or unsubstituted ($C_1$-$C_5$)-alkyl, substituted or unsubstituted ($C_3$-$C_6$)-cycloalkyl, substituted or unsubstituted 3-6 membered heterocycloalkyl, hydroxyl, halide, $CF_3$, $C(H)F_2$, $C(F)H_2$, —($C_1$-$C_4$)-alkoxy, —$OCF_3$ —CN, and substituted or unsubstituted ($C_1$-$C_4$)-alkylene-($C_1$-$C_4$)-alkoxy;

$R_{3d}$ is selected from the group consisting of H, substituted or unsubstituted ($C_1$-$C_5$)-alkyl, hydroxyl, halide, and —($C_1$-$C_4$)-alkoxy;

$R_4$ is H, or substituted or unsubstituted ($C_1$-$C_4$)-alkyl;

$R_{5a}$ and $R_{5e}$ are independently selected from the group consisting of H, CN, halide, $CF_3$, $C(H)F_2$, $C(F)H_2$, —$CH_2CF_3$, substituted or unsubstituted ($C_3$-$C_6$)-cycloalkyl, substituted or unsubstituted ($C_1$-$C_5$)-alkyl, substituted or unsubstituted 3-6 membered heterocycloalkyl hydroxyl, and ($C_1$-$C_4$)-alkoxy; and $R_{5b}$, $R_{5c}$, and $R_{5d}$ are independently selected from the group consisting of H, CN, halide, $CF_3$, $C(H)F_2$, $C(F)H_2$, —$CH_2CF_3$, substituted or unsubstituted ($C_1$-$C_5$)-alkyl, substituted or unsubstituted ($C_3$-$C_6$)-cycloalkyl, substituted or unsubstituted 3-6 membered heterocycloalkyl, hydroxyl, and ($C_1$-$C_4$)-alkoxy;

or a pharmaceutically acceptable salt thereof.

In some aspects of the invention, a compound of Formula (I) can be a compound wherein one and only one of $R_a$, $R_b$, and $R_c$ is substituted or unsubstituted —($C_1$-$C_5$)alkylene-N—$(R_x)(R_y)$; $R_1$ is ($C_1$-$C_6$) alkyl (e.g., isobutyl); $R_{3a}$ and $R_{3b}$ are independently selected from the group consisting of H, ($C_1$-$C_4$)-alkyl (e.g., methyl), halide (e.g., F or Cl), $CF_3$, $C(H)F_2$, and $C(F)H_2$, provided that $R_{3a}$ and $R_{3b}$ are not both H; and $R_4$ is H.

In some examples, a compound of Formula (I) can be a compound wherein one and only one of $R_a$, $R_b$, and $R_c$ is substituted or unsubstituted —($C_1$-$C_5$)alkylene-N—$(R_x)(R_y)$; $R_x$ and $R_y$ are each independently unsubstituted ($C_1$-$C_6$)-alkyl (e.g., methyl) or $R_x$ and $R_y$ taken together with the N to which they are attached form a substituted or unsubstituted 4-6 membered heterocyclyl ring; $R_1$ is unsubstituted ($C_1$-$C_6$) alkyl (e.g., isobutyl); $R_{3a}$ and $R_{3b}$ are independently selected from the group consisting of H, unsubstituted ($C_1$-$C_4$)-alkyl (e.g., methyl, ethyl, etc.), halide (e.g., F or Cl), $CF_3$, $C(H)F_2$, and $C(F)H_2$, provided that $R_{3a}$ and $R_{3b}$ are not both H; $R_{3c}$ is selected from the group consisting of: H, F, Cl, hydroxyl, substituted or unsubstituted ($C_1$-$C_4$)-alkyl (e.g., methyl), substituted or unsubstituted ($C_3$-$C_6$)-cycloalkyl (e.g., cyclopropyl), ($C_1$-$C_4$)-alkoxy (e.g., methoxy); $R_{3d}$ is selected from the group consisting of H, halide (e.g., F, or Cl), substituted or unsubstituted ($C_1$-$C_4$)-alkyl (e.g., methyl), and hydroxyl; and $R_4$ is H. In some examples, a compound of Formula (I), Formula (Ia) and/or Formula (Ib) can be a compound wherein one and only one of $R_a$, $R_b$, and $R_c$ is substituted or unsubstituted —($C_1$-$C_5$)alkylene-N—$(R_x)(R_y)$; $R_x$ and $R_y$ each independently unsubstituted methyl or $R_x$ and $R_y$ taken together with the N to which they are attached form a substituted or unsubstituted 4-6 membered heterocyclyl ring; $R_1$ is isobutyl; $R_{3a}$ and $R_{3b}$ are independently selected from the group consisting of unsubstituted ($C_1$-$C_4$)-alkyl (e.g., methyl), halide (e.g., F or Cl), $CF_3$, $C(H)F_2$, and $C(F)H_2$, $R_{3c}$ and $R_{3d}$ are both H; and $R_4$ is H. For instance, a compound of Formula (I), Formula (Ia) and/or Formula (Ib) can be a compound wherein $R_1$ is isobutyl; $R_{3a}$ and $R_{3b}$ are independently selected from the group consisting of unsubstituted ($C_1$-$C_4$)-alkyl (e.g., methyl), halide (e.g., F or Cl), $CF_3$, $C(H)F_2$, and $C(F)H_2$, $R_{3c}$ and $R_{3d}$ are both H; $R_4$ is H; and $R_{5a}$, and $R_{5e}$ are each substituted or unsubstituted ($C_1$-$C_4$)-alkyl (e.g., methyl). A compound of Formula (I) can be a compound wherein one and only one of $R_a$, $R_b$, and $R_c$ is substituted or unsubstituted —($C_1$-$C_5$)alkylene-N—$(R_x)(R_y)$; $R_x$ and $R_y$ each independently unsubstituted methyl or $R_x$ and $R_y$ taken together with the N to which they are attached form a 4-6 membered heterocyclyl ring optionally substituted with halide (e.g., F); $R_1$ is isobutyl; $R_{3a}$ and $R_{3b}$ are independently selected from the group consisting of unsubstituted ($C_1$-$C_4$)-alkyl (e.g., methyl), halide (e.g., F or Cl), $CF_3$, $C(H)F_2$, and $C(F)H_2$, $R_{3c}$ and $R_{3d}$ are both H; $R_4$ is H; $R_{5a}$, and $R_{5e}$ are each substituted or unsubstituted ($C_1$-$C_4$)-alkyl (e.g., methyl), and $R_{5b}$, $R_{5c}$, and $R_{5d}$ are each independently selected from the group consisting of H, CN, halide (e.g., F, Cl), $CF_3$, $C(H)F_2$, $C(F)H_2$, ($C_1$-$C_5$)-alkyl, hydroxyl, and ($C_1$-$C_4$)-alkoxy. In certain embodiments, the invention relates to a method of treating auto-inflammatory/autoimmune diseases, such as Crohn's disease, and ulcerative colitis; comprising the step of: administering to a subject in need thereof a therapeutically effective amount of any one of the compounds described herein.

Methods of preparing and isolating the compounds of Formula (I), Formula (Ia) and/or Formula (Ib) are also provided herein.

DETAILED DESCRIPTION

Figure 1:
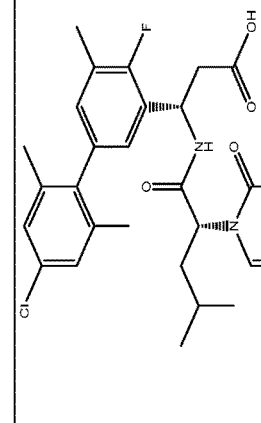
FIG. 1 is a table (Table 1) summarizing in vitro inhibition of $\alpha_4\beta_7$ integrin by exemplary compounds (i.e., data obtained from the fluorescence polarization assay of Example 5, and the ligand binding assay of Example 6).
Figure 1:
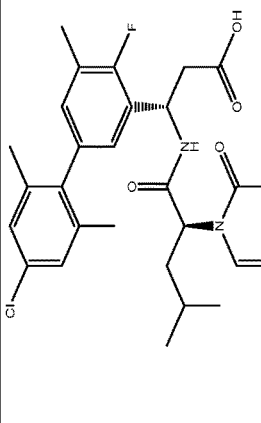
Figure 1:
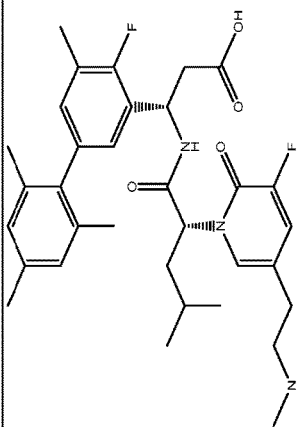
Figure 1:
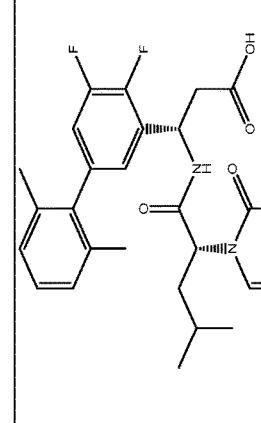
Figure 1:
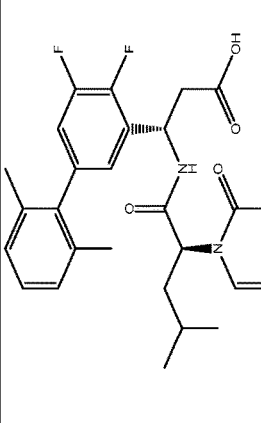
Figure 1:
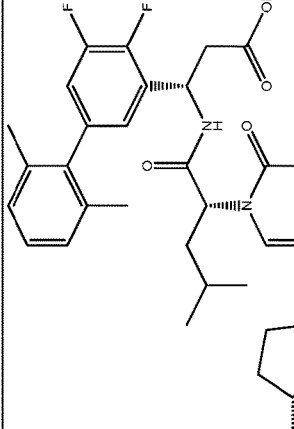
Figure 1:
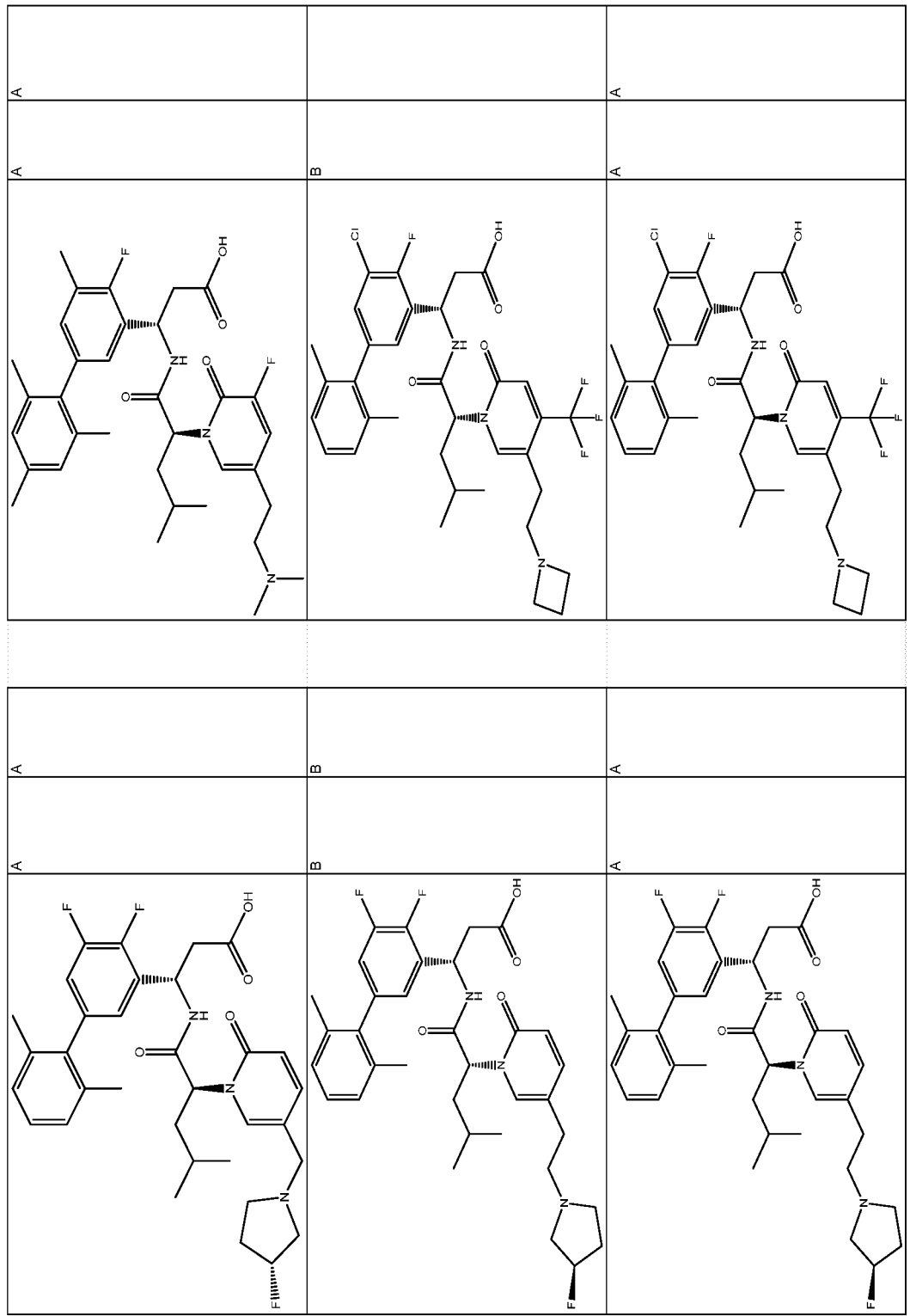
Figure 1:
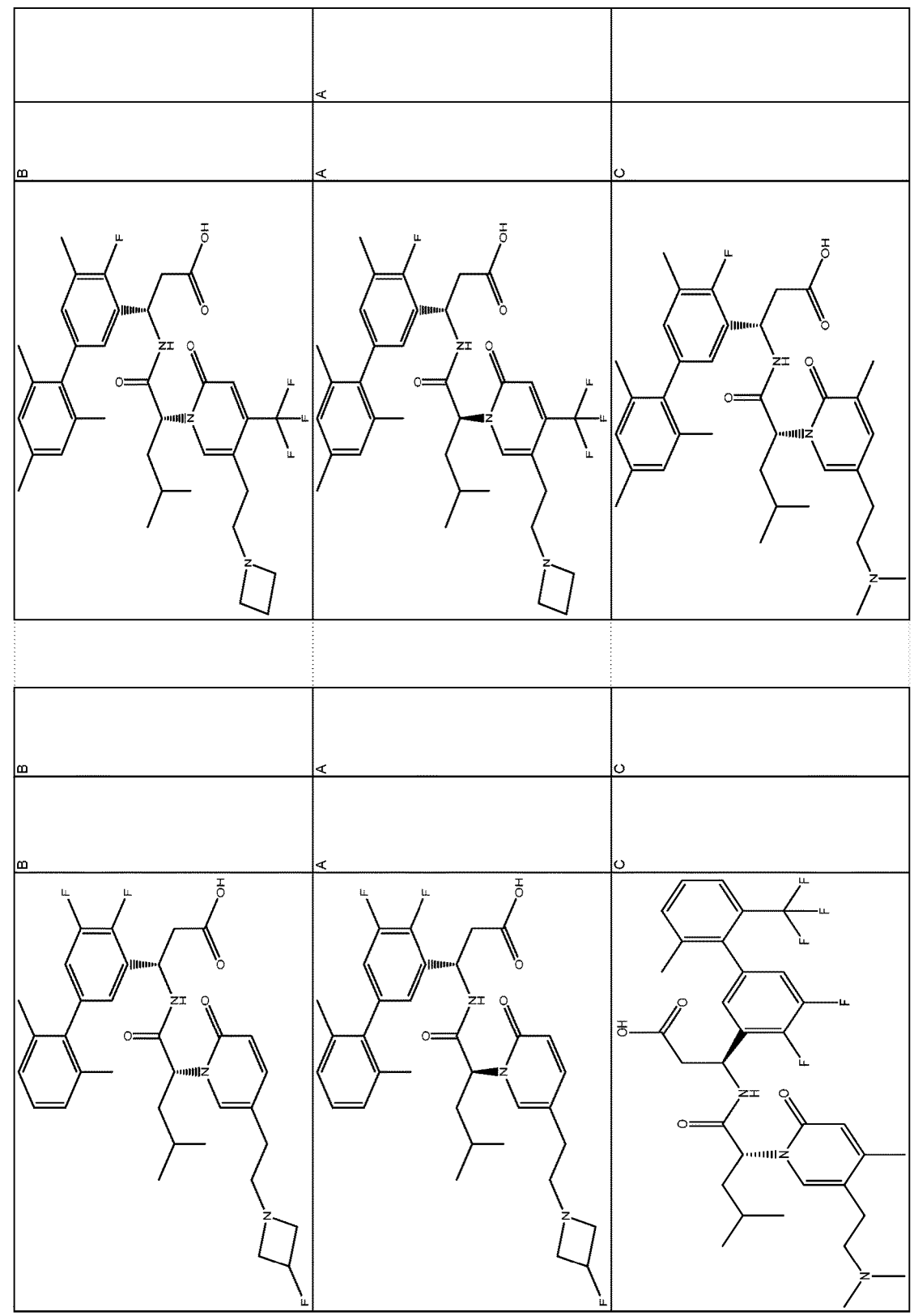
Figure 1:
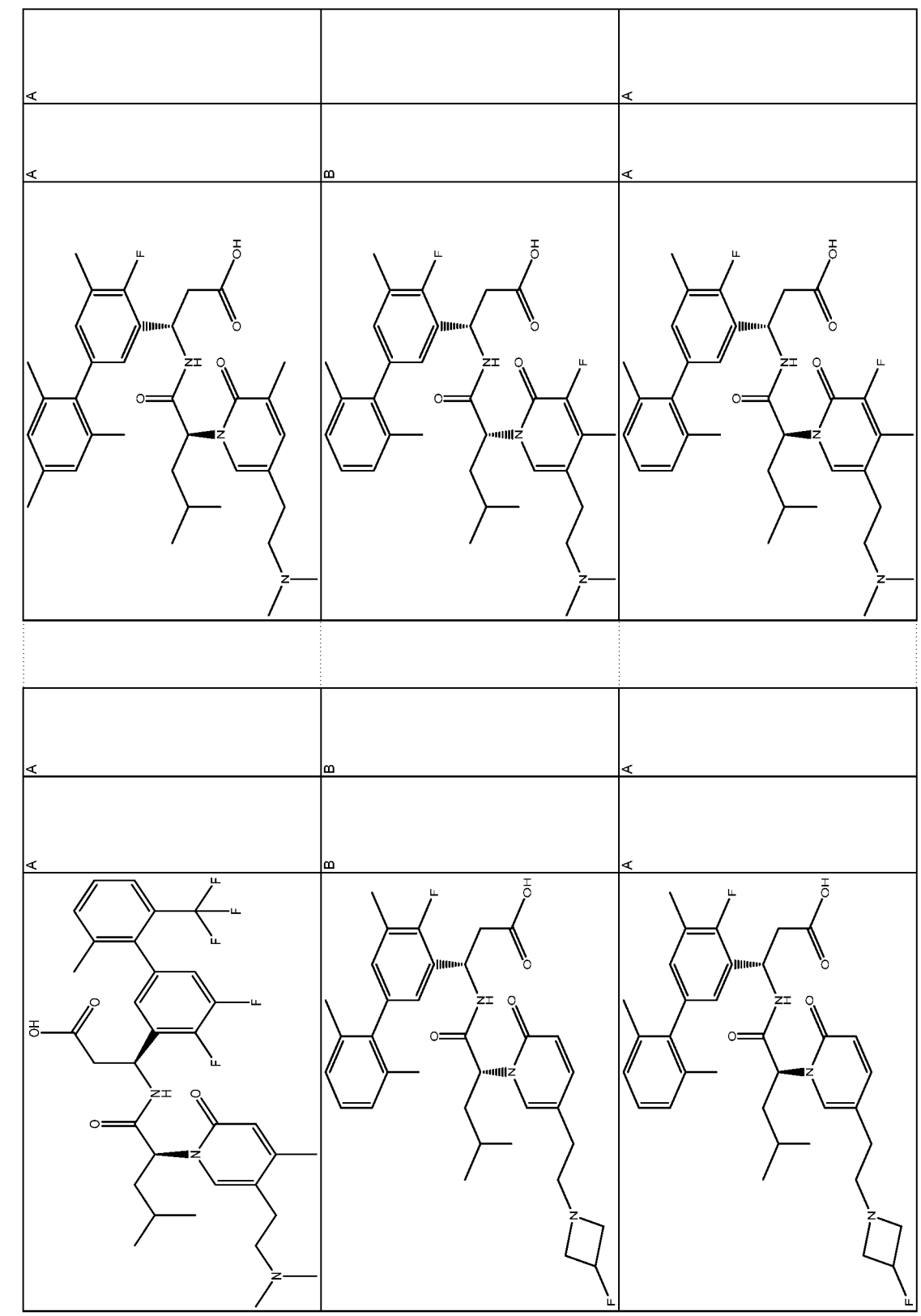
Figure 1:
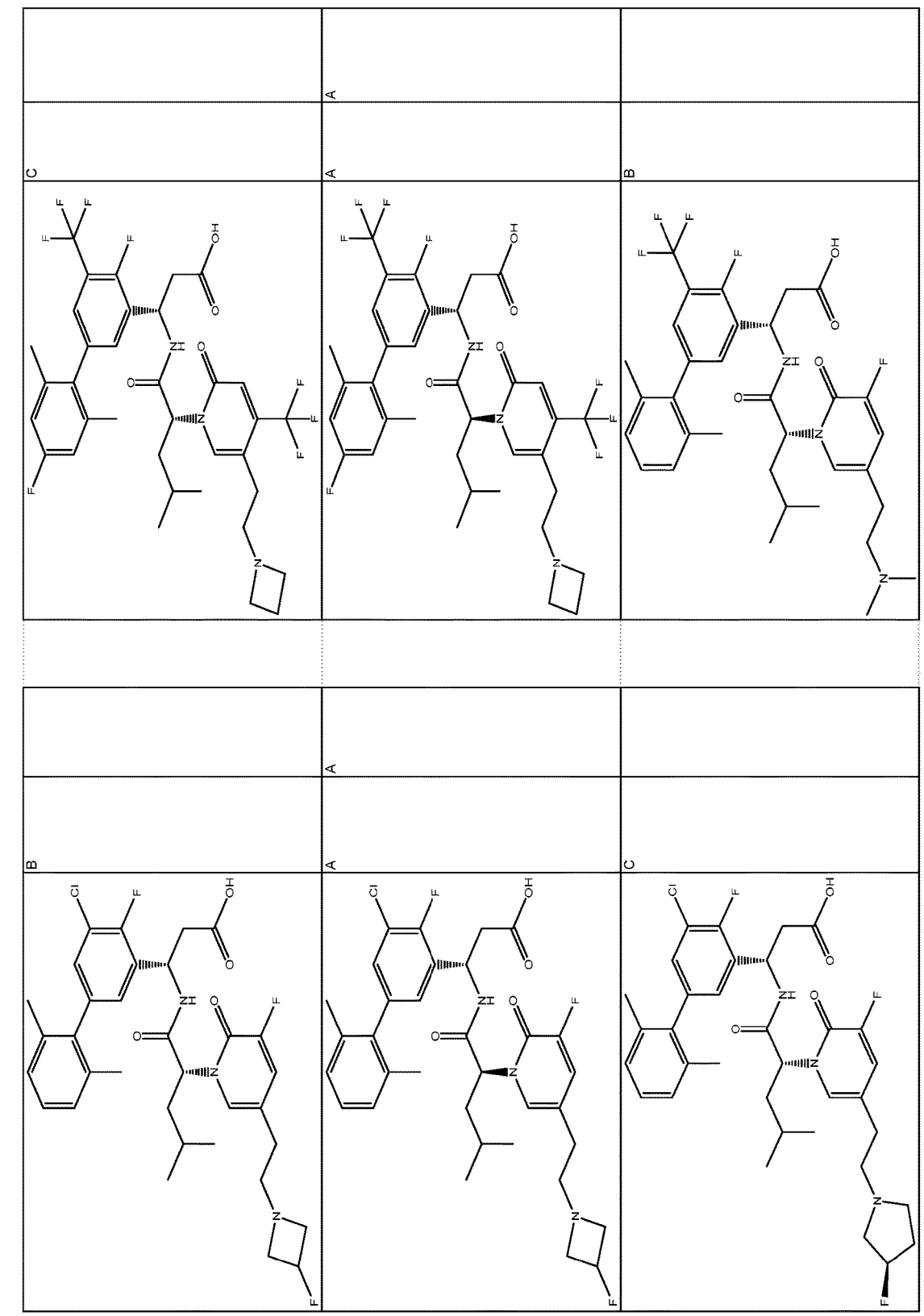
Figure 1:
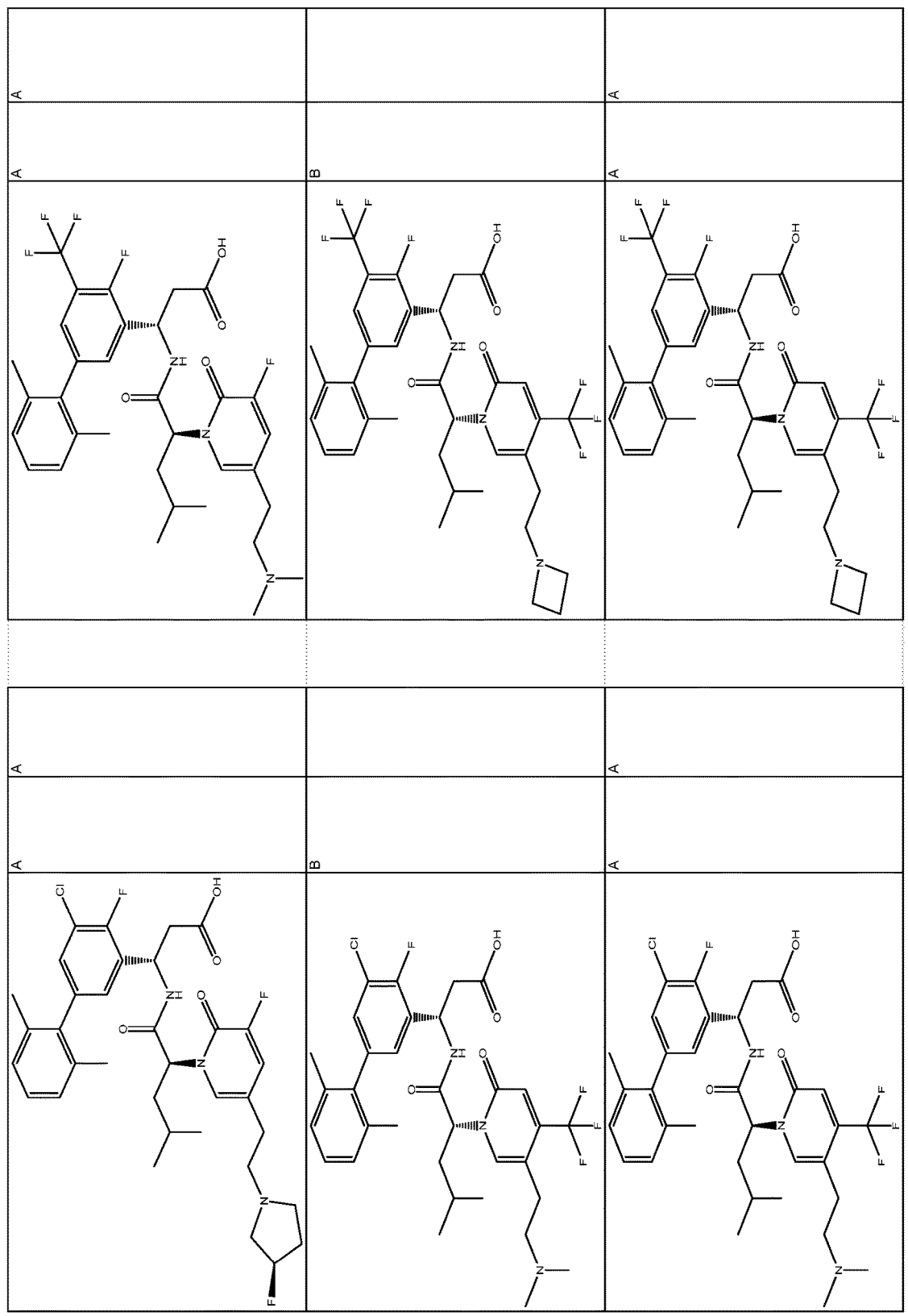
Figure 1:
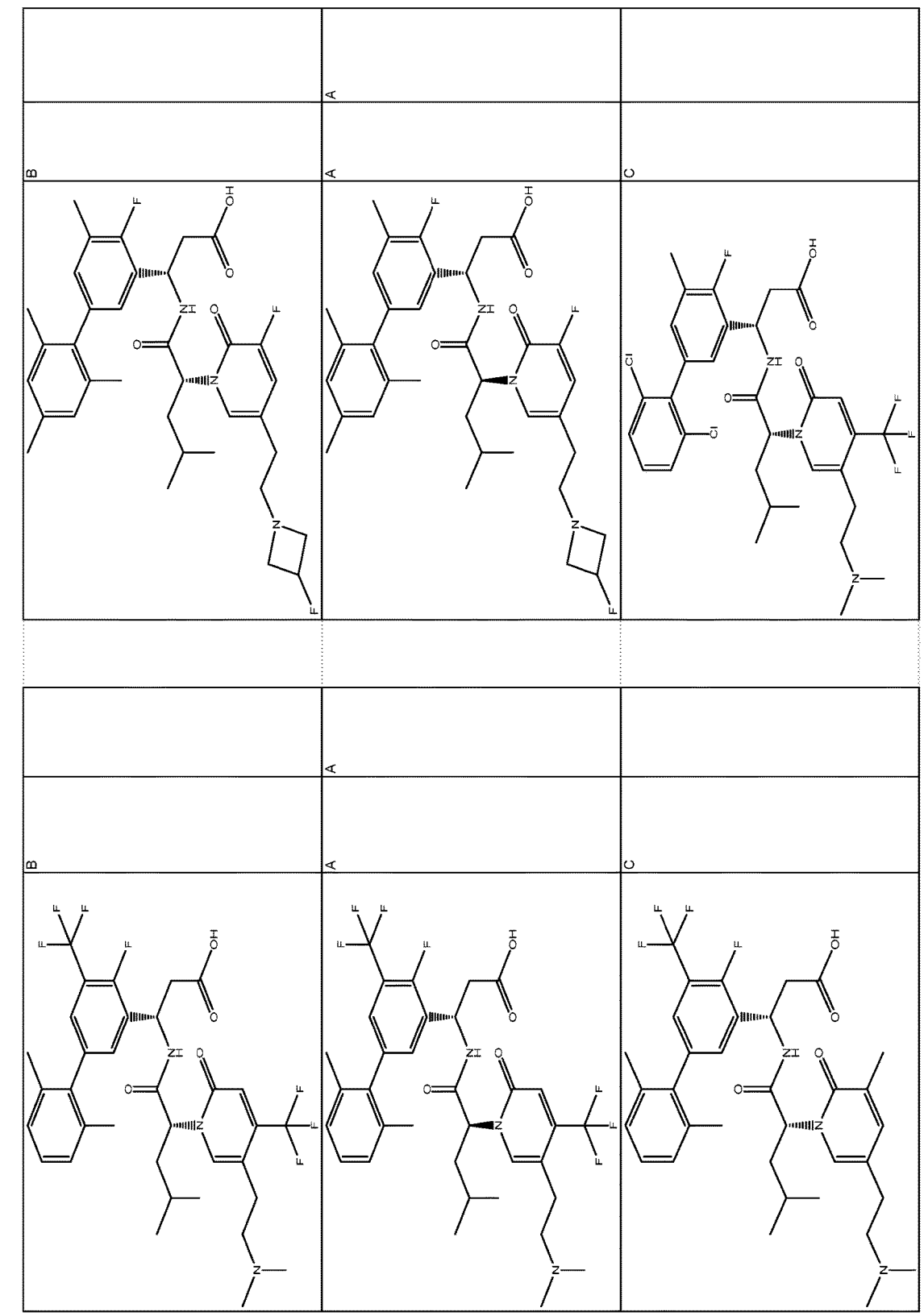
Figure 1:
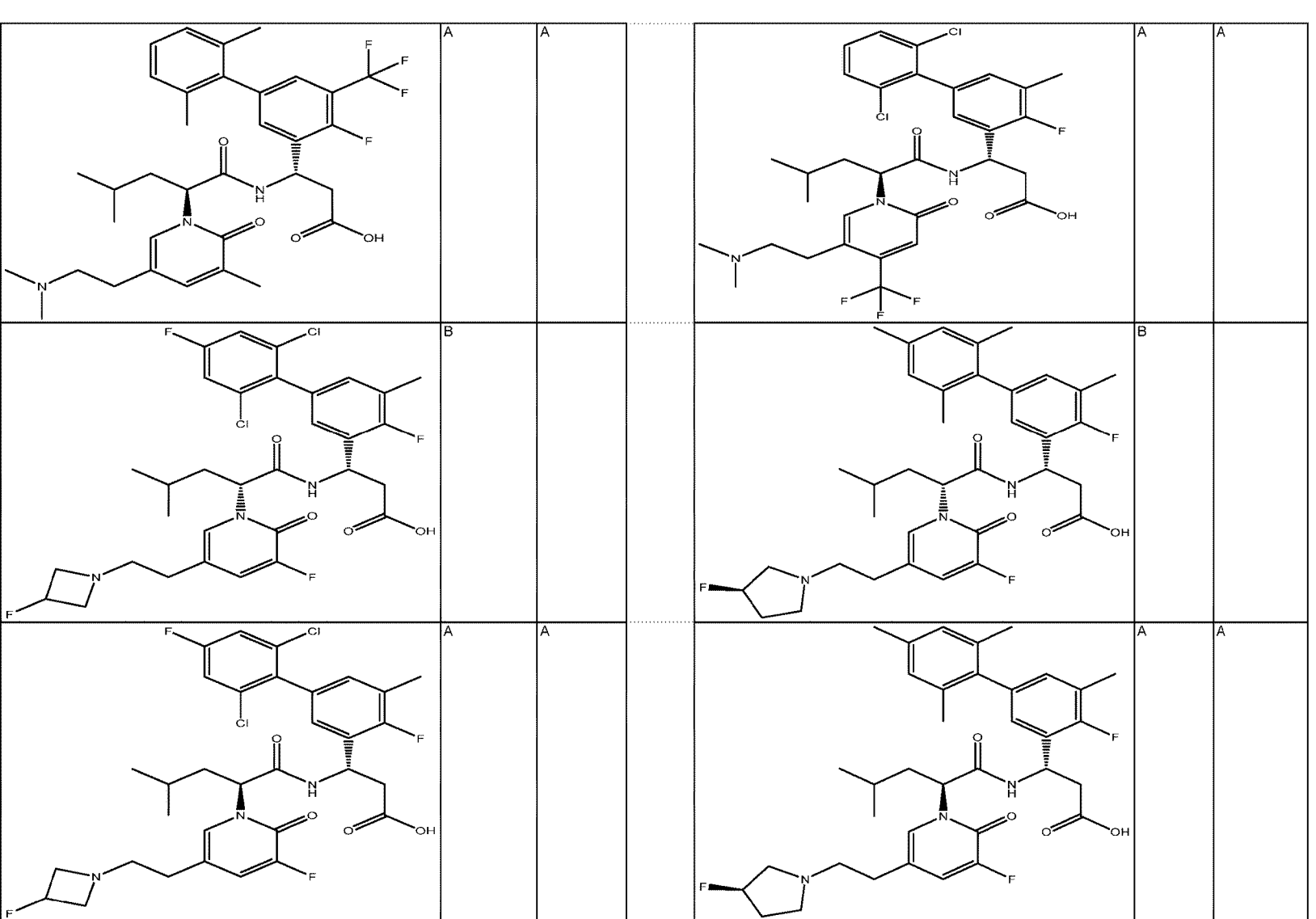
Figure 1:
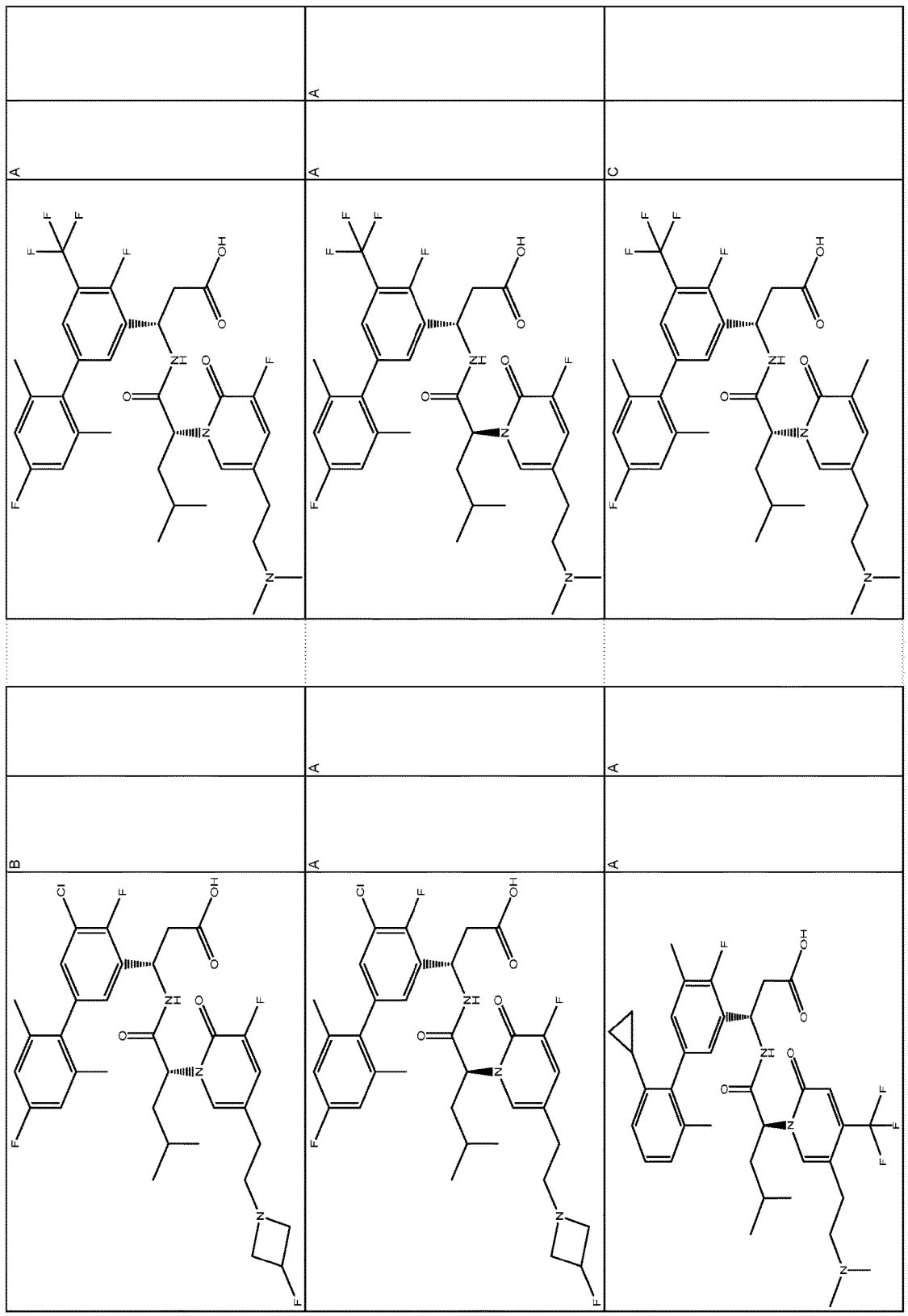
Figure 1:
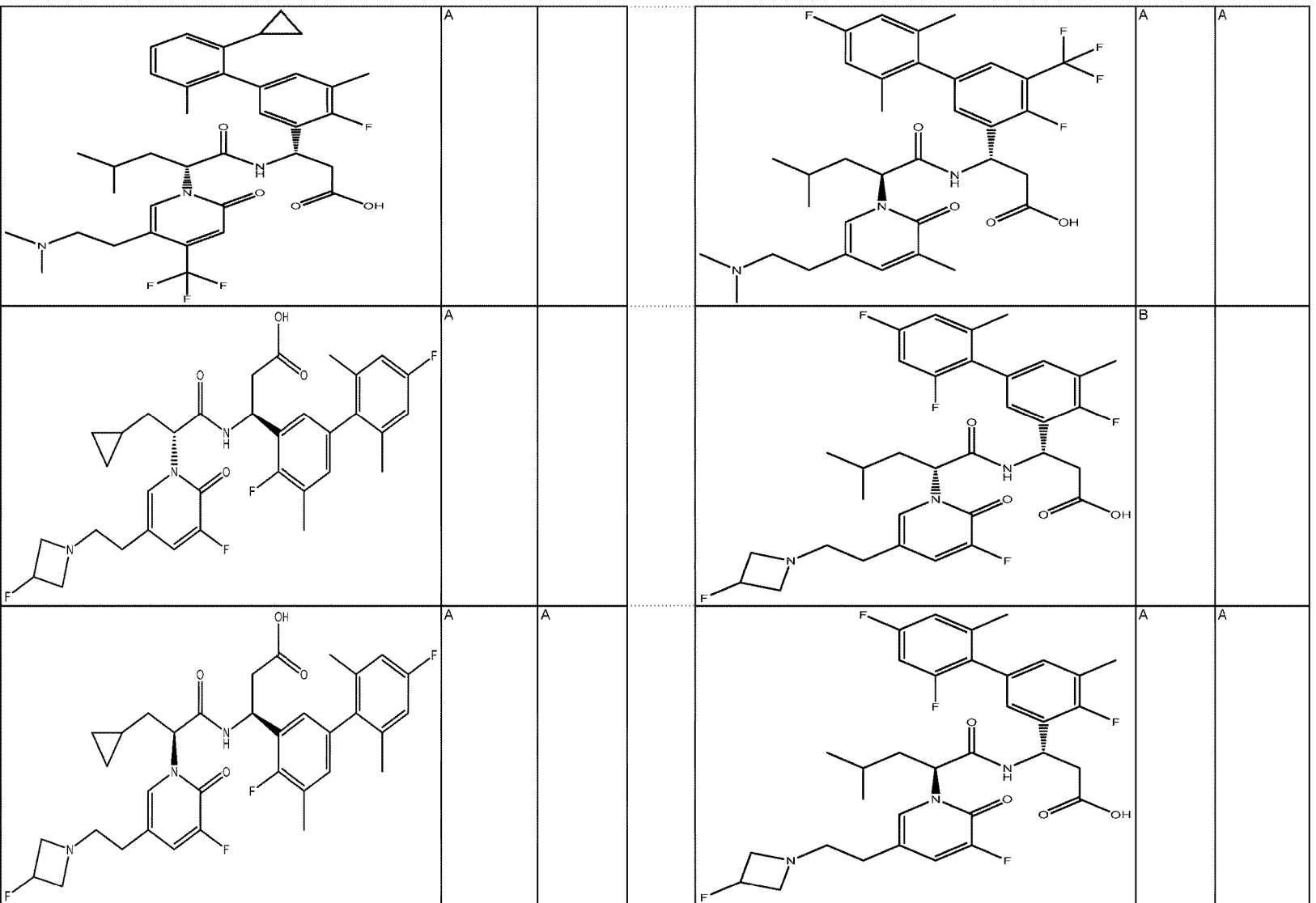
Figure 1:
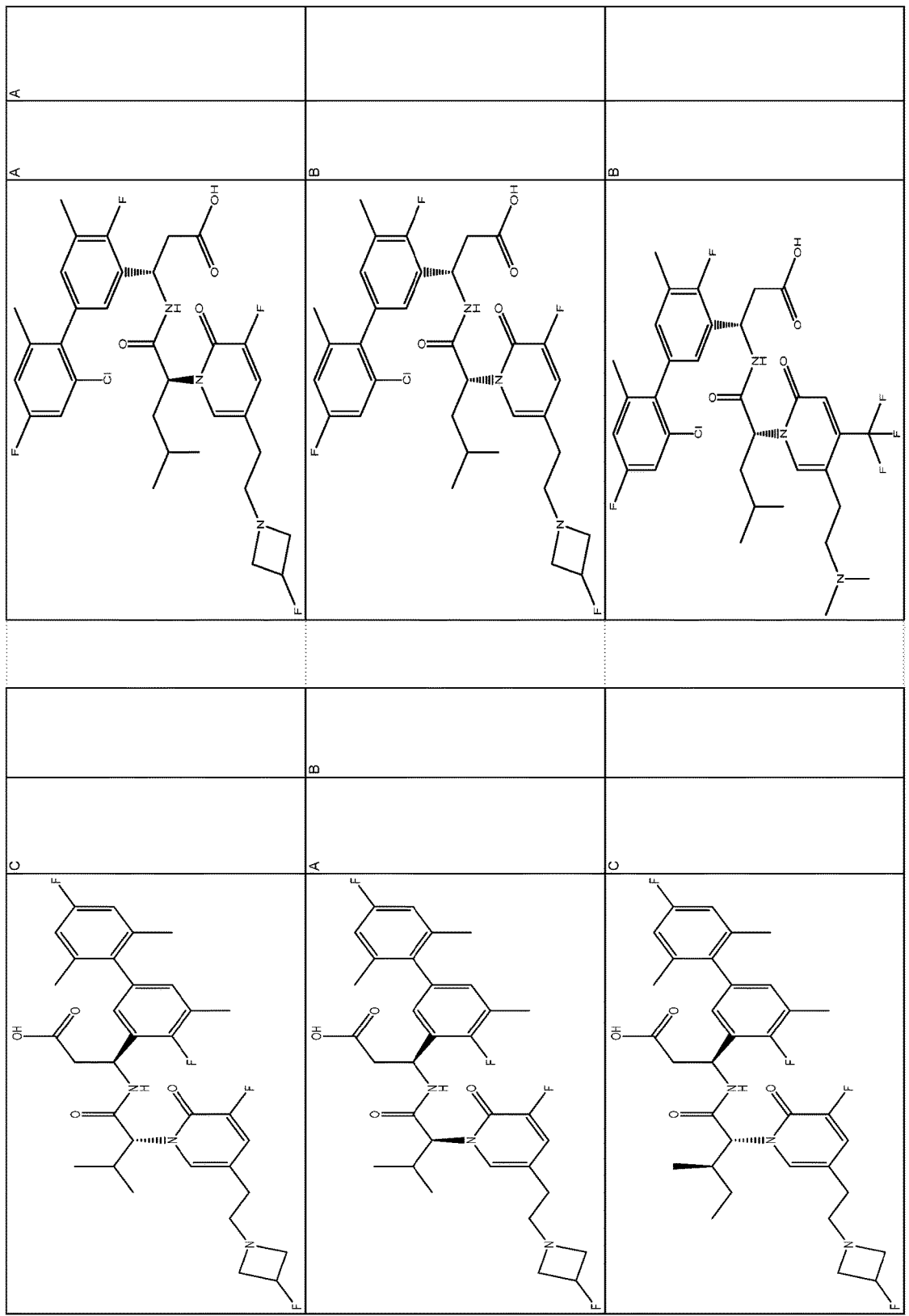
Figure 1:
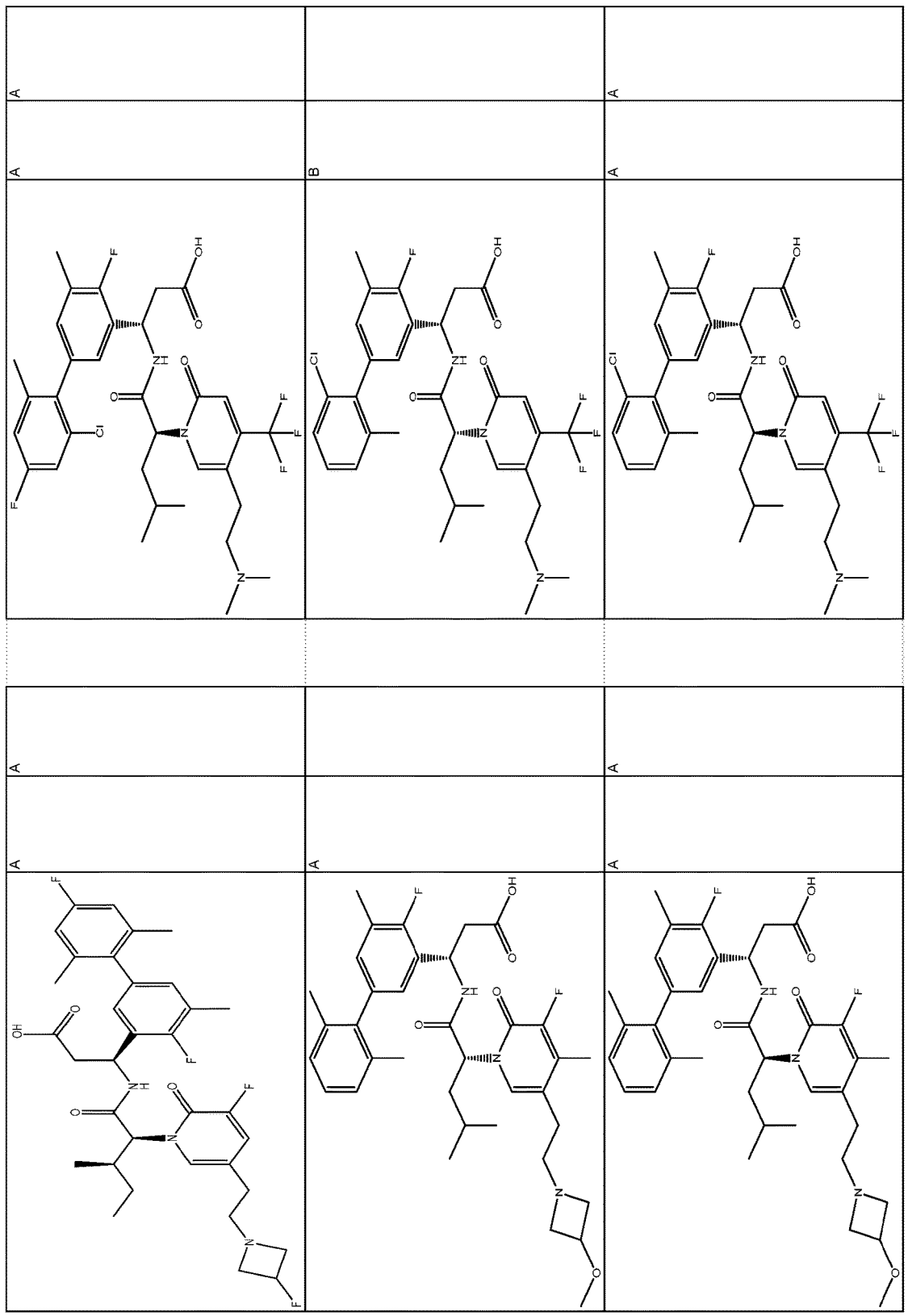
Figure 1:
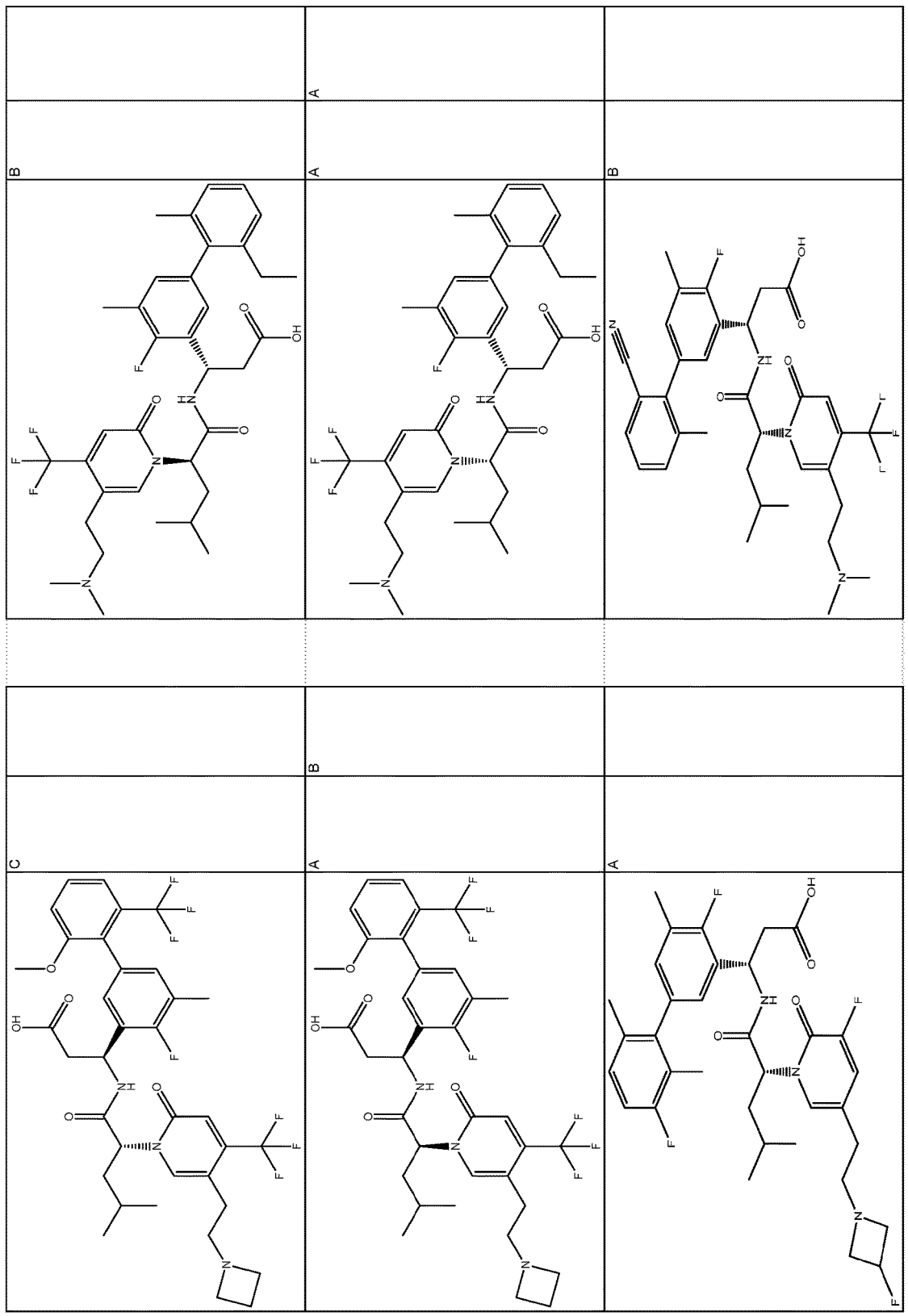
Figure 1:
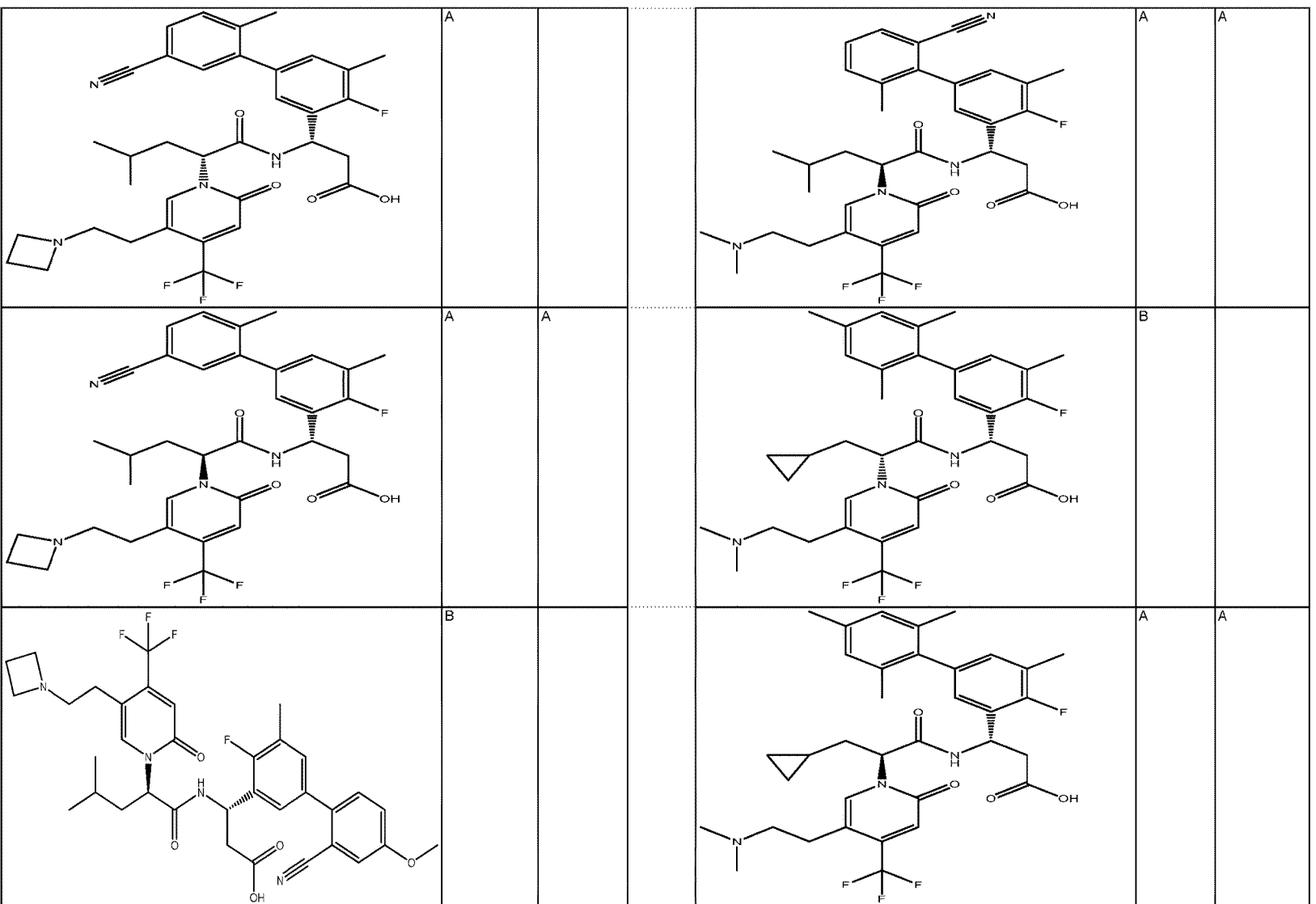
Figure 1:
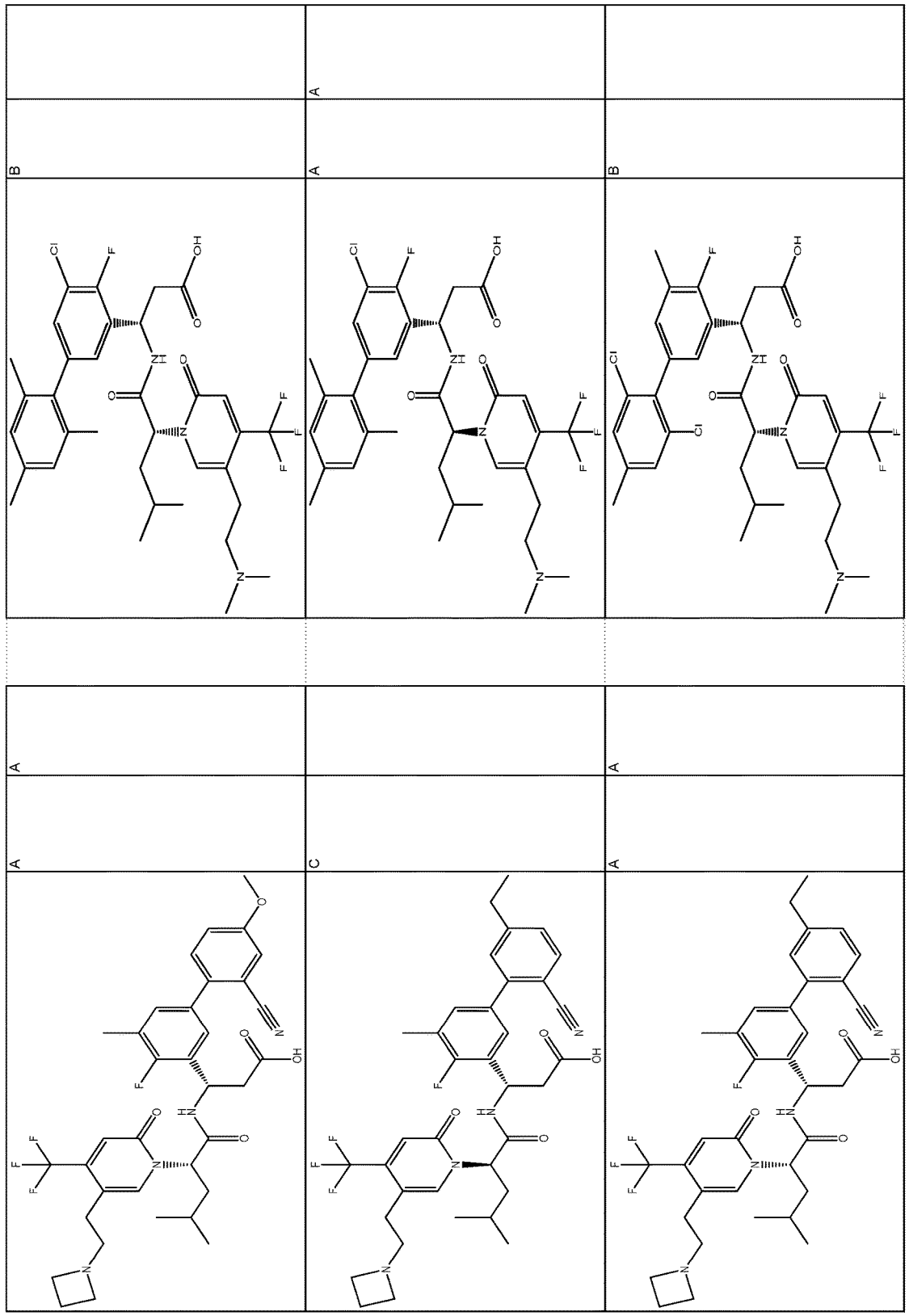
Figure 1:
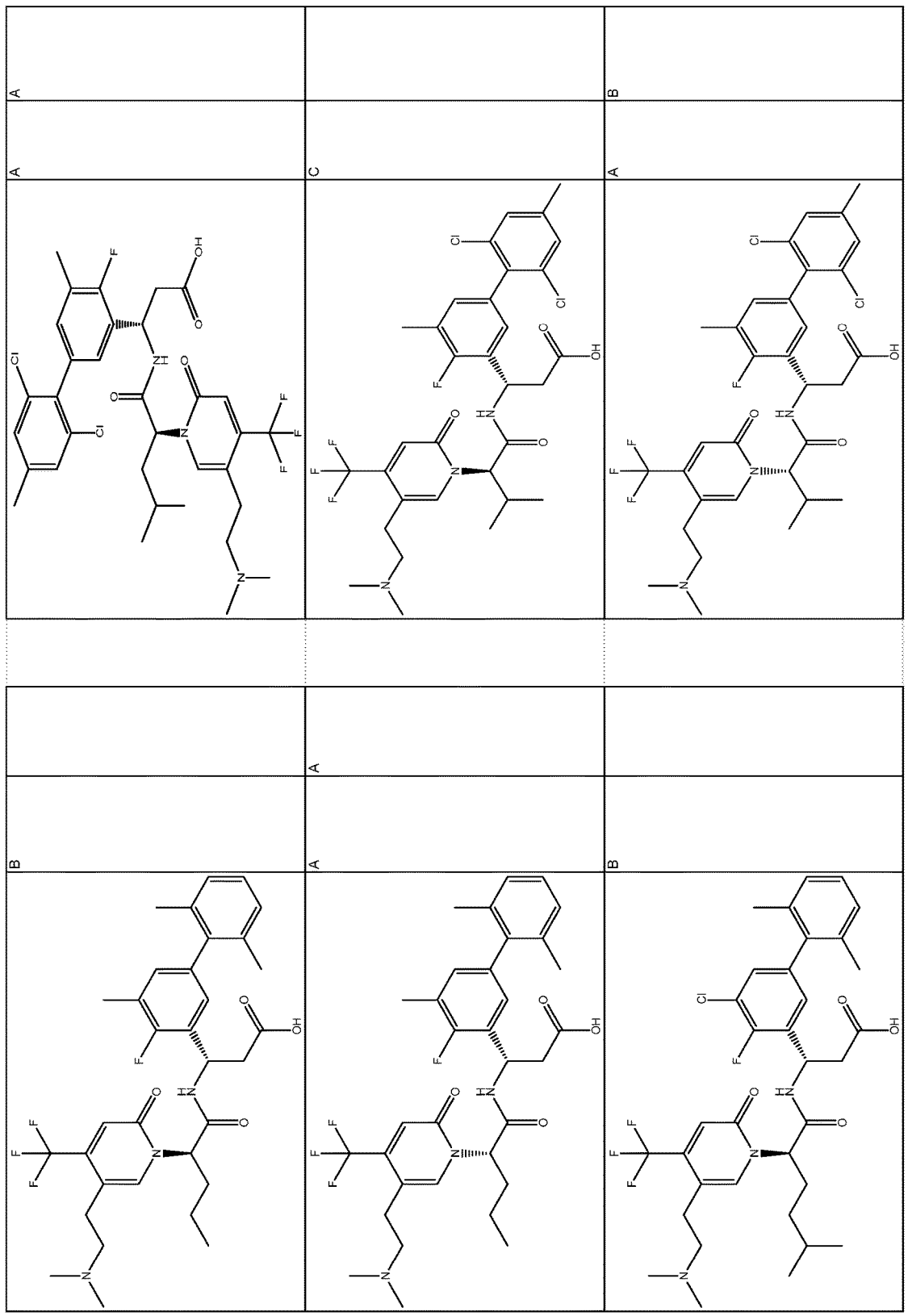
Figure 1:
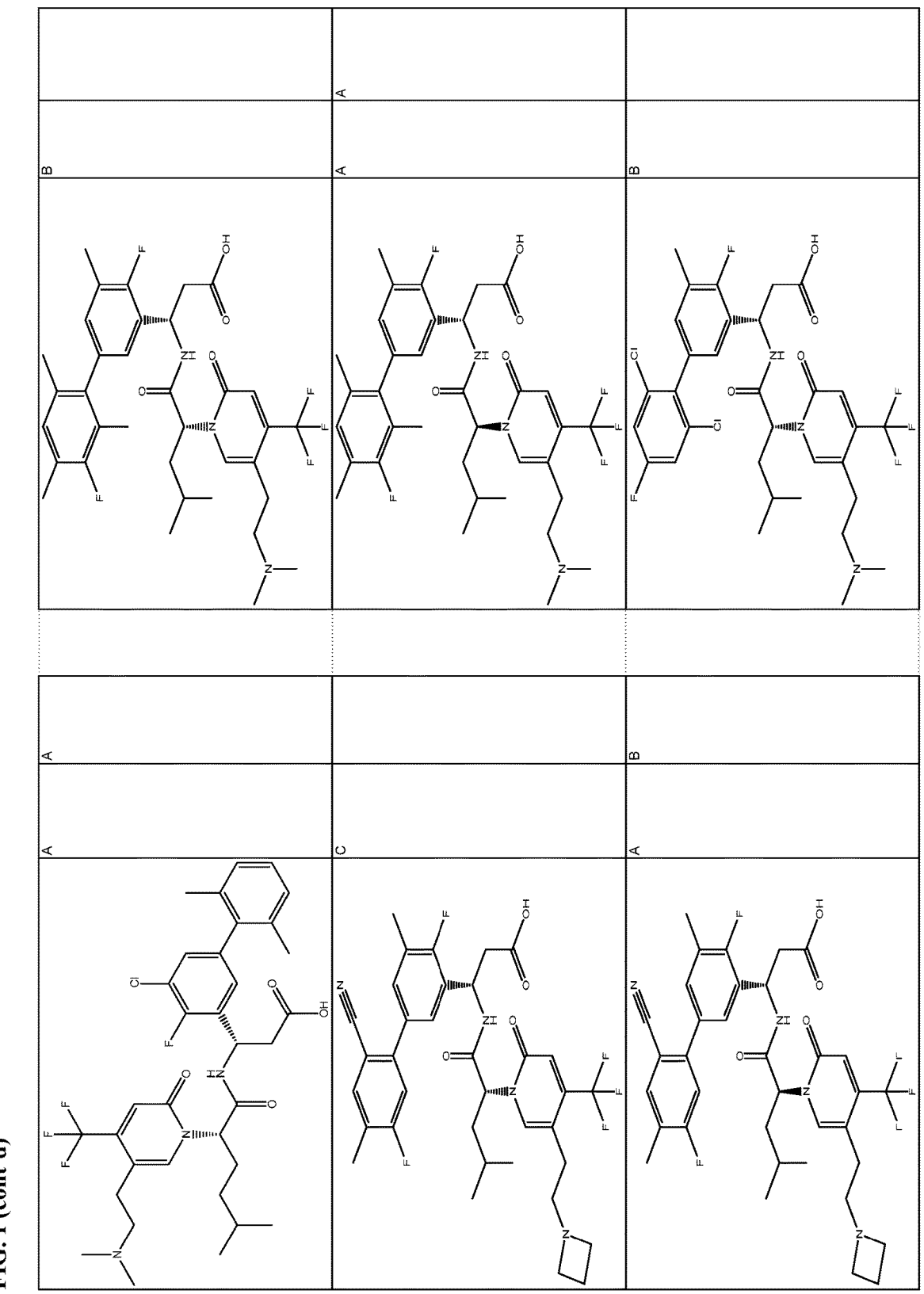
Figure 1:
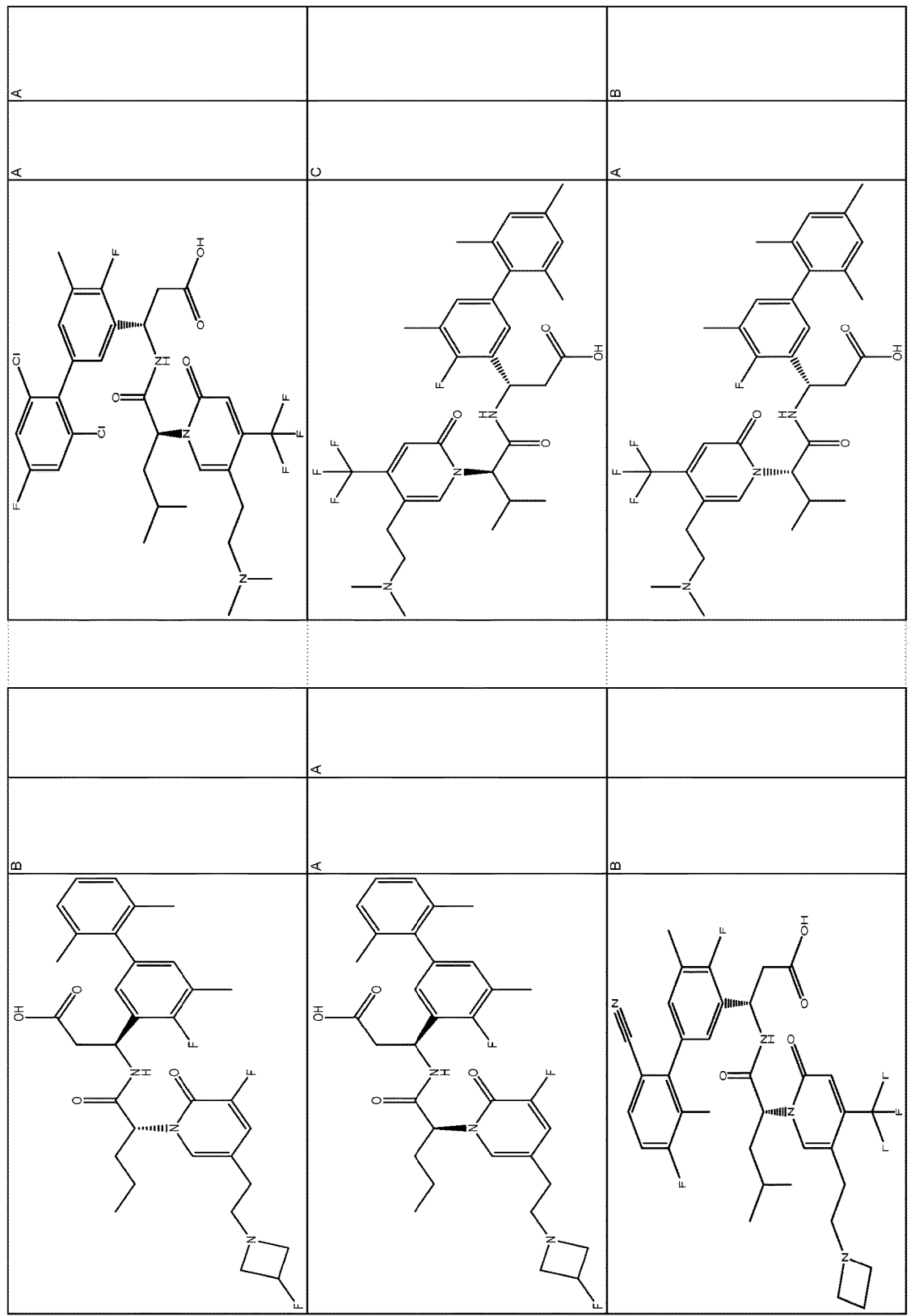
Figure 1:
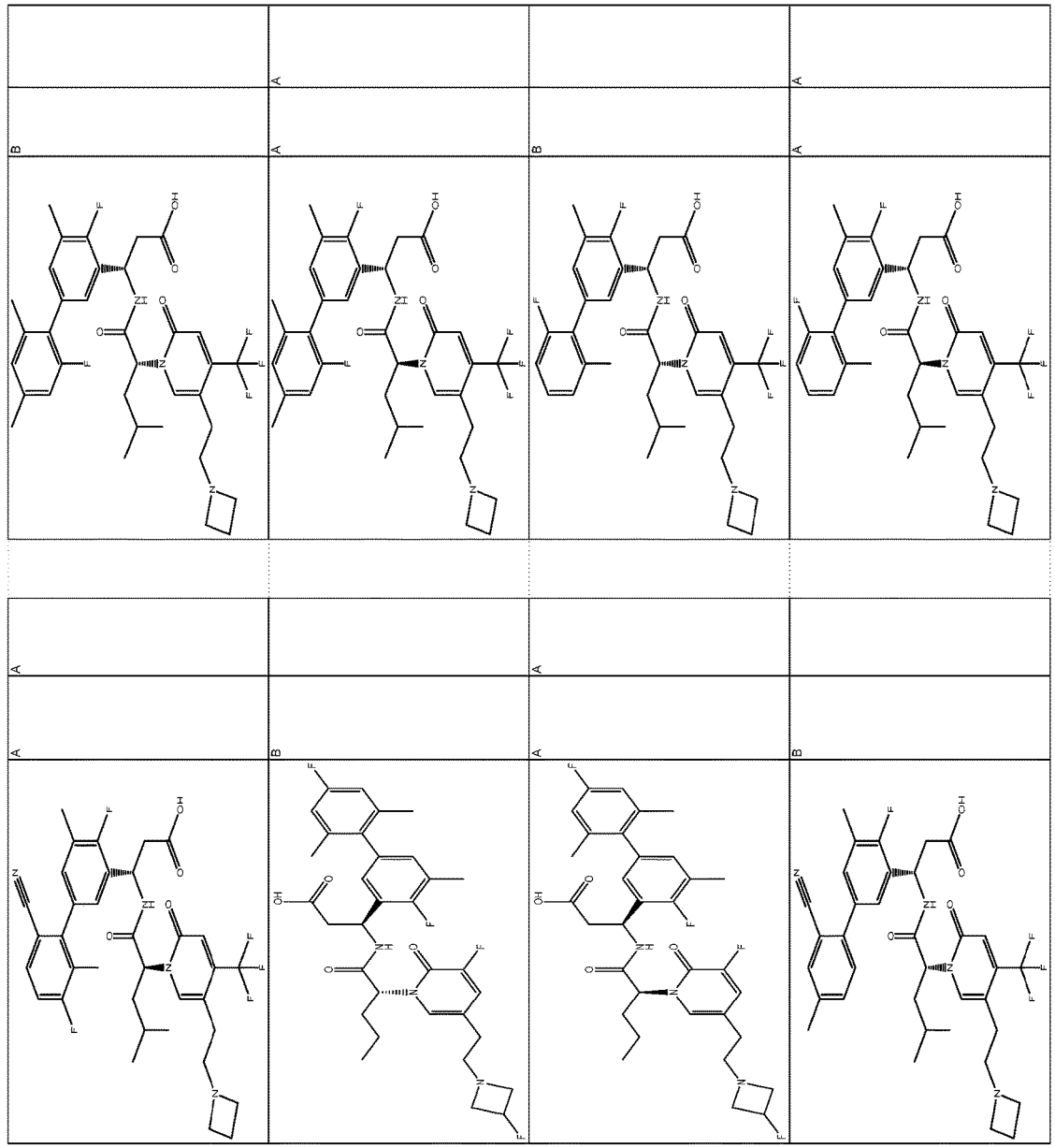
Figure 1:
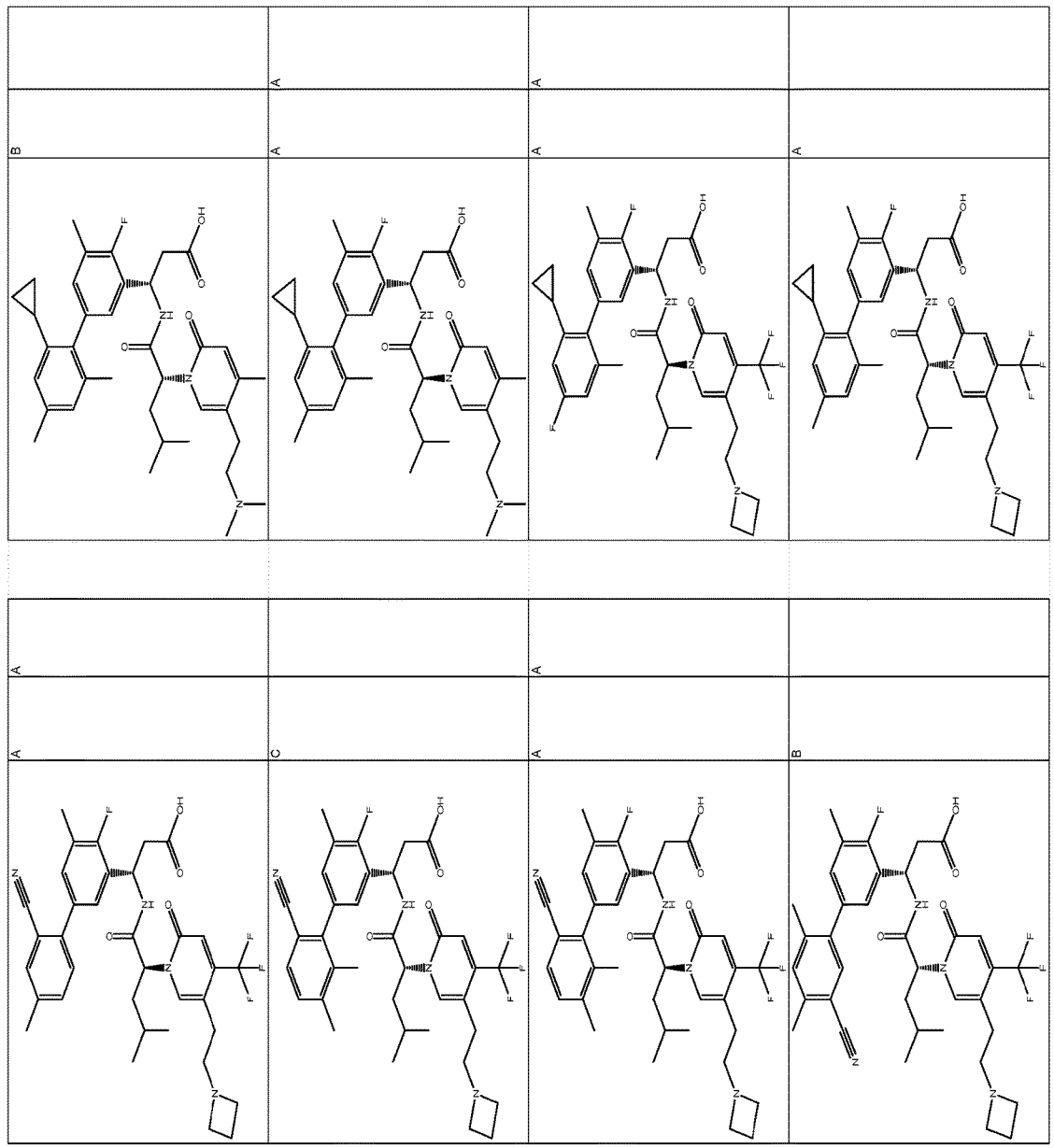
Figure 1:
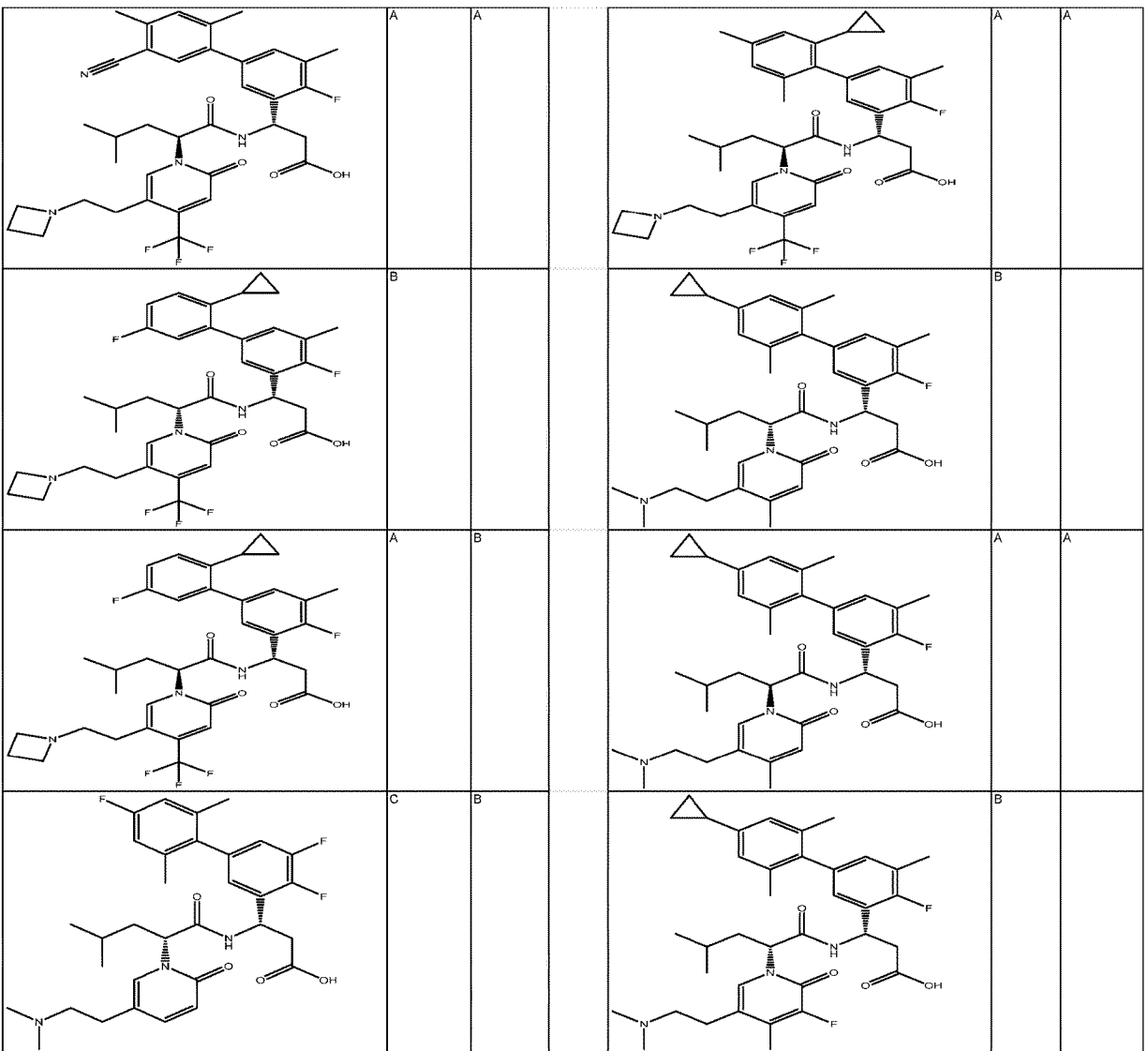
Figure 1:
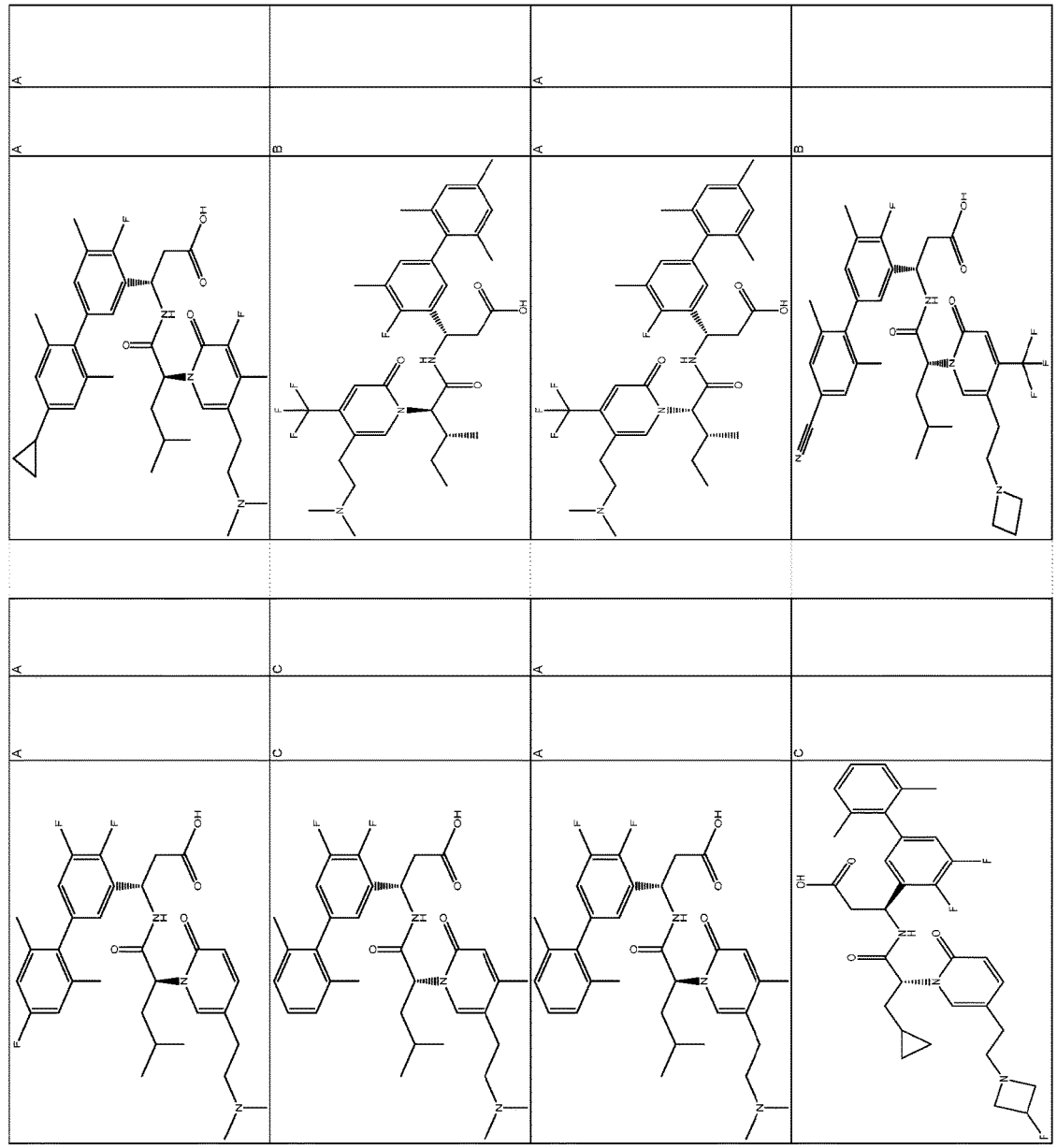
Figure 1:
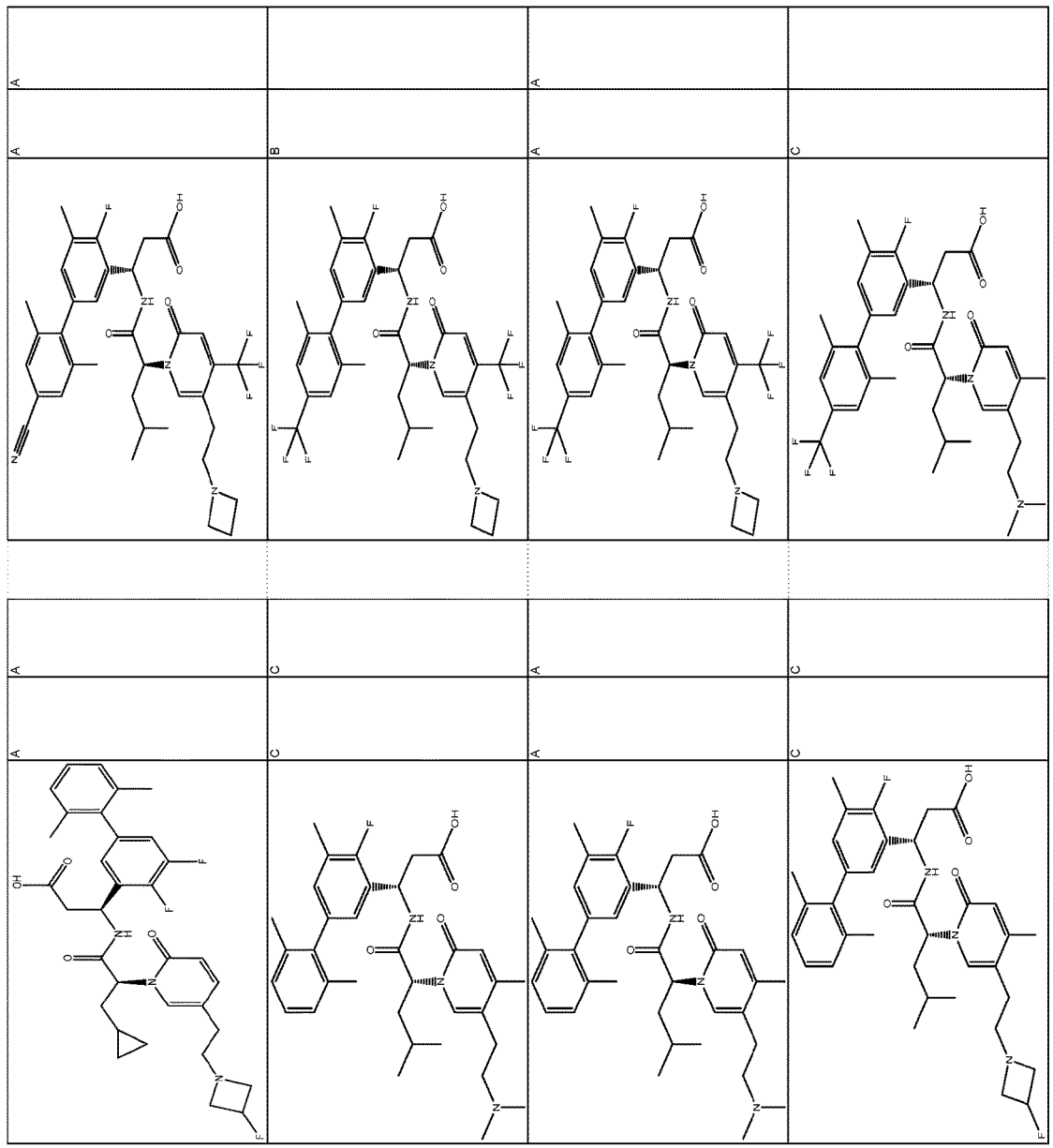
Figure 1:
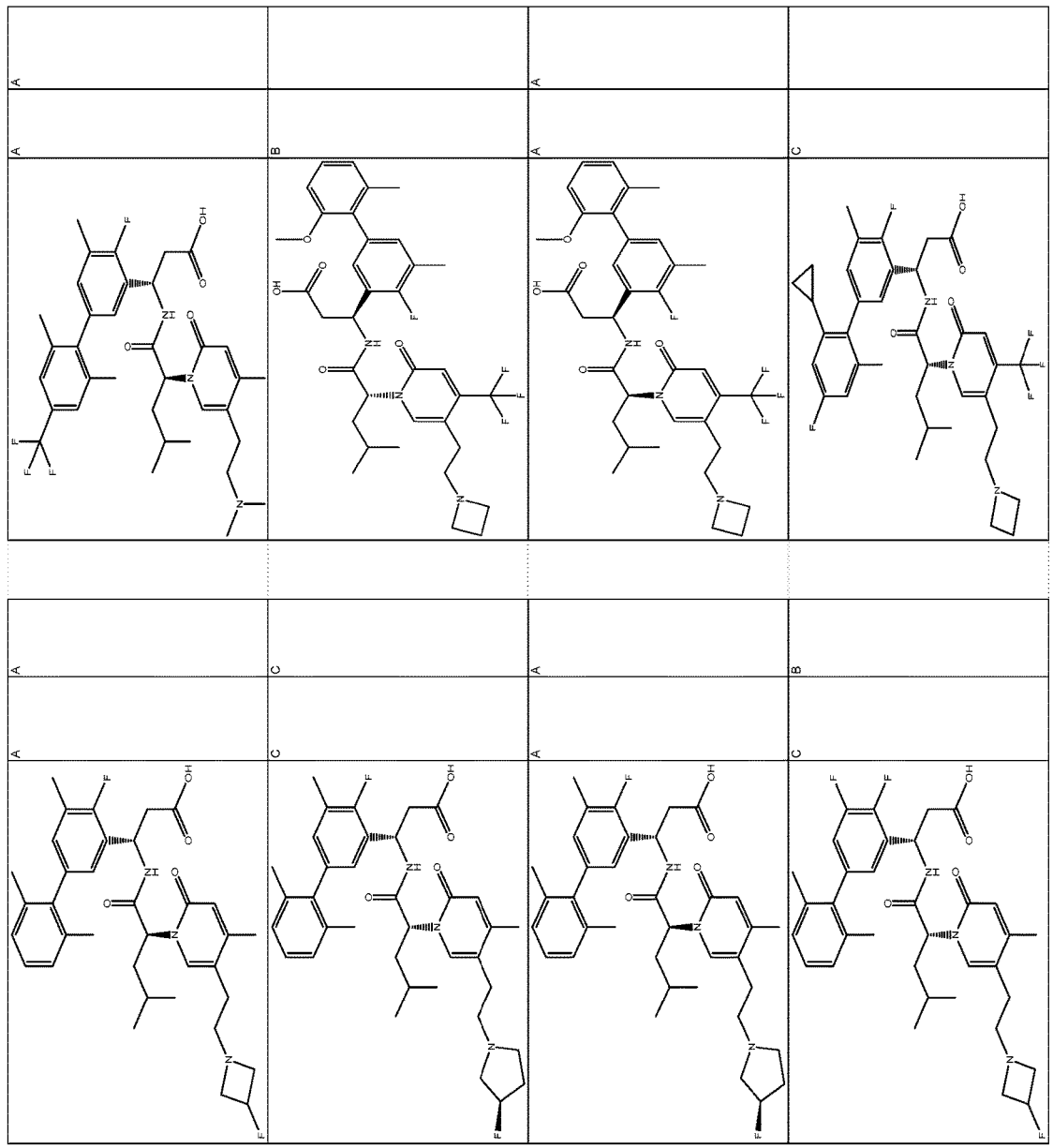
Figure 1:
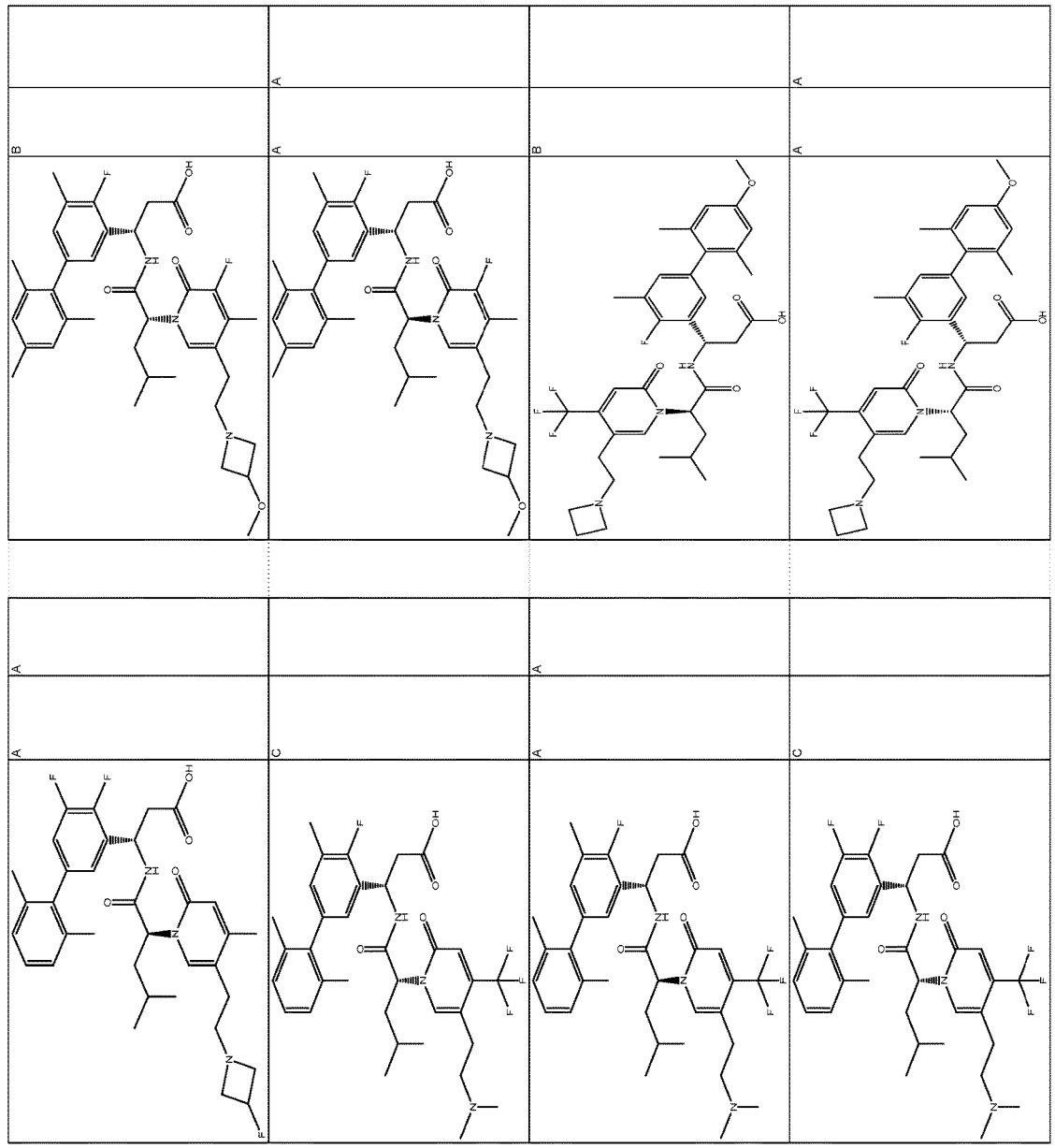
Figure 1:
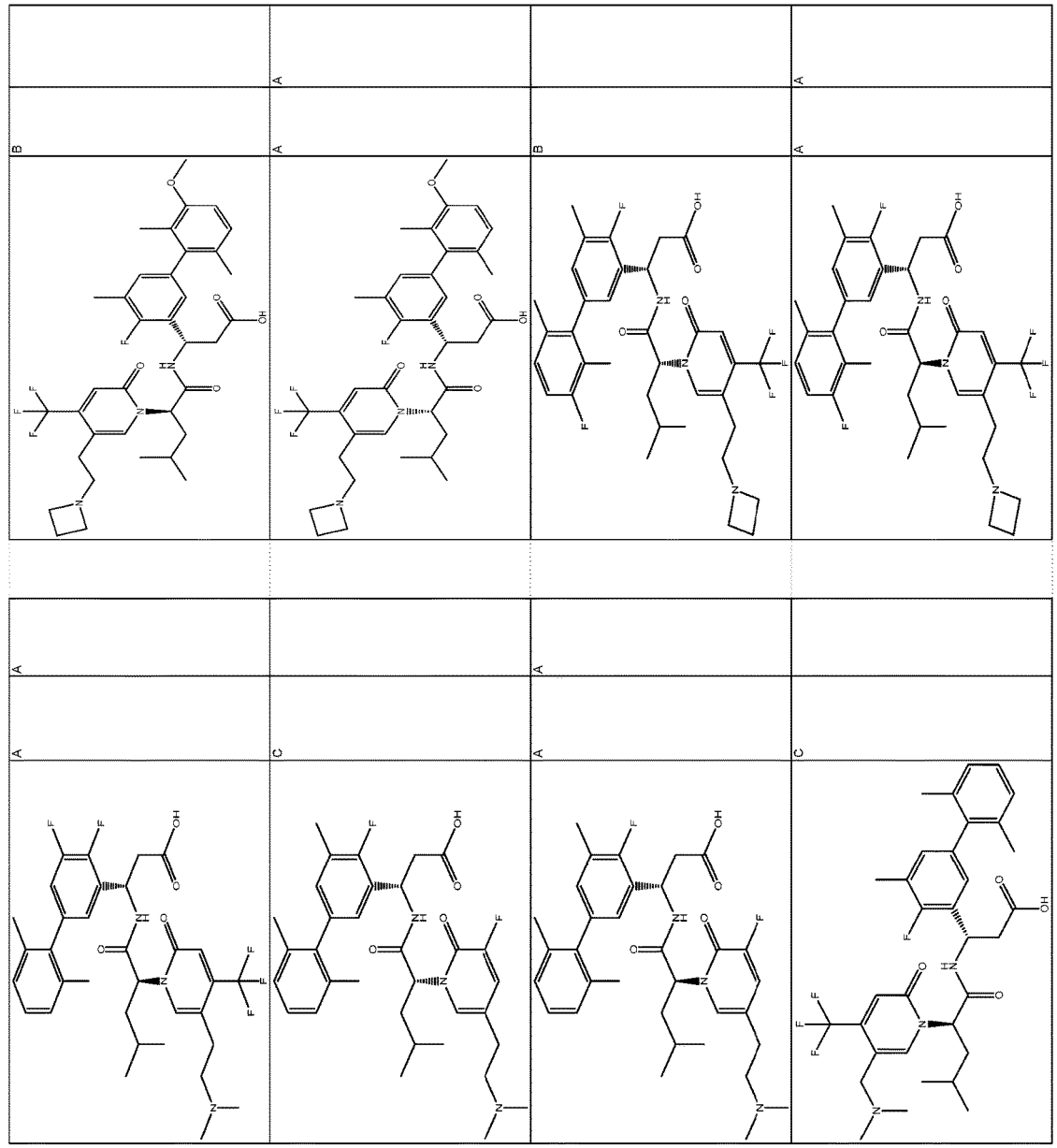
Figure 1:
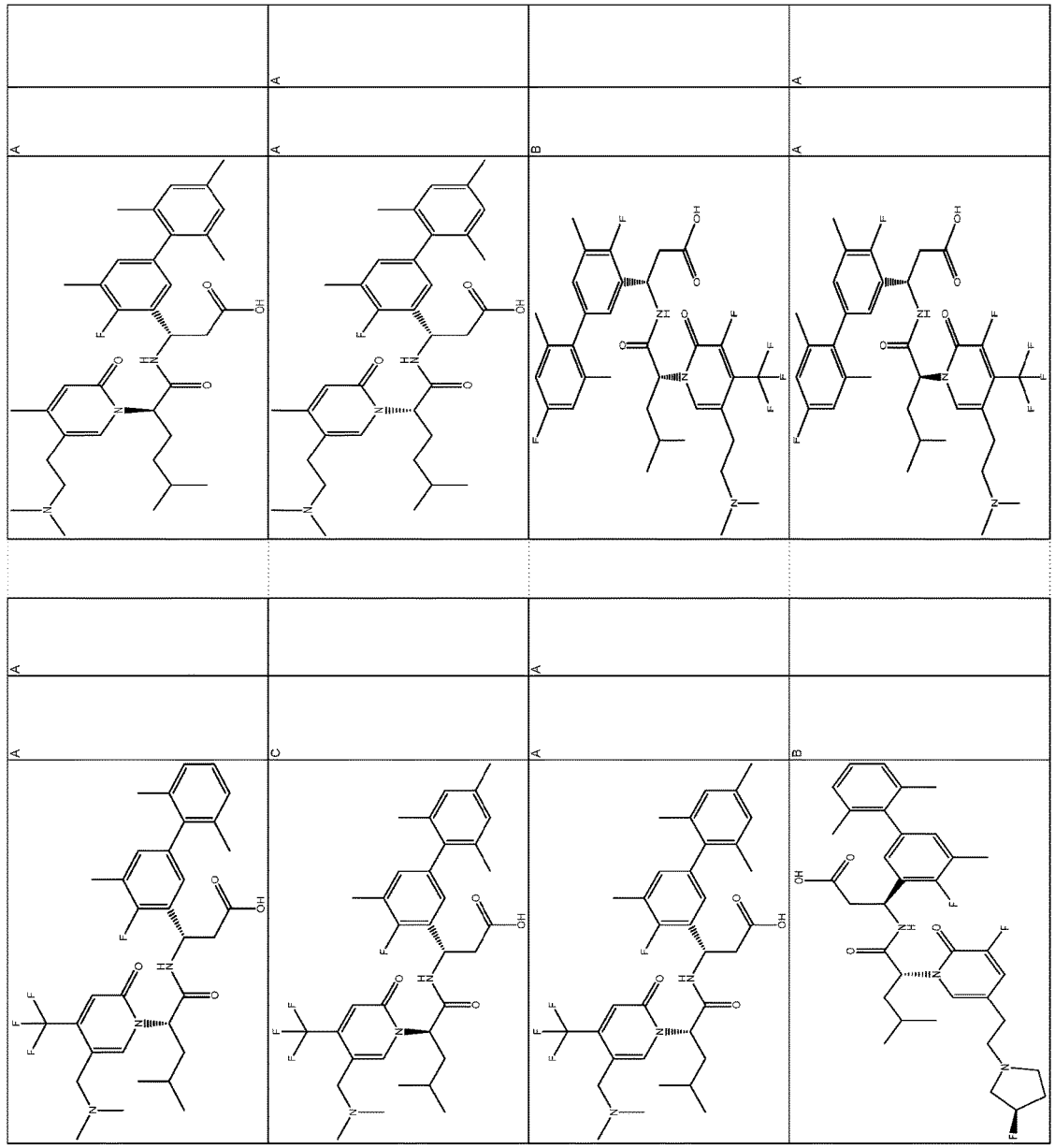
Figure 1:
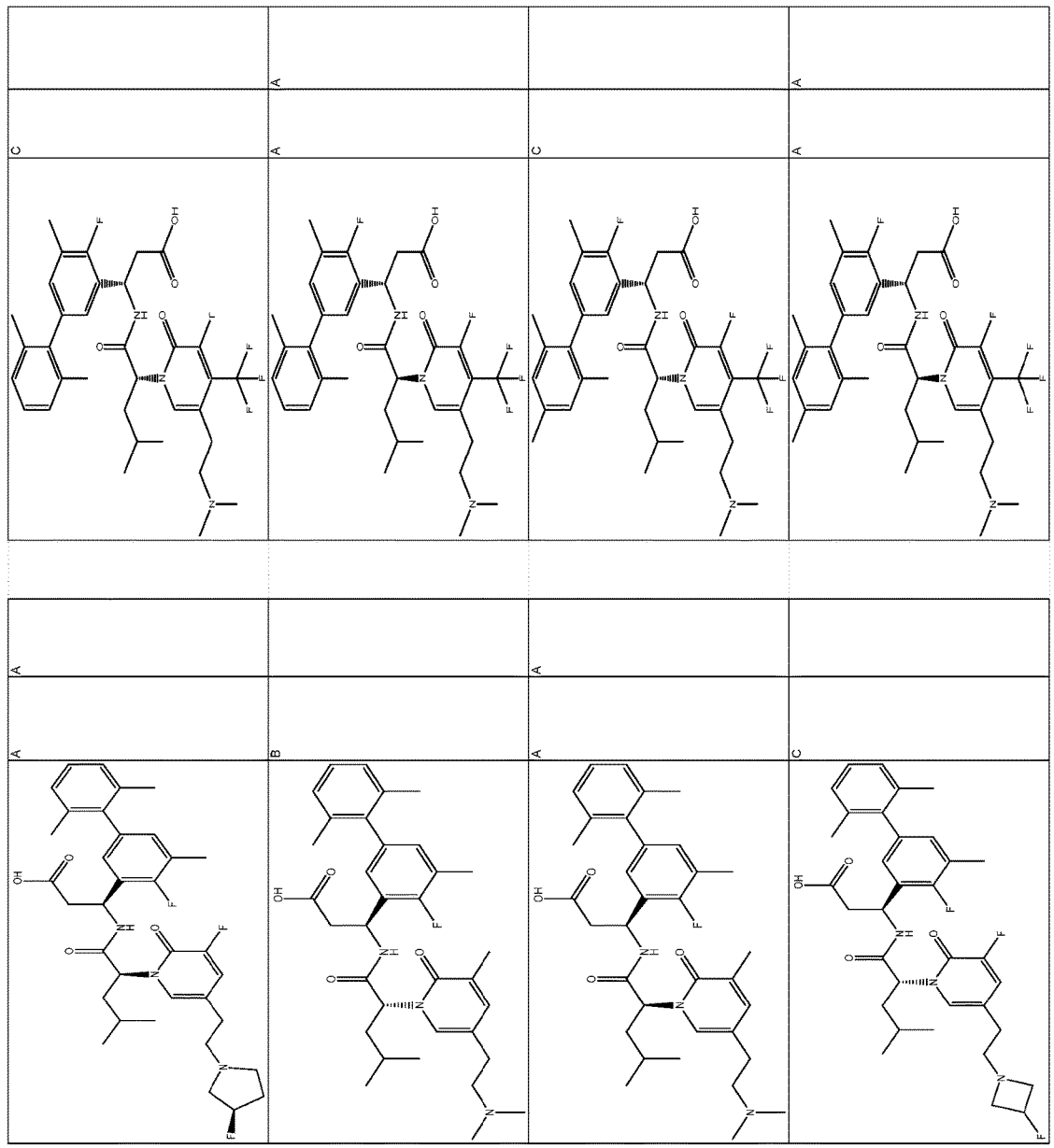
Figure 1:
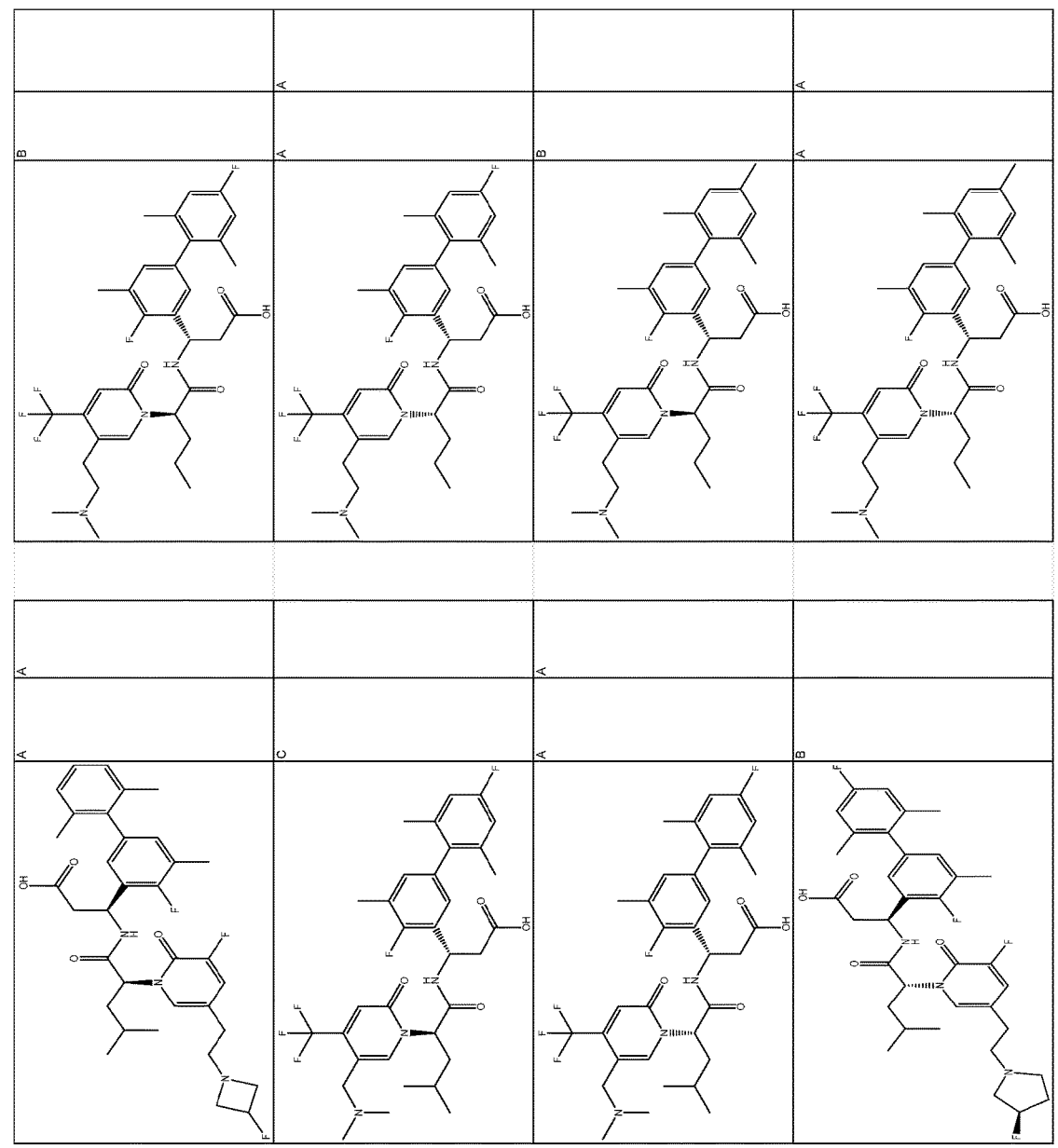
Figure 1:
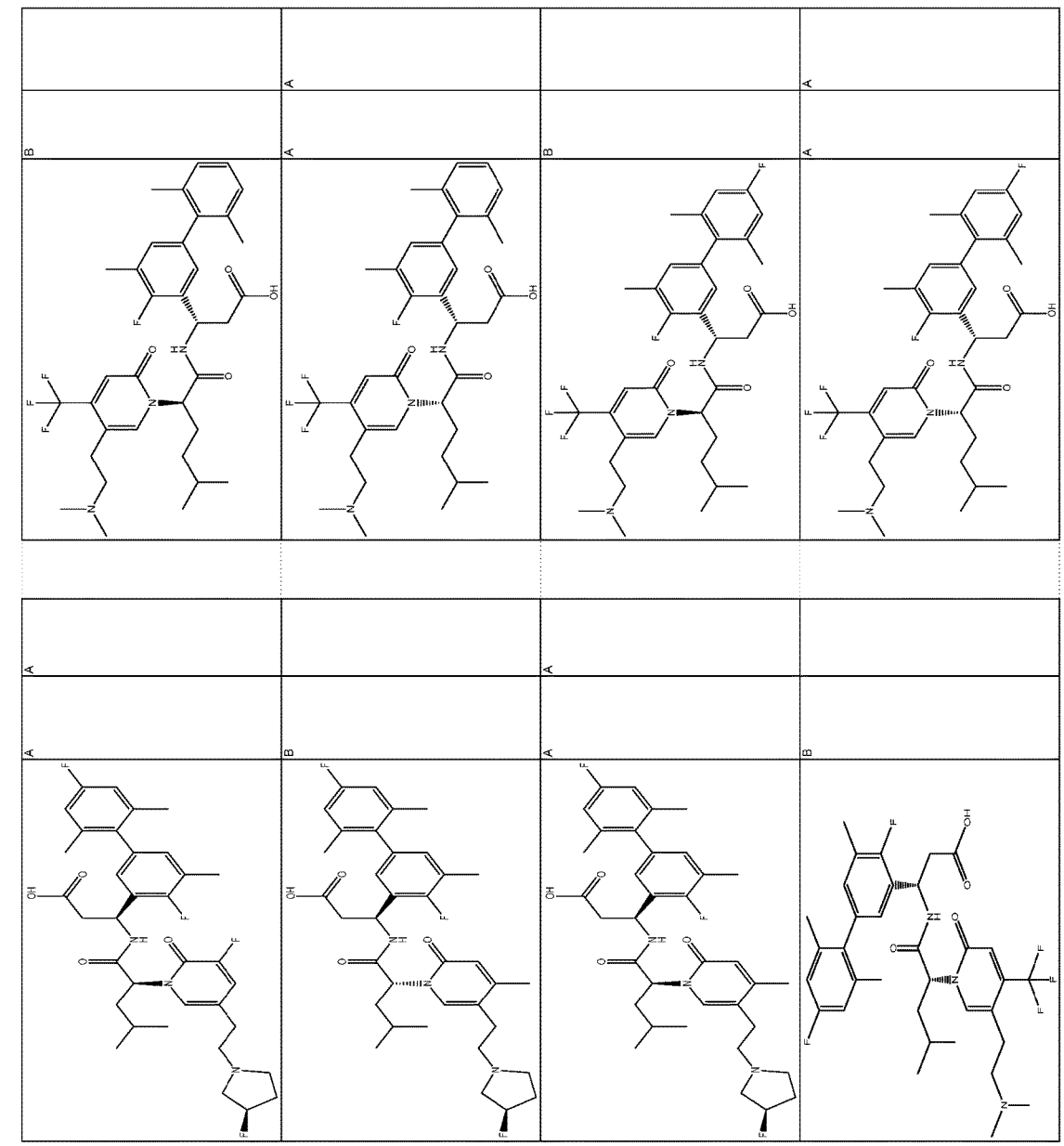
Figure 1:
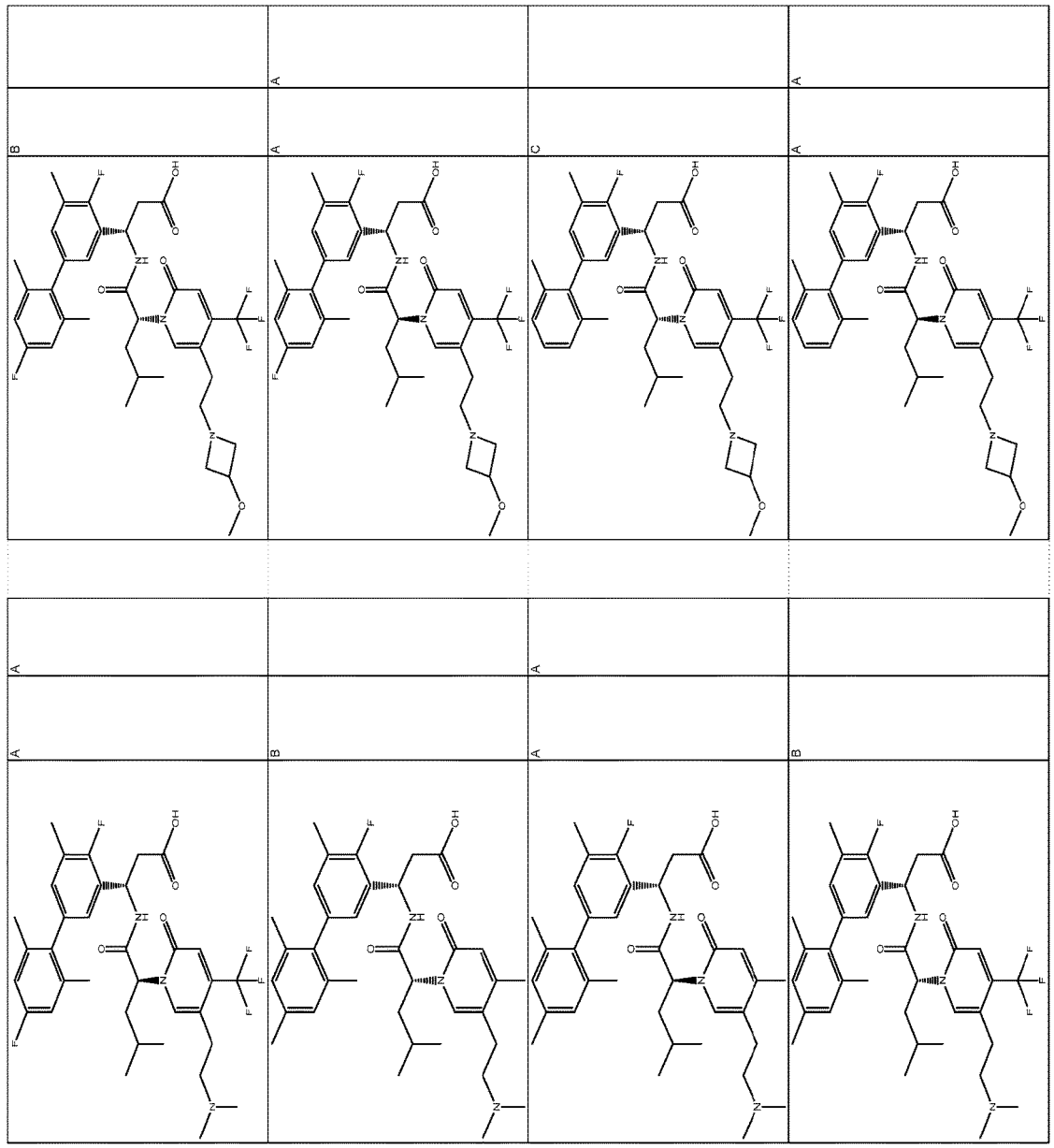
Figure 1:
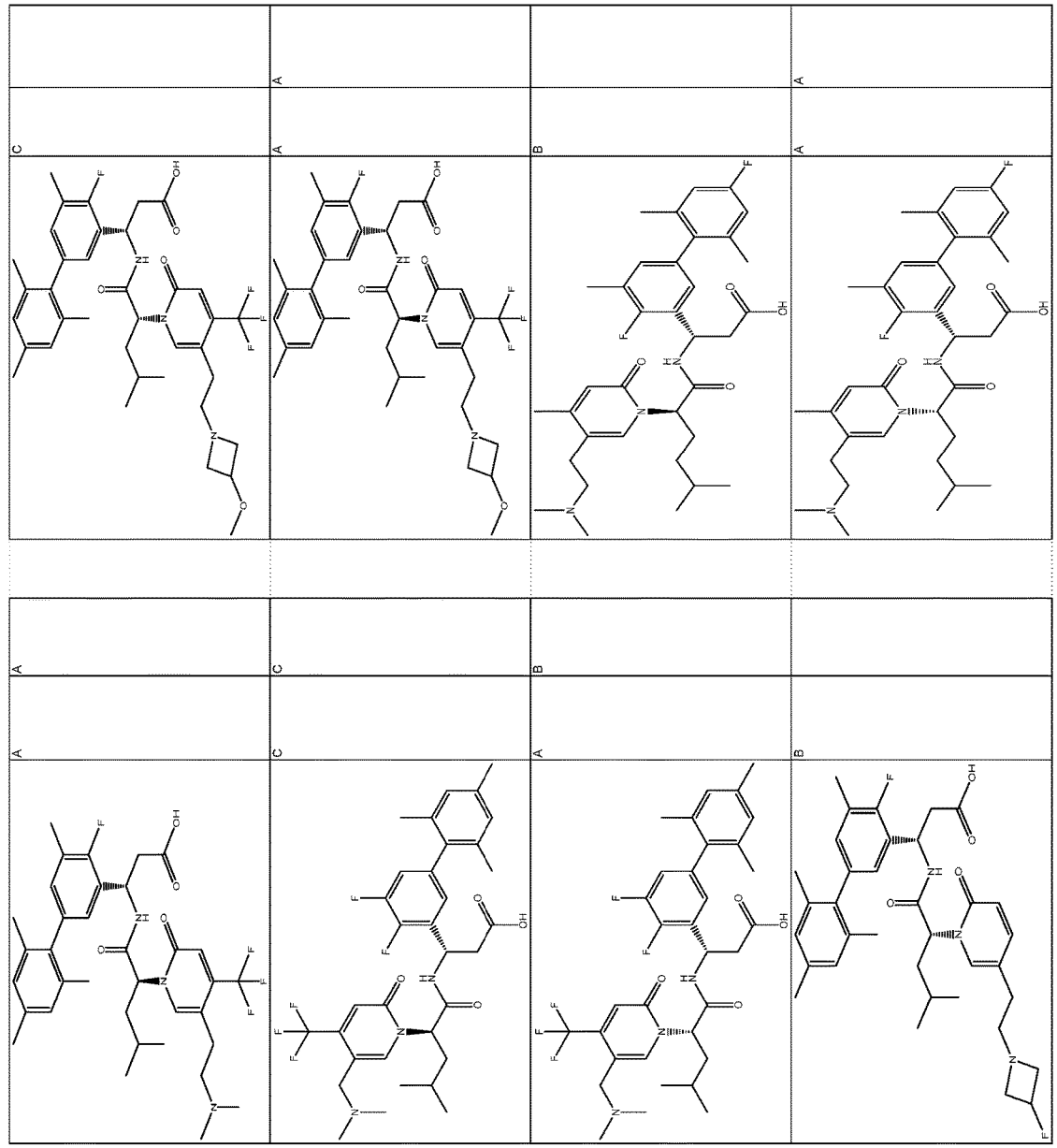
Figure 1:
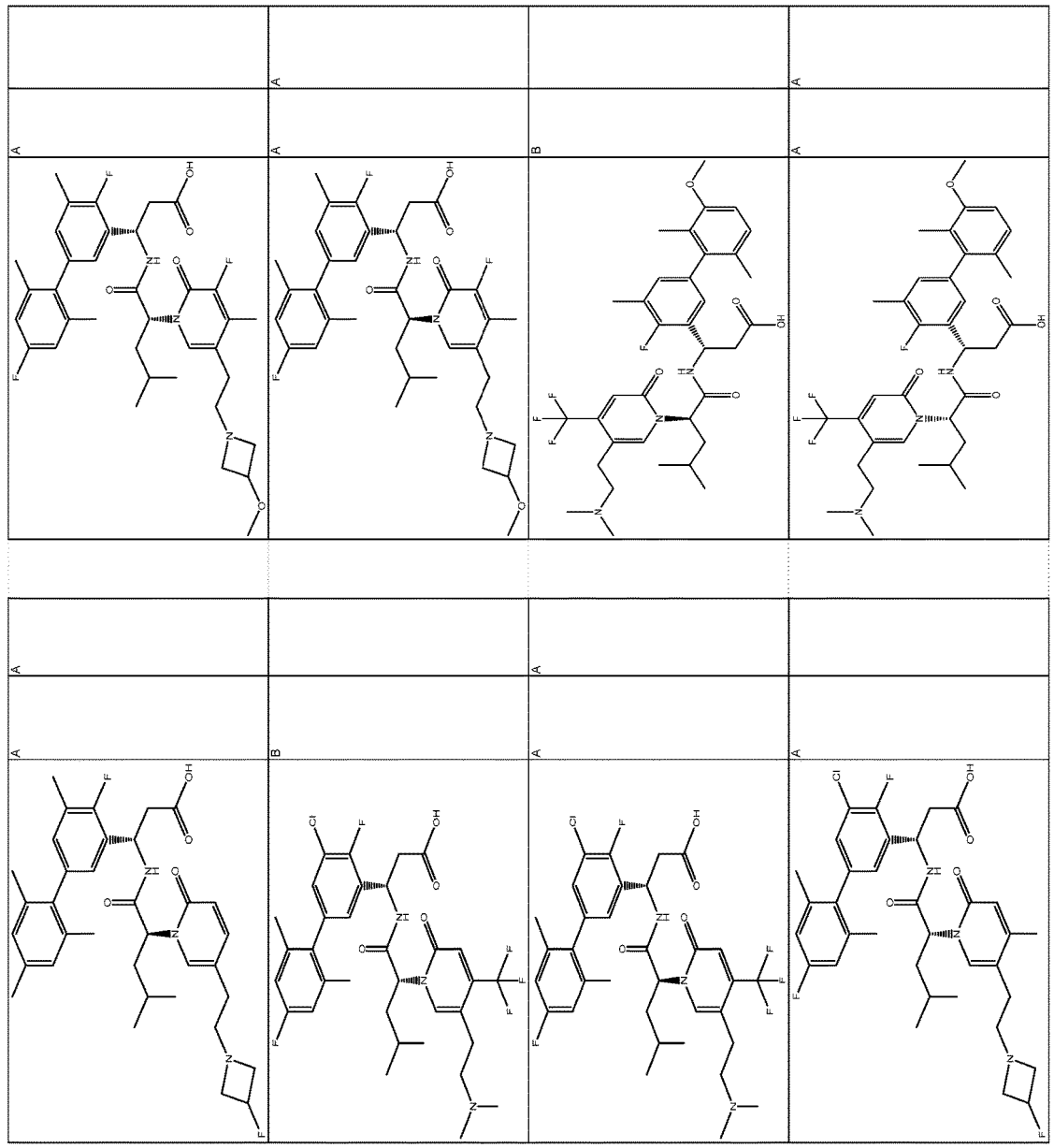
Figure 1:
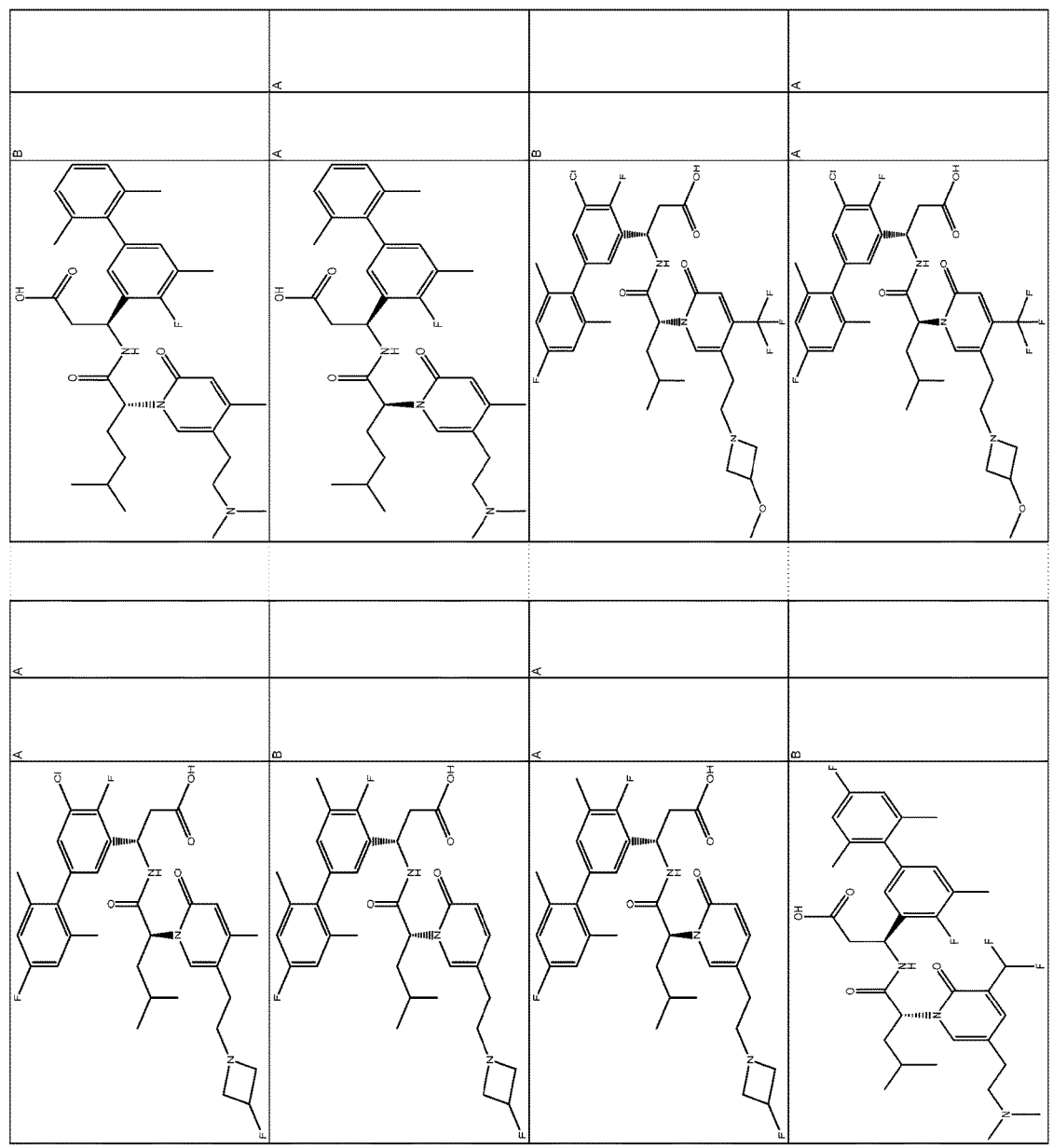
Figure 1:
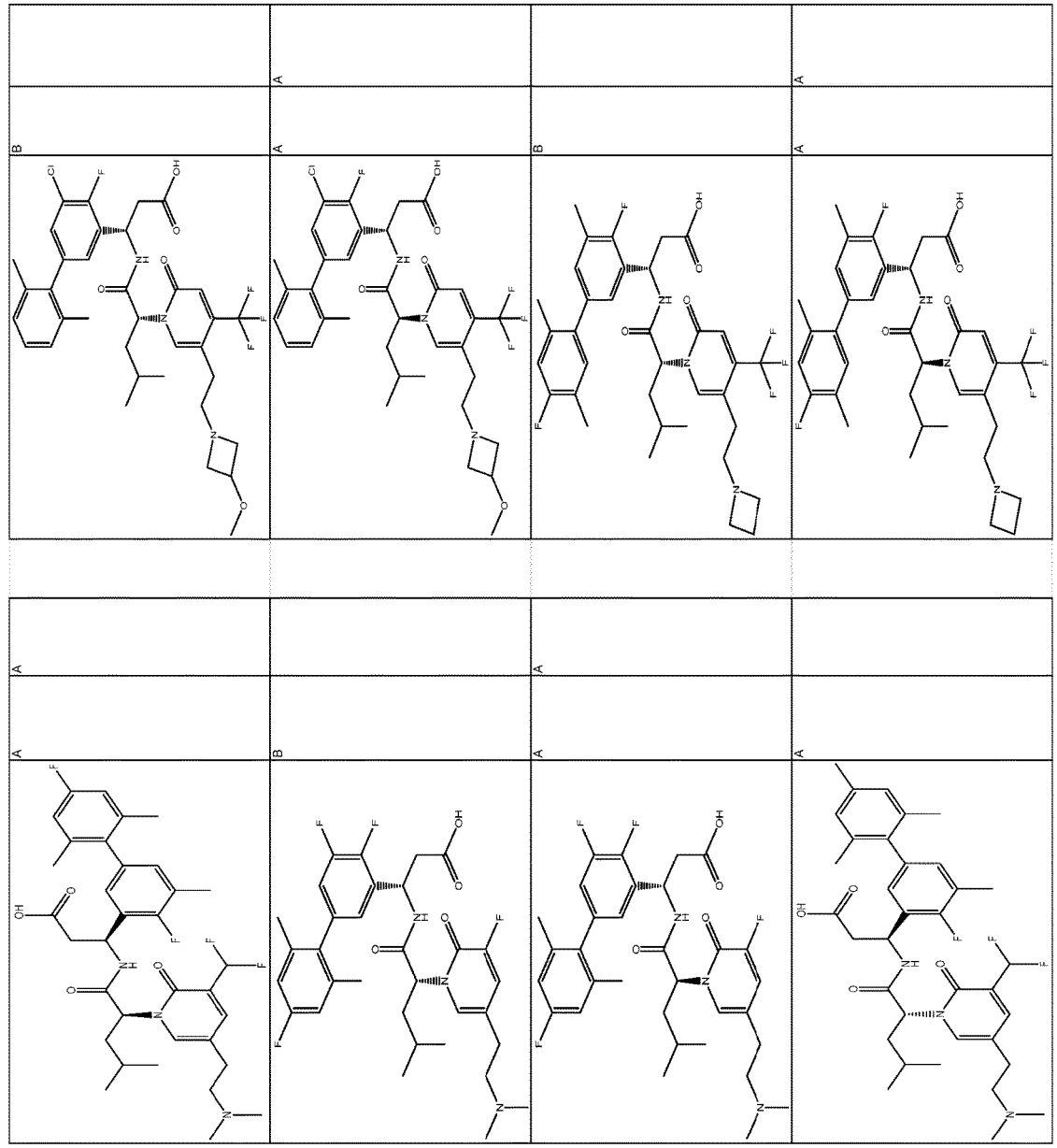
Figure 1:
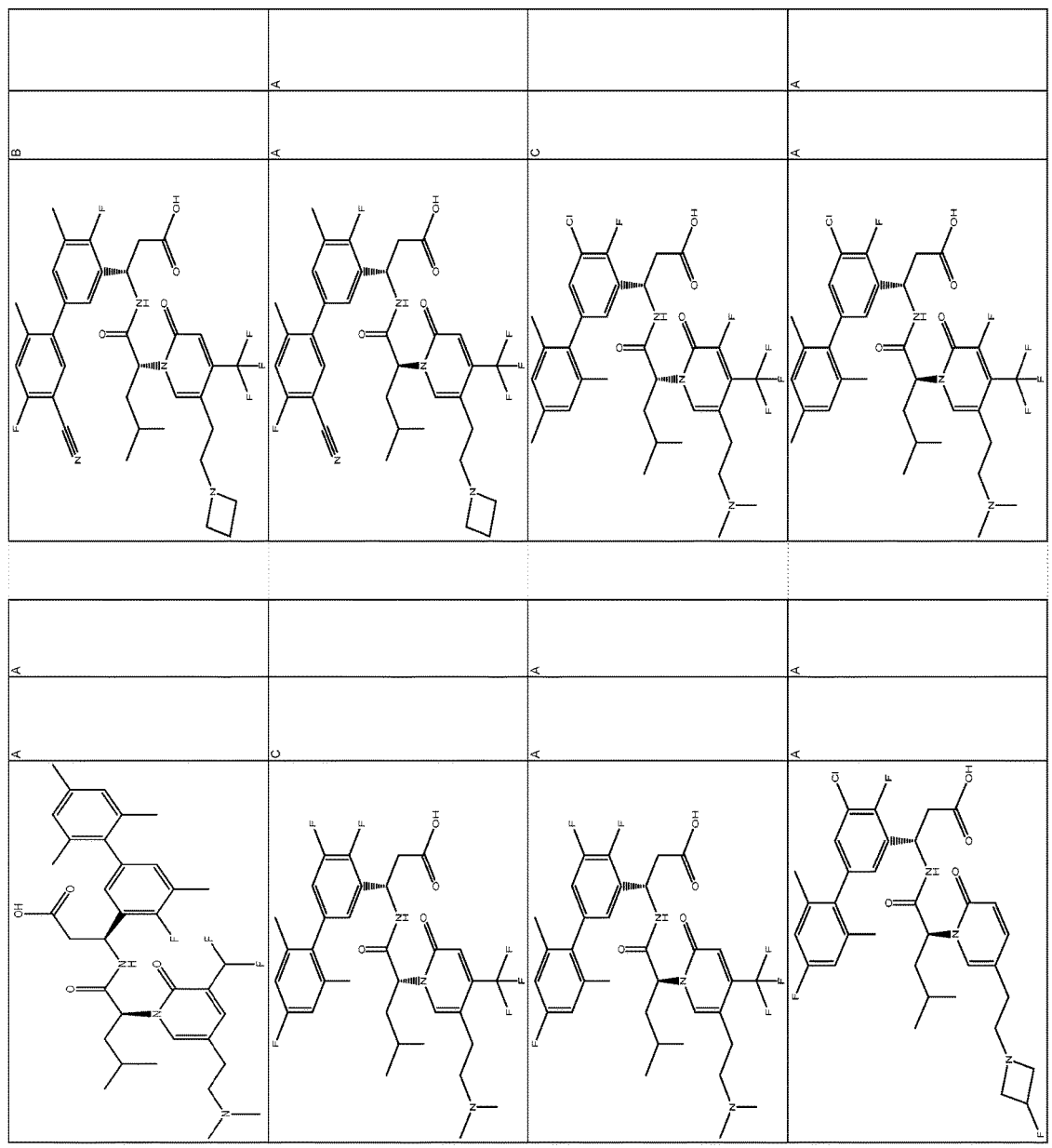
Figure 1:
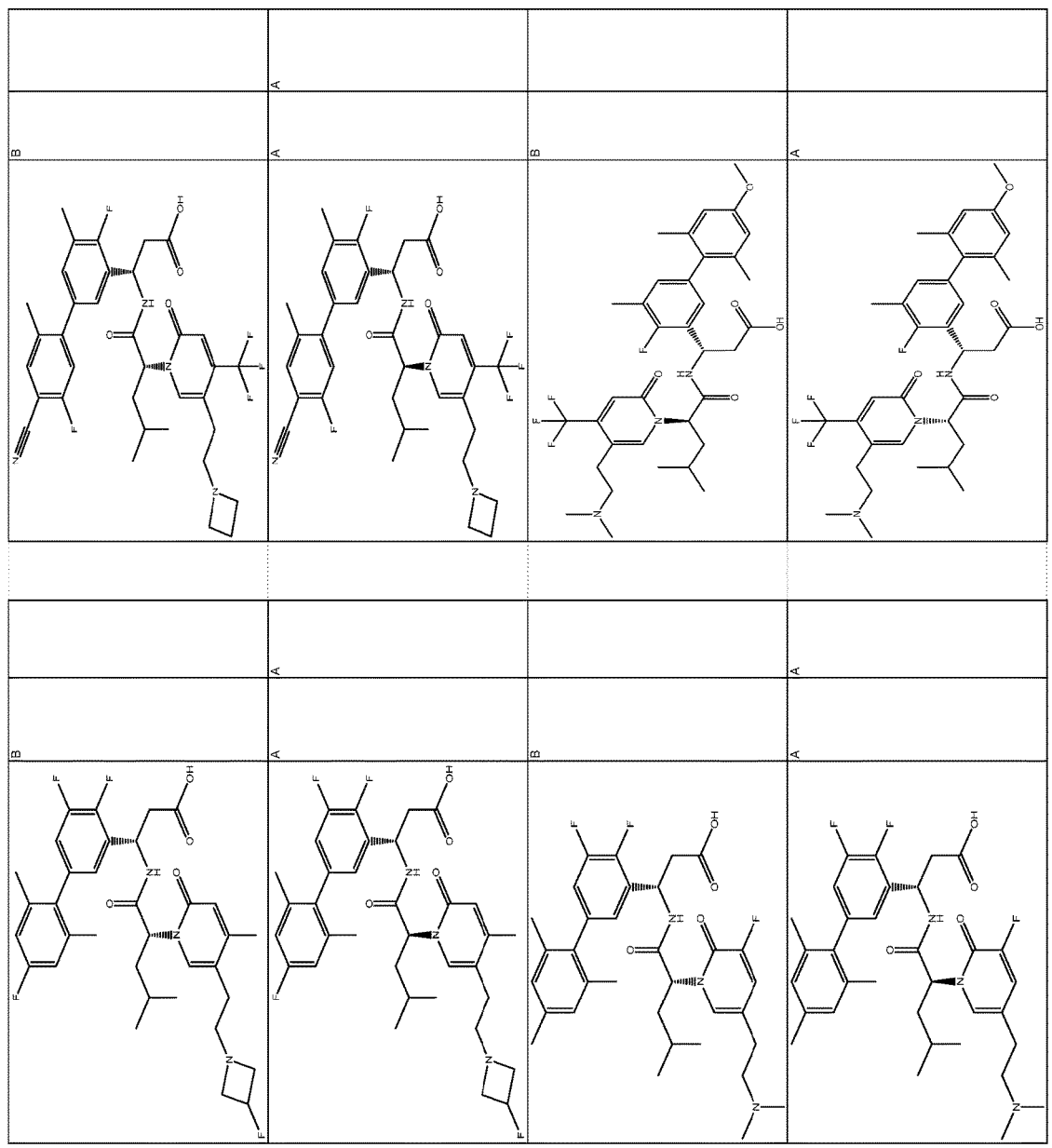
Figure 1:
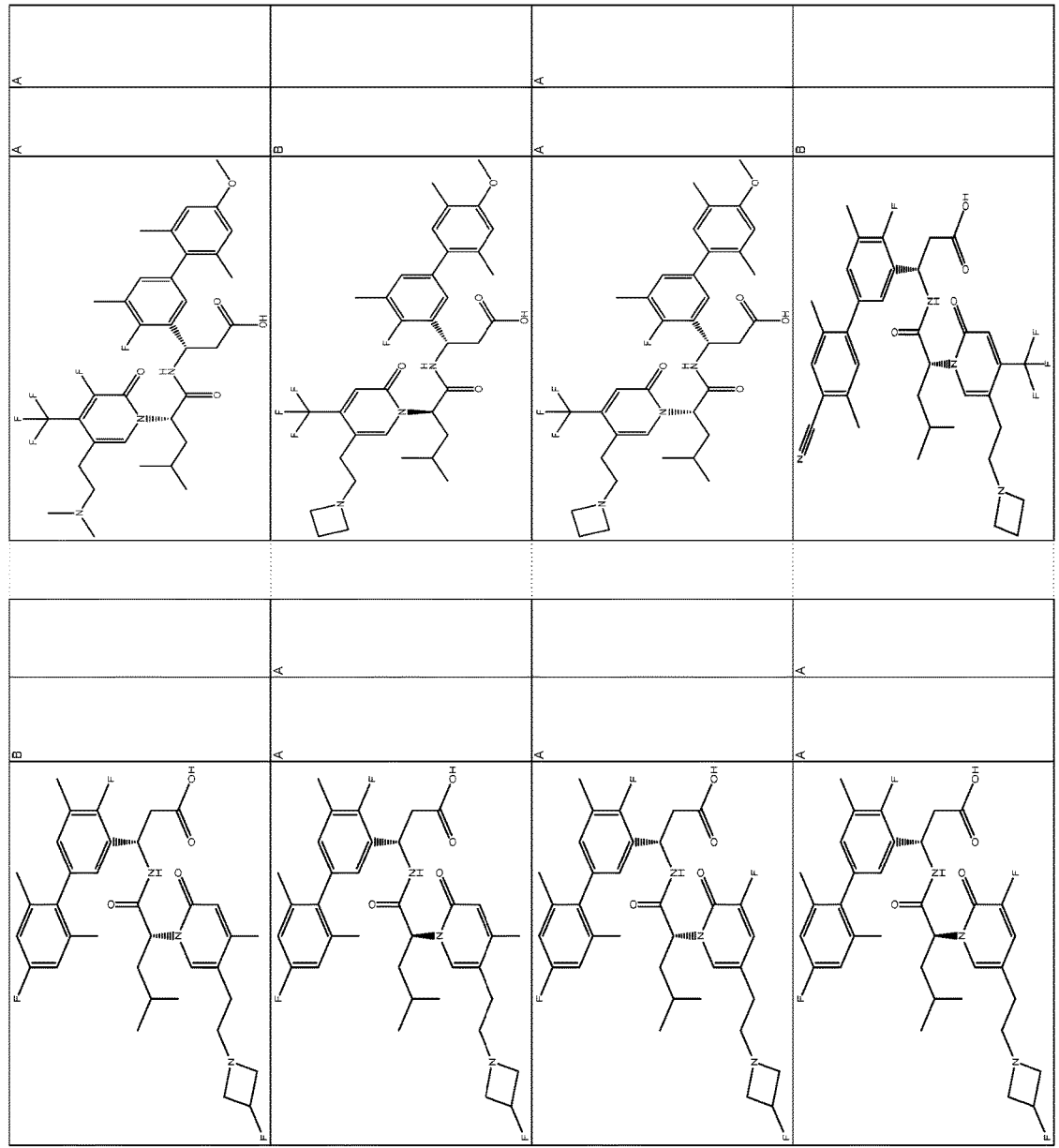
Figure 1:
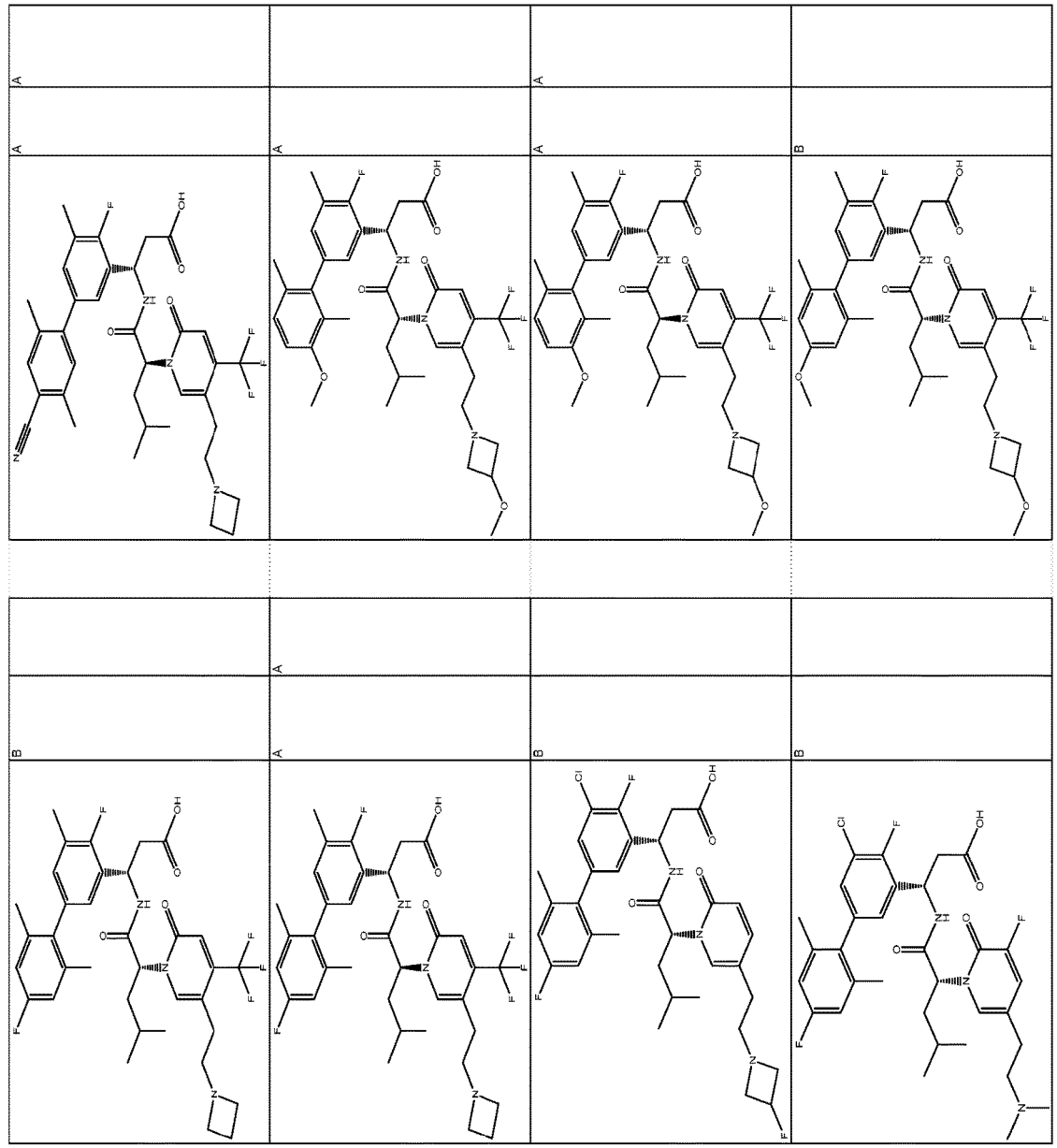
Figure 1:
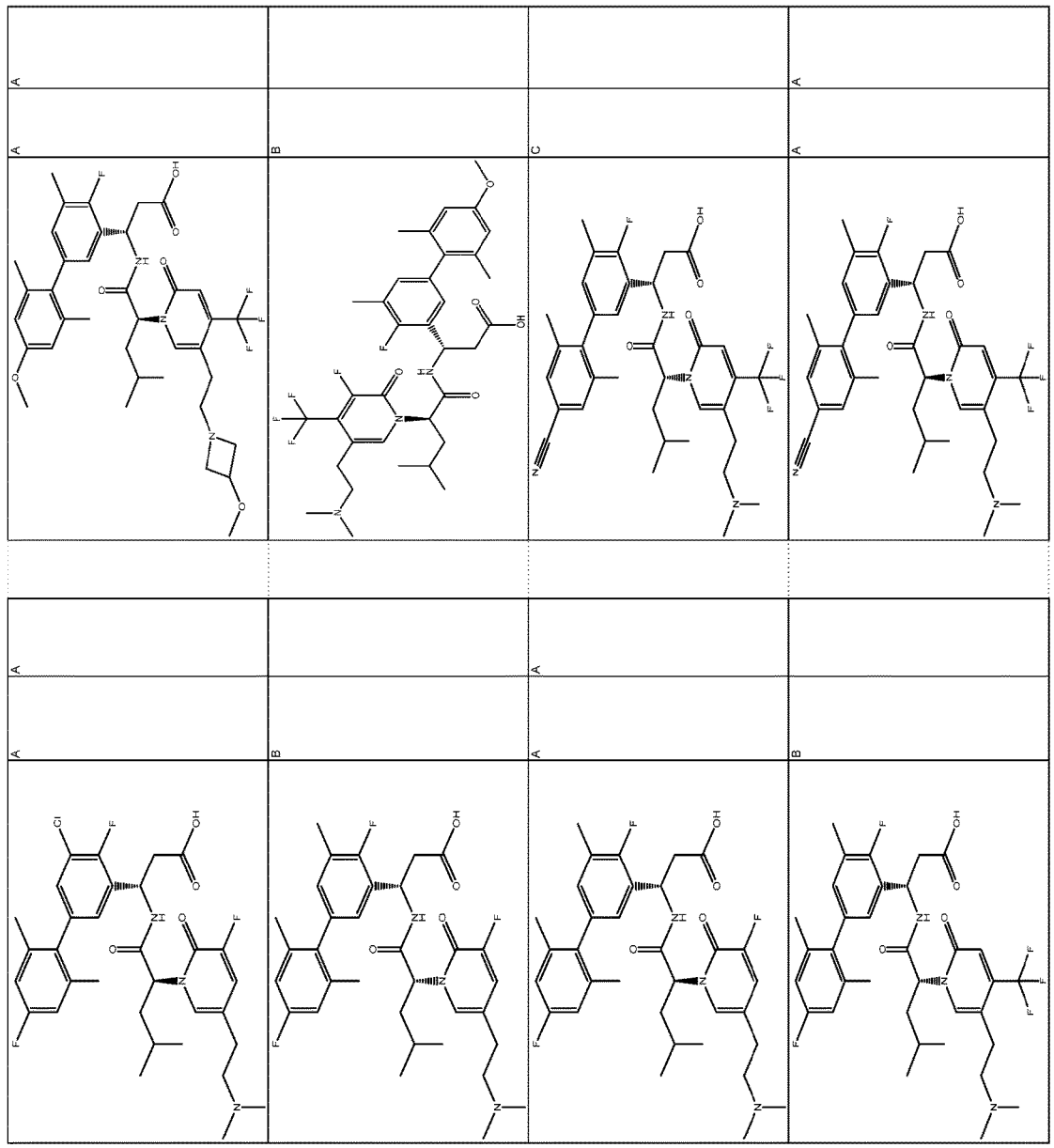
Figure 1:
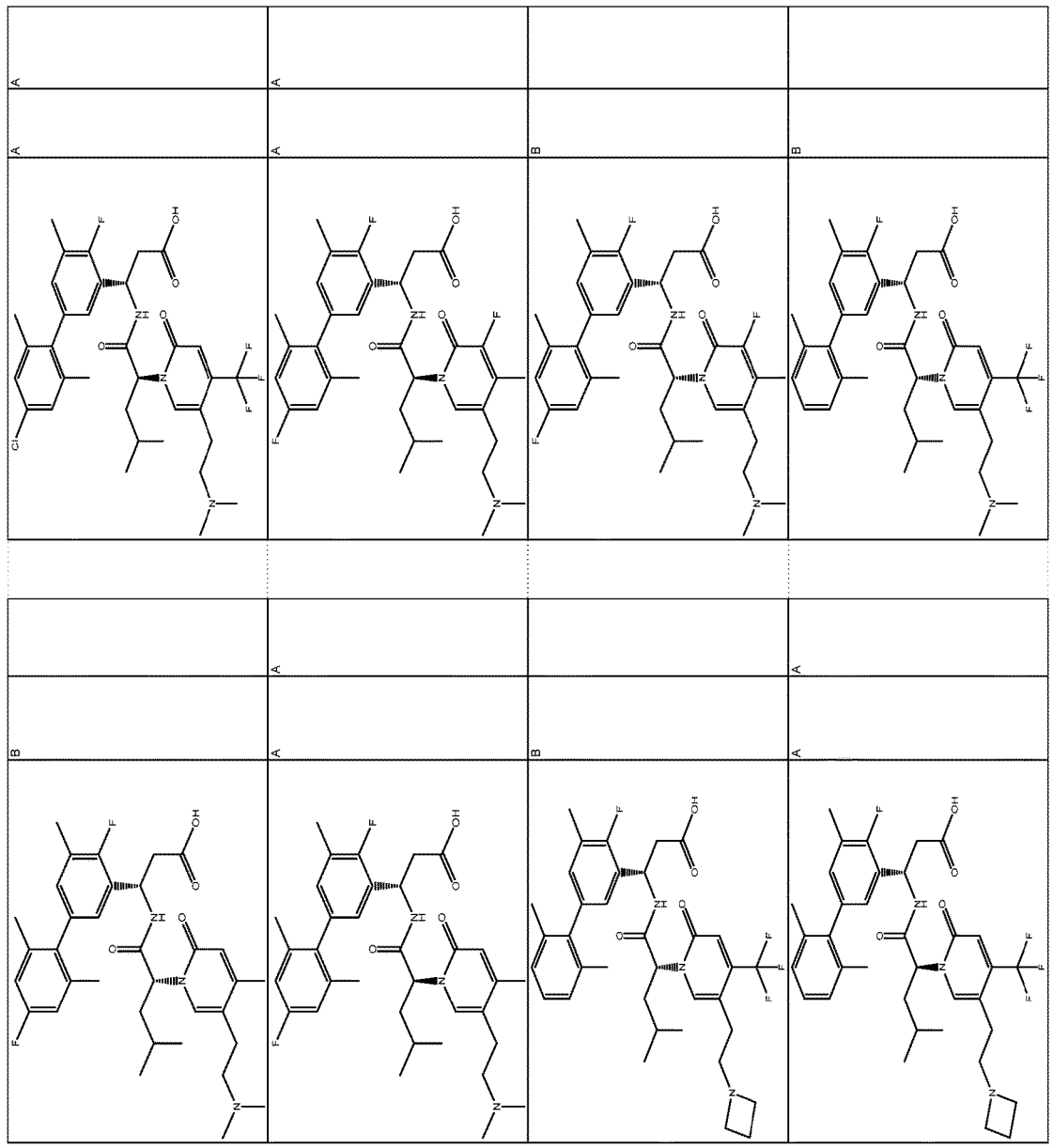
Figure 2:
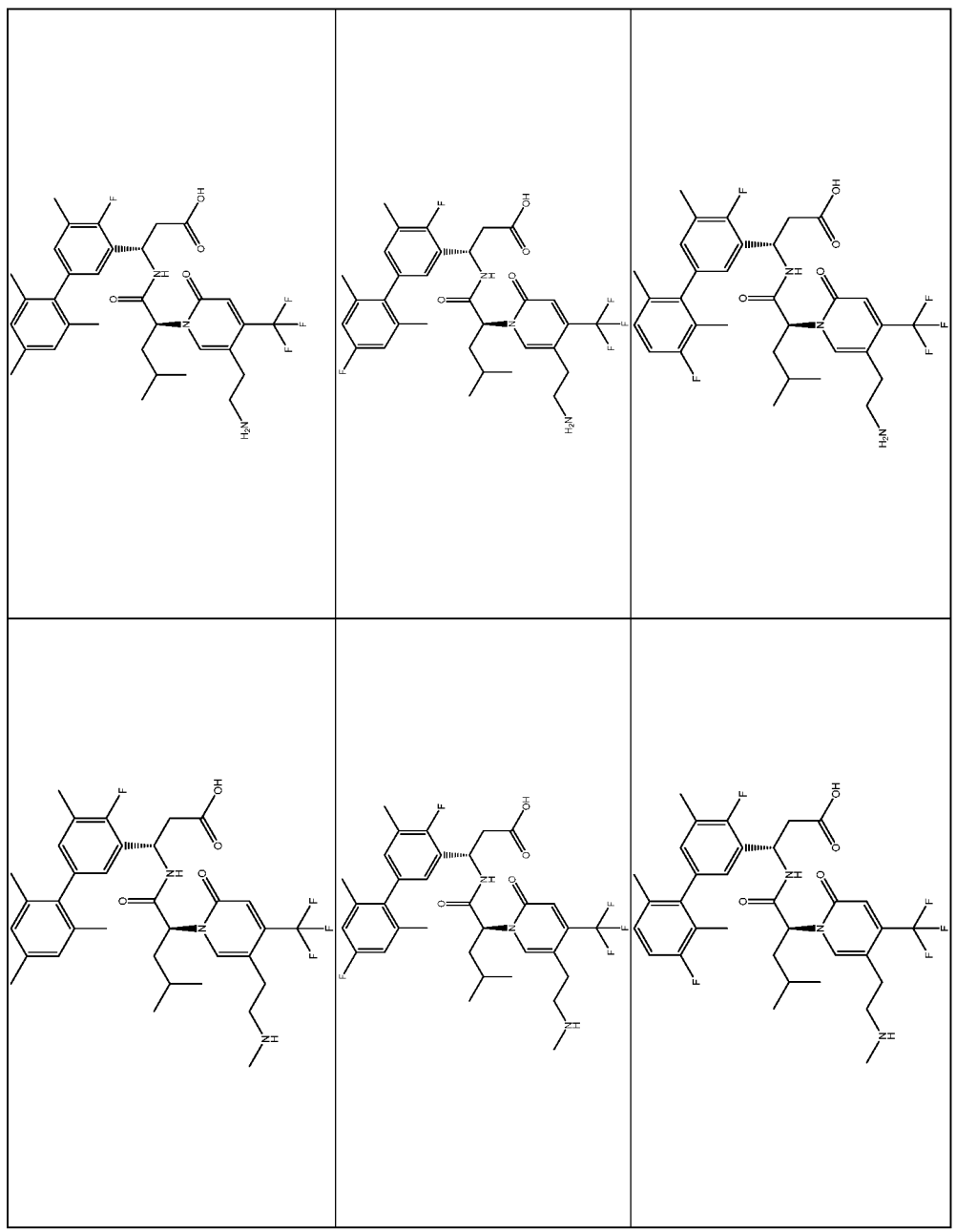
FIG. 2 is a table (Table 2) providing additional exemplary compounds.
Figure 2:
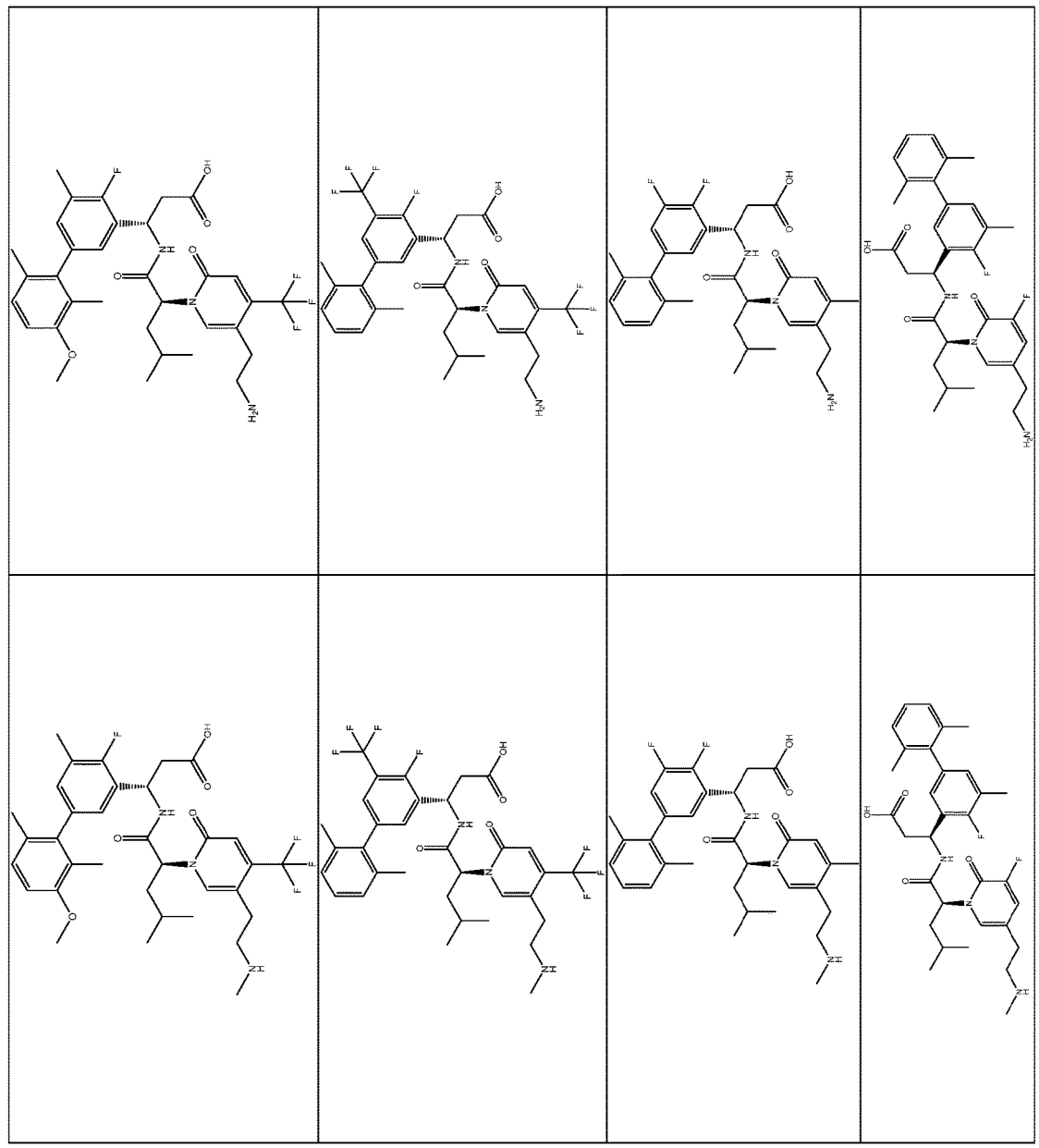
Figure 2:
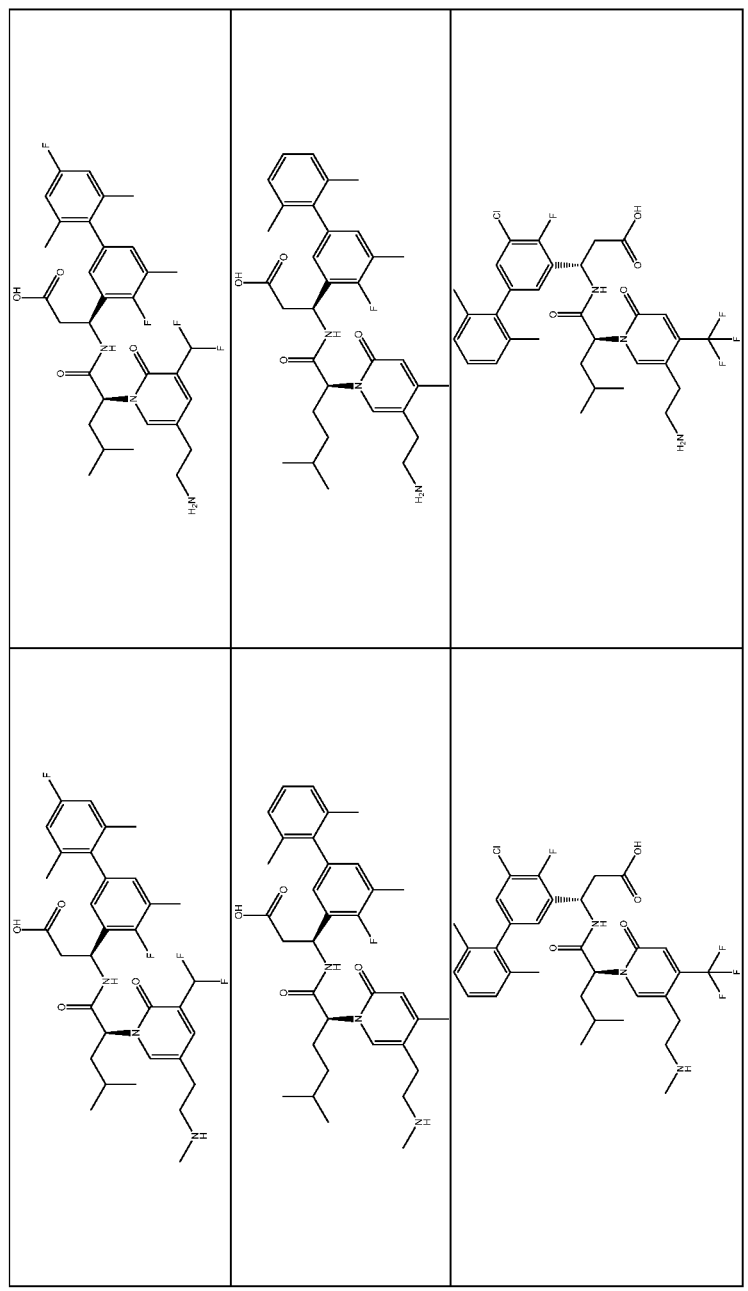

In certain embodiments, the invention relates to compounds that antagonize $\alpha_4\beta_7$ integrin.

The compounds will be useful for the treatment of diseases that are treatable by the inhibition of $\alpha_4\beta_7$ integrin (e.g., Crohn's disease (CD), and ulcerative colitis (UC)).

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

In order for the present invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items.

Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention.

Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Structures depicted herein are also meant to include compounds that differ only in the presence of one or more isotopically enriched atoms. For example, compounds produced by the replacement of a hydrogen with deuterium or tritium, or of a carbon with a $^{13}$C- or $^{14}$C-enriched carbon are within the scope of this invention.

The terms "$\alpha_4\beta_7$", "a4B7", "a4b7", "alpha-4 beta-7" and "alpha 4 beta 7" and the like as used herein all refer to $\alpha_4\beta_7$.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salts" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, for example, Berge et al. (1977) "Pharmaceutical Salts", *J. Pharm. Sci.* 66:1-19.)

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound(s). These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

A "therapeutically effective amount" (or "effective amount") of a compound with respect to use in treatment, refers to an amount of the compound in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "patient" refers to a mammal in need of a particular treatment. In certain embodiments, a patient is a primate, canine, feline, or equine. In certain embodiments, a patient is a human.

An aliphatic chain comprises the classes of alkyl, alkenyl and alkynyl defined below. A straight aliphatic chain is limited to unbranched carbon chain moieties. As used herein, the term "aliphatic group" refers to a straight chain, branched-chain, or cyclic aliphatic hydrocarbon group and includes saturated and unsaturated aliphatic groups, such as an alkyl group, an alkenyl group, or an alkynyl group.

"Alkyl" refers to a fully saturated cyclic or acyclic, branched or unbranched carbon chain moiety having the number of carbon atoms specified, or 1 up to 30 carbon atoms if no specification is made. For example, alkyl of 1 to 8 carbon atoms refers to moieties such as methyl, ethyl, propyl, butyl, pentyl, hexyl, heptyl, and octyl, and those moieties which are positional isomers of these moieties. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Alkyl groups may be substituted or unsubstituted. As used herein, "Me" and —$CH_3$ both refer to methyl.

As used herein, the term "alkylene" refers to an alkyl group having the specified number of carbons, for example from 2 to 12 carbon atoms, that contains two points of attachment to the rest of the compound on its longest carbon chain. Non-limiting examples of alkylene groups include methylene —($CH_2$)—, ethylene —($CH_2CH_2$)—, n-propylene —($CH_2CH_2CH_2$)—, isopropylene —($CH_2CH(CH_3)$)—, and the like. Alkylene groups can be cyclic or acyclic, branched or unbranched carbon chain moiety, and may be optionally substituted with one or more substituents.

"Cycloalkyl" means mono- or bicyclic or bridged or spirocyclic, or polycyclic saturated carbocyclic rings, each having from 3 to 12 carbon atoms. Likewise, preferred cycloalkyls have from 3-10 carbon atoms in their ring structure, and more preferably have 3-6 carbons in the ring structure. Cycloalkyl groups may be substituted or unsubstituted.

Unless the number of carbons is otherwise specified, "lower alkyl," as used herein, means an alkyl group, as defined above, but having from one to ten carbons, more preferably from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, preferred alkyl groups are lower alkyls. In certain embodiments, a substituent designated herein as alkyl is a lower alkyl.

The term "aryl" as used herein includes 3- to 12-membered substituted or unsubstituted single-ring aromatic groups in which each atom of the ring is carbon (i.e., carbocyclic aryl) or where one or more atoms are heteroatoms (i.e., heteroaryl). Preferably, aryl groups include 5- to 12-membered rings, more preferably 6- to 10-membered rings The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Carbocyclic aryl groups include benzene, naphthalene, phenanthrene, phenol, aniline, and the like. Heteroaryl groups include substituted or unsubstituted aromatic 3- to 12-membered ring structures, more preferably 5- to 12-membered rings, more preferably 5- to 10-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine and pyrimidine, and the like. Aryl and heteroaryl can be monocyclic, bicyclic, or polycyclic.

The term "halo", "halide", or "halogen" as used herein means halogen and includes, for example, and without being limited thereto, fluoro, chloro, bromo, iodo and the like, in both radioactive and non-radioactive forms. In a preferred embodiment, halo is selected from the group consisting of fluoro, chloro and bromo.

The terms "heterocyclyl" or "heterocyclic group" refer to 3- to 12-membered ring structures, more preferably 5- to 12-membered rings, more preferably 5- to 10-membered rings, whose ring structures include one to four heteroatoms. Heterocycles can be monocyclic, bicyclic, spirocyclic, or polycyclic. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —CF$_3$, —CN, and the like.

The term "carbonyl" is art-recognized and includes such moieties as can be represented by the formula:

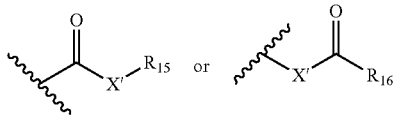

wherein X' is a bond or represents an oxygen or a sulfur, and R$_1$1 represents a hydrogen, an alkyl, an alkenyl, —(CH$_2$)$_m$—R$_{10}$ or a pharmaceutically acceptable salt, R$_{16}$ represents a hydrogen, an alkyl, an alkenyl or —(CH$_2$)$_m$—R$_{10}$, where m and R$_{10}$ are as defined above. Where X' is an oxygen and R$_{15}$ or R$_{16}$ is not hydrogen, the formula represents an "ester." Where X' is an oxygen, and R$_{15}$ is as defined above, the moiety is referred to herein as a carboxyl group, and particularly when R$_{15}$ is a hydrogen, the formula represents a "carboxylic acid". Where X' is an oxygen, and R$_{16}$ is a hydrogen, the formula represents a "formate." On the other hand, where X' is a bond, and R$_{15}$ is not hydrogen, the above formula represents a "ketone" group. Where X' is a bond, and R$_{15}$ is a hydrogen, the above formula represents an "aldehyde" group.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above, and for example substituted with one or more substituents selected from alkyl, cycloalkyl, heterocyclylakyl, halogen, OH, OMe, C(H)F$_2$, C(F)H$_2$, CF$_3$, C(H)$_2$CF$_3$, SF$_5$, CHFCH$_2$amine, CH$_2$amine, and CN. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "nitro" means —NO$_2$; the term "halogen" designates —F, —Cl, —Br, or —I; the term "hydroxyl" means —OH; and the term "cyano" means —CN;

As used herein, the definition of each expression, e.g., alkyl, m, n, etc., when it occurs more than once in any structure, is intended to be independent of its definition elsewhere in the same structure.

The term "prodrug" as used herein encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

For purposes of this invention, the chemical elements are identified in accordance with the Periodic Table of the Elements, CAS version, Handbook of Chemistry and Physics, 67th Ed., 1986-87, inside cover.

Exemplary Compounds

In some embodiments, the invention relates to a compound of Formula (I), Formula (Ia), or Formula (Ib):

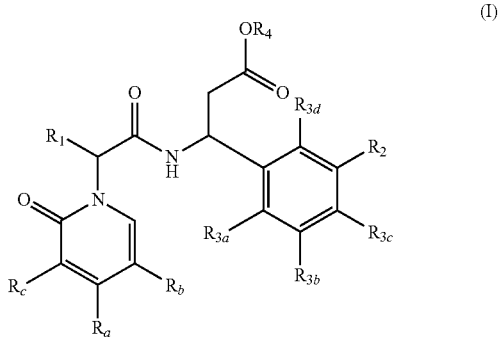

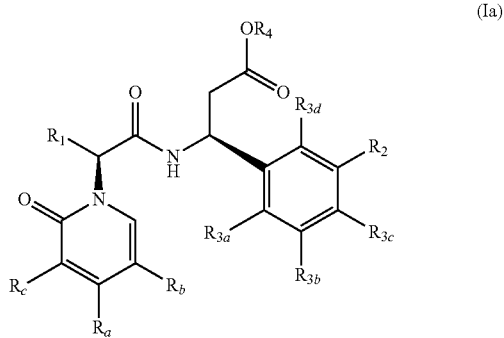

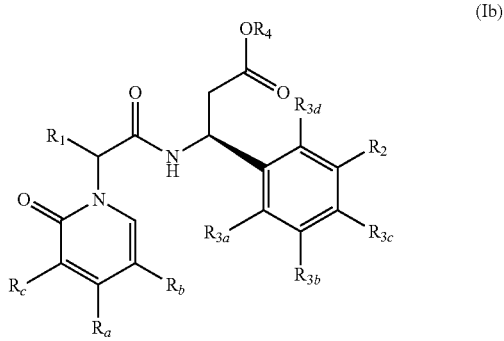

or a pharmaceutically acceptable salt thereof;

wherein

R$_a$, R$_b$, and R$_c$ are independently selected from the group consisting of H, Me, halide, CF$_3$, C(H)F$_2$, C(F)H$_2$, —CN, —OCF$_3$, substituted or unsubstituted (C$_1$-C$_5$)-alkyl, substituted or unsubstituted (C$_1$-C$_5$)-alkoxy, —CH$_2$CF$_3$, and substituted or unsubstituted —(C$_1$-C$_5$)alkylene-N—(R$_x$)(R$_y$); provided that at least one of R$_a$, R$_b$, and R$_c$ is —(C$_1$-C$_5$) alkylene-N—(R$_x$)(R$_y$);

R$_x$ and R$_y$ are independently selected from the group consisting of H and substituted or unsubstituted (C$_1$-C$_6$)-alkyl; or R$_x$ and R$_y$ taken together with the N to which they are attached form a 4-6 membered ring;

$R_1$ is substituted or unsubstituted $(C_1$-$C_6)$-alkyl, substituted or unsubstituted $(C_1$-$C_4)$-alkylene-$(C_3$-$C_6)$-cycloalkyl, or substituted or unsubstituted $(C_1$-$C_4)$-alkylene-$(C_1$-$C_4)$-alkoxy;

$R_2$ is

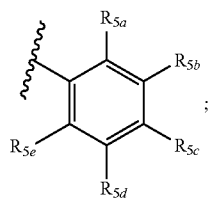

$R_{3a}$ and $R_{3b}$ are independently selected from the group consisting of H, substituted or unsubstituted $(C_1$-$C_5)$-alkyl, substituted or unsubstituted $(C_3$-$C_6)$-cycloalkyl, substituted or unsubstituted 3-6 membered heterocycloalkyl, —OH, —CN, halide, $CF_3$, $C(H)F_2$, $C(F)H_2$, —$(C_1$-$C_4)$-alkoxy, —$OCF_3$, and substituted or unsubstituted $(C_1$-$C_4)$-alkylene-$(C_1$-$C_4)$-alkoxy; provided that $R_{3a}$ and $R_{3b}$ are not both H;

$R_{3c}$ is selected from the group consisting of H, substituted or unsubstituted $(C_1$-$C_5)$-alkyl, substituted or unsubstituted $(C_3$-$C_6)$-cycloalkyl, substituted or unsubstituted 3-6 membered heterocycloalkyl, hydroxyl, halide, $CF_3$, $C(H)F_2$, $C(F)H_2$, —$(C_1$-$C_4)$-alkoxy, —$OCF_3$ —CN, and substituted or unsubstituted $(C_1$-$C_4)$-alkylene-$(C_1$-$C_4)$-alkoxy;

$R_{3d}$ is selected from the group consisting of H, substituted or unsubstituted $(C_1$-$C_5)$-alkyl, hydroxyl, halide, and —$(C_1$-$C_4)$-alkoxy;

$R_4$ is H, or substituted or unsubstituted $(C_1$-$C_4)$-alkyl;

$R_{5a}$, and $R_{5e}$ are independently selected from the group consisting of H, CN, halide, $CF_3$, $C(H)F_2$, $C(F)H_2$, —$CH_2CF_3$, substituted or unsubstituted $(C_3$-$C_6)$-cycloalkyl, substituted or unsubstituted $(C_1$-$C_5)$-alkyl, substituted or unsubstituted 3-6 membered heterocycloalkyl hydroxyl, and $(C_1$-$C_4)$-alkoxy; and $R_{5b}$, $R_{5c}$, and $R_{5d}$ are independently selected from the group consisting of H, CN, halide, $CF_3$, $C(H)F_2$, $C(F)H_2$, —$CH_2CF_3$, substituted or unsubstituted $(C_1$-$C_5)$-alkyl, substituted or unsubstituted $(C_3$-$C_6)$-cycloalkyl, substituted or unsubstituted 3-6 membered heterocycloalkyl, hydroxyl, and $(C_1$-$C_4)$-alkoxy.

In some embodiments, a compound of Formula (I) can be a compound of Formula (Ia), Formula (Ib), Formula (Ic) and/or Formula (Id):

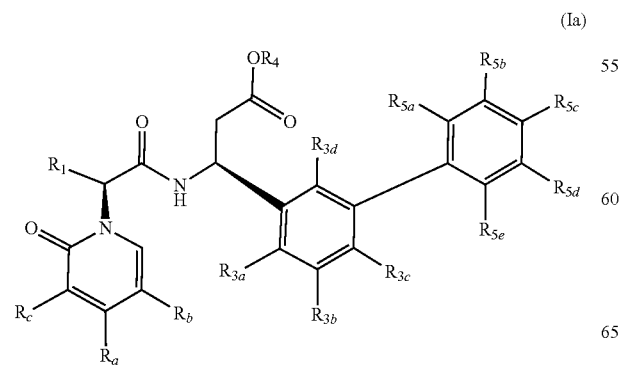

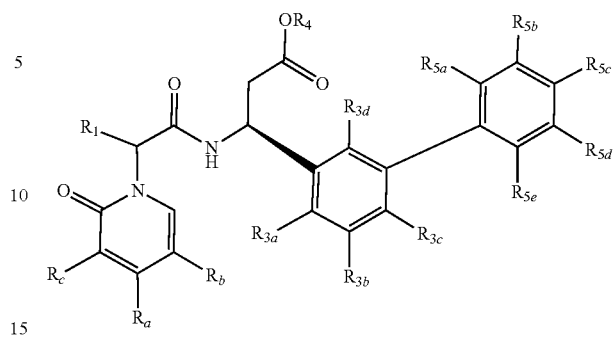

wherein $R_a$, $R_b$, $R_c$, $R_1$, $R_{3a}$, $R_{3b}$, $R_{3c}$, $R_{3d}$, $R_{5a}$, $R_{5b}$, $R_{5c}$, $R_{5d}$, $R_{5e}$, and $R_4$ in Formula (Ia), Formula (Ib), Formula (Ic) and Formula (Id) are each independently defined as above with respect to Formula (I).

In some embodiments, a compound of Formula (I) can be a compound of Formula (II), including compounds of Formula (IIa), Formula (IIb) or Formula (IIc):

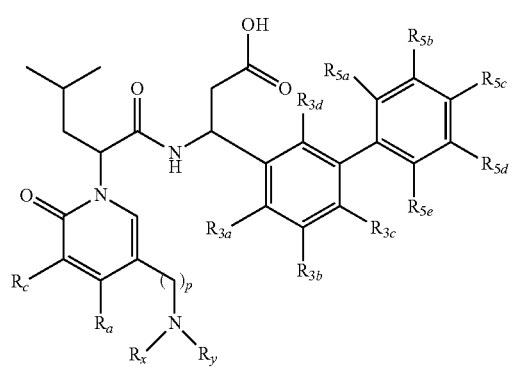

-continued

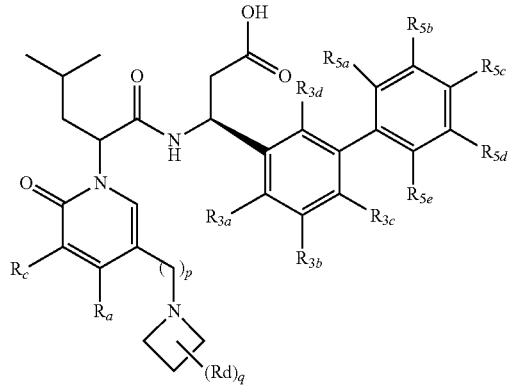

(IIa)

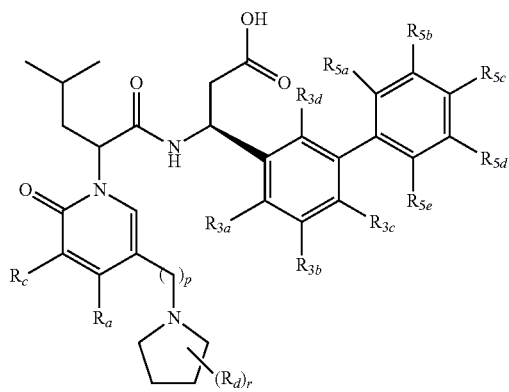

(IIb)

(IIc)

wherein $R_a$, $R_c$, $R_{3a}$, $R_{3b}$, $R_{3c}$, $R_{3d}$, $R_{5a}$, $R_{5b}$, $R_{5c}$, $R_{5d}$, and $R_{5e}$, are as described in Formula (I); p is 1, 2, or 3; q is 0, 1, 2 or 3; r is an 0, 1, 2, 3 or 4; s is 0, 1, 2, 3, 4 or 5; and each $R_a$ is independently selected from the group consisting of halide, $(C_1-C_5)$-alkyl, $(C_1-C_4)$-alkoxy, —$CF_3$, —$C(H)F_2$, —$OCF_3$, and —CN. In some embodiments, at least one instance of $R_d$ is F or Cl. In some embodiments, at least one instance of $R_d$ is methyl. In some embodiments, at least one instance of $R_d$ is methoxy. In certain embodiments, the invention relates to any one of the aforementioned compounds of Formula (IIa), wherein q is 1. In certain embodiments, the invention relates to any one of the aforementioned compounds of Formula (IIb), wherein r is 1. In certain embodiments, the invention relates to any one of the aforementioned compounds of Formula (IIc), wherein s is 1.

In certain embodiments, the invention relates to any one of the aforementioned compounds, wherein $R_1$ is unsubstituted $(C_1-C_6)$-alkyl. In certain embodiments, the invention relates to any one of the aforementioned compounds, wherein $R_1$ is substituted $(C_1-C_6)$-alkyl. In certain embodiments, the invention relates to any one of the aforementioned compounds, wherein $R_1$ is substituted or unsubstituted $(C_1-C_4)$-alkyl. In certain embodiments, $R_1$ is methyl, ethyl, isopropyl, n-propyl, i-butyl, n-butyl, sec-butyl, or t-butyl. In certain embodiments, the invention relates to any one of the aforementioned compounds, wherein $R_1$ is selected from the group consisting of

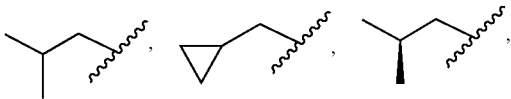

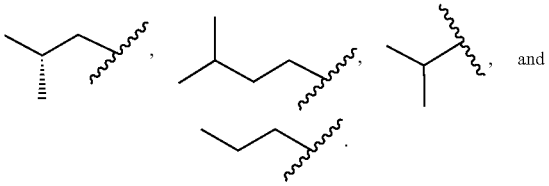

and

In certain embodiments, the invention relates to any one of the aforementioned compounds, wherein $R_1$ is substituted $(C_1-C_4)$-alkylene-$(C_3-C_6)$-cycloalkyl. In certain embodiments, the invention relates to any one of the aforementioned compounds, wherein $R_1$ is unsubstituted $(C_1-C_4)$-alkylene-$(C_3-C_6)$-cycloalkyl. In certain embodiments, $R_1$ is

In certain embodiments, the invention relates to any one of the aforementioned compounds, wherein $R_1$ is substituted $(C_1-C_4)$-alkylene- $(C_1-C_4)$-alkoxy. In certain embodiments, the invention relates to any one of the aforementioned compounds, wherein $R_1$ is unsubstituted $(C_1-C_4)$-alkylene- $(C_1-C_4)$-alkoxy. In certain embodiments, $R_1$ is

In certain embodiments, the invention relates to any one of the aforementioned compounds, wherein $R_{3a}$ is H; provided that $R_{3a}$ and $R_{3b}$ are not both H. In certain embodiments, the invention relates to any one of the aforementioned compounds, wherein $R_{3a}$ is unsubstituted $(C_1-C_4)$-alkyl. In certain embodiments, the invention relates to any one of the aforementioned compounds, wherein $R_{3a}$ is substituted $(C_1-C_4)$-alkyl. In certain embodiments, the substituted $(C_1-C_5)$-alkyl, is substituted with a halogen. In certain embodiments, the halogen is Cl or F. In certain embodiments, $R_{3a}$ is methyl, ethyl, isopropyl, n-propyl, i-butyl, n-butyl, or t-butyl. In certain embodiments, the invention relates to any one of the aforementioned compounds, wherein $R_{3a}$ is substituted $(C_3-C_6)$-cycloalkyl. In certain embodiments, the invention relates to any one of the aforementioned compounds, wherein $R_{3a}$ is substituted or unsubstituted $(C_3-C_6)$-cycloalkyl. In certain embodiments, the invention relates to any one of the aforementioned compounds, wherein $R_{3a}$ is cyclopropyl. In certain embodiments, the invention relates to any one of the aforementioned compounds, wherein $R_{3a}$ is halide. In some embodiments, the halide is Cl or F. In certain embodiments, the invention relates to any one of the aforementioned compounds, wherein $R_{3a}$ is $CF_3$. In certain embodiments, the invention relates to any one of the aforementioned compounds, wherein $R_{3a}$ is $C(H)F_2$. In certain embodiments, the invention relates to any one of the aforementioned compounds, wherein $R_{3a}$ is $C(F)H_2$. In certain embodiments, the invention relates to any one of the aforementioned compounds, wherein $R_{3a}$ is substituted $—(C_1-C_4)$-alkoxy. In certain embodiments, the invention relates to any one of the aforementioned compounds, wherein $R_{3a}$ is unsubstituted $—(C_1-C_4)$-alkoxy. In certain embodiments, the invention relates to any one of the aforementioned compounds, wherein $R_{3a}$ is $—OCF_3$. In certain embodiments, the invention relates to any one of the aforementioned compounds, wherein $R_{3a}$ is substituted $(C_1-C_4)$-alkylene-$(C_1-C_4)$-alkoxy. In certain embodiments, the invention relates to any one of the aforementioned compounds, wherein $R_{3a}$ is unsubstituted $(C_1-C_4)$-alkylene-$(C_1-C_4)$-alkoxy. In certain embodiments, $(C_1-C_4)$-alkylene-$(C_1-C_4)$-alkoxy is $—CH_2OMe$.

In certain embodiments, the invention relates to any one of the aforementioned compounds, wherein $R_{3b}$ is H; provided that $R_{3a}$ and $R_{3b}$ are not both H. In certain embodiments, the invention relates to any one of the aforementioned compounds, wherein $R_{3b}$ is unsubstituted $(C_1-C_4)$-alkyl. In certain embodiments, the invention relates to any one of the aforementioned compounds, wherein $R_{3b}$ is substituted $(C_1-C_4)$-alkyl. In certain embodiments, the substituted $(C_1-C_5)$-alkyl, is substituted with a halogen. In certain embodiments, the halogen is Cl or F. In certain embodiments, $R_{3b}$ is methyl, ethyl, isopropyl, n-propyl, i-butyl, n-butyl, or t-butyl. In certain embodiments, the invention relates to any one of the aforementioned compounds, wherein $R_{3b}$ is substituted $(C_3-C_6)$-cycloalkyl. In certain embodiments, the invention relates to any one of the aforementioned compounds, wherein $R_{3b}$ is substituted or unsubstituted $(C_3-C_6)$-cycloalkyl. In certain embodiments, the invention relates to any one of the aforementioned compounds, wherein $R_{3b}$ is cyclopropyl. In certain embodiments, the invention relates to any one of the aforementioned compounds, wherein $R_{3b}$ is halide. In some embodiments, the halide is Cl or F. In certain embodiments, the invention relates to any one of the aforementioned compounds, wherein $R_{3b}$ is $CF_3$. In certain embodiments, the invention relates to any one of the aforementioned compounds, wherein $R_{3b}$ is $C(H)F_2$. In certain embodiments, the invention relates to any one of the aforementioned compounds, wherein $R_{3b}$ is $C(F)H_2$. In certain embodiments, the invention relates to any one of the aforementioned compounds, wherein $R_{3b}$ is substituted $—(C_1-C_4)$-alkoxy. In certain embodiments, the invention relates to any one of the aforementioned compounds, wherein $R_{3b}$ is unsubstituted $—(C_1-C_4)$-alkoxy. In certain embodiments, the invention relates to any one of the aforementioned compounds, wherein $R_{3b}$ is $—OCF_3$. In certain embodiments, the invention relates to any one of the aforementioned compounds, wherein $R_{3b}$ is substituted $(C_1-C_4)$-alkylene-$(C_1-C_4)$-alkoxy. In certain embodiments, the invention relates to any one of the aforementioned compounds, wherein $R_{3b}$ is unsubstituted $(C_1-C_4)$-alkylene-$(C_1-C_4)$-alkoxy. In certain embodiments, $(C_1-C_4)$-alkylene-$(C_1-C_4)$-alkoxy is $—CH_2OMe$.

In certain embodiments, $R_{3a}$ and $R_{3b}$ are independently selected from the group consisting of H, $(C_1-C_5)$-alkyl, halide, $CF_3$, $C(H)F_2$, and $C(F)H_2$; provided that $R_{3a}$ and $R_{3b}$ are not both H.

For example, $R_{3a}$ and $R_{3b}$ can be independently selected from the group consisting of H, methyl, Cl, F, $CF_3$, $C(H)F_2$, and $C(F)H_2$; provided that $R_{3a}$ and $R_{3b}$ are not both H.

In certain embodiments, the invention relates to any one of the aforementioned compounds, wherein $R_{3c}$ is selected from the group consisting of: H, substituted or unsubstituted $(C_1-C_5)$-alkyl, substituted or unsubstituted cyclopropyl, hydroxyl, methoxy, halide, $CF_3$, $C(H)F_2$, $C(F)H_2$, and —CN. In certain embodiments, the invention relates to any one of the aforementioned compounds, wherein $R_{3c}$ is H. In certain embodiments, the invention relates to any one of the aforementioned compounds, wherein $R_{3c}$ is unsubstituted $(C_1-C_4)$-alkyl. In certain embodiments, the invention relates to any one of the aforementioned compounds, wherein $R_{3c}$ is substituted $(C_1-C_4)$-alkyl. In certain embodiments, the substituted $(C_1-C_5)$-alkyl, is substituted with a halogen. In certain embodiments, the halogen is Cl or F. In certain embodiments, $R_{3c}$ is methyl, ethyl, isopropyl, n-propyl, i-butyl, n-butyl, or t-butyl. In certain embodiments, the invention relates to any one of the aforementioned compounds, wherein $R_{3c}$ is substituted $(C_3-C_6)$-cycloalkyl. In certain embodiments, the invention relates to any one of the aforementioned compounds, wherein $R_{3c}$ is substituted or unsubstituted $(C_3-C_6)$-cycloalkyl. In certain embodiments, the invention relates to any one of the aforementioned compounds, wherein $R_{3c}$ is cyclopropyl. In certain embodiments, the invention relates to any one of the aforementioned compounds, wherein $R_{3c}$ is halide. In some embodiments, the halide is Cl or F. In certain embodiments, the invention relates to any one of the aforementioned compounds, wherein $R_{3c}$ is $CF_3$. In certain embodiments, the invention relates to any one of the aforementioned compounds, wherein $R_{3c}$ is $C(H)F_2$. In certain embodiments, the invention relates to any one of the aforementioned compounds, wherein $R_{3c}$ is $C(F)H_2$. In certain embodiments, the invention relates to any one of the aforementioned compounds, wherein $R_{3c}$ is substituted $—(C_1-C_4)$-alkoxy.

In certain embodiments, the invention relates to any one of the aforementioned compounds, wherein $R_{3c}$ is unsubstituted $—(C_1-C_4)$-alkoxy. In certain embodiments, the invention relates to any one of the aforementioned compounds, wherein $R_{3c}$ is $—OCF_3$. In certain embodiments, the invention relates to any one of the aforementioned compounds, wherein $R_{3c}$ is substituted $(C_1-C_4)$-alkylene-$(C_1-C_4)$-alkoxy. In certain embodiments, the invention relates to any one of the aforementioned compounds, wherein $R_{3c}$ is unsubstituted $(C_1-C_4)$-alkylene-$(C_1-C_4)$-alkoxy. In certain embodiments, $(C_1-C_4)$-alkylene-$(C_1-C_4)$-alkoxy is $—CH_2OMe$.

In certain embodiments, the invention relates to any one of the aforementioned compounds, wherein $R_{3d}$ is selected from the group consisting of H, substituted or unsubstituted $(C_1-C_5)$-alkyl, hydroxyl, halide, methoxy, halide, $CF_3$, $C(H)F_2$, and $C(F)H_2$. In certain embodiments, the invention relates to any one of the aforementioned compounds, wherein $R_{3d}$ H. In certain embodiments, the invention relates to any one of the aforementioned compounds, wherein $R_{3d}$ is unsubstituted $(C_1-C_4)$-alkyl. In certain embodiments, the invention relates to any one of the aforementioned compounds, wherein $R_{3d}$ is substituted $(C_1-C_4)$-alkyl. In certain embodiments, the substituted $(C_1-C_5)$-alkyl, is substituted with a halogen. In certain embodiments, the halogen is F. In certain embodiments, $R_{3d}$ is methyl. In certain embodiments, the invention relates to any one of the aforementioned compounds, wherein $R_{3d}$ is substituted $(C_3-C_6)$-cycloalkyl. In certain embodiments, the invention relates to any one of the aforementioned compounds, wherein $R_{3c}$ is substituted or unsubstituted $(C_3-C_6)$-cycloalkyl. In certain embodiments, the invention relates to any one of the aforementioned compounds, wherein $R_{3d}$ is cyclopropyl. In certain embodiments, the invention relates to any one of the aforementioned compounds, wherein $R_{3d}$ is halide. In some embodiments, the halide is Cl or F. In certain embodiments, the invention relates to any one of the aforementioned compounds, wherein $R_{3d}$ is $CF_3$. In certain embodiments, the invention relates to any one of the aforementioned compounds, wherein $R_{3d}$ is $C(H)F_2$. In certain embodiments, the invention relates to any one of the aforementioned compounds, wherein $R_{3d}$ is $C(F)H_2$. In certain embodiments, the invention relates to any one of the aforementioned compounds, wherein $R_3$ is substituted $—(C_1-C_4)$-alkoxy. In certain embodiments, the invention relates to any one of the aforementioned compounds, wherein $R_{3d}$ is unsubstituted $—(C_1-C_4)$-alkoxy. In certain embodiments, $—(C_1-C_4)$-alkoxy is methoxy. In certain embodiments, the invention relates to any one of the aforementioned compounds, wherein $R_{3d}$ is $—OCF_3$. In certain embodiments, the invention relates to any one of the aforementioned compounds, wherein $R_{3d}$ is substituted $(C_1-C_4)$-alkylene-$(C_1-C_4)$-alkoxy. In certain embodiments, the invention relates to any one of the aforementioned compounds, wherein $R_{3d}$ is unsubstituted $(C_1-C_4)$-alkylene-$(C_1-C_4)$-alkoxy. In certain embodiments, $(C_1-C_4)$-alkylene-$(C_1-C_4)$-alkoxy is $—CH_2OMe$.

In some embodiments, $R_{3c}$ and $R_{3d}$ are the same. In some embodiments, $R_{3c}$ and $R_{3d}$ are different. In some embodiments, $R_{3c}$ and $R_{3d}$ are both H.

In certain embodiments, the invention relates to any one of the aforementioned compounds, wherein $R_4$ is H. In certain embodiments, the invention relates to any one of the aforementioned compounds, wherein $R_4$ is substituted $(C_1-C_4)$-alkyl. In certain embodiments, the invention relates to any one of the aforementioned compounds, wherein $R_4$ is unsubstituted $(C_1-C_4)$-alkyl. In certain embodiments, the invention relates to any one of the aforementioned compounds, wherein $R_4$ is methyl, ethyl, n-propyl, or i-propyl. In certain embodiments, the invention relates to any one of the aforementioned compounds, wherein $R_4$ is methyl or ethyl.

In certain embodiments, $R_{5a}$ is H. In certain embodiments, the invention relates to any one of the aforementioned compounds, wherein $R_{5a}$ is substituted or unsubstituted $(C_1-C_4)$-alkyl. In certain embodiments, the invention relates to any one of the aforementioned compounds, wherein $R_{5a}$ is unsubstituted $(C_1-C_4)$-alkyl. In certain embodiments, the invention relates to any one of the aforementioned compounds, wherein $R_{5a}$ is substituted $(C_1-C_4)$-alkyl. In certain embodiments, the substituted $(C_1-C_5)$-alkyl, is substituted with one or more halogen. In certain embodiments, the halogen is Cl or F. In certain embodiments, $R_{5a}$ is methyl, ethyl, isopropyl, n-propyl, i-butyl, n-butyl, or t-butyl. In certain embodiments, the invention relates to any one of the aforementioned compounds, wherein $R_{5a}$ is halide. In some embodiments, the halide is Cl or F. In certain embodiments, $R_{5a}$ is substituted $(C_3-C_6)$-cycloalkyl. In certain embodiments, $R_{5a}$ is unsubstituted $(C_3-C_6)$-cycloalkyl. In some embodiments, $(C_3-C_6)$-cycloalkyl is cyclopropyl. In certain embodiments, the invention relates to any one of the aforementioned compounds, wherein $R_{5a}$ is $CF_3$. In certain embodiments, the invention relates to any one of the aforementioned compounds, wherein $R_{5a}$ is $C(H)F_2$. In certain embodiments, the invention relates to any one of the aforementioned compounds, wherein $R_{5a}$ is $C(F)H_2$. In certain embodiments, the invention relates to any one of the aforementioned compounds, wherein $R_{5a}$ is $(C_1-C_4)$-alkoxy. In some embodiments, $(C_1-C_4)$-alkoxy is methoxy. In certain embodiments, the invention relates to any one of the aforementioned compounds, wherein $R_{5a}$ is methoxy. In certain embodiments, the invention relates to any one of the aforementioned compounds, wherein $R_{5a}$ is hydroxyl. In certain embodiments, the invention relates to any one of the aforementioned compounds, wherein $R_{5a}$ is $—OCF_3$. In certain embodiments, $R_{5a}$ is CN. In certain embodiments, the invention relates to any one of the aforementioned compounds, wherein $R_{5a}$ is substituted $(C_1-C_4)$-alkylene-$(C_1-C_4)$-alkoxy. In certain embodiments, the invention relates to any one of the aforementioned compounds, wherein $R_{5a}$ is unsubstituted $(C_1-C_4)$-alkylene-$(C_1-C_4)$-alkoxy. In certain embodiments, $(C_1-C_4)$-alkylene-$(C_1-C_4)$-alkoxy is $—CH_2OMe$. In certain embodiments, $R_{5a}$ is $CH_2OH$.

In certain embodiments, the invention relates to any one of the aforementioned compounds, wherein $R_{5b}$ is CN. In certain embodiments, the invention relates to any one of the aforementioned compounds, wherein $R_{5b}$ is unsubstituted $(C_1-C_4)$-alkyl. In certain embodiments, the invention relates to any one of the aforementioned compounds, wherein $R_{5b}$ is substituted $(C_1-C_4)$-alkyl. In certain embodiments, the substituted $(C_1-C_5)$-alkyl, is substituted with a halogen. In certain embodiments, the halogen is Cl or F. In certain embodiments, $R_{5b}$ is methyl, ethyl, isopropyl, n-propyl, i-butyl, n-butyl, or t-butyl. In certain embodiments, the invention relates to any one of the aforementioned compounds, wherein $R_{5b}$ is halide. In some embodiments, the halide is Cl or F. In certain embodiments, $R_{5b}$ is substituted $(C_3-C_6)$-cycloalkyl. In certain embodiments, $R_{5b}$ is unsubstituted $(C_3-C_6)$-cycloalkyl. In certain embodiments, the invention relates to any one of the aforementioned compounds, wherein $R_{5b}$ is $CF_3$. In certain embodiments, the invention relates to any one of the aforementioned compounds, wherein $R_{5b}$ is $C(H)F_2$. In certain embodiments, the invention relates to any one of the aforementioned compounds, wherein $R_{5b}$ is $C(F)H_2$. In certain embodiments, the invention relates to any one of the aforementioned compounds, wherein $R_{5b}$ is $(C_1-C_4)$-alkoxy. In certain embodiments, the invention relates to any one of the aforementioned compounds, wherein $R_{5b}$ is methoxy. In certain embodiments, the invention relates to any one of the aforementioned compounds, wherein $R_{5b}$ is hydroxyl. In certain embodiments, the invention relates to any one of the aforementioned compounds, wherein $R_{5b}$ is $—OCF_3$. In certain embodiments, the invention relates to any one of the aforementioned compounds, wherein $R_{5b}$ is substituted $(C_1-C_4)$-alkylene-$(C_1-C_4)$-alkoxy. In certain embodiments, the invention relates to any one of the aforementioned compounds, wherein $R_{5b}$ is unsubstituted $(C_1-C_4)$-alkylene-$(C_1-C_4)$-alkoxy. In certain embodiments, $(C_1-C_4)$-alkylene-$(C_1-C_4)$-alkoxy is $—CH_2OMe$.

In certain embodiments, the invention relates to any one of the aforementioned compounds, wherein $R_{5c}$ is CN. In certain embodiments, the invention relates to any one of the aforementioned compounds, wherein $R_{5c}$ is unsubstituted $(C_1-C_4)$-alkyl. In certain embodiments, the invention relates to any one of the aforementioned compounds, wherein $R_{5c}$ is substituted $(C_1-C_4)$-alkyl. In certain embodiments, the substituted $(C_1-C_5)$-alkyl, is substituted with a halogen. In certain embodiments, the halogen is Cl or F. In certain embodiments, $R_{5c}$ is methyl, ethyl, isopropyl, n-propyl, i-butyl, n-butyl, or t-butyl. In certain embodiments, the invention relates to any one of the aforementioned compounds, wherein $R_{5c}$ is halide. In some embodiments, the halide is Cl or F. In certain embodiments, $R_{5c}$ is substituted $(C_3-C_6)$-cycloalkyl. In certain embodiments, $R_{5c}$ is unsubstituted $(C_3-C_6)$-cycloalkyl. In certain embodiments, the invention relates to any one of the aforementioned compounds, wherein $R_{5c}$ is $CF_3$. In certain embodiments, the invention relates to any one of the aforementioned compounds, wherein $R_{5c}$ is $C(H)F_2$. In certain embodiments, the invention relates to any one of the aforementioned compounds, wherein $R_{5c}$ is $C(F)H_2$. In certain embodiments, the invention relates to any one of the aforementioned compounds, wherein $R_{5c}$ is $(C_1-C_4)$-alkoxy. In certain embodiments, the invention relates to any one of the aforementioned compounds, wherein $R_{5c}$ is methoxy. In certain embodiments, the invention relates to any one of the aforementioned compounds, wherein $R_{5c}$ is hydroxyl. In certain embodiments, the invention relates to any one of the aforementioned compounds, wherein $R_{5c}$ is —$OCF_3$. In certain embodiments, the invention relates to any one of the aforementioned compounds, wherein $R_{5c}$ is substituted $(C_1-C_4)$-alkylene-$(C_1-C_4)$-alkoxy. In certain embodiments, the invention relates to any one of the aforementioned compounds, wherein $R_{5c}$ is unsubstituted $(C_1-C_4)$-alkylene-$(C_1-C_4)$-alkoxy. In certain embodiments, $(C_1-C_4)$-alkylene-$(C_1-C_4)$-alkoxy is —$CH_2OMe$.

In certain embodiments, the invention relates to any one of the aforementioned compounds, wherein $R_{5d}$ is CN. In certain embodiments, the invention relates to any one of the aforementioned compounds, wherein $R_{5d}$ is unsubstituted $(C_1-C_4)$-alkyl. In certain embodiments, the invention relates to any one of the aforementioned compounds, wherein $R_{5d}$ is substituted $(C_1-C_4)$-alkyl. In certain embodiments, the substituted $(C_1-C_5)$-alkyl, is substituted with a halogen. In certain embodiments, the halogen is Cl or F. In certain embodiments, $R_{5d}$ is methyl, ethyl, isopropyl, n-propyl, i-butyl, n-butyl, or t-butyl. In certain embodiments, the invention relates to any one of the aforementioned compounds, wherein $R_{5d}$ is halide. In some embodiments, the halide is Cl or F. In certain embodiments, $R_{5d}$ is substituted $(C_3-C_6)$-cycloalkyl. In certain embodiments, $R_{5d}$ is unsubstituted $(C_3-C_6)$-cycloalkyl. In certain embodiments, the invention relates to any one of the aforementioned compounds, wherein $R_{5d}$ is $CF_3$. In certain embodiments, the invention relates to any one of the aforementioned compounds, wherein $R_{5d}$ is $C(H)F_2$. In certain embodiments, the invention relates to any one of the aforementioned compounds, wherein $R_{5d}$ is $C(F)H_2$. In certain embodiments, the invention relates to any one of the aforementioned compounds, wherein $R_{5d}$ is $(C_1-C_4)$-alkoxy. In certain embodiments, the invention relates to any one of the aforementioned compounds, wherein $R_{5d}$ is methoxy. In certain embodiments, the invention relates to any one of the aforementioned compounds, wherein $R_{5d}$ is hydroxyl. In certain embodiments, the invention relates to any one of the aforementioned compounds, wherein $R_{5d}$ is —$OCF_3$. In certain embodiments, the invention relates to any one of the aforementioned compounds, wherein $R_{5d}$ is substituted $(C_1-C_4)$-alkylene-$(C_1-C_4)$-alkoxy. In certain embodiments, the invention relates to any one of the aforementioned compounds, wherein $R_{5d}$ is unsubstituted $(C_1-C_4)$-alkylene-$(C_1-C_4)$-alkoxy. In certain embodiments, $(C_1-C_4)$-alkylene-$(C_1-C_4)$-alkoxy is —$CH_2OMe$.

In certain embodiments, the invention relates to any one of the aforementioned compounds, wherein $R_{5e}$ is CN. In certain embodiments, the invention relates to any one of the aforementioned compounds, wherein $R_{5e}$ is unsubstituted $(C_1-C_4)$-alkyl. In certain embodiments, the invention relates to any one of the aforementioned compounds, wherein $R_{5e}$ is substituted $(C_1-C_4)$-alkyl. In certain embodiments, the substituted $(C_1-C_5)$-alkyl, is substituted with a halogen. In certain embodiments, the halogen is Cl or F. In certain embodiments, $R_{5e}$ is methyl, ethyl, isopropyl, n-propyl, i-butyl, n-butyl, or t-butyl. In certain embodiments, the invention relates to any one of the aforementioned compounds, wherein $R_{5e}$ is halide. In some embodiments, the halide is Cl or F. In certain embodiments, $R_{5e}$ is substituted $(C_3-C_6)$-cycloalkyl. In certain embodiments, $R_{5e}$ is unsubstituted $(C_3-C_6)$-cycloalkyl. In certain embodiments, the invention relates to any one of the aforementioned compounds, wherein $R_{5e}$ is $CF_3$. In certain embodiments, the invention relates to any one of the aforementioned compounds, wherein $R_{5e}$ is $C(H)F_2$. In certain embodiments, the invention relates to any one of the aforementioned compounds, wherein $R_{5e}$ is $C(F)H_2$. In certain embodiments, the invention relates to any one of the aforementioned compounds, wherein $R_{5e}$ is $(C_1-C_4)$-alkoxy. In certain embodiments, the invention relates to any one of the aforementioned compounds, wherein $R_{5e}$ is methoxy. In certain embodiments, the invention relates to any one of the aforementioned compounds, wherein $R_{5e}$ is hydroxyl. In certain embodiments, the invention relates to any one of the aforementioned compounds, wherein $R_{5e}$ is —$OCF_3$. In certain embodiments, the invention relates to any one of the aforementioned compounds, wherein $R_{5e}$ is substituted $(C_1-C_4)$-alkylene-$(C_1-C_4)$-alkoxy. In certain embodiments, the invention relates to any one of the aforementioned compounds, wherein $R_{5e}$ is unsubstituted $(C_1-C_4)$-alkylene-$(C_1-C_4)$-alkoxy. In certain embodiments, $(C_1-C_4)$-alkylene-$(C_1-C_4)$-alkoxy is —$CH_2OMe$.

In certain embodiments, $R_{5b}$ is H. In certain embodiments, the invention relates to any one of the aforementioned compounds, wherein $R_{5b}$ is substituted or unsubstituted $(C_1-C_4)$-alkyl. In certain embodiments, the invention relates to any one of the aforementioned compounds, wherein $R_{5b}$ is unsubstituted $(C_1-C_4)$-alkyl. In certain embodiments, the invention relates to any one of the aforementioned compounds, wherein $R_{5b}$ is substituted $(C_1-C_4)$-alkyl. In certain embodiments, the substituted $(C_1-C_5)$-alkyl, is substituted with one or more halogen. In certain embodiments, the halogen is Cl or F. In certain embodiments, $R_{5b}$ is methyl, ethyl, isopropyl, n-propyl, i-butyl, n-butyl, or t-butyl. In certain embodiments, the invention relates to any one of the aforementioned compounds, wherein $R_{5b}$ is halide. In some embodiments, the halide is Cl or F. In certain embodiments, $R_{5b}$ is substituted $(C_3-C_6)$-cycloalkyl. In certain embodiments, $R_{5b}$ is unsubstituted $(C_3-C_6)$-cycloalkyl. In some embodiments, $(C_3-C_6)$-cycloalkyl is cyclopropyl. In certain embodiments, the invention relates to any one of the aforementioned compounds, wherein $R_{5b}$ is $CF_3$. In certain embodiments, the invention relates to any one of the aforementioned compounds, wherein $R_{5b}$ is $C(H)F_2$. In certain embodiments, the invention relates to any one of the aforementioned compounds, wherein $R_{5b}$ is $C(F)H_2$. In certain embodiments, the invention relates to any one of the aforementioned compounds, wherein $R_{5a}$ is $(C_1-C_4)$-alkoxy. In some embodiments, $(C_1-C_4)$-alkoxy is methoxy. In certain embodiments, the invention relates to any one of the aforementioned compounds, wherein $R_{5b}$ is methoxy. In certain embodiments, the invention relates to any one of the aforementioned compounds, wherein $R_{5b}$ is hydroxyl. In certain embodiments, the invention relates to any one of the aforementioned compounds, wherein $R_{5b}$ is —$OCF_3$. In certain embodiments, $R_{5b}$ is CN. In certain embodiments, the invention relates to any one of the aforementioned compounds, wherein $R_{5b}$ is substituted $(C_1-C_4)$-alkylene-$(C_1-C_4)$-alkoxy.

In certain embodiments, the invention relates to any one of the aforementioned compounds, wherein $R_{5b}$ is unsubstituted $(C_1-C_4)$-alkylene-$(C_1-C_4)$-alkoxy. In certain embodiments, $(C_1-C_4)$-alkylene-$(C_1-C_4)$-alkoxy is —CH$_2$OMe. In certain embodiments, $R_{5b}$ is CH$_2$OH.

In certain embodiments, $R_{5c}$ is H. In certain embodiments, the invention relates to any one of the aforementioned compounds, wherein $R_{5c}$ is substituted or unsubstituted $(C_1-C_4)$-alkyl. In certain embodiments, the invention relates to any one of the aforementioned compounds, wherein $R_{5a}$ is unsubstituted $(C_1-C_4)$-alkyl. In certain embodiments, the invention relates to any one of the aforementioned compounds, wherein $R_{5c}$ is substituted $(C_1-C_4)$-alkyl. In certain embodiments, the substituted $(C_1-C_5)$-alkyl, is substituted with one or more halogen. In certain embodiments, the halogen is Cl or F. In certain embodiments, $R_{5c}$ is methyl, ethyl, isopropyl, n-propyl, i-butyl, n-butyl, or t-butyl. In certain embodiments, the invention relates to any one of the aforementioned compounds, wherein $R_{5c}$ is halide. In some embodiments, the halide is Cl or F. In certain embodiments, $R_{5c}$ is substituted $(C_3-C_6)$-cycloalkyl. In certain embodiments, $R_{5c}$ is unsubstituted $(C_3-C_6)$-cycloalkyl. In some embodiments, $(C_3-C_6)$-cycloalkyl is cyclopropyl. In certain embodiments, the invention relates to any one of the aforementioned compounds, wherein $R_{5c}$ is CF$_3$. In certain embodiments, the invention relates to any one of the aforementioned compounds, wherein $R_{5c}$ is C(H)F$_2$. In certain embodiments, the invention relates to any one of the aforementioned compounds, wherein $R_{5c}$ is C(F)H$_2$. In certain embodiments, the invention relates to any one of the aforementioned compounds, wherein $R_{5c}$ is $(C_1-C_4)$-alkoxy. In some embodiments, $(C_1-C_4)$-alkoxy is methoxy. In certain embodiments, the invention relates to any one of the aforementioned compounds, wherein $R_{5c}$ is methoxy. In certain embodiments, the invention relates to any one of the aforementioned compounds, wherein $R_{5c}$ is hydroxyl. In certain embodiments, the invention relates to any one of the aforementioned compounds, wherein $R_{5c}$ is —OCF$_3$. In certain embodiments, $R_{5c}$ is CN. In certain embodiments, the invention relates to any one of the aforementioned compounds, wherein $R_{5a}$ is substituted $(C_1-C_4)$-alkylene-$(C_1-C_4)$-alkoxy. In certain embodiments, the invention relates to any one of the aforementioned compounds, wherein $R_{5c}$ is unsubstituted $(C_1-C_4)$-alkylene-$(C_1-C_4)$-alkoxy. In certain embodiments, $(C_1-C_4)$-alkylene-$(C_1-C_4)$-alkoxy is —CH$_2$OMe. In certain embodiments, $R_{5c}$ is CH$_2$OH.

In certain embodiments, $R_{5d}$ is H. In certain embodiments, the invention relates to any one of the aforementioned compounds, wherein $R_{5d}$ is substituted or unsubstituted $(C_1-C_4)$-alkyl. In certain embodiments, the invention relates to any one of the aforementioned compounds, wherein $R_{5d}$ is unsubstituted $(C_1-C_4)$-alkyl. In certain embodiments, the invention relates to any one of the aforementioned compounds, wherein $R_{5d}$ is substituted $(C_1-C_4)$-alkyl. In certain embodiments, the substituted $(C_1-C_5)$-alkyl, is substituted with one or more halogen. In certain embodiments, the halogen is Cl or F. In certain embodiments, $R_{5d}$ is methyl, ethyl, isopropyl, n-propyl, i-butyl, n-butyl, or t-butyl. In certain embodiments, the invention relates to any one of the aforementioned compounds, wherein $R_{5d}$ is halide. In some embodiments, the halide is Cl or F. In certain embodiments, $R_{5d}$ is substituted $(C_3-C_6)$-cycloalkyl. In certain embodiments, $R_{5d}$ is unsubstituted $(C_3-C_6)$-cycloalkyl. In some embodiments, $(C_3-C_6)$-cycloalkyl is cyclopropyl. In certain embodiments, the invention relates to any one of the aforementioned compounds, wherein $R_{5d}$ is CF$_3$. In certain embodiments, the invention relates to any one of the aforementioned compounds, wherein $R_{5d}$ is C(H)F$_2$. In certain embodiments, the invention relates to any one of the aforementioned compounds, wherein $R_{5d}$ is C(F)H$_2$. In certain embodiments, the invention relates to any one of the aforementioned compounds, wherein $R_{5d}$ is $(C_1-C_4)$-alkoxy. In some embodiments, $(C_1-C_4)$-alkoxy is methoxy. In certain embodiments, the invention relates to any one of the aforementioned compounds, wherein $R_{5d}$ is methoxy. In certain embodiments, the invention relates to any one of the aforementioned compounds, wherein $R_{5d}$ is hydroxyl. In certain embodiments, the invention relates to any one of the aforementioned compounds, wherein $R_{5d}$ is —OCF$_3$. In certain embodiments, $R_{5d}$ is CN. In certain embodiments, the invention relates to any one of the aforementioned compounds, wherein $R_{5d}$ is substituted $(C_1-C_4)$-alkylene-$(C_1-C_4)$-alkoxy. In certain embodiments, the invention relates to any one of the aforementioned compounds, wherein $R_{5d}$ is unsubstituted $(C_1-C_4)$-alkylene-$(C_1-C_4)$-alkoxy. In certain embodiments, $(C_1-C_4)$-alkylene-$(C_1-C_4)$-alkoxy is —CH$_2$OMe. In certain embodiments, $R_{5d}$ is CH$_2$OH.

In certain embodiments, $R_{5e}$ is H. In certain embodiments, the invention relates to any one of the aforementioned compounds, wherein $R_{5e}$ is substituted or unsubstituted $(C_1-C_4)$-alkyl. In certain embodiments, the invention relates to any one of the aforementioned compounds, wherein $R_{5e}$ is unsubstituted $(C_1-C_4)$-alkyl. In certain embodiments, the invention relates to any one of the aforementioned compounds, wherein $R_{5e}$ is substituted $(C_1-C_4)$-alkyl. In certain embodiments, the substituted $(C_1-C_5)$-alkyl, is substituted with one or more halogen. In certain embodiments, the halogen is Cl or F. In certain embodiments, $R_{5e}$ is methyl, ethyl, isopropyl, n-propyl, i-butyl, n-butyl, or t-butyl. In certain embodiments, the invention relates to any one of the aforementioned compounds, wherein $R_{5e}$ is halide. In some embodiments, the halide is Cl or F. In certain embodiments, $R_{5e}$ is substituted $(C_3-C_6)$-cycloalkyl. In certain embodiments, $R_{5e}$ is unsubstituted $(C_3-C_6)$-cycloalkyl. In some embodiments, $(C_3-C_6)$-cycloalkyl is cyclopropyl. In certain embodiments, the invention relates to any one of the aforementioned compounds, wherein $R_{5e}$ is CF$_3$. In certain embodiments, the invention relates to any one of the aforementioned compounds, wherein $R_{5e}$ is C(H)F$_2$. In certain embodiments, the invention relates to any one of the aforementioned compounds, wherein $R_{5e}$ is C(F)H$_2$. In certain embodiments, the invention relates to any one of the aforementioned compounds, wherein $R_{5e}$ is $(C_1-C_4)$-alkoxy. In some embodiments, $(C_1-C_4)$-alkoxy is methoxy. In certain embodiments, the invention relates to any one of the aforementioned compounds, wherein $R_{5e}$ is methoxy. In certain embodiments, the invention relates to any one of the aforementioned compounds, wherein $R_{5e}$ is hydroxyl. In certain embodiments, the invention relates to any one of the aforementioned compounds, wherein $R_{5e}$ is —OCF$_3$. In certain embodiments, $R_{5e}$ is CN. In certain embodiments, the invention relates to any one of the aforementioned compounds, wherein $R_{5e}$ is substituted $(C_1-C_4)$-alkylene-$(C_1-C_4)$-alkoxy. In certain embodiments, the invention relates to any one of the aforementioned compounds, wherein $R_{5e}$ is unsubstituted $(C_1-C_4)$-alkylene-$(C_1-C_4)$-alkoxy. In certain embodiments, $(C_1-C_4)$-alkylene-$(C_1-C_4)$-alkoxy is —CH$_2$OMe. In certain embodiments, $R_{5e}$ is CH$_2$OH.

In some embodiments, $R_{5a}$ and $R_{5e}$ are identical. For example, $R_{5a}$ and $R_{5e}$ can both be substituted or unsubstituted $(C_1-C_4)$-alkyl. In some examples, $R_{5a}$ and $R_{5e}$ are both unsubstituted $(C_1-C_4)$-alkyl (e.g., methyl). In some examples, $R_{5a}$ and $R_{5e}$ are both unsubstituted methyl.

In some embodiments, $R_{5b}$ and $R_{5d}$ are identical. For example, $R_5$ and $R_{5e}$ can both be hydrogen.

In some embodiments, $R_{5a}$ and $R_{5e}$ are both substituted, and $R_{5b}$ and $R_{5d}$ are both hydrogen. For example, $R_{5a}$ and $R_{5e}$ can both be (the same or different) substituted or unsubstituted $(C_1-C_4)$-alkyl. In some examples, $R_{5a}$ and $R_{5e}$ can both be unsubstituted $(C_1-C_4)$-alkyl (e.g., methyl) and $R_{5b}$ and $R_{5d}$ are both hydrogen. In some examples, $R_{5a}$ and $R_{5e}$ are both unsubstituted methyl and $R_{5b}$ and $R_{5d}$ are both hydrogen. In some embodiments, $R_{5a}$, and $R_{5e}$ are independently selected from the group consisting of H, CN, halide, $CF_3$, $C(H)F_2$, $C(F)H_2$, $(C_1-C_5)$-alkyl, hydroxyl, and $(C_1-C_4)$-alkoxy.

In some embodiments, $R_{5c}$ is hydrogen, halide (e.g., F), substituted or unsubstituted $(C_1-C_4)$-alkoxy (e.g., methoxy), or substituted or unsubstituted $(C_1-C_4)$-alkyl (e.g., methyl).

In some embodiments, $R_{5a}$ and $R_{5e}$ are both substituted or unsubstituted $(C_1-C_5)$-alkyl, both $R_{5b}$ and $R_{5d}$ are hydrogen and $R_{5c}$ is hydrogen, halide (e.g., F), substituted or unsubstituted $(C_1-C_4)$-alkoxy (e.g., methoxy), or substituted or unsubstituted $(C_1-C_4)$-alkyl (e.g., methyl). For example, $R_{5a}$ and $R_{5e}$ can both be methyl; $R_{5b}$ and $R_{5d}$ are both hydrogen; and $R_{5c}$ is selected from the group consisting of hydrogen, halide (e.g., F), substituted or unsubstituted $(C_1-C_4)$-alkoxy (e.g., methoxy), and substituted or unsubstituted $(C_1-C_4)$-alkyl (e.g., methyl). In some examples, $R_{5a}$ and $R_{5e}$ can both be methyl; $R_{5b}$ and $R_{5d}$ are both hydrogen; and $R_{5c}$ is selected from the group consisting of hydrogen, F, Cl, methoxy, and methyl. In some examples, $R_{5a}$, $R_{5c}$ and $R_{5e}$ are each methyl; and $R_{5b}$ and $R_{5d}$ are both hydrogen. In some embodiments, $R_{5b}$, $R_{5c}$, and $R_{5e}$ are independently selected from the group consisting of H, CN, halide, $CF_3$, $C(H)F_2$, $C(F)H_2$, $(C_1-C_5)$-alkyl, hydroxyl, and $(C_1-C_4)$-alkoxy.

In certain embodiments, the invention relates to any one of the aforementioned compounds, wherein $R_a$, $R_b$ and $R_c$ comprise a charged amine. At least one of $R_a$, $R_b$ and $R_c$ can be a substituted or unsubstituted —$(C_1-C_5)$alkylene-N—$(R_x)(R_y)$; wherein $R_x$ and $R_y$ are independently selected from the group consisting of H, substituted or unsubstituted $(C_1-C_6)$-alkyl, or substituted or unsubstituted $(C_1-C_4)$-alkylene-$(C_1-C_4)$-alkoxy; or $R_x$ and $R_y$ taken together with the N to which they are attached form a substituted or unsubstituted 4-6 membered heterocyclyl ring.

In certain embodiments, the invention relates to any one of the aforementioned compounds, wherein only one of $R_a$, $R_b$ and $R_c$ is a substituted or unsubstituted —$(C_1-C_5)$alkylene-N—$(R_x)(R_y)$; wherein $R_x$ and $R_y$ are independently selected from the group consisting of H, substituted or unsubstituted $(C_1-C_6)$-alkyl, or substituted or unsubstituted $(C_1-C_4)$-alkylene-$(C_1-C_4)$-alkoxy. In certain embodiments, the invention relates to any one of the aforementioned compounds, wherein only one of $R_a$, $R_b$ and $R_c$ is a substituted or unsubstituted —$(C_1-C_5)$alkylene-N—$(R_x)(R_y)$; wherein $R_x$ and $R_y$ are independently selected from the group consisting of substituted or unsubstituted $(C_1-C_6)$-alkyl, or substituted or unsubstituted $(C_1-C_4)$-alkylene-$(C_1-C_4)$-alkoxy. In certain embodiments, the invention relates to any one of the aforementioned compounds, wherein only one of $R_a$, $R_b$ and $R_c$ is a substituted or unsubstituted —$(C_1-C_5)$ alkylene-N—$(R_x)(R_y)$; wherein $R_x$ and $R_y$ are independently selected from the group consisting of substituted or unsubstituted $(C_1-C_6)$-alkyl.

In certain embodiments, the invention relates to any one of the aforementioned compounds, wherein only one of $R_a$, $R_b$ and $R_c$ is a substituted or unsubstituted —$(C_1-C_5)$alkylene-N—$(R_x)(R_y)$; wherein $R_x$ and $R_y$ taken together with the N to which they are attached form a substituted or unsubstituted 4-6 membered heterocyclyl ring. In certain embodiments, the invention relates to any one of the aforementioned compounds, wherein only one of $R_a$, $R_b$ and $R_c$ is a substituted or unsubstituted —$(C_1-C_5)$alkylene-N—$(R_x)(R_y)$; wherein $R_x$ and $R_y$ taken together with the N to which they are attached form a 4-6 membered heterocyclyl ring optionally substituted with one or more halide (e.g., F, Cl).

In some embodiments, $R_a$, $R_b$, and $R_c$ are independently selected from the group consisting of H, substituted or unsubstituted $(C_1-C_5)$-alkyl, halide, $CF_3$, $C(H)F_2$, $C(F)H_2$, substituted or unsubstituted $(C_1-C_4)$-alkoxy, —$OCF_3$, and at least one of $R_a$, $R_b$, and $R_c$ is —$(C_1-C_3)$alkylene-N—$(R_x)(R_y)$ wherein $R_x$ and $R_y$ are independently selected from the group consisting of H and $(C_1-C_6)$-alkyl; or $R_x$ and $R_y$ taken together with the N to which they are attached form a 4-6 membered heterocyclyl ring optionally substituted with one or more halide (e.g., F, or Cl).

In some embodiments, $R_a$, $R_b$, and $R_c$ are independently selected from the group consisting of H, substituted or unsubstituted $(C_1-C_5)$-alkyl, halide, $CF_3$, $C(H)F_2$, $C(F)H_2$, substituted or unsubstituted $(C_1-C_4)$-alkoxy, —$OCF_3$, and at least one of $R_a$, $R_b$, and $R_c$ is —$(C_1-C_3)$alkylene-N—$(R_x)(R_y)$ wherein $R_x$ and $R_y$ are independently selected from the group consisting of $(C_1-C_6)$-alkyl (e.g., methyl); or $R_x$ and $R_y$ taken together with the N to which they are attached form a 4-6 membered heterocyclyl ring optionally substituted with one or more halide (e.g., F, or Cl).

In certain embodiments, the invention relates to any one of the aforementioned compounds, wherein only one of $R_a$, $R_b$ and $R_c$ is selected from the group consisting of

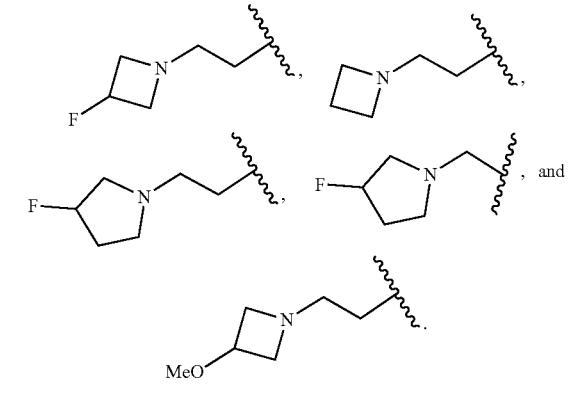

some embodiments, $R_a$ is

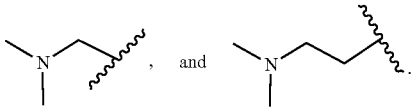

In certain embodiments, the invention relates to any one of the aforementioned compounds, wherein $R_a$ is selected from the group consisting of H, substituted or unsubstituted $(C_1-C_5)$-alkyl, halide, $CF_3$, $C(H)F_2$, $C(F)H_2$, substituted or unsubstituted $(C_1-C_4)$-alkoxy, and —$OCF_3$. In certain embodiments, the invention relates to any one of the aforementioned compounds, wherein $R_a$ is selected from the group consisting of H, substituted or unsubstituted $(C_1-C_5)$-alkyl, halide, $CF_3$, $C(H)F_2$, $C(F)H_2$, substituted or unsubstituted $(C_1-C_4)$-alkoxy, and —$OCF_3$; and one of $R_b$ and $R_c$ is a substituted or unsubstituted —(C₁-C₅)alkylene-N—(R_x)(R_y); wherein R_x and R_y are independently selected from the group consisting of H, substituted or unsubstituted (C₁-C₆)-alkyl, or substituted or unsubstituted (C₁-C₄)-alkylene-(C₁-C₄)-alkoxy; or R_x and R_y taken together with the N to which they are attached form a substituted or unsubstituted 4-6 membered heterocyclyl ring.

In certain embodiments, the invention relates to any one of the aforementioned compounds, wherein R_a is H. In certain embodiments, the invention relates to any one of the aforementioned compounds, wherein R_a is Me. In certain embodiments, the invention relates to any one of the aforementioned compounds, wherein R_a is halide. In some embodiments, halide is Cl or F. In certain embodiments, the invention relates to any one of the aforementioned compounds, wherein R_a is CF₃. In certain embodiments, the invention relates to any one of the aforementioned compounds, wherein R_a is C(H)F₂. In certain embodiments, the invention relates to any one of the aforementioned compounds, wherein R_a is C(F)H₂. In certain embodiments, the invention relates to any one of the aforementioned compounds, wherein R_a is substituted (C₁-C₄)-alkoxy. In certain embodiments, the invention relates to any one of the aforementioned compounds, wherein R_a is unsubstituted (C₁-C₄)-alkoxy. In some embodiments, (C₁-C₄)-alkoxy is methoxy. In certain embodiments, the invention relates to any one of the aforementioned compounds, wherein R_a is —OCF₃. In certain embodiments, the invention relates to any one of the aforementioned compounds, wherein R_a is substituted —(C₁-C₅)alkylene-N—(R_x)(R_y). In certain embodiments, the invention relates to any one of the aforementioned compounds, wherein R_a is unsubstituted —(C₁-C₅)alkylene-N—(R_x)(R_y). In some embodiments, —(C₁-C₅)alkylene of —(C₁-C₅)alkylene-N—(R_x)(R_y) is substituted with one or more halide or —(C₁-C₄)alkyl. In certain embodiments, the invention relates to any one of the aforementioned compounds, wherein (C₁-C₅)alkylene-N—(R_x)(R_y) is —(C₁-C₄)alkylene-N—(R_x)(R_y).

In some embodiments, R_a is substituted (C₁-C₅)-alkyl, substituted (C₁-C₄)-alkoxy, or substituted —(C₁-C₅)alkylene-N—(R_x)(R_y), wherein substituted means substituted with halide or (C₁-C₄)-alkoxy. In some embodiments, R_a is substituted (C₁-C₅)-alkyl, substituted (C₁-C₄)-alkoxy, or substituted —(C₁-C₅)alkylene-N—(R_x)(R_y), wherein substituted means substituted with F or methoxy.

In some embodiments, R_a is selected from the group consisting of

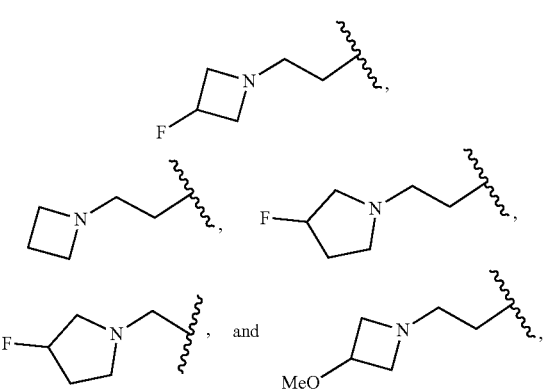

In some embodiments, R_a

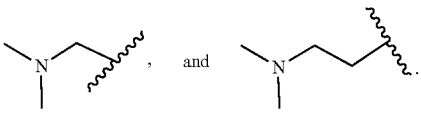

In certain embodiments, the invention relates to any one of the aforementioned compounds, wherein R_a is selected from the group consisting of H, substituted or unsubstituted (C₁-C₅)-alkyl, halide, CF₃, C(H)F₂, C(F)H₂, substituted or unsubstituted (C₁-C₄)-alkoxy, and —OCF; and R_b is a substituted or unsubstituted —(C₁-C₅)alkylene-N—(R_x)(R_y); wherein R_x and R_y are independently selected from the group consisting of H, substituted or unsubstituted (C₁-C₆)-alkyl, or substituted or unsubstituted (C₁-C₄)-alkylene-(C₁-C₄)-alkoxy; or R_x and R_y taken together with the N to which they are attached form a substituted or unsubstituted 4-6 membered heterocyclyl ring.

In certain embodiments, the invention relates to any one of the aforementioned compounds, wherein R_b is H. In certain embodiments, the invention relates to any one of the aforementioned compounds, wherein R_b is Me. In certain embodiments, the invention relates to any one of the aforementioned compounds, wherein R_b is halide. In some embodiments, halide is Cl or F. In certain embodiments, the invention relates to any one of the aforementioned compounds, wherein R_b is CF₃. In certain embodiments, the invention relates to any one of the aforementioned compounds, wherein R_b is C(H)F₂. In certain embodiments, the invention relates to any one of the aforementioned compounds, wherein R_b is C(F)H₂. In certain embodiments, the invention relates to any one of the aforementioned compounds, wherein R_b is substituted (C₁-C₄)-alkoxy. In certain embodiments, the invention relates to any one of the aforementioned compounds, wherein R_b is unsubstituted (C₁-C₄)-alkoxy. In some embodiments, (C₁-C₄)-alkoxy is methoxy. In certain embodiments, the invention relates to any one of the aforementioned compounds, wherein R_b is —OCF₃. In certain embodiments, the invention relates to any one of the aforementioned compounds, wherein R_b is substituted —(C₁-C₅)alkylene-N—(R_x)(R_y). In certain embodiments, the invention relates to any one of the aforementioned compounds, wherein R_b is unsubstituted —(C₁-C₅)alkylene-N—(R_x)(R_y). In some embodiments, —(C₁-C₅)alkylene of —(C₁-C₅)alkylene-N—(R_x)(R_y) is substituted with one or more halide or —(C₁-C₄)alkyl. In certain embodiments, the invention relates to any one of the aforementioned compounds, wherein (C₁-C₅)alkylene-N—(R_x)(R_y) is —(C₁-C₄)alkylene-N—(R_x)(R_y).

In some embodiments, R_b is substituted (C₁-C₅)-alkyl, substituted (C₁-C₄)-alkoxy, or substituted —(C₁-C₅)alkylene-N—(R_x)(R_y), wherein substituted means substituted with halide or (C₁-C₄)-alkoxy. In some embodiments, R_b is substituted (C₁-C₅)-alkyl, substituted (C₁-C₄)-alkoxy, or substituted —(C₁-C₅)alkylene-N—(R_x)(R_y), wherein substituted means substituted with F or methoxy.

In some embodiments, R_b is selected from the group consisting of

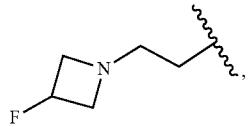

-continued

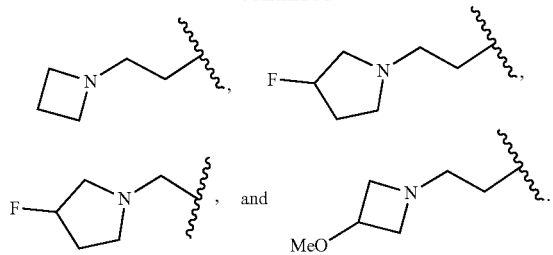

In some embodiments, $R_b$

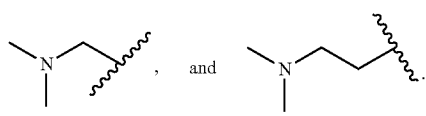

In certain embodiments, the invention relates to any one of the aforementioned compounds, wherein $R_c$ is H. In certain embodiments, the invention relates to any one of the aforementioned compounds, wherein $R_c$ is Me. In certain embodiments, the invention relates to any one of the aforementioned compounds, wherein $R_c$ is halide. In some embodiments, halide is Cl or F. In certain embodiments, the invention relates to any one of the aforementioned compounds, wherein $R_c$ is $CF_3$. In certain embodiments, the invention relates to any one of the aforementioned compounds, wherein $R_c$ is $C(H)F_2$. In certain embodiments, the invention relates to any one of the aforementioned compounds, wherein $R_c$ is $C(F)H_2$. In certain embodiments, the invention relates to any one of the aforementioned compounds, wherein $R_c$ is substituted $(C_1-C_4)$-alkoxy. In some embodiments, $(C_1-C_4)$-alkoxy is methoxy. In certain embodiments, the invention relates to any one of the aforementioned compounds, wherein $R_c$ is unsubstituted $(C_1-C_4)$-alkoxy. In certain embodiments, the invention relates to any one of the aforementioned compounds, wherein $R_c$ is —$OCF_3$. In certain embodiments, the invention relates to any one of the aforementioned compounds, wherein $R_c$ is substituted —$(C_1-C_5)$alkylene-N—$(R_x)(R_y)$. In certain embodiments, the invention relates to any one of the aforementioned compounds, wherein $R_c$ is unsubstituted —$(C_1-C_5)$alkylene-N—$(R_x)(R_y)$. In some embodiments, —$(C_1-C_5)$ alkylene of —$(C_1-C_5)$alkylene-N—$(R_x)(R_y)$ is substituted with one or more halide or —$(C_1-C_4)$alkyl. In certain embodiments, the invention relates to any one of the aforementioned compounds, wherein $(C_1-C_5)$alkylene-N—$(R_x)(R_y)$ is —$(C_1-C_4)$alkylene-N—$(R_x)(R_y)$.

In some embodiments, $R_c$ is substituted $(C_1-C_5)$-alkyl, substituted $(C_1-C_4)$-alkoxy, or substituted —$(C_1-C_5)$alkylene-N—$(R_x)(R_y)$, wherein substituted means substituted with halide or $(C_1-C_4)$-alkoxy. In some embodiments, $R_c$ is substituted $(C_1-C_5)$-alkyl, substituted $(C_1-C_4)$-alkoxy, or substituted —$(C_1-C_5)$alkylene-N—$(R_x)(R_y)$, wherein substituted means substituted with F or methoxy.

In some embodiments, $R_c$ is selected from the group consisting of

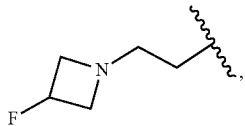

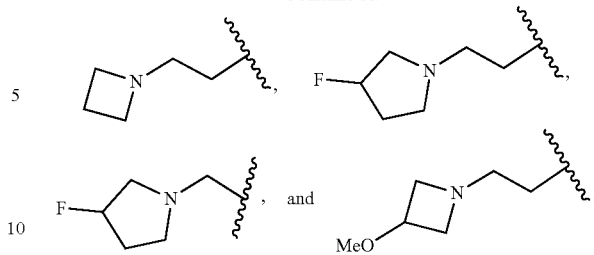

In some embodiments, $R_c$

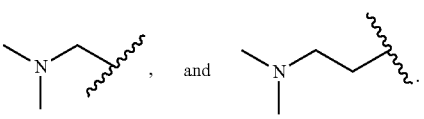

In some embodiments, at least one of $R_a$, $R_b$, and $R_c$ is H.

In some embodiments, at least one of $R_a$, $R_b$, and $R_c$ is a charged amine; and at least one of $R_a$, $R_b$, and $R_c$ is H.

In certain embodiments, the invention relates to any one of the aforementioned compounds, wherein $R_x$ is H. In certain embodiments, the invention relates to any one of the aforementioned compounds, wherein $R_x$ is substituted $(C_1-C_6)$-alkyl. In certain embodiments, the invention relates to any one of the aforementioned compounds, wherein $R_x$ is unsubstituted $(C_1-C_6)$-alkyl. In certain embodiments, the invention relates to any one of the aforementioned compounds, wherein $R_x$ is substituted $(C_1-C_4)$-alkyl. In some embodiments $(C_1-C_6)$-alkyl is substituted with OMe, CN, or halide. In certain embodiments, the invention relates to any one of the aforementioned compounds, wherein $R_x$ is unsubstituted $(C_1-C_4)$-alkyl. In certain embodiments, the invention relates to any one of the aforementioned compounds, wherein $R_x$ is $(C_1-C_4)$-alkylene-$(C_1-C_4)$-alkoxy. In some embodiments, $(C_1-C_4)$-alkylene-$(C_1-C_4)$-alkoxy is —$(CH_2)_2$OMe. In certain embodiments, the invention relates to any one of the aforementioned compounds, wherein $R_x$ is Me.

In certain embodiments, the invention relates to any one of the aforementioned compounds, wherein $R_y$ is H. In certain embodiments, the invention relates to any one of the aforementioned compounds, wherein $R_y$ is substituted $(C_1-C_6)$-alkyl. In certain embodiments, the invention relates to any one of the aforementioned compounds, wherein $R_y$ is unsubstituted $(C_1-C_6)$-alkyl. In certain embodiments, the invention relates to any one of the aforementioned compounds, wherein $R_y$ is substituted $(C_1-C_4)$-alkyl. In some embodiments $(C_1-C_6)$-alkyl is substituted with OMe, CN, or halide. In certain embodiments, the invention relates to any one of the aforementioned compounds, wherein $R_y$ is unsubstituted $(C_1-C_4)$-alkyl. In certain embodiments, the invention relates to any one of the aforementioned compounds, wherein $R_y$ is $(C_1-C_4)$-alkylene-$(C_1-C_4)$-alkoxy. In some embodiments, $(C_1-C_4)$-alkylene-$(C_1-C_4)$-alkoxy is —$(CH_2)_2$OMe. In certain embodiments, the invention relates to any one of the aforementioned compounds, wherein $R_y$ is Me.

In certain embodiments, the invention relates to any one of the aforementioned compounds, wherein $R_x$ is Me; and $R_y$ is Me.

In certain embodiments, the invention relates to any one of the aforementioned compounds, wherein $R_x$ and $R_y$ taken together with the N to which they are attached form a substituted or unsubstituted 4-6 membered ring. In some embodiments, the 4-6 membered ring is a substituted or unsubstituted heterocycloalkyl. In some embodiments, the substituted 4-6 membered heterocyclalkyl is substituted with halide of $(C_1-C_6)$alkyl. In some embodiments, the 4-6 membered ring is a substituted or unsubstituted heteroaryl. In some embodiments, the substituted 4-6 membered heteroaryl is substituted with halide of $(C_1-C_6)$alkyl. In some embodiments, the 4-6 membered ring is selected from

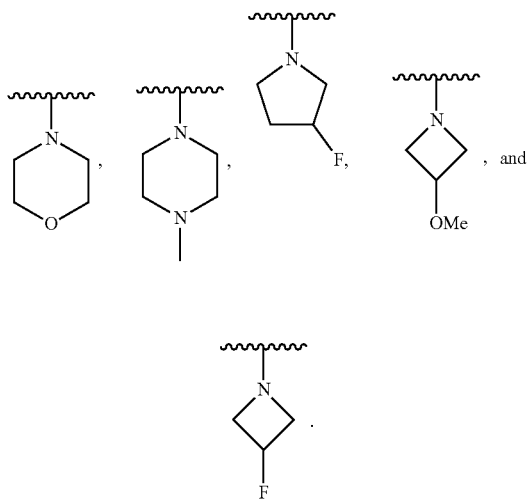

In certain embodiments, the invention relates to a compound of Formula (Ia) or (Ib):

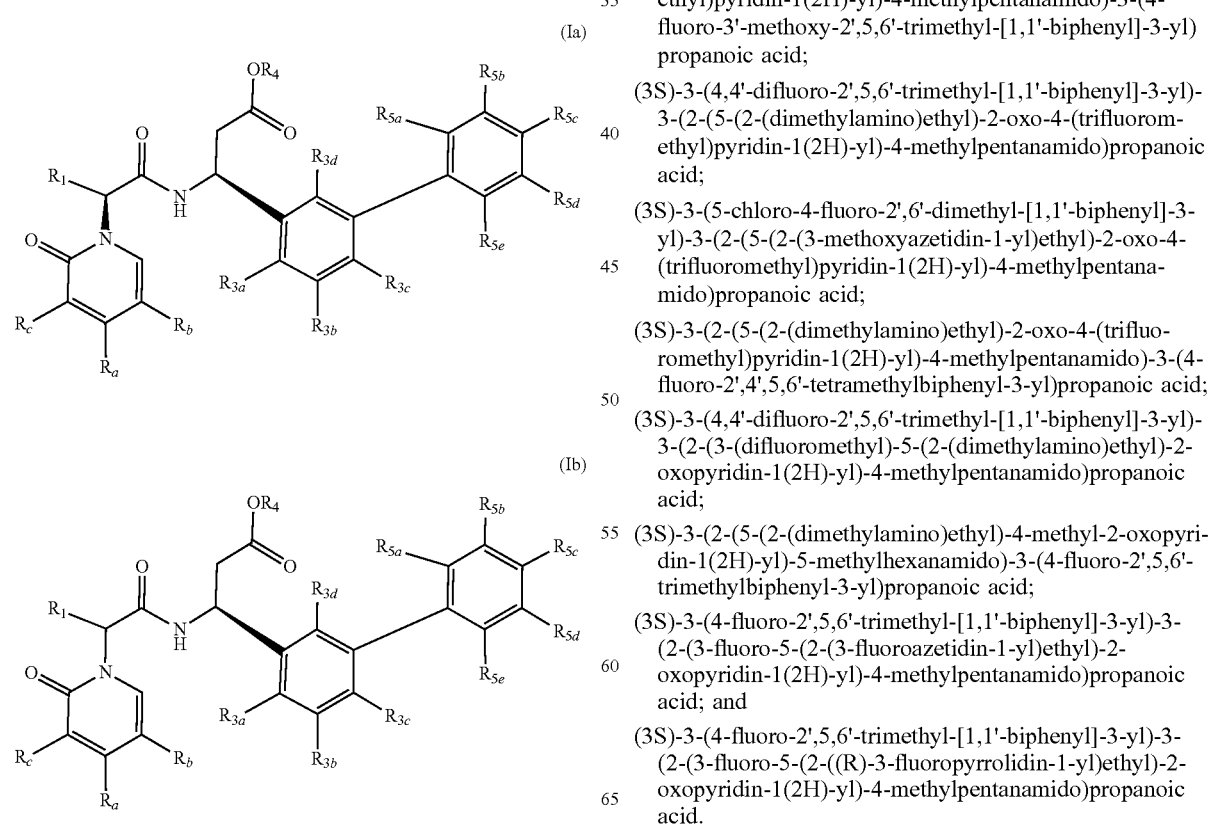

wherein $R_1$, $R_{3c}$, $R_{3d}$, $R_{5a}$, $R_{5b}$, $R_{5c}$, $R_{5d}$, $R_{5e}$, $R_a$, $R_b$, and $R_c$ are as defined above with respect to Formula (I);

$R_4$ is H; and at least one of $R_a$, $R_b$, and $R_c$ is —$(C_1-C_3)$alkylene-N($R_x$)($R_y$);

$R_x$ and $R_y$ are independently selected from the group consisting of H and methyl; or $R_x$ and $R_y$ taken together with the N to which they are attached form a 4-6 membered ring; and $R_{3a}$, and $R_{3b}$ are each independently selected from the group consisting of methyl and F.

In certain embodiments, the invention relates to any of the compounds depicted in FIG. 1.

In certain embodiments, the invention relates to a compound selected from the group consisting of:

(3S)-3-(4,5-difluoro-2',6'-dimethylbiphenyl-3-yl)-3-(2-(5-(2-(3-fluoroazetidin-1-yl)ethyl)-4-methyl-2-oxopyridin-1(2H)-yl)-4-methylpentanamido)propanoic acid;

(3S)-3-(2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)biphenyl-3-yl)propanoic acid;

(3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic acid;

(3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic acid;

(3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid;

(3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid;

(3S)-3-(2-(5-(2-(dimethylamino)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoic acid;

(3S)-3-(4,4'-difluoro-2',5,6'-trimethyl-[1,1'-biphenyl]-3-yl)-3-(2-(3-(difluoromethyl)-5-(2-(dimethylamino)ethyl)-2-oxopyridin-1(2H)-yl)-4-methylpentanamido)propanoic acid;

(3S)-3-(2-(5-(2-(dimethylamino)ethyl)-4-methyl-2-oxopyridin-1(2H)-yl)-5-methylhexanamido)-3-(4-fluoro-2',5,6'-trimethylbiphenyl-3-yl)propanoic acid;

(3S)-3-(4-fluoro-2',5,6'-trimethyl-[1,1'-biphenyl]-3-yl)-3-(2-(3-fluoro-5-(2-(3-fluoroazetidin-1-yl)ethyl)-2-oxopyridin-1(2H)-yl)-4-methylpentanamido)propanoic acid; and (3S)-3-(4-fluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic acid.

or a pharmaceutically acceptable salt thereof.

In certain embodiments, the invention relates to a compound selected from the group consisting of.
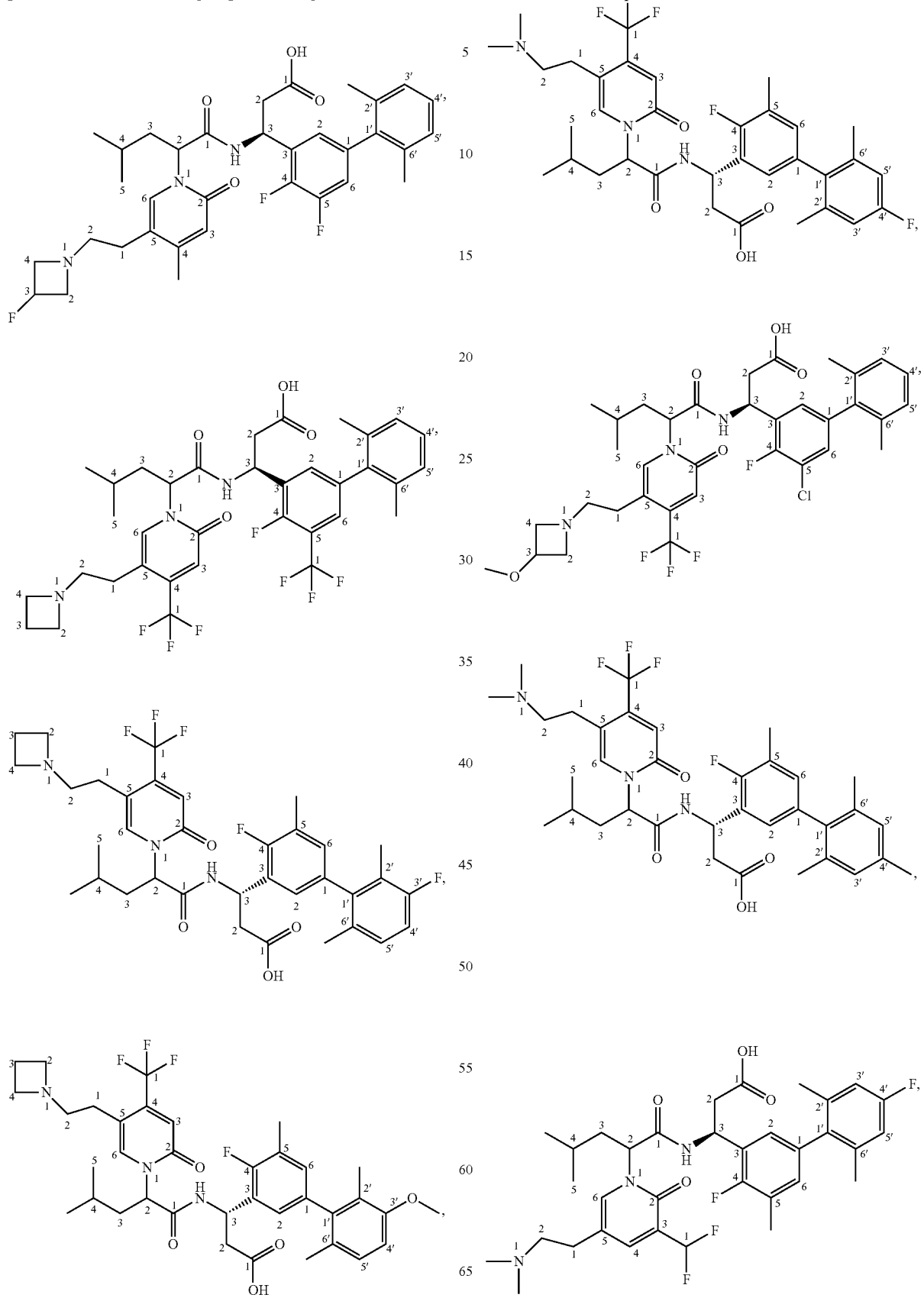

-continued

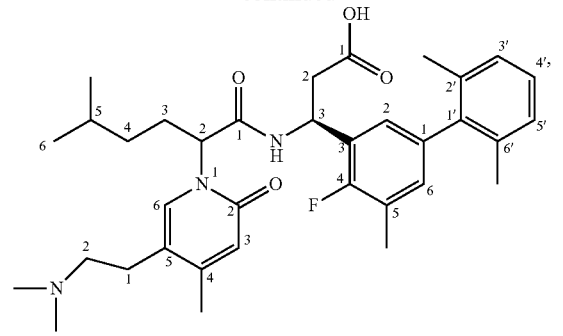

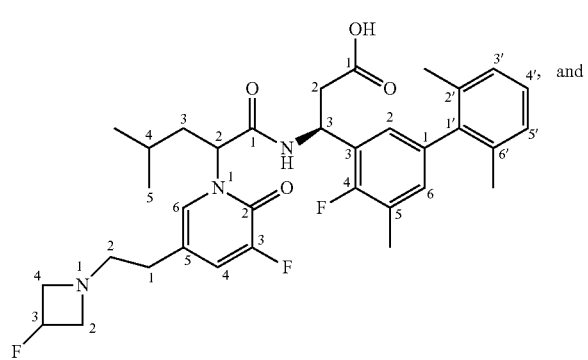

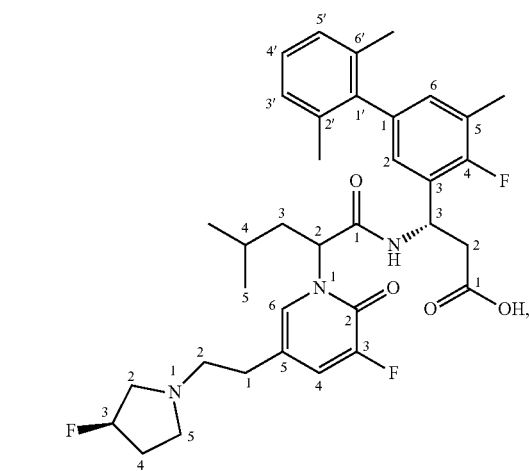

or a pharmaceutically acceptable salt thereof.

In certain embodiments, the invention relates to a compound selected from the group consisting of:

(S)-3-(4,5-difluoro-2',6'-dimethyl-[1,1'-biphenyl]-3-yl)-3-((S)-2-(5-(2-(3-fluoroazetidin-1-yl)ethyl)-4-methyl-2-oxopyridin-1(2H)-yl)-4-methylpentanamido)propanoic acid;

(S)-3-((S)-2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoic acid;

(S)-3-((S)-2-(5-(2-(azetidin-1-yl)ethyl)-2-oxo-4-(trifluoromethyl)pyridin-1(2H)-yl)-4-methylpentanamido)-3-(3',4-difluoro-2',5',6'-trimethyl-[1,1'-biphenyl]-3-yl)propanoic acid;

(S)-3-((S)-2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5',6'-trimethyl-[1,1'-biphenyl]-3-yl)propanoic acid;

(S)-3-(4,4'-difluoro-2',5',6'-trimethyl-[1,1'-biphenyl]-3-yl)-3-((S)-2-(5-(2-(dimethylamino)ethyl)-2-oxo-4-(trifluoromethyl)pyridin-1(2H)-yl)-4-methylpentanamido)propanoic acid;

(S)-3-(5-chloro-4-fluoro-2',6'-dimethyl-[1,1'-biphenyl]-3-yl)-3-((S)-2-(5-(2-(3-methoxyazetidin-1-yl)ethyl)-2-oxo-4-(trifluoromethyl)pyridin-1(2H)-yl)-4-methylpentanamido)propanoic acid;

(S)-3-((S)-2-(5-(2-(dimethylamino)ethyl)-2-oxo-4-(trifluoromethyl)pyridin-1(2H)-yl)-4-methylpentanamido)-3-(4-fluoro-2',4',5',6'-tetramethyl-[1,1'-biphenyl]-3-yl)propanoic acid;

(S)-3-(4,4'-difluoro-2',5',6'-trimethyl-[1,1'-biphenyl]-3-yl)-3-((S)-2-(3-(difluoromethyl)-5-(2-(dimethylamino)ethyl)-2-oxopyridin-1(2H)-yl)-4-methylpentanamido)propanoic acid;

(S)-3-((S)-2-(5-(2-(dimethylamino)ethyl)-4-methyl-2-oxopyridin-1(2H)-yl)-5-methylhexanamido)-3-(4-fluoro-2',5',6'-trimethyl-[1,1'-biphenyl]-3-yl)propanoic acid;

(S)-3-(4-fluoro-2',5',6'-trimethyl-[1,1'-biphenyl]-3-yl)-3-((S)-2-(3-fluoro-5-(2-(3-fluoroazetidin-1-yl)ethyl)-2-oxopyridin-1(2H)-yl)-4-methylpentanamido)propanoic acid; and (S)-3-(4-fluoro-2',5',6'-trimethyl-[1,1'-biphenyl]-3-yl)-3-((S)-2-(3-fluoro-5-(2-((R)-3-fluoropyrrolidin-1-yl)ethyl)-2-oxopyridin-1(2H)-yl)-4-methylpentanamido)propanoic acid;

or a pharmaceutically acceptable salt thereof.

In certain embodiments, the invention relates to a compound selected from the group consisting of:

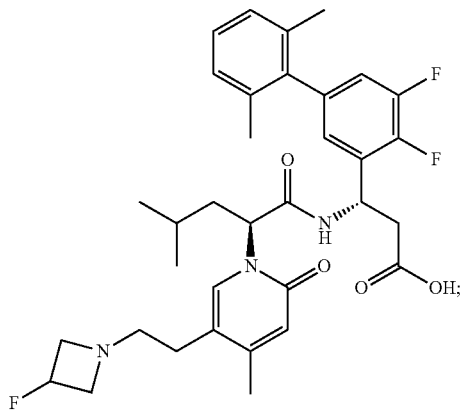

(S)-3-(4,5-difluoro-2',6'-dimethyl-[1,1'-biphenyl]-3-yl)-3-((S)-2-(5-(2-(3-fluoroazetidin-1-yl)ethyl)-4-methyl-2-oxopyridin-1(2H)-yl-4-methylpentanamido)propanoic acid

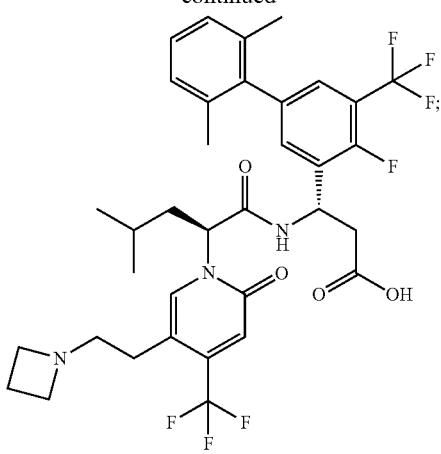

(S)-3-((S)-2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoic acid;

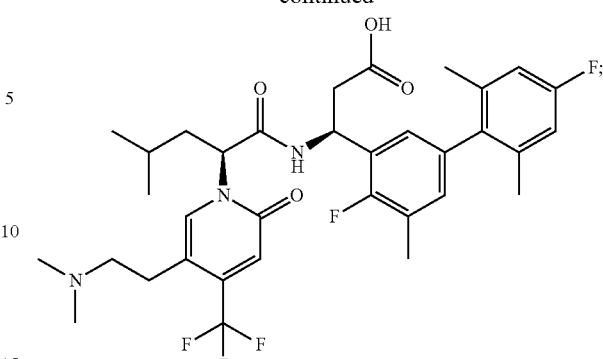

(S)-3-(4,4'-difluoro-2',5,6'-trimethyl-[1,1'-biphenyl]-3-yl)-3-((S)-2-(5-(2-(dimethylamino)ethyl)-2-oxo-4-(trifluoromethyl)pyridin-1(2H)-yl)-4-methylpentanamido)propanoic acid;

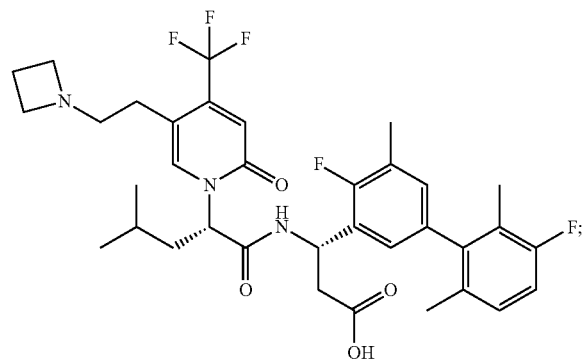

(S)-3-((S)-2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic acid;

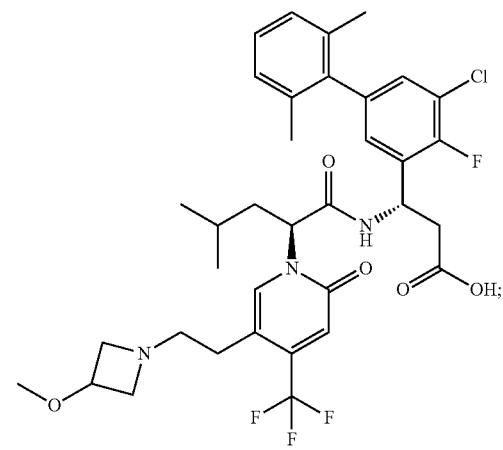

(S)-3-(5-chloro-4-fluoro-2',6'-dimethyl-[1,1'-biphenyl]-3-yl)-3-((S)-2-(5-(2-(3-methoxyazetidin-1-yl)ethyl)-2-oxo-4-(trifluoromethyl)pyridin-1(2H)-yl)-4-methylpentanamido)propanoic acid;

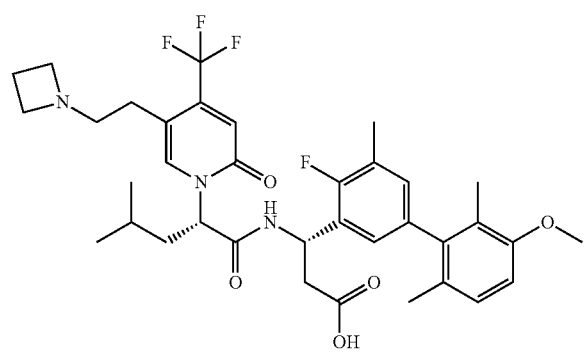

(S)-3-((S)-2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic acid;

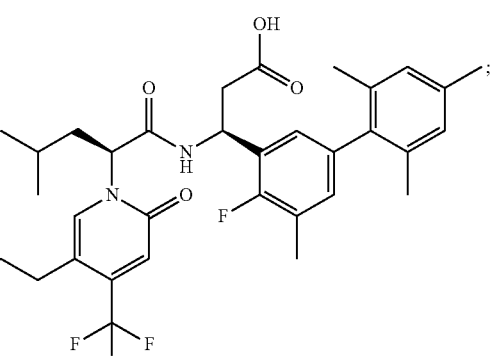

(S)-3-((S-2-(5-(2-(dimethylamino)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoic acid;

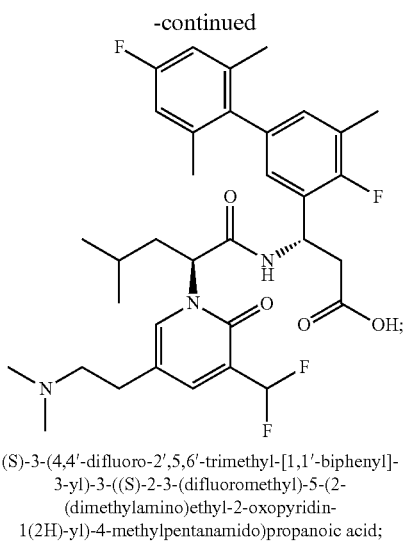

(S)-3-(4,4'-difluoro-2',5,6'-trimethyl-[1,1'-biphenyl]-
3-yl)-3-((S)-2-3-(difluoromethyl)-5-(2-
(dimethylamino)ethyl-2-oxopyridin-
1(2H)-yl)-4-methylpentanamido)propanoic acid;

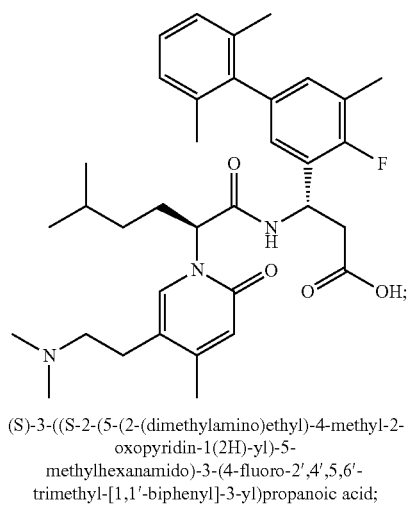

(S)-3-((S-2-(5-(2-(dimethylamino)ethyl)-4-methyl-2-
oxopyridin-1(2H)-yl)-5-
methylhexanamido)-3-(4-fluoro-2',4',5,6'-
trimethyl-[1,1'-biphenyl]-3-yl)propanoic acid;

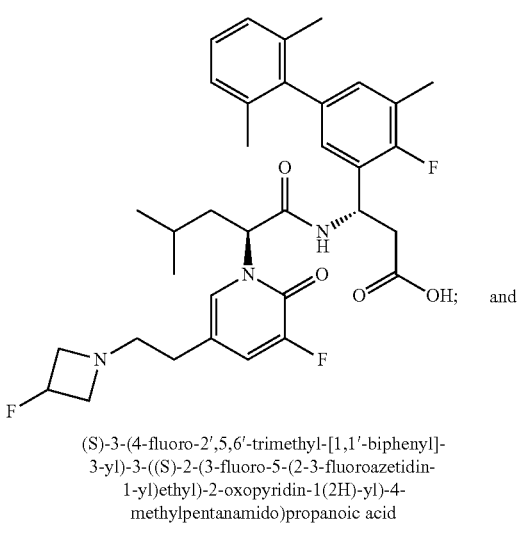

(S)-3-(4-fluoro-2',5,6'-trimethyl-[1,1'-biphenyl]-
3-yl)-3-((S)-2-3-fluoro-5-(2-3-fluoroazetidin-
1-yl)ethyl)-2-oxopyridin-1(2H)-yl)-4-
methylpentanamido)propanoic acid and

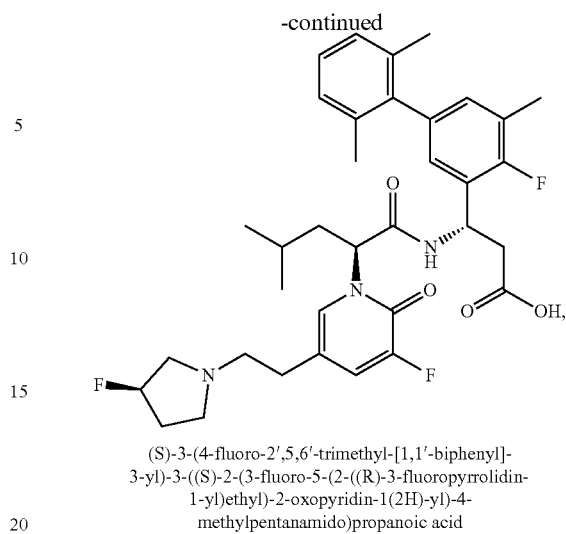

(S)-3-(4-fluoro-2',5,6'-trimethyl-[1,1'-biphenyl]-
3-yl)-3-((S)-2-(3-fluoro-5-(2-((R)-3-fluoropyrrolidin-
1-yl)ethyl)-2-oxopyridin-1(2H)-yl)-4-
methylpentanamido)propanoic acid In certain embodiments, the invention relates to any one of the aforementioned compounds, wherein the compound is in the form of a pharmaceutically acceptable salt.

Exemplary Pharmaceutical Compositions Compounds of Formula (I) can be formulated in various pharmaceutical compositions. A compound of Formula (I) (including compounds of Formula (Ia) and Formula (Ib) as provided herein), as well as pharmaceutically acceptable salts thereof, may be the active pharmaceutical ingredient (API) combined with one or more other ingredients to form a drug substance pharmaceutical composition. The drug substance (DS) pharmaceutical composition can comprise the API (i.e., a compound of Formula (I) or pharmaceutically acceptable salt thereof) and one or more pharmaceutically acceptable carriers, diluents, and/or excipients. The carrier(s), diluent(s) or excipient(s) can be selected to be compatible with the other ingredients of the formulation and appropriately safe and effective for an intended therapy. A desired weight concentration of the compound of Formula (I) as the active pharmaceutical ingredient (API) can be combined with the other inactive ingredients to form a drug substance (DS) in a formulation batch. Pharmaceutically acceptable compositions can be formulated for administration by an appropriate route, for example by the oral delivery (including as a capsule or tablet) in unit dosage forms. Such compositions may be prepared by bringing into association the active pharmaceutical ingredient (API) comprising a compound of Formula (I) with the carrier(s) or excipient(s).

In certain embodiments, the invention provides a pharmaceutical composition comprising the compound of Formula (I), or a pharmaceutically acceptable salt thereof as the active pharmaceutical ingredient (API).

In certain embodiments, the invention provides a pharmaceutical composition comprising the compound of Formula (Ia), or a pharmaceutically acceptable salt thereof as the active pharmaceutical ingredient (API).

In certain embodiments, the invention provides a pharmaceutical composition comprising the compound of Formula (Ib), or a pharmaceutically acceptable salt thereof as the active pharmaceutical ingredient (API).

In certain embodiments, the invention provides a pharmaceutical composition comprising the compound (3S)-3-(4,5-difluoro-2',6'-dimethylbiphenyl-3-yl)-3-(2-(5-(2-(3-fluoroazetidin-1-yl)ethyl)-4-methyl-2-oxopyridin-1(2H)- yl)-4-methylpentanamido)propanoic acid or a pharmaceutically acceptable salt thereof as the active pharmaceutical ingredient (API).

In certain embodiments, the invention provides a pharmaceutical composition comprising the compound (3S)-3-(2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)biphenyl-3-yl)propanoic acid or a pharmaceutically acceptable salt thereof as the active pharmaceutical ingredient (API).

In certain embodiments, the invention provides a pharmaceutical composition comprising the compound (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic acid or a pharmaceutically acceptable salt thereof as the active pharmaceutical ingredient (API).

In certain embodiments, the invention provides a pharmaceutical composition comprising the compound (3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic acid or a pharmaceutically acceptable salt thereof as the active pharmaceutical ingredient (API).

In certain embodiments, the invention provides a pharmaceutical composition comprising the compound (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid or a pharmaceutically acceptable salt thereof as the active pharmaceutical ingredient (API).

In certain embodiments, the invention provides a pharmaceutical composition comprising the compound (3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid or a pharmaceutically acceptable salt thereof as the active pharmaceutical ingredient (API).

In certain embodiments, the invention provides a pharmaceutical composition comprising the compound (3S)-3-(2-(5-(2-(dimethylamino)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoic acid or a pharmaceutically acceptable salt thereof as the active pharmaceutical ingredient (API).

In certain embodiments, the invention provides a pharmaceutical composition comprising the compound (3S)-3-(4,4'-difluoro-2',5,6'-trimethyl-[1,1'-biphenyl]-3-yl)-3-(2-(3-(difluoromethyl)-5-(2-(dimethylamino)ethyl)-2-oxopyridin-1(2H)-yl)-4-methylpentanamido)propanoic acid or a pharmaceutically acceptable salt thereof as the active pharmaceutical ingredient (API).

In certain embodiments, the invention provides a pharmaceutical composition comprising the compound (3S)-3-(2-(5-(2-(dimethylamino)ethyl)-4-methyl-2-oxopyridin-1(2H)-yl)-5-methylhexanamido)-3-(4-fluoro-2',5,6'-trimethylbiphenyl-3-yl)propanoic acid or a pharmaceutically acceptable salt thereof as the active pharmaceutical ingredient (API).

In certain embodiments, the invention provides a pharmaceutical composition comprising the compound (3S)-3-(4-fluoro-2',5,6'-trimethyl-[1,1'-biphenyl]-3-yl)-3-(2-(3-fluoro-5-(2-(3-fluoroazetidin-1-yl)ethyl)-2-oxopyridin-1(2H)-yl)-4-methylpentanamido)propanoic acid or a pharmaceutically acceptable salt thereof as the active pharmaceutical ingredient (API).

In certain embodiments, the invention provides a pharmaceutical composition comprising the compound (3S)-3-(4-fluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic acid or a pharmaceutically acceptable salt thereof as the active pharmaceutical ingredient (API).

In certain embodiments, the invention provides a pharmaceutical composition comprising the compound (S)-3-(4,5-difluoro-2',6'-dimethyl-[1,1'-biphenyl]-3-yl)-3-((S)-2-(5-(2-(3-fluoroazetidin-1-yl)ethyl)-4-methyl-2-oxopyridin-1(2H)-yl)-4-methylpentanamido)propanoic acid or a pharmaceutically acceptable salt thereof as the active pharmaceutical ingredient (API).

In certain embodiments, the invention provides a pharmaceutical composition comprising the compound (S)-3-((S)-2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoic acid or a pharmaceutically acceptable salt thereof as the active pharmaceutical ingredient (API).

In certain embodiments, the invention provides a pharmaceutical composition comprising the compound (S)-3-((S)-2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic acid or a pharmaceutically acceptable salt thereof as the active pharmaceutical ingredient (API).

In certain embodiments, the invention provides a pharmaceutical composition comprising the compound (S)-3-((S)-2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic acid or a pharmaceutically acceptable salt thereof as the active pharmaceutical ingredient (API).

In certain embodiments, the invention provides a pharmaceutical composition comprising the compound (S)-3-(4,4'-difluoro-2',5,6'-trimethyl-[1,1'-biphenyl]-3-yl)-3-((S)-2-(5-(2-(dimethylamino)ethyl)-2-oxo-4-(trifluoromethyl)pyridin-1(2H)-yl)-4-methylpentanamido)propanoic acid or a pharmaceutically acceptable salt thereof as the active pharmaceutical ingredient (API).

In certain embodiments, the invention provides a pharmaceutical composition comprising the compound (S)-3-(5-chloro-4-fluoro-2',6'-dimethyl-[1,1'-biphenyl]-3-yl)-3-((S)-2-(5-(2-(3-methoxyazetidin-1-yl)ethyl)-2-oxo-4-(trifluoromethyl)pyridin-1(2H)-yl)-4-methylpentanamido)propanoic acid or a pharmaceutically acceptable salt thereof as the active pharmaceutical ingredient (API).

In certain embodiments, the invention provides a pharmaceutical composition comprising the compound (S)-3-((S)-2-(5-(2-(dimethylamino)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoic acid or a pharmaceutically acceptable salt thereof as the active pharmaceutical ingredient (API).

In certain embodiments, the invention provides a pharmaceutical composition comprising the compound (S)-3-(4,4'-difluoro-2',5,6'-trimethyl-[1,1'-biphenyl]-3-yl)-3-((S)-2-(3-(difluoromethyl)-5-(2-(dimethylamino)ethyl)-2-oxopyridin-1(2H)-yl)-4-methylpentanamido)propanoic acid or a pharmaceutically acceptable salt thereof as the active pharmaceutical ingredient (API).

In certain embodiments, the invention provides a pharmaceutical composition comprising the compound (S)-3-((S)-2-(5-(2-(dimethylamino)ethyl)-4-methyl-2-oxopyridin-1(2H)-yl)-5-methylhexanamido)-3-(4-fluoro-2',5,6'- trimethyl-[1,1'-biphenyl]-3-yl)propanoic acid or a pharmaceutically acceptable salt thereof as the active pharmaceutical ingredient (API).

In certain embodiments, the invention provides a pharmaceutical composition comprising the compound (S)-3-(4-fluoro-2',5,6'-trimethyl-[1,1'-biphenyl]-3-yl)-3-((S)-2-(3-fluoro-5-(2-(3-fluoroazetidin-1-yl)ethyl)-2-oxopyridin-1(2H)-yl)-4-methylpentanamido)propanoic acid or a pharmaceutically acceptable salt thereof as the active pharmaceutical ingredient (API).

In certain embodiments, the invention provides a pharmaceutical composition comprising the compound (S)-3-(4-fluoro-2',5,6'-trimethyl-[1,1'-biphenyl]-3-yl)-3-((S)-2-(3-fluoro-5-(2-((R)-3-fluoropyrrolidin-1-yl)ethyl)-2-oxopyridin-1(2H)-yl)-4-methylpentanamido)propanoic acid or a pharmaceutically acceptable salt thereof as the active pharmaceutical ingredient (API).

In certain embodiments, the invention relates to a pharmaceutical composition comprising a compound selected from the group consisting of:

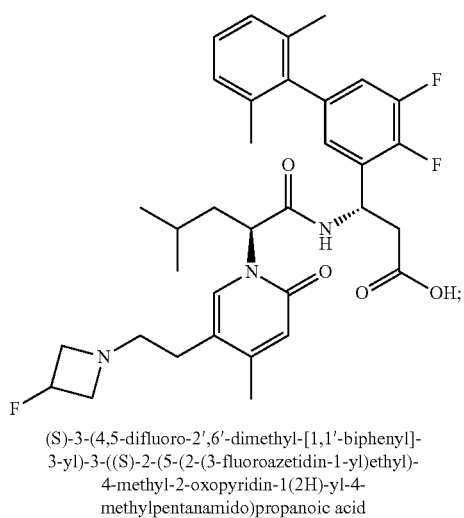

(S)-3-(4,5-difluoro-2',6'-dimethyl-[1,1'-biphenyl]-3-yl)-3-((S)-2-(5-(2-(3-fluoroazetidin-1-yl)ethyl)-4-methyl-2-oxopyridin-1(2H)-yl-4-methylpentanamido)propanoic acid

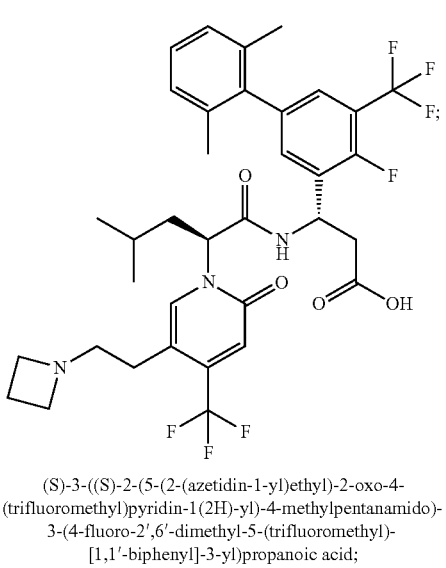

(S)-3-((S)-2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoic acid;

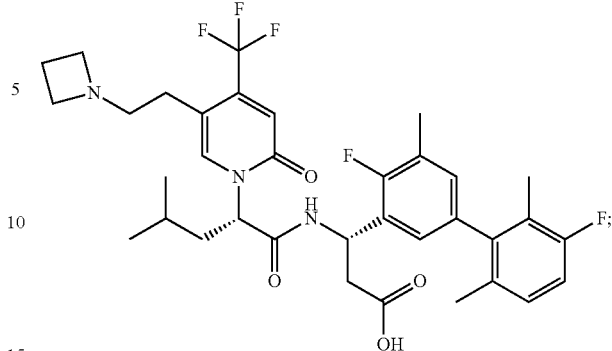

(S)-3-((S)-2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic acid;

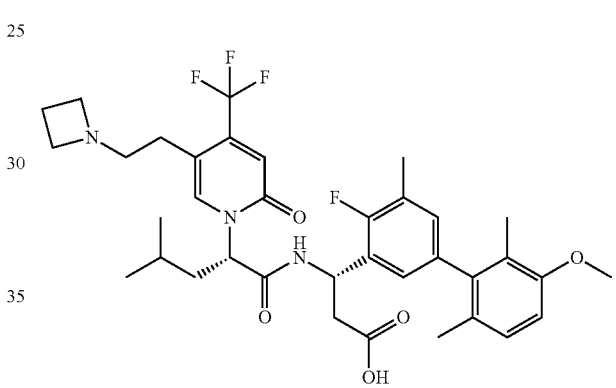

(S)-3-((S)-2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic acid;

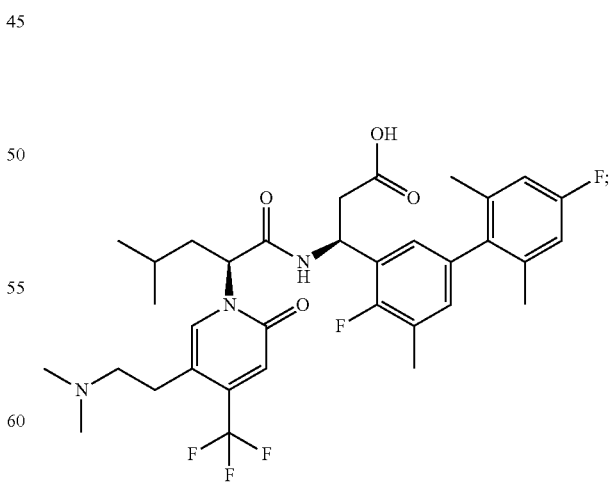

(S)-3-(4,4'-difluoro-2',5,6'-trimethyl-[1,1'-biphenyl]-3-yl)-3-3-((S)-2-(5-(2-(dimethylamino)ethyl)-2-oxo-4-(trifluoromethyl)pyridin-1(2H)-yl)-4-methylpentanamido)propanoic acid;

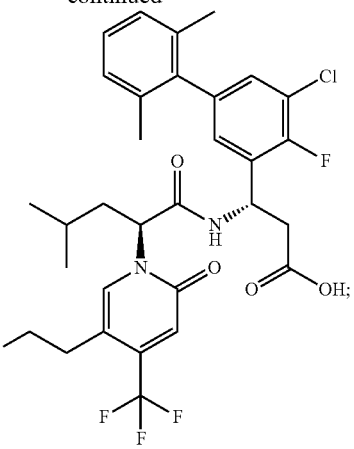

(S)-3-(5-chloro-4-fluoro-2',6'-dimethyl-[1,1'-biphenyl]-
3-yl)-3-((S)-2-(5-(2-(3-methoxyazetidin-1-yl)ethyl)-2-
oxo-4-(trifluoromethyl)pyridin-1(2H)-yl)-
4-methylpentanamido)propanoic acid;

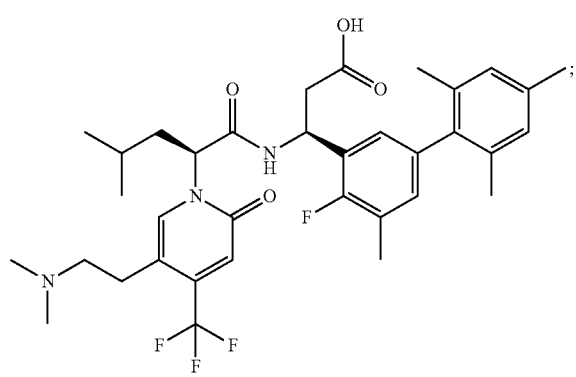

(S)-3-((S-2-(5-(2-(dimethylamino)ethyl)-2-oxo-4-
(trifluoromethyl)pyridin-1(2H)-yl)-4-
methylpentanamido)-3-(4-fluoro-2',4',5,6'-
tetramethyl-[1,1'-biphenyl]-3-yl)propanoic acid;

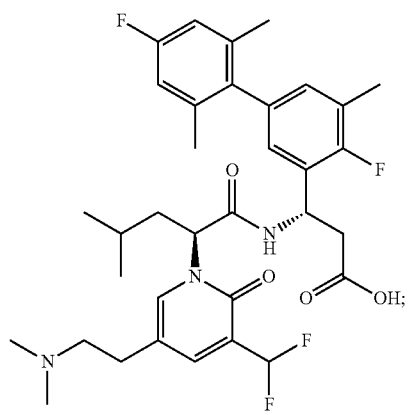

(S)-3-(4,4'-difluoro-2',5,6'-trimethyl-[1,1'-biphenyl]-
3-yl)-3-((S)-2-3-(difluoromethyl)-5-(2-
(dimethylamino)ethyl-2-oxopyridin-
1(2H)-yl)-4-methylpentanamido)propanoic acid;

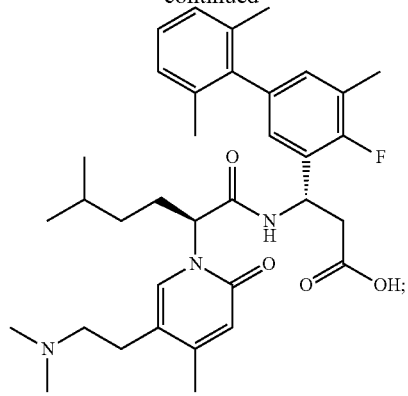

(S)-3-((S-2-(5-(2-(dimethylamino)ethyl)-4-methyl-2-
oxopyridin-1(2H)-yl)-5-
methylhexanamido)-3-(4-fluoro-2',4',5,6'-
trimethyl-[1,1'-biphenyl]-3-yl)propanoic acid;

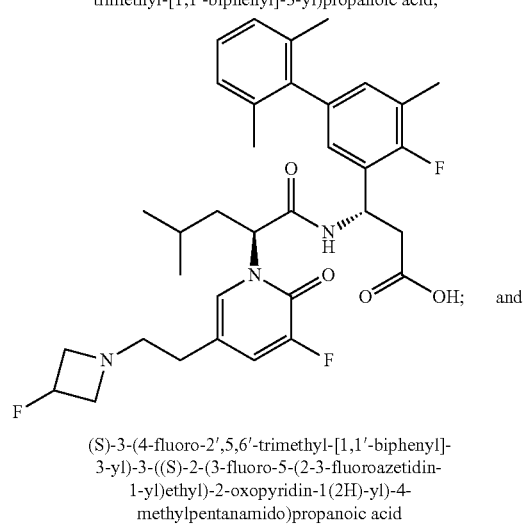

(S)-3-(4-fluoro-2',5,6'-trimethyl-[1,1'-biphenyl]-
3-yl)-3-((S)-2-(3-fluoro-5-(2-3-fluoroazetidin-
1-yl)ethyl)-2-oxopyridin-1(2H)-yl)-4-
methylpentanamido)propanoic acid and

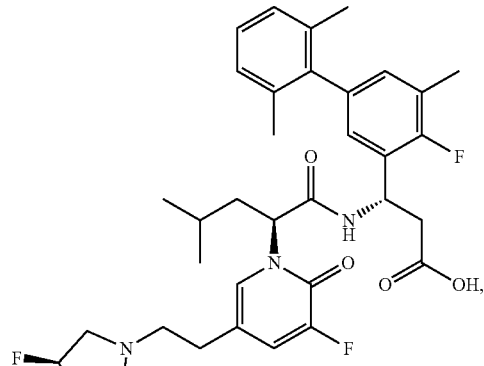

(S)-3-(4-fluoro-2',5,6'-trimethyl-[1,1'-biphenyl]-
3-yl)-3-((S)-2-(3-fluoro-5-(2-((R)-3-fluoropyrrolidin-
1-yl)ethyl)-2-oxopyridin-1(2H)-yl)-4-
methylpentanamido)propanoic acid or a pharmaceutically acceptable salt thereof.

Pharmaceutically acceptable compositions comprising the compound of Formula (I) can be prepared by various procedures. For example, the compounds of Formula (I) can be formulated with suitable excipients, diluents, or carriers, and formed into tablets, or capsules, and other suitable dosage forms.

Pharmaceutical compositions can be provided in unit dose forms containing a predetermined amount of API comprising a compound of Formula (I) per unit dose. Such a unit may contain, a desired amount of a compound of the Formula (I) or pharmaceutically acceptable salt thereof, depending on the condition being treated, the route of administration and the age, weight and condition of the patient. Such unit doses may therefore be administered at a desired dose interval. The concentration of active compound in the drug composition will depend on various applicable parameters and considerations such as the absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted overtime according to the individual need and the professional judgment of the person administering or supervising the administration of the compositions, and that the concentration ranges set forth herein are exemplary only and are not intended to limit the scope or practice of the claimed composition. The active ingredient can be administered at once, or can be divided into a number of smaller doses to be administered at varying intervals of time.

In certain embodiments, the mode of administration of the active compound is oral. Oral compositions will generally include an inert diluent or an edible carrier. They can be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition. Pharmaceutical compositions comprising a compound of Formula (I) formulated for oral delivery can be prepared in a unit dosage form, such as a capsule at a desired dosage strength of the compound of Formula (I). For oral administration in liquid form, the oral drug components can be combined with any oral, non-toxic, pharmaceutically acceptable inert carrier such as ethanol, glycerol, water and the like. For oral administration in the form of a tablet or capsule, the compound of Formula (I) can be combined with an oral, non-toxic, pharmaceutically acceptable, inert carrier. Other examples of excipients, diluents, and carriers that are suitable for such formulations include the following: fillers and extenders such as starch, and sugars; and binding agents such as cellulose derivatives. Moreover, when desired or necessary, suitable binders, lubricants, disintegrating agents and coloring agents can also be incorporated into the mixture. Suitable binders include starch, natural sugars, natural and synthetic gums, and the like. Lubricants and/or glidants can be used in these dosage forms.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, unit dosage forms can contain various other materials that modify the physical form of the dosage unit, for example, coatings of sugar, or other enteric agents.

The compound can be administered as a component of an elixir, suspension, syrup, wafer, or the like. A syrup can contain, in addition to the active compound(s), sucrose or sweetener as a sweetening agent and certain preservatives, dyes and colorings and flavors.

The compounds can be formulated as solutions appropriate for parenteral administration, for example, by intramuscular, subcutaneous or intravenous routes. For example, a compound of Formula (I) can be dissolved in a suitable buffer. A pharmaceutical composition comprising a desired concentration of a compound of Formula (I) can be formulated as an injectable drug solution in (useful, e.g., in preclinical animal studies).

Exemplary Methods Compounds inhibiting $\alpha_4\beta_7$ are useful for development of medicaments to treat ulcerative colitis and Crohn's disease patients. Ulcerative colitis (UC) and Crohn's disease (CD) patients suffer from autoimmune inflammation in the digestive tract and for many of these patients, the $CD4^+$ memory T cells drive the progression and flare ups of the disease via their ability to secrete pro-inflammatory, effector cytokines within the gut, impacting the surrounding immune cells and tissue. The progression and flare ups of these disease conditions are believed to include extravasation of T cells leaving the blood to enter tissue in the gut leading to inflammatory conditions found in UC and CD via integrin related mechanisms. The inhibition of $\alpha_4\beta_7$ can disrupt this mechanism, thereby preventing the localization of T cells to the tissue and effectively treating and preventing disease such as UC and CD. T cell homing to the gut requires surface expression of integrin $\alpha_4\beta_7$ and chemokine receptor CCR9. While CCR9 is utilized by the cell to migrate against the gradient of CCL25 expressed in the small intestine, $\alpha_4\beta_7$ is a tethering molecule which binds the ligand, mucosal addressin cell adhesion molecule 1 (MAdCAM-1). Integrin $\alpha_4\beta_7$ binds MAdCAM-1 with high affinity facilitating rolling and firm adhesion of cells followed by extravasation into tissue.

Pharmaceutical compositions can comprise compounds that inhibit the $\alpha_4\beta_7$ integrin on inflammatory cells that enables adhesion of these cells to mucosal addressin cell adhesion molecule-1 (MAdCAM-1), and inhibiting or preventing these cells from entering the gut lamina propria and gut associated lymphoid tissue.

Compounds of Formula (I) were evaluated using a fluorescent polarization (FP) assay. FP assays are used to evaluate potency of compounds on purified protein. The FP assays consists of measuring purified integrin αβ heterodimer ecto domains or headpiece binding to surrogate or truncated ligands. Results of the FP assay for exemplary compounds of Formula (I) are provided herein.

Compounds of Formula (I) were further evaluated using a Ligand binding assay (LBA) to examine compound potency of free ligand binding to receptors expressed on cells. The MAdCAM ligand binding assay uses flow cytometry to measure the binding of fluorescently-labeled MAd-CAM-1-Fc to RPMI 8866 cells in the presence of Mn++. This assay assesses the binding of compounds to native full-length receptors on the cell surface. One advantage of the MAdCAM ligand binding assay is its ability to quantify and discriminate the activity of potent compounds that exceed the FP assay's functional sensitivity limit [~10 nM in Mn]. Ligand binding assays (LBA) are used to examine compound potency and selectivity of free ligand binding to receptors expressed on cells.

In some embodiments, compounds of the invention can be selected from one or more of the following numbered embodiments:

1. A compound of Formula (I):

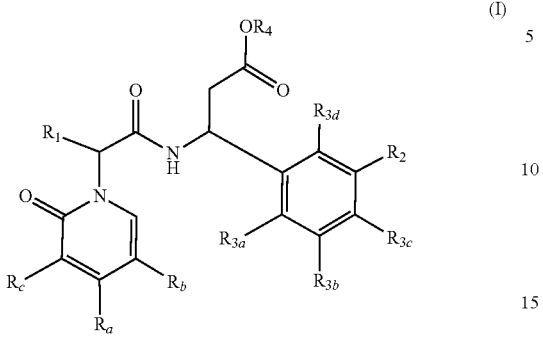

wherein $R_a$, $R_b$, and $R_c$ are independently selected from the group consisting of H, Me, halide, $CF_3$, $C(H)F_2$, $C(F)H_2$, and —$(C_1$-$C_5)$alkylene-N—$(R_x)(R_y)$; provided that at least one of $R_a$, $R_b$, and $R_c$ is —$(C_1$-$C_5)$alkylene-N—$(R_x)(R_y)$;

$R_x$ and $R_y$ are independently selected from the group consisting of H and substituted or unsubstituted $(C_1$-$C_6)$-alkyl; or $R_x$ and $R_y$ taken together with the N to which they are attached form a 4-6 membered ring;

$R_1$ is substituted or unsubstituted $(C_1$-$C_6)$-alkyl, substituted or unsubstituted $(C_1$-$C_4)$-alkylene-$(C_3$-$C_6)$-cycloalkyl, or substituted or unsubstituted $(C_1$-$C_4)$-alkylene- $(C_1$-$C_4)$-alkoxy;

$R_2$ is

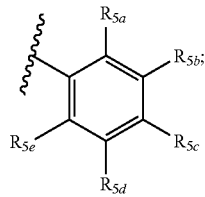

$R_{3a}$ and $R_{3b}$ are independently selected from the group consisting of H, substituted or unsubstituted $(C_1$-$C_5)$-alkyl, substituted or unsubstituted $(C_3$-$C_6)$-cycloalkyl, substituted or unsubstituted 3-6 membered heterocycloalkyl, —OH, —CN, halide, $CF_3$, $C(H)F_2$, $C(F)H_2$, —$(C_1$-$C_4)$-alkoxy, —$OCF_3$, and substituted or unsubstituted $(C_1$-$C_4)$-alkylene-$(C_1$-$C_4)$-alkoxy; provided that $R_{3a}$ and $R_{3b}$ are not both H;

$R_{3c}$, and $R_{3d}$ are H;

$R_4$ is H, or substituted or unsubstituted $(C_1$-$C_4)$-alkyl;

$R_{5a}$, and $R_{5e}$ are independently selected from the group consisting of H, CN, halide, $CF_3$, $C(H)F_2$, $C(F)H_2$, substituted or unsubstituted $(C_3$-$C_6)$-cycloalkyl, substituted or unsubstituted $(C_1$-$C_5)$-alkyl, hydroxyl, and $(C_1$-$C_4)$-alkoxy; and $R_{5b}$, $R_{5c}$, and $R_{5d}$ are independently selected from the group consisting of H, CN, halide, $CF_3$, $C(H)F_2$, $C(F)H_2$, substituted or unsubstituted $(C_1$-$C_5)$-alkyl, substituted or unsubstituted $(C_3$-$C_6)$-cycloalkyl, substituted or unsubstituted 3-6 membered heterocycloalkyl, hydroxyl, and $(C_1$-$C_4)$-alkoxy;

or a pharmaceutically acceptable salt thereof.

2. The compound of embodiment 1, wherein $R_1$ is methyl, ethyl, n-propyl, iso-propyl, n-butyl, iso-butyl, sec-butyl, or t-butyl.

3. The compound of embodiment 2, wherein $R_1$ is iso-butyl.

4. The compound of embodiment 1, wherein $R_1$ is

5. The compound of embodiment 1, wherein $R_1$ is

6. The compound of any one of embodiments 1-5, wherein $R_{3a}$ and $R_{3b}$ are independently selected from the group consisting of halide, substituted or unsubstituted $(C_1$-$C_5)$-alkyl, substituted or unsubstituted $(C_3$-$C_6)$-cycloalkyl, substituted or unsubstituted $(C_1$-$C_4)$-alkoxy, $CF_3$, $C(H)F_2$, and $C(F)H_2$.

7. The compound of embodiment 6, wherein $R_{3a}$ and $R_{3b}$ are independently selected from the group consisting of halide and $(C_1$-$C_4)$-alkyl.

8. The compound of embodiment 7, wherein halide is Cl or F.

9. The compound of embodiment 7 or 8, wherein $(C_1$-$C_4)$-alkyl is methyl.

10. The compound of any one of embodiments 1-7, wherein $R_{3a}$ is methyl; and $R_{3b}$ is F.

11. The compound of any one of embodiments 1-7, wherein $R_{3a}$ is F; and $R_{3b}$ is methyl.

12. The compound of any one of embodiments 1-11, wherein $R_4$ is H.

13. The compound of any one of embodiments 1-11, wherein $R_4$ is methyl, ethyl, n-propyl, iso-propyl.

14. The compound of any one of embodiments 1-13, wherein $R_{5a}$ and $R_{5e}$ are independently selected from the group consisting of halide, $CF_3$, $C(H)F_2$, $C(F)H_2$, and substituted or unsubstituted $(C_1$-$C_4)$-alkyl.

15. The compound of any one of embodiments 1-14, wherein $R_{5a}$ is halide.

16. The compound of embodiment 15, wherein $R_{5a}$ is F or Cl.

17. The compound of any one of embodiments 1-14, wherein $R_{5a}$ is $CF_3$.

18. The compound of any one of embodiments 1-14, wherein $R_{5a}$ is $C(H)F_2$.

19. The compound of any one of embodiments 1-14, wherein $R_{5a}$ is $C(F)H_2$.

20. The compound of any one of embodiments 1-14, wherein $R_{5a}$ is unsubstituted $(C_1$-$C_4)$-alkyl.

21. The compound of embodiment 20, wherein $R_{5a}$ is methyl.

22. The compound of any one of embodiments 1-14, wherein $R_{5a}$ is substituted $(C_1$-$C_5)$-alkyl, substituted with at least one halide.

23. The compound of any one of embodiments 1-14, wherein $R_{5a}$ is unsubstituted $(C_1$-$C_4)$-alkoxy.

24. The compound of embodiment 23, wherein $R_{5a}$ is OMe.

25. The compound of any one of embodiments 1-24, wherein $R_{5e}$ is halide.

26. The compound of embodiment 25, wherein $R_{5e}$ is F or Cl.

27. The compound of any one of embodiments 1-24, wherein $R_{5e}$ is $CF_3$.
28. The compound of any one of embodiments 1-24, wherein $R_{5e}$ is $C(H)F_2$.
29. The compound of any one of embodiments 1-24, wherein $R_{5e}$ is $C(F)H_2$.
30. The compound of any one of embodiments 1-24, wherein $R_{5e}$ is unsubstituted $(C_1-C_4)$-alkyl.
31. The compound of embodiment 30, wherein $R_{5e}$ is methyl.
32. The compound of any one of embodiments 1-24, wherein $R_{5e}$ is substituted $(C_1-C_5)$-alkyl, substituted with at least one halide.
33. The compound of any one of embodiments 1-24, wherein $R_{5e}$ is unsubstituted $(C_1-C_4)$-alkoxy.
34. The compound of embodiment 33, wherein $R_{5e}$ is OMe.
35. The compound of any one of embodiments 1-34, wherein $R_{5b}$, $R_{5c}$, and $R_{5d}$ are independently selected from the group consisting of H, halide, $CF_3$, $C(H)F_2$, $C(F)H_2$, substituted or unsubstituted $(C_1-C_5)$-alkyl, and substituted or unsubstituted $(C_1-C_4)$-alkoxy.
36. The compound of any one of embodiments 1-35, wherein $R_{5b}$ is H.
37. The compound of any one of embodiments 1-35, wherein $R_{5b}$ is halide.
38. The compound of embodiment 37, wherein $R_{5b}$ is Cl or F.
39. The compound of any one of embodiments 1-35, wherein $R_{5b}$ is $CF_3$.
40. The compound of any one of embodiments 1-35, wherein $R_{5b}$ is $C(H)F_2$.
41. The compound of any one of embodiments 1-35, wherein $R_{5b}$ is $C(F)H_2$.
42. The compound of any one of embodiments 1-35, wherein $R_{5b}$ is unsubstituted $(C_1-C_4)$-alkyl.
43. The compound of embodiment 37, wherein $R_{5b}$ is methyl.
44. The compound of any one of embodiments 1-35, wherein $R_{5b}$ is unsubstituted $(C_1-C_4)$-alkoxy.
45. The compound of embodiment 44, wherein $R_{5b}$ is OMe.
46. The compound of any one of embodiments 1-35, wherein $R_{5b}$ is unsubstituted $(C_3-C_6)$-cycloalkyl.
47. The compound of embodiment 46, wherein $R_{5b}$ is cyclopropyl.
48. The compound of any one of embodiments 1-47, wherein $R_{5c}$ is H.
49. The compound of any one of embodiments 1-47, wherein $R_{5c}$ is halide.
50. The compound of embodiment 49, wherein $R_{5c}$ is Cl or F.
51. The compound of any one of embodiments 1-47, wherein $R_{5c}$ is $CF_3$.
52. The compound of any one of embodiments 1-47, wherein $R_{5c}$ is $C(H)F_2$.
53. The compound of any one of embodiments 1-47, wherein $R_{5c}$ is $C(F)H_2$.
54. The compound of any one of embodiments 1-47, wherein $R_{5c}$ is unsubstituted $(C_1-C_4)$-alkyl.
55. The compound of embodiment 54, wherein $R_{5c}$ is methyl.
56. The compound of any one of embodiments 1-47, wherein $R_{5c}$ is unsubstituted $(C_1-C_4)$-alkoxy.
57. The compound of embodiment 56, wherein $R_{5c}$ is OMe.
58. The compound of any one of embodiments 1-47, wherein $R_{5c}$ is unsubstituted $(C_3-C_6)$-cycloalkyl.
59. The compound of embodiment 58, wherein $R_{5b}$ is cyclopropyl.
60. The compound of any one of embodiments 1-59, wherein $R_5$ is H.
61. The compound of any one of embodiments 1-59, wherein $R_{5d}$ is halide.
62. The compound of embodiment 61, wherein $R_{5d}$ is Cl or F.
63. The compound of any one of embodiments 1-59, wherein $R_{5d}$ is $CF_3$.
64. The compound of any one of embodiments 1-59, wherein $R_{5d}$ is $C(H)F_2$.
65. The compound of any one of embodiments 1-59, wherein $R_{5d}$ is $C(F)H_2$.
66. The compound of any one of embodiments 1-59, wherein $R_{5d}$ is unsubstituted $(C_1-C_4)$-alkyl.
67. The compound of embodiment 66, wherein $R_{5d}$ is methyl.
68. The compound of any one of embodiments 1-67, wherein $R_{5d}$ is unsubstituted $(C_1-C_4)$-alkoxy.
69. The compound of embodiment 68, wherein $R_{5d}$ is OMe.
70. The compound of any one of embodiments 1-67, wherein $R_{5d}$ is unsubstituted $(C_3-C_6)$-cycloalkyl.
71. The compound of embodiment 70, wherein $R_{5d}$ is cyclopropyl.
72. The compound of any one of embodiments 1-35, wherein $R_{5b}$, and $R_{5d}$ are each H.
73. The compound of any one of embodiments 1-72, wherein $R_a$ is H.
74. The compound of any one of embodiments 1-72, wherein $R_a$ is Me.
75. The compound of any one of embodiments 1-72, wherein $R_a$ is halide.
76. The compound of embodiment 75, wherein $R_a$ is Cl or F.
77. The compound of any one of embodiments 1-72, wherein $R_a$ is $CF_3$.
78. The compound of any one of embodiments 1-72, wherein $R_a$ is $C(H)F_2$.
79. The compound of any one of embodiments 1-72, wherein $R_a$ is $C(F)H_2$.
80. The compound of any one of embodiments 1-72, wherein $R_a$ is unsubstituted —$(C_1-C_3)$alkylene-N—$(R_x)(R_y)$.
81. The compound of any one of embodiments 1-72, wherein $R_a$ is substituted —$(C_1-C_3)$alkylene-N—$(R_x)(R_y)$, substituted with F or OMe.
82. The compound of any one of embodiments 1-81, wherein $R_b$ is H.
83. The compound of any one of embodiments 1-81, wherein $R_b$ is Me.
84. The compound of any one of embodiments 1-81, wherein $R_b$ is halide.
85. The compound of embodiment 84, wherein $R_b$ is Cl or F.
86. The compound of any one of embodiments 1-81, wherein $R_b$ is $CF_3$.
87. The compound of any one of embodiments 1-81, wherein $R_b$ is $C(H)F_2$.
88. The compound of any one of embodiments 1-81, wherein $R_b$ is $C(F)H_2$.
89. The compound of any one of embodiments 1-81, wherein $R_b$ is unsubstituted —$(C_1-C_3)$alkylene-N—$(R_x)(R_y)$.

90. The compound of any one of embodiments 1-81, wherein $R_b$ is substituted —$(C_1$-$C_3)$alkylene-N—$(R_x)$$(R_y)$, substituted with F or OMe.

91. The compound of any one of embodiments 1-90, wherein $R_c$ is H.

92. The compound of any one of embodiments 1-90, wherein $R_c$ is Me.

93. The compound of any one of embodiments 1-90, wherein $R_c$ is halide.

94. The compound of embodiment 93, wherein $R_c$ is Cl or F.

95. The compound of any one of embodiments 1-90, wherein $R_c$ is $CF_3$.

96. The compound of any one of embodiments 1-90, wherein $R_c$ is $C(H)F_2$.

97. The compound of any one of embodiments 1-90, wherein $R_c$ is $C(F)H_2$.

98. The compound of any one of embodiments 1-90, wherein $R_c$ is unsubstituted —$(C_1$-$C_3)$alkylene-N—$(R_x)$$(R_y)$.

99. The compound of any one of embodiments 1-90, wherein $R_c$ is substituted —$(C_1$-$C_3)$alkylene-N—$(R_x)$$(R_y)$, substituted with F or OMe.

100. The compound of any one of embodiments 1-99, wherein $R_x$ is H.

101. The compound of any one of embodiments 1-99, wherein $R_x$ is unsubstituted $(C_1$-$C_6)$-alkyl.

102. The compound of any one of embodiments 1-100, wherein $R_y$ is H.

103. The compound of any one of embodiments 1-100, wherein $R_y$ is unsubstituted $(C_1$-$C_6)$-alkyl.

104. The compound of any one of embodiments 1-72, 80-81, 89-90, and 98-99, wherein $R_x$ and $R_y$ taken together with the N to which they are attached form a unsubstituted 4-6 membered ring.

105. The compound of any one of embodiments 1-72, 80-81, 89-90, and 98-99, wherein $R_x$ and $R_y$ taken together with the N to which they are attached form a substituted 4-6 membered ring, substituted with at least one halide, substituted or unsubstituted $(C_1$-$C_4)$ alkyl, or OMe.

106. The compound of embodiment 104 or 105, wherein the 4-6 membered ring is a 3-6 membered heterocycloalkyl.

107. The compound of embodiment 104 or 105, wherein the 4-6 membered ring is a 4-5 membered heterocycloalkyl.

108. The compound of embodiment 1, wherein the compound is a compound of Formula (Ia):

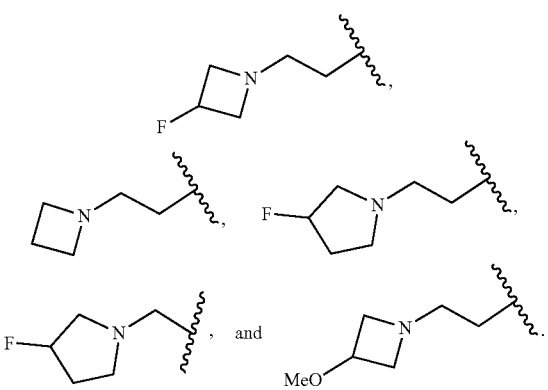

(Ia)

wherein
at least one of $R_a$, $R_b$, and $R_c$ is —$(C_1$-$C_3)$alkylene-N$(R_x)$$(R_y)$;
$R_x$ and $R_y$ are independently selected from the group consisting of H and methyl; or
$R_x$ and $R_y$ taken together with the N to which they are attached form a substituted or unsubstituted 4-6 membered ring; and
$R_{3a}$, and $R_{3b}$ are each independently selected from the group consisting of methyl and F.

109. The compound of embodiment 108, wherein $R_{5a}$, and $R_{5e}$ are independently unsubstituted $(C_1$-$C_4)$ alkyl.

110. The compound of embodiment 108 or 109, wherein $R_b$ is unsubstituted —$(C_1$-$C_3)$alkylene-N$(R_x)$$(R_y)$.

111. The compound of embodiment 1 or 108, wherein $R_a$ is selected from the group consisting of H, $C(H)F_2$, $CF_3$, and Me.

112. The compound of embodiment 1 or 108, wherein $R_b$ is selected from the group consisting of

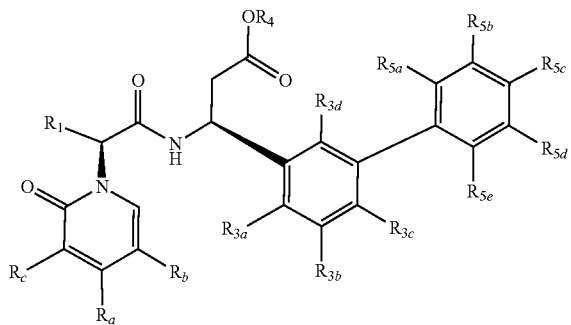

113. The compound of embodiment 1 or 108, wherein $R_b$ is selected from the group consisting of

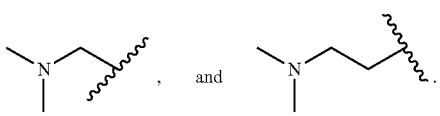

114. The compound of embodiment 1 or 108, wherein $R_c$ is H or F.

115. The compound of any one of embodiments 1 and 108-114, wherein $R_1$ is selected from the group consisting of

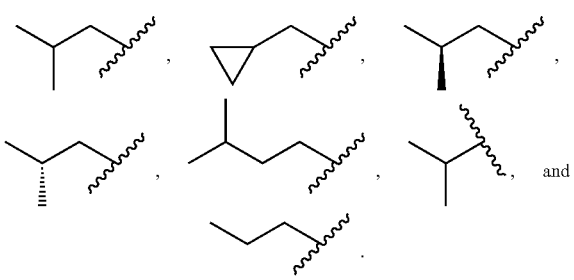

116. The compound of any one of embodiments 108-115, wherein $R_{5a}$ is CF.

117. The compound of any one of embodiments 108-115, wherein $R_{5a}$ is $C(H)F_2$.
118. The compound of any one of embodiments 108-115, wherein $R_{5a}$ is $C(F)H_2$.
119. The compound of any one of embodiments 108-115, wherein $R_{5a}$ is methyl.
120. The compound of any one of embodiments 108-115, wherein $R_{5a}$ is OMe.
121. The compound of any one of embodiments 108-115, wherein $R_{5a}$ is F or Cl.
122. The compound of any one of embodiments 108-121, wherein $R_{5b}$ is H.
123. The compound of any one of embodiments 108-121, wherein $R_{5b}$ is C.
124. The compound of any one of embodiments 108-121, wherein $R_{5b}$ is $C(H)F_2$.
125. The compound of any one of embodiments 108-121, wherein $R_{5b}$ is $C(F)H_2$.
126. The compound of any one of embodiments 108-121, wherein $R_{5b}$ is methyl.
127. The compound of any one of embodiments 108-121, wherein $R_{5b}$ is OMe.
128. The compound of any one of embodiments 108-121, wherein $R_{5b}$ is F or Cl.
129. The compound of any one of embodiments 108-128, wherein $R_{5b}$ is H.
130. The compound of any one of embodiments 108-128, wherein $R_{5c}$ is C.
131. The compound of any one of embodiments 108-128, wherein $R_{5c}$ is $C(H)F_2$.
132. The compound of any one of embodiments 108-128, wherein $R_{5c}$ is $C(F)H_2$.
133. The compound of any one of embodiments 108-128, wherein $R_{5c}$ is methyl.
134. The compound of any one of embodiments 108-128, wherein $R_{5c}$ is OMe.
135. The compound of any one of embodiments 108-128, wherein $R_{5c}$ is F or Cl.
136. The compound of any one of embodiments 108-135, wherein $R_{5d}$ is H.
137. The compound of any one of embodiments 108-135, wherein $R_{5d}$ is $CF_3$.
138. The compound of any one of embodiments 108-135, wherein $R_{5d}$ is $C(H)F_2$.
139. The compound of any one of embodiments 108-135, wherein $R_{5d}$ is $C(F)H_2$.
140. The compound of any one of embodiments 108-135, wherein $R_{5d}$ is methyl.
141. The compound of any one of embodiments 108-135, wherein $R_{5d}$ is OMe.
142. The compound of any one of embodiments 108-135, wherein $R_{5d}$ is F or Cl.
143. The compound of any one of embodiments 108-142, wherein $R_{5d}$ is $CF_3$.
144. The compound of any one of embodiments 108-142, wherein $R_{5e}$ is $C(H)F_2$.
145. The compound of any one of embodiments 108-142, wherein $R_{5e}$ is $C(F)H_2$.
146. The compound of any one of embodiments 108-142, wherein $R_{5e}$ is methyl.
147. The compound of any one of embodiments 108-142, wherein $R_{5e}$ is OMe.
148. The compound of any one of embodiments 108-142, wherein $R_{5e}$ is F or Cl.
149. The compound of any one of embodiments 1, and 108-121, wherein at least one of $R_{5b}$, $R_{5c}$, and $R_{5d}$ is H.
150. The compound of any one of embodiments 1, and 108-121, wherein at least two of $R_{5b}$, $R_{5c}$, and $R_{5d}$ is H.
151. The compound of any one of embodiments 1, and 108-121, wherein $R_{5b}$, $R_{5c}$, and $R_{5d}$ are H.
152. The compound of any one of embodiments 1, and 108-151, wherein $R_{3a}$ is H.
153. The compound of any one of embodiments 1, and 108-151, wherein $R_{3a}$ is methyl.
154. The compound of any one of embodiments 1, and 108-151, wherein $R_{3a}$ is halide.
155. The compound of any one of embodiments 1, and 108-151, wherein $R_{3a}$ is $CF_3$.
156. The compound of any one of embodiments 1, and 108-151, wherein $R_{3a}$ is $C(H)F_2$.
157. The compound of any one of embodiments 1, and 108-151, wherein $R_{3a}$ is $C(F)H_2$.
158. The compound of any one of embodiments 1, and 108-151, wherein $R_{3a}$ is OMe.
159. The compound of any one of embodiments 1, and 108-158, wherein $R_{3b}$ is H.
160. The compound of any one of embodiments 1, and 108-158, wherein $R_{3b}$ is methyl.
161. The compound of any one of embodiments 1, and 108-158, wherein $R_{3b}$ is halide.
162. The compound of any one of embodiments 1, and 108-158, wherein $R_{3b}$ is $CF_3$.
163. The compound of any one of embodiments 1, and 108-158, wherein $R_{3b}$ is $C(H)F_2$.
164. The compound of any one of embodiments 1, and 108-158, wherein $R_{3b}$ is $C(F)H_2$.
165. The compound of any one of embodiments 1, and 108-158, wherein $R_{3b}$ is OMe.
166. The compound of any one of embodiments 1, and 108-158, wherein $R_{3b}$ is $OCF_3$.
167. The compound of any one of embodiments 1, and 108-158, wherein $R_{3b}$ is cyclopropyl.
168. The compound of any one of embodiments 108-151, wherein $R_{3a}$ is methyl and $R_{3b}$ is F.
169. The compound of any one of embodiments 108-151, wherein $R_{3a}$ is F and $R_{3b}$ is methyl.
170. The compound of embodiment 1, wherein the compound is selected from any one of the compounds of FIG. 1, or an enantiomer thereof.
171. The compound of embodiment 1, wherein the compound is a compound of Formula (Ic)

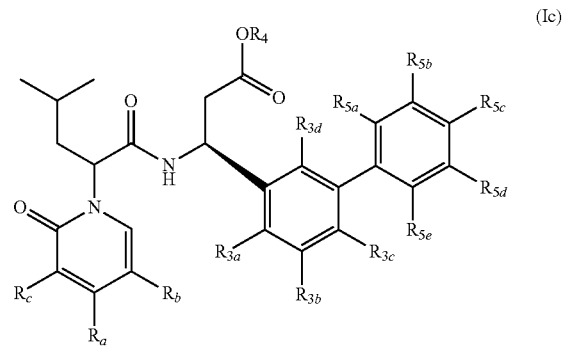

(Ic)

or a pharmaceutically acceptable salt thereof, wherein $R_a$, $R_b$, and $R_c$ are independently selected from the group consisting of H, substituted or unsubstituted $(C_1$-$C_5)$-alkyl, halide, $CF_3$, $C(H)F_2$, $C(F)H_2$, substituted or unsubstituted $(C_1$-$C_4)$-alkoxy, $-OCF_3$, and substituted or unsubstituted —(C₁-C₅)alkylene-N—(R$_x$)(R$_y$); provided that one of R$_a$, R$_b$, and R$_c$ is —(C₁-C₅)alkylene-N—(R$_x$)(R$_y$);

R$_x$ and R$_y$ are independently selected from the group consisting of H, substituted or unsubstituted (C₁-C₆)-alkyl, or substituted or unsubstituted (C₁-C₄)-alkylene-(C₁-C₄)-alkoxy; or R$_x$ and R$_y$ taken together with the N to which they are attached form a substituted or unsubstituted 4-6 membered heterocyclyl ring;

R$_{3a}$ and R$_{3b}$ are independently selected from the group consisting of H, substituted or unsubstituted (C₁-C₅)-alkyl, substituted or unsubstituted (C₃-C₆)-cycloalkyl, substituted or unsubstituted 3-6 membered heterocycloalkyl, —OH, —CN, halide, CF₃, C(H)F₂, C(F)H₂, —(C₁-C₄)-alkoxy, —OCF₃, and substituted or unsubstituted (C₁-C₄)-alkylene-(C₁-C₄)-alkoxy; provided that R$_{3a}$ and R$_{3b}$ are not both H;

R$_{3c}$ is selected from the group consisting of H, substituted or unsubstituted (C₁-C₅)-alkyl, substituted or unsubstituted (C₃-C₆)-cycloalkyl, substituted or unsubstituted 3-6 membered heterocycloalkyl, hydroxyl, halide, CF₃, C(H)F₂, C(F)H₂, —(C₁-C₄)-alkoxy, —OCF₃ —CN, and substituted or unsubstituted (C₁-C₄)-alkylene-(C₁-C₄)-alkoxy;

R$_{3d}$ is selected from the group consisting of H, substituted or unsubstituted (C₁-C₅)-alkyl, hydroxyl, halide, and —(C₁-C₄)-alkoxy;

R$_{5a}$, and R$_{5e}$ are independently selected from the group consisting of H, CN, halide, CF₃, C(H)F₂, C(F)H₂, substituted or unsubstituted (C₁-C₅)-alkyl, hydroxyl, and (C₁-C₄)-alkoxy; and R$_{5b}$, R$_{5c}$, and R$_{5d}$ are independently selected from the group consisting of H, CN, halide, CF₃, C(H)F₂, C(F)H₂, substituted or unsubstituted (C₁-C₅)-alkyl, hydroxyl, and (C₁-C₄)-alkoxy; or a pharmaceutically acceptable salt thereof.

172. A compound selected from the group consisting of:
(3S)-3-(4,5-difluoro-2',6'-dimethylbiphenyl-3-yl)-3-(2-(5-(2-(3-fluoroazetidin-1-yl)ethyl)-4-methyl-2-oxopyridin-1(2H)-yl)-4-methylpentanamido)propanoic acid;
(3S)-3-(2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)biphenyl-3-yl)propanoic acid;
(3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',5',6'-trimethyl-[1,1'-biphenyl]-3-yl)propanoic acid;
(3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5',6'-trimethyl-[1,1'-biphenyl]-3-yl)propanoic acid;
(3S)-3-(4,4'-difluoro-2',5',6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid;
(3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid;
(3S)-3-(2-(5-(2-(dimethylamino)ethyl)-2-oxo-4-(trifluoromethyl)pyridin-1(2H)-yl)-4-methylpentanamido)-3-(4-fluoro-2',4',5',6'-tetramethylbiphenyl-3-yl)propanoic acid;
(3S)-3-(4,4'-difluoro-2',5',6'-trimethyl-[1,1'-biphenyl]-3-yl)-3-(2-(3-(difluoromethyl)-5-(2-(dimethylamino)ethyl)-2-oxopyridin-1(2H)-yl)-4-methylpentanamido)propanoic acid;
(3S)-3-(2-(5-(2-(dimethylamino)ethyl)-4-methyl-2-oxopyridin-1(2H)-yl)-5-methylhexanamido)-3-(4-fluoro-2',5',6'-trimethylbiphenyl-3-yl)propanoic acid;
(3S)-3-(4-fluoro-2',5',6'-trimethyl-[1,1'-biphenyl]-3-yl)-3-(2-(3-fluoro-5-(2-(3-fluoroazetidin-1-yl)ethyl)-2-oxopyridin-1(2H)-yl)-4-methylpentanamido)propanoic acid;

(3S)-3-(4-fluoro-2',5',6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic acid; and
(3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid,
or a pharmaceutically acceptable salt thereof.

173. The compound of embodiment 1, wherein the compound is the compound:

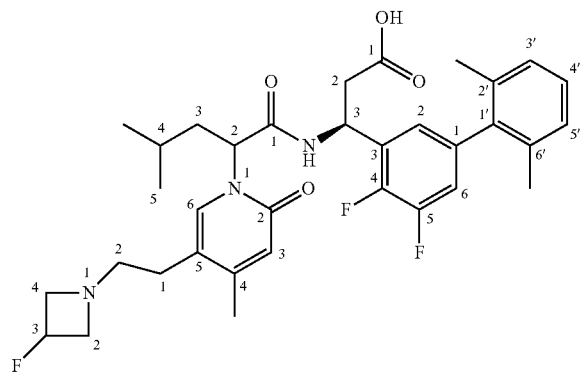 [SMILES: Cc1cc(=O)n(C(CC(C)C)C(=O)N[C@@H](CC(=O)O)c2cc(-c3c(C)cccc3C)cc(F)c2F)cc1CCN1CC(F)C1]

or a pharmaceutically acceptable salt thereof.

174. The compound of embodiment 1, wherein the compound is the compound:

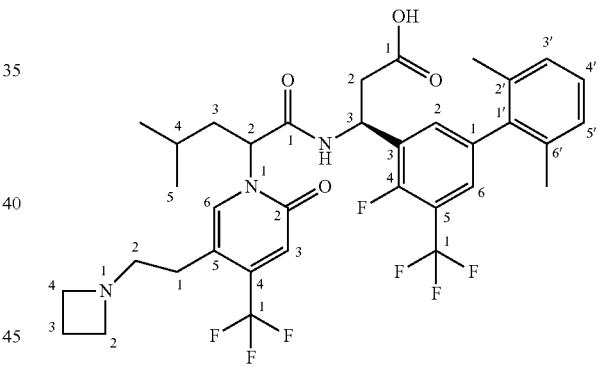

or a pharmaceutically acceptable salt thereof.

175. The compound of embodiment 1, wherein the compound is the compound:

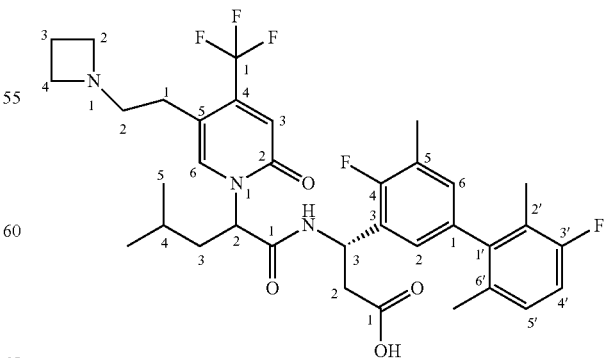

or a pharmaceutically acceptable salt thereof.

176. The compound of embodiment 1, wherein the compound is the compound:

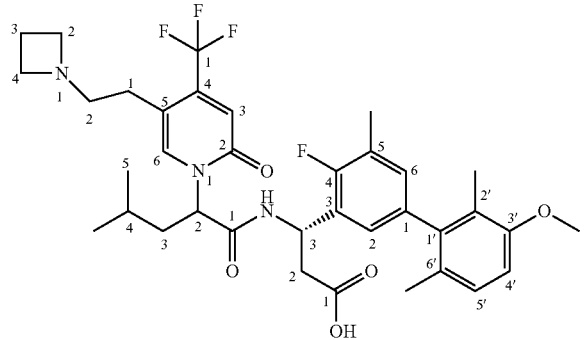 [SMILES: COc1ccc(C)c(-c2cc(C)c(F)c([C@H](CC(=O)O)NC(=O)C(CC(C)C)n3cc(CCN4CCC4)c(C(F)(F)F)cc3=O)c2)c1C]

or a pharmaceutically acceptable salt thereof.

177. The compound of embodiment 1, wherein the compound is the compound:

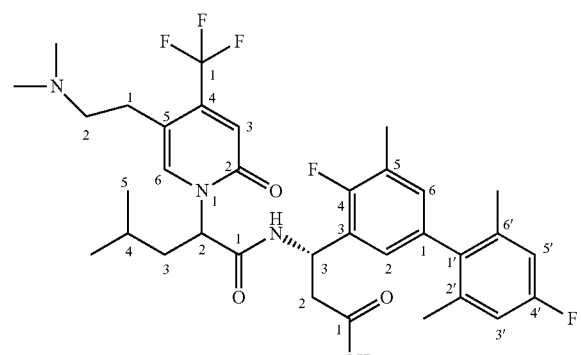

or a pharmaceutically acceptable salt thereof.

178. The compound of embodiment 1, wherein the compound is the compound:

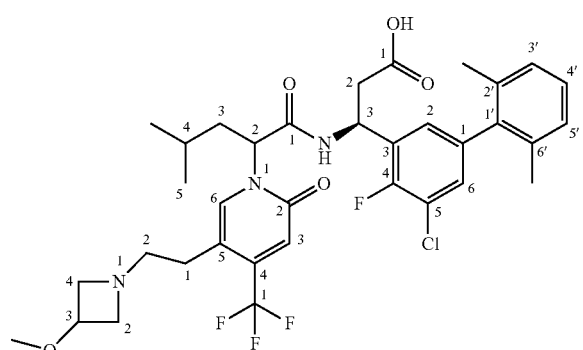

or a pharmaceutically acceptable salt thereof.

179. The compound of embodiment 1, wherein the compound is the compound:

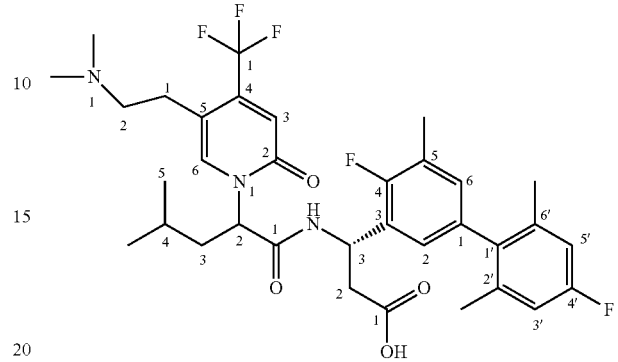

or a pharmaceutically acceptable salt thereof

180. The compound of embodiment 1, wherein the compound is the compound:

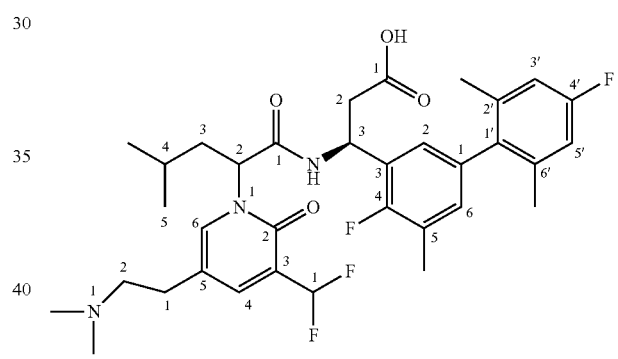

or a pharmaceutically acceptable salt thereof.

181. The compound of embodiment 1, wherein the compound is the compound:

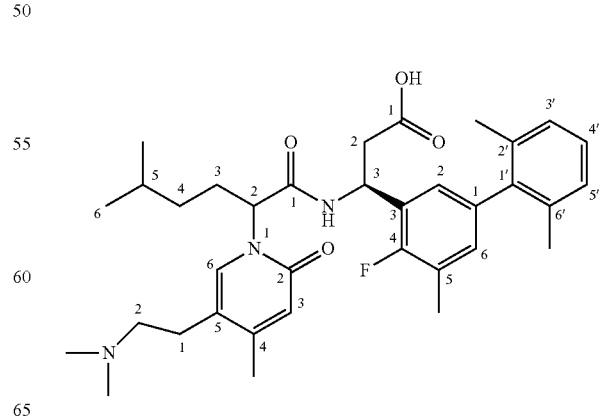

or a pharmaceutically acceptable salt thereof.

182. The compound of embodiment 1, wherein the compound is the compound:

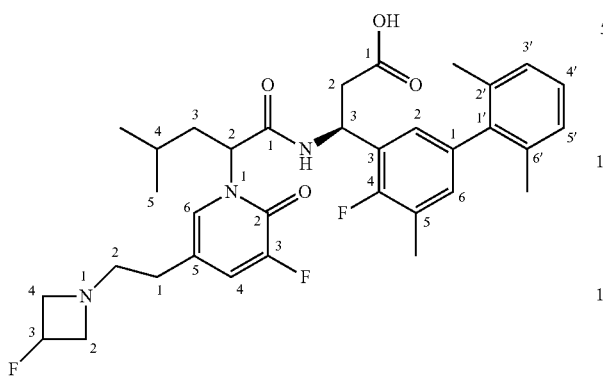

or a pharmaceutically acceptable salt thereof

183. The compound of embodiment 1, wherein the compound is the compound:

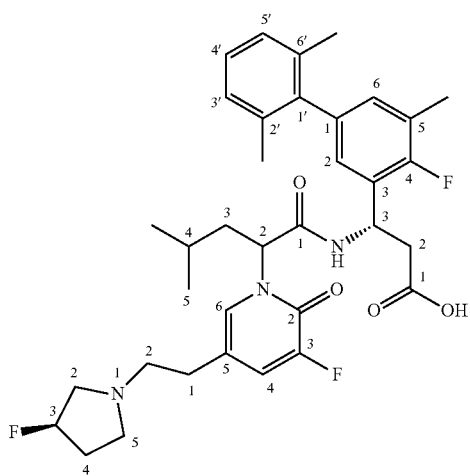 [SMILES: Cc1cc(-c2c(C)cccc2C)cc([C@H](CC(=O)O)NC(=O)C(CC(C)C)n2cc(CCN3CC[C@@H](F)C3)cc(F)c2=O)c1F]

or a pharmaceutically acceptable salt thereof.

184. The compound of embodiment 1, wherein the compound is the compound:

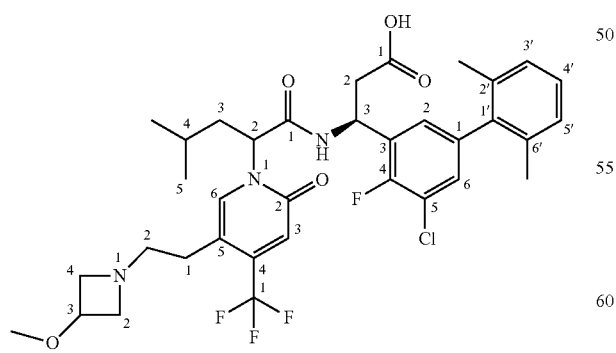

or a pharmaceutically acceptable salt thereof.

185. The compound of embodiment 1, wherein the compound is (3S)-3-(4,5-difluoro-2',6'-dimethylbiphenyl-3-yl)-3-(2-(5-(2-(3-fluoroazetidin-1-yl)ethyl)-4-methyl-2-oxopyridin-1(2H)-yl)-4-methylpentanamido)propanoic acid, or a pharmaceutically acceptable salt thereof.

186. The compound of embodiment 1, wherein the compound is (3S)-3-(2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)biphenyl-3-yl)propanoic acid, or a pharmaceutically acceptable salt thereof.

187. The compound of embodiment 1, wherein the compound is (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic acid, or a pharmaceutically acceptable salt thereof.

188. The compound of embodiment 1, wherein the compound is (3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic acid, or a pharmaceutically acceptable salt thereof.

189. The compound of embodiment 1, wherein the compound is (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid, or a pharmaceutically acceptable salt thereof.

190. The compound of embodiment 1, wherein the compound is (3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid, or a pharmaceutically acceptable salt thereof.

191. The compound of embodiment 1, wherein the compound is (3S)-3-(2-(5-(2-(dimethylamino)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoic acid, or a pharmaceutically acceptable salt thereof.

192. The compound of embodiment 1, wherein the compound is (3S)-3-(4,4'-difluoro-2',5,6'-trimethyl-[1,1'-biphenyl]-3-yl)-3-(2-(3-(difluoromethyl)-5-(2-(dimethylamino)ethyl)-2-oxopyridin-1(2H)-yl)-4-methylpentanamido)propanoic acid, or a pharmaceutically acceptable salt thereof.

193. The compound of embodiment 1, wherein the compound is (3S)-3-(2-(5-(2-(dimethylamino)ethyl)-4-methyl-2-oxopyridin-1(2H)-yl)-5-methylhexanamido)-3-(4-fluoro-2',5,6'-trimethylbiphenyl-3-yl)propanoic acid, or a pharmaceutically acceptable salt thereof.

194. The compound of embodiment 1, wherein the compound is (3S)-3-(4-fluoro-2',5,6'-trimethyl-[1,1'-biphenyl]-3-yl)-3-(2-(3-fluoro-5-(2-(3-fluoroazetidin-1-yl)ethyl)-2-oxopyridin-1(2H)-yl)-4-methylpentanamido)propanoic acid, or a pharmaceutically acceptable salt thereof.

195. The compound of embodiment 1, wherein the compound is (3S)-3-(4-fluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic acid, or a pharmaceutically acceptable salt thereof.

196. The compound of embodiment 1, wherein the compound is (3S)-3-(5-chloro-4-fluoro-2',6'-dimethyl-[1, 1'-biphenyl]-3-yl)-3-(2-(5-(2-(3-methoxyazetidin-1-yl)ethyl)-2-oxo-4-(trifluoromethyl)pyridin-1(2H)-yl)-4- methylpentanamido)propanoic acid, or a pharmaceutically acceptable salt thereof.

197. The compound of embodiment 1, wherein the compound is (S)-3-(4,5-difluoro-2',6'-dimethyl-[1,1'-biphenyl]-3-yl)-3-((S)-2-(5-(2-(3-fluoroazetidin-1-yl)ethyl)-4-methyl-2-oxopyridin-1(2H)-yl)-4-methylpentanamido)propanoic acid, or a pharmaceutically acceptable salt thereof.

198. The compound of embodiment 1, wherein the compound is (S)-3-((S)-2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoic acid, or a pharmaceutically acceptable salt thereof.

199. The compound of embodiment 1, wherein the compound is (S)-3-((S)-2-(5-(2-(azetidin-1-yl)ethyl)-2-oxo-4-(trifluoromethyl)pyridin-1(2H)-yl)-4-methylpentanamido)-3-(3',4-difluoro-2',5',6'-trimethyl-[1,1'-biphenyl]-3-yl)propanoic acid, or a pharmaceutically acceptable salt thereof.

200. The compound of embodiment 1, wherein the compound is (S)-3-((S)-2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5',6'-trimethyl-[1,1'-biphenyl]-3-yl)propanoic acid, or a pharmaceutically acceptable salt thereof.

201. The compound of embodiment 1, wherein the compound is (S)-3-(4,4'-difluoro-2',5',6'-trimethyl-[1,1'-biphenyl]-3-yl)-3-((S)-2-(5-(2-(dimethylamino)ethyl)-2-oxo-4-(trifluoromethyl)pyridin-1(2H)-yl)-4-methylpentanamido)propanoic acid, or a pharmaceutically acceptable salt thereof.

202. The compound of embodiment 1, wherein the compound is (S)-3-(5-chloro-4-fluoro-2',6'-dimethyl-[1,1'-biphenyl]-3-yl)-3-((S)-2-(5-(2-(3-methoxyazetidin-1-yl)ethyl)-2-oxo-4-(trifluoromethyl)pyridin-1(2H)-yl)-4-methylpentanamido)propanoic acid, or a pharmaceutically acceptable salt thereof.

203. The compound of embodiment 1, wherein the compound is (S)-3-((S)-2-(5-(2-(dimethylamino)ethyl)-2-oxo-4-(trifluoromethyl)pyridin-1(2H)-yl)-4-methylpentanamido)-3-(4-fluoro-2',4',5',6'-tetramethyl-[1,1'-biphenyl]-3-yl)propanoic acid, or a pharmaceutically acceptable salt thereof.

204. The compound of embodiment 1, wherein the compound is (S)-3-(4,4'-difluoro-2',5',6'-trimethyl-[1,1'-biphenyl]-3-yl)-3-((S)-2-(3-(difluoromethyl)-5-(2-(dimethylamino)ethyl)-2-oxopyridin-1(2H)-yl)-4-methylpentanamido)propanoic acid, or a pharmaceutically acceptable salt thereof.

205. The compound of embodiment 1, wherein the compound is (S)-3-((S)-2-(5-(2-(dimethylamino)ethyl)-4-methyl-2-oxopyridin-1(2H)-yl)-5-methylhexanamido)-3-(4-fluoro-2',5',6'-trimethyl-[1,1'-biphenyl]-3-yl) propanoic acid, or a pharmaceutically acceptable salt thereof.

206. The compound of embodiment 1, wherein the compound is (S)-3-(4-fluoro-2',5',6'-trimethyl-[1,1'-biphenyl]-3-yl)-3-((S)-2-(3-fluoro-5-(2-(3-fluoroazetidin-1-yl)ethyl)-2-oxopyridin-1(2H)-yl)-4-methylpentanamido)propanoic acid, or a pharmaceutically acceptable salt thereof.

207. The compound of embodiment 1, wherein the compound is (S)-3-(4-fluoro-2',5',6'-trimethyl-[1,1'-biphenyl]-3-yl)-3-((S)-2-(3-fluoro-5-(2-((R)-3-fluoropyrrolidin-1-yl)ethyl)-2-oxopyridin-1(2H)-yl)-4-methylpentanamido)propanoic acid, or a pharmaceutically acceptable salt thereof.

208. The compound of embodiment 1, wherein the compound is (S)-3-(5-chloro-4-fluoro-2',6'-dimethyl-[1,1'-biphenyl]-3-yl)-3-((S)-2-(5-(2-(3-methoxyazetidin-1-yl)ethyl)-2-oxo-4-(trifluoromethyl)pyridin-1(2H)-yl)-4-methylpentanamido)propanoic acid, or a pharmaceutically acceptable salt thereof.

209. A pharmaceutical composition, comprising a compound of any one of embodiments 1-208; and a pharmaceutically acceptable excipient.

210. A method of inhibiting $\alpha_4\beta_7$ integrin in a cell, comprising contacting the cell with a compound of any one of embodiments 1-208 under conditions effective to reduce the adhesion of the cell to MAdCAM-1.

211. A method of reducing the adhesion of a cell comprising an $\alpha_4\beta_7$ integrin to MAdCAM-1, the method comprising contacting the cell with a compound of any one of embodiments 1-208 under conditions effective to reduce the adhesion of the cell to MAdCAM-1.

212. A method of treating inflammatory bowel disease, ulcerative colitis, or Crohn's disease, comprising administering to a subject in need thereof a therapeutically effective amount of a compound of any one of embodiments 1-208

In some embodiments, compounds of the invention can be a compound of Formula (I):

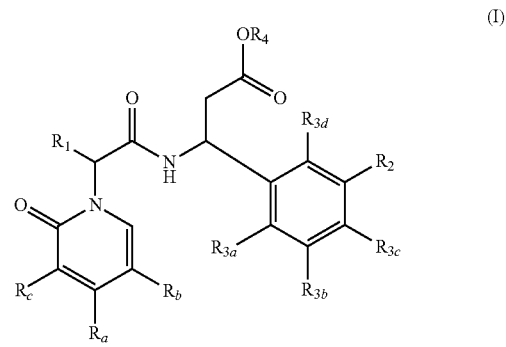

wherein $R_a$, $R_b$, and $R_c$ are independently selected from the group consisting of H, Me, halide, $CF_3$, $C(H)F_2$, $C(F)H_2$, and —$(C_1$-$C_5)$alkylene-N—$(R_x)(R_y)$; provided that at least one of $R_a$, $R_b$, and $R_c$ is —$(C_1$-$C_5)$alkylene-N—$(R_x)(R_y)$;

$R_x$ and $R_y$ are independently selected from the group consisting of H and substituted or unsubstituted $(C_1$-$C_6)$-alkyl; or $R_x$ and $R_y$ taken together with the N to which they are attached form a 4-6 membered ring;

$R_1$ is methyl, ethyl, n-propyl, iso-propyl, n-butyl, iso-butyl, sec-butyl, or t-butyl;

$R_2$ is

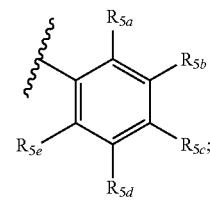

$R_{3a}$ and $R_{3b}$ are independently selected from the group consisting of halide, substituted or unsubstituted ($C_1$-$C_5$)-alkyl, substituted or unsubstituted ($C_3$-$C_6$)-cycloalkyl, substituted or unsubstituted ($C_1$-$C_4$)-alkoxy, $CF_3$, $C(H)F_2$, and $C(F)H_2$;

$R_{3c}$, and $R_{3d}$ are H;

$R_4$ is H;

$R_{5a}$ is methyl;

$R_{5b}$ is selected from the group consisting of H, CN, halide, $CF_3$, $C(H)F_2$, $C(F)H_2$, substituted or unsubstituted ($C_1$-$C_5$)-alkyl, substituted or unsubstituted ($C_3$-$C_6$)-cycloalkyl, substituted or unsubstituted 3-6 membered heterocycloalkyl, hydroxyl, and ($C_1$-$C_4$)-alkoxy;

$R_{5c}$ is methyl;

$R_{5d}$ is H;

$R_{5e}$ is selected from the group consisting of H, CN, halide, $CF_3$, $C(H)F_2$, $C(F)H_2$, substituted or unsubstituted ($C_3$-$C_6$)-cycloalkyl, substituted or unsubstituted ($C_1$-$C_5$)-alkyl, hydroxyl, and ($C_1$-$C_4$)-alkoxy;

or a pharmaceutically acceptable salt thereof.

In some embodiments, compounds of the invention can be a compound of Formula (Ia):

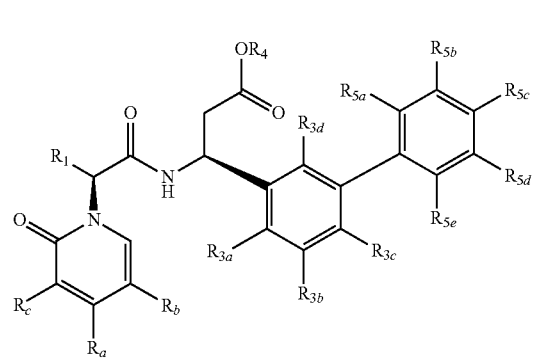

(Ia)

wherein $R_a$, $R_b$, and $R_c$ are independently selected from the group consisting of H, Me, halide, $CF_3$, $C(H)F_2$, $C(F)H_2$, and —($C_1$-$C_5$)alkylene-N—($R_x$)($R_y$); provided that at least one of $R_a$, $R_b$, and $R_c$ is —($C_1$-$C_5$)alkylene-N—($R_x$)($R_y$);

at least one of $R_a$, $R_b$, and $R_c$ is —($C_1$-$C_3$)alkylene-N($R_x$)($R_y$);

$R_x$ and $R_y$ are independently selected from the group consisting of H and methyl; or $R_x$ and $R_y$ taken together with the N to which they are attached form a substituted or unsubstituted 4-6 membered ring;

$R_1$ is substituted or unsubstituted ($C_1$-$C_6$)-alkyl, substituted or unsubstituted ($C_1$-$C_4$)-alkylene-($C_3$-$C_6$)-cycloalkyl, or substituted or unsubstituted ($C_1$-$C_4$)-alkylene- ($C_1$-$C_4$)-alkoxy;

$R_2$ is

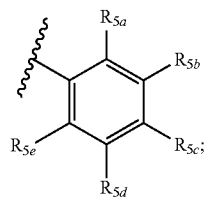

$R_{3a}$, and $R_{3b}$ are each independently selected from the group consisting of methyl and F, and $R_{3a}$ is halide;

$R_{3c}$, and $R_{3d}$ are H;

$R_4$ is H, or substituted or unsubstituted ($C_1$-$C_4$)-alkyl;

$R_{5a}$ is selected from the group consisting of H, CN, halide, $CF_3$, $C(H)F_2$, $C(F)H_2$, substituted or unsubstituted ($C_3$-$C_6$)-cycloalkyl, substituted or unsubstituted ($C_1$-$C_5$)-alkyl, hydroxyl, and ($C_1$-$C_4$)-alkoxy; and $R_{5b}$, and $R_{5c}$ are independently selected from the group consisting of H, CN, halide, $CF_3$, $C(H)F_2$, $C(F)H_2$, substituted or unsubstituted ($C_1$-$C_5$)-alkyl, substituted or unsubstituted ($C_3$-$C_6$)-cycloalkyl, substituted or unsubstituted 3-6 membered heterocycloalkyl, hydroxyl, and ($C_1$-$C_4$)-alkoxy; and $R_{5d}$ is H;

$R_{5e}$ is methyl;

or a pharmaceutically acceptable salt thereof.

In some embodiments, compounds of the invention can be a compound of Formula (Ic)

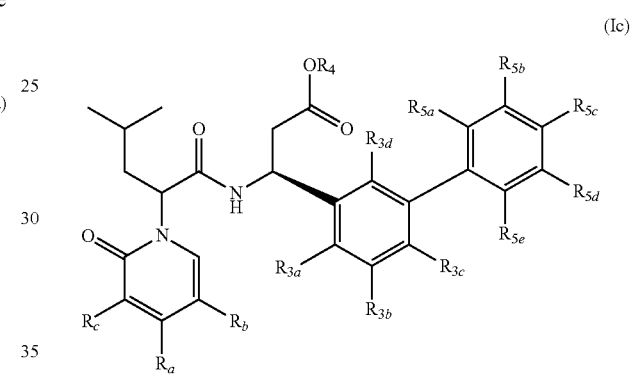

(Ic)

wherein $R_a$, $R_b$, and $R_c$ are independently selected from the group consisting of H, substituted or unsubstituted ($C_1$-$C_5$)-alkyl, halide, $CF_3$, $C(H)F_2$, $C(F)H_2$, substituted or unsubstituted ($C_1$-$C_4$)-alkoxy, —$OCF_3$, and substituted or unsubstituted —($C_1$-$C_5$)alkylene-N—($R_x$)($R_y$); provided that one of $R_a$, $R_b$, and $R_c$ is —($C_1$-$C_5$)alkylene-N—($R_x$)($R_y$);

$R_x$ and $R_y$ are independently selected from the group consisting of H, substituted or unsubstituted ($C_1$-$C_6$)-alkyl, or substituted or unsubstituted ($C_1$-$C_4$)-alkylene-($C_1$-$C_4$)-alkoxy; or $R_x$ and $R_y$ taken together with the N to which they are attached form a substituted or unsubstituted 4-6 membered heterocyclyl ring;

$R_{3a}$ is halide and $R_{3b}$ is selected from the group consisting of H, substituted or unsubstituted ($C_1$-$C_5$)-alkyl, substituted or unsubstituted ($C_3$-$C_6$)-cycloalkyl, substituted or unsubstituted 3-6 membered heterocycloalkyl, —OH, —CN, halide, $CF_3$, $C(H)F_2$, $C(F)H_2$, —($C_1$-$C_4$)-alkoxy, —$OCF_3$, and substituted or unsubstituted ($C_1$-$C_4$)-alkylene-($C_1$-$C_4$)-alkoxy;

$R_{3c}$ is H, substituted or unsubstituted ($C_1$-$C_5$)-alkyl, substituted or unsubstituted ($C_3$-$C_6$)-cycloalkyl, substituted or unsubstituted 3-6 membered heterocycloalkyl, hydroxyl, halide, $CF_3$, $C(H)F_2$, $C(F)H_2$, —($C_1$-$C_4$)-alkoxy, —$OCF_3$ —CN, and substituted or unsubstituted ($C_1$-$C_4$)-alkylene-($C_1$-$C_4$)-alkoxy;

$R_{3d}$ is selected from the group consisting of H, substituted or unsubstituted ($C_1$-$C_5$)-alkyl, hydroxyl, halide, and —($C_1$-$C_4$)-alkoxy;

$R_{5a}$, and $R_{5e}$ are independently selected from the group consisting of H, CN, halide, $CF_3$, $C(H)F_2$, $C(F)H_2$, substituted or unsubstituted ($C_1$-$C_5$)-alkyl, hydroxyl, and ($C_1$-$C_4$)-alkoxy; and $R_{5b}$, $R_{5c}$, and $R_{5d}$ are independently selected from the group consisting of H, CN, halide, $CF_3$, $C(H)F_2$, $C(F)H_2$, substituted or unsubstituted ($C_1$-$C_5$)-alkyl, hydroxyl, and ($C_1$-$C_4$)-alkoxy; or a pharmaceutically acceptable salt thereof.

In some embodiments, compounds of the invention can be a compound (3S)-3-(2-(5-(2-(dimethylamino)ethyl)-2-oxo-4-(trifluoromethyl)pyridin-1(2H)-yl)-4-methylpentanamido)-3-(2-fluoro-3-methyl-5-((S)-2-methylpiperidin-1-yl)phenyl)propanoic acid

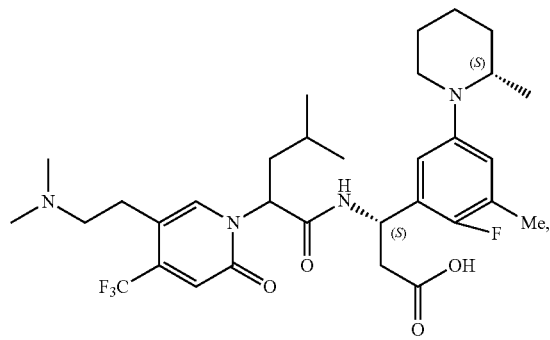

or a pharmaceutically acceptable salt thereof.

In certain embodiments, the invention relates to any one of the aforementioned methods, wherein the subject is a mammal. In certain embodiments, the invention relates to any one of the aforementioned methods, wherein the subject is human.

EXAMPLES

The invention now being generally described, it will be more readily understood by reference to the following examples, which are included merely for purposes of illustration of certain aspects and embodiments of the present invention, and are not intended to limit the invention.

Examples 1-4 describe the synthesis of certain compounds presented in FIG. 1, including compounds of Formula (Ia) and Formula (Ib). Compounds in FIG. 1 can be prepared as a mixture of diastereomeric compounds (e.g., as disclosed in Examples 1-4) having a (3S) configuration (i.e., at the stereocenter beta to the carboxylic acid moiety), and a mixture of diastereomersat the chiral center covalently bound to the pyridone ring nitrogen atom of Formula (I) (e.g., as shown in Formula (Ib)).

In FIG. 1, compounds having greater activity in the fluorescence polarization (FP) assay of Example 5 are shown with the stereochemistry of Formula (Ia). Example 5 describes a fluorescence polarization (FP) assay. Example 6 describes a ligand binding (LB) assay. Example 7 describes a cell adhesion (CA) assay.

Additional Embodiments

In some embodiments, a compound can be selected from one or more of the enumerated embodiments provided below:
1. A compound of Formula (I):

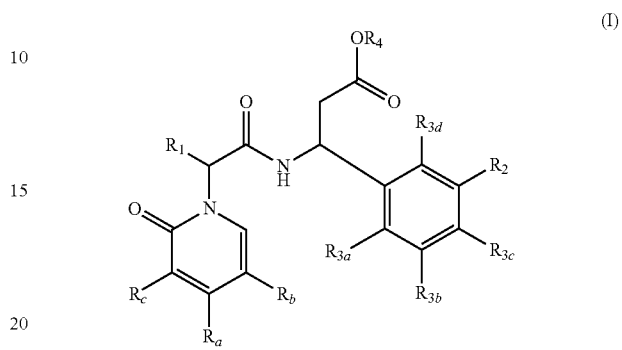

wherein
$R_a$, $R_b$, and $R_c$ are independently selected from the group consisting of H, Me, halide, $CF_3$, $C(H)F_2$, $C(F)H_2$, and —($C_1$-$C_5$)alkylene-N—$(R_x)(R_y)$; provided that at least one of $R_a$, $R_b$, and $R_c$ is —($C_1$-$C_5$)alkylene-N—$(R_x)(R_y)$;
$R_x$ and $R_y$ are independently selected from the group consisting of H and substituted or unsubstituted ($C_1$-$C_6$)-alkyl; or $R_x$ and $R_y$ taken together with the N to which they are attached form a 4-6 membered ring;
$R_1$ is substituted or unsubstituted ($C_1$-$C_6$)-alkyl, substituted or unsubstituted ($C_1$-$C_4$)-alkylene-($C_3$-$C_6$)-cycloalkyl, or substituted or unsubstituted ($C_1$-$C_4$)-alkylene- ($C_1$-$C_4$)-alkoxy;
$R_2$ is

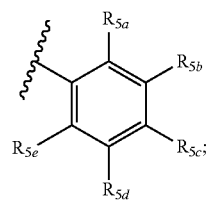

$R_{3a}$ and $R_{3b}$ are independently selected from the group consisting of H, substituted or unsubstituted ($C_1$-$C_5$)-alkyl, substituted or unsubstituted ($C_3$-$C_6$)-cycloalkyl, substituted or unsubstituted 3-6 membered heterocycloalkyl, —OH, —CN, halide, $CF_3$, $C(H)F_2$, $C(F)H_2$, —($C_1$-$C_4$)-alkoxy, —$OCF_3$, and substituted or unsubstituted ($C_1$-$C_4$)-alkylene-($C_1$-$C_4$)-alkoxy; provided that $R_{3a}$ and $R_{3b}$ are not both H;
$R_{3c}$ and $R_{3d}$ are H;
$R_4$ is H, or substituted or unsubstituted ($C_1$-$C_4$)-alkyl;
$R_{5a}$, and $R_{5e}$ are independently selected from the group consisting of H, CN, halide, $CF_3$, $C(H)F_2$, $C(F)H_2$, substituted or unsubstituted ($C_3$-$C_6$)-cycloalkyl, substituted or unsubstituted ($C_1$-$C_5$)-alkyl, hydroxyl, and ($C_1$-$C_4$)-alkoxy; and $R_{5b}$, $R_{5c}$, and $R_{5d}$ are independently selected from the group consisting of H, CN, halide, $CF_3$, $C(H)F_2$, $C(F)H_2$, substituted or unsubstituted ($C_1$-$C_5$)-alkyl, substituted or unsubstituted ($C_3$-$C_6$)-cycloalkyl, substituted or unsubstituted 3-6 membered heterocycloalkyl, hydroxyl, and ($C_1$-$C_4$)-alkoxy;
or a pharmaceutically acceptable salt thereof.

2. The compound of embodiment 1, wherein $R_1$ is methyl, ethyl, n-propyl, iso-propyl, n-butyl, iso-butyl, sec-butyl, or t-butyl.
3. The compound of embodiment 2, wherein $R_1$ is iso-butyl.
4. The compound of embodiment 1, wherein $R_1$ is

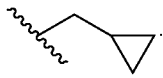 [SMILES: *CC1CC1]

5. The compound of embodiment 1, wherein $R_1$ is OMe

6. The compound of any one of embodiments 1-5, wherein $R_{3a}$ and $R_{3b}$ are independently selected from the group consisting of halide, substituted or unsubstituted $(C_1-C_5)$-alkyl, substituted or unsubstituted $(C_3-C_6)$-cycloalkyl, substituted or unsubstituted $(C_1-C_4)$-alkoxy, $CF_3$, $C(H)F_2$, and $C(F)H_2$.
7. The compound of embodiment 6, wherein $R_{3a}$ and $R_{3b}$ are independently selected from the group consisting of halide and $(C_1-C_4)$-alkyl. 8. The compound of embodiment 7, wherein halide is Cl or F.
9. The compound of embodiment 7 or 8, wherein $(C_1-C_4)$-alkyl is methyl.
10. The compound of any one of embodiments 1-7, wherein $R_{3a}$ is methyl; and $R_{3b}$ is F.
11. The compound of any one of embodiments 1-7, wherein $R_{3a}$ is F; and $R_{3b}$ is methyl.
12. The compound of any one of embodiments 1-11, wherein $R_4$ is H.
13. The compound of any one of embodiments 1-11, wherein $R_4$ is methyl, ethyl, n-propyl, iso-propyl.
14. The compound of any one of embodiments 1-13, wherein $R_{5a}$ and $R_{5e}$ are independently selected from the group consisting of halide, $CF_3$, $C(H)F_2$, $C(F)H_2$, and substituted or unsubstituted $(C_1-C_4)$-alkyl.
15. The compound of any one of embodiments 1-14, wherein $R_{5a}$ is halide.
16. The compound of embodiment 15, wherein $R_{5a}$ is F or Cl.
17. The compound of any one of embodiments 1-14, wherein $R_{5a}$ is $CF_3$.
18. The compound of any one of embodiments 1-14, wherein $R_{5a}$ is $C(H)F_2$.
19. The compound of any one of embodiments 1-14, wherein $R_{5a}$ is $C(F)H_2$.
20. The compound of any one of embodiments 1-14, wherein $R_{5a}$ is unsubstituted $(C_1-C_4)$-alkyl.
21. The compound of embodiment 20, wherein $R_{5a}$ is methyl.
22. The compound of any one of embodiments 1-14, wherein $R_{5a}$ is substituted $(C_1-C_5)$-alkyl, substituted with at least one halide.
23. The compound of any one of embodiments 1-14, wherein $R_{5a}$ is unsubstituted $(C_1-C_4)$-alkoxy.
24. The compound of embodiment 23, wherein $R_{5a}$ is OMe.
25. The compound of any one of embodiments 1-24, wherein $R_{5a}$ is halide.
26. The compound of embodiment 25, wherein $R_{5a}$ is F or Cl.
27. The compound of any one of embodiments 1-24, wherein $R_{5e}$ is $CF_3$.
28. The compound of any one of embodiments 1-24, wherein $R_{5e}$ is $C(H)F_2$.
29. The compound of any one of embodiments 1-24, wherein $R_{5e}$ is $C(F)H_2$.
30. The compound of any one of embodiments 1-24, wherein $R_{5e}$ is unsubstituted $(C_1-C_4)$-alkyl.
31. The compound of embodiment 30, wherein $R_{5e}$ is methyl.
32. The compound of any one of embodiments 1-24, wherein $R_5$ is substituted $(C_1-C_5)$-alkyl, substituted with at least one halide.
33. The compound of any one of embodiments 1-24, wherein $R_{5e}$ is unsubstituted $(C_1-C_4)$-alkoxy.
34. The compound of embodiment 33, wherein $R_{5e}$ is OMe.
35. The compound of any one of embodiments 1-34, wherein $R_{5b}$, $R_{5c}$, and $R_{5d}$ are independently selected from the group consisting of H, halide, $CF_3$, $C(H)F_2$, $C(F)H_2$, substituted or unsubstituted $(C_1-C_5)$-alkyl, and substituted or unsubstituted $(C_1-C_4)$-alkoxy.
36. The compound of any one of embodiments 1-35, wherein $R_{5b}$ is H.
37. The compound of any one of embodiments 1-35, wherein $R_{5b}$ is halide.
38. The compound of embodiment 37, wherein $R_{5b}$ is Cl or F.
39. The compound of any one of embodiments 1-35, wherein $R_{5b}$ is $CF_3$.
40. The compound of any one of embodiments 1-35, wherein $R_{5b}$ is $C(H)F_2$.
41. The compound of any one of embodiments 1-35, wherein $R_{5b}$ is $C(F)H_2$.
42. The compound of any one of embodiments 1-35, wherein $R_{5b}$ is unsubstituted $(C_1-C_4)$-alkyl.
43. The compound of embodiment 37, wherein $R_{5b}$ is methyl.
44. The compound of any one of embodiments 1-35, wherein $R_{5b}$ is unsubstituted $(C_1-C_4)$-alkoxy.
45. The compound of embodiment 44, wherein $R_{5b}$ is OMe.
46. The compound of any one of embodiments 1-35, wherein $R_{5b}$ is unsubstituted $(C_3-C_6)$-cycloalkyl.
47. The compound of embodiment 46, wherein $R_{5b}$ is cyclopropyl.
48. The compound of any one of embodiments 1-47, wherein $R_{5c}$ is H.
49. The compound of any one of embodiments 1-47, wherein $R_{5c}$ is halide.
50. The compound of embodiment 49, wherein $R_{5c}$ is Cl or F.
51. The compound of any one of embodiments 1-47, wherein $R_{5c}$ is $CF_3$.
52. The compound of any one of embodiments 1-47, wherein $R_{5c}$ is $C(H)F_2$.
53. The compound of any one of embodiments 1-47, wherein $R_{5c}$ is $C(F)H_2$.
54. The compound of any one of embodiments 1-47, wherein $R_{5c}$ is unsubstituted $(C_1-C_4)$-alkyl.
55. The compound of embodiment 54, wherein $R_{5c}$ is methyl.
56. The compound of any one of embodiments 1-47, wherein $R_{5c}$ is unsubstituted $(C_1-C_4)$-alkoxy.
57. The compound of embodiment 56, wherein $R_{5c}$ is OMe.
58. The compound of any one of embodiments 1-47, wherein $R_{5c}$ is unsubstituted $(C_3-C_6)$-cycloalkyl.

59. The compound of embodiment 58, wherein $R_{5b}$ is cyclopropyl.
60. The compound of any one of embodiments 1-59, wherein $R_{5d}$ is H.
61. The compound of any one of embodiments 1-59, wherein $R_{5d}$ is halide.
62. The compound of embodiment 61, wherein $R_{5d}$ is Cl or F.
63. The compound of any one of embodiments 1-59, wherein $R_{5d}$ is $CF_3$.
64. The compound of any one of embodiments 1-59, wherein $R_{5d}$ is $C(H)F_2$.
65. The compound of any one of embodiments 1-59, wherein $R_{5d}$ is $C(F)H_2$.
66. The compound of any one of embodiments 1-59, wherein $R_{5d}$ is unsubstituted $(C_1-C_4)$-alkyl.
67. The compound of embodiment 66, wherein $R_{5d}$ is methyl.
68. The compound of any one of embodiments 1-67, wherein $R_{5d}$ is unsubstituted $(C_1-C_4)$-alkoxy.
69. The compound of embodiment 68, wherein $R_{5d}$ is OMe.
70. The compound of any one of embodiments 1-67, wherein $R_{5d}$ is unsubstituted $(C_3-C_6)$-cycloalkyl.
71. The compound of embodiment 70, wherein $R_{5d}$ is cyclopropyl.
72. The compound of any one of embodiments 1-35, wherein $R_{5b}$, and $R_{5d}$ are each H.
73. The compound of any one of embodiments 1-72, wherein $R_a$ is H.
74. The compound of any one of embodiments 1-72, wherein $R_a$ is Me.
75. The compound of any one of embodiments 1-72, wherein $R_a$ is halide.
76. The compound of embodiment 75, wherein $R_a$ is Cl or F.
77. The compound of any one of embodiments 1-72, wherein $R_a$ is $CF_3$.
78. The compound of any one of embodiments 1-72, wherein $R_a$ is $C(H)F_2$.
79. The compound of any one of embodiments 1-72, wherein $R_a$ is $C(F)H_2$.
80. The compound of any one of embodiments 1-72, wherein $R_a$ is unsubstituted —$(C_1-C_3)$alkylene-N—$(R_x)$$(R_y)$.
81. The compound of any one of embodiments 1-72, wherein $R_a$ is substituted —$(C_1-C_3)$alkylene-N—$(R_x)$$(R_y)$, substituted with F or OMe.
82. The compound of any one of embodiments 1-81, wherein $R_b$ is H.
83. The compound of any one of embodiments 1-81, wherein $R_b$ is Me.
84. The compound of any one of embodiments 1-81, wherein $R_b$ is halide.
85. The compound of embodiment 84, wherein $R_b$ is Cl or F.
86. The compound of any one of embodiments 1-81, wherein $R_b$ is $CF_3$.
87. The compound of any one of embodiments 1-81, wherein $R_b$ is $C(H)F_2$.
88. The compound of any one of embodiments 1-81, wherein $R_b$ is $C(F)H_2$.
89. The compound of any one of embodiments 1-81, wherein $R_b$ is unsubstituted —$(C_1-C_3)$alkylene-N—$(R_x)$$(R_y)$.
90. The compound of any one of embodiments 1-81, wherein $R_b$ is substituted —$(C_1-C_3)$alkylene-N—$(R_x)$$(R_y)$, substituted with F or OMe.
91. The compound of any one of embodiments 1-90, wherein $R_c$ is H.
92. The compound of any one of embodiments 1-90, wherein $R_c$ is Me.
93. The compound of any one of embodiments 1-90, wherein $R_c$ is halide.
94. The compound of embodiment 93, wherein $R_c$ is Cl or F.
95. The compound of any one of embodiments 1-90, wherein $R_c$ is $CF_3$.
96. The compound of any one of embodiments 1-90, wherein $R_c$ is $C(H)F_2$.
97. The compound of any one of embodiments 1-90, wherein $R_c$ is $C(F)H_2$.
98. The compound of any one of embodiments 1-90, wherein $R_c$ is unsubstituted —$(C_1-C_3)$alkylene-N—$(R_x)$$(R_y)$.
99. The compound of any one of embodiments 1-90, wherein $R_c$ is substituted —$(C_1-C_3)$alkylene-N—$(R_x)$$(R_y)$, substituted with F or OMe.
100. The compound of any one of embodiments 1-99, wherein $R_x$ is H.
101. The compound of any one of embodiments 1-99, wherein $R_x$ is unsubstituted $(C_1-C_6)$-alkyl.
102. The compound of any one of embodiments 1-100, wherein $R_y$ is H.
103. The compound of any one of embodiments 1-100, wherein $R_y$ is unsubstituted $(C_1-C_6)$-alkyl.
104. The compound of any one of embodiments 1-72, 80-81, 89-90, and 98-99, wherein $R_x$ and $R_y$ taken together with the N to which they are attached form a unsubstituted 4-6 membered ring.
105. The compound of any one of embodiments 1-72, 80-81, 89-90, and 98-99, wherein $R_x$ and $R_y$ taken together with the N to which they are attached form a substituted 4-6 membered ring, substituted with at least one halide, substituted or unsubstituted $(C_1-C_4)$ alkyl, or OMe.
106. The compound of embodiment 104 or 105, wherein the 4-6 membered ring is a 3-6 membered heterocycloalkyl.
107. The compound of embodiment 104 or 105, wherein the 4-6 membered ring is a 4-5 membered heterocycloalkyl.
108. The compound of embodiment 1, wherein the compound is a compound of Formula (Ia):

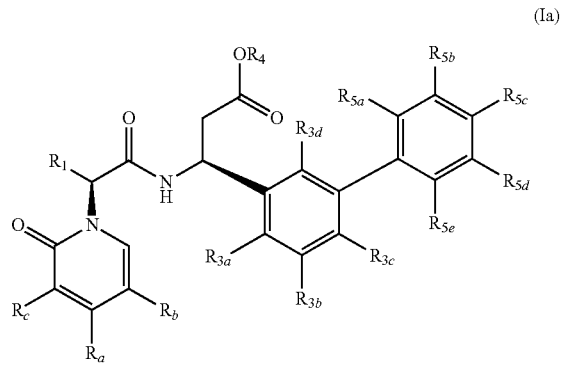

(Ia)

wherein
at least one of $R_a$, $R_b$, and $R_c$ is —$(C_1-C_3)$alkylene-N$(R_x)$$(R_y)$;
$R_x$ and $R_y$ are independently selected from the group consisting of H and methyl; or $R_x$ and $R_y$, taken together with the N to which they are attached form a substituted or unsubstituted 4-6 membered ring; and $R_{3a}$, and $R_{3b}$ are each independently selected from the group consisting of methyl and F.

109. The compound of embodiment 108, wherein $R_{5a}$, and $R_{5e}$ are independently unsubstituted $(C_1$-$C_4)$ alkyl.

110. The compound of embodiment 108 or 109, wherein $R_b$ is unsubstituted —$(C_1$-$C_3)$alkylene-$N(R_x)(R_y)$.

111. The compound of embodiment 1 or 108, wherein $R_a$ is selected from the group consisting of H, C(H)F$_2$, CF$_3$, and Me.

112. The compound of embodiment 1 or 108, wherein $R_b$ is selected from the group consisting of

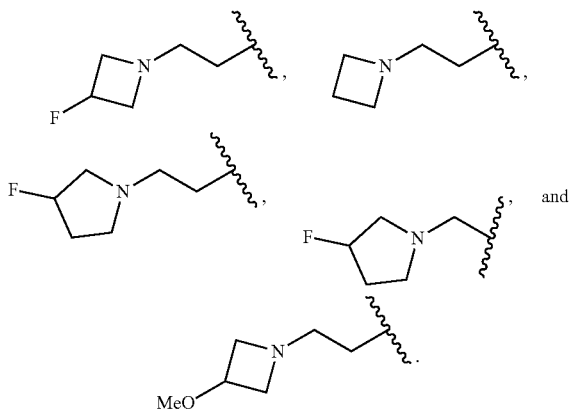

113. The compound of embodiment 1 or 108, wherein $R_b$ is selected from the group consisting of

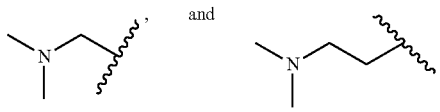

114. The compound of embodiment 1 or 108, wherein $R_c$ is H or F.

115. The compound of any one of embodiments 1 and 108-114, wherein $R_1$ is selected from the group consisting of

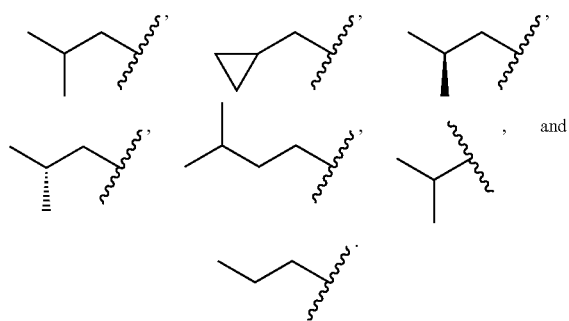

116. The compound of any one of embodiments 108-115, wherein $R_{5a}$ is CF$_3$.

117. The compound of any one of embodiments 108-115, wherein $R_{5a}$ is C(H)F$_2$.

118. The compound of any one of embodiments 108-115, wherein $R_{5a}$ is C(F)H$_2$.

119. The compound of any one of embodiments 108-115, wherein $R_{5a}$ is methyl.

120. The compound of any one of embodiments 108-115, wherein $R_{5a}$ is OMe.

121. The compound of any one of embodiments 108-115, wherein $R_{5a}$ is F or Cl.

122. The compound of any one of embodiments 108-121, wherein $R_{5b}$ is H.

123. The compound of any one of embodiments 108-121, wherein $R_{5b}$ is CF$_3$.

124. The compound of any one of embodiments 108-121, wherein $R_{5b}$ is C(H)F$_2$.

125. The compound of any one of embodiments 108-121, wherein $R_{5b}$ is C(F)H$_2$.

126. The compound of any one of embodiments 108-121, wherein $R_{5b}$ is methyl.

127. The compound of any one of embodiments 108-121, wherein $R_{5b}$ is OMe.

128. The compound of any one of embodiments 108-121, wherein $R_{5b}$ is F or Cl.

129. The compound of any one of embodiments 108-128, wherein $R_{5c}$ is H.

130. The compound of any one of embodiments 108-128, wherein $R_{5c}$ is CF$_3$.

131. The compound of any one of embodiments 108-128, wherein $R_{5c}$ is C(H)F$_2$.

132. The compound of any one of embodiments 108-128, wherein $R_{5c}$ is C(F)H$_2$.

133. The compound of any one of embodiments 108-128, wherein $R_{5c}$ is methyl.

134. The compound of any one of embodiments 108-128, wherein $R_{5c}$ is OMe.

135. The compound of any one of embodiments 108-128, wherein $R_{5c}$ is F or Cl.

136. The compound of any one of embodiments 108-135, wherein $R_{5d}$ is H.

137. The compound of any one of embodiments 108-135, wherein $R_{5d}$ is CF$_3$.

138. The compound of any one of embodiments 108-135, wherein $R_{5d}$ is C(H)F$_2$.

139. The compound of any one of embodiments 108-135, wherein $R_{5d}$ is C(F)H$_2$.

140. The compound of any one of embodiments 108-135, wherein $R_{5d}$ is methyl.

141. The compound of any one of embodiments 108-135, wherein $R_{5d}$ is OMe.

142. The compound of any one of embodiments 108-135, wherein $R_{5d}$ is F or Cl.

143. The compound of any one of embodiments 108-142, wherein $R_e$ is CF$_3$.

144. The compound of any one of embodiments 108-142, wherein $R_{5e}$ is C(H)F$_2$.

145. The compound of any one of embodiments 108-142, wherein $R_{5e}$ is C(F)H$_2$.

146. The compound of any one of embodiments 108-142, wherein $R_{5e}$ is methyl.

147. The compound of any one of embodiments 108-142, wherein $R_{5e}$ is OMe.

148. The compound of any one of embodiments 108-142, wherein $R_{5e}$ is F or Cl.

149. The compound of any one of embodiments 1, and 108-121, wherein at least one of $R_{5b}$, $R_{5c}$, and $R_{5d}$ is H.

150. The compound of any one of embodiments 1, and 108-121, wherein at least two of $R_{5b}$, $R_{5c}$, and $R_{5d}$ is H.

151. The compound of any one of embodiments 1, and 108-121, wherein $R_{5b}$, $R_{5c}$, and $R_{5d}$ are H.
152. The compound of any one of embodiments 1, and 108-151, wherein $R_{3a}$ is H.
153. The compound of any one of embodiments 1, and 108-151, wherein $R_{3a}$ is methyl.
154. The compound of any one of embodiments 1, and 108-151, wherein $R_{3a}$ is halide.
155. The compound of any one of embodiments 1, and 108-151, wherein $R_{3a}$ is $CF_3$.
156. The compound of any one of embodiments 1, and 108-151, wherein $R_{3a}$ is $C(H)F_2$.
157. The compound of any one of embodiments 1, and 108-151, wherein $R_{3a}$ is $C(F)H_2$.
158. The compound of any one of embodiments 1, and 108-151, wherein $R_{3a}$ is OMe.
159. The compound of any one of embodiments 1, and 108-158, wherein $R_{3b}$ is H.
160. The compound of any one of embodiments 1, and 108-158, wherein $R_{3b}$ is methyl.
161. The compound of any one of embodiments 1, and 108-158, wherein $R_{3b}$ is halide.
162. The compound of any one of embodiments 1, and 108-158, wherein $R_{3b}$ is $CF_3$.
163. The compound of any one of embodiments 1, and 108-158, wherein $R_{3b}$ is $C(H)F_2$.
164. The compound of any one of embodiments 1, and 108-158, wherein $R_{3b}$ is $C(F)H_2$.
165. The compound of any one of embodiments 1, and 108-158, wherein $R_{3b}$ is OMe.
166. The compound of any one of embodiments 1, and 108-158, wherein $R_{3b}$ is $OCF_3$.
167. The compound of any one of embodiments 1, and 108-158, wherein $R_{3b}$ is cyclopropyl.
168. The compound of any one of embodiments 108-151, wherein $R_{3a}$ is methyl and $R_{3b}$ is F.
169. The compound of any one of embodiments 108-151, wherein $R_{3a}$ is F and $R_{3b}$ is methyl.
170. The compound of embodiment 1, wherein the compound is selected from any one of the compounds of FIG. 1, or an enantiomer thereof.
171. The compound of embodiment 1, wherein the compound is a compound of Formula (Ic)

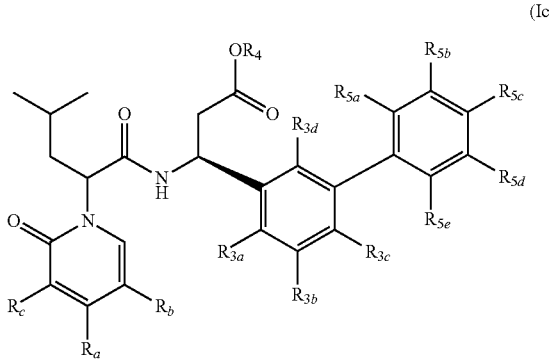

(Ic)

or a pharmaceutically acceptable salt thereof, wherein
$R_a$, $R_b$, and $R_c$ are independently selected from the group consisting of H, substituted or unsubstituted ($C_1$-$C_5$)-alkyl, halide, $CF_3$, $C(H)F_2$, $C(F)H_2$, substituted or unsubstituted ($C_1$-$C_4$)-alkoxy, —$OCF_3$, and substituted or unsubstituted —($C_1$-$C_5$)alkylene-N—($R_x$)($R_y$); provided that one of $R_a$, $R_b$, and $R_c$ is —($C_1$-$C_5$)alkylene-N—($R_x$)($R_y$);

$R_x$ and $R_y$ are independently selected from the group consisting of H, substituted or unsubstituted ($C_1$-$C_6$)-alkyl, or substituted or unsubstituted ($C_1$-$C_4$)-alkylene-($C_1$-$C_4$)-alkoxy; or $R_x$ and $R_y$ taken together with the N to which they are attached form a substituted or unsubstituted 4-6 membered heterocyclyl ring;

$R_{3a}$ and $R_{3b}$ are independently selected from the group consisting of H, substituted or unsubstituted ($C_1$-$C_5$)-alkyl, substituted or unsubstituted ($C_3$-$C_6$)-cycloalkyl, substituted or unsubstituted 3-6 membered heterocycloalkyl, —OH, —CN, halide, $CF_3$, $C(H)F_2$, $C(F)H_2$, —($C_1$-$C_4$)-alkoxy, —$OCF_3$, and substituted or unsubstituted ($C_1$-$C_4$)-alkylene-($C_1$-$C_4$)-alkoxy; provided that $R_{3a}$ and $R_{3b}$ are not both H;

$R_{3c}$ is selected from the group consisting of H, substituted or unsubstituted ($C_1$-$C_5$)-alkyl, substituted or unsubstituted ($C_3$-$C_6$)-cycloalkyl, substituted or unsubstituted 3-6 membered heterocycloalkyl, hydroxyl, halide, $CF_3$, $C(H)F_2$, $C(F)H_2$, —($C_1$-$C_4$)-alkoxy, —$OCF_3$ —CN, and substituted or unsubstituted ($C_1$-$C_4$)-alkylene-($C_1$-$C_4$)-alkoxy;

$R_{3d}$ is selected from the group consisting of H, substituted or unsubstituted ($C_1$-$C_5$)-alkyl, hydroxyl, halide, and —($C_1$-$C_4$)-alkoxy;

$R_{5a}$, and $R_{5e}$ are independently selected from the group consisting of H, CN, halide, $CF_3$, $C(H)F_2$, $C(F)H_2$, substituted or unsubstituted ($C_1$-$C_5$)-alkyl, hydroxyl, and ($C_1$-$C_4$)-alkoxy; and $R_{5b}$, $R_{5c}$, and $R_d$ are independently selected from the group consisting of H, CN, halide, $CF_3$, $C(H)F_2$, $C(F)H_2$, substituted or unsubstituted ($C_1$-$C_5$)-alkyl, hydroxyl, and ($C_1$-$C_4$)-alkoxy; or a pharmaceutically acceptable salt thereof.

172. A compound selected from the group consisting of:
(3S)-3-(4,5-difluoro-2',6'-dimethylbiphenyl-3-yl)-3-(2-(5-(2-(3-fluoroazetidin-1-yl)ethyl)-4-methyl-2-oxopyridin-1(2H)-yl)-4-methylpentanamido)propanoic acid;
(3S)-3-(2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)biphenyl-3-yl)propanoic acid;
(3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic acid;
(3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic acid;
(3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid;
(3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid;
(3S)-3-(2-(5-(2-(dimethylamino)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoic acid;
(3S)-3-(4,4'-difluoro-2',5,6'-trimethyl-[1,1'-biphenyl]-3-yl)-3-(2-(3-(difluoromethyl)-5-(2-(dimethylamino)ethyl)-2-oxopyridin-1(2H)-yl)-4-methylpentanamido)propanoic acid;

(3S)-3-(2-(5-(2-(dimethylamino)ethyl)-4-methyl-2-oxopyridin-1(2H)-yl)-5-methylhexanamido)-3-(4-fluoro-2',5,6'-trimethylbiphenyl-3-yl)propanoic acid;

(3S)-3-(4-fluoro-2',5,6'-trimethyl-[1,1'-biphenyl]-3-yl)-3-(2-(3-fluoro-5-(2-(3-fluoroazetidin-1-yl)ethyl)-2-oxopyridin-1(2H)-yl)-4-methylpentanamido)propanoic acid;

(3S)-3-(4-fluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic acid; and (3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid, or a pharmaceutically acceptable salt thereof.

173. The compound of embodiment 1, wherein the compound is the compound:

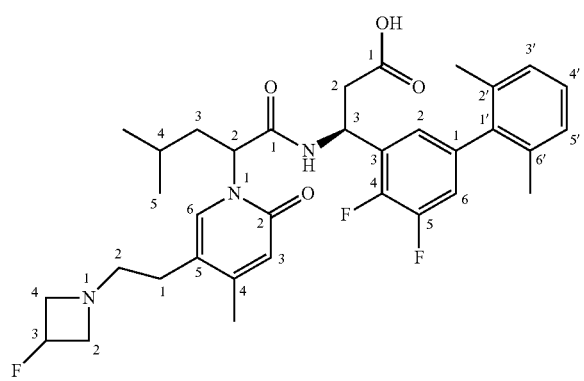 [SMILES: Cc1cc(=O)n(C(CC(C)C)C(=O)N[C@@H](CC(=O)O)c2cc(-c3c(C)cccc3C)cc(F)c2F)cc1CCN1CC(F)C1]

or a pharmaceutically acceptable salt thereof.

174. The compound of embodiment 1, wherein the compound is the compound:

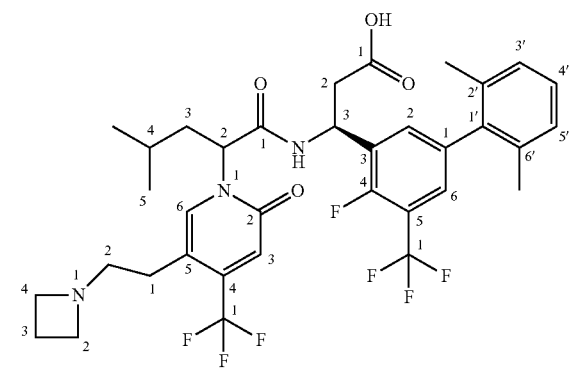 [SMILES: Cc1cccc(C)c1-c1cc([C@H](CC(=O)O)NC(=O)C(CC(C)C)n2cc(CCN3CCC3)c(C(F)(F)F)cc2=O)c(F)c(C(F)(F)F)c1]

or a pharmaceutically acceptable salt thereof.

175. The compound of embodiment 1, wherein the compound is the compound:

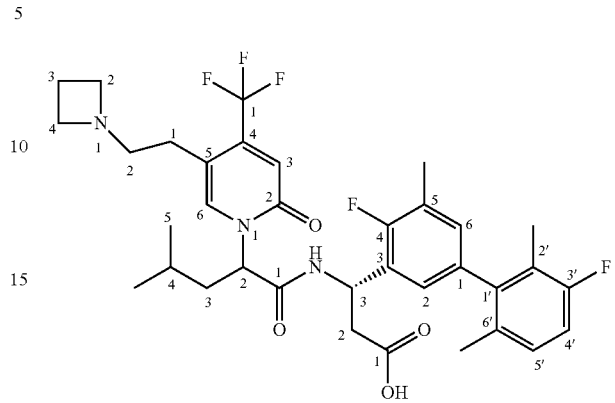

or a pharmaceutically acceptable salt thereof.

176. The compound of embodiment 1, wherein the compound is the compound:

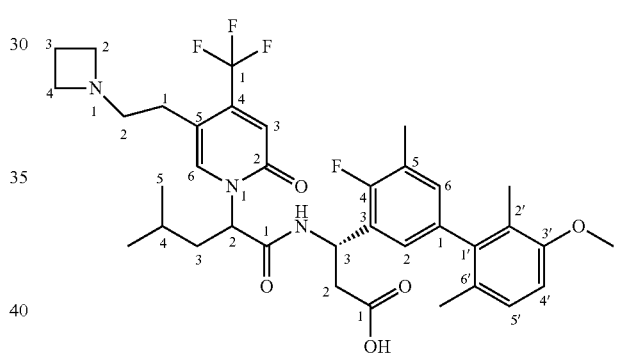

or a pharmaceutically acceptable salt thereof.

177. The compound of embodiment 1, wherein the compound is the compound:

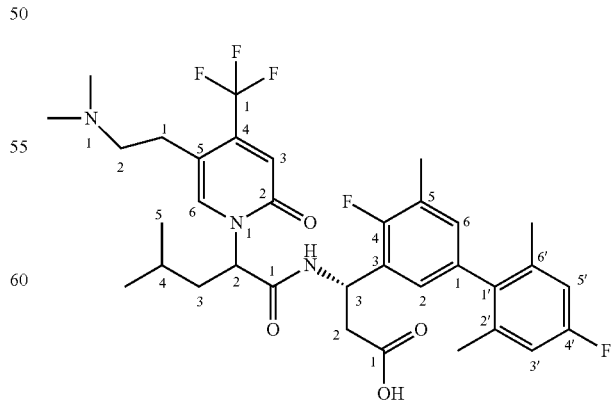

or a pharmaceutically acceptable salt thereof.

178. The compound of embodiment 1, wherein the compound is the compound:

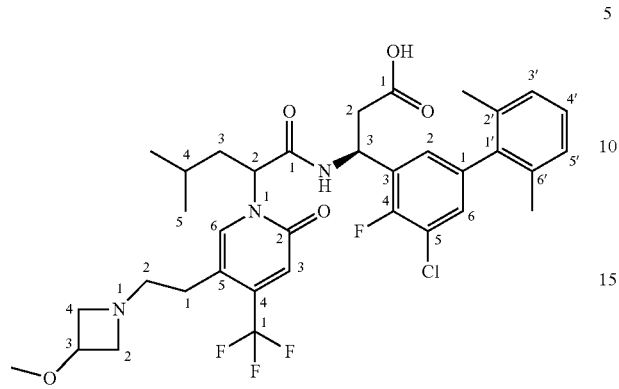

or a pharmaceutically acceptable salt thereof.

179. The compound of embodiment 1, wherein the compound is the compound:

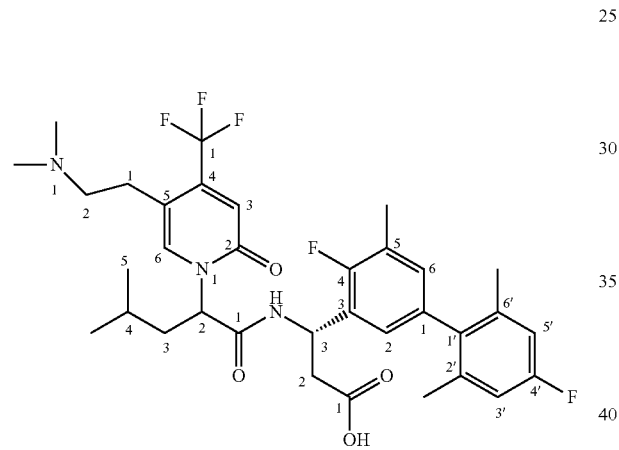

or a pharmaceutically acceptable salt thereof

180. The compound of embodiment 1, wherein the compound is the compound:

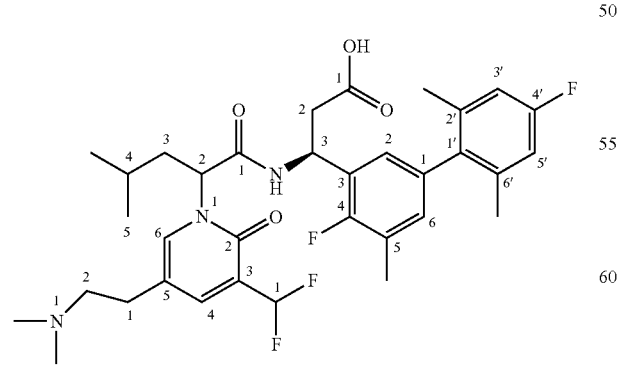

or a pharmaceutically acceptable salt thereof.

181. The compound of embodiment 1, wherein the compound is the compound:

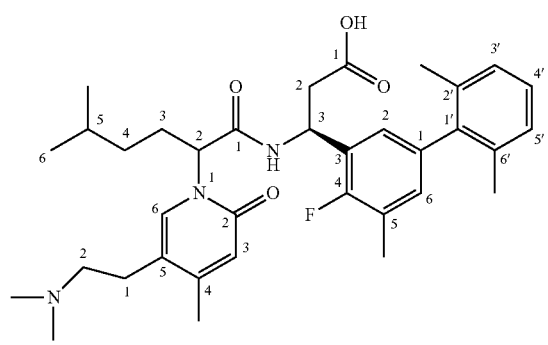 [SMILES: Cc1cc(=O)n(C(CCC(C)C)C(=O)N[C@@H](CC(=O)O)c2cc(-c3c(C)cccc3C)cc(C)c2F)cc1CCN(C)C]

or a pharmaceutically acceptable salt thereof.

182. The compound of embodiment 1, wherein the compound is the compound:

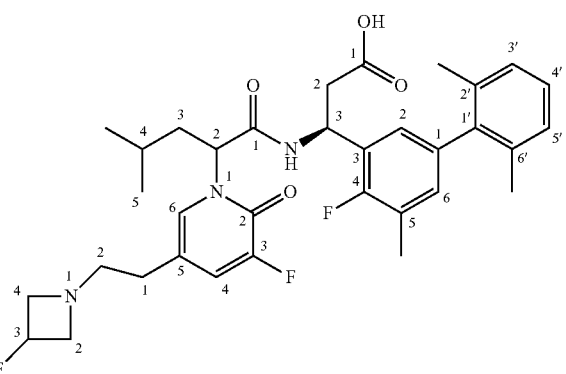

or a pharmaceutically acceptable salt thereof.

183. The compound of embodiment 1, wherein the compound is the compound:

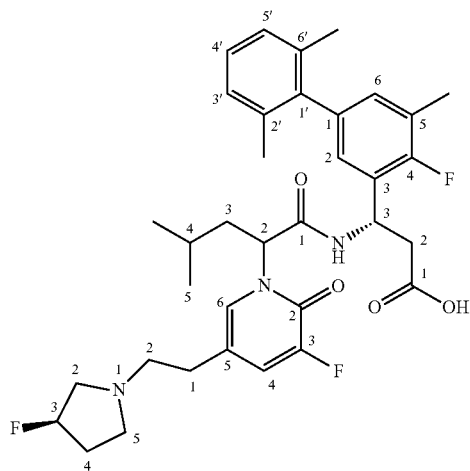 [SMILES: Cc1cc(-c2c(C)cccc2C)cc([C@H](CC(=O)O)NC(=O)C(CC(C)C)n2cc(CCN3CC[C@@H](F)C3)cc(F)c2=O)c1F]

or a pharmaceutically acceptable salt thereof.

184. The compound of embodiment 1, wherein the compound is the compound:

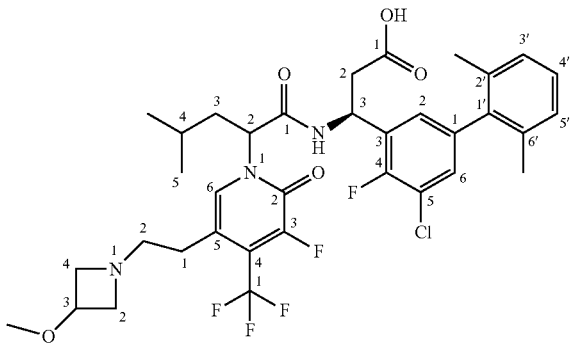 [SMILES: COC1CN(CCc2cn(C(CC(C)C)C(=O)N[C@@H](CC(=O)O)c3cc(-c4c(C)cccc4C)cc(Cl)c3F)c(=O)c(F)c2C(F)(F)F)C1]

or a pharmaceutically acceptable salt thereof.
185. The compound of embodiment 1, wherein the compound is (3S)-3-(4,5-difluoro-2',6'-dimethylbiphenyl-3-yl)-3-(2-(5-(2-(3-fluoroazetidin-1-yl)ethyl)-4-methyl-2-oxopyridin-1(2H)-yl)-4-methylpentanamido)propanoic acid, or a pharmaceutically acceptable salt thereof.
186. The compound of embodiment 1, wherein the compound is (3S)-3-(2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)biphenyl-3-yl)propanoic acid, or a pharmaceutically acceptable salt thereof.
187. The compound of embodiment 1, wherein the compound is (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic acid, or a pharmaceutically acceptable salt thereof.
188. The compound of embodiment 1, wherein the compound is (3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic acid, or a pharmaceutically acceptable salt thereof.
189. The compound of embodiment 1, wherein the compound is (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid, or a pharmaceutically acceptable salt thereof.
190. The compound of embodiment 1, wherein the compound is (3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid, or a pharmaceutically acceptable salt thereof.
191. The compound of embodiment 1, wherein the compound is (3S)-3-(2-(5-(2-(dimethylamino)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoic acid, or a pharmaceutically acceptable salt thereof.
192. The compound of embodiment 1, wherein the compound is (3S)-3-(4,4'-difluoro-2',5,6'-trimethyl-[1,1'-biphenyl]-3-yl)-3-(2-(3-(difluoromethyl)-5-(2-(dimethylamino)ethyl)-2-oxopyridin-1(2H)-yl)-4-methylpentanamido)propanoic acid, or a pharmaceutically acceptable salt thereof.
193. The compound of embodiment 1, wherein the compound is (3S)-3-(2-(5-(2-(dimethylamino)ethyl)-4-methyl-2-oxopyridin-1(2H)-yl)-5-methylhexanamido)-3-(4-fluoro-2',5,6'-trimethylbiphenyl-3-yl)propanoic acid, or a pharmaceutically acceptable salt thereof.
194. The compound of embodiment 1, wherein the compound is (3S)-3-(4-fluoro-2',5,6'-trimethyl-[1,1'-biphenyl]-3-yl)-3-(2-(3-fluoro-5-(2-(3-fluoroazetidin-1-yl)ethyl)-2-oxopyridin-1(2H)-yl)-4-methylpentanamido)propanoic acid, or a pharmaceutically acceptable salt thereof.
195. The compound of embodiment 1, wherein the compound is (3S)-3-(4-fluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic acid, or a pharmaceutically acceptable salt thereof.
196. The compound of embodiment 1, wherein the compound is (3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid, or a pharmaceutically acceptable salt thereof.
197. The compound of embodiment 1, wherein the compound is (S)-3-(4,5-difluoro-2',6'-dimethyl-[1,1'-biphenyl]-3-yl)-3-((S)-2-(5-(2-(3-fluoroazetidin-1-yl)ethyl)-4-methyl-2-oxopyridin-1(2H)-yl)-4-methylpentanamido)propanoic acid, or a pharmaceutically acceptable salt thereof.
198. The compound of embodiment 1, wherein the compound is (S)-3-((S)-2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoic acid, or a pharmaceutically acceptable salt thereof.
199. The compound of embodiment 1, wherein the compound is (S)-3-((S)-2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic acid, or a pharmaceutically acceptable salt thereof.
200. The compound of embodiment 1, wherein the compound is (S)-3-((S)-2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic acid, or a pharmaceutically acceptable salt thereof.
201. The compound of embodiment 1, wherein the compound is (S)-3-(4,4'-difluoro-2',5,6'-trimethyl-[1,1'-biphenyl]-3-yl)-3-((S)-2-(5-(2-(dimethylamino)ethyl)-2-oxo-4-(trifluoromethyl)pyridin-1(2H)-yl)-4-methylpentanamido)propanoic acid, or a pharmaceutically acceptable salt thereof.
202. The compound of embodiment 1, wherein the compound is (S)-3-(5-chloro-4-fluoro-2',6'-dimethyl-[1,1'-biphenyl]-3-yl)-3-((S)-2-(5-(2-(3-methoxyazetidin-1-yl)ethyl)-2-oxo-4-(trifluoromethyl)pyridin-1(2H)-yl)-4-methylpentanamido)propanoic acid, or a pharmaceutically acceptable salt thereof.
203. The compound of embodiment 1, wherein the compound is (S)-3-((S)-2-(5-(2-(dimethylamino)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoic acid, or a pharmaceutically acceptable salt thereof.
204. The compound of embodiment 1, wherein the compound is (S)-3-(4,4'-difluoro-2',5,6'-trimethyl-[1,1'-biphenyl]-3-yl)-3-((S)-2-(3-(difluoromethyl)-5-(2-(dimethylamino)ethyl)-2-oxopyridin-1(2H)-yl)-4-methylpentanamido)propanoic acid, or a pharmaceutically acceptable salt thereof.
205. The compound of embodiment 1, wherein the compound is (S)-3-((S)-2-(5-(2-(dimethylamino)ethyl)-4-methyl-2-oxopyridin-1(2H)-yl)-5-methylhexanamido)-3-(4-fluoro-2',5,6'-trimethyl-[1,1'-biphenyl]-3-yl)propanoic acid, or a pharmaceutically acceptable salt thereof.
206. The compound of embodiment 1, wherein the compound is (S)-3-(4-fluoro-2',5,6'-trimethyl-[1,1'-biphenyl]-3-yl)-3-((S)-2-(3-fluoro-5-(2-(3-fluoroazetidin-1-yl)ethyl)-2-oxopyridin-1(2H)-yl)-4-methylpentanamido)propanoic acid, or a pharmaceutically acceptable salt thereof.
207. The compound of embodiment 1, wherein the compound is (S)-3-(4-fluoro-2',5,6'-trimethyl-[1,1'-biphenyl]-3-yl)-3-((S)-2-(3-fluoro-5-(2-((R)-3-fluoropyrrolidin-1-yl)ethyl)-2-oxopyridin-1(2H)-yl)-4-methylpentanamido)propanoic acid, or a pharmaceutically acceptable salt thereof.
208. The compound of embodiment 1, wherein the compound is (S)-3-(5-chloro-4-fluoro-2',6'-dimethyl-[1,1'-biphenyl]-3-yl)-3-((S)-2-(5-(2-(3-methoxyazetidin-1-yl)ethyl)-2-oxo-4-(trifluoromethyl)pyridin-1(2H)-yl)-4-methylpentanamido)propanoic acid, or a pharmaceutically acceptable salt thereof.
209. A pharmaceutical composition, comprising a compound of any one of embodiments 1-208; and a pharmaceutically acceptable excipient.
210. A method of inhibiting $\alpha_4\beta_7$ integrin in a cell, comprising contacting the cell with a compound of any one of embodiments 1-208 under conditions effective to reduce the adhesion of the cell to MAdCAM-1.
211. A method of reducing the adhesion of a cell comprising an $\alpha_4\beta_7$ integrin to MAdCAM-1, the method comprising contacting the cell with a compound of any one of embodiments 1-208 under conditions effective to reduce the adhesion of the cell to MAdCAM-1.
212. A method of treating inflammatory bowel disease, ulcerative colitis, or Crohn's disease, comprising administering to a subject in need thereof a therapeutically effective amount of a compound of any one of embodiments 1-208.

Example 1. General Schemes for the Synthesis of $\alpha_4\beta_7$ Inhibitors β-Amino Acid Synthesis The synthesis of β-amino acids can be achieved using well known procedures described in the literature, such as but not limited to "Enantioselective Synthesis of β-Amino Acids," Second
Edition, Editors: Eusebio Juaristi, Vadim A. Soloshonok, First published:27 Jan. 2005, John Wiley & Sons, Inc.; Ellman et. Al Acc. Chem. Res. 2002. 35, 984-995; Franklin A. Davis and Bang-Chi Chen Chem. Soc. Rev., 1998, 27, 13-18; Jacobsen, M. F.; Skrydstrup, T. J. Org. Chem. 2003, 68, 7122; Tang, T. P.; Ellman, J. A. J. Org. Chem. 2002, 67, 7819; and Tang, T. P.; Ellman, J. A. J. Org. Chem. 1999, 64, 12.
Reductive Aminations

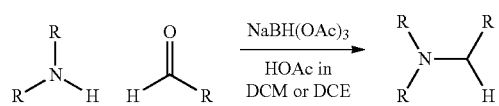

Procedure A: A mixture of amine (1 equiv.), aldehyde (1.2 equiv.) in DCM (1-2 mL/mmol amine) was stirred at room temperature for 30 min. Then NaBH(OAc)$_3$ (1.5 equiv.) was added portion-wise and stirred at room temperature overnight. The solvent was concentrated in vacuo and the residue was purified by silica gel chromatography to give the desired amine.

Procedure B: A mixture of aldehyde (1 equiv.), amine (1.05-2 equiv.) in DCE (3-4 mL/mmol of aldehyde) was stirred at room temperature for 10-30 mins. Then NaBH(OAc)$_3$ (3-4 equiv.) was added portion-wise and stirred at room temperature 1-16 until complete by LC/MS. The solvent was concentrated in vacuo and the residue was purified by silica gel chromatography to give the desired amine.

Procedure C: A mixture of aldehyde (1 equiv.), AcOH (1.2 equiv), amine (1.05-2 equiv.) in DCM (2-3 mL/mmol aldehyde) and MeOH (0.5 mL/mmol aldehyde) was stirred at room temperature for 15-30 mins Then NaBH(OAc)$_3$ (2 equiv.) was added portion-wise and stirred at room temperature 1-16 until complete by LC/MS. The solvent was concentrated in vacuo and the residue was purified by silica gel chromatography to give the desired amine.
Alkylations

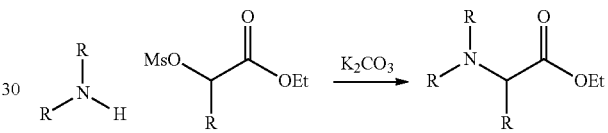

Procedure A: To a solution of amine (1 equiv.) in MeCN (3-4 mL/mmol amine) was added mesylate (1.5 equiv.) and K$_2$CO$_3$ (3 equiv.). The reaction mixture was stirred at 80° C. for 16 hours. The reaction mixture was concentrated in vacuo and the residue was purified by reverse phase HPLC to give the alkylated product.

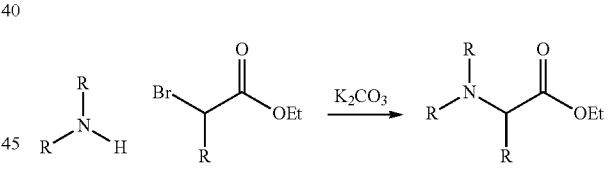

Procedure B: To a solution of amine (1 equiv.) in MeCN (3-4 mL/mmol amine) was added alkylbromide (2 equiv.) and K$_2$CO$_3$ (2 equiv.). The reaction mixture was stirred at 80° C. for 16 hours. The reaction mixture was concentrated in vacuo and the residue was purified by reverse phase HPLC to give the alkylated product.
Phenol Deprotections

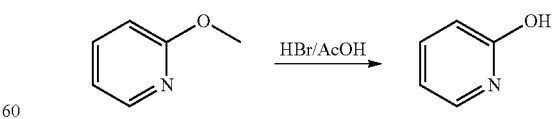

does this need R groups on pyridine?
A mixture of methoxypyridine (1 equiv.) in 44% HBr/AcOH (10 mL/mmol of substrate) was heated at 55-75° C. for 5-16 hours until complete by LCMS. The reaction was concentrated in vacuo and the residue purified by reverse phase HPLC to give the phenol product.

Wittig Reactions

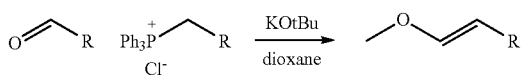

Procedure A: A mixture of (methoxymethyl)triphenylphosphonium chloride (1.5 equiv.), t-BuOK (2.5 equiv.) in dioxane (2 mL/mmol phosphonium salt) was stirred at room temperature for 15 minutes. Then aldehyde (1 equiv.) in THF (1 mL/mmol aldehyde) was added. The mixture was stirred for 2-16 h at room temperature. The reaction mixture was worked up (diluted with water and extracted with EtOAc; combined exacts dried over $Na_2SO_4$, filtered and concentrated) and purified by silica gel chromatography to give the enol ether product.

Procedure B: A mixture of (methoxymethyl)triphenylphosphonium chloride (1.1 equiv.), t-BuOK (2.5 equiv.) in THF (4 mL/mmol phosphonium salt) was stirred at 0° C. for 1 h. Then aldehyde (1 equiv.) in THF (2 mL/mmol aldehyde) was added. The mixture was stirred for 16 h at room temperature. The reaction mixture was worked up (diluted with water and extracted with EtOAc; combined exacts dried over $Na_2SO_4$, filtered, and concentrated) and purified by silica gel chromatography to give the enol ether product.

Enol Ether to Aldehyde

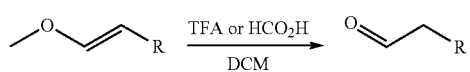

Procedure A: Enol ether (1 equiv.) was treated with TFA (2 mL/mmol) at room temperature for 4 hours. The solvent was removed in vacuo to provide the desired aldehyde.

Procedure B: Enol ether (1 equiv.) was treated with HCOOH (2 mL/mmol) at 70° C. for 2 hours. The solvent was removed in vacuo to provide the desired aldehyde.

Procedure C: To a solution of enol ether (1 equiv.) in DCM (15 mL/mmol enol ether) was added TFA (2 mL/mmol) and water (0.25 mL/mmol enol ether). The reaction was stirred at 45° C. for 18 h. The reaction was worked up (quenched with $NaHCO_3$, extracted with DCM; combined extracts dried over $Na_2SO_4$, filtered, and concentrated) to provide the desired aldehyde.

Stille Reaction

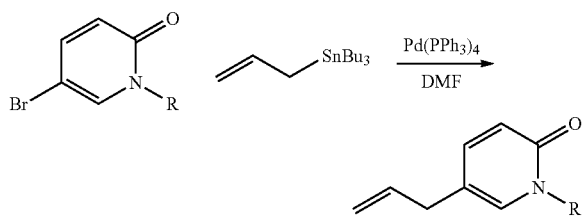

To a solution of arylbromide (1 equiv.) and allylstannane (1.2 equiv.) under $N_2$ in DMF (3 mL/mmol arylbromide) was added $Pd(PPh_3)_4$ (0.1 equiv.). The reaction was stirred at 100° C. for 16 hours. The reaction was concentration in vacuo then diluted with EtOAc, poured into 20% aq. KF and stirred for 1 h and extracted. The combined organic layers were dried over $Na_2SO_4$, filtered and concentrated, and purified by silica gel chromatography to provide the desired product.

Alkene to Aldehyde

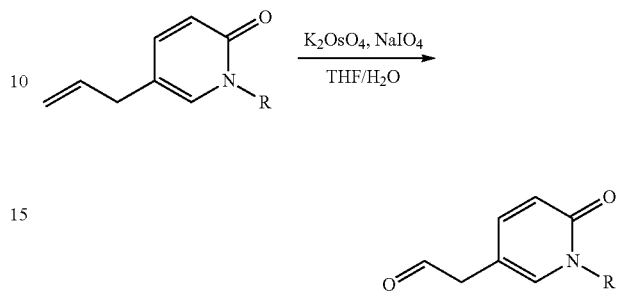

To a solution of alkene (1 equiv.) in $THF/H_2O$ (1:1) (10 mL/mmol of alkene) at 0° C. was added $K_2OsO_4 \cdot 2H_2O$ (0.01 equiv.). The mixture was stirred at 0° C. for 5 min then $NaIO_4$ (3 equiv.) in $H_2O$ (1 mL/mmol alkene) was added dropwise and stirred at 0° C. for 1 h then warmed to room temperature and stirred until complete by LCMS. The reaction was worked up (dilute with water and extract with EtOAc; combined organic layers were dried over $Na_2SO_4$, filtered, and concentrated) to give the desired aldehyde.

Ester to Acid

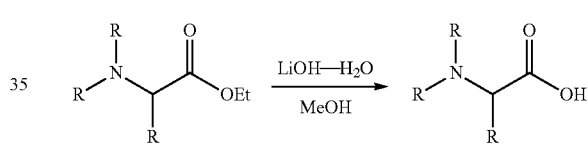

The ester (1 equiv.) was treated with $LiOH—H_2O$ (3-5 equiv.) in MeOH (1-3 mL/mmol ester) and water (1-3 mL/mmol ester) at room temperature for 1-5 h. The reaction was acidified with 1N HCl to pH=3 and concentrated. The residue was purified by prep HPLC to give the desired carboxylic acid product.

Amine Protection

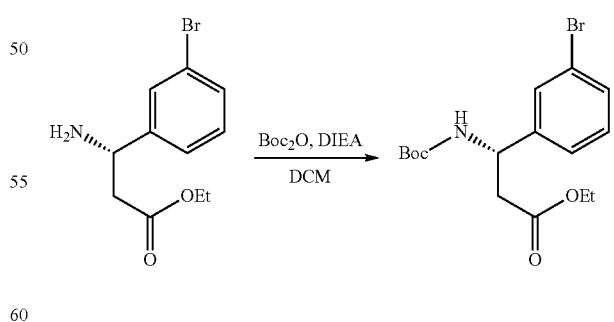

A mixture of amine (1 equiv.), DIEA (3 equiv.), and Boc2O (2 equiv.) was stirred in DCM (5 mL/mmole amine) at room temperature for 16 h until complete by LCMS. The reaction was worked up (wash with 0.5 N HCl, sat. $NaHCO_3$, brine, extract with DCM; combined organic layers were dried over $Na_2SO_4$, filtered, and concentrated) and purified by silica gel chromatography.

Preparation of Arylborane

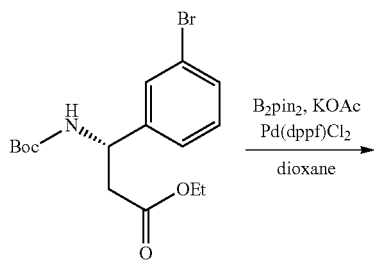

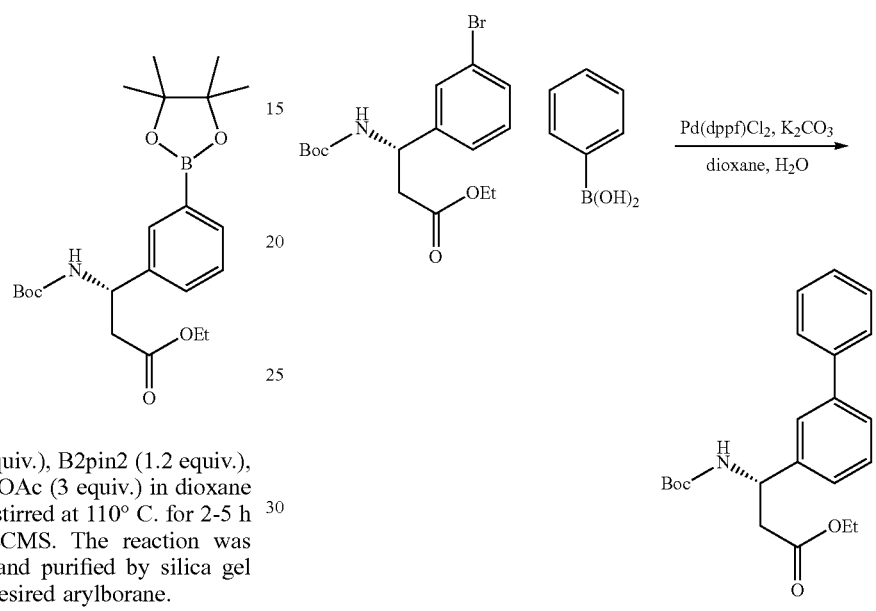

A mixture of arylbromide (1 equiv.), B2pin2 (1.2 equiv.), Pd(dppf)Cl2 (0.05 equiv.), and KOAc (3 equiv.) in dioxane (10 mL/mmol arylbromide) was stirred at 110° C. for 2-5 h under N2 until complete by LCMS. The reaction was filtered, concentrated in vacuo, and purified by silica gel chromotagraphy to provide the desired arylborane.

Suzuki Coupling

"Palladium-Catalyzed Cross-Coupling Reactions of Organoboron Compounds" N. Miyaura; A. Suzuki *Chem. Rev.* 1995, 957, 2457-2483.

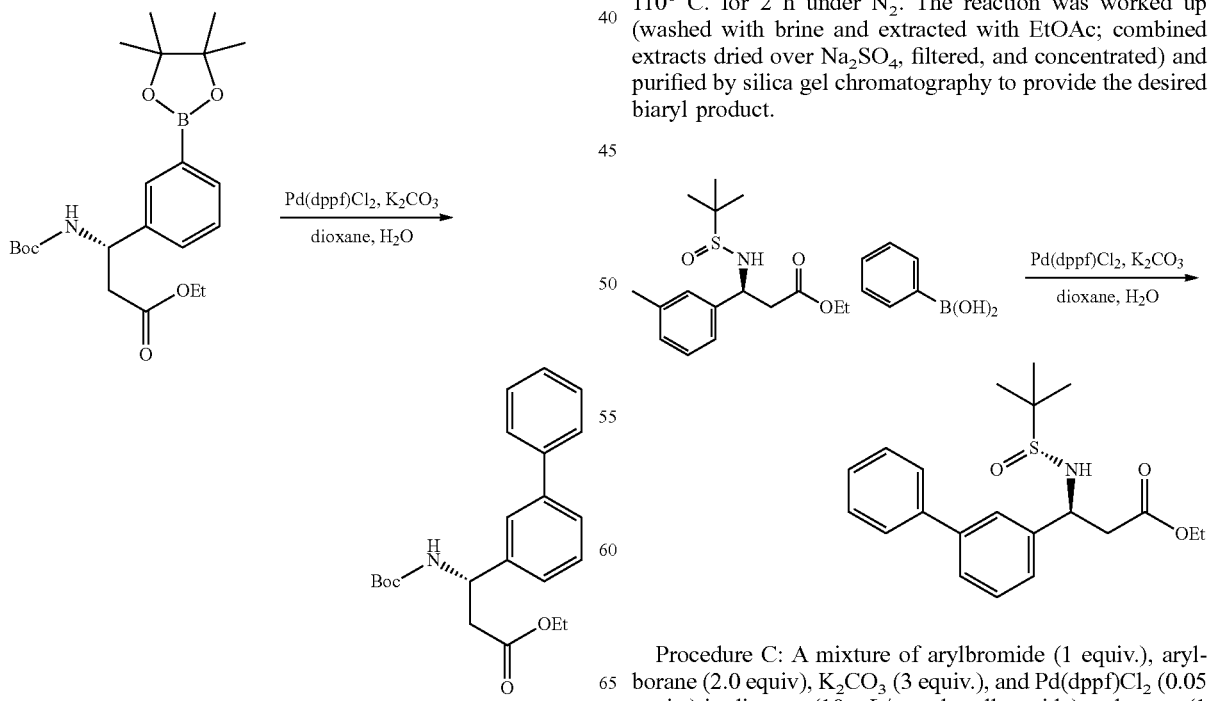

Procedure A: To a solution of arylborane (1 equiv.) in dioxane (10 mL/mmol arylborane) was added arylbromide (1.2 equiv.), Pd(dppf)Cl2 (0.1 equiv.), $K_2CO_3$ (2 equiv.), and water (2 mL/mmol). The reaction was stirred at 110° C. for 3 h under $N_2$. The reaction was worked up (washed with brine and extracted with EtOAc; combined extracts dried over $Na_2SO_4$, filtered, and concentrated) and purified by silica gel chromatography to provide the desired biaryl product.

Procedure B: To a solution of arylbromide (1 equiv.) and arylborane (1.1 equiv.) in dioxane (10 mL/mmol arylbromide) was added $K_2CO_3$ (2 equiv.) in water (2 mL/mmol) and Pd(dppf)Cl2 (0.1 equiv.). The reaction was stirred at 110° C. for 2 h under $N_2$. The reaction was worked up (washed with brine and extracted with EtOAc; combined extracts dried over $Na_2SO_4$, filtered, and concentrated) and purified by silica gel chromatography to provide the desired biaryl product.

Procedure C: A mixture of arylbromide (1 equiv.), arylborane (2.0 equiv), $K_2CO_3$ (3 equiv.), and Pd(dppf)Cl2 (0.05 equiv.) in dioxane (10 mL/mmol arylbromide) and water (1 mL/mmol) was stirred at 110° C. for 2 h under $N_2$ until complete by LCMS. The reaction was worked up (washed with brine and extracted with EtOAc; combined extracts dried over Na₂SO₄, filtered, and concentrated) and purified by silica gel chromatography to provide the desired biaryl product.

Boc Deprotection

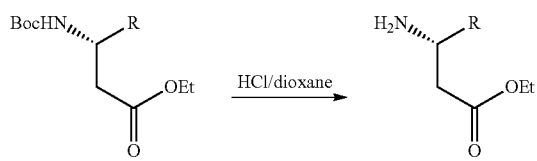

Boc-protected amine (1 equiv.) in DCM (4 mL/mmol amine) was added 4M HCl-dioxane (12 equiv.). The reaction was stirred for 1-2 h until complete by LCMS. The reaction was concentrated in vacuo to give the desired amine.

t-Butylsulfinyl Deprotection

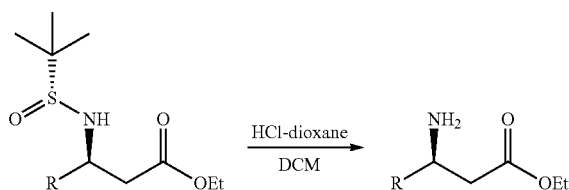

To a solution of t-butylsulfinylamine (1 equiv.) in DCM (0.5 mL/mmol amine) was added 4M HCl-dioxane (1.7 equiv.). The reaction was stirred for 0.5-1 h until complete by LCMS. The reaction was concentrated and purified by prep HPLC to give the desired amine.

Amide Bond Formation

"Peptide Coupling Reagents, More than a Letter Soup" A. El-Faham, F. Albericio Chem. Rev. 2011, 111, 11, 6557-6602; "Amide bond formation and peptide coupling" C. A. G. N. Montalbetti; V. Falque Tetrahedron 2005, 61, 10827-10852.

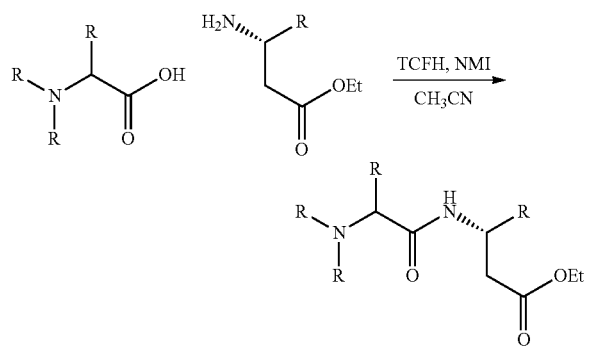

A mixture of amine (1 equiv.), carboxylic acid (1 equiv.), TCFH (2 equiv.), and NMI (4 equiv.) in CH₃CN (10 mL/mmol amine) was stirred at room temperature for 1-2 h until complete by LCMS. The reaction was concentrated in vacuo and purified by silica gel chromatography to give the desired amide product.

Ester Hydrolysis

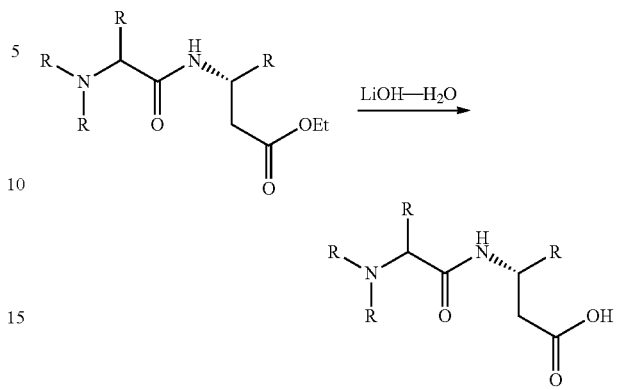

The ester (1 equiv.) was treated with LiOH—H₂O (3-5 equiv.) in MeOH (1-3 mL/mmol ester) and water (1-3 mL/mmol ester) at room temperature for 1-5 h. The reaction was acidified with 1N HCl to pH=4-5 and concentrated. The residue was purified by prep HPLC to give the desired carboxylic acid product.

Analytical Methods

LCMS Analytical Methods

Final compounds were analyzed using LC/MS conditions, with UV detector monitoring at 214 nm and 254 nm, and mass spectrometry scanning 110-800 amu in ESI+ ionization mode.

LC/MS A: column: XBridge C18, 4.6×50 mm, 3.5 μm; mobile phase: A water (10 mM ammonium hydrogen carbonate), B CH₃CN; gradient: 5%-95% B in 1.4 min, then 1.6 min hold; flow rate: 1.8 mL/min; oven temperature 50° C.

LC/MS B: column: SunFire C18, 4.6×50 mm, 3.5 μm; mobile phase: A water (0.01% TFA), B CH₃CN; gradient: 5%-95% B in 1.5 min, then 1.5 min hold; flow rate: 2.0 mL/min; oven temperature 50° C.

LC/MS C: column: XBridge C18, 4.6×50 mm, 3.5 μm; mobile phase: A water (10 mM ammonium hydrogen carbonate), B CH₃CN; gradient: 5%-95% B in 1.5 min, then 1.5 min hold; flow rate: 1.8 mL/min; oven temperature 50° C.

LC/MS D: column: Poroshell 120 EC-C18, 4.6×30 mm, 2.7 μm; mobile phase: A water (0.01% TFA), B CH₃CN (0.01% TFA); gradient: 5%-95% B in 1.2 min, then 1.8 min hold; flow rate: 2.2 mL/min; oven temperature 50° C.

Example 2. Preparation of Intermediates

Preparation of ethyl (S)-3-(5-bromo-2-fluoro-3-methylphenyl)-3-((tert-butoxycarbonyl)amino)propanoate Step 1: 5-bromo-2-fluoro-3-methylbenzaldehyde

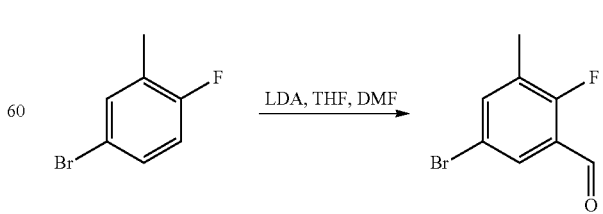

To a mixture of 4-bromo-1-fluoro-2-methylbenzene (10.0 g, 52.9 mmol, 1.0 eq) in anhydrous THF (100.0 mL) under nitrogen atmosphere at −78° C. was added Lithium diisopropylamide (2.0 M, 39.7 mL, 79.4 mmol, 1.5 eq) dropwise over the period of 10 mins and stirred at −78° C. for 1 hour. DMF (15.0 mL) was added dropwise and the mixture was stirred at −78° C. for 2 hours. LCMS showed that the reaction was completed. The reaction mixture was quenched with a saturated NH$_4$Cl solution (aq) (100 mL) at 0° C., extracted with EtOAc (100 mL×2). The organic layer was washed with brine (100 mL), dried over anhydrous Na$_2$SO$_4$, filtered and concentrated in vacuo. The residue obtained was purified by silica gel column (pet ether: EtOAc 9:1) to provide 5-bromo-2-fluoro-3-methylbenzaldehyde as a white solid (8.0 g). Yield 70% (ESI 218.9 [M+H]$^+$).

Step 2: (R, E)-N-(5-bromo-2-fluoro-3-methylbenzylidene)-2-methylpropane-2-sulfinamide

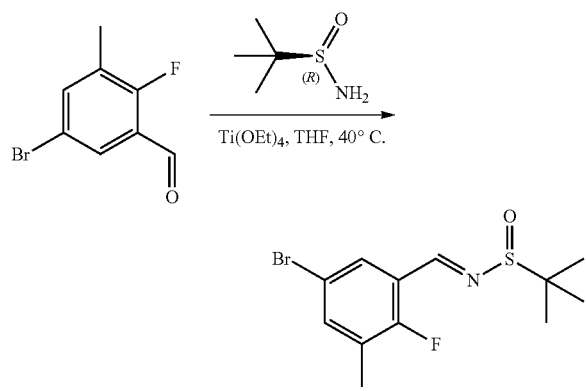

To a mixture of 5-bromo-2-fluoro-3-methylbenzaldehyde (8.0 g, 36.9 mmol, 1.00 eq) and (R)-2-methylpropane-2-sulfinamide (5.4 g, 44.3 mmol, 1.2 eq) in anhydrous THF (80 mL) under nitrogen atmosphere was added Ti(OEt)$_4$ (12.6 g, 55.4 mmol, 1.50 eq) dropwise at room temperature with the temperature maintained below 30° C. The reaction mixture was warmed to 40° C. and stirred for 1 hour. LCMS showed that the reaction was completed. Water (80 mL) and EtOAc (80 mL) was added into the mixture and stirred at room temperature for 5 mins. The mixture was filtered and washed with EtOAc (50 mL). The filtrate was separated. The organic layer was washed with water (100 mL) and brine (100 mL), dried over anhydrous Na$_2$SO$_4$, filtered and concentrated in vacuo to give crude product (R, E)-N-(5-bromo-2-fluoro-3-methylbenzylidene)-2-methylpropane-2-sulfinamide as a yellow solid (12.0 g, crude) which was used in the next step without further purification. Yield 100% (ESI 320.0 [M+H]$^+$).

Step 3: ethyl (S)-3-(5-bromo-2-fluoro-3-methylphenyl)-3-(((R)-tert-butylsulfinyl)amino)propanoate ethyl 2-bromoacetate+

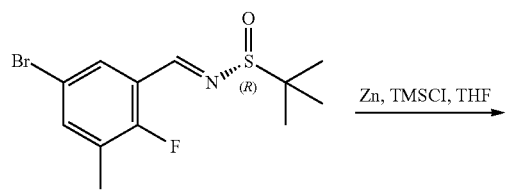

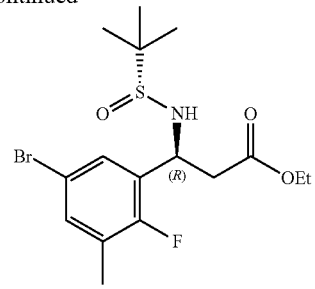

To a mixture of Zn (12.2 g, 187.5 mmol, 5.0 eq) in anhydrous THF (200 mL) under nitrogen atmosphere was added chlorotrimethylsilane (0.8 g, 7.5 mmol, 0.2 eq) dropwise at room temperature. The mixture was stirred at 60° C. for 1 hour under nitrogen atmosphere and cooled to 20-30° C. Ethyl 2-bromoacetate (1.57 g, 9.4 mmol, 0.25 eq) was added dropwise at 20-30° C. When the reaction mixture started to be exothermic, the rest of ethyl 2-bromoacetate (14.4 g, 86.3 mmol, 2.3 eq) was added dropwise during which time the reaction mixture was kept at 50-60° C. After the completion of the addition, the reaction mixture was stirred at 60° C. for 1 hour under nitrogen atmosphere. The reaction mixture was cooled to 0° C., (R, E)-N-(5-bromo-2-fluoro-3-methylbenzylidene)-2-methylpropane-2-sulfinamide (12.0 g, 37.5 mmol) in anhydrous THF (30 mL) was added dropwise and stirred at 25° C. for 1 hour. LCMS showed that the reaction was completed. MTBE (150 mL) and a solution of citric acid (3 g) in water (100 mL) were added into the mixture. The mixture was separated. The aqueous layer was extracted with MTBE (150 mL×2). The combined organic phase was washed with brine (200 mL), dried over anhydrous Na$_2$SO$_4$, filtered and concentrated in vacuo. The residue was purified by silica gel column (pet ether: EtOAc 3:1) to provide ethyl (S)-3-(5-bromo-2-fluoro-3-methylphenyl)-3-(((R)-tert-butylsulfinyl)amino)propanoate (9.0 g). Yield 59% (ESI 408.0 [M+H]$^+$).

Step 4: ethyl (S)-3-amino-3-(5-bromo-2-fluoro-3-methylphenyl)propanoate

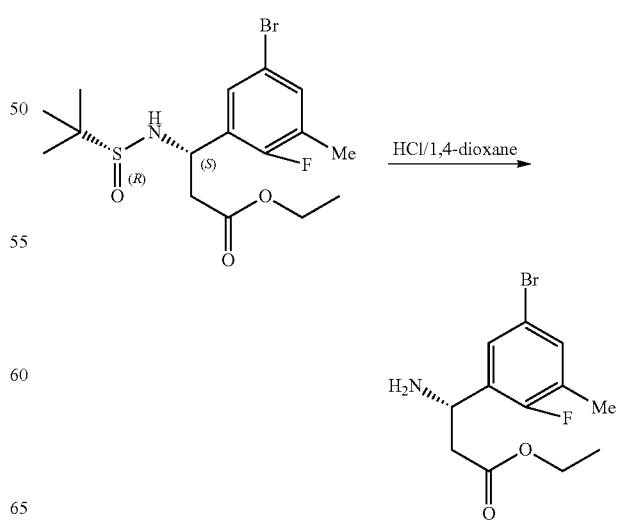

To a solution of ethyl (S)-3-(5-bromo-2-fluoro-3-methylphenyl)-3-(((R)-tert-butylsulfinyl)amino)propanoate (8.0 g, 19.6 mmol, 1.00 eq) in DCM (20 mL) was added HCl-dioxane (4 M, 20 mL, 80.0 mmol, 4.08 eq) and stirred at room temperature for 4 hours. LCMS showed that the reaction was completed. The mixture was filtered and concentrated in vacuo to give crude product ethyl (S)-3-amino-3-(5-bromo-2-fluoro-3-methylphenyl)propanoate as a yellow oil (8.0 g) used in the next step without further purification. Yield 100% (ESI 304.2 [M+H]$^+$).

Step 5: ethyl (S)-ethyl 3-(5-bromo-2-fluoro-3-methylphenyl)-3-(tert-butoxycarbonylamino)propanoate

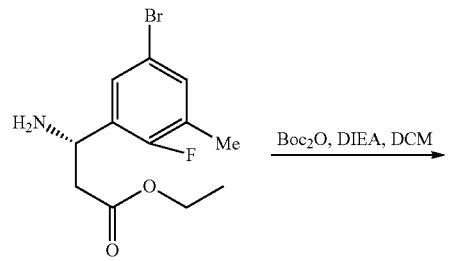

To a solution of ethyl (S)-3-amino-3-(5-bromo-2-fluoro-3-methylphenyl)propanoate (8.0 g, 19.6 mmol, 1.00 eq) in DCM (100 mL) was added DIEA (7.6 g, 59.0 mmol, 3.00 eq) and Boc20 (8.6 g, 39.2 mmol, 2.00 eq). The reaction mixture was stirred at room temperature for 16 hours. LCMS showed that the reaction was completed. The reaction mixture was diluted with DCM (200 mL) and washed with 0.5 N HCl (50 mL×3), saturated NaHCO$_3$ (50 mL) and brine (50 mL). The organic phase was dried over Na$_2$SO$_4$, filtered and concentrated in vacuo. The residue was purified by silica gel column (pet ether: EtOAc 3:1) to provide ethyl (S)-3-(5-bromo-2-fluoro-3-methylphenyl)-3-((tert-butoxycarbonyl)amino)propanoate as a brown oil (6.0 g). Yield 75% (ESI 404.1 (M+H)$^+$).

Preparation of ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate

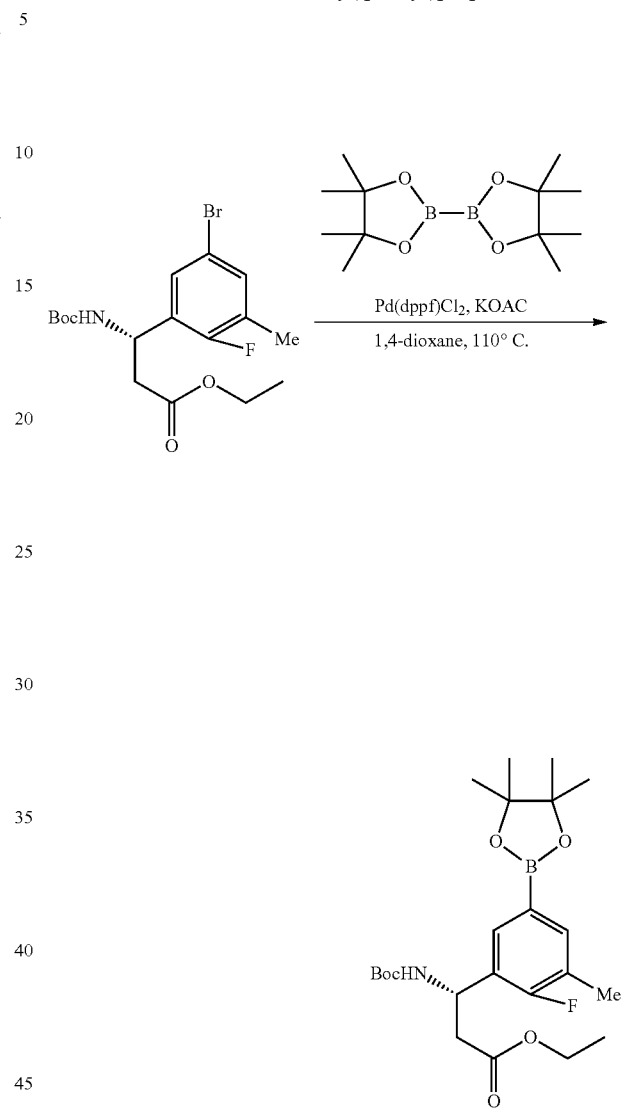

A mixture of ethyl (S)-3-(5-bromo-2-fluoro-3-methylphenyl)-3-((tert-butoxycarbonyl)amino)propanoate (1.0 g, 2.48 mmol, 1.0 eq), bis(pinacolato)diboron (756.28 mg, 2.98 mmol, 1.2 eq), Pd(dppf)Cl$_2$ (90.65 mg, 0.13 mmol, 0.05 eq) and KOAc (729.12 mg, 7.44 mmol, 3.0 eq) in 1,4-dioxane (20 mL) was stirred at 110° C. for 3 hours under nitrogen atmosphere. The reaction mixture was cooled to room temperature, filtered and concentrated in vacuo. The residue was purified by silica gel column (petroleum ether: EtOAc 2:1) to give (S)-ethyl 3-(tert-butoxycarbonylamino)-3-(2-fluoro-3-methyl-5-(4,4,5,5-tetramethyl-1,3,2-dioxaborolan-2-yl)phenyl)propanoate as a colorless oil (1.0 g). Yield 89% (ESI 452.2 (M+H)$^+$).

Preparation of ethyl (S)-3-amino-3-(2',4-difluoro-5,6'-dimethyl-[1,1'-biphenyl]-3-yl)propanoate

Step 1: ethyl(S)-3-((tert-butoxycarbonyl)amino)-3-(2',4-difluoro-5,6'-dimethyl-[1,1'-biphenyl]-3-yl)propanoate

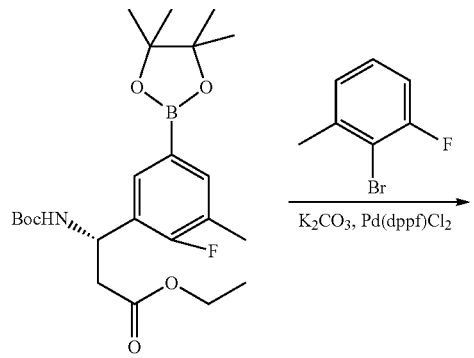

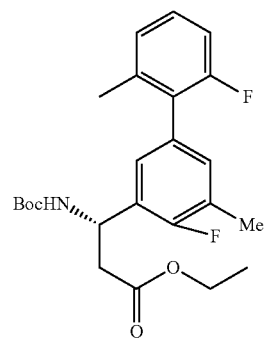

To a solution of ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate (300 mg, 0.66 mmol, 1.0 eq) in dioxane (5 mL) was added 2-bromo-1-fluoro-3-methylbenzene (150 mg, 0.79 mmol, 1.2 eq), Pd(dppf)Cl$_2$ (48 mg, 0.066 mmol, 0.1 eq), K$_2$CO$_3$ (182 mg, 1.32 mmol, 2.0 eq) and water (1 mL). The reaction mixture was stirred at 110° C. for 3 hours under nitrogen atmosphere. Water (10 mL) was added and the solution was extracted with EtOAc (20 mL×3). The combined organic phases were washed with brine (100 mL), dried over anhydrous Na$_2$SO$_4$, filtered and concentrated in vacuo. The residue was purified by silica gel column (petroleum ether: EtOAc 8:1) to provide ethyl (S)-3-((tert-butoxycarbonyl)amino)-3-(2',4-difluoro-5,6'-dimethyl-[1,1'-biphenyl]-3-yl)propanoate as a colorless oil (210 mg). Yield 73% (ESI 334.1 [M+H-100]$^+$).

Step 2: ethyl (S)-3-amino-3-(2',4-difluoro-5,6'-dimethyl-[1,1'-biphenyl]-3-yl)propanoate

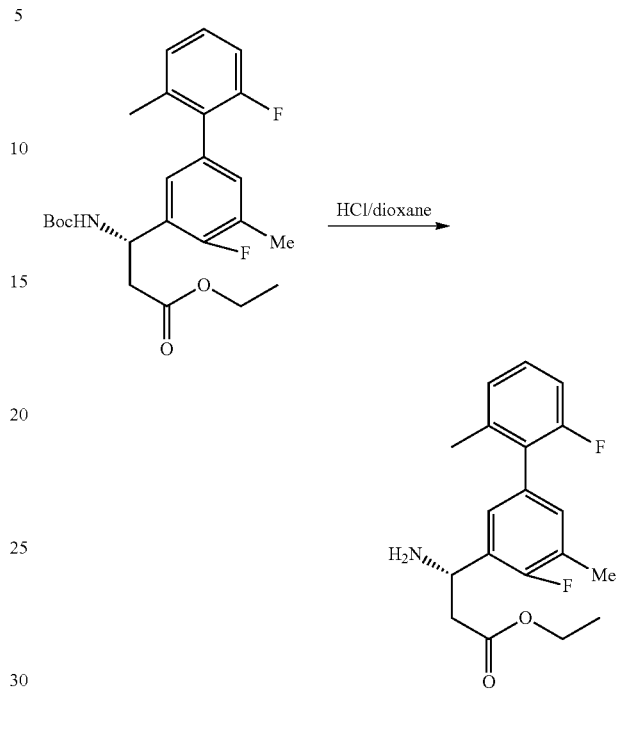

To a stirred solution of ethyl (S)-3-((tert-butoxycarbonyl)amino)-3-(2',4-difluoro-5,6'-dimethyl-[1,1'-biphenyl]-3-yl)propanoate (210 mg, 0.48 mmol, 1.0 eq) in DCM (2 mL) was added HCl-dioxane (4 M, 3.0 mL, 6.0 mmol, 12.5 eq). The mixture was stirred at room temperature for 2 hours. LCMS showed that the reaction was completed. The mixture was concentrated in vacuo to provide ethyl (S)-3-amino-3-(2',4-difluoro-5,6'-dimethyl-[1,1'-biphenyl]-3-yl)propanoate as a colorless oil (160 mg). Yield 99% (ESI 334.1 [M+H]$^+$).

Preparation of ethyl (S)-3-amino-3-(2'-cyano-4-fluoro-5,6'-dimethyl-[1,1'-biphenyl]-3-yl)propanoate hydrochloride

Step 1: ethyl (S)-3-((tert-butoxycarbonyl)amino)-3-(2'-cyano-4-fluoro-5,6'-dimethyl-[1,1'-biphenyl]-3-yl)propanoate

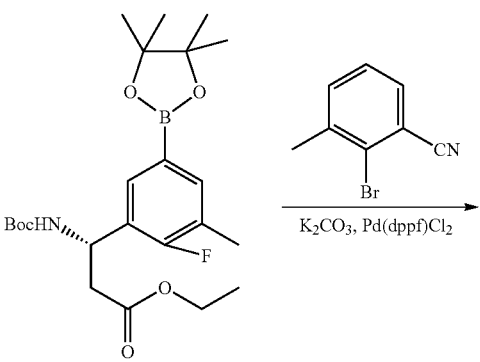

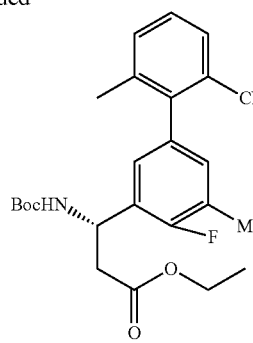

To a solution of ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate (350 mg, 0.77 mmol, 1.0 eq) in dioxane (10 mL) was added 2-bromo-3-methylbenzonitrile (226 mg, 1.16 mmol, 1.5 eq), Pd(dppf)Cl$_2$ (56 mg, 0.077 mmol), K$_2$CO$_3$ (193 mg, 1.4 mmol, 1.8 eq) and water (2 mL). The reaction mixture was stirred at 110° C. for 3 hours under nitrogen atmosphere. Water (20 mL) was added and the solution was extracted with EtOAc (20 mL×3). The combined organic phases were washed with brine (50 mL), dried over anhydrous Na$_2$SO$_4$, filtered and concentrated in vacuo. The residue was purified by silica gel column (petroleum ether: EtOAc 4:1) to provide ethyl (S)-3-((tert-butoxycarbonyl)amino)-3-(2'-cyano-4-fluoro-5,6'-dimethyl-[1,1'-biphenyl]-3-yl)propanoate as a colorless oil (260 mg). Yield 76% (ESI 341.1 [M+H-100]$^+$).

Step 2: ethyl(S)-3-amino-3-(2'-cyano-4-fluoro-5,6'-dimethyl-[1,1'-biphenyl]-3-yl)propanoate hydrochloride

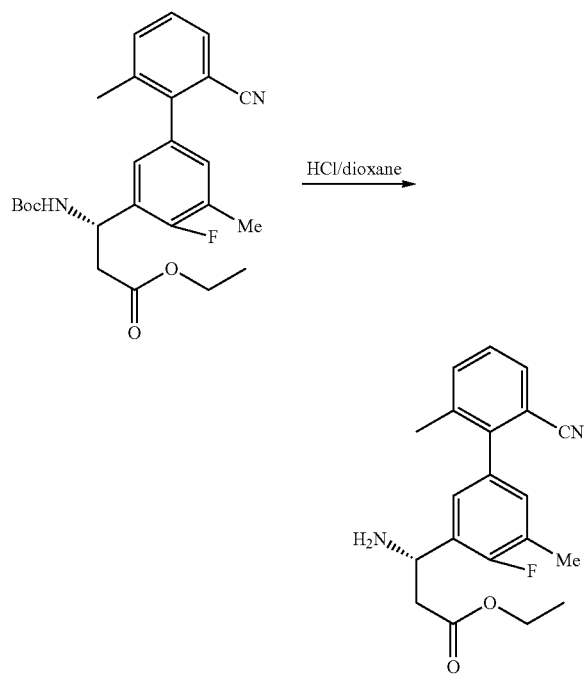

To a stirred solution of ethyl (S)-3-((tert-butoxycarbonyl)amino)-3-(2'-cyano-4-fluoro-5,6'-dimethyl-[1,1'-biphenyl]-3-yl)propanoate (230 mg, 0.52 mmol, 1.0 eq) in DCM (2 mL) was added HCl-dioxane (4 M, 2.0 mL, 4.0 mmol, 7.7 eq). The mixture was stirred at room temperature for 1 hour. LCMS showed that the reaction was completed. The mixture was concentrated in vacuo to provide ethyl (S)-3-amino-3-(2'-cyano-4-fluoro-5,6'-dimethyl-[1,1'-biphenyl]-3-yl)propanoate hydrochloride as a yellow oil (180 mg). Yield 91% (ESI 341.1 [M+H]$^+$).

Preparation of ethyl (S)-3-amino-3-(2'-chloro-4-fluoro-5,6'-dimethyl-[1,1'-biphenyl]-3-yl)propanoate Step 1: ethyl (S)-3-((tert-butoxycarbonyl)amino)-3-(2'-chloro-4-fluoro-5,6'-dimethyl-[1,1'-biphenyl]-3-yl)propanoate

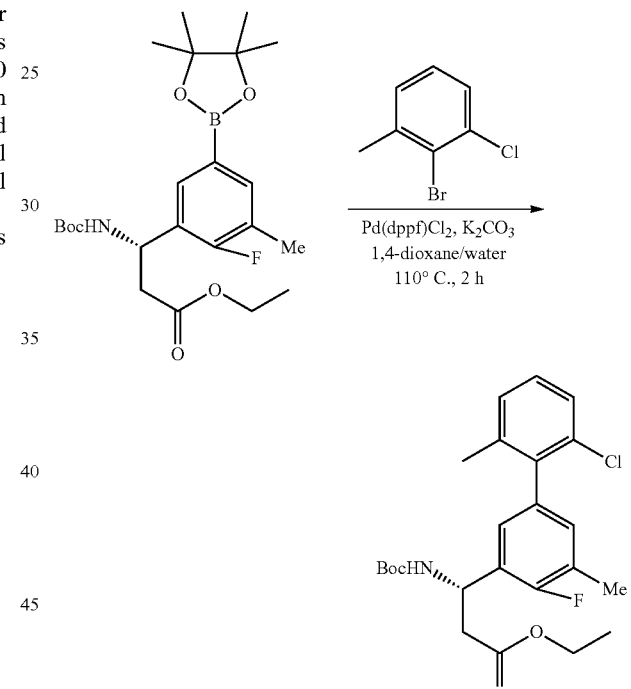

A mixture of ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate (1.0 g, 2.22 mmol, 1.00 eq), 2-bromo-1-chloro-3-methylbenzene (543 mg, 2.66 mmol, 1.20 eq), K$_2$CO$_3$ (613 mg, 4.44 mmol, 2.0 eq) and Pd(dppf)Cl$_2$ (81 mg, 0.11 mmol, 0.05 eq) in dioxane (10 mL) and H$_2$O (2 mL) was stirred at 110° C. for 2 hours under nitrogen atmosphere. Water (30 mL) was added and the solution was extracted with EtOAc (30 mL×3). The combined organic phases were washed with brine (100 mL), dried over anhydrous Na$_2$SO$_4$, filtered and concentrated in vacuo. The residue was purified by silica gel column (petroleum ether: EtOAc 2:1) to provide ethyl (S)-3-((tert-butoxycarbonyl)amino)-3-(2'-chloro-4-fluoro-5,6'-dimethyl-[1,1'-biphenyl]-3-yl)propanoate as a colorless oil (800 mg). Yield 80% (ESI 450.18 [M+H]$^+$).

Step 2: ethyl (S)-3-amino-3-(2'-chloro-4-fluoro-5,6'-dimethyl-[1,1'-biphenyl]-3-yl)propanoate

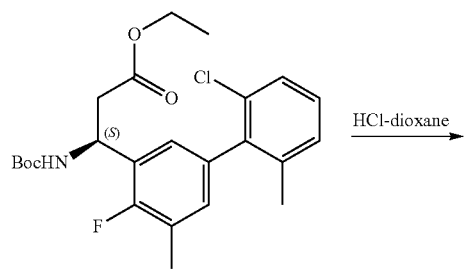

To a mixture of ethyl (S)-3-((tert-butoxycarbonyl)amino)-3-(2'-chloro-4-fluoro-5,6'-dimethyl-[1,1'-biphenyl]-3-yl)propanoate (300 mg, 0.67 mmol, 1.00 eq) in DCM (9 mL) was added HCl-dioxane (4 M, 9.0 mL, 36.0 mmol, 53.73 eq) and stirred at room temperature for 1 hour. LCMS showed that the reaction was completed. The mixture was concentrated in vacuo to provide ethyl (S)-3-amino-3-(2'-chloro-4-fluoro-5,6'-dimethyl-[1,1'-biphenyl]-3-yl)propanoate as a white solid (200 mg) used directly in the next reaction without further purification. Yield 86% (ESI 350.1[M+H]$^+$).

Preparation of ethyl (S)-3-amino-3-(2'-cyclopropyl-4-fluoro-5,6'-dimethyl-[1,1'-biphenyl]-3-yl)propanoate Step 1: ethyl (S)-3-((tert-butoxycarbonyl)amino)-3-(2'-cyclopropyl-4-fluoro-5,6'-dimethyl-[1,1'-biphenyl]-3-yl)propanoate

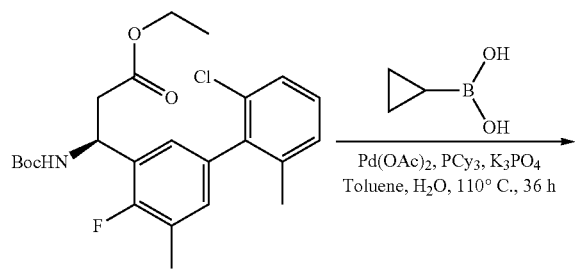

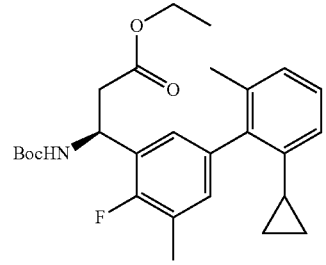

A mixture of ethyl (S)-3-((tert-butoxycarbonyl)amino)-3-(2'-chloro-4-fluoro-5,6'-dimethyl-[1,1'-biphenyl]-3-yl)propanoate (500 mg, 1.12 mmol, 1.00 eq), cyclopropylboronic acid (116 mg, 1.35 mmol, 1.20 eq), K$_3$PO$_4$ (475 mg, 2.24 mmol, 2.00 eq), PCy$_3$ (31 mg, 0.11 mmol, 0.10 eq) and Pd(OAc)$_2$ (11 mg, 0.11 mmol, 0.10 eq) in dioxane (10 mL) and H$_2$O (2 mL) was stirred at 110° C. for 36 hours under nitrogen atmosphere. Water (30 mL) was added and the solution was extracted with EtOAc (30 mL×3). The combined organic phases were washed with brine (20 mL), dried over anhydrous Na$_2$SO$_4$, filtered and concentrated in vacuo. The residue was purified by silica gel column (petroleum ether: EtOAc 2:1) to provide ethyl (S)-3-((tert-butoxycarbonyl)amino)-3-(2'-cyclopropyl-4-fluoro-5,6'-dimethyl-[1,1'-biphenyl]-3-yl)propanoate as a colorless oil (400 mg). Yield 79% (ESI 456.2 [M+H]$^+$).

Step 2: ethyl (S)-3-amino-3-(2'-cyclopropyl-4-fluoro-5,6'-dimethyl-[1,1'-biphenyl]-3-yl)propanoate

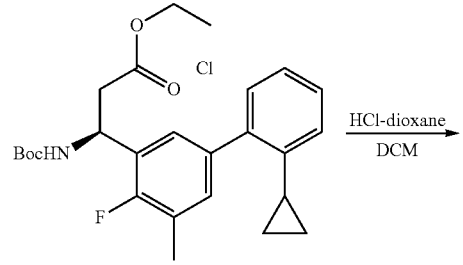

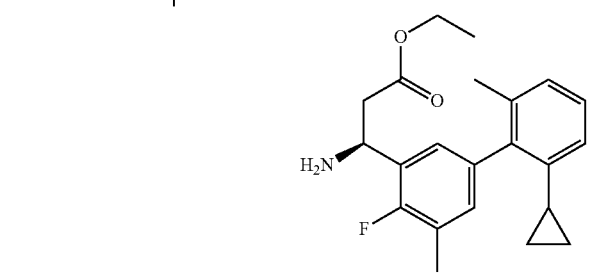

To a mixture of ethyl (S)-3-((tert-butoxycarbonyl)amino)-3-(2'-cyclopropyl-4-fluoro-5,6'-dimethyl-[1,1'-biphenyl]-3-yl)propanoate (400 mg, 0.88 mmol, 1.0 eq) in DCM (9 mL) was added HCl-dioxane (4 M, 9.0 mL, 36.0 mmol, 40.9 eq) and stirred at room temperature for 1 hour. LCMS showed that the reaction was completed. The mixture was concentrated in vacuo to provide ethyl (S)-3-amino-3-(2'-cyclopropyl-4-fluoro-5,6'-dimethyl-[1,1'-biphenyl]-3-yl)propanoate as a white solid (300 mg) used directly in the next reaction without further purification. Yield 96% (ESI 356.2 [M+H]$^+$).

Preparation of ethyl (S)-3-amino-3-(4-fluoro-4'-methoxy-2',5,6'-trimethyl-[1,1'-biphenyl]-3-yl)propanoate hydrochloride Step 1: ethyl (S)-3-amino-3-(2'-ethyl-4-fluoro-5,6'-dimethyl-[1,1'-biphenyl]-3-yl)propanoate hydrochloride

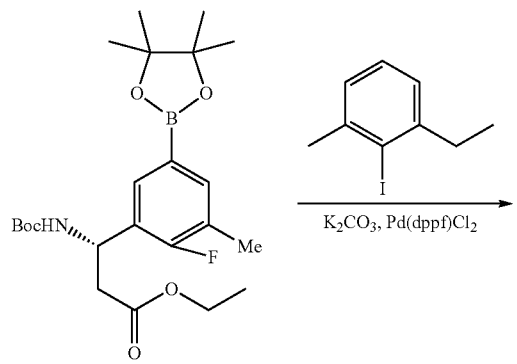

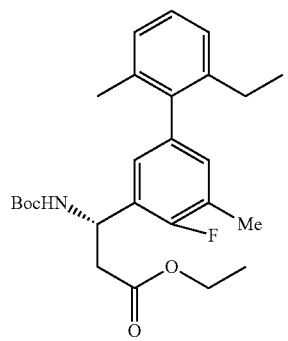

To a solution of ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate (350 mg, 0.77 mmol, 1.0 eq) in dioxane (10 mL) was added 1-ethyl-2-iodo-3-methylbenzene (286 mg, 1.16 mmol, 1.5 eq), Pd(dppf)Cl$_2$ (56 mg, 0.077 mmol, 0.1 eq), K$_2$CO$_3$ (193 mg, 1.4 mmol, 1.8 eq) and water (2 mL). The reaction mixture was stirred at 110° C. for 3 hours under nitrogen atmosphere. Water (10 mL) was added and the solution was extracted with EtOAc (20 mL×3). The combined organic phases were washed with brine (60 mL), dried over anhydrous Na$_2$SO$_4$, filtered and concentrated in vacuo. The residue was purified by silica gel column (petroleum ether: EtOAc 4:1) to provide ethyl (S)-3-((tert-butoxycarbonyl)amino)-3-(2'-ethyl-4-fluoro-5,6'-dimethyl-[1,1'-biphenyl]-3-yl)propanoate as a colorless oil (240 mg). Yield 70% (ESI 344.2 [M+H-100]$^+$).

Step 2: ethyl (S)-3-amino-3-(2'-ethyl-4-fluoro-5,6'-dimethyl-[1,1'-biphenyl]-3-yl)propanoate hydrochloride

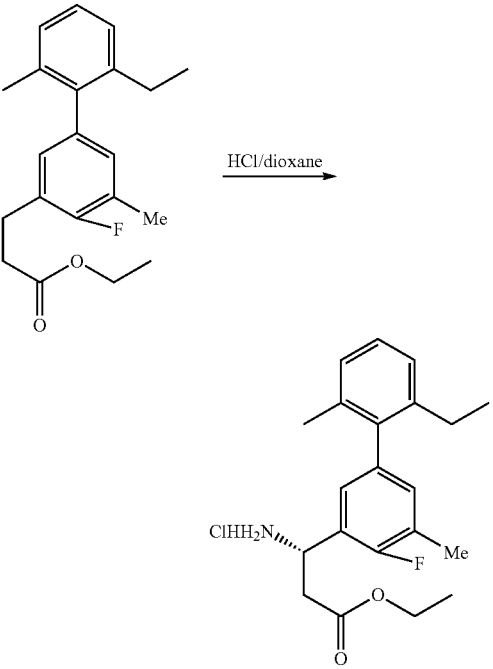

To a stirred solution of ethyl (S)-3-((tert-butoxycarbonyl)amino)-3-(2'-ethyl-4-fluoro-5,6'-dimethyl-[1,1'-biphenyl]-3-yl)propanoate (210 mg, 0.47 mmol, 1.0 eq) in DCM (2 mL) was added HCl-dioxane (4 M, 3.0 mL, 6.0 mmol, 12.8 eq). The mixture was stirred at room temperature for 1 hour. LCMS showed that the reaction was completed. The mixture was concentrated in vacuo to provide ethyl (S)-3-amino-3-(2'-ethyl-4-fluoro-5,6'-dimethyl-[1,1'-biphenyl]-3-yl)propanoate hydrochloride as a colorless oil (170 mg). Yield 94% (ESI 344.1 [M+H]$^+$).

Preparation of (S)-ethyl 3-amino-3-(4-fluoro-2'-methoxy-5,6'-dimethylbiphenyl-3-yl)propanoate Step 1: ethyl(S)-3-(((R)-tert-butylsulfinyl)amino)-3-(4-fluoro-2',4',5,6'-tetramethyl-[1,1'-biphenyl]-3-yl)propanoate

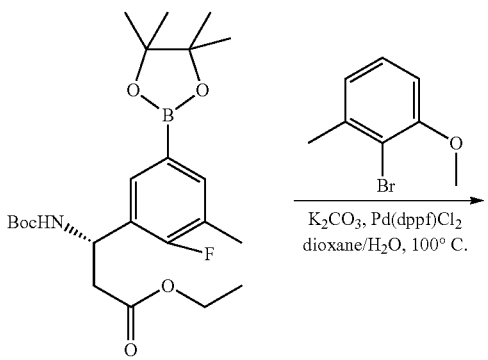

-continued

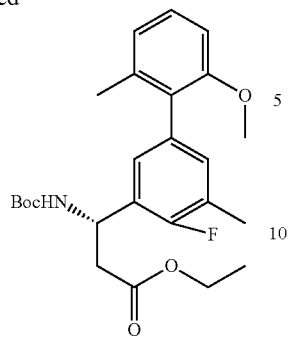

A mixture of (S)-ethyl 3-(tert-butoxycarbonylamino)-3-(2-fluoro-3-methyl-5-(4,4,5,5-tetramethyl-1,3,2-dioxaborolan-2-yl)phenyl)propanoate (1 g, 2.22 mmol, 1.0 eq), 2-bromo-1-methoxy-3-methylbenzene (666 mg, 3.33 mmol, 1.5 eq), K$_2$CO$_3$ (919 mg, 6.66 mmol, 3.0 eq) and Pd(dppf)Cl$_2$ (162 mg, 0.222 mmol, 0.1 eq) in dioxane (15 mL) and H$_2$O (1.5 mL) was stirred at 100° C. under nitrogen atmosphere for 3 hours. LCMS showed the reaction was completed. The reaction mixture was cooled to room temperature. Water (50 mL) was added and the mixture was extracted with EtOAc (50 mL×3). The combined organic layers were washed with brine (100 mL), dried over Na$_2$SO$_4$, filtered and concentrated in vacuo. The residue was purified by silica gel column (pet ether: EtOAc 2:1) to provide (S)-ethyl 3-(tert-butoxycarbonylamino)-3-(4-fluoro-2'-methoxy-5,6'-dimethylbiphenyl-3-yl)propanoate as a yellow oil (0.96 g). Yield 97% (ESI 346.1 [M+H]$^+$).

Step 2: (S)-ethyl 3-amino-3-(4-fluoro-2'-methoxy-5,6'-dimethylbiphenyl-3-yl)propanoate

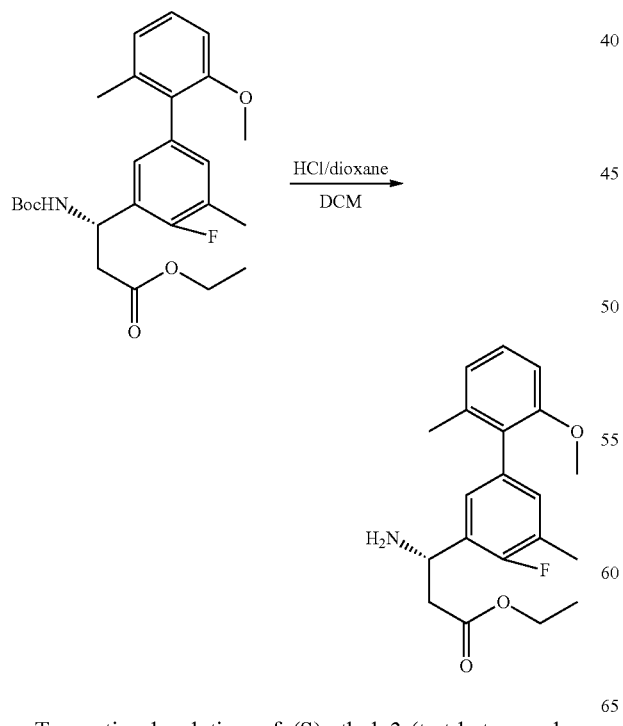

To a stirred solution of (S)-ethyl 3-(tert-butoxycarbonylamino)-3-(4-fluoro-2'-methoxy-5,6'-dimethylbiphenyl-3-yl)propanoate (0.96 g, 2.15 mmol, 1.0 eq) in DCM (7 mL) was added HCl-dioxane (4 M, 2.15 mL, 4 eq) and stirred at 25° C. for 2 hours. LCMS showed that the reaction was completed. The mixture was concentrated in vacuo and the residue was purified by reverse phase HPLC on a C18/40 g column (A: water 10 mM NH$_4$HCO$_3$, B: MeOH, 0~100%) to provide (S)-ethyl 3-amino-3-(4-fluoro-2'-methoxy-5,6'-dimethylbiphenyl-3-yl)propanoate as a yellow oil (0.6 g). Yield 81% (ESI 346.1 [M+H]$^+$).

Preparation of (S)-ethyl 3-amino-3-(4-fluoro-2'-methoxy-5-methyl-6'-(trifluoromethyl)biphenyl-3-yl)propanoate Step 1:
1-methoxy-2-nitro-3-(trifluoromethyl)benzene

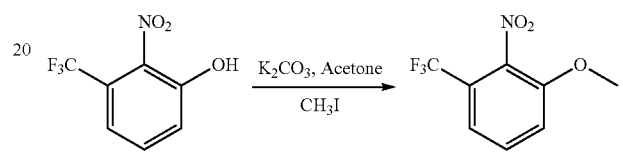

To a mixture of 2-nitro-3-(trifluoromethyl)phenol (1.5 g, 7.25 mmol, 1.0 eq) in acetone (20 mL) was added K$_2$CO$_3$ (3 g, 21.75 mmol, 3 eq) and CH$_3$I (5.15 g, 36.25 mmol, 5 eq) and stirred at room temperature for 16 hours. LCMS showed that the reaction was completed. The reaction mixture was filtered, washed with EtOAc (20 mL). The filtrate was concentrated in vacuo and the residue was purified by silica gel column (pet ether: EtOAc 2:1) to provide 1-methoxy-2-nitro-3-(trifluoromethyl)benzene as a white solid (1.3 g). Yield 81%.

Step 2: 2-methoxy-6-(trifluoromethyl)aniline

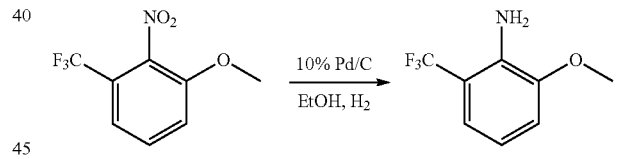

To a mixture of 1-methoxy-2-nitro-3-(trifluoromethyl)benzene (1.3 g, 5.88 mmol, 1.0 eq) in EtOH (20 mL) was added 10% Pd/C (700 mg) and stirred at room temperature for 16 hours under H$_2$ atmosphere (2 L, 1 atm). LCMS showed that the reaction was completed. The reaction mixture was filtered and the filtrated concentrated in vacuo to provide 2-methoxy-6-(trifluoromethyl)aniline as a white solid (0.75 g). Yield 67% (ESI 192.1 [M+H]$^+$).

Step 3:
2-bromo-1-methoxy-3-(trifluoromethyl)benzene

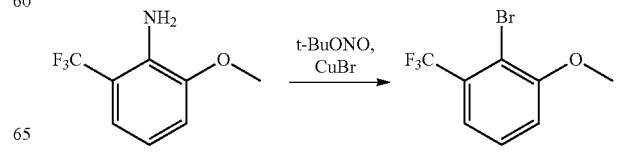

To a mixture of 2-methoxy-6-(trifluoromethyl)aniline (700 mg, 3.66 mmol, 1.0 eq) in MeCN (15 mL) was added t-BuONO (565 mg, 5.49 mmol, 1.5 eq) and CuBr (628 mg, 4.39 mmol, 1.2 eq). The mixture was stirred at 60° C. for 2 hours. LCMS showed that the reaction was completed. The reaction mixture was concentrated in vacuo and the residue was purified by silica gel column (pet ether: EtOAc 10:1) to provide 2-bromo-1-methoxy-3-(trifluoromethyl)benzene as a colorless oil (400 mg). Yield 43%.

Step 4: (S)-ethyl 3-(tert-butoxycarbonylamino)-3-(4-fluoro-2'-methoxy-5-methyl-6'-(trifluoromethyl)biphenyl-3-yl)propanoate

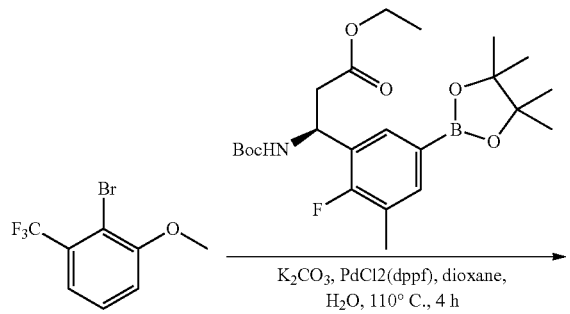

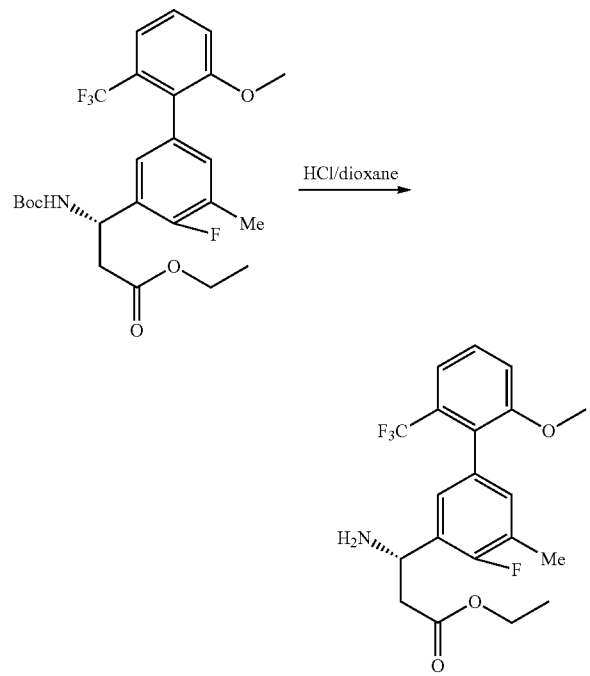

A mixture of 2-bromo-1-methoxy-3-(trifluoromethyl)benzene (400 mg, 1.57 mmol, 1.00 eq), (S)-ethyl 3-(tert-butoxycarbonylamino)-3-(2-fluoro-3-methyl-5-(4,4,5,5-tetramethyl-1,3,2-dioxaborolan-2-yl)phenyl)propanoate (708 mg, 1.57 mmol, 1.0 eq), K$_2$CO$_3$ (650 mg, 4.71 mmol, 3.0 eq) and Pd(dppf)Cl$_2$ (115 mg, 0.157 mmol, 0.1 eq) in dioxane (8 mL) and H$_2$O (0.8 mL) was stirred at 110° C. for 4 hours under nitrogen atmosphere. LCMS showed that the reaction was completed. The mixture was cooled to room temperature. Water (30 mL) was added and the mixture was extracted with EtOAc (30 mL×3). The combined organic phases was washed with brine (30 mL), dried over anhydrous Na$_2$SO$_4$, filtered and concentrated in vacuo. The residue was purified by silica gel column (pet ether: EtOAc 10:1) to provide (S)-ethyl 3-(tert-butoxycarbonylamino)-3-(4-fluoro-2'-methoxy-5-methyl-6'-(trifluoromethyl)biphenyl-3-yl)propanoate (400 mg) as a colorless oil. Yield 51% (ESI 400.1 [M-Boc]$^+$).

Step 5: (S)-ethyl 3-amino-3-(4-fluoro-2'-methoxy-5-methyl-6'-(trifluoromethyl)biphenyl-3-yl)propanoate

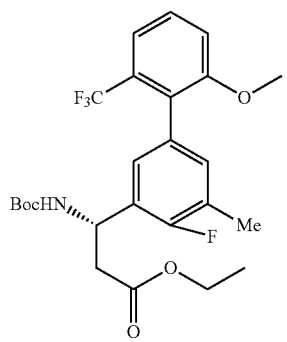

To a stirred solution of (S)-ethyl 3-(tert-butoxycarbonylamino)-3-(4-fluoro-2'-methoxy-5-methyl-6'-(trifluoromethyl)biphenyl-3-yl)propanoate (400 mg, 0.8 mmol, 1.00 eq) in DCM (6 mL) was added HCl-dioxane (4 M, 0.8 mL, 3.2 mmol, 4 eq) and stirred at room temperature for 2 hours. LCMS showed that the reaction was completed. The mixture was concentrated in vacuo and the residue was purified by reverse phase HPLC on a C18/120 g column (A: water 10 mM NH$_4$HCO$_3$, B: MeOH, 0~100%) to provide (S)-ethyl 3-amino-3-(4-fluoro-2'-methoxy-5-methyl-6'-(trifluoromethyl)biphenyl-3-yl)propanoate (280 mg) as a colorless oil. Yield 87% (ESI 400.1 [M+H]$^+$).

Preparation of (S)-ethyl 3-amino-3-(2',6'-dichloro-4-fluoro-5-methylbiphenyl-3-yl)propanoate Step 1: (S)-ethyl 3-(tert-butoxycarbonylamino)-3-(2',6'-dichloro-4-fluoro-5-methylbiphenyl-3-yl)propanoate

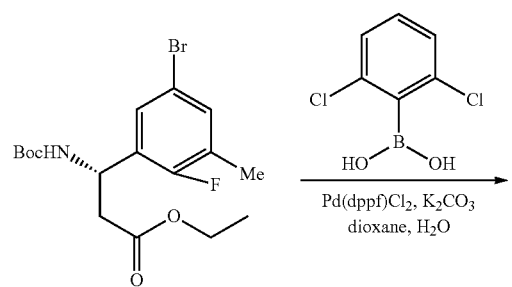

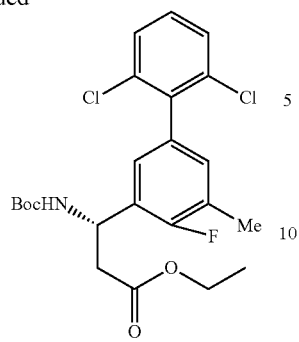

To a mixture of methyl (S)-ethyl 3-(5-bromo-2-fluoro-3-methylphenyl)-3-(tert-butoxycarbonylamino)propanoate (0.5 g, 1.29 mmol, 1 eq) and 2,6-dichlorophenylboronic acid (0.26 g, 1.36 mmol, 1.1 eq) in dioxane (10 mL) was added a solution of $K_2CO_3$ (0.34 g, 2.48 mmol, 2 eq) in $H_2O$ (2 mL) and Pd(dppf)Cl$_2$ (90 mg, 0.124 mmol, 0.1 eq). The mixture was heated to 110° C. for 2 hours under nitrogen atmosphere. The mixture was cooled to room temperature. Water (20 mL) was added and the solution was extracted with EtOAc (20 mL×3). The combined organic phases were concentrated in vacuo and the residue was purified by silica gel column (pet ether: EtOAc 1:1) to provide (S)-ethyl 3-(tert-butoxycarbonylamino)-3-(2',6'-dichloro-4-fluoro-5-methylbiphenyl-3-yl)propanoate a colorless oil (0.550 g). Yield 94% (ESI 470.4 [M+H]$^+$).

Step 2: (S)-methyl 3-amino-3-(2',6'-dichloro-4-fluoro-5-methylbiphenyl-3-yl)propanoate

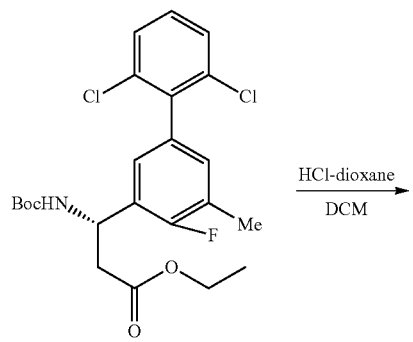

To a mixture of methyl (S)-ethyl 3-(tert-butoxycarbonylamino)-3-(2',6'-dichloro-4-fluoro-5-methylbiphenyl-3-yl)propanoate (0.55 g, 1.21 mmol, 1 eq) in DCM (6 mL) was added HCl-dioxane (4 M, 3 mL, 12 mmol, 10 eq). The mixture was stirred at room temperature for 1 hour. LCMS showed that the reaction was completed. The mixture was concentrated in vacuo to give crude product (S)-ethyl 3-amino-3-(2',6'-dichloro-4-fluoro-5-methylbiphenyl-3-yl)propanoate as a white solid (0.42 g) used directly in the next reaction without further purification. Yield 98% (ESI 370.3 [M+H]$^+$).

Preparation of ethyl (S)-3-amino-3-(2',4-difluoro-4',5,6'-trimethyl-[1,1'-biphenyl]-3-yl)propanoate Step 1: 2-fluoro-4,6-dimethylaniline

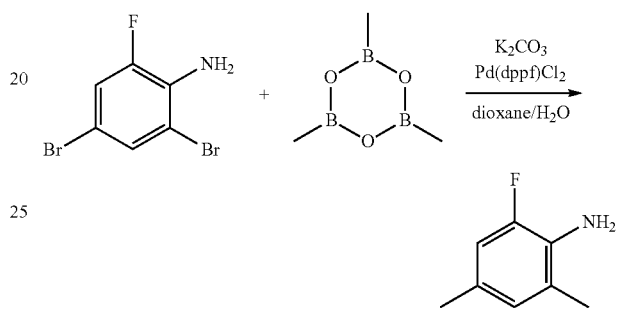

A mixture of 2,4-dibromo-6-fluoroaniline (5.0 g, 18.59 mmol, 1.0 eq), 2,4,6-trimethyl-1,3,5,2,4,6-trioxatriborinane (3.5 M in THF, 21.2 mL, 74.36 mmol, 4.0 eq), Pd(dppf)Cl$_2$ (680 mg, 0.93 mmol, 0.05 eq) and $K_2CO_3$ (7.71 g, 55.78 mmol, 3.0 eq) in dioxane (60 mL) and $H_2O$ (8 mL) was stirred at 110° C. for 12 hours under nitrogen atmosphere. The mixture was cooled to room temperature. Water (30 mL) was added and the solution was extracted with EtOAc (35 mL×3). The combined organic phases were washed with brine (20 mL), dried over anhydrous Na$_2$SO$_4$, filtered and concentrated in vacuo. The residue was purified by silica gel column (petroleum ether: EtOAc 20:1) to provide 2-fluoro-4,6-dimethylaniline as a yellow oil (2.16 g). Yield 83.5% (ESI 140.2 [M+H]$^+$).

Step 2: 2-bromo-1-fluoro-3,5-dimethylbenzene

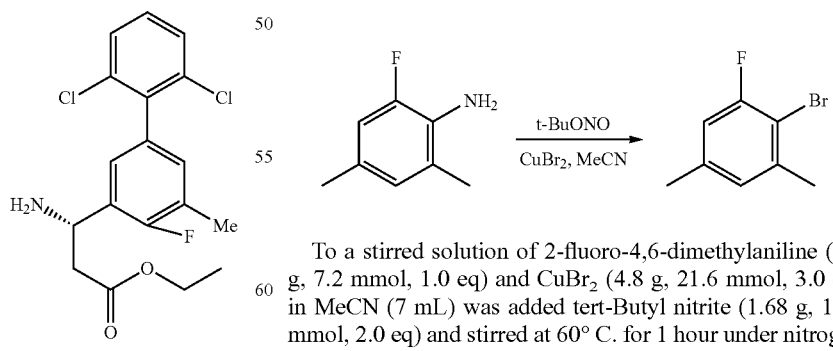

To a stirred solution of 2-fluoro-4,6-dimethylaniline (1.0 g, 7.2 mmol, 1.0 eq) and CuBr$_2$ (4.8 g, 21.6 mmol, 3.0 eq) in MeCN (7 mL) was added tert-Butyl nitrite (1.68 g, 14.4 mmol, 2.0 eq) and stirred at 60° C. for 1 hour under nitrogen atmosphere. LCMS showed that the reaction was completed. The mixture was filtered and concentrated in vacuo. The residue was purified by silica gel column (petroleum ether) to provide 2-bromo-1-fluoro-3,5-dimethylbenzene as a yellow oil (560 mg). Yield 38%.

Step 3: ethyl (S)-3-((tert-butoxycarbonyl)amino)-3-(2',4-difluoro-4',5,6'-trimethyl-[1,1'-biphenyl]-3-yl)propanoate

Step 4: ethyl (S)-3-amino-3-(2',4-difluoro-4',5,6'-trimethyl-[1,1'-biphenyl]-3-yl)propanoate

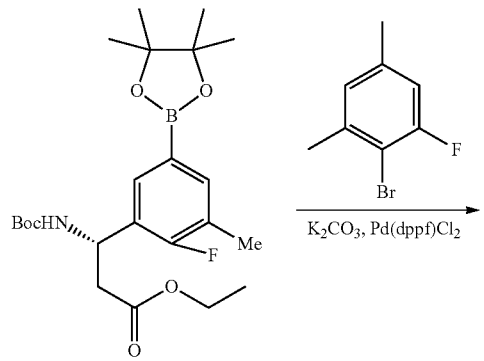

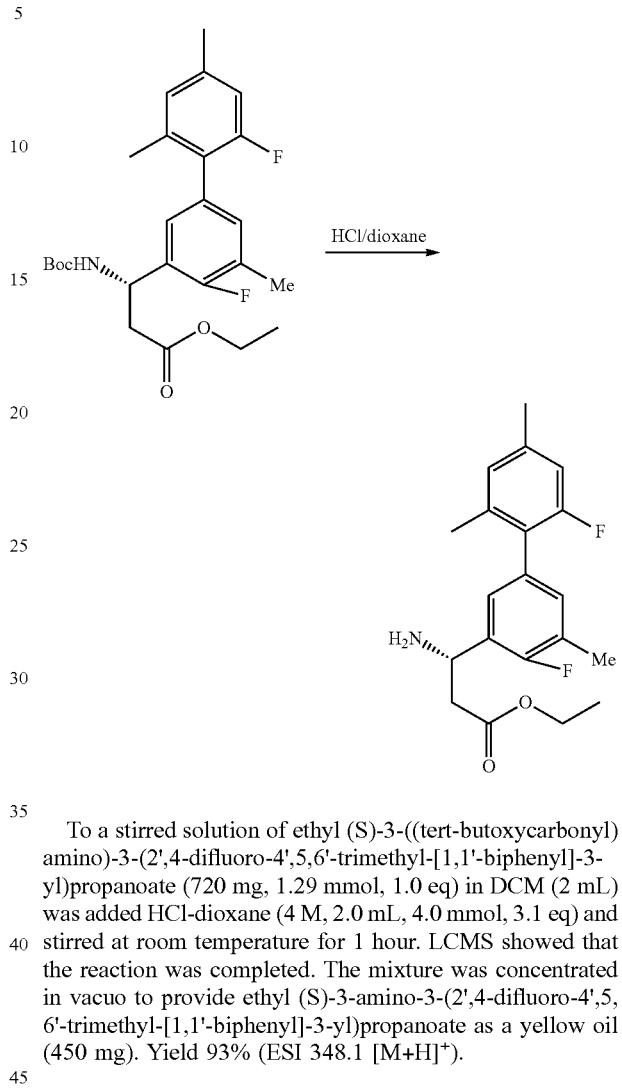

A mixture of ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate (556 mg, 1.23 mmol, 1.0 eq), 2-bromo-1-fluoro-3,5-dimethylbenzene (250 mg, 1.23 mmol, 1.0 eq), Pd(dppf)Cl$_2$ (45 mg, 0.062 mmol, 0.05 eq) and K$_2$CO$_3$ (510 mg, 3.69 mmol, 3.0 eq) in dioxane (6 mL) and water (2 mL) was stirred at 110° C. for 2 hours under nitrogen atmosphere. Water (35 mL) was added and the solution was extracted with EtOAc (25 mL×3). The combined organic phases were washed with brine (50 mL), dried over anhydrous Na$_2$SO$_4$, filtered and concentrated in vacuo. The residue was purified by silica gel column (petroleum ether: EtOAc 7:1) to provide ethyl (S)-3-((tert-butoxycarbonyl)amino)-3-(2',4-difluoro-4',5,6'-trimethyl-[1,1'-biphenyl]-3-yl)propanoate as a yellow oil (365 mg). Yield 66% (ESI 348.1 [M+H-100]$^+$).

To a stirred solution of ethyl (S)-3-((tert-butoxycarbonyl)amino)-3-(2',4-difluoro-4',5,6'-trimethyl-[1,1'-biphenyl]-3-yl)propanoate (720 mg, 1.29 mmol, 1.0 eq) in DCM (2 mL) was added HCl-dioxane (4 M, 2.0 mL, 4.0 mmol, 3.1 eq) and stirred at room temperature for 1 hour. LCMS showed that the reaction was completed. The mixture was concentrated in vacuo to provide ethyl (S)-3-amino-3-(2',4-difluoro-4',5,6'-trimethyl-[1,1'-biphenyl]-3-yl)propanoate as a yellow oil (450 mg). Yield 93% (ESI 348.1 [M+H]$^+$).

Preparation of (S)-ethyl 3-amino-3-(2',6'-dichloro-4-fluoro-4',5-dimethylbiphenyl-3-yl)propanoate

Step 1: 1,3-dichloro-2-iodo-5-methylbenzene

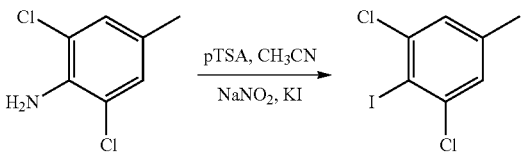

To a mixture of 2,6-dichloro-4-methylaniline (2.5 g, 14.3 mmol, 1.0 eq) in acetonitrile (10 mL) and water (1 mL) was added 4-methylbenzenesulfonic acid (9.8 g, 57.1 mmol, 4 eq) and stirred at 0° C. for 10 mins. A solution of NaNO$_2$ (2.0 g, 28.6 mmol, 2 eq) in H$_2$O (2 mL) was added dropwise and the mixture was stirred at 0° C. for 30 mins. Then a solution of potassium iodide (3.0 g, 17.9 mmol, 1.5 eq) in H$_2$O (2 mL) was added and heated to 50° C. for 2 hours under nitrogen atmosphere. Water (20 mL) was added and the solution was extracted with EtOAc (20 mL×3). The combined organic phases were concentrated in vacuo and the residue was purified by silica gel column (pet ether: EtOAc 1:1) to give 1,3-dichloro-2-iodo-5-methylbenzene as a colorless oil (1.8 g). Yield 44.2% (ESI 286.9[M+H]$^+$).

Step 2: (S)-ethyl 3-(tert-butoxycarbonylamino)-3-(2',6'-dichloro-4-fluoro-4',5-dimethylbiphenyl-3-yl)propanoate

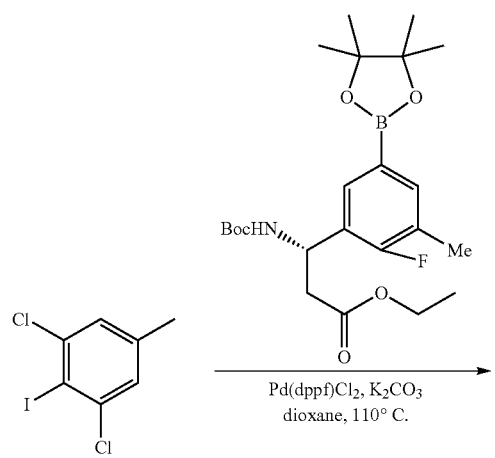

To a mixture of methyl (S)-ethyl 3-(tert-butoxycarbonylamino)-3-(2-fluoro-3-methyl-5-(4,4,5,5-tetramethyl-1,3,2-dioxaborolan-2-yl)phenyl)propanoate (1.5 g, 3.43 mmol, 1 eq) and 1,3-dichloro-2-iodo-5-methylbenzene (2.0 g, 6.86 mmol, 2 eq) in dioxane (10 mL) was added a solution of K$_2$CO$_3$ (1.9 g, 13.72 mmol, 4 eq) in H$_2$O (2 mL) and Pd(dppf)Cl$_2$ (250 mg, 0.343 mmol, 0.1 eq). The mixture was heated to 110° C. for 2 hours under nitrogen atmosphere. Water (20 mL) was added and the solution was extracted with EtOAc (20 mL×3). The combined organic phases were concentrated in vacuo and the residue was purified by silica gel column (pet ether: EtOAc 1:1) to give methyl (S)-ethyl 3-(tert-butoxycarbonylamino)-3-(2',6'-dichloro-4-fluoro-4',5-dimethylbiphenyl-3-yl)propanoate as a colorless oil (1.3 g). Yield 78.3% (ESI 484.4 [M+H]$^+$).

Step 3: (S)-ethyl 3-amino-3-(2',6'-dichloro-4-fluoro-4',5-dimethylbiphenyl-3-yl)propanoate

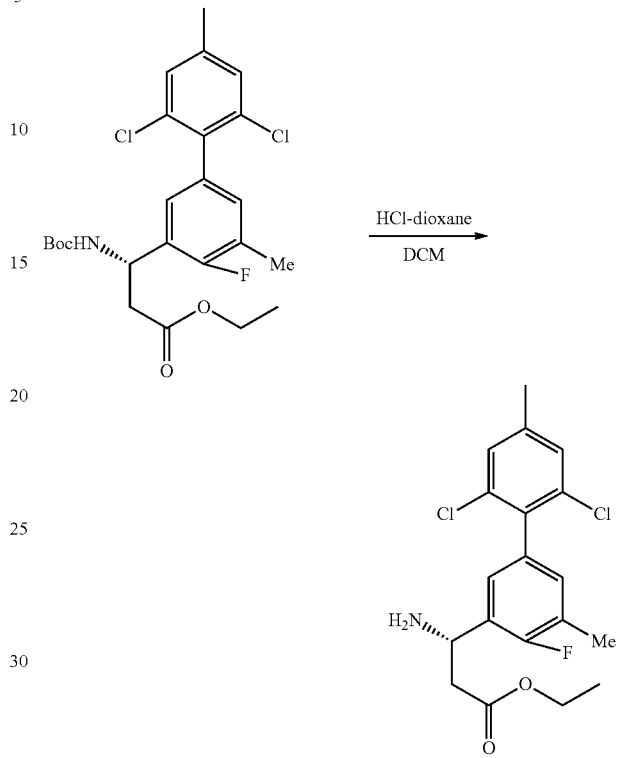

To a mixture of methyl (S)-ethyl 3-(tert-butoxycarbonylamino)-3-(2',6'-dichloro-4-fluoro-4',5-dimethylbiphenyl-3-yl)propanoate (1.3 g, 2.76 mmol, 4 eq) in DCM (6 mL) was added HCl-dioxane (4 M, 3 mL, 12 mmol, 4.3 eq). The mixture was stirred at room temperature for 1 hour. LCMS showed that the reaction was completed. The mixture was concentrated in vacuo to give crude (S)-ethyl 3-amino-3-(2',6'-dichloro-4-fluoro-4',5-dimethylbiphenyl-3-yl)propanoate as a white solid (1.0 g) used directly in the next reaction without further purification. Yield 91% (ESI 384.3 [M+H]$^+$).

Preparation of ethyl (S)-3-amino-3-(4-fluoro-2',5,6'-trimethyl-[1,1'-biphenyl]-3-yl)propanoate Step 1: ethyl(S)-3-(((R)-tert-butylsulfinyl)amino)-3-(4-fluoro-2',5,6'-trimethyl-[1,1'-biphenyl]-3-yl)propanoate

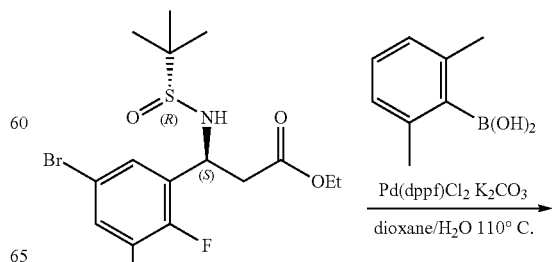

-continued

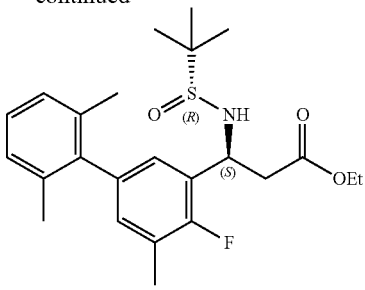

A mixture of ethyl (S)-3-(5-bromo-2-fluoro-3-methylphenyl)-3-(((R)-tert-butylsulfinyl)amino)propanoate (4.0 g, 9.8 mmol, 1.00 eq), (2,6-dimethylphenyl)boronic acid (2.9 g, 19.6 mmol, 2.00 eq), $K_2CO_3$ (4.1 g, 29.4 mmol, 3.0 eq), Pd(dppf)Cl$_2$ (717 mg, 0.98 mmol, 0.05 eq) in dioxane (24 mL) and H$_2$O (9 mL) was stirred at 110° C. for 2 hours under nitrogen atmosphere. LCMS showed that the reaction was completed. The mixture was cooled to room temperature. Water (30 mL) was added and the solution was extracted with EtOAc (30 mL×3). The combined organic phases were washed with brine (30 mL), dried over anhydrous Na$_2$SO$_4$, filtered and concentrated in vacuo. The residue was purified by silica gel column (pet ether:EtOAc 1:1) to provide ethyl (S)-3-(((R)-tert-butylsulfinyl)amino)-3-(4-fluoro-2',5,6'-trimethyl-[1,1'-biphenyl]-3-yl)propanoate (4.0 g) as a yellow oil. Yield 94% (ESI 434.1 [M+H]$^+$).

Step 2: ethyl(S)-3-amino-3-(4-fluoro-2',5,6'-trimethyl-[1,1'-biphenyl]-3-yl)propanoate

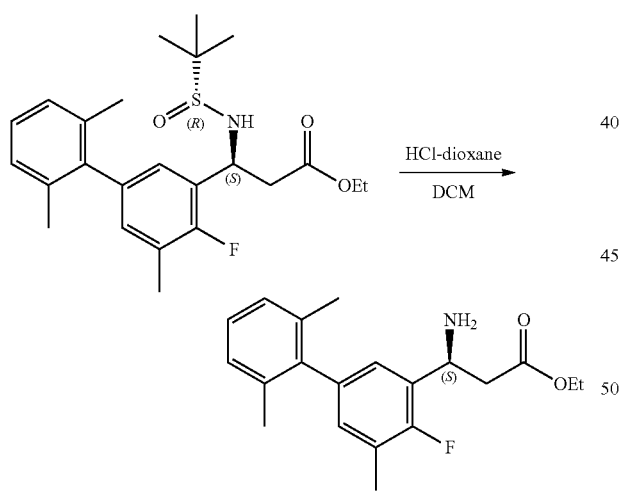

To a stirred solution of ethyl (S)-3-(((R)-tert-butylsulfinyl)amino)-3-(4-fluoro-2',5,6'-trimethyl-[1,1'-biphenyl]-3-yl)propanoate (4.0 g, 9.2 mmol, 1.00 eq) in DCM (6 mL) was added HCl-dioxane (4 M, 4 mL, 16.0 mmol, 1.7 eq). The mixture was stirred at room temperature for 30 mins. LCMS showed that the reaction was completed. The mixture was concentrated in vacuo and the residue was purified by reverse phase HPLC on a C18/120 g column (A: water 10 mM NH$_4$HCO$_3$, B: MeOH, 0~100%) to provide ethyl (S)-3-amino-3-(4-fluoro-2',5,6'-trimethyl-[1,1'-biphenyl]-3-yl)propanoate (2.0 g) as a colorless oil. Yield 61% (ESI 330.1 [M+H]$^+$).

Preparation of ethyl (S)-3-amino-3-(4,4'-difluoro-2',5,6'-trimethyl-[1,1'-biphenyl]-3-yl)propanoate Step 1: ethyl (S)-3-(((R)-tert-butylsulfinyl)amino)-3-(4,4'-difluoro-2',5,6'-trimethyl-[1,1'-biphenyl]-3-yl)propanoate

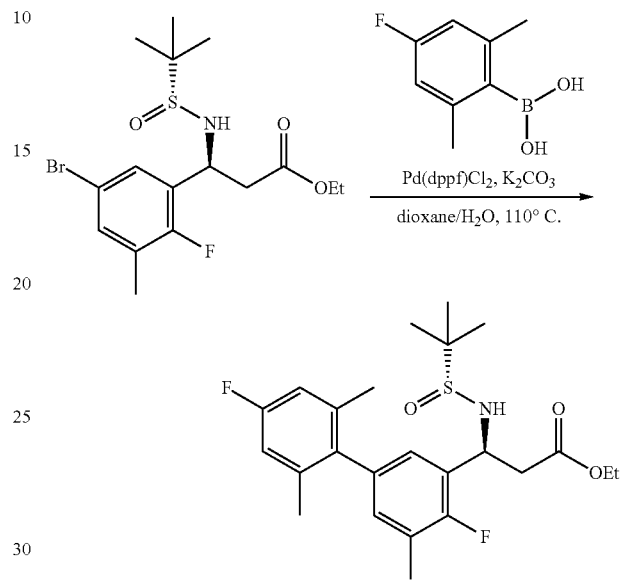

A mixture of ethyl (S)-3-(5-bromo-2-fluoro-3-methylphenyl)-3-(((R)-tert-butylsulfinyl)amino)propanoate (6.0 g, 14.7 mmol, 1.00 eq), (4-fluoro-2,6-dimethylphenyl)boronic acid (3.7 g, 22.1 mmol, 1.5 eq), $K_2CO_3$ (6.1 g, 44.1 mmol, 3.0 eq) and Pd(dppf)Cl$_2$ (1.1 g, 1.47 mmol, 0.01 eq) in dioxane (50 mL) and H$_2$O (5 mL) was stirred at 110° C. under nitrogen atmosphere for 1 hour. LCMS showed that the reaction was completed. The mixture was cooled to room temperature. Water (50 mL) was added and the solution was extracted with EtOAc (50 mL×3). The combined organic phases were washed with brine (30 mL), dried over anhydrous Na$_2$SO$_4$, filtered and concentrated in vacuo. The residue was purified by silica gel column (pet ether: EtOAc 1:1) to provide ethyl (S)-3-(((R)-tert-butylsulfinyl)amino)-3-(4,4'-difluoro-2',5,6'-trimethyl-[1,1'-biphenyl]-3-yl)propanoate as a yellow oil (5.5 g). Yield 83% (ESI 452.0 (M+H)$^+$)

Step 2: ethyl (S)-3-amino-3-(4,4'-difluoro-2',5,6'-trimethyl-[1,1'-biphenyl]-3-yl)propanoate

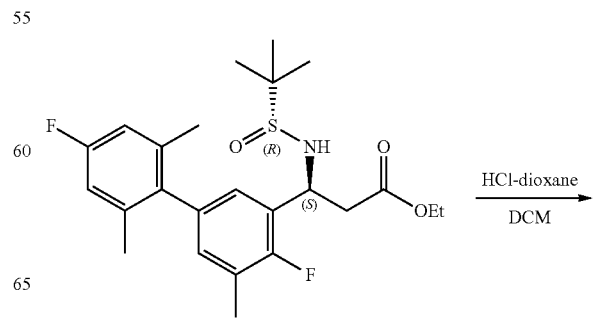

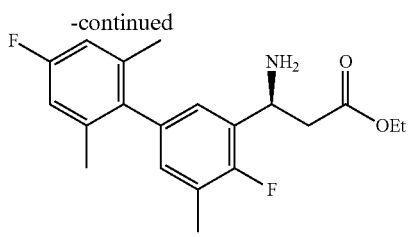

To the solution of ethyl (S)-3-(((R)-tert-butylsulfinyl)amino)-3-(4,4'-difluoro-2',5,6'-trimethyl-[1,1'-biphenyl]-3-yl)propanoate (5.5 g, 12.2 mmol, 1.00 eq) in DCM (6 mL) was added HCl-dioxane (4M, 6 mL, 24.0 mmol, 1.97 eq) and stirred at room temperature for 1 hour. The mixture was concentrated in vacuo and the residue was purified by reverse phase HPLC on a C18/120 g column (A: water/0.01% TFA, B: MeOH, 0~100%) to provide ethyl (S)-3-amino-3-(4,4'-difluoro-2',5,6'-trimethyl-[1,1'-biphenyl]-3-yl)propanoate as a yellow solid (4.0 g). Yield 95% (ESI 348.1 (M+H)$^+$).

Preparation of ethyl (S)-3-amino-3-(4'-chloro-4-fluoro-2',5,6'-trimethyl-[1,1'-biphenyl]-3-yl)propanoate Step 1: 2-(4-chloro-2,6-dimethylphenyl)-4,4,5,5-tetramethyl-1,3,2-dioxaborolane

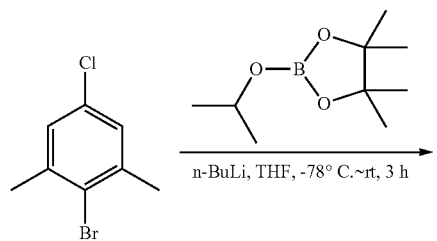

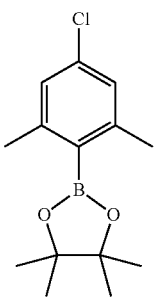

To a solution of 2-bromo-5-chloro-1,3-dimethylbenzene (4.0 g, 18.2 mmol, 1.0 eq) in anhydrous THF (40 mL) under nitrogen atmosphere was added n-BuLi (2 N, 11.0 mL, 22.0 mmol, 1.2 eq) at −78° C. The reaction mixture was stirred at −78° C. for 40 mins and 2-isopropoxy-4,4,5,5-tetramethyl-1,3,2-dioxaborolane (5.1 g, 27.5 mmol, 1.5 eq) in anhydrous THF (40 mL) was added and stirred at −78° C. for 3 hours. After completion, a saturated NH$_4$Cl solution (aq) (100 mL) was added. The mixture was extracted with EtOAc (100 mL×3). The combined organic layers were washed with brine (50 mL), dried over anhydrous Na$_2$SO$_4$, filtered and concentrated in vacuo. The residue obtained was purified by silica gel (petroleum ether: EtOAc 2:1) to give the desired 2-(4-chloro-2,6-dimethylphenyl)-4,4,5,5-tetramethyl-1,3,2-dioxaborolane as a white solid (4.4 g). Yield 90%.

Step 2: ethyl (S)-3-amino-3-(4'-chloro-4-fluoro-2',5,6'-trimethyl-[1,1'-biphenyl]-3-yl)propanoate

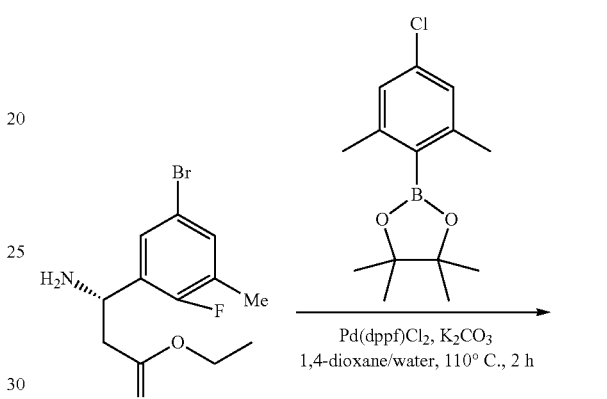

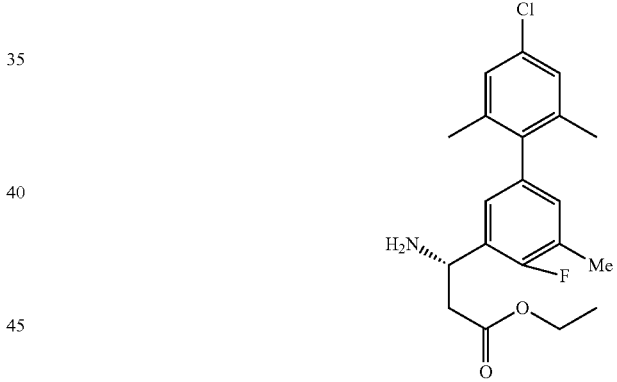

A mixture of ethyl (S)-3-amino-3-(5-bromo-2-fluoro-3-methylphenyl)propanoate (500 mg, 1.7 mmol, 1.0 eq), 2-(4-chloro-2,6-dimethylphenyl)-4,4,5,5-tetramethyl-1,3,2-dioxaborolane (544 mg, 2.04 mmol, 1.2 eq), Pd(dppf)Cl$_2$ (62 mg, 0.085 mmol, 0.05 eq) and K$_2$CO$_3$ (704 mg, 5.1 mmol, 3.0 eq) in 1,4-dioxane (10 mL) and water (2 mL) was stirred at 110° C. for 2 hours under nitrogen atmosphere. Water (20 mL) was added and the solution was extracted with EtOAc (30 mL×3). The combined organic layers were washed with brine (20 mL), dried over anhydrous Na$_2$SO$_4$, filtered and concentrated in vacuo. The residue was purified by silica gel column (petroleum ether: EtOAc 1:2) to provide ethyl (S)-3-amino-3-(4'-chloro-4-fluoro-2',5,6'-trimethyl-[1,1'-biphenyl]-3-yl)propanoate as a colorless oil (250 mg). Yield 41% (ESI 364.2 [M+H]$^+$).

115

Preparation of ethyl (S)-3-amino-3-(4-fluoro-2',4',5,6'-tetramethyl-[1,1'-biphenyl]-3-yl)propanoate Step 1: ethyl (S)-3-(((R)-tert-butylsulfinyl)amino)-3-(4-fluoro-2',4',5,6'-tetramethyl-[1,1'-biphenyl]-3-yl)propanoate

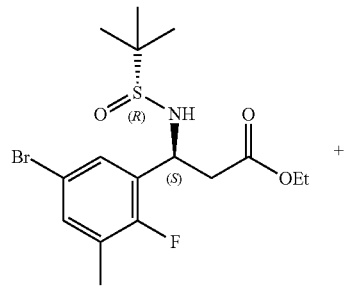

+

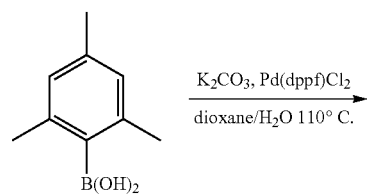

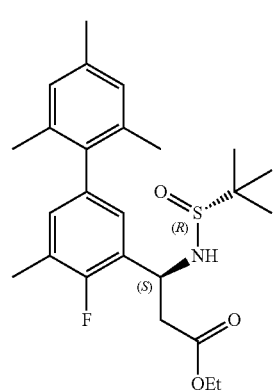

A mixture of ethyl (S)-3-(5-bromo-2-fluoro-3-methylphenyl)-3-(((R)-tert-butylsulfinyl)amino)propanoate (3.8 g, 9.3 mmol, 1.0 eq), mesitylboronic acid (3.05 g, 18.6 mmol, 2.0 eq), K₂CO₃ (3.85 g, 27.9 mmol, 3.0 eq) and Pd(dppf)Cl₂ (340 mg, 0.465 mmol, 0.05 eq) in Dioxane (30 mL) and H₂O (5 mL) was stirred at 110° C. under nitrogen atmosphere for 2 hours. LCMS showed the reaction was complete. The reaction mixture was cooled to room temperature. Water (80 mL) was added and the mixture was extracted with EtOAc (100 mL×3). The combined organic layers were washed with brine (150 mL), dried over Na₂SO₄, filtered and concentrated in vacuo. The residue was purified by silica gel column (pet ether: EtOAc 1:1) to provide ethyl (S)-3-(((R)-tert-butylsulfinyl)amino)-3-(4-fluoro-2',4',5,6'-tetramethyl-[1,1'-biphenyl]-3-yl)propanoate as a yellow oil (3.1 g). Yield 75% (ESI 448.2 [M+H]⁺).

116

Step 2: ethyl(S)-3-amino-3-(4-fluoro-2',4',5,6'-tetramethyl-[1,1'-biphenyl]-3-yl)propanoate

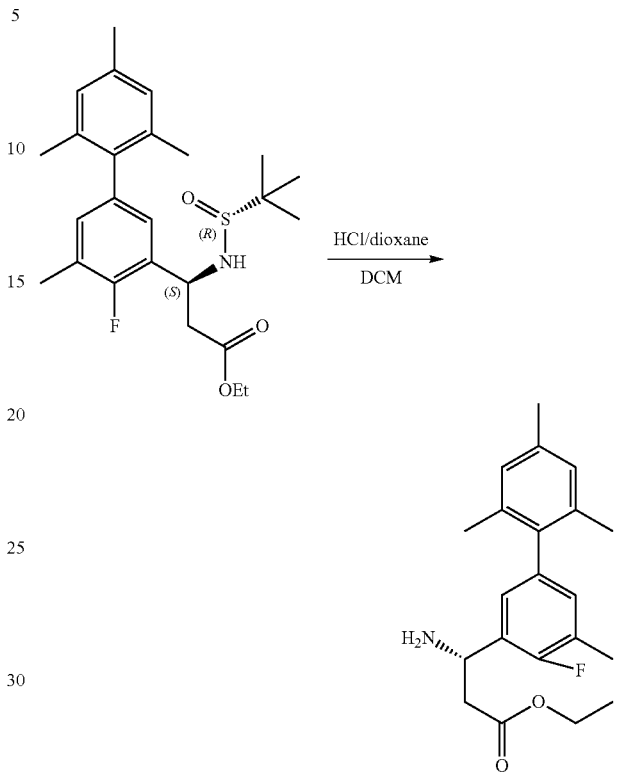

To a stirred solution of ethyl (S)-3-(((R)-tert-butylsulfinyl)amino)-3-(4-fluoro-2',4',5,6'-tetramethyl-[1,1'-biphenyl]-3-yl)propanoate (3.1 g, 6.94 mmol, 1.0 eq) in DCM (7 mL) was added HCl-dioxane (4 M, 6.8 mL, 3.9 eq) and stirred at 25° C. for 2 hours. LCMS showed that the reaction was completed. The mixture was concentrated in vacuo and the residue was purified by reverse phase HPLC on a C18/40 g column (A: water 10 mM NH₄HCO₃, B: MeOH, 0~100%) to provide (S)-ethyl 3-amino-3-(4-fluoro-2',4',5,6'-tetramethylbiphenyl-3-yl)propanoate as a yellow oil (1.6 g). Yield 67% (ESI 344.2 [M+H]⁺).

Example: Preparation of ethyl (S)-3-amino-3-(4-fluoro-2',5,6'-trimethyl-4'-(trifluoromethyl)-[1,1'-biphenyl]-3-yl)propanoate hydrochloride Step 1: 2,6-dimethyl-4-(trifluoromethyl)aniline

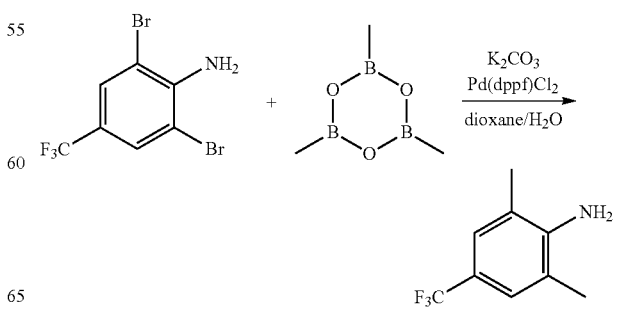

A mixture of 2,6-dibromo-4-(trifluoromethyl)aniline (638 mg, 2.00 mmol, 1.0 eq), 2,4,6-trimethyl-1,3,5,2,4,6-trioxatriborinane (3.5 M in THF, 3.43 mL, 12.00 mmol, 6.0 eq), K$_2$CO$_3$ (1.10 g, 7.96 mmol, 3.98 eq) and Pd(dppf)Cl$_2$ (245 mg, 0.30 mmol, 0.15 eq) in dioxane (6 mL) and water (1 mL) was stirred at 90° C. for 8 hours under nitrogen atmosphere. The mixture was filtered through a pad of Celite, washed with ethyl acetate (100 mL) and the filtrate was concentrated in vacuo. The residue was purified by silica gel column (petroleum ether: EtOAc 20:1) to provide 2,6-dimethyl-4-(trifluoromethyl)aniline as a colorless oil (1.63 g). Yield 48% (ESI 190.1 (M+H)$^+$).

Step 2:
2-bromo-1,3-dimethyl-5-(trifluoromethyl)benzene

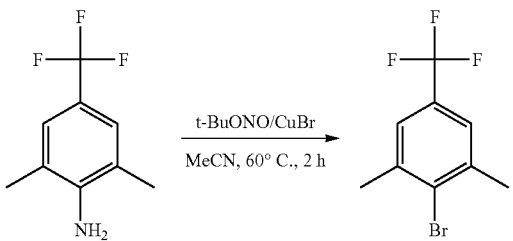

A mixture of 2,6-dimethyl-4-(trifluoromethyl)aniline (793 mg, 4.19 mmol, 1.0 eq), tert-butyl nitrite (0.94 mL, 7.84 mmol, 1.9 eq) and copper(I) bromide (794 mg, 5.53 mmol, 1.3 eq) in anhydrous acetonitrile (16 mL) was stirred at 60° C. for 2 hours under nitrogen atmosphere. LCMS showed that the reaction was completed. The mixture was filtered through a pad of Celite and the filtrate was concentrated in vacuo. The residue was purified by silica gel column (petroleum ether: EtOAc 6:1) to provide 2-bromo-1,3-dimethyl-5-(trifluoromethyl)benzene as a colorless oil (975 mg). Yield 46%. $^1$H NMR (400 MHz, DMSO-d$_6$) δ: 7.55 (s, 2H), 2.42 (s, 6H).

Step 3: ethyl (S)-3-((tert-butoxycarbonyl)amino)-3-(4-fluoro-2',5,6'-trimethyl-4'-(trifluoromethyl)-[1,1'-biphenyl]-3-yl)propanoate

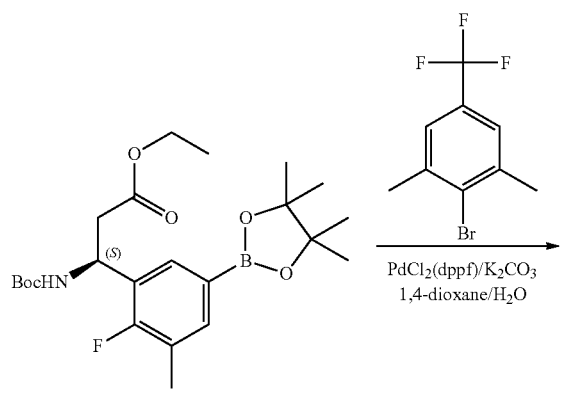

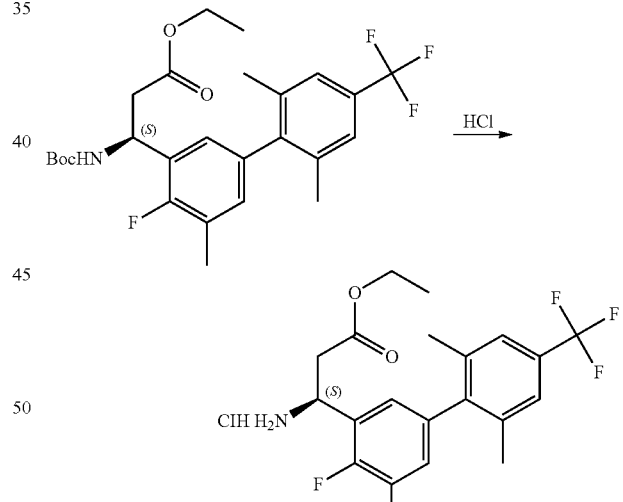

To a solution of ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate (519 mg, 1.15 mmol, 1.0 eq) in dioxane (36 mL) was added 2-bromo-1,3-dimethyl-5-(trifluoromethyl)benzene (306 mg, 1.21 mmol, 1.1 eq), Pd(dppf)Cl$_2$ (188 mg, 0.23 mmol, 0.2 eq), K$_2$CO$_3$ (477 mg, 3.45 mmol, 3.0 eq) and water (3.6 mL). The reaction mixture was stirred at 110° C. for 18 hours under nitrogen atmosphere. The mixture was filtered and concentrated in vacuo. The residue was purified by silica gel column (petroleum ether: EtOAc 6:1) to provide ethyl (S)-3-((tert-butoxycarbonyl)amino)-3-(4-fluoro-2',5,6'-trimethyl-4'-(trifluoromethyl)-[1,1'-biphenyl]-3-yl)propanoate as a light brown oil (308 mg). Yield 54%. (ESI 398.1 [M+H-100]$^+$).

Step 5: ethyl(S)-3-amino-3-(4-fluoro-2',5,6'-trimethyl-4'-(trifluoromethyl)-[1,1'-biphenyl]-3-yl)propanoate hydrochloride To a stirred solution of ethyl (S)-3-((tert-butoxycarbonyl)amino)-3-(4-fluoro-2',5,6'-trimethyl-4'-(trifluoromethyl)-[1,1'-biphenyl]-3-yl)propanoate (308 mg, 0.62 mmol, 1.0 eq) in DCM (4 mL) was added HCl-dioxane (4 M, 4.0 mL, 16.0 mmol, 25.8 eq). The mixture was stirred at room temperature for 2 hours. LCMS showed that the reaction was completed. The mixture was concentrated in vacuo to provide ethyl (S)-3-amino-3-(4-fluoro-2',5,6'-trimethyl-4'-(trifluoromethyl)-[1,1'-biphenyl]-3-yl)propanoate hydrochloride as a yellow oil (260 mg). Yield 97% (ESI 398.1 [M+H]$^+$).

119

Preparation of ethyl (S)-3-amino-3-(4'-cyclopropyl-4-fluoro-2',5,6'-trimethyl-[1,1'-biphenyl]-3-yl)propanoate Step 1: 4-cyclopropyl-2,6-dimethylaniline

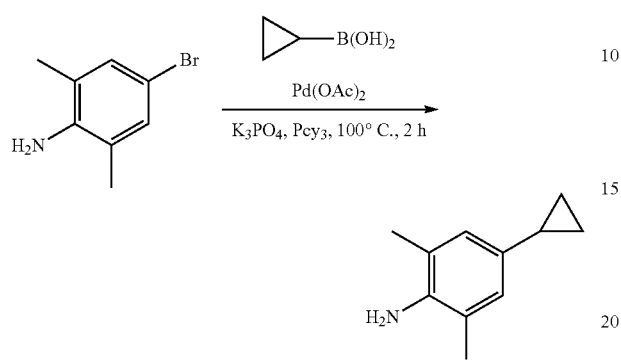

To a mixture of 4-bromo-2,6-dimethylaniline (2.0 g, 10.0 mmol, 1.0 eq), cyclopropylboronic acid (1.03 g, 12.0 mmol, 1.2 eq) in toluene (15 mL) under nitrogen atmosphere was added a solution of $K_3PO_4$ (4.2 g, 20.0 mmol, 2.0 eq) in $H_2O$ (3 mL), tricyclohexyl phosphine (280.0 mg, 1.0 mmol, 0.1 eq) and $Pd(OAc)_2$ (224.0 mg, 1.0 mmol, 0.1 eq). The mixture was stirred at 100° C. for 4 hours under nitrogen atmosphere. Water (30 mL) was added and the solution was extracted with EtOAc (30 mL×3). The combined organic layers were washed with brine (50 mL), dried over anhydrous $Na_2SO_4$, filtered and concentrated in vacuo. The residue was purified by silica gel column (petroleum ether: EtOAc 2:1) to provide 4-cyclopropyl-2,6-dimethylaniline (0.8 g) used in the next step without further purification. Yield 93% (ESI 162.2 [M+H]$^+$).

Step 2: 2-bromo-5-cyclopropyl-1,3-dimethylbenzene

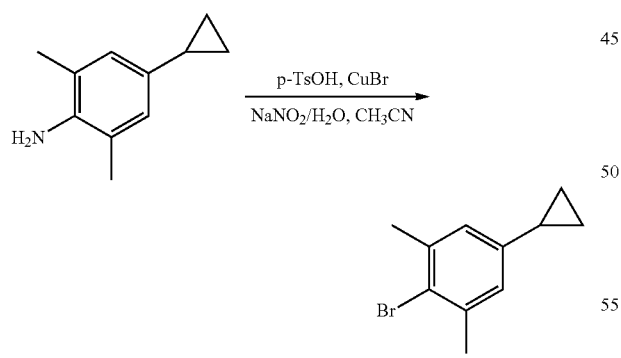

To a mixture of 4-cyclopropyl-2,6-dimethylaniline (800.0 mg, 4.9 mmol, 1.0 eq) in ACN (10 mL) and $H_2O$ (1 mL) was added p-toluenesulphonic acid (3.4 g, 19.8 mmo, 4.0 eq). The mixture was stirred at 0° C. for 10 mins under under nitrogen atmosphere. A solution of $NaNO_2$ (685.0 mg, 9.93 mmol, 2.0 eq) in $H_2O$ (2 mL) was added dropwise and the mixture was stirred 0° C. for 30 mins. CuBr (4.4 g, 19.8 mmol, 4.0 eq) was added to the reaction mixture and stirred at room temperature for 4 hours. Water (50 mL) was added and the solution was extracted with DCM (50 mL×3). The combined organic layers were washed with brine (50 mL), dried over anhydrous $Na_2SO_4$, filtered and concentrated in vacuo. The residue was purified by silica gel column (petroleum ether: EtOAc 19:1) to provide 2-bromo-5-cyclopropyl-1,3-dimethylbenzene as a yellow oil (800.0 mg) used in the next step without further purification. Yield 49% (ESI 225.1 (M+H)$^+$, 227.1 (M+H)$^+$).

Step 3: ethyl (S)-3-((tert-butoxycarbonyl)amino)-3-(4'-cyclopropyl-4-fluoro-2',5,6'-trimethyl-[1,1'-biphenyl]-3-yl)propanoate

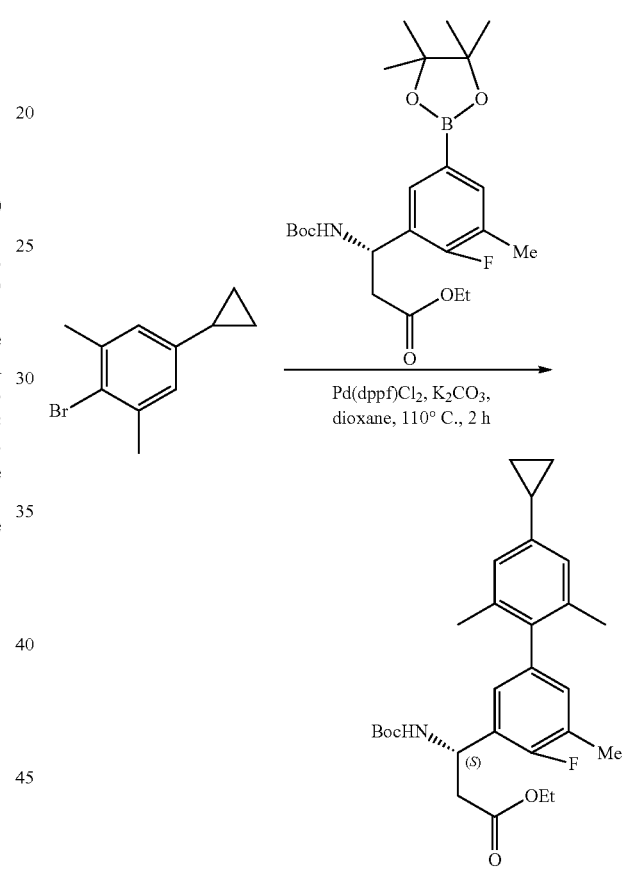

To a mixture of 2-bromo-5-cyclopropyl-1,3-dimethylbenzene (800 mg, 3.6 mmol, 1.0 eq) and ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate (1.6 g, 3.6 mmol, 1.0 eq) in 1,4-dioxane (10 mL) under nitrogen atmosphere was added a solution of $K_2CO_3$ (1.0 g, 7.2 mmol, 2.0 eq) in $H_2O$ (1 mL) and $Pd(dppf)Cl_2$ (260 mg, 0.36 mmol, 0.1 eq). The mixture was stirred at 110° C. for 2 hours under nitrogen atmosphere. Water (30 mL) was added and the solution was extracted with EtOAc (50 mL×3). The combined organic phases were washed with brine (50 mL), dried over anhydrous $Na_2SO_4$, filtered and concentrated in vacuo. The residue was purified by silica gel column (petroleum ether: EtOAc 19:1) to provide ethyl (S)-3-((tert-butoxycarbonyl)amino)-3-(4'-cyclopropyl-4-fluoro-2',5,6'-trimethyl-[1,1'-biphenyl]-3-yl)propanoateas a brown oil (500 mg). Yield 30% (ESI 370.1 [M-100+H]$^+$).

121

Step 4: ethyl (S)-3-amino-3-(4'-cyclopropyl-4-fluoro-2',5',6'-trimethyl-[1,1'-biphenyl]-3-yl)propanoate hydrochloride

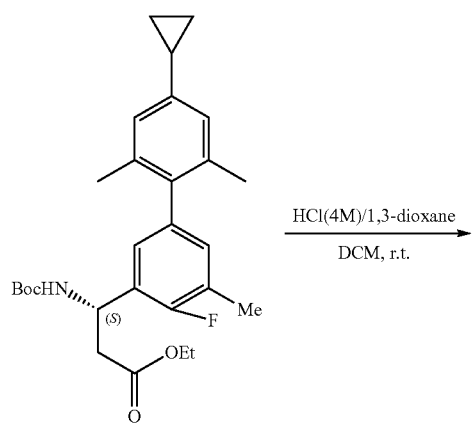

To a stirred solution of ethyl (S)-3-((tert-butoxycarbonyl) amino)-3-(4'-cyclopropyl-4-fluoro-2',5',6'-trimethyl-[1,1'-biphenyl]-3-yl)propanoate (900 mg, 1.91 mmol, 1.0 eq) in DCM (5 mL) was added HCl-dioxane (4 M, 5.0 mL, 20.0 mmol, 10.47 eq) and stirred at room temperature for 1 hour. LCMS showed that the reaction was completed. The mixture was concentrated in vacuo to provide ethyl (S)-3-amino-3-(4'-cyclopropyl-4-fluoro-2',5',6'-trimethyl-[1,1'-biphenyl]-3-yl)propanoate hydrochloride as a green-yellow foam (710 mg). Yield 91% (ESI 370.2 [M+H]$^+$).

122

Preparation of ethyl (S)-3-amino-3-(4-fluoro-4'-methoxy-2',5',6'-trimethyl-[1,1'-biphenyl]-3-yl)propanoate hydrochloride Step 1: ethyl(S)-3-((tert-butoxycarbonyl)amino)-3-(4-fluoro-4'-methoxy-2',5',6'-trimethyl-[1,1'-biphenyl]-3-yl)propanoate

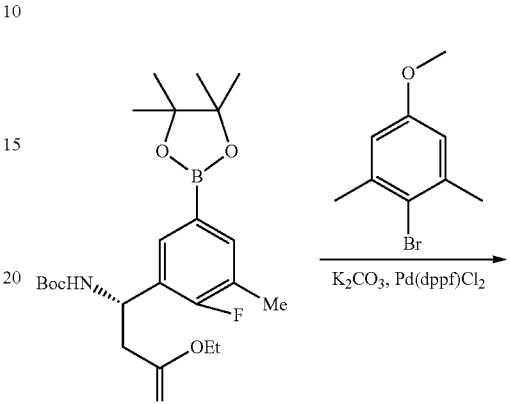

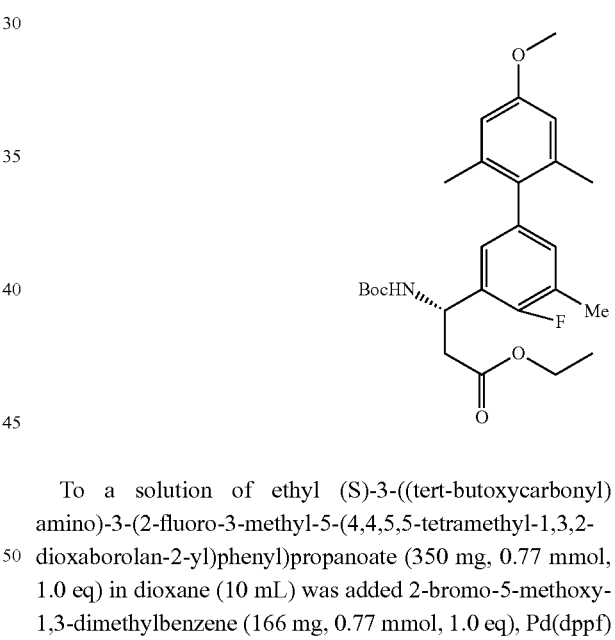

To a solution of ethyl (S)-3-((tert-butoxycarbonyl) amino)-3-(2-fluoro-3-methyl-5-(4,4,5,5-tetramethyl-1,3,2-dioxaborolan-2-yl)phenyl)propanoate (350 mg, 0.77 mmol, 1.0 eq) in dioxane (10 mL) was added 2-bromo-5-methoxy-1,3-dimethylbenzene (166 mg, 0.77 mmol, 1.0 eq), Pd(dppf)Cl$_2$ (56 mg, 0.077 mmol, 0.1 eq), K$_2$CO$_3$ (213 mg, 1.54 mmol, 2.0 eq) and water (2 mL). The reaction mixture was stirred at 110° C. for 3 hours under nitrogen atmosphere. Water (10 mL) was added and the solution was extracted with EtOAc (20 mL×3). The combined organic layers were washed with brine (60 mL), dried over anhydrous Na$_2$SO$_4$, filtered and concentrated in vacuo. The residue was purified by silica gel column (petroleum ether: EtOAc 7:1) to provide ethyl (S)-3-((tert-butoxycarbonyl)amino)-3-(4-fluoro-4'-methoxy-2',5',6'-trimethyl-[1,1'-biphenyl]-3-yl)propanoate as a colorless oil (230 mg). Yield 65% (ESI 360.2 [M+H-100]$^+$).

123

Step 2: ethyl (S)-3-amino-3-(4-fluoro-4'-methoxy-2',5,6'-trimethyl-[1,1'-biphenyl]-3-yl)propanoate hydrochloride

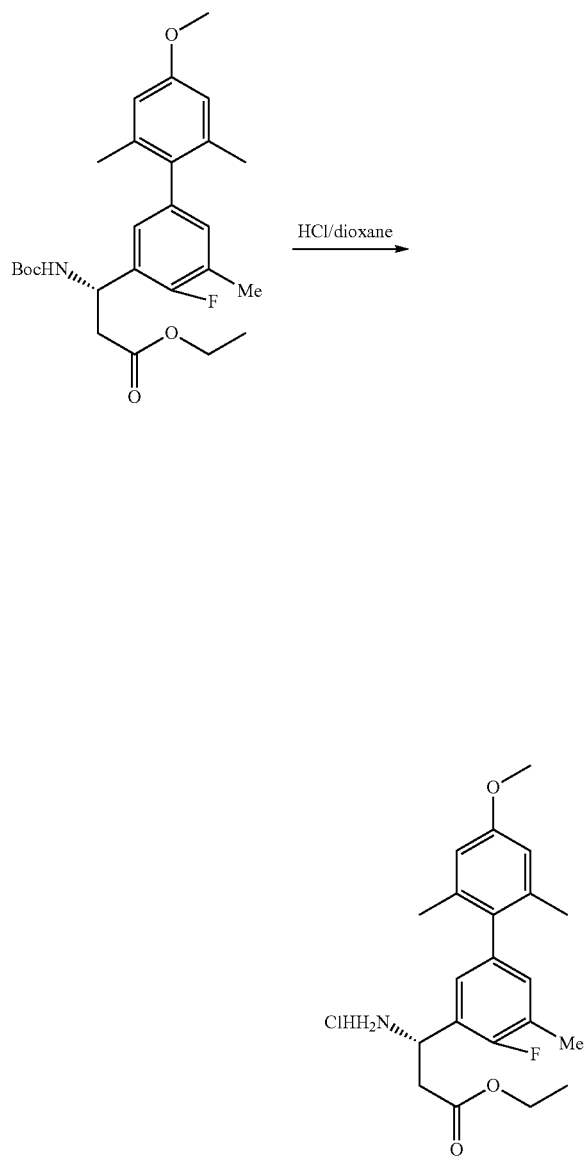

To a stirred solution of ethyl (S)-3-((tert-butoxycarbonyl)amino)-3-(4-fluoro-4'-methoxy-2',5,6'-trimethyl-[1,1'-biphenyl]-3-yl)propanoate (200 mg, 0.43 mmol, 1.0 eq) in DCM (7 mL) was added HCl-dioxane (4 M, 2.0 mL, 4.0 mmol, 9.3 eq). The mixture was stirred at room temperature for 1 hour. LCMS showed that the reaction was completed. The mixture was concentrated in vacuo to provide ethyl (S)-3-amino-3-(4-fluoro-4'-methoxy-2',5,6'-trimethyl-[1,1'-biphenyl]-3-yl)propanoate hydrochloride as a yellow oil (160 mg). Yield 93% (ESI 360.2 [M+H]$^+$).

124

Preparation of ethyl (S)-3-amino-3-(4'-cyano-4-fluoro-2',5,6'-trimethyl-[1,1'-biphenyl]-3-yl)propanoate Step 1: ethyl (S)-3-((tert-butoxycarbonyl)amino)-3-(4'-cyano-4-fluoro-2',5,6'-trimethyl-[1,1'-biphenyl]-3-yl)propanoate

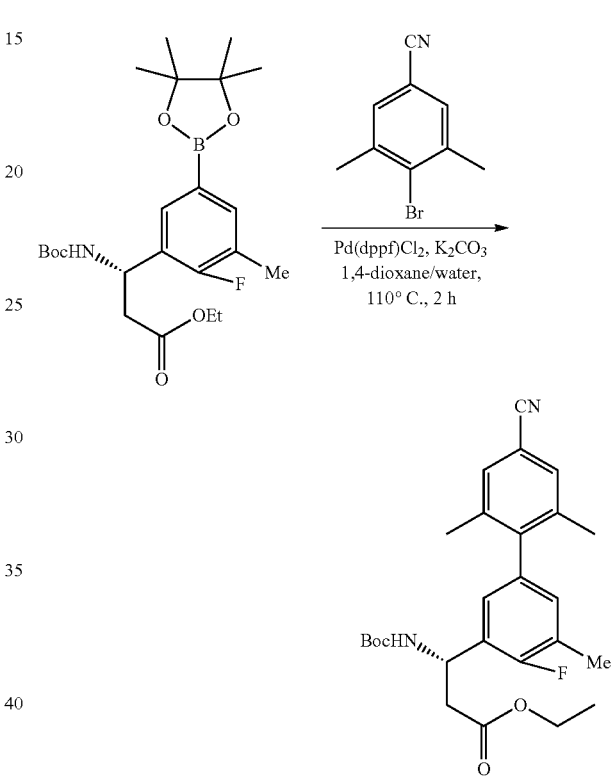

A mixture of ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate (450 mg, 1 mmol, 1.0 eq), 4-bromo-3,5-dimethylbenzonitrile (316 mg, 1.5 mmol, 1.5 eq), Pd(dppf)Cl$_2$ (37 mg, 0.05 mmol, 0.05 eq) and K$_2$CO$_3$ (414 mg, 3 mmol, 3.0 eq) in 1,4-dioxane (8 mL) and water (2 mL) was stirred at 110° C. for 2 hours under nitrogen atmosphere. Water (10 mL) was added and the solution was extracted with EtOAc (20 mL×3). The combined organic layers were washed with brine (20 mL), dried over anhydrous Na$_2$SO$_4$, filtered and concentrated in vacuo. The residue was purified by silica gel column (petroleum ether: EtOAc 1:1) to provide ethyl (S)-3-((tert-butoxycarbonyl)amino)-3-(4'-cyano-4-fluoro-2',5,6'-trimethyl-[1,1'-biphenyl]-3-yl)propanoate as a colorless oil (320 mg). Yield 70% (ESI 455.2 [M+H]$^+$).

125

Step 2: ethyl (S)-3-amino-3-(4'-cyano-4-fluoro-2',5,6'-trimethyl-[1,1'-biphenyl]-3-yl)propanoate

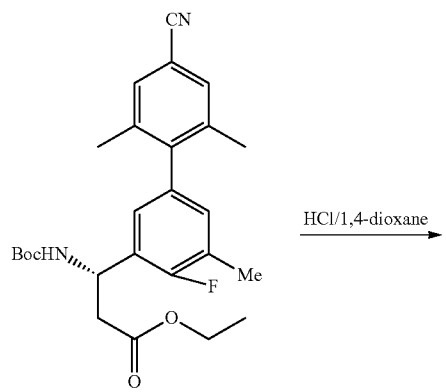

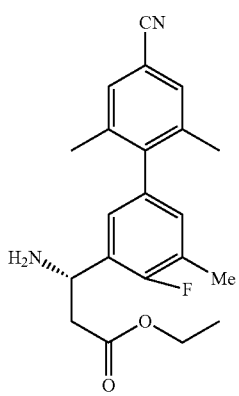

To a stirred solution of ethyl (S)-3-((tert-butoxycarbonyl)amino)-3-(4'-cyano-4-fluoro-2',5,6'-trimethyl-[1,1'-biphenyl]-3-yl)propanoate (320 mg, 0.7 mmol, 1.0 eq) in DCM (2 mL) was added HCl-dioxane (4 M, 2.0 mL, 4.0 mmol, 5.7 eq). The mixture was stirred at room temperature for 2 hours. LCMS showed that the reaction was completed. The mixture was concentrated in vacuo to provide ethyl (S)-3-amino-3-(4'-cyano-4-fluoro-2',5,6'-trimethyl-[1,1'-biphenyl]-3-yl)propanoate as a colorless oil (250 mg). Yield 100% (ESI 355.1 [M+H]$^+$).

126

Preparation of ethyl (S)-3-amino-3-(4'-((dimethylamino)methyl)-4-fluoro-2',5,6'-trimethyl-[1,1'-biphenyl]-3-yl)propanoate Step 1: ethyl (S)-3-((tert-butoxycarbonyl)amino)-3-(4-fluoro-4'-formyl-2',5,6'-trimethyl-[1,1'-biphenyl]-3-yl)propanoate

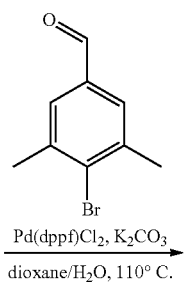

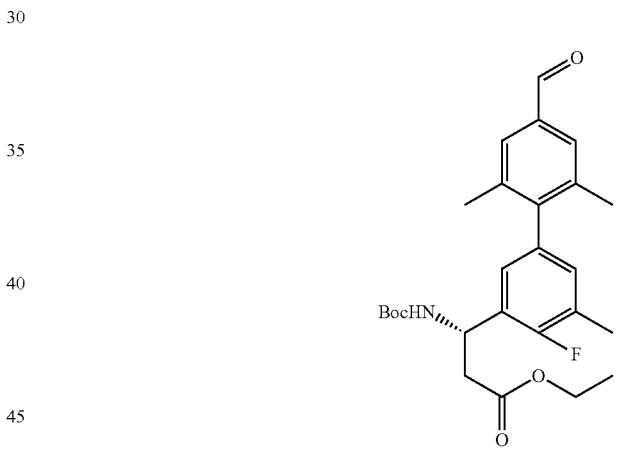

A mixture of ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate (465 mg, 1.03 mmol, 1.1 eq), 4-bromo-3,5-dimethylbenzaldehyde (200 mg, 0.93 mmol, 1.0 eq), K$_2$CO$_3$ (259 mg, 1.87 mmol, 2.0 eq) and 1,1'-Bis (diphenylphosphino) ferrocene-palladium(II)dichloride dichloromethane complex (68 mg, 0.09 mmol, 0.1 eq) in dioxane (10 mL) and H$_2$O (1 mL) was stirred at 80° C. for 3 hours under nitrogen atmosphere. LCMS showed that the reaction was completed. The mixture was cooled to room temperature. Water (50 mL) was added and the solution was extracted with EtOAc (50 mL×3). The combined organic layers were washed with brine (100 mL), dried over anhydrous Na$_2$SO$_4$, filtered and concentrated in vacuo. The residue was purified by silica gel column (pet ether: EtOAc 1:3) to provide ethyl (S)-3-((tert-butoxycarbonyl)amino)-3-(4-fluoro-4'-formyl-2',5,6'-trimethyl-[1,1'-biphenyl]-3-yl) propanoate as a yellow oil (300 mg). Yield 64% (ESI 358.1 [M+H-100]$^+$)

127

Step 2: ethyl (S)-3-((tert-butoxycarbonyl)amino)-3-(4'-((dimethylamino)methyl)-4-fluoro-2',5,6'-trimethyl-[1,1'-biphenyl]-3-yl)propanoate

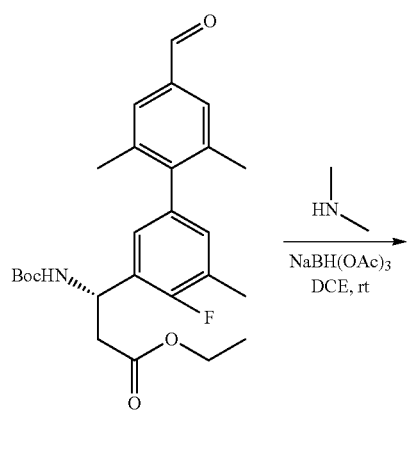

128

Step 3: ethyl (S)-3-amino-3-(4'-((dimethylamino)methyl)-4-fluoro-2',5,6'-trimethyl-[1,1'-biphenyl]-3-yl)propanoate

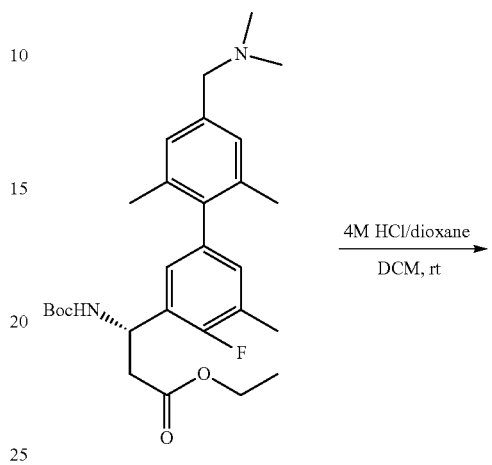

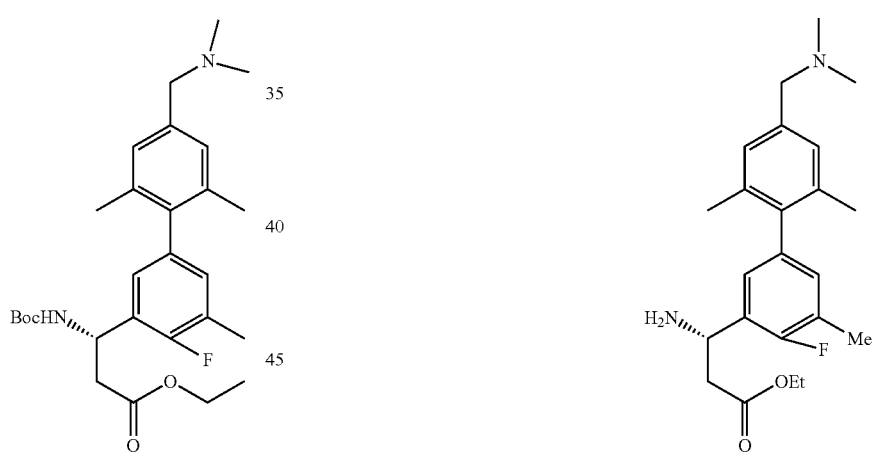

A mixture of ethyl (S)-3-((tert-butoxycarbonyl)amino)-3-(4-fluoro-4'-formyl-2',5,6'-trimethyl-[1,1'-biphenyl]-3-yl)propanoate (1.3 g, 2.8 mmol, 1.0 eq) and dimethylamine hydrochloride (233 mg, 2.9 mmol, 1.05 eq) in DCE (10 mL) was stirred at room temperature for 30 mins. Sodium triacetoxyborohydride (1.2 g, 5.6 mmol, 2.0 eq) was added and stirred at room temperature for 16 hours. The solvent was removed in vacuo and the residue was purified by silica gel column (DCM:MeOH 9:1) to provide ethyl (S)-3-((tert-butoxycarbonyl)amino)-3-(4'-((dimethylamino)methyl)-4-fluoro-2',5,6'-trimethyl-[1,1'-biphenyl]-3-yl)propanoate as a yellow oil (800 mg). Yield 58.7% (ESI 487.2 (M+H)$^+$).

To a stirred solution of ethyl (S)-3-((tert-butoxycarbonyl)amino)-3-(4'-((dimethylamino)methyl)-4-fluoro-2',5,6'-trimethyl-[1,1'-biphenyl]-3-yl)propanoate (800 mg, 1.64 mmol, 1.0 eq) in DCM (10 mL) was added HCl-dioxane (4 M, 3 mL, 12.0 mmol) and stirred at room temperature for 1 hour. LCMS showed that the reaction was completed. The mixture was concentrated in vacuo and the residue was purified by reverse phase on a C18/40 g column (A: water 10 mM NH$_4$HCO$_3$, B: MeOH, 0~100%) to provide ethyl (S)-3-amino-3-(4'-((dimethylamino)methyl)-4-fluoro-2',5,6'-trimethyl-[1,1'-biphenyl]-3-yl)propanoate as a white solid (600 mg). Yield 94% (ESI 387.2 (M+H)$^+$).

129

Preparation of ethyl (S)-3-amino-3-(4-fluoro-4'-((3-fluoroazetidin-1-yl)methyl)-2',5,6'-trimethyl-[1,1'-biphenyl]-3-yl)propanoate Step 1: ethyl(S)-3-((tert-butoxycarbonyl)amino)-3-(4-fluoro-4'-((3-fluoroazetidin-1-yl)methyl)-2',5,6'-trimethyl-[1,1'-biphenyl]-3-yl)propanoate

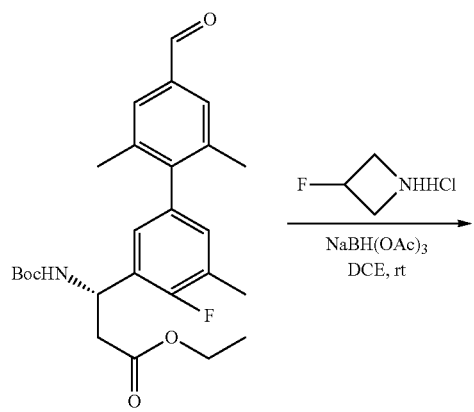

130

Step 2: ethyl (S)-3-amino-3-(4-fluoro-4'-((3-fluoroazetidin-1-yl)methyl)-2',5,6'-trimethyl-[1,1'-biphenyl]-3-yl)propanoate

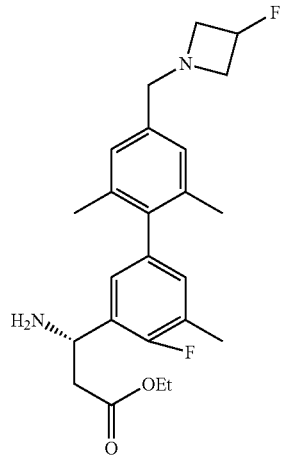

A mixture of ethyl (S)-3-((tert-butoxycarbonyl)amino)-3-(4-fluoro-4'-formyl-2',5,6'-trimethyl-[1,1'-biphenyl]-3-yl)propanoate (1.3 g, 2.8 mmol, 1.0 eq) and 3-fluoroazetidine hydrochloride (233 mg, 2.9 mmol, 1.05 eq) in DCM (10 mL) was stirred at room temperature for 30 mins. Sodium triacetoxyborohydride (1.2 g, 5.6 mmol, 2.0 eq) was added and stirred at room temperature for 16 hours. The solvent was removed in vacuo and the residue was purified by silica gel column (DCM:MeOH 9:1) to provide ethyl (S)-3-(((R)-tert-butylsulfinyl)amino)-3-(4-fluoro-4'-((3-fluorocyclobutyl)methyl)-2',5,6'-trimethyl-[1,1'-biphenyl]-3-yl)propanoate as yellow oil (800 mg). Yield 54.7% (ESI 517.2 [M+H]$^+$).

To a solution of ethyl (S)-3-((tert-butoxycarbonyl)amino)-3-(4-fluoro-4'-((3-fluoroazetidin-1-yl)methyl)-2',5,6'-trimethyl-[1,1'-biphenyl]-3-yl)propanoate (800 mg, 1.5 mmol, 1.0 eq) in DCM (10 mL) was added HCl-dioxane (4M, 10.0 mL, 40.0 mmol, 26.7 eq) and stirred at room temperature for 1 hour. The mixture was concentrated in vacuo and the residue was purified by reverse phase HPLC on a C18/120 g column (A: water/0.01% TFA, B: MeOH, 0~100%) to provide ethyl (S)-3-amino-3-(4-fluoro-4'-((3-fluoroazetidin-1-yl)methyl)-2',5,6'-trimethyl-[1,1'-biphenyl]-3-yl)propanoate as a white solid (500 mg). Yield 78% (ESI 417.1 [M+H]$^+$).

131

Preparation of ethyl (S)-3-amino-3-(2'-cyclopropyl-4-fluoro-4',5,6'-trimethyl-[1,1'-biphenyl]-3-yl)propanoate Step 1: 2-bromo-1-chloro-3,5-dimethylbenzene

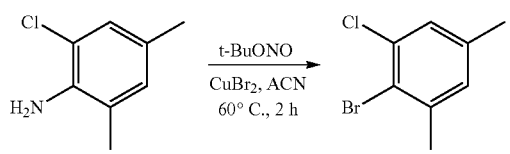

To a mixture of 2-chloro-4,6-dimethylaniline (3.0 g, 19.3 mmol, 1.00 eq) and $CuBr_2$ (21.5 g, 96.5 mmol, 5.00 eq) in ACN (50 mL) was added t-BuONO (5.96 g, 58.9 mmol, 3.00 eq) and stirred at 60° C. for 2 hours under nitrogen atmosphere. The mixture was filtered through a pad of Celite and the filtrate was concentrated in vacuo. The residue was purified by silica gel column (pet ether 100%) to give compound 2-bromo-1-chloro-3,5-dimethylbenzene as colorless oil (2.8 g). Yield: 67% (ESI 220 [M+H]$^+$).

Step 2: ethyl (S)-3-((tert-butoxycarbonyl)amino)-3-(2'-chloro-4-fluoro-4',5,6'-trimethyl-[1,1'-biphenyl]-3-yl)propanoate

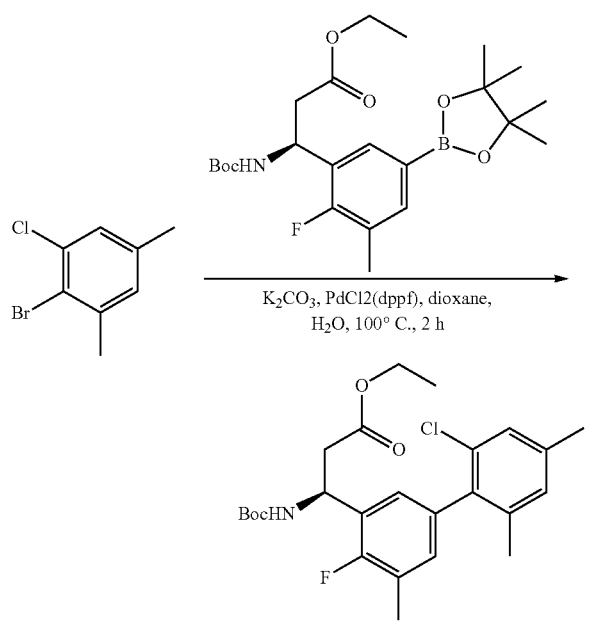

To a mixture of 2-bromo-1-chloro-3,5-dimethylbenzene (483 mg, 2.2 mmol, 1.10 eq), ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate (902 mg, 2.0 mmol, 1.00 eq) in dioxane (10 mL) under nitrogen atmosphere was added a solution of $K_2CO_3$ (552 mg, 4.0 mmol, 2.00 eq) in $H_2O$ (5 mL) and Pd(dppf)$Cl_2$ (146 mg, 0.2 mmol, 0.10 eq). The mixture was stirred at 100° C. for 2 hours under nitrogen atmosphere. Water (30 mL) was added and the solution was extracted with EtOAc (30 mL×3). The combined organic layers were washed with brine (70 mL), dried over anhydrous $Na_2SO_4$, filtered and concentrated in vacuo. The residue was purified by silica gel column (pet ether: EtOAc 10:1) to provide ethyl (S)-3-((tert-butoxycarbonyl)amino)-3-(2'-chloro-4-fluoro-4',5,6'-trimethyl-[1,1'-biphenyl]-3-yl)propanoate as colorless oil (880 mg). Yield 95% (ESI 364 [M-100+H]$^+$).

Step 3: ethyl (S)-3-((tert-butoxycarbonyl)amino)-3-(2'-cyclopropyl-4-fluoro-4',5,6'-trimethyl-[1,1'-biphenyl]-3-yl)propanoate

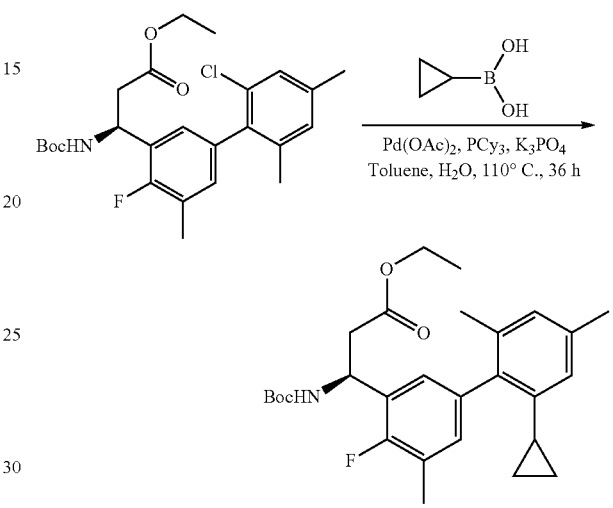

To a solution of ethyl (S)-3-((tert-butoxycarbonyl)amino)-3-(2'-chloro-4-fluoro-4',5,6'-trimethyl-[1,1'-biphenyl]-3-yl)propanoate (880 mg, 1.9 mmol, 1.00 eq), cyclopropylboronic acid (327 mg, 3.8 mmol, 2.00 eq) in toluene (10 mL) under nitrogen atmosphere was added a solution of $K_3PO_4$ (807 mg, 3.8 mmol, 2.00 eq) in $H_2O$ (2 mL), Pd(OAc)$_2$ (43 mg, 0.19 mmol, 0.10 eq) and PCy$_3$ (107 mg, 0.38 mmol, 0.20 eq). The mixture was stirred at 110° C. for 36 hours under nitrogen atmosphere. Water (30 mL) was added and the solution was extracted with EtOAc (30 mL×3). The combined organic layers were washed with brine (70 mL), dried over anhydrous $Na_2SO_4$, filtered and concentrated in vacuo. The residue was purified by silica gel column (pet ether EtOAc 2:1) to provide ethyl (S)-3-((tert-butoxycarbonyl)amino)-3-(2'-cyclopropyl-4-fluoro-4',5,6'-trimethyl-[1,1'-biphenyl]-3-yl)propanoate as a gray solid (625 mg). Yield 70% (ESI 370 [M-100+H]$^+$).

Step 4: ethyl (S)-3-amino-3-(2'-cyclopropyl-4-fluoro-4',5,6'-trimethyl-[1,1'-biphenyl]-3-yl)propanoate hydrochloride

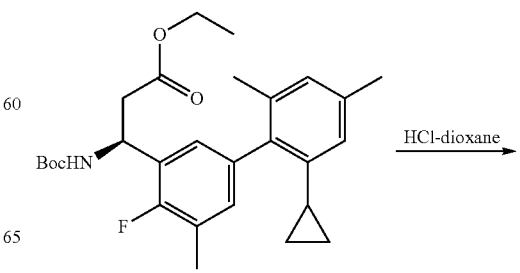

-continued

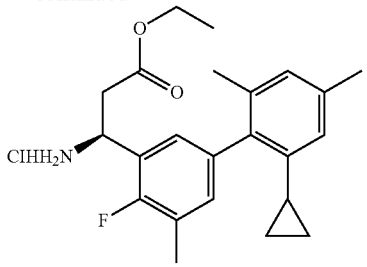

To a solution of ethyl (S)-3-((tert-butoxycarbonyl)amino)-3-(2'-cyclopropyl-4-fluoro-4',5,6'-trimethyl-[1,1'-biphenyl]-3-yl)propanoate (250 mg, 0.53 mmol, 1.00 eq) in 1,4-dioxane (6 mL) was added HCl-dioxane (4M 4.0 mL, 16.0 mmol, 30.2 eq). The mixture was stirred at room temperature for 1 hour. LCMS showed that the reaction was completed. The mixture was concentrated in vacuo to provide ethyl (S)-3-amino-3-(2'-cyclopropyl-4-fluoro-4',5,6'-trimethyl-[1,1'-biphenyl]-3-yl)propanoate hydrochloride as a white solid (215 mg), used directly in the next reaction without further purification. Yield 100% (ESI 370 [M+H]$^+$).

Preparation of ethyl (S)-3-amino-3-(3',4-difluoro-2',5,6'-trimethyl-[1,1'-biphenyl]-3-yl)propanoate Step 1: 2-bromo-6-fluoro-3-methylbenzaldehyde

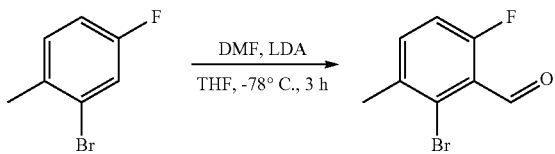

To a mixture of 2-bromo-4-fluoro-1-methylbenzene (5.0 g, 26.5 mmol, 1.00 eq) in anhydrous THF (50 mL) under nitrogen atmosphere was added lithium diisopropylamide (2.0 M, 14.6 mL, 29.2 mmol, 1.10 eq) at −78° C. and stirred at −78° C. for 1 hour. DMF (3.87 g, 53 mmol, 2.00 eq) was added to the reaction mixture at −78° C. and stirred at −78° C. for 0.5 hour, then slowly warmed to room temperature and stirred for 2 hours. The reaction was quenched with water (20 mL), extracted with EtOAc (50 mL×3). The combined organic layers were washed with brine (20 mL×3), dried over anhydrous Na$_2$SO$_4$, filtered and concentrated in vacuo to give the crude product 2-bromo-6-fluoro-3-methylbenzaldehyde as a brown liquid (4.2 g). Yield 73%. $^1$H NMR (400 MHz, MeOD) δ 10.02 (s, 1H), 7.45-7.17 (m, 1H), 7.05-7.00 (m, 1H), 2.26 (s, 3H).

Step 2: (2-bromo-6-fluoro-3-methylphenyl)methanol

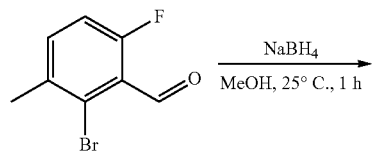

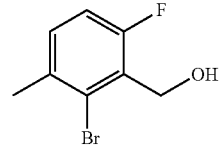

To a mixture of 2-bromo-6-fluoro-3-methylbenzaldehyde (3.0 g, 13.8 mmol, 1.00 eq) in MeOH (30 mL) under nitrogen atmosphere was added NaBH$_4$ (1.5 g, 41.4 mmol, 3.00 eq) at 0° C. and stirred at room temperature for 2 hours. The mixture was quenched with water (50 mL), extracted with EtOAc (50 mL×3). The combined organic phase was washed with brine (80 mL), dried over anhydrous Na$_2$SO$_4$, filtered and concentrated in vacuo. The residue was purified by silica gel column (pet ether: EtOAc 10:1) to provide (2-bromo-6-fluoro-3-methylphenyl)methanol as a white solid (2.7 g). Yield 90%

Step 3: (2-bromo-3-(bromomethyl)-4-fluoro-1-methylbenzene

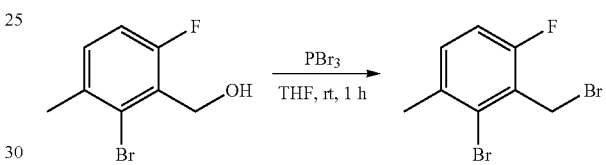

To a mixture of (2-bromo-6-fluoro-3-methylphenyl)methanol (3.2 g, 14.6 mmol, 1.00 eq) in THF (50 mL) under nitrogen atmosphere was added PBr$_3$ (3 mL, 29.2 mmol, 2.00 eq) at room temperature and stirred for 1 hour. The reaction mixture was concentrated in vacuo and the residue was purified by silica gel column (pet ether: EtOAc 99:1) to provide 2-bromo-3-(bromomethyl)-4-fluoro-1-methylbenzene as a white solid (3.58 g). Yield 90% $^1$H NMR (400 MHz, MeOD) δ 7.33-7.30 (m, 1H), 7.09-7.04 (m, 1H), 4.72 (d, J=2.0 Hz, 2H), 2.40 (s, 3H).

Step 4: 2-bromo-4-fluoro-1,3-dimethylbenzene

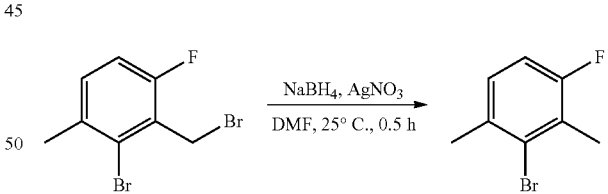

To a mixture of 2-bromo-3-(bromomethyl)-4-fluoro-1-methylbenzene (2.0 g, 7.09 mmol, 1.00 eq) in DMF (20 mL) was added NaBH$_4$ (0.536 g, 14.18 mmol, 2.00 eq) and AgNO$_3$ (2.4 g, 14.18 mmol, 2.00 eq) at room temperature. The reaction was stirred at room temperature for 0.5 hour. The mixture was quenched with water (50 mL) and extracted with EtOAc (50 mL×3). The combined organic layers were washed with brine (100 mL), dried over anhydrous Na$_2$SO$_4$, filtered and concentrated in vacuo. The residue was purified by silica gel column (DCM 100%) to provide 2-bromo-4-fluoro-1,3-dimethylbenzene as colorless oil (1.00 g). Yield 69% $^1$H NMR (400 MHz, CDCl$_3$) δ 7.09-7.01 (m, 1H), 6.90 (t, J=8.7 Hz, 1H), 2.37 (s, 3H), 2.34 (d, J=2.4 Hz, 3H).

Step 5: ethyl(S)-3-((tert-butoxycarbonyl)amino)-3-(3',4-difluoro-2',5,6'-trimethyl-[1,1'-biphenyl]-3-yl)propanoate

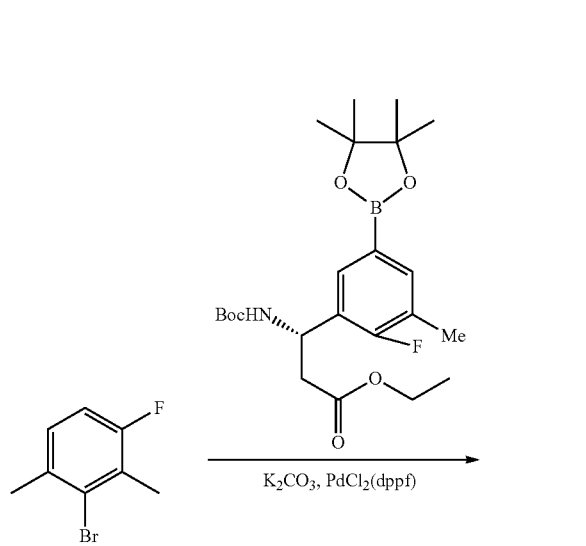

To a mixture of 2-bromo-4-fluoro-1,3-dimethylbenzene (800 mg, 3.93 mmol, 1.00 eq), ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate (1.77 g, 3.93 mmol, 1.00 eq) in dioxane (12 mL) under nitrogen atmosphere was added a solution of K$_2$CO$_3$ (1.08 g, 7.86 mmol, 2.00 eq) in H$_2$O (2 mL) and Pd(dppf)Cl$_2$ (658 mg, 0.39 mmol, 0.10 eq). The mixture was stirred at 100° C. for 2 hours under nitrogen atmosphere. Water (30 mL) was added and the solution was extracted with EtOAc (30 mL×3). The combined organic layers were washed with brine (70 mL), dried over anhydrous Na$_2$SO$_4$, filtered and concentrated in vacuo. The residue was purified by reverse phase HPLC on a C18/40 g column (A: water 10 mM NH$_4$HCO$_3$, B: MeOH, 0~100%) to provide ethyl (S)-3-((tert-butoxycarbonyl)amino)-3-(3',4-difluoro-2',5,6'-trimethyl-[1,1'-biphenyl]-3-yl)propanoate as colorless oil (1.2 g). Yield 68% (ESI 348.1 [M-100+H]$^+$).

Step 6: ethyl (S)-3-amino-3-(3',4-difluoro-2',5,6'-trimethyl-[1,1'-biphenyl]-3-yl)propanoate hydrochloride

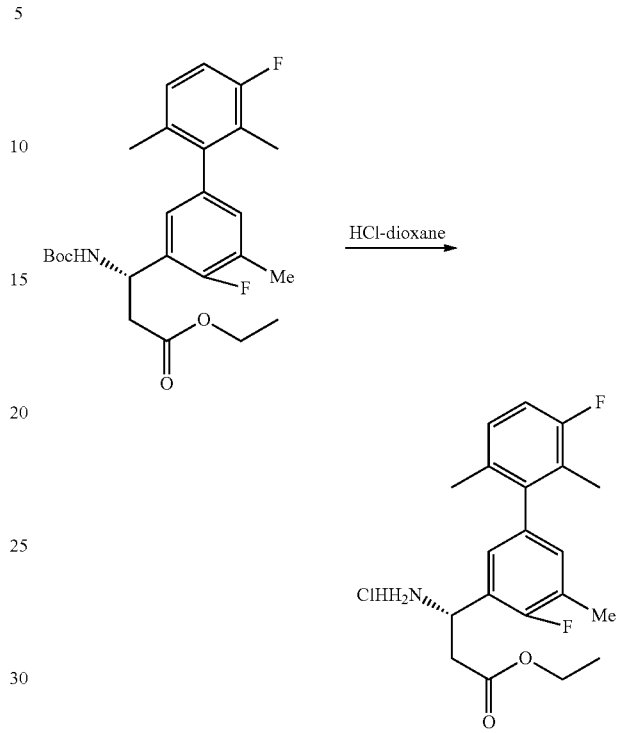

To a mixture of product ethyl (S)-3-((tert-butoxycarbonyl)amino)-3-(3',4-difluoro-2',5,6'-trimethyl-[1,1'-biphenyl]-3-yl)propanoate (1.2 g, 2.68 mmol, 1.00 eq) in 1,4-dioxane (6 mL) was added HCl-dioxane (4M 4.0 mL, 16.0 mmol, 5.97 eq). The mixture was stirred at room temperature for 1 hour. LCMS showed that the reaction was completed. The mixture was concentrated in vacuo to provide ethyl (S)-3-amino-3-(3',4-difluoro-2',5,6'-trimethyl-[1,1'-biphenyl]-3-yl)propanoate hydrochloride (1.0 g crude) used directly in the next reaction without further purification. (ESI 348.2 [M+H]$^+$).

Preparation of (S)-ethyl 3-amino-3-(4-fluoro-3'-methoxy-2',5,6'-trimethylbiphenyl-3-yl)propanoate

Step 1: 1-bromo-2,4-dimethyl-3-nitrobenzene

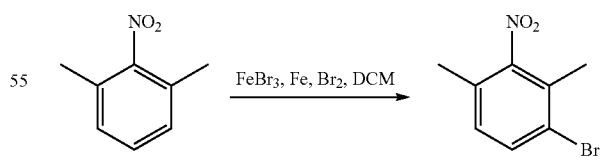

To a mixture of 1,3-dimethyl-2-nitrobenzene (10 g, 66 mmol, 1.0 eq) in DCM (100 mL) was added FeBr$_3$ (390 mg, 211.32 mmol, 0.02 eq) and Fe (1.12 g, 20 mmol, 0.3 eq). Br$_2$ (11.6 g, 72.6 mmol, 1.1 eq) was added dropwise and stirred at 60° C. for 16 hours. The reaction mixture was concentrated in vacuo and the residue was purified by silica gel column (pet ether) to provide 1-bromo-2,4-dimethyl-3-nitrobenzene as a white solid (10 g). Yield 66%.

Step 2: 1-methoxy-2,4-dimethyl-3-nitrobenzene

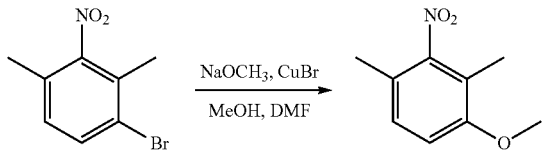

To a mixture of 1-bromo-2,4-dimethyl-3-nitrobenzene (8 g, 35 mmol, 1.0 eq) in MeOH (80 mL) and DMF (80 mL) was added NaOCH$_3$ (5.67 g, 105 mmol, 3 eq) and CuBr (1 g, 7 mmol, 0.2 eq) at room temperature. The mixture was stirred at 110° C. for 16 hours. The reaction mixture was filtered. The filtrate was diluted with water (100 mL), extracted with EtOAc (100 mL×3). The combined organic layers were washed with brine (100 mL), dried over anhydrous Na$_2$SO$_4$, filtered and concentrated in vacuo. The residue was purified by silica gel column (100% pet ether) to provide 1-methoxy-2,4-dimethyl-3-nitrobenzene as a colorless oil (5.8 g). Yield 91% (ESI 182.2 [M+H]$^+$).

Step 3: 3-methoxy-2,6-dimethylaniline

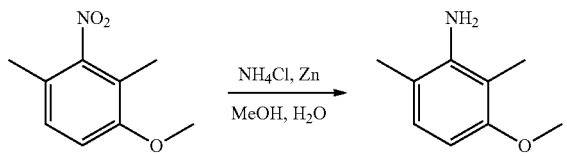

To a mixture of 1-methoxy-2,4-dimethyl-3-nitrobenzene (5.8 g, 32 mmol, 1.0 eq) in MeOH (60 mL) and H$_2$O (6 mL) at 0° C. was added NH$_4$Cl (5.18 g, 96 mmol, 3.0 eq) and Zn (20.8 g, 320 mmol, 10 eq). The mixture was stirred at room temperature for 4 hours. LCMS showed that the reaction was completed. The reaction mixture was filtered and concentrated in vacuo. The residue was purified by silica gel column (pet ether: EtOAc 1:1) to provide 3-methoxy-2,6-dimethylaniline as yellow oil (2.8 g). Yield 58% (ESI 152.2[M+H]$^+$).

Step 4: 2-bromo-4-methoxy-1,3-dimethylbenzene

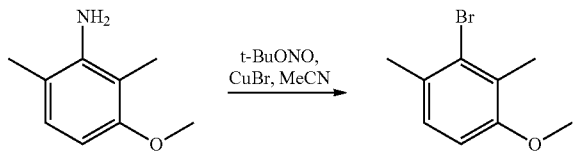

To a mixture of 3-methoxy-2,6-dimethylaniline (2 g, 13.24 mmol, 1.0 eq) in MeCN (30 mL) was added t-BuONO (2.06 g, 20 mmol, 1.5 eq) at 0° C., then CuBr (2.27 g, 15.89 mmol, 1.2 eq) was added. The mixture was stirred at 60° C. for 2 hours. LCMS showed that the reaction was completed. The reaction mixture was concentrated in vacuo and purified by silica gel column (pet ether) to provide 2-bromo-4-methoxy-1,3-dimethylbenzene as a colorless oil (800 mg). Yield 28%.

Step 5: (S)-ethyl 3-(tert-butoxycarbonylamino)-3-(4-fluoro-3'-methoxy-2',5,6'-trimethylbiphenyl-3-yl)propanoate

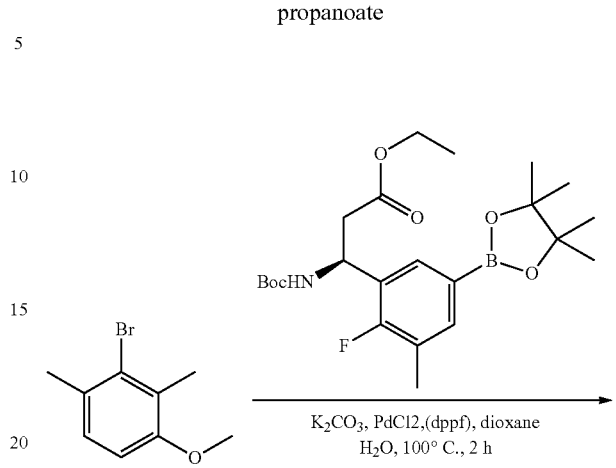

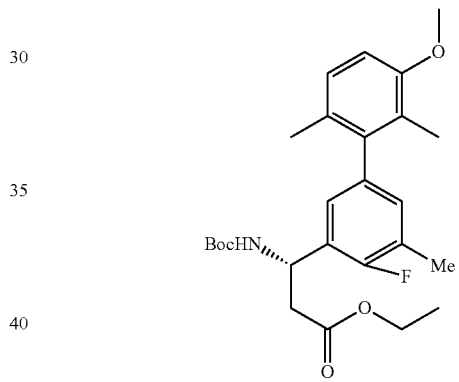

A mixture of 2-bromo-4-methoxy-1,3-dimethylbenzene (700 mg, 3.27 mmol, 1.00 eq), (S)-ethyl 3-(tert-butoxycarbonylamino)-3-(2-fluoro-3-methyl-5-(4,4,5,5-tetramethyl-1,3,2-dioxaborolan-2-yl)phenyl)propanoate (1.47 g, 3.27 mmol, 1.0 eq), K$_2$CO$_3$ (1.35 g, 9.81 mmol, 3 eq) and Pd(dppf)Cl$_2$ (239 mg, 0.327 mmol, 0.1 eq) in dioxane (10 mL) and H$_2$O (1 mL) was stirred at 110° C. for 4 hours under nitrogen atmosphere. LCMS showed that the reaction was completed. The mixture was cooled to room temperature. Water (30 mL) was added and the solution was extracted with EtOAc (30 mL×3). The combined organic layers were washed with brine (30 mL), dried over anhydrous Na$_2$SO$_4$, filtered and concentrated in vacuo. The residue was purified by silica gel column (pet ether: EtOAc 5:1) to provide (S)-ethyl 3-(tert-butoxycarbonylamino)-3-(4-fluoro-3'-methoxy-2',5,6'-trimethylbiphenyl-3-yl)propanoate (1 g) as a colorless oil. Yield 67% (ESI 360.1 [M-Boc+1]$^+$).

139

Step 6: (S)-ethyl 3-amino-3-(4-fluoro-3'-methoxy-2', 5,6'-trimethylbiphenyl-3-yl)propanoate

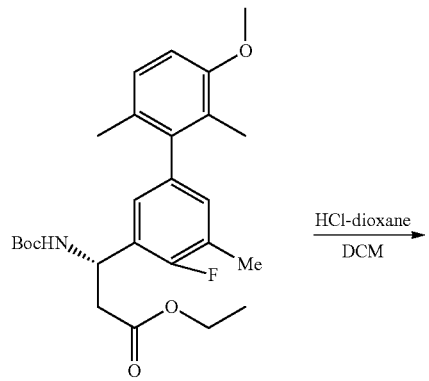

To a stirred solution of (S)-ethyl 3-(tert-butoxycarbonylamino)-3-(4-fluoro-3'-methoxy-2',5,6'-trimethylbiphenyl-3-yl)propanoate (1 g, 2.18 mmol, 1.00 eq) in DCM (8 mL) was added HCl-dioxane (4 M, 2.18 mL, 8.72 mmol, 4 eq). The mixture was stirred at room temperature for 2 hours. LCMS showed that the reaction was completed. The mixture was concentrated in vacuo and the residue was purified by reverse phase IPLC on a C18/80 g column (A: water 10 mM NH$_4$HCO$_3$, B: MeOH, 0~100%) to provide (S)-ethyl 3-amino-3-(4-fluoro-3'-methoxy-2',5,6'-trimethylbiphenyl-3-yl)propanoate (600 mg) as a colorless oil. Yield 77% (ESI 360.1 [M+H]$^+$).

140

Preparation of ethyl (S)-3-amino-3-(6'-cyano-4-fluoro-2',3',5-trimethyl-[1,1'-biphenyl]-3-yl)propanoate Step 1: ethyl (S)-3-(((R)-tert-butylsulfinyl)amino)-3-(6'-cyano-4-fluoro-2',3',5-trimethyl-[1,1'-biphenyl]-3-yl)propanoate

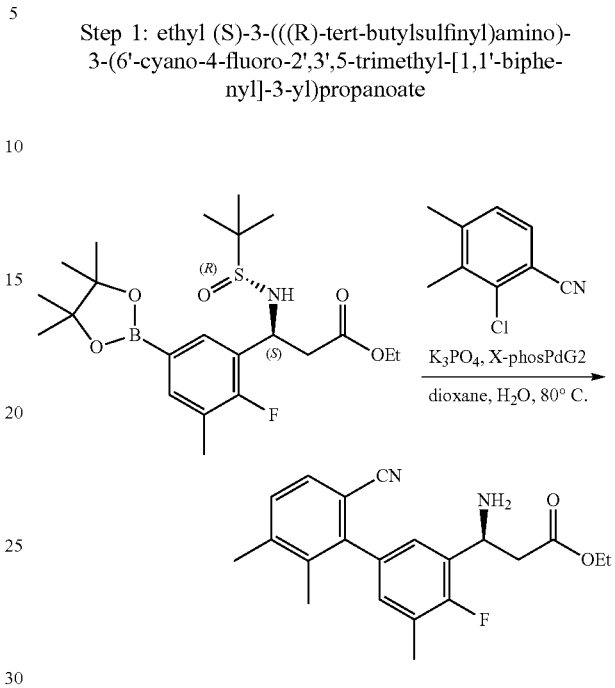

A mixture of ethyl (S)-3-(((R)-tert-butylsulfinyl)amino)-3-(2-fluoro-3-methyl-5-(4,4,5,5-tetramethyl-1,3,2-dioxaborolan-2-yl)phenyl)propanoate (1.7 g, 3.6 mmol, 2.0 eq), 2-chloro-3,4-dimethylbenzonitrile (300 mg, 1.8 mmol, 1.0 eq), K$_3$PO$_4$ (1.2 g, 5.4 mmol, 3.0 eq) and XPhosPdG2 (140 mg, 0.18 mmol, 0.1 eq) in dioxane (30 mL) and H$_2$O (3 mL) was stirred at 80° C. for 2 hours under nitrogen atmosphere. LCMS showed that the reaction was completed. The mixture was cooled to room temperature. Water (20 mL) was added and the solution was extracted with EtOAc (20 mL×3). The combined organic layers were washed with brine (50 mL), dried over anhydrous Na$_2$SO$_4$, filtered and concentrated in vacuo. The residue was purified by silica gel column (pet ether: EtOAc 1:1) to provide ethyl (S)-3-(((R)-tert-butylsulfinyl)amino)-3-(6'-cyano-4-fluoro-2',3',5-trimethyl-[1, 1'-biphenyl]-3-yl)propanoate (500 mg) as a yellow oil. Yield 60% (ESI 459.3 [M+H]$^+$).

Step 2: ethyl (S)-3-amino-3-(6'-cyano-4-fluoro-2',3', 5-trimethyl-[1,1'-biphenyl]-3-yl)propanoate

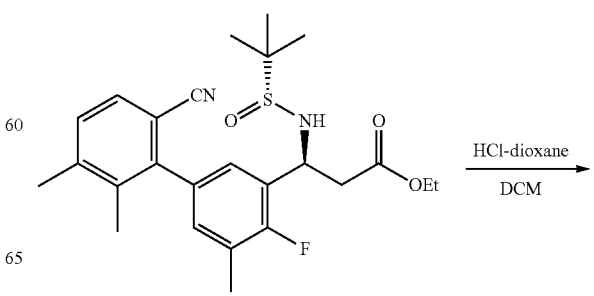

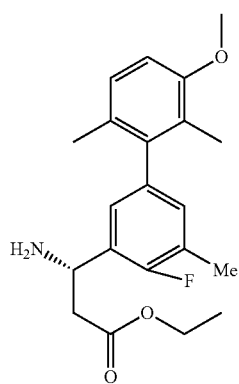

-continued

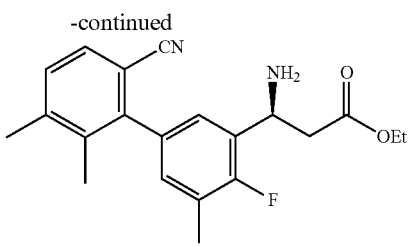

To a stirred solution of ethyl (S)-3-(((R)-tert-butylsulfinyl)amino)-3-(6'-cyano-4-fluoro-2',3',5-trimethyl-[1,1'-biphenyl]-3-yl)propanoate (500 mg, 1.1 mmol, 1.0 eq) in DCM (10 mL) was added HCl-dioxane (4 M, 10 mL, 40.0 mmol, 36.4 eq). The mixture was stirred at room temperature for 1 hour. LCMS showed that the reaction was completed. The mixture was concentrated in vacuo and the residue was purified by reverse phase HPLC on a C18/40 g column (A: water 10 mM NH$_4$HCO$_3$, B: MeOH, 0~100%) to provide ethyl (S)-3-amino-3-(6'-cyano-4-fluoro-2',3',5-trimethyl-[1,1'-biphenyl]-3-yl)propanoate (200 mg) as a colorless oil. Yield 51.8% (ESI 355.2 [M+H]$^+$).

Preparation of (S)-ethyl 3-amino-3-(3',4-difluoro-2',4',5,6'-tetramethylbiphenyl-3-yl)propanoate Step 1: (S)-ethyl 3-(tert-butoxycarbonylamino)-3-(3',4-difluoro-2',4',5,6'-tetramethylbiphenyl-3-yl)propanoate To a mixture of (S)-ethyl 3-(tert-butoxycarbonylamino)-3-(2-fluoro-3-methyl-5-(4,4,5,5-tetramethyl-1,3,2-dioxaborolan-2-yl)phenyl)propanoate (500 mg, 1.14 mmol, 1 eq) and 2-bromo-4-fluoro-1,3,5-trimethylbenzene (309 mg, 1.43 mmol, 1.2 eq) in dioxane (10 mL) was added a solution of K$_2$CO$_3$ (314.6 mg, 2.28 mmol, 2 eq) in H$_2$O (2 mL) and Pd(dppf)Cl$_2$ (80 mg, 0.11 mmol, 0.1 eq). The mixture was heated to 110° C. for 2 hours under nitrogen atmosphere. Water (20 mL) was added and the solution was extracted with EtOAc (20 mL×3). The combined organic layers were concentrated in vacuo and the residue was purified by silica gel column (pet ether: EtOAc 1:1) to give methyl (S)-ethyl 3-(tert-butoxycarbonylamino)-3-(3',4-difluoro-2',4',5,6'-tetramethylbiphenyl-3-yl)propanoate as a colorless oil (500 mg). Yield 97.8% (ESI 461.5 [M+H]$^+$).

Step 2: (S)-ethyl 3-amino-3-(3',4-difluoro-2',4',5,6'-tetramethylbiphenyl-3-yl)propanoate

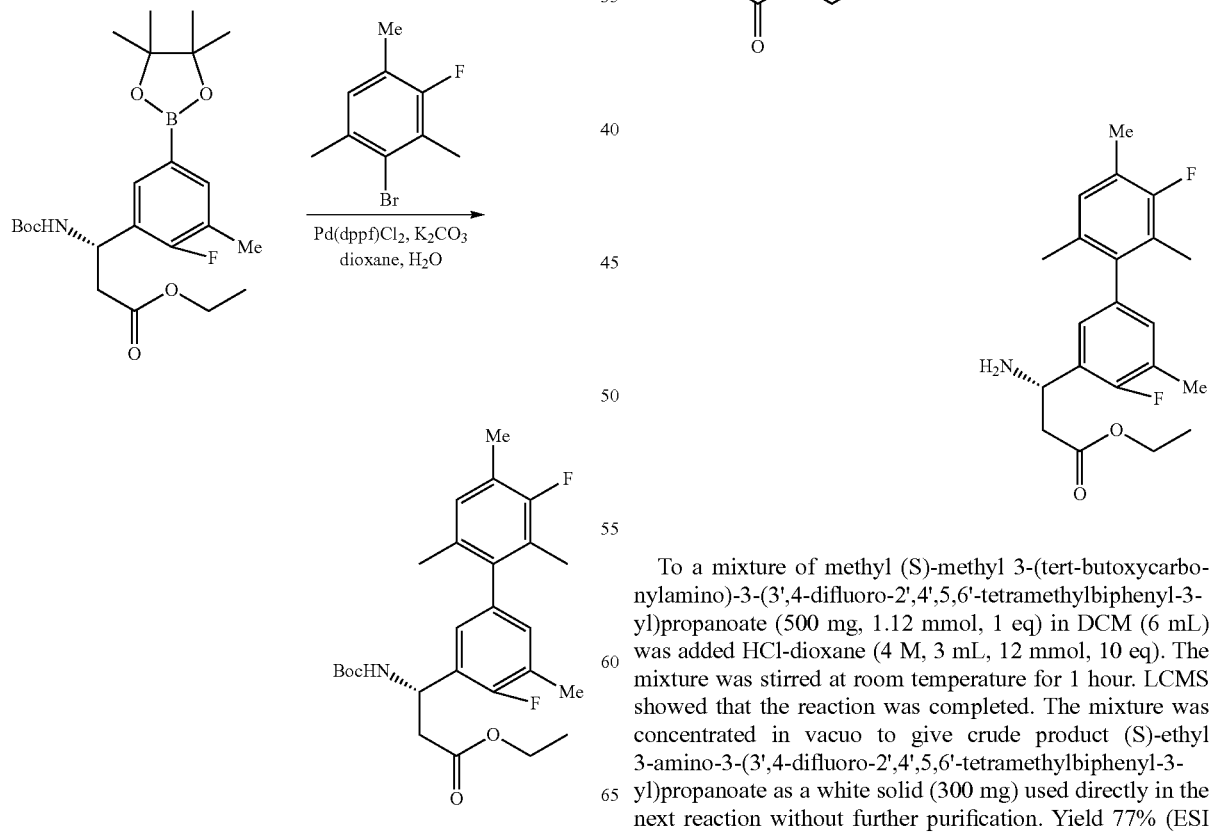

To a mixture of methyl (S)-methyl 3-(tert-butoxycarbonylamino)-3-(3',4-difluoro-2',4',5,6'-tetramethylbiphenyl-3-yl)propanoate (500 mg, 1.12 mmol, 1 eq) in DCM (6 mL) was added HCl-dioxane (4 M, 3 mL, 12 mmol, 10 eq). The mixture was stirred at room temperature for 1 hour. LCMS showed that the reaction was completed. The mixture was concentrated in vacuo to give crude product (S)-ethyl 3-amino-3-(3',4-difluoro-2',4',5,6'-tetramethylbiphenyl-3-yl)propanoate as a white solid (300 mg) used directly in the next reaction without further purification. Yield 77% (ESI 361.4s [M+H]$^+$).

Preparation of ethyl (S)-3-(5-bromo-3-chloro-2-fluorophenyl)-3-(((R)-tert-butylsulfinyl)amino)propanoate

Step 1: (R,E)-N-(5-bromo-3-chloro-2-fluorobenzylidene)-2-methylpropane-2-sulfinamide

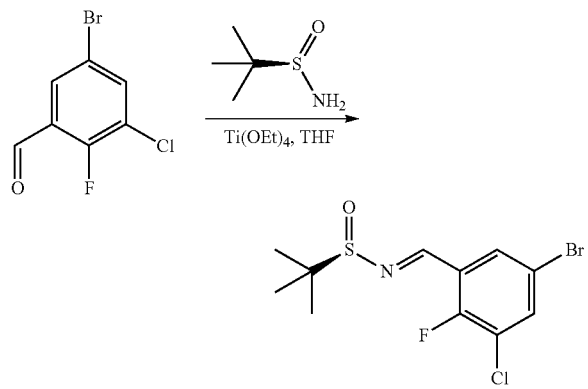

To a mixture of 5-bromo-3-chloro-2-fluorobenzaldehyde (10.0 g, 42.2 mmol, 1.00 eq) and (R)-2-methylpropane-2-sulfinamide (5.6 g, 46.4 mmol, 1.1 eq) in anhydrous THF (100 mL) under nitrogen atmosphere was added Ti(OEt)$_4$ (14.4 g, 63.3 mmol, 1.50 eq) dropwise at room temperature and the temperature maintained below 30° C. The reaction mixture was warmed to 35° C. and stirred for 1 hour. LCMS showed that the reaction was completed. Water (100 mL) and EtOAc (100 mL) were added into the mixture and stirred at room temperature for 5 mins. The mixture was filtered and washed with EtOAc (50 mL). The filtrate was separated. The organic layer was washed with brine (100 mL), dried over anhydrous Na$_2$SO$_4$, filtered and concentrated in vacuo. The residue was purified by silica gel column (pet ether: EtOAc 4:1) to provide (R, E)-N-(5-bromo-3-chloro-2-fluorobenzylidene)-2-methylpropane-2-sulfinamide as a yellow oil (14.0 g). Yield 98% (ESI 341.9 (M+H)$^+$).

Step 2: ethyl(S)-3-(5-bromo-3-chloro-2-fluorophenyl)-3-(((R)-tert-butylsulfinyl)amino)propanoate

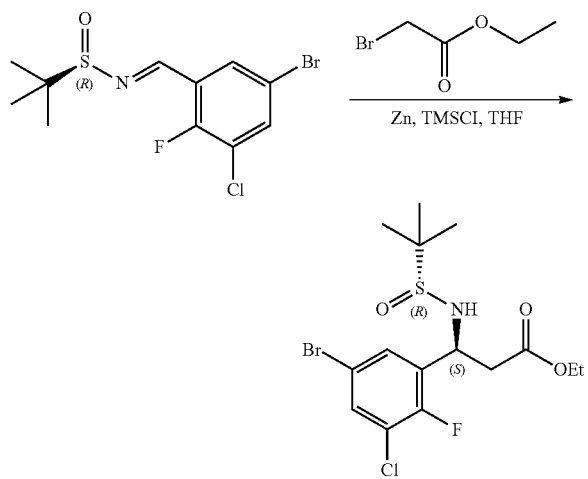

To a mixture of Zn (13.0 g, 205.5 mmol, 5.00 eq) in anhydrous THF (200 mL) under nitrogen atmosphere was added chlorotrimethylsilane (888 mg, 8.22 mmol, 0.2 eq) dropwise at room temperature and stirred at 50° C. under nitrogen atmosphere for 1 hour. The mixture was cooled to 20-30° C. Ethyl 2-bromoacetate (17.1 g, 102.7 mmol, 2.50 eq) was added dropwise at room temperature under nitrogen atmosphere and stirred at 60° C. under for 1 hour. The reaction mixture was cooled to room temperature. A solution of (R, E)-N-(5-bromo-3-chloro-2-fluorobenzylidene)-2-methylpropane-2-sulfinamide (14.0 g, 41.1 mmol, 1.00 eq) in anhydrous THF (20 mL) was added dropwise into the mixture at room temperature under nitrogen atmosphere and stirred at room temperature for 1 hour. LCMS showed that the reaction was completed. Water (100 mL) and EtOAc (100 mL) was added into the mixture and stirred at room temperature for 5 mins. The mixture was filtered. The filtrate was extracted with EtOAc (100 mL). The combined organic layers were washed with water (30 mL) and brine (30 mL), dried over anhydrous Na$_2$SO$_4$, filtered and concentrated in vacuo. The residue was purified by silica gel column (pet ether: EtOAc 4:1) to provide ethyl (S)-3-(5-bromo-3-chloro-2-fluorophenyl)-3-(((R)-tert-butylsulfinyl)amino)propanoate as a yellow oil (12.0 g). Yield 73% (ESI 429.9 (M+H)$^+$).

Preparation of ethyl (S)-3-amino-3-(5-chloro-4-fluoro-2',6'-dimethyl-[1,1'-biphenyl]-3-yl)propanoate

Step 1: ethyl(S)-3-(((R)-tert-butylsulfinyl)amino)-3-(5-chloro-4-fluoro-2',6'-dimethyl-[1,1'-biphenyl]-3-yl)propanoate

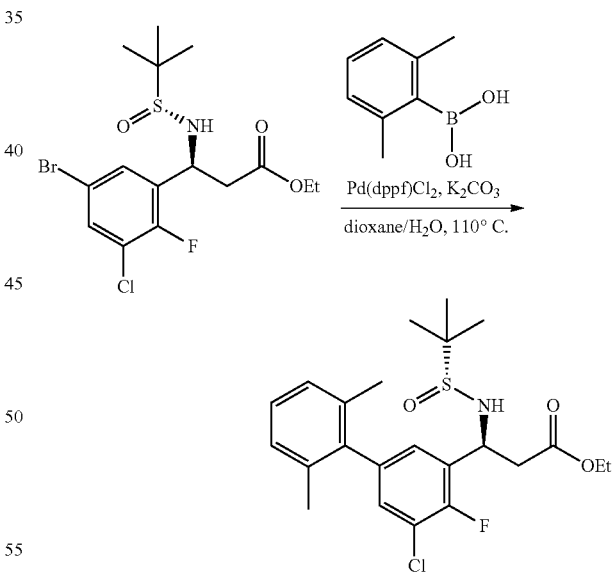

A mixture of ethyl (S)-3-(5-bromo-3-chloro-2-fluorophenyl)-3-(((R)-tert-butylsulfinyl)amino)propanoate (4.0 g, 9.6 mmol, 1.00 eq), K$_2$CO$_3$ (8.0 g, 57.6 mmol, 2.0 eq) Pd(dppf)Cl$_2$ (1.4 g, 1.9 mmol, 0.1 eq) and (2,6-dimethylphenyl)boronic acid (2.8 g, 19.2 mmol, 2.00 eq) in dioxane (40 mL) and H$_2$O (4 mL) was stirred at 80° C. for 16 hours under nitrogen atmosphere. The reaction mixture was cooled to room temperature and poured into 50 mL of water and extracted with EtOAc (50 mL×3). The combined organic layers were washed with brine (100 mL), dried over anhydrous Na₂SO₄, filtered and concentrated in vacuo. The residue was purified by silica gel column (pet ether: EtOAc 10:1) to provide ethyl (S)-3-(((R)-tert-butylsulfinyl)amino)-3-(5-chloro-4-fluoro-2',6'-dimethyl-[1,1'-biphenyl]-3-yl) propanoate as a yellow oil (3.0 g). Yield 71% (ESI 454.1 (M+H)⁺)

Step 2: ethyl (S)-3-amino-3-(5-chloro-4-fluoro-2',6'-dimethyl-[1,1'-biphenyl]-3-yl)propanoate

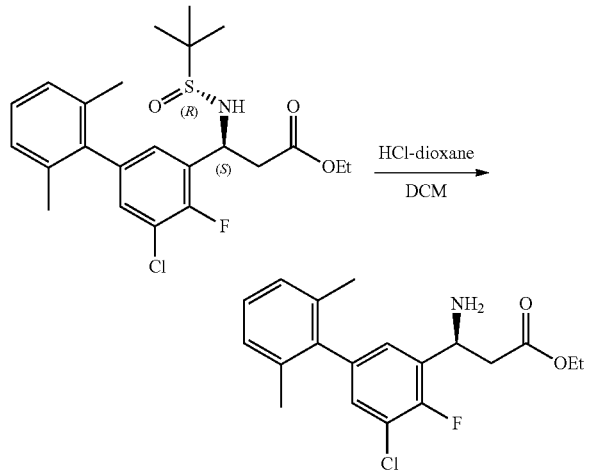

To a mixture of ethyl (S)-3-(((R)-tert-butylsulfinyl) amino)-3-(5-chloro-4-fluoro-2',6'-dimethyl-[1,1'-biphenyl]-3-yl)propanoate (3.0 g, 43.66 mmol, 1.0 eq) in DCM (20 mL) was added HCl-dioxane (4 M, 20 mL, 80 mmol, 1.8 eq). The mixture was stirred at room temperature for 1 hour. LCMS showed that the reaction was completed. The mixture was concentrated in vacuo and the residue was purified by reverse phase HPLC on a C18/120 g column (A: water 10 mM NH₄HCO₃, B: MeOH, 0~100%) to provide ethyl (S)-3-amino-3-(5-chloro-4-fluoro-2',6'-dimethyl-[1,1'-biphenyl]-3-yl)propanoate as a white solid (1.8 g). Yield 78% (ESI 350.0 [M+H]⁺).

Preparation of ethyl (S)-3-amino-3-(5-chloro-4,4'-difluoro-2',6'-dimethyl-[1,1'-biphenyl]-3-yl)propanoate Step 1: ethyl(S)-3-(((R)-tert-butylsulfinyl)amino)-3-(5-chloro-4,4'-difluoro-2',6'-dimethyl-[1,1'-biphenyl]-3-yl)propanoate

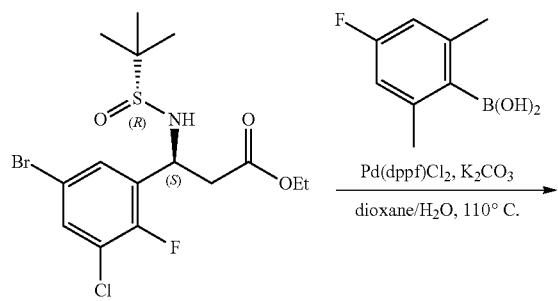

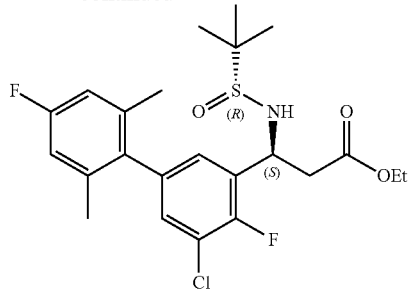

To a mixture of ethyl (S)-3-(5-bromo-3-chloro-2-fluorophenyl)-3-(((R)-tert-butylsulfinyl)amino)propanoate (2.0 g, 4.66 mmol, 1.0 eq) and (4-fluoro-2,6-dimethylphenyl)boronic acid (940 mg, 5.59 mmol, 1.2 eq) in dioxane (20 mL) was added a solution of K₂CO₃ (1.3 g, 9.32 mmol, 2.0 eq) in H₂O (2 mL) and Pd(dppf)Cl₂ (341 mg, 0.47 mmol, 0.1 eq). The mixture was heated to 110° C. for 2 hours under nitrogen atmosphere. The reaction mixture was cooled to room temperature and poured into water (50 mL) and extracted with EtOAc (50 mL×3). The combined organic layers were washed with brine (100 mL) and dried over anhydrous Na₂SO₄, filtered and concentrated in vacuo. The residue was purified by silica gel column (pet ether: EtOAc 1:1) to provide ethyl (S)-3-(((R)-tert-butylsulfinyl)amino)-3-(5-chloro-4,4'-difluoro-2',6'-dimethyl-[1,1'-biphenyl]-3-yl)propanoate as a colorless oil (1.2 g). Yield 54% (ESI 472.1 [M+H]⁺).

Step 2: ethyl(S)-3-amino-3-(5-chloro-4,4'-difluoro-2',6'-dimethyl-[1,1'-biphenyl]-3-yl)propanoate

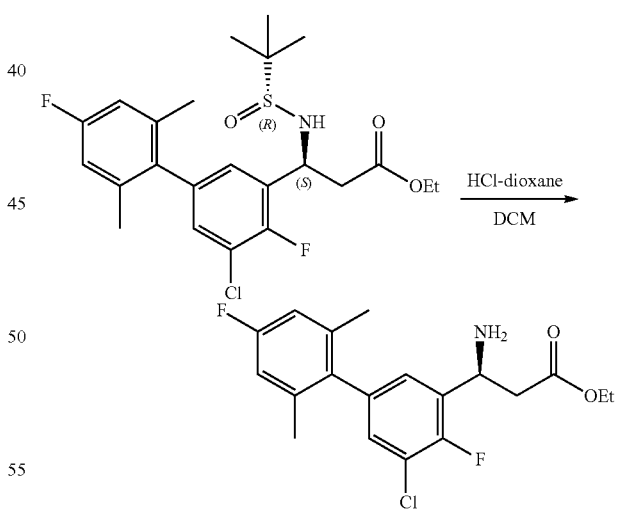

To a mixture of ethyl (S)-3-(((R)-tert-butylsulfinyl) amino)-3-(5-chloro-4,4'-difluoro-2',6'-dimethyl-[1,1'-biphenyl]-3-yl)propanoate (1.2 g, 2.54 mmol, 1.0 eq) in DCM (6 mL) was added HCl-dioxane (4 M, 3 mL, 12 mmol, 4.7 eq). The mixture was stirred at room temperature for 1 hour. LCMS showed that the reaction was completed. The mixture was concentrated in vacuo and the residue was purified by reverse phase IPLC on a C18/80 g column (A: water 0.01% TFA, B: MeOH, 0~100%) to provide ethyl (S)-3-amino-3-

(5-chloro-4,4'-difluoro-2',6'-dimethyl-[1,1'-biphenyl]-3-yl) propanoate as a white solid (900 mg). Yield 96% (ESI 368.1 [M+H]⁺).

Preparation of ethyl (S)-3-amino-3-(5-chloro-4-fluoro-2',4',6'-trimethyl-[1,1'-biphenyl]-3-yl)propanoate Step 1: ethyl (S)-3-(((R)-tert-butylsulfinyl)amino)-3-(5-chloro-4-fluoro-2',4',6'-trimethyl-[1,1'-biphenyl]-3-yl)propanoate

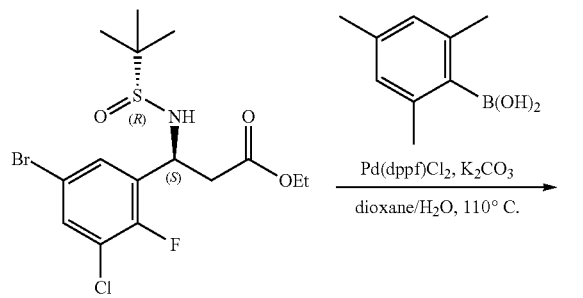

A mixture of ethyl (S)-3-(5-bromo-3-chloro-2-fluorophenyl)-3-(((R)-tert-butylsulfinyl)amino)propanoate (2.0 g, 4.66 mmol, 1.0 eq), mesitylboronic acid (1.5 g, 9.33 mmol, 2.0 eq), K₂CO₃ (1.29 g, 9.32 mmol, 2.0 eq) and Pd(dppf)Cl₂ (341 mg, 0.466 mmol, 0.1 eq) in dioxane (20 mL) and H₂O (2 mL) was stirred at 110° C. under nitrogen atmosphere overnight. After completion and cooling to room temperature, the reaction mixture was poured into water (50 mL), extracted with EtOAc (50 mL×3). The combined organic layers were washed with brine (100 mL) and dried over anhydrous Na₂SO₄, filtered and concentrated in vacuo. The residue was purified by silica gel column (pet ether: EtOAc 1:1) to provide ethyl (S)-3-(((R)-tert-butylsulfinyl)amino)-3-(5-chloro-4-fluoro-2',4',6'-trimethyl-[1,1'-biphenyl]-3-yl) propanoate as a yellow oil (1.9 g). Yield 87% (ESI 468 (M+H)⁺).

Step 2: ethyl (S)-3-amino-3-(5-chloro-4-fluoro-2',4',6'-trimethyl-[1,1'-biphenyl]-3-yl)propanoate

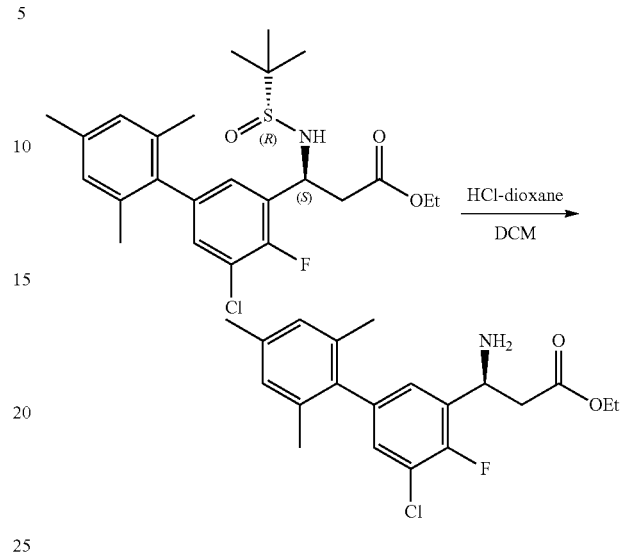

To a mixture of ethyl (S)-3-(((R)-tert-butylsulfinyl) amino)-3-(5-chloro-4-fluoro-2',4',6'-trimethyl-[1,1'-biphenyl]-3-yl)propanoate (1.9 g, 4.06 mmol, 1.0 eq) in DCM (20 mL) was added HCl-dioxane (4 M, 3 mL, 12 mmol, 3.0 eq). The mixture was stirred at room temperature for 1 hour. LCMS showed that the reaction was completed. The mixture was concentrated in vacuo and the residue was purified by reverse phase HPLC on a C18/120 g column (A: water 10 mM NH₄HCO₃, B: MeOH, 0~100%) to provide ethyl (S)-3-amino-3-(5-chloro-4-fluoro-2',4',6'-trimethyl-[1,1'-biphenyl]-3-yl)propanoate as a white solid (1.3 g). Yield 88% (ESI 364.1 (M+H)⁺).

Preparation of ethyl (S)-3-(5-bromo-2,3-difluorophenyl)-3-(((R)-tert-butylsulfinyl)amino)propanoate Step 1: (R, E)-N-(5-bromo-2,3-difluorobenzylidene)-2-methylpropane-2-sulfinamide

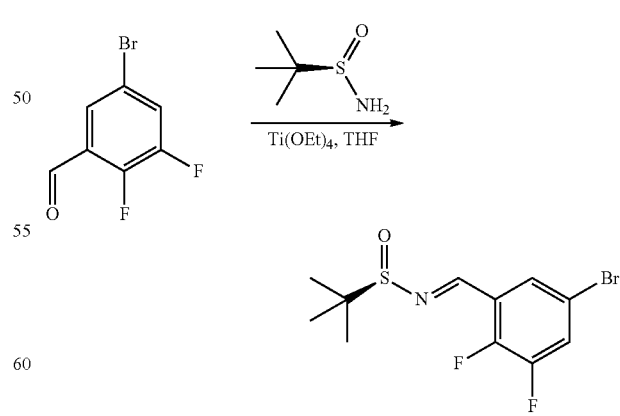

To a mixture of 5-bromo-2,3-difluorobenzaldehyde (4.5 g, 20.36 mmol, 1.0 eq) and (R)-2-methylpropane-2-sulfinamide (2.7 g, 22.40 mmol, 1.1 eq) in anhydrous THF (50 mL) under nitrogen atmosphere was added Ti(OEt)₄ (9.3 g, 40.72 mmol, 2.0 eq) dropwise at room temperature while maintaining the temperature below 30° C. The reaction mixture was warmed to 35° C. and stirred for 1 hour. LCMS showed that the reaction was completed. Water (50 mL) and EtOAc (50 mL) was added into the mixture and stirred at room temperature for 10 mins. The mixture was filtered and washed with EtOAc (50 mL). The filtrate was separated. The organic layer was washed with water (70 mL) and brine (70 mL), dried over anhydrous Na$_2$SO$_4$, filtered and concentrated in vacuo. The residue was purified by silica gel column (pet ether: EtOAc 4:1) to provide (R, E)-N-(5-bromo-2,3-difluorobenzylidene)-2-methylpropane-2-sulfinamide as a yellow oil (6.0 g). Yield 91% (ESI 325.9 (M+H)$^+$).

Step 2: ethyl (S)-3-(5-bromo-2,3-difluorophenyl)-3-(((R)-tert-butylsulfinyl)amino)propanoate

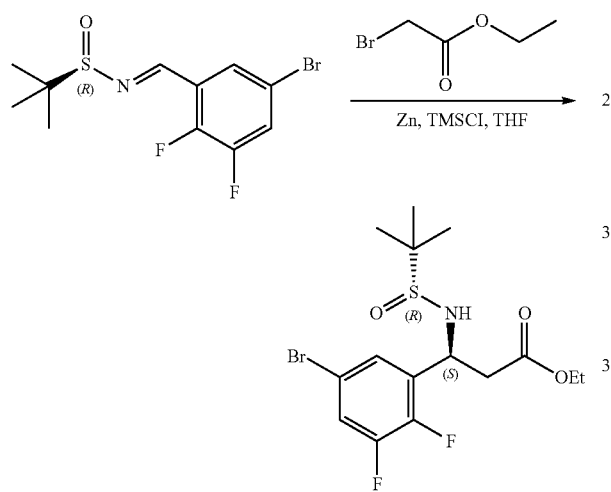

To a mixture of Zn (3.2 g, 49.2 mmol, 4.00 eq) in anhydrous THF (20 mL) under nitrogen atmosphere was added chlorotrimethylsilane (267 mg, 2.46 mmol, 0.2 eq) dropwise at room temperature. The mixture was stirred at 50° C. for 1 hour under nitrogen atmosphere and cooled to 20-30° C. Ethyl 2-bromoacetate (5.1 g, 30.75 mmol, 2.50 eq) was added dropwise at room temperature under nitrogen atmosphere and then stirred at 60° C. for 1 hour under nitrogen atmosphere. The reaction mixture was cooled to room temperature. A solution of (R,E)-N-(5-bromo-2,3-difluorobenzylidene)-2-methylpropane-2-sulfinamide (4.0 g, 12.3 mmol, 1.00 eq) in anhydrous THF (5 mL) was added dropwise into the mixture at room temperature under nitrogen atmosphere and stirred at room temperature for 1 hour. LCMS showed that the reaction was completed. Water (150 mL) and EtOAc (150 mL) were added into the mixture and stirred at room temperature for 10 mins. The mixture was filtered and washed with EtOAc (50 mL). The filtrate was separated. The organic layer was washed with water (100 mL) and brine (100 mL), dried over anhydrous Na$_2$SO$_4$, filtered and concentrated in vacuo. The residue was purified by silica gel column (pet ether: EtOAc 3:1) to provide ethyl (S)-3-(5-bromo-2,3-difluorophenyl)-3-(((R)-tert-butylsulfinyl)amino)propanoate as a colorless oil (2.7 g). Yield 53% (ESI 412.0 (M+H)$^+$).

Preparation of ethyl (S)-3-amino-3-(4,5-difluoro-2',6'-dimethyl-[1,1'-biphenyl]-3-yl)propanoate Step 1: ethyl (S)-3-(((R)-tert-butylsulfinyl)amino)-3-(4,5-difluoro-2',6'-dimethyl-[1,1'-biphenyl]-3-yl)propanoate

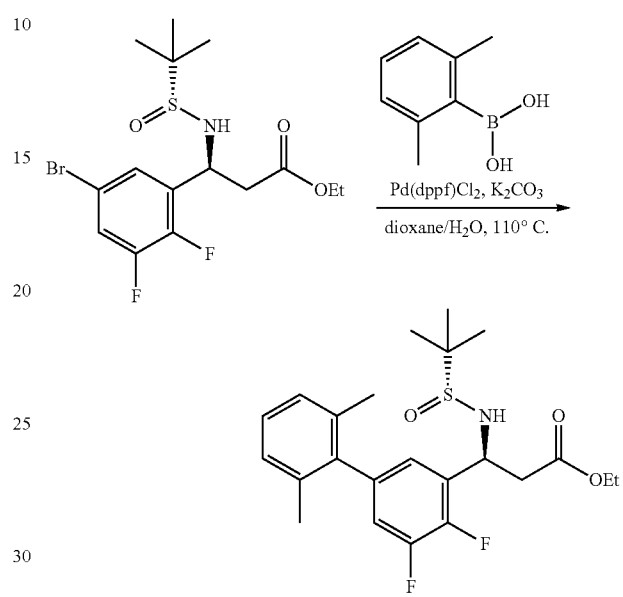

A mixture of ethyl (S)-3-(5-bromo-2,3-difluorophenyl)-3-(((R)-tert-butylsulfinyl)amino)propanoate (1.0 g, 2.4 mmol, 1.00 eq), K$_2$CO$_3$ (664 mg, 4.8 mmol, 2.0 eq) Pd(dppf)Cl$_2$ (175 mg, 0.24 mmol, 0.1 eq) and (2,6-dimethylphenyl)boronic acid (720 mg, 4.8 mmol, 2.00 eq) in dioxane (12 mL) and H$_2$O (1.2 mL) was stirred at 110° C. under nitrogen atmosphere for 2 hours. LCMS showed that the reaction was completed. The reaction mixture was poured into 50 mL of water and extracted with EtOAc (50 mL×3). The combined organic layers were washed with brine (100 mL), dried over anhydrous Na$_2$SO$_4$, filtered and concentrated in vacuo. The residue was purified by silica gel column (pet ether: EtOAc 2:1) to provide ethyl (S)-3-(((R)-tert-butylsulfinyl)amino)-3-(4,5-difluoro-2',6'-dimethyl-[1,1'-biphenyl]-3-yl)propanoateas a yellow oil (900 mg). Yield 85% (ESI 438.1 (M+H)$^+$).

Step 2: ethyl (S)-3-amino-3-(4,5-difluoro-2',6'-dimethyl-[1,1'-biphenyl]-3-yl)propanoate

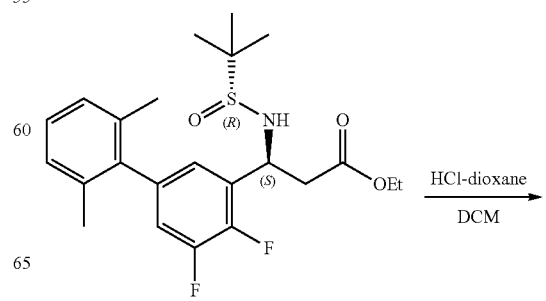

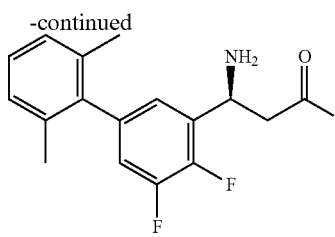

To a mixture of ethyl (S)-3-(((R)-tert-butylsulfinyl)amino)-3-(4,5-difluoro-2',6'-dimethyl-[1,1'-biphenyl]-3-yl)propanoate (900 mg, 2.06 mmol, 1.0 eq) in DCM (4 mL) was added HCl-dioxane (4 M, 2 mL, 8.0 mmol, 3.88 eq). The mixture was stirred at room temperature for 1 hour. LCMS showed that the reaction was completed. The mixture was concentrated in vacuo and the residue was purified by reverse phase HPLC on a C18/40 g column (A: water/0.01% TFA, B: MeOH, 0~100%) to provide ethyl (S)-3-amino-3-(4,5-difluoro-2',6'-dimethyl-[1,1'-biphenyl]-3-yl)propanoate as a light yellow solid (800 mg). Yield 90% (ESI 334.1 [M+H]$^+$).

Preparation of ethyl (S)-3-amino-3-(4,4',5-trifluoro-2',6'-dimethyl-[1,1'-biphenyl]-3-yl)propanoate Step 1: ethyl(S)-3-(((R)-tert-butylsulfinyl)amino)-3-(4,4',5-trifluoro-2',6'-dimethyl-[1,1'-biphenyl]-3-yl)propanoate

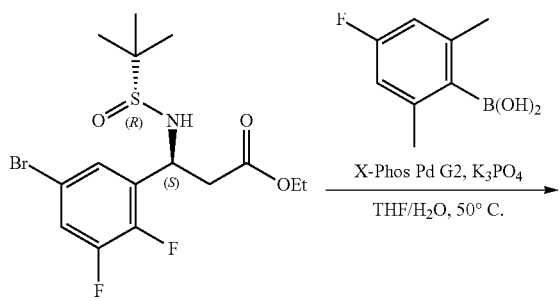

A mixture of ethyl (S)-3-(5-bromo-2,3-difluorophenyl)-3-(((R)-tert-butylsulfinyl)amino)propanoate (1.1 g, 2.68 mmol, 1.00 eq), K$_3$PO$_4$ (1.7 g, 8.04 mmol, 3.00 eq), X-Phos Pd G2 (212 mg, 0.27 mmol, 0.10 eq) and (4-fluoro-2,6-dimethylphenyl)boronic acid (900 mg, 5.36 mmol, 2.00 eq) in THF (10 mL) and H$_2$O (2 mL) was stirred at 50° C. under nitrogen atmosphere for 2 hours. LCMS showed that the reaction was completed. The reaction mixture was poured into 50 mL of water and extracted with EtOAc (50 mL×3). The combined organic layers were washed with brine (100 mL), dried over anhydrous Na$_2$SO$_4$, filtered and concentrated in vacuo. The residue was purified by silica gel column (pet ether: EtOAc 1:1) to provide ethyl (S)-3-(((R)-tert-butylsulfinyl)amino)-3-(4,4',5-trifluoro-2',6'-dimethyl-[1,1'-biphenyl]-3-yl)propanoate as a brown oil (1 g). Yield 82% (ESI 456.1 (M+H)$^+$)

Step 2: ethyl (S)-3-amino-3-(4,4',5-trifluoro-2',6'-dimethyl-[1,1'-biphenyl]-3-yl)propanoate

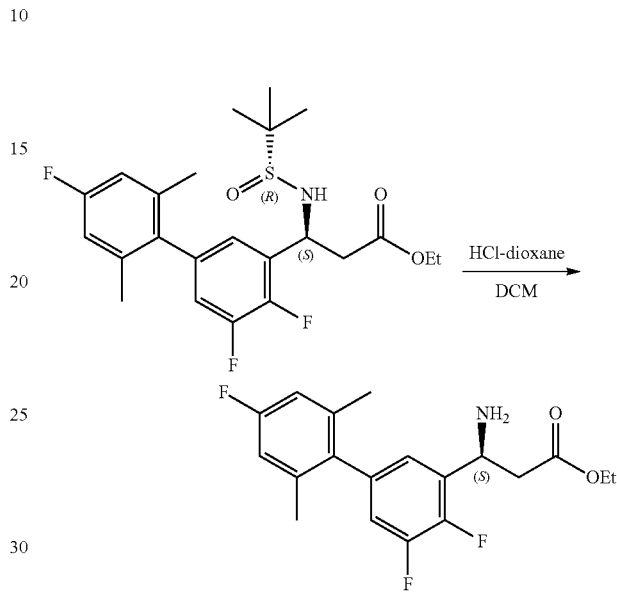

To a mixture of ethyl (S)-3-(((R)-tert-butylsulfinyl)amino)-3-(4,4',5-trifluoro-2',6'-dimethyl-[1,1'-biphenyl]-3-yl)propanoate (1.0 g, 2.2 mmol, 1.0 eq) in DCM (4 mL) was added HCl-dioxane (4 M, 2 mL, 4.0 mmol, 1.8 eq). The mixture was stirred at room temperature for 1 hour. LCMS showed that the reaction was completed. The mixture was concentrated in vacuo and the residue was purified by reverse phase HPLC on a C18/80 g column (A: water 10 mM NH$_4$HCO$_3$, B: MeOH, 0~100%) to provide ethyl (S)-3-amino-3-(4,4',5-trifluoro-2',6'-dimethyl-[1,1'-biphenyl]-3-yl)propanoate as a white solid (750 mg). Yield 97% (ESI 352.1 [M+H]$^+$).

Preparation of ethyl (S)-3-amino-3-(4,5-difluoro-2',4',6'-trimethyl-[1,1'-biphenyl]-3-yl)propanoate Scheme:

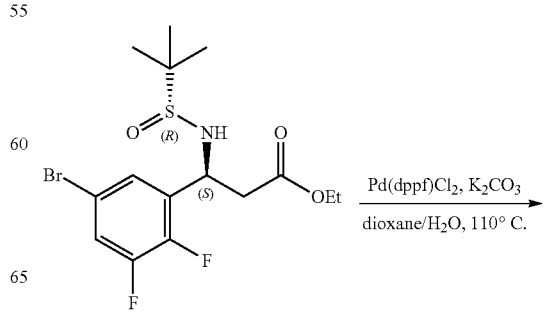

3-(4,5-difluoro-2',4',6'-trimethyl-[1,1'-biphenyl]-3-yl)propanoate as a yellow oil (1.4 g). Yield 85% (ESI 452.2 (M+H)⁺).

Step 2: ethyl (S)-3-amino-3-(4,5-difluoro-2',4',6'-trimethyl-[1,1'-biphenyl]-3-yl)propanoate

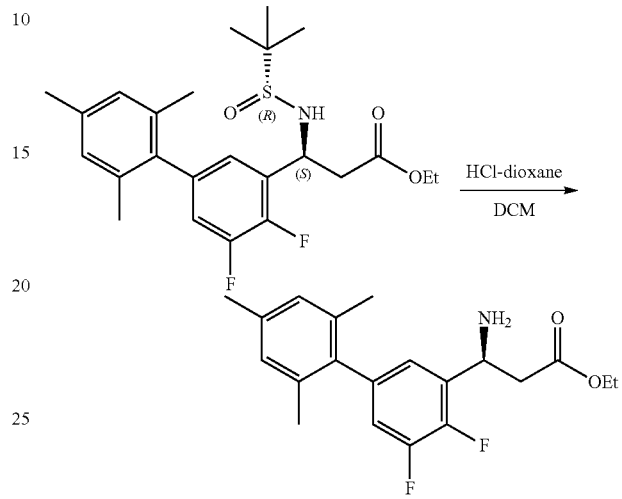

To a mixture of ethyl (S)-3-(((R)-tert-butylsulfinyl)amino)-3-(4,5-difluoro-2',4',6'-trimethyl-[1,1'-biphenyl]-3-yl)propanoate (1.4 g, 3.1 mmol, 1.0 eq) in DCM (20 mL) was added HCl-dioxane (4 M, 2 mL, 8.0 mmol, 2.58 eq). The mixture was stirred at room temperature for 1 hour. LCMS showed that the reaction was completed. The mixture was concentrated in vacuo and the residue was purified by reverse phase HPLC on a C18/120 g column (A: water/0.01% TFA, B: MeOH, 0~100%) to provide ethyl (S)-3-amino-3-(4,5-difluoro-2',4',6'-trimethyl-[1,1'-biphenyl]-3-yl)propanoate as a light yellow solid (1.0 g). Yield 93% (ESI 348.1 (M+H)⁺).

Preparation of ethyl (S)-3-(5-bromo-2-fluoro-3-(trifluoromethyl)phenyl)-3-(((R)-tert-butylsulfinyl)amino)propanoate Step 1:
5-bromo-2-fluoro-3-(trifluoromethyl)benzaldehyde

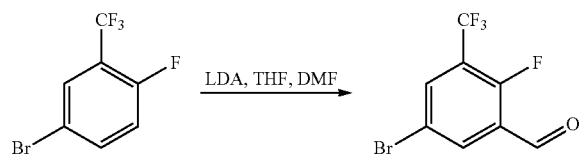 [SMILES: Fc1ccc(Br)cc1C(F)(F)F ; O=Cc1cc(Br)cc(C(F)(F)F)c1F]

To a solution of 4-bromo-1-fluoro-2-(trifluoromethyl)benzene (10.0 g, 41.15 mmol, 1.00 eq) in anhydrous THF (50 mL) under nitrogen atmosphere at −78° C. was added Lithium diisopropylamide (2.0 M, 30.9 mL, 61.73 mmol, 1.50 eq) dropwise and stirred at −78° C. for 1 hour under nitrogen atmosphere. DMF (15 mL) was added dropwise and the mixture was stirred at −78° C. for 1 hour. The mixture was quenched with 1M HCl aqueous solution (30 mL) and extracted with EtOAc (30 mL×3). The combined

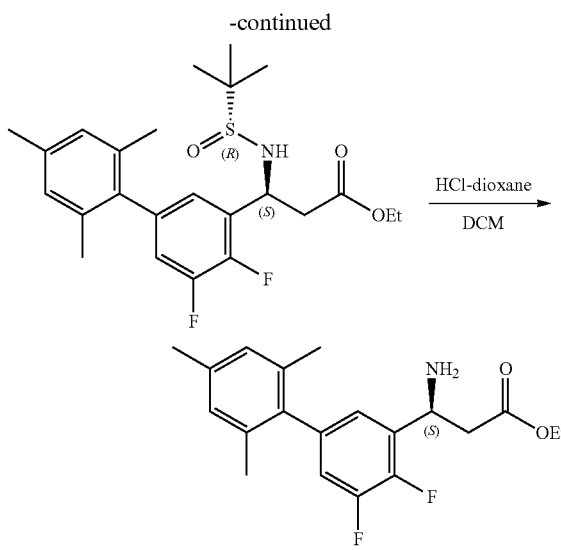

Step 1: ethyl (S)-3-(((R)-tert-butylsulfinyl)amino)-3-(4,5-difluoro-2',4',6'-trimethyl-[1,1'-biphenyl]-3-yl)propanoate

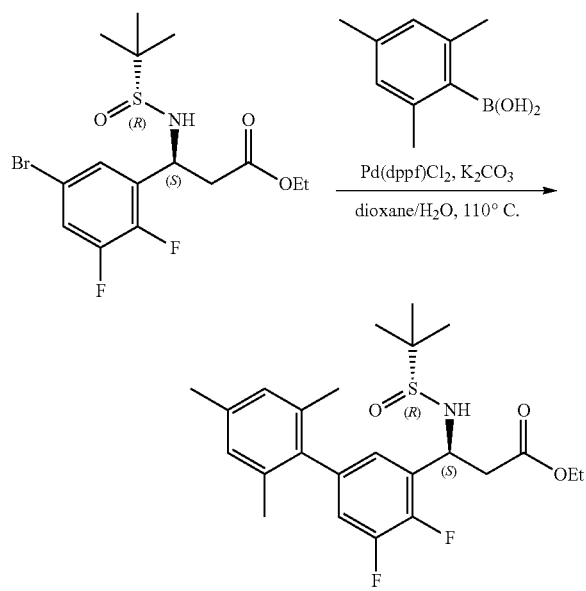

A mixture of ethyl (S)-3-(5-bromo-2,3-difluorophenyl)-3-(((R)-tert-butylsulfinyl)amino)propanoate (1.5 g, 3.65 mmol, 1.0 eq), mesitylboronic acid (1.2 g, 7.30 mmol, 2.0 eq), K₂CO₃ (1.5 g, 10.95 mmol, 3.0 eq) and Pd(dppf)Cl₂ (267 mg, 0.365 mmol, 0.1 eq) in dioxane (10 mL) and H₂O (1 mL) was stirred at 110° C. under nitrogen atmosphere for 1 hour. LCMS showed that the reaction was completed. The mixture was cooled to room temperature, poured into water (30 mL), extracted with EtOAc (30 mL×3). The combined organic layers were washed with brine (100 mL), dried over anhydrous Na₂SO₄, filtered and concentrated in vacuo. The residue was purified by silica gel column (pet ether: EtOAc 2:1) to provide ethyl (S)-3-(((R)-tert-butylsulfinyl)amino)- organic layers were washed with brine (50 mL), dried over anhydrous Na$_2$SO$_4$, filtered and concentrated in vacuo. The residue obtained was purified by silica gel column (pet ether: EtOAc 20:1) to provide 5-bromo-2-fluoro-3-(trifluoromethyl)benzaldehyde as a white solid (8.0 g). Yield 72%. $^1$H NMR (400 MHz, CDCl$_3$) δ 10.34 (s, 1H), 8.19 (dd, J=5.4, 2.4 Hz, 1H), 7.98 (dd, J=6.1, 2.5 Hz, 1H).

Step 2: (R, E)-N-(5-bromo-2-fluoro-3-(trifluoromethyl)benzylidene)-2-methylpropane-2-sulfinamide

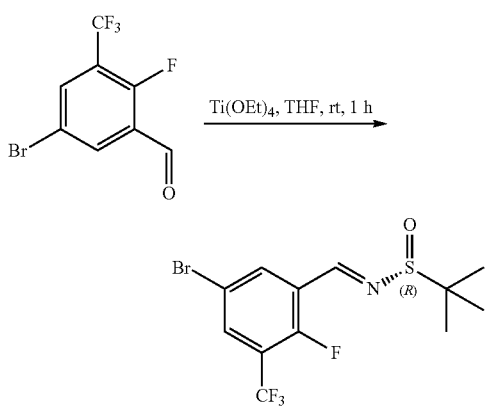

To a mixture of 5-bromo-2-fluoro-3-(trifluoromethyl)benzaldehyde (8.0 g, 29.50 mmol, 1.00 eq) and (R)-2-methylpropane-2-sulfinamide (3.9 g, 32.45 mmol, 1.1 eq) in anhydrous THF (100 mL) under nitrogen atmosphere was added Ti(OEt)$_4$ (13.0 g, 59.00 mmol, 2.00 eq) dropwise at room temperature and maintained the temperature below 30° C. The reaction mixture was stirred at room temperature for 1 hour under nitrogen atmosphere. LCMS showed that the reaction was completed. Water (100 mL) and EtOAc (100 mL) was added into the mixture and stirred at room temperature for 5 mins. The mixture was filtered and washed with EtOAc (50 mL). The filtrate was separated. The organic layer was washed with water (50 mL) and brine (50 mL), dried over anhydrous Na$_2$SO$_4$, filtered and concentrated in vacuo. The residue was purified by silica gel column (pet ether: EtOAc 5:1) to provide (R, E)-N-(5-bromo-2-fluoro-3-(trifluoromethyl)benzylidene)-2-methylpropane-2-sulfinamide as a yellow oil (8.0 g). Yield 72% (ESI 373.9 (M+H)$^+$).

Step 3: ethyl (S)-3-(5-bromo-2-fluoro-3-(trifluoromethyl)phenyl)-3-(((R)-tert-butylsulfinyl)amino)propanoate

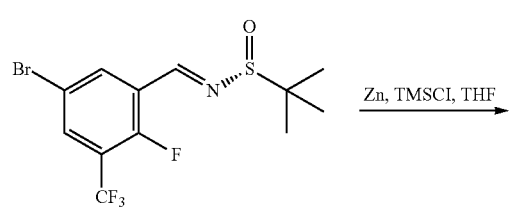

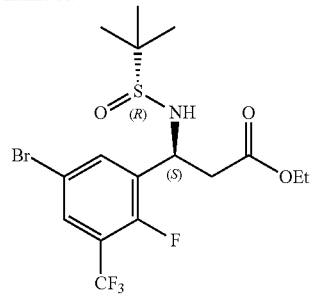

To a mixture of Zn (5.6 g, 85.6 mmol, 4.00 eq) in anhydrous THF (100 mL) under nitrogen atmosphere was added chlorotrimethylsilane (465 mg, 4.28 mmol, 0.2 eq) dropwise at room temperature. The mixture was stirred at 45° C. for 1 hour under nitrogen atmosphere and cooled to 20-30° C. Ethyl 2-bromoacetate (8.9 g, 53.5 mmol, 2.50 eq) was added dropwise at room temperature. The reaction mixture was stirred at 50° C. for 1 hour under nitrogen atmosphere and then cooled to room temperature. A solution of (R,E)-N-(5-bromo-2-fluoro-3-(trifluoromethyl)benzylidene)-2-methylpropane-2-sulfinamide (8.0 g, 21.4 mmol, 1.00 eq) in anhydrous THF (10 mL) was added dropwise into the mixture at room temperature under nitrogen atmosphere. The mixture was stirred at room temperature for 1 hour. LCMS showed that the reaction was completed. Water (100 mL) and EtOAc (100 mL) was added into the mixture and stirred at room temperature for 5 mins. The mixture was filtered and washed with EtOAc (100 mL). The filtrate was separated. The organic layer was washed with water (100 mL) and brine (100 mL), dried over anhydrous Na$_2$SO$_4$, filtered and concentrated in vacuo. The residue was purified by silica gel column (pet ether: EtOAc 4:1) to provide ethyl (S)-3-(5-bromo-2-fluoro-3-(trifluoromethyl) phenyl)-3-(((R)-tert-butylsulfinyl)amino)propanoate as a colorless oil (6.3 g). Yield 64% (ESI 462.0 (M+H)$^+$).

Preparation of ethyl (S)-ethyl 3-amino-3-(4-fluoro-2',6'-dimethyl-5-(trifluoromethyl)biphenyl-3-yl)propanoate Step 1: ethyl(S)-3-(((R)-tert-butylsulfinyl)amino)-3-(4-fluoro-2',6'-dimethyl-5-(trifluoromethyl)-[1,1'-biphenyl]-3-yl)propanoate

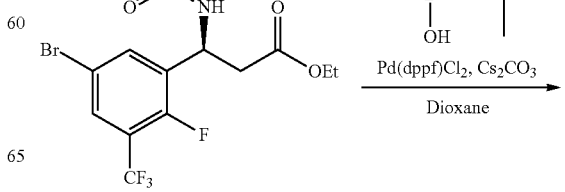

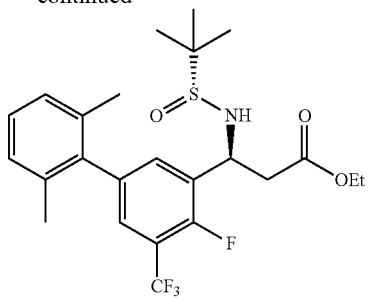

To a solution of ethyl (S)-3-(5-bromo-2-fluoro-3-(trifluoromethyl)phenyl)-3-(((R)-tert-butylsulfinyl)amino)propanoate (3 g, 6.49 mmol) and (2,6-dimethylphenyl)boronic acid (1.46 g, 9.73 mmol) in Dioxane (24 mL) was added a solution of Cs2CO3 (4.23 g, 12.98 mmol) in Water (8 mL). The reaction was purged with N2 for 5 min, followed by addition of PdCl2(dppf) (0.712 g, 0.973 mmol) and another N2 purge for 1 min. The reaction was stirred at 70 C for 4 hours. The reaction mixture was diluted into 250 mL EtOAc, then washed with 1N HCl (250 mL), Sat. NaHCO$_3$ (205 mL) and Brine (250 mL). The residue was concentrated and purified by silica gel chromatography to provide ethyl (S)-3-(((R)-tert-butylsulfinyl)amino)-3-(4-fluoro-2',6'-dimethyl-5-(trifluoromethyl)-[1,1'-biphenyl]-3-yl)propanoate (2.71 g). Yield 86% (ESI 488 (M+H)+).

Step 2: (S)-ethyl 3-amino-3-(4-fluoro-2',6'-dimethyl-5-(trifluoromethyl)biphenyl-3-yl)propanoate

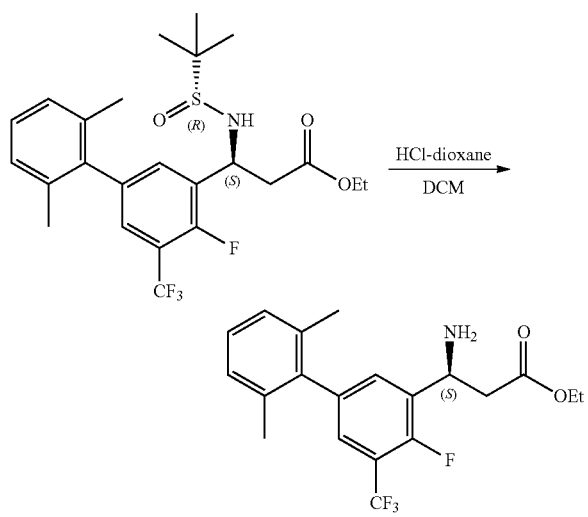

To a solution of (S)-ethyl 3-((R)-1,1-dimethylethylsulfinamido)-3-(4-fluoro-2',6'-dimethyl-5-(trifluoromethyl)biphenyl-3-yl)propanoate (0.93 g, 1.9 mmol, 1.00 eq) in DCM (8 mL) was added HCl-dioxane (4M, 1.9 mL, 7.6 mmol, 4 eq) and stirred at room temperature for 2 hours. The mixture was concentrated in vacuo and the residue was purified by reverse phase IPLC on a C18/120 g column (A: water/0.01% TFA, B: MeOH, 0~100%) to provide (R)-ethyl 3-amino-3-(4-fluoro-2',6'-dimethyl-5-(trifluoromethyl)biphenyl-3-yl) propanoate as a yellow solid (0.6 g). Yield 82% (ESI 384.1 (M+H)+).

Preparation of ethyl (S)-3-amino-3-(4,4'-difluoro-2',6'-dimethyl-5-(trifluoromethyl)-[1,1'-biphenyl]-3-yl) propanoate Step 1: ethyl(S)-3-(((R)-tert-butylsulfinyl)amino)-3-(4,4'-difluoro-2',6'-dimethyl-5-(trifluoromethyl)-[1,1'-biphenyl]-3-yl)propanoate

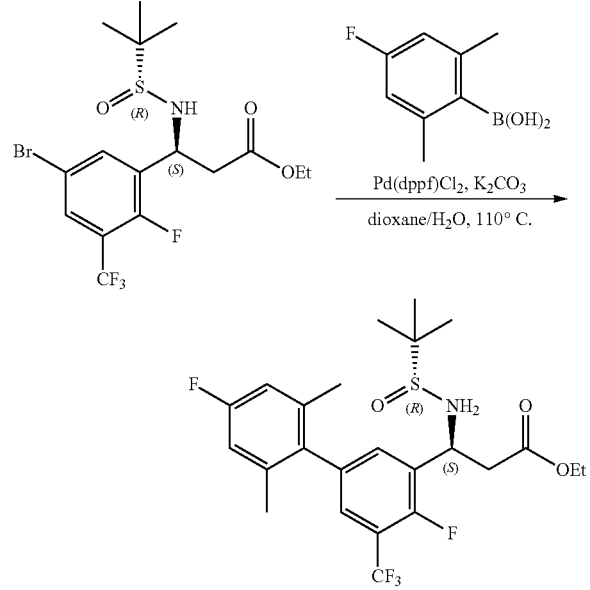

A mixture of ethyl (S)-3-(5-bromo-2-fluoro-3-(trifluoromethyl)phenyl)-3-(((R)-tert-butylsulfinyl)amino)propanoate (2.0 g, 4.3 mmol, 1.00 eq), K$_2$CO$_3$ (1.8 g, 12.9 mmol, 3.00 eq), Pd(dppf)Cl$_2$ (315 mg, 0.43 mmol, 0.10 eq) and (4-fluoro-2,6-dimethylphenyl)boronic acid (1.1 g, 6.45 mmol, 1.50 eq) in dioxane (50 mL) and H$_2$O (5 mL) was stirred at 110° C. for 2 hours under nitrogen atmosphere. LCMS showed that the reaction was completed. The reaction mixture was poured into 50 mL of water, extracted with EtOAc (50 mL×3). The combined organic layers were washed with brine (15 mL), dried over anhydrous Na$_2$SO$_4$, filtered and concentrated in vacuo. The residue was purified by silica gel column (pet ether: EtOAc 3:1) to provide ethyl (S)-3-(((R)-tert-butylsulfinyl)amino)-3-(4,4'-difluoro-2',6'-dimethyl-5-(trifluoromethyl)-[1,1'-biphenyl]-3-yl)propanoate as a colorless oil (1.4 g). Yield 64% (ESI 506.0 (M+H)$^+$)

Step 2: ethyl (S)-3-amino-3-(4,4'-difluoro-2',6'-dimethyl-5-(trifluoromethyl)-[1,1'-biphenyl]-3-yl)propanoate

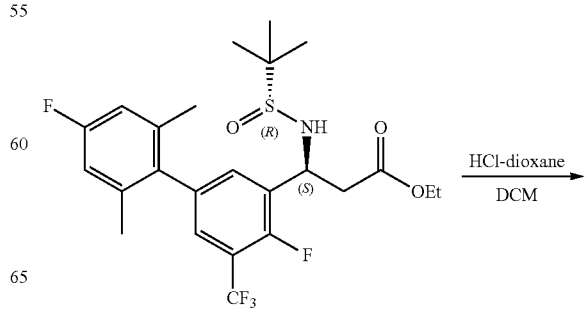

-continued

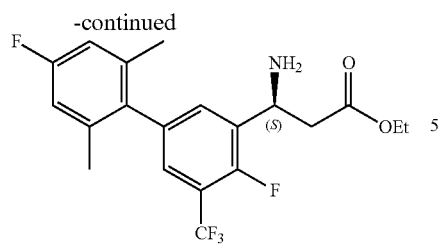

To a mixture of ethyl (S)-3-(((R)-tert-butylsulfinyl)amino)-3-(4,4'-difluoro-2',6'-dimethyl-5-(trifluoromethyl)-[1,1'-biphenyl]-3-yl)propanoate (1.4 g, 2.77 mmol, 1.0 eq) in DCM (10 mL) was added HCl-dioxane (4 M, 6 mL, 24.0 mmol, 8.66 eq). The mixture was stirred at room temperature for 1 hour. LCMS showed that the reaction was completed. The mixture was concentrated in vacuo and the residue was purified by reverse phase HPLC on a C18/120 g column (A: water/0.01% TFA, B: MeOH, 0~100%) to provide ethyl (S)-3-amino-3-(4,4'-difluoro-2',6'-dimethyl-5-(trifluoromethyl)-[1,1'-biphenyl]-3-yl)propanoate as a colorless oil (880 mg). Yield 79% (ESI 402.1 [M+H]$^+$).

Preparation of 2-(5-((dimethylamino)methyl)-2-oxopyridin-1(2H)-yl)-4-methylpentanoic acid Step 1:
5-((dimethylamino)methyl)pyridin-2(1H)-one

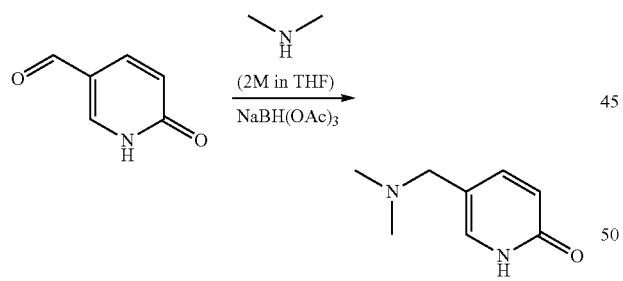

A mixture of 6-oxo-1,6-dihydropyridine-3-carbaldehyde (2 g, 16.2 mmol), dimethylamine (2M in THF, 4 mL) in DCM (10 mL) was stirred at room temperature for 30 mins. Then NaBH(OAc)$_3$ (5.2 g, 24.39 mmol) was added portionwise and stirred at room temperature overnight. The solvent was concentrated in vacuo and the residue purified by reverse phase HPLC (Eluent A: water 10 mM NH$_4$HCO$_3$, Eluent B: MeOH, gradient A→B 0~100%) to provide 5-((dimethylamino)methyl)pyridin-2(1H)-one as a yellow oil (1 g). Yield 41% (ESI 153 (M+H)$^+$).

Step 2: ethyl 2-(5-((dimethylamino)methyl)-2-oxopyridin-1(2H)-yl)-4-methylpentanoate

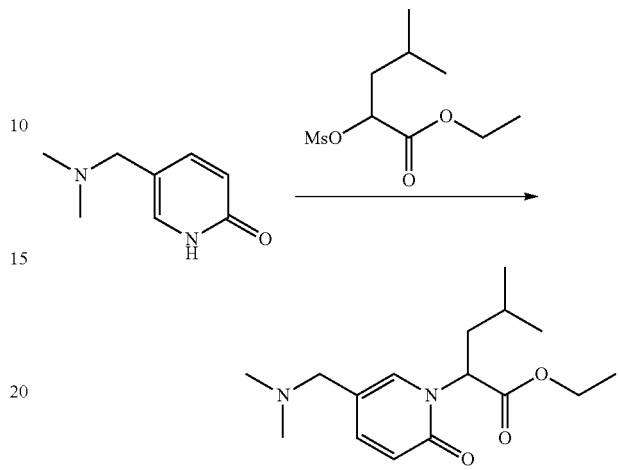

A mixture of 5-((dimethylamino)methyl)pyridin-2(1H)-one (500 mg, 3.28 mmol), K$_2$CO$_3$ (1.36 g, 9.86 mmol) and ethyl 4-methyl-2-(methylsulfonyloxy)pentanoate (1.17 g, 4.93 mmol) in CH$_3$CN (20 mL) was stirred at 70° C. overnight. The solvent was concentrated in vacuo and the residue was purified by silica gel column (pet ether: EtOAc 1:2) to provide ethyl 2-(5-((dimethylamino)methyl)-2-oxopyridin-1(2H)-yl)-4-methylpentanoate as a yellow oil (300 mg). Yield 31% (ESI 295 (M+H)$^+$).

Step 3: 2-(5-((dimethylamino)methyl)-2-oxopyridin-1(2H)-yl)-4-methylpentanoic acid

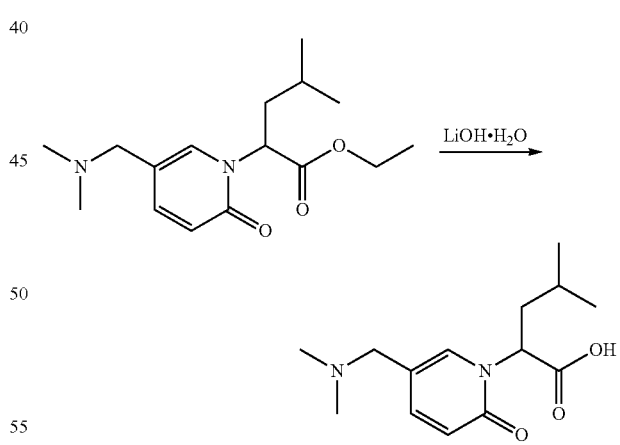

Ethyl 2-(5-((dimethylamino)methyl)-2-oxopyridin-1(2H)-yl)-4-methylpentanoate (300 mg, 1.02 mmol) was treated with LiOH—H$_2$O (120 mg, 3.02 mmol) in methanol (2 mL) and water (1 mL) at room temperature for 2 hours. The reaction was acidified with 1N HCl to pH=3. The solvent was removed in vacuo and the residue was purified by preparatory-HPLC A conditions (30-80% MeCN) to provide 2-(5-((dimethylamino)methyl)-2-oxopyridin-1(2H)-yl)-4-methylpentanoic acid as a white solid (100 mg). Yield 37% (ESI 267 (M+H)$^+$).

161

Preparation of 2-(4-((dimethylamino)methyl)-2-oxopyridin-1(2H)-yl)-4-methylpentanoic acid Step 1: 2-oxo-2,3-dihydropyridine-4-carbaldehyde

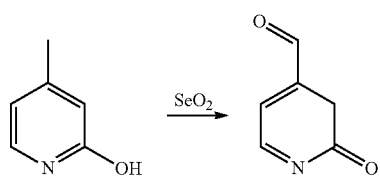

A mixture of 4-methylpyridin-2-ol (3 g, 27.5 mmol) and SeO$_2$ (4 g, 35.8 mmol) in dioxane (40 mL) was refluxed under N$_2$ atmosphere overnight and filtered. The filtrate was removed in vacuo and the residue was purified by silica gel column (DCM:MeOH=1:10) to provide 2-oxo-2,3-dihydropyridine-4-carbaldehyde as a yellow oil (300 mg). Yield 9% (ESI 124 (M+H)$^+$)

Step 2: 4-((dimethylamino)methyl)pyridin-2(1H)-one

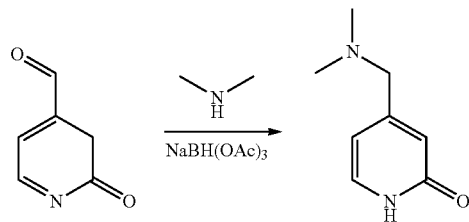

A mixture of 2-oxo-2,3-dihydropyridine-4-carbaldehyde (300 mg, 2.4 mmol), dimethylamine (2M in THF, 6 mL) in DCM (5 mL) was stirred at room temperature for 30 minutes. NaBH(OAc)$_3$ (775.6 mg, 3.65 mmol) was added portion-wise and stirred at room temperature overnight. The solvent was concentrated in vacuo and the residue was purified by reverse phase HPLC (Eluent A: water 10 mM NH$_4$HCO$_3$, Eluent B: MeOH, gradient A→B 0~100%) to provide 4-((dimethylamino)methyl)pyridin-2(1H)-one as a yellow oil (150 mg). Yield 41% (ESI 153 (M+H)$^+$).

Step 3: ethyl 2-(4-((dimethylamino)methyl)-2-oxopyridin-1(2H)-yl)-4-methylpentanoate

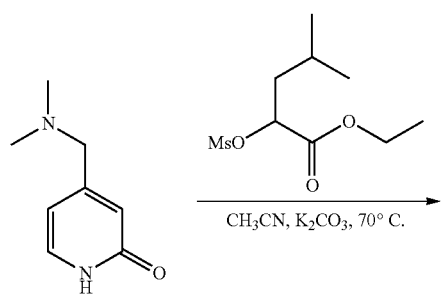

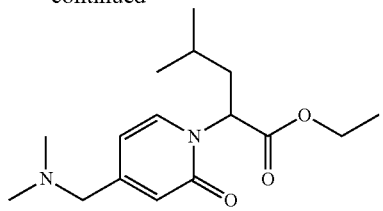

A mixture of 4-((dimethylamino)methyl)pyridin-2(1H)-one (150 mg, 0.98 mmol), K$_2$CO$_3$ (409 mg, 2.96 mmol) and ethyl 4-methyl-2-(methylsulfonyloxy)pentanoate (350 mg, 1.47 mmol) in CH$_3$CN (5 mL) was stirred at 70° C. overnight. The solvent was concentrated in vacuo and the residue was purified by silica gel column (pet ether: EtOAc 1:2) to provide ethyl 2-(4-((dimethylamino)methyl)-2-oxopyridin-1(2H)-yl)-4-methylpentanoate as a yellow oil (100 mg). Yield 35% (ESI 295 (M+H)$^+$).

Step 4: 2-(4-((dimethylamino)methyl)-2-oxopyridin-1(2H)-yl)-4-methylpentanoic acid

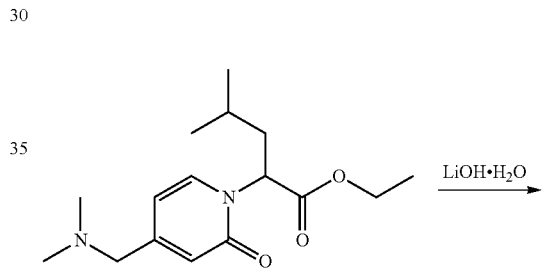

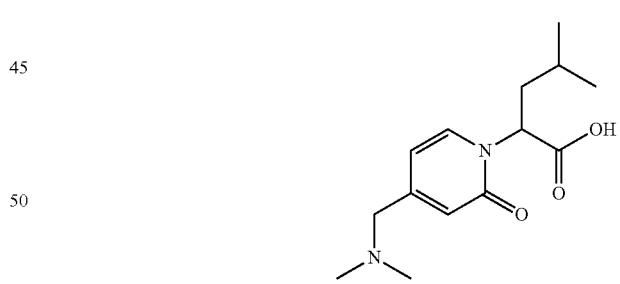

Ethyl 2-(4-((dimethylamino)methyl)-2-oxopyridin-1(2H)-yl)-4-methylpentanoate (100 mg, 0.33 mmol) was treated with LiOH—H$_2$O (40 mg, 1.01 mmol) in methanol (2 mL) and water (1 mL) at room temperature for 2 hours. The solvent was removed in vacuo and the residue was purified by preparatory-HPLC A (30-80% MeCN) to provide 2-(4-((dimethylamino)methyl)-2-oxopyridin-1(2H)-yl)-4-methylpentanoic acid as a white solid (80 mg). Yield 90% (ESI 267 (M+H)$^+$).

Preparation of Acid 3: 2-(5-((3, 3-difluoroazetidin-1-yl)methyl)-2-oxopyridin-1(2H)-yl)-4-methylpentanoic acid Step 1: 5-((3, 3-difluoroazetidin-1-yl)methyl)pyridin-2(1H)-one

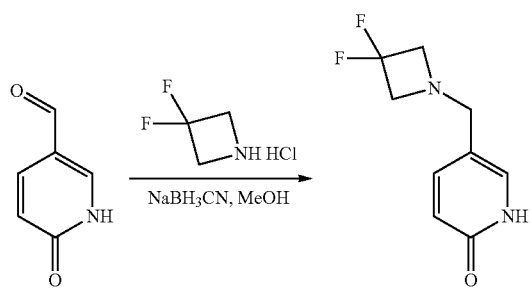

A mixture of 6-oxo-1,6-dihydropyridine-3-carbaldehyde (153 mg, 1.24 mmol) and 3,3-difluoroazetidine hydrochloride (193 mg, 1.49 mmol) in MeOH (3 mL) was stirred at room temperature for 30 mins. NaBH$_3$CN (231 mg, 3.73 mmol) was added and stirred at room temperature for 1 hour. The solvent was removed in vacuo to provide the crude 5-((3, 3-difluoroazetidin-1-yl)methyl)pyridin-2(1H)-one as white solid (248 mg) used without further purification. (ESI 201.1 (M+H)$^+$).

Step 2: ethyl 2-(5-((3, 3-difluoroazetidin-1-yl)methyl)-2-oxopyridin-1(2H)-yl)-4-methylpentanoate

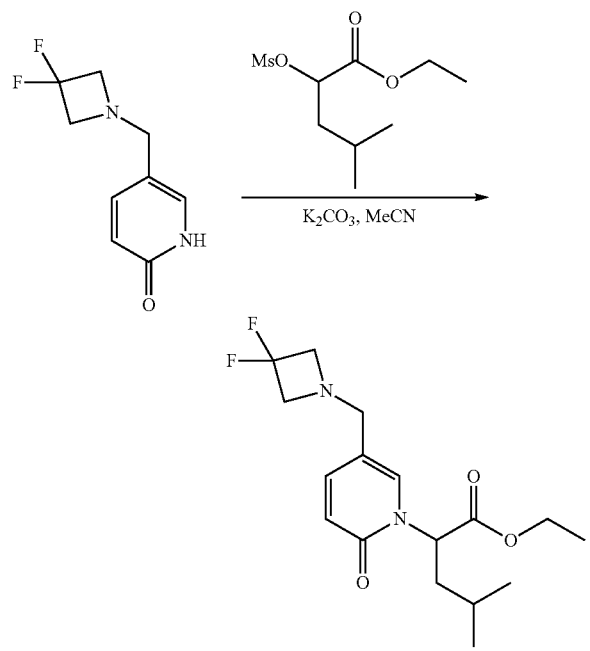

A mixture of 5-((3,3-difluoroazetidin-1-yl)methyl)pyridin-2(1H)-one (248 mg, 1.24 mmol), ethyl 4-methyl-2-(methylsulfonyloxy)pentanoate (443 mg, 1.86 mmol) and K$_2$CO$_3$ (514 mg, 3.72 mmol) in MeCN (5 mL) was stirred at 80° C. overnight. The mixture was filtered and washed with MeCN (5 mL). The filtrate was concentrated in vacuo and the residue was purified by silica gel column (petroleum ether: EtOAc 2:1) to provide ethyl 2-(5-((3, 3-difluoroazetidin-1-yl)methyl)-2-oxopyridin-1(2H)-yl)-4-methylpentanoate as a colorless oil (150 mg). Yield 36% (ESI 343.1 (M+H)$^+$).

Step 3: 2-(5-((3, 3-difluoroazetidin-1-yl)methyl)-2-oxopyridin-1(2H)-yl)-4-methylpentanoic acid

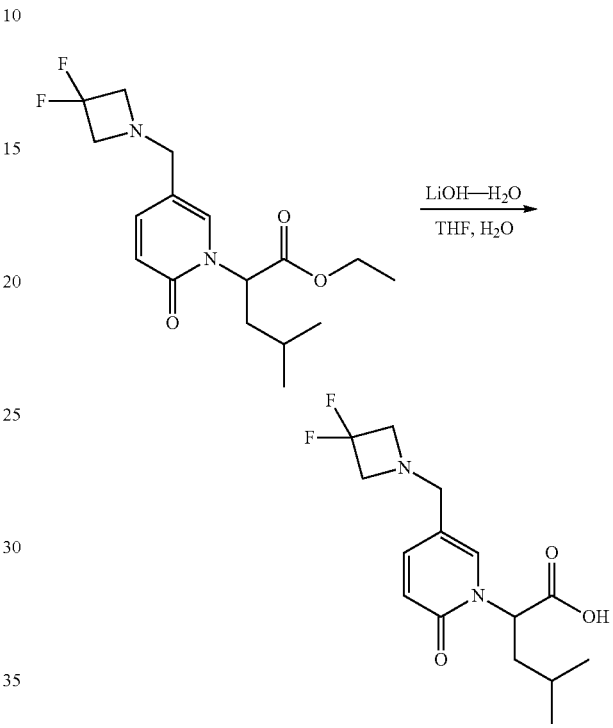

Ethyl 2-(5-((3,3-difluoroazetidin-1-yl)methyl)-2-oxopyridin-1(2H)-yl)-4-methylpentanoate (151 mg, 0.44 mmol) was treated with LiOH—H$_2$O (28 mg, 0.66 mmol) in THF (3 mL) and H$_2$O (0.5 mL) at room temperature for 30 mins. The mixture was acidified to pH 4~5 with 1N HCl. The mixture was concentrated in vacuo to provide 2-(5-((3, 3-difluoroazetidin-1-yl)methyl)-2-oxopyridin-1(2H)-yl)-4-methylpentanoic acid as white solid (138 mg) used without further purification. Yield 100% (ESI 315.1 (M+H)$^+$).

Preparation of 4-methyl-2-(5-(morpholinomethyl)-2-oxopyridin-1(2H)-yl)pentanoic acid Step 1: ethyl 2-(5-formyl-2-oxopyridin-1(2H)-yl)-4-methylpentanoate

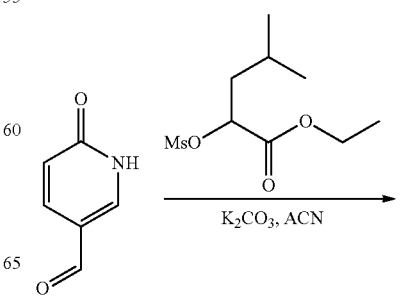

-continued

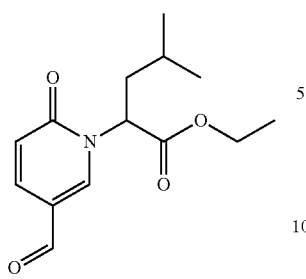

A mixture of 6-oxo-1,6-dihydropyridine-3-carbaldehyde (400 mg, 3.2 mmol), ethyl 4-methyl-2-(methylsulfonyloxy) pentanoate (1 g, 4.2 mmol) and $K_2CO_3$ (1.1 g, 8 mmol) in MeCN (10 mL) was stirred at 80° C. overnight. The mixture was filtered and washed with MeCN (5 mL). The filtrate was concentrated in vacuo and purified by silica gel column (pet ether: EtOAc 4:1) to provide ethyl 2-(5-formyl-2-oxopyridin-1(2H)-yl)-4-methylpentanoate as a colorless oil (650 mg). Yield 70% (ESI 266.3 (M+H)$^+$).

Step 2: ethyl 2-(5-((3-fluoroazetidin-1-yl)methyl)-2-oxopyridin-1(2H)-yl)-4-methylpentanoate

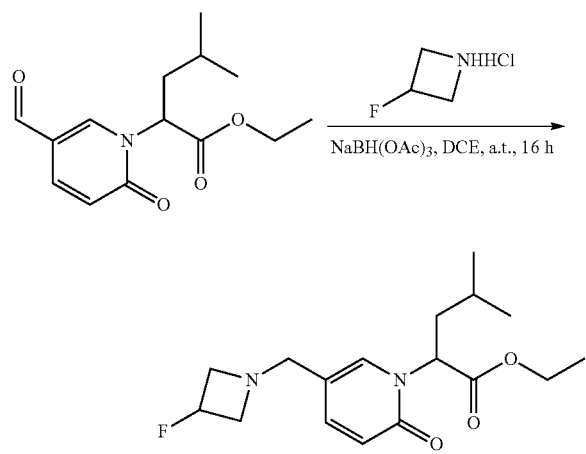

A mixture of ethyl 2-(5-formyl-2-oxopyridin-1(2H)-yl)-4-methylpentanoate (300 mg, 1.13 mmol) and 3-fluoroazetidine hydrochloride (251 mg, 2.26 mmol) in DCE (4 mL) was stirred at room temperature for 30 mins. Sodium triacetoxyborohydride (959 mg, 4.52 mmol) was added and stirred at room temperature overnight. The mixture was concentrated in vacuo and purified by silica gel column (DCM:MeOH 10:1) to provide ethyl 2-(5-((3-fluoroazetidin-1-yl)methyl)-2-oxopyridin-1(2H)-yl)-4-methylpentanoate as a colorless oil (264 mg). Yield 72% (ESI 325.2 (M+H)$^+$).

Step 3:2-(5-((3-fluoroazetidin-1-yl)methyl)-2-oxopyridin-1(2H)-yl)-4-methylpentanoic acid

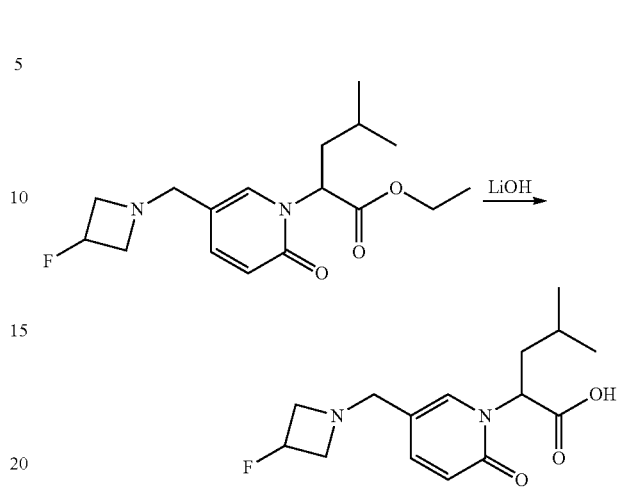

Ethyl 2-(5-((3-fluoroazetidin-1-yl)methyl)-2-oxopyridin-1(2H)-yl)-4-methylpentanoate (264 mg, 0.81 mmol) was treated with LiOH—$H_2O$ (171 mg, 4 mmol) in EtOH (4 mL) and $H_2O$ (1 mL) at room temperature for 2 hours. The mixture was acidified to pH 4~5 with 1N HCL. The mixture was concentrated in vacuo and purified by silica gel column (DCM:MeOH 10:1) to provide 2-(5-((3-fluoroazetidin-1-yl) methyl)-2-oxopyridin-1(2H)-yl)-4-methylpentanoic acid as a white solid (217 mg). Yield 90% (ESI 297.1 (M+H)$^+$).

Preparation of 4-methyl-2-(5-(morpholinomethyl)-2-oxopyridin-1(2H)-yl)pentanoic acid Step 1: ethyl 4-methyl-2-(5-(morpholinomethyl)-2-oxopyridin-1(2H)-yl)pentanoate

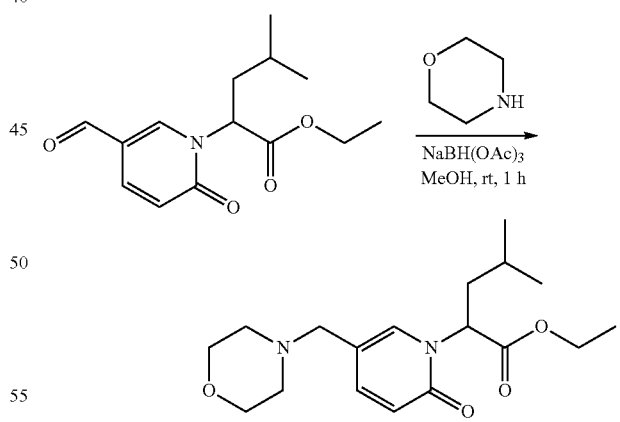

A mixture of ethyl 2-(5-formyl-2-oxopyridin-1(2H)-yl)-4-methylpentanoate (300 mg, 1.13 mmol) and morpholine (147 mg, 1.70 mmol) in DCE (5 mL) was stirred at room temperature for 30 mins. NaBH(OAc)$_3$ (715 mg, 3.39 mmol) was added and stirred at room temperature for 1 hour. The solvent was removed in vacuo and the residue purified by silica gel column (DCM:MeOH 2:1) to provide ethyl 4-methyl-2-(5-(morpholinomethyl)-2-oxopyridin-1(2H)-yl) pentanoate as yellow oil (150 mg). Yield 39% (ESI 337.2 (M+H)$^+$).

Step 2: 4-methyl-2-(5-(morpholinomethyl)-2-oxopyridin-1(2H)-yl)pentanoic acid

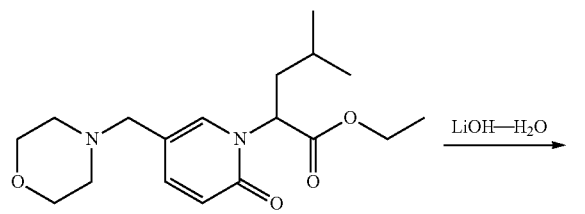

Ethyl 4-methyl-2-(5-(morpholinomethyl)-2-oxopyridin-1(2H)-yl)pentanoate (150 mg, 0.45 mmol) was treated with LiOH—H$_2$O (56 mg, 1.34 mmol) in THF (3 mL) and H$_2$O (0.5 mL) at room temperature for 2 hours. The mixture was acidified to pH 4~5 with 1N HCl. The mixture was concentrated in vacuo and the residue was purified by reverse phase HPLC on a C18/40 g column (A: water 10 mM NH$_4$HCO$_3$, B: MeOH, 0~100%) to provide 4-methyl-2-(5-(morpholinomethyl)-2-oxopyridin-1(2H)-yl)pentanoic acid as white solid (110 mg). Yield 80% (ESI 309.3 (M+H)$^+$).

Preparation of 2-(5-(2-(dimethylamino)ethyl)-2-oxopyridin-1(2H)-yl)-4-methylpentanoic acid

Step 1: ethyl 2-(5-(((R)-3-fluoropyrrolidin-1-yl)methyl)-2-oxopyridin-1(2H)-yl)-4-methylpentanoate

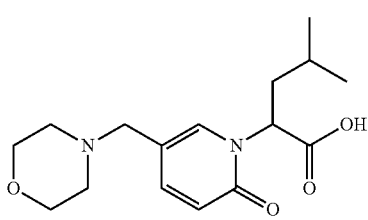

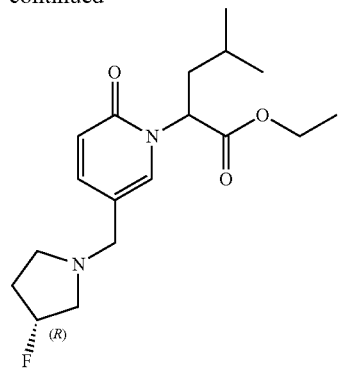

A mixture of ethyl 2-(5-formyl-2-oxopyridin-1(2H)-yl)-4-methylpentanoate (300 mg, 1.13 mmol), (R)-3-fluoropyrrolidine hydrochloride (284 mg, 2.26 mmol) and triethylamine (0.31 mL, 2.26 mmol) in DCE (10 mL) was stirred at room temperature for 30 mins. Sodium triacetoxyborohydride (959 mg, 4.52 mmol) was added and stirred at room temperature overnight. The mixture was concentrated in vacuo and purified by silica gel column (DCM:MeOH 10:1) to provide ethyl 2-(5-(((R)-3-fluoropyrrolidin-1-yl)methyl)-2-oxopyridin-1(2H)-yl)-4-methylpentanoate as a colorless oil (237 mg). Yield 62% (ESI 339.2 (M+H)$^+$).

Step 2: 2-(5-(((R)-3-fluoropyrrolidin-1-yl)methyl)-2-oxopyridin-1(2H)-yl)-4-methylpentanoic acid

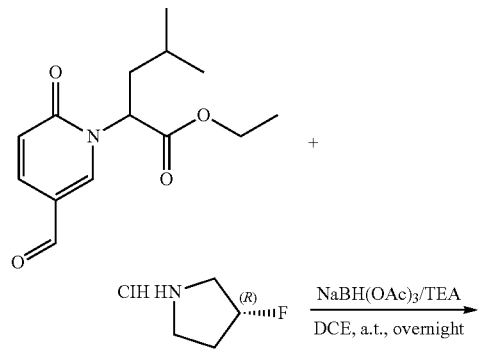

Ethyl 2-(5-(((R)-3-fluoropyrrolidin-1-yl)methyl)-2-oxopyridin-1(2H)-yl)-4-methylpentanoate (426 mg, 1.13 mmol) was treated with LiOH—H$_2$O (237 mg, 5.65 mmol) in EtOH (6 mL) and H$_2$O (0.6 mL) at room temperature for 2 hours. The mixture was acidified to pH 4~5 with 1N HCl. The mixture was concentrated in vacuo and the residue purified by silica gel column (DCM:MeOH 10:1) to provide 2-(5-(((R)-3-fluoropyrrolidin-1-yl)methyl)-2-oxopyridin-1(2H)-yl)-4-methylpentanoic acid as a white solid (348 mg). Yield 99% (ESI 311.1 (M+H)$^+$).

Preparation of 2-(5-(3-(dimethylamino)azetidin-1-yl)-4-methyl-2-oxopyridin-1(2H)-yl)-4-methylpentanoic acid Step 1: ethyl 2-(5-bromo-4-methyl-2-oxopyridin-1(2H)-yl)-4-methylpentanoate

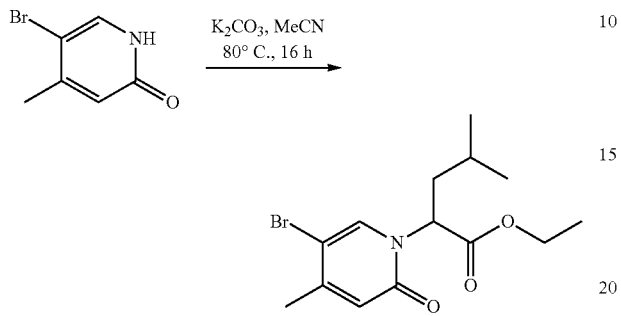

A mixture of 5-bromo-4-methylpyridin-2(1H)-one (3.0 g, 16 mmol, 1.0 eq), K$_2$CO$_3$ (4.4 g, 32 mmol, 2.0 eq) and ethyl 4-methyl-2-((methylsulfonyl)oxy)pentanoate (5.7 g, 24 mmol, 1.5 eq) in CH$_3$CN (50 mL) was stirred at 80° C. for 16 h. LCMS showed the reaction was completed. The mixture was filtered and washed with CH$_3$CN (20 mL). The filtrate was concentrated in vacuo and the residue was purified by silica gel column (pet ether: EtOAc 3:1) to provide ethyl 2-(5-bromo-4-methyl-2-oxopyridin-1(2H)-yl)-4-methylpentanoate as a yellow oil (4.5 g). Yield 85% (ESI 330 (M+H)$^+$). $^1$H NMR (500 MHz, CDCl$_3$) δ 7.46 (s, 1H), 6.49 (d, J=0.6 Hz, 1H), 5.67 (dd, J=10.6, 5.3 Hz, 1H), 4.20 (qd, J=7.1, 0.8 Hz, 2H), 2.24 (d, J=0.8 Hz, 3H), 1.97-1.93 (m, 1H), 1.87-1.80 (m, 1H), 1.51-1.43 (m, 1H), 1.27 (t, J=7.1 Hz, 3H), 0.95 (t, J=6.3 Hz, 6H).

Step 2: ethyl 2-(5-(3-(dimethylamino)azetidin-1-yl)-4-methyl-2-oxopyridin-1(2H)-yl)-4-methylpentanoate

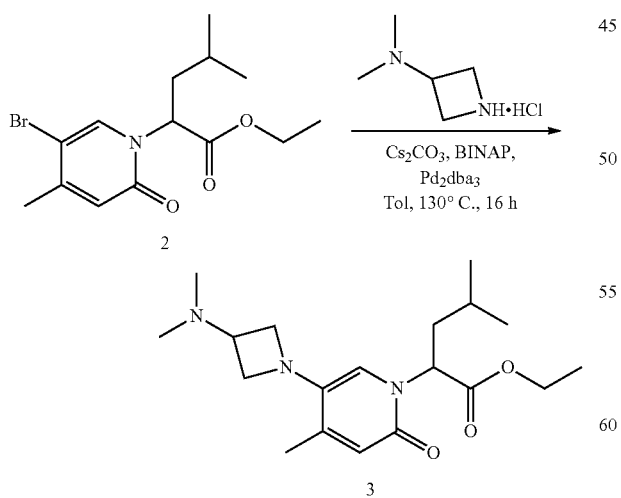

To a solution of ethyl 2-(5-bromo-4-methyl-2-oxopyridin-1(2H)-yl)-4-methylpentanoate (2.0 g, 6.06 mmol, 1.0 eq), N,N-dimethylazetidin-3-amine dihydrochloride (1.57 g, 9.07 mmol, 1.5 eq), and CsCO$_3$ (8.0 g, 24.5 mmol, 4.0 eq) in toluene (50 mL) was added BINAP (376 mg, 0.606 mmol, 0.1 eq) and Pd$_2$dba$_3$ (250 mg, 0.27 mmol, 0.05 eq) under N$_2$ and then heated to 120° C. for 3 h. LCMS showed the reaction was completed. The mixture was filtered and washed with both EtOAc (20 mL) and EtOH (20 mL). The filtrate was concentrated in vacuo and the residue was purified by silica gel column (pet ether: EtOAc 1:1) to provide ethyl 2-(5-(3-(dimethylamino)azetidin-1-yl)-4-methyl-2-oxopyridin-1(2H)-yl)-4-methylpentanoate (1.4 g). Yield 66% (ESI 350 (M+H)$^+$).

Step 3: 2-(5-(3-(dimethylamino)azetidin-1-yl)-4-methyl-2-oxopyridin-1(2H)-yl)-4-methylpentanoic acid

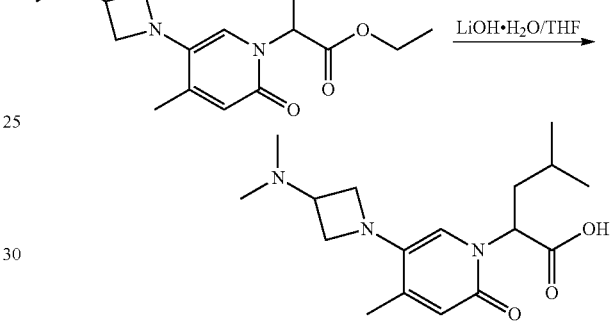

Ethyl 2-(5-(3-(dimethylamino)azetidin-1-yl)-4-methyl-2-oxopyridin-1(2H)-yl)-4-methylpentanoate (1.4 g, 4.0 mmol, 1.0 eq) was treated with LiOH—H$_2$O (840 mg, 20.0 mmol, 5.0 eq) in THF (20 mL) and water (6 mL) at room temperature for 2 hours. The MeOH was removed and the aqueous material acidified with 1N HCl to pH 4. The mixture was purified by reverse phase HPLC in neutral condition (A: water, B: MeOH, 60% B) to provide 2-(5-(3-(dimethylamino)azetidin-1-yl)-4-methyl-2-oxopyridin-1(2H)-yl)-4-methylpentanoic acid as a white solid (800 mg). Yield 62% (ESI 322 (M+H)$^+$). 1H-NMR (400 MHz, MeOD) δ 6.75 (s, 1H), 6.31 (s, 1H), 5.45-5.38 (m, 1H), 3.87-3.28 (m, 2H), 3.24 (s, 3H), 3.17-2.42 (m, 6H), 2.19-2.06 (m, 3H), 1.24-1.19 (m, 1H), 0.85-0.74 (m, 6H).

Preparation of 2-(5-((dimethylamino)methyl)-2-oxo-4-(trifluoromethyl)pyridin-1(2H)-yl)-4-methylpentanoic acid Step 1: 1-(6-methoxy-4-(trifluoromethyl)pyridin-3-yl)-N,N-dimethylmethanamine

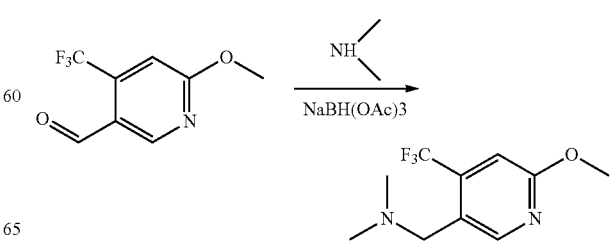

A mixture of 6-methoxy-4-(trifluoromethyl)nicotinaldehyde (0.5 g, 2.44 mmol), dimethylamine (2.0 M in THF, 1.5 mL, 2.92 mmol) in DCE (10 mL) was stirred at room temperature for 15 mins. NaBH(OAc)$_3$ (1.03 g, 4.88 mmol) was added and stirred at room temperature for 3 hours. The solvent was removed in vacuo and the residue purified by silica gel column (DCM:MeOH 10:1) to provide 1-(6-methoxy-4-(trifluoromethyl)pyridin-3-yl)-N,N-dimethylmethanamine as yellow oil (220 mg). Yield 38% (ESI 235.1 (M+H)$^+$).

Step 2: 5-((dimethylamino)methyl)-4-(trifluoromethylpridin-2-ol

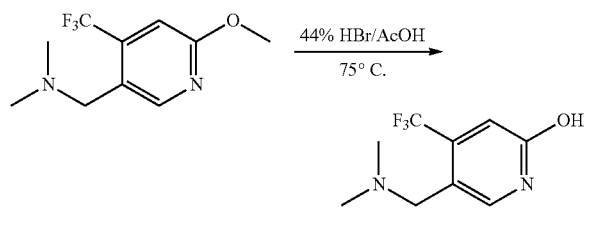

A mixture of 1-(6-methoxy-4-(trifluoromethyl)pyridin-3-yl)-N,N-dimethylmethanamine (220 mg, 0.94 mmol) in 33% HBr/AcOH (10 mL) was heated at 75° C. for 16 hours. The solvent was removed in vacuo and the residue was purified by reverse phase HPLC on a C18/40 g column (A: water 10 mM NH$_4$HCO$_3$, B: MeOH, 0~100%) to provide 5-((dimethylamino)methyl)-4-(trifluoromethyl)pyridin-2-ol as a red solid (180 mg). Yield 87% (ESI 221.1 (M+H)$^+$).

Step 3: ethyl 2-(5-((dimethylamino)methyl)-2-oxo-4-(trifluoromethyl)pyridin-1(2H)-yl)-4-methylpentanoate

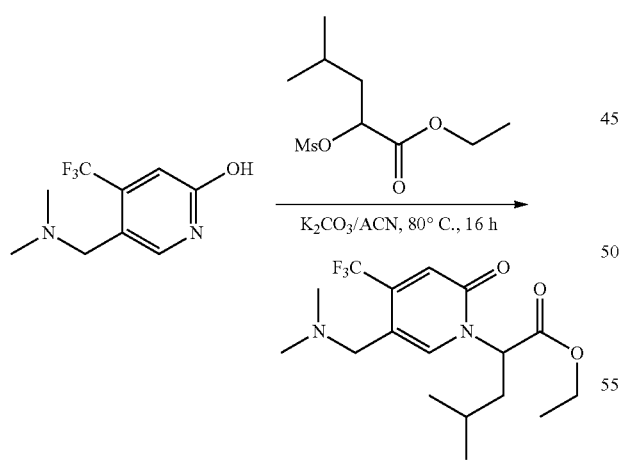

A mixture of 5-((dimethylamino)methyl)-4-(trifluoromethyl)pyridin-2-ol (150 mg, 0.68 mmol), ethyl 4-methyl-2-(methylsulfonyloxy)pentanoate (194 mg, 0.816 mmol) and K$_2$CO$_3$ (281.5 mg, 2.04 mmol) in MeCN (10 mL) was stirred at 80° C. overnight. The solvent was removed in vacuo and the residue was purified by reverse phase HPLC on a C18/40 g column (A: water 10 mM NH$_4$HCO$_3$, B: MeOH, 0~100%) to provide ethyl 2-(5-((dimethylamino) methyl)-2-oxo-4-(trifluoromethyl)pyridin-1(2H)-yl)-4-methylpentanoate (170 mg). Yield 68% (ESI 363.1 (M+H)$^+$).

Step 4: 2-(5-((dimethylamino)methyl)-2-oxo-4-(trifluoromethyl)pyridin-1(2H)-yl)-4-methylpentanoic acid

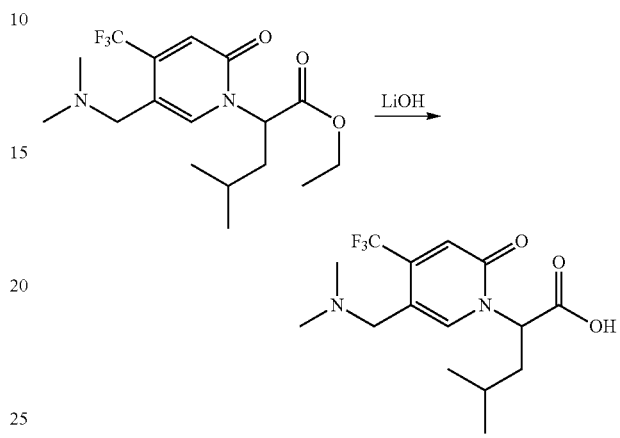

Ethyl 2-(5-((dimethylamino)methyl)-2-oxo-4-(trifluoromethyl)pyridin-1(2H)-yl)-4-methylpentanoate (170 mg, 0.47 mmol) was treated with LiOH—H$_2$O (98.7 mg, 2.35 mmol) in MeOH (10 mL) and H$_2$O (2 mL) at room temperature for 2 hours. The mixture was acidified to pH 4~5 with 1N HCl and purified by reverse phase HPLC on a C18/40 g column (A: water 10 mM NH$_4$HCO$_3$, B: MeOH, 0~100%) to provide 2-(5-((dimethylamino)methyl)-2-oxo-4-(trifluoromethyl)pyridin-1(2H)-yl)-4-methylpentanoic acid as white solid (120 mg). Yield 76% (ESI 335.2 (M+H)$^+$).

Preparation of 2-(5-(2-(dimethylamino)ethyl)-2-oxopyridin-1(2H)-yl)-4-methylpentanoic acid Step 1: 5-(2-methoxyvinyl)pyridin-2(1H)-one

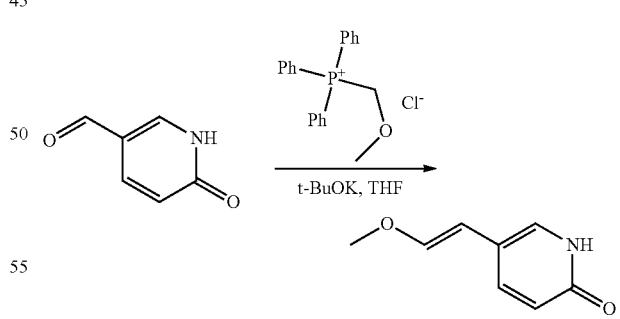

A mixture of (methoxymethyl)triphenylphosphonium chloride (12.5 g, 36.6 mmol), t-BuOK (6.83 g, 61 mmol) in dioxane (60 mL) was stirred at room temperature for 15 minutes. Then 6-oxo-1,6-dihydropyridine-3-carbaldehyde (3 g, 24.4 mmol) in 20 mL THF was added. The mixture was stirred for 16 h at room temperature. To the reaction mixture was added 80 mL water. The mixture was extracted with EtOAc (80 mL×2) and the aqueous phase concentrated in vacuo. The residue was purified by reverse phase HPLC (Eluent A: water 10 mM NH₄HCO₃, Eluent B: MeOH, gradient A→B 0~100%) to provide 5-(2-methoxyvinyl)pyridin-2(1H)-one as a red oil (1.3 g). Yield 35% (ESI 152.2 (M+H)⁺).

Step 2:2-(6-oxo-1,6-dihydropyridin-3-yl)acetaldehyde

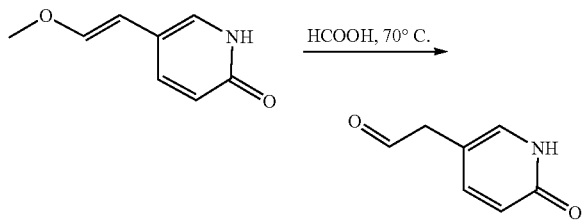

5-(2-methoxyvinyl)pyridin-2(1H)-one (1.2 g, 7.95 mmol) was treated with HCOOH (20 mL) at 70° C. for 2 hours. The solvent was removed in vacuo to provide the crude product 2-(6-oxo-1,6-dihydropyridin-3-yl)acetaldehyde as a red oil (0.8 g, crude). (ESI 138.3 (M+H)⁺).

Step 3: 5-(2-(dimethylamino)ethyl)pyridin-2(1H)-one

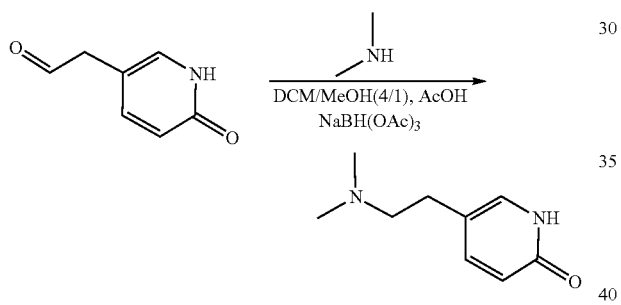

A mixture of methyl 2-(6-oxo-1,6-dihydropyridin-3-yl)acetaldehyde (750 mg, 5.47 mmol), AcOH (394 mg, 6.56 mmol) and dimethylamine (40% in water) (1.23 g, 10.94 mmol) in DCM (10 mL) and MeOH (2.5 mL) was stirred at room temperature for 30 minutes then NaBH(OAc)₃ (2.32 g, 10.94 mmol) was added. The mixture was stirred at room temperature overnight. The solvent was removed in vacuo and the residue was purified by silica gel column (DCM:MeOH 2:1) to provide 5-(2-(dimethylamino)ethyl)pyridin-2(1H)-one as yellow oil (500 mg). Yield 55% (ESI 167.2 (M+H)⁺).

Step 4: ethyl 2-(5-(2-(dimethylamino)ethyl-2-oxopyridin-1(2H)-yl)-4-methylpentanoate

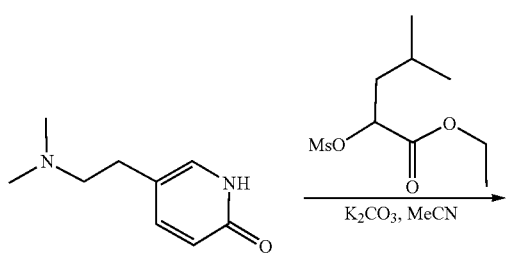

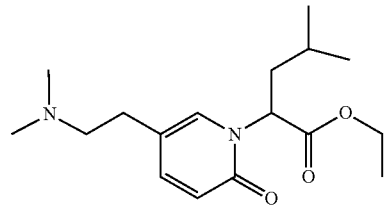

A mixture of methyl 5-(2-(dimethylamino)ethyl)pyridin-2(1H)-one (500 mg, 3 mmol), ethyl 4-methyl-2-(methylsulfonyloxy)pentanoate (1.07 g, 4.5 mmol) and K₂CO₃ (828 mg, 6 mmol) in MeCN (15 mL) was stirred at 70° C. overnight. The solvent was removed in vacuo and the residue was purified by silica gel column (DCM:MeOH 1:2) to provide methyl ethyl 2-(5-(2-(dimethylamino)ethyl)-2-oxopyridin-1(2H)-yl)-4-methylpentanoate as a white solid (100 mg). Yield 11% (ESI 309.2 (M+H)⁺).

Step 5:2-(5-(2-(dimethylamino)ethyl 2-oxopyridin-1(2H)-yl)-4-methylpentanoic acid

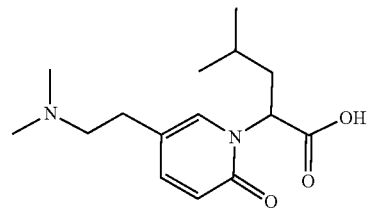

Ethyl 2-(5-(2-(dimethylamino)ethyl)-2-oxopyridin-1(2H)-yl)-4-methylpentanoate (100 mg, 0.32 mmol) was treated with LiOH—H₂O (54 mg, 1.28 mmol) in EtOH (3 mL) and H₂O (1 mL) at room temperature for 2 hours. The reaction mixture was acidified to pH 4~5 with 1 N HCl. The solvent was removed in vacuo and the residue was purified by reverse phase HPLC (Eluent A: water 10 mM NH₄HCO₃, Eluent B: MeOH, gradient A→B 0~100%) to provide 2-(5-(2-(dimethylamino)ethyl)-2-oxopyridin-1(2H)-yl)-4-methylpentanoic acid as a white solid (70 mg). Yield 78% (ESI 281.2 (M+H)⁺).

Preparation of 2-(4-(2-(dimethylamino)ethyl)-2-oxopyridin-1(2H)-yl)-4-methylpentanoic acid

Step 1: ethyl 2-(4-bromo-2-oxopyridin-1(2H)-yl)-4-methylpentanoate

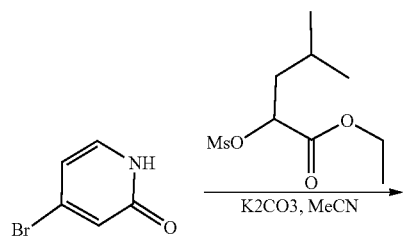

A mixture of 4-bromopyridin-2(1H)-one (1.2 g, 6.94 mmol), K$_2$CO$_3$ (1.92 g, 13.88 mmol) and ethyl 4-methyl-2-(methylsulfonyloxy)pentanoate (1.98 g, 8.33 mmol) in CH$_3$CN (20 mL) was stirred at 80° C. overnight. The solvent was concentrated in vacuo and the residue was purified by silica gel column (pet ether: EtOAc 1:1) to give ethyl 2-(4-bromo-2-oxopyridin-1(2H)-yl)-4-methylpentanoate as a yellow oil (1.6 g). Yield 73% (ESI 316.1 (M+H)$^+$).

Step 2: ethyl 2-(4-(2-(benzyloxycarbonylamino)ethyl)-2-oxopyridin-1(2H)-yl)-4-methylpentanoate

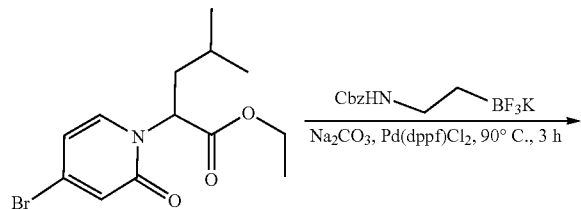

A mixture of ethyl 2-(4-bromo-2-oxopyridin-1(2H)-yl)-4-methylpentanoate (1.6 g, 5.0 mmol), potassium benzyl N-[2-(trifluoroboraly)ethyl]carbamate (1.71 g, 6 mmol), Pd(dppf)Cl$_2$ (366 mg, 0.5 mmol) and Na$_2$CO$_3$ (1.06 g, 10 mmol) in 1,4-dioxane (20 mL) and H$_2$O (10 mL) was stirred at 90° C. under N$_2$ atmosphere for 4 hours. The reaction was concentrated and purified by reverse phase HPLC on a C18/40 g column (A: water/0.01% TFA, B: MeOH, 0~100%) to provide ethyl 2-(4-(2-(benzyloxycarbonylamino)ethyl)-2-oxopyridin-1(2H)-yl)-4-methylpentanoate as a yellow oil (700 mg). Yield 35% (ESI 415.1 (M+H)$^+$).

Step 3: ethyl 2-(4-(2-aminoethyl)-2-oxopyridin-1(2H)-yl)-4-methylpentanoate

Ethyl 2-(4-(2-(benzyloxycarbonylamino)ethyl)-2-oxopyridin-1(2H)-yl)-4-methylpentanoate (0.7 g, 1.7 mmol) was treated with TFA (10 mL) at 50° C. for 4 hours. The solvent was removed in vacuo and the residue was purified by reverse phase HPLC on a C18/40 g column (A: water 10 mM NH$_4$HCO$_3$, B: MeOH, 0~100%) to provide ethyl 2-(4-(2-aminoethyl)-2-oxopyridin-1(2H)-yl)-4-methylpentanoate as a red oil (0.4 g). Yield 84%. (ESI 281.2 (M+H)$^+$).

Step 4: ethyl 2-(4-(2-(dimethylamino)ethyl)-2-oxopyridin-1(2H)-yl)-4-methylpentanoate

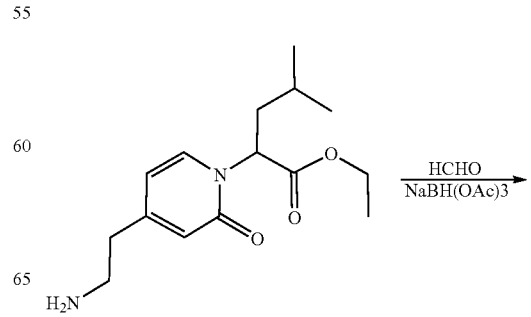

-continued

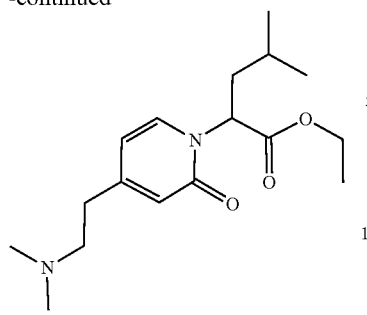

To a mixture of ethyl 2-(4-(2-aminoethyl)-2-oxopyridin-1(2H)-yl)-4-methylpentanoate (400 mg, 1.43 mmol) in MeOH (10 mL) was added HCHO (37% in H$_2$O, 1 mL) and stirred at room temperature for 5 mins. NaBH(OAc)$_3$ (1.21 g, 5.72 mmol) was added and stirred at room temperature for 1 hour. The solvent was removed in vacuo and the residue was purified by reverse phase HPLC on a C18/40 g column (A: water 10 mM NH$_4$HCO$_3$, B: MeOH, 0~100%) to provide ethyl 2-(4-(2-(dimethylamino)ethyl)-2-oxopyridin-1(2H)-yl)-4-methylpentanoate as yellow oil (400 mg). Yield 91% (ESI 309.2 (M+H)$^+$).

Step 5: 2-(4-(2-(dimethylamino)ethyl)-2-oxopyridin-1(2H)-yl)-4-methylpentanoic acid

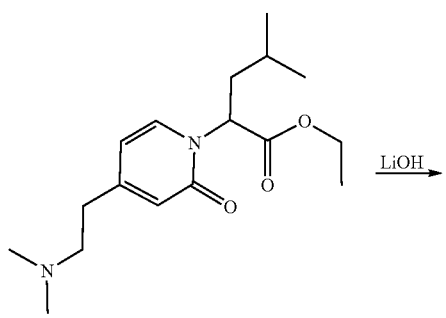

Ethyl 2-(4-(2-(dimethylamino)ethyl)-2-oxopyridin-1(2H)-yl)-4-methylpentanoate (400 mg, 1.3 mmol) was treated with LiOH—H$_2$O (218 mg, 5.2 mmol) in MeOH (4 mL) and H$_2$O (1 mL) at room temperature for 1 hour. The mixture was acidified to pH 4~5 with 1N HCl. The mixture was concentrated in vacuo and the residue was purified by reverse phase HPLC on a C18/40 g column (A: water/0.01% TFA, B: MeOH, 0~100%) to give 2-(4-(2-(dimethylamino)ethyl)-2-oxopyridin-1(2H)-yl)-4-methylpentanoic acid as white solid (310 mg). Yield 85% (ESI 281.2 (M+H)$^+$).

Preparation of 2-(3-(2-(dimethylamino)ethyl)-2-oxopyridin-1(2H)-yl)-4-methylpentanoic acid Step 1: ethyl 2-(3-bromo-2-oxopyridin-1(2-yl)-4-methylpentanoate

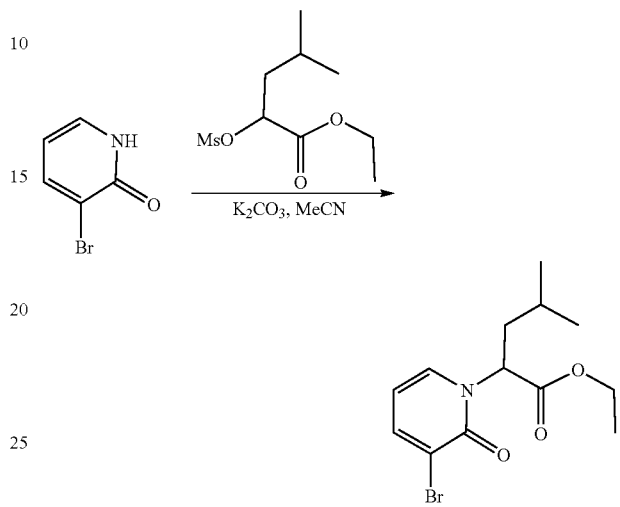

A mixture of 3-bromopyridin-2(1H)-one (1 g, 5.78 mmol), K$_2$CO$_3$ (1.6 g, 11.56 mmol) and ethyl 4-methyl-2-(methylsulfonyloxy)pentanoate (1.65 g, 6.94 mmol) in CH$_3$CN (20 mL) was stirred at 80° C. overnight. The solvent was concentrated in vacuo and purified by silica gel column (petroleum ether: EtOAc 1:1) to provide ethyl 2-(3-bromo-2-oxopyridin-1(2H)-yl)-4-methylpentanoate as a white solid (1.6 g). Yield 88% (ESI 316.1 (M+H)$^+$).

Step 2: ethyl 2-(3-(2-(benzyloxycarbonylamino) ethyl)-2-oxopyridin-1(2H)-yl)-4-methylpentanoate

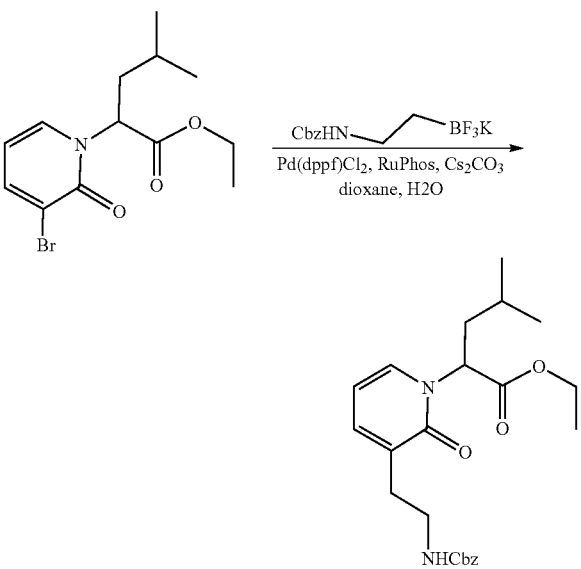

A mixture of ethyl 2-(3-bromo-2-oxopyridin-1(2H)-yl)-4-methylpentanoate (1 g, 3.17 mmol), potassium benzyl N-[2-(trifluoroboryl)ethyl]carbamate (1.08 g, 3.8 mmol), Pd(dppf)Cl$_2$ (36 mg, 0.16 mmol), Cs2CO$_3$ (2 g, 6.34 mmol) and RuPhos (144 mg, 0.32 mmol) in 1,4-dioxane (20 mL) and H$_2$O (10 mL) was stirred at 110° C. for 2 hours. The reaction was concentrated and purified by reverse phase HPLC on a C18/40 g column (A: water/0.01% TFA, B: MeOH, 0~100%) to give ethyl 2-(3-(2-(benzyloxycarbonylamino)ethyl)-2-oxopyridin-1(2H)-yl)-4-methylpentanoate as a yellow oil (1.1 g). Yield 84% (ESI 415.2 (M+H)$^+$).

Step 3: ethyl 2-(3-(2-aminoethyl)-2-oxopyridin-1(2H)-yl)-4-methylpentanoate

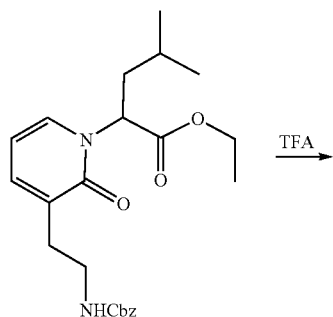

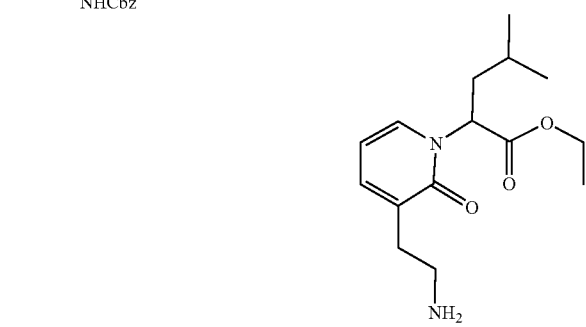

Ethyl 2-(3-(2-(benzyloxycarbonylamino)ethyl)-2-oxopyridin-1(2H)-yl)-4-methylpentanoate (1.07 g, 2.58 mmol) was treated with TFA (20 mL) at 50° C. for 4 hours. The solvent was removed in vacuo and the residue purified by reverse phase HPLC on a C18/40 g column (A: water 10 mM NH$_4$HCO$_3$, B: MeOH, 0~100%) to provide ethyl 2-(3-(2-aminoethyl)-2-oxopyridin-1(2H)-yl)-4-methylpentanoate as a yellow oil (0.6 g). Yield 83%. (ESI 281.2 (M+H)$^+$).

Step 4 ethyl 2-(3-(2-(dimethylamino)ethyl)-2-oxopyridin-1(2H)-yl)-4-methylpentanoate

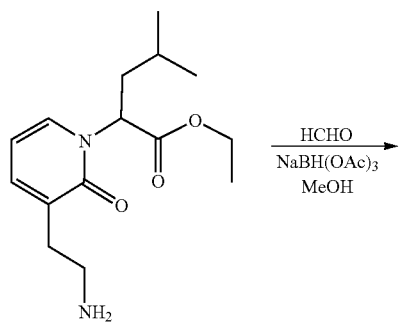

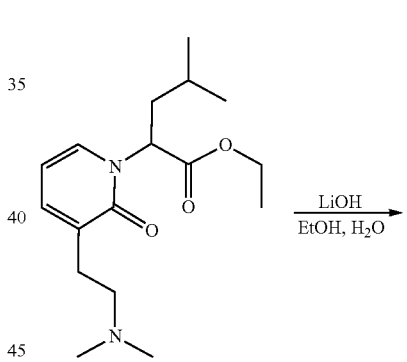

To a mixture of ethyl 2-(3-(2-aminoethyl)-2-oxopyridin-1(2H)-yl)-4-methylpentanoate (600 mg, 2.14 mmol) in MeOH (10 mL) was added HCHO (37% in H$_2$O, 1 mL). The mixture was stirred at room temperature for 5 mins. NaBH(OAc)$_3$ (1.81 g, 8.56 mmol) was added and stirred at room temperature for 1 hour. The solvent was removed in vacuo and the residue purified by reverse phase HPLC on a C18/40 g column (A: water 10 mM NH$_4$HCO$_3$, B: MeOH, 0~100%) to provide ethyl 2-(3-(2-(dimethylamino)ethyl)-2-oxopyridin-1(2H)-yl)-4-methylpentanoate as yellow oil (600 mg). Yield 91% (ESI 309.2 (M+H)$^+$).

Step 5: 2-(3-(2-(dimethylamino)ethyl)-2-oxopyridin-1(2H)-yl)-4-methylpentanoic acid

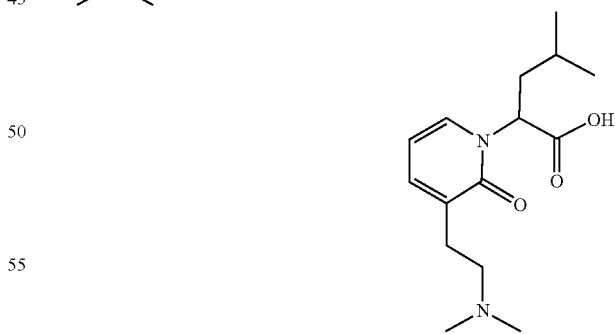

Ethyl 2-(3-(2-(dimethylamino)ethyl)-2-oxopyridin-1(2H)-yl)-4-methylpentanoate (600 mg, 1.95 mmol) was treated with LiOH monohydrate (328 mg, 7.8 mmol) in EtOH (4 mL) and H$_2$O (1 mL) at room temperature for 1 hour. The mixture was acidified to pH 4~5 with 1N HCl aqueous solution. The mixture was concentrated in vacuo and the residue purified by reverse phase HPLC on a C18/40 g column (A: water/0.01% TFA, B: MeOH, 0~100%) to give 2-(3-(2-(dimethylamino)ethyl)-2-oxopyridin-1(2H)-yl)-4-methylpentanoic acid as white solid (500 mg). Yield 92% (ESI 281.2 (M+H)$^+$).

Preparation of Acid 9: 2-(5-(2-(3-fluoroazetidin-1-yl)ethyl)-2-oxopyridin-1(2H)-yl)-4-methylpentanoic acid Step 1: 5-(2-(azetidin-1-yl)ethyl)pyridin-2(1H)-one

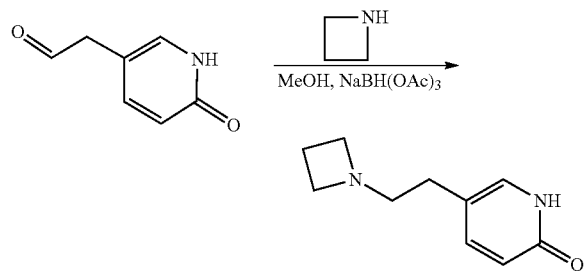

A mixture of methyl 2-(6-oxo-1,6-dihydropyridin-3-yl)acetaldehyde (1.0 g, 7.29 mmol) and azetidine (416 mg, 7.30 mmol) in MeOH (10 mL) was stirred at room temperature for 30 mins. NaBH(OAc)$_3$ (4.6 g, 21.9 mmol) was added and stirred at room temperature for 1 hour. The solvent was removed in vacuo and the residue purified by silica gel column (DCM:MeOH 2:1) to provide 5-(2-(azetidin-1-yl)ethyl)pyridin-2(1H)-one as yellow oil (800 mg). Yield 62% (ESI 179.1 (M+H)$^+$).

Step 2: ethyl 2-(5-(2-(azetidin-1-yl)ethyl)-2-oxopyridin-1(2H)-yl)-4-methylpentanoate

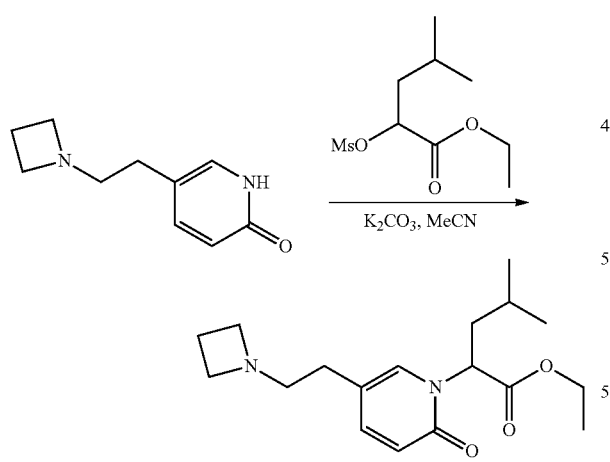

A mixture of 5-(2-(azetidin-1-yl)ethyl)pyridin-2(1H)-one (800 mg, 4.49 mmol), ethyl 4-methyl-2-(methylsulfonyloxy)pentanoate (2.2 g, 6.74 mmol) and K$_2$CO$_3$ (1.8 g, 13.47 mmol) in MeCN (40 mL) was stirred at 80° C. overnight. The mixture was filtered and washed with MeCN (5 mL). The filtrate was concentrated in vacuo and the residue purified by reverse phase HPLC on a C18/80 g column (A: water/0.01% TFA, B: MeOH, 0~100%) to provide ethyl 2-(5-(2-(azetidin-1-yl)ethyl)-2-oxopyridin-1(2H)-yl)-4-methylpentanoate as a colorless oil (600 mg). Yield 42% (ESI 321.2 (M+H)$^+$).

Step 3: 2-(5-(2-(azetidin-1-yl)ethyl)-2-oxopyridin-1(2H)-yl)-4-methylpentanoic acid

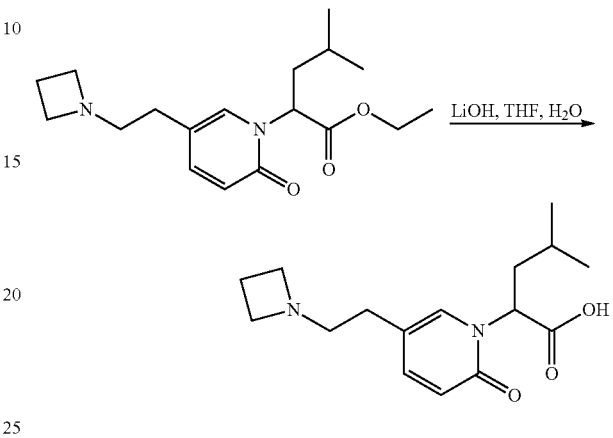

Ethyl 2-(5-(2-(azetidin-1-yl)ethyl)-2-oxopyridin-1(2H)-yl)-4-methylpentanoate (600 mg, 1.88 mmol) was treated with LiOH—H$_2$O (394 mg, 9.40 mmol) in THF (10 mL) and H$_2$O (2 mL) at room temperature for 1 hour. The mixture was acidified to pH 4~5 with 1N HCl. The mixture was concentrated in vacuo and the residue purified by reverse phase HPLC on a C18/40 g column (A: water 10 mM NH$_4$HCO$_3$, B: MeOH, 0~100%) to provide 2-(5-(2-(azetidin-1-yl)ethyl)-2-oxopyridin-1(2H)-yl)-4-methylpentanoic acid as red solid (150 mg). Yield 27% (ESI 293.2 (M+H)$^+$).

Preparation of 2-(5-(2-(3-fluoroazetidin-1-yl)ethyl)-2-oxopyridin-1(2H)-yl)-4-methylpentanoic acid Step 1: 5-(2-(3-fluoroazetidin-1-yl)ethyl)pyridin-2(1H)-one

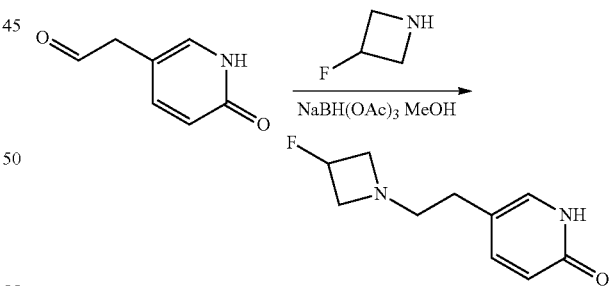

A mixture of 2-(6-oxo-1,6-dihydropyridin-3-yl)acetaldehyde (1.5 g, 11 mmol), AcOH (0.8 g, 13.2 mmol) and 3-fluoroazetidine hydrochloride (1.47 g, 13.2 mmol) in MeOH (30 mL) was stirred at room temperature for 30 mins. NaBH(OAc)$_3$ (4.66 g, 22 mmol) was added and stirred at room temperature for 3 hours. The solvent was removed in vacuo and the residue was purified by reverse phase HPLC on a C18/120 g column (A: water 10 mM NH$_4$HCO$_3$, B: MeOH, 0~100%) to provide 5-(2-(3-fluoroazetidin-1-yl)ethyl)pyridin-2(1H)-one as a yellow oil (2 g, crude). (ESI 197.2 (M+H)$^+$).

Step 2: ethyl 2-(5-(2-(3-fluoroazetidin-1-yl)ethyl)-2-oxopyridin-1(2H)-yl)-4-methylpentanoate

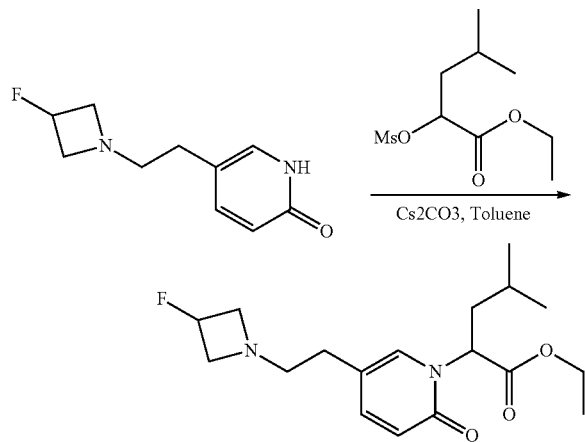

A mixture of 5-(2-(3-fluoroazetidin-1-yl)ethyl)pyridin-2(1H)-one (1.9 g, 9.7 mmol), ethyl 4-methyl-2-(methylsulfonyloxy)pentanoate (3.45 g, 14.5 mmol) and Cs$_2$CO$_3$ (9.5 g, 29.1 mmol) in toluene (40 mL) was stirred 110° C. overnight. The solvent was removed in vacuo and the residue purified by reverse phase HPLC on a C18/120 g column (A: water 10 mM NH$_4$HCO$_3$, B: MeOH, 0~100%) to provide ethyl 2-(5-(2-(3-fluoroazetidin-1-yl)ethyl)-2-oxopyridin-1(2H)-yl)-4-methylpentanoate as a yellow oil (650 mg). Yield 20% (ESI 339.1 (M+H)$^+$).

Step 3: 2-(5-(2-(3-fluoroazetidin-1-yl)ethyl)-2-oxopyridin-1(2H)-yl)-4-methylpentanoic acid

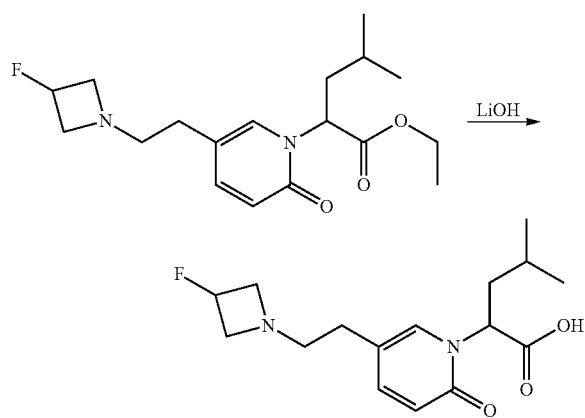

Ethyl 2-(5-(2-(3-fluoroazetidin-1-yl)ethyl)-2-oxopyridin-1(2H)-yl)-4-methylpentanoate (650 mg, 1.92 mmol) was treated with LiOH—H$_2$O (322 mg, 7.68 mmol) in MeOH (10 mL) and H$_2$O (2.5 mL) at room temperature for 2 hours. The mixture was acidified to pH 4~5 with 1N HCl, purified by reverse phase HPLC on a C18/40 g column (A: water 10 mM NH$_4$HCO$_3$, B: MeOH, 0~100%) to provide 2-(5-(2-(3-fluoroazetidin-1-yl)ethyl)-2-oxopyridin-1(2H)-yl)-4-methylpentanoic acid as a white solid (350 mg). Yield 59% (ESI 311.2 (M+H)$^+$).

Preparation of 3-cyclopropyl-2-(5-(2-(3-fluoroazetidin-1-yl)ethyl)-2-oxopyridin-1(2H)-yl)propanoic acid Step 1: (S)-2-bromo-3-cyclopropylpropanoic acid

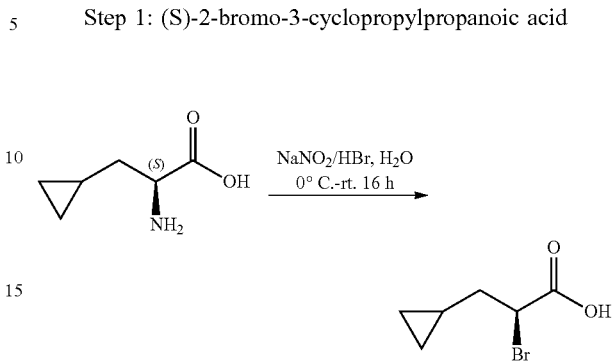

To a solution of (S)-2-amino-3-cyclopropylpropanoic acid (5.0 g, 38.7 mmol) in H$_2$O (50 mL) was added 40% HBr (60 mL). The reaction mixture was stirred at 0° C. for 10 min. A solution of sodium nitrite (4.5 g, 24 mmol) in H$_2$O (10 mL) was added. The reaction mixture was stirred at 0° C. for 30 min and warmed to room temperature overnight. The reaction mixture was extracted with EtOAc (100 mL×3). The organic layer was washed with brine (100 mL) and dried over Na$_2$SO$_4$, filtered and concentrated in vacuo to provide (S)-2-bromo-3-cyclopropylpropanoic acid as a colorless oil used directly in the next reaction without further purification (5.0 g). Yield 74% (ESI 194 (M+H)$^+$).

Step 2: ethyl (S)-2-bromo-3-cyclopropylpropanoate

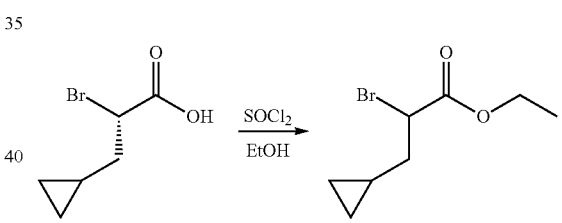

To a solution of (S)-2-bromo-3-cyclopropylpropanoic acid (1 g, 5.2 mmol) in EtOH (20 mL) was added SOCl$_2$ (1.8 g, 15.6 mmol) and stirred at ambient temperature for 2 hours. The solvent was removed in vacuo to provide ethyl 2-bromo-3-cyclopropylpropanoate as a white solid (1.2 g, crude) used directly in the next reaction. (ESI 221.0 (M+H)$^+$).

Step 3: ethyl 3-cyclopropyl-2-(5-(2-(3-fluoroazetidin-1-yl)ethyl)-2-oxopyridin-1(2H)-yl)propanoate

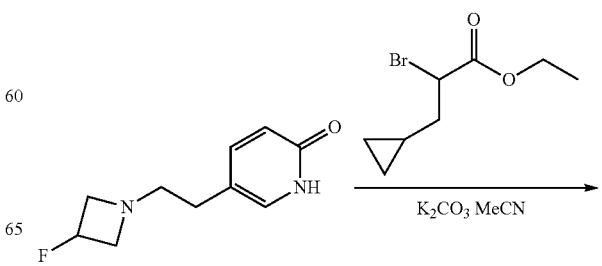

185

-continued

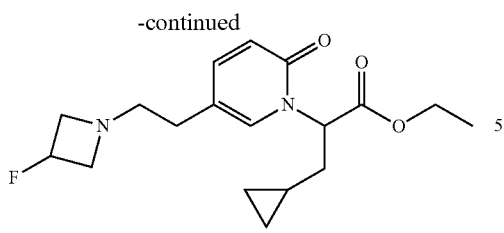

A mixture of ethyl 2-bromo-3-cyclopropylpropanoate (800 mg, 3.64 mmol), 5-(2-(3-fluoroazetidin-1-yl)ethyl)pyridin-2(1H)-one (1.07 g, 5.46 mmol) and $K_2CO_3$ (1.5 g, 10.92 mmol) in MeCN (10 mL) was stirred at 80° C. overnight. The mixture was filtered and washed with MeCN (10 mL). The filtrate was concentrated in vacuo and the residue was purified by silica gel column (petroleum ether: EtOAc 2:1) to provide ethyl 3-cyclopropyl-2-(5-(2-(3-fluoroazetidin-1-yl)ethyl)-2-oxopyridin-1(2H)-yl)propanoate as a colorless oil (400 mg). Yield 32% (ESI 337.2 $(M+H)^+$).

Step 4: 3-cyclopropyl-2-(5-(2-(3-fluoroazetidin-1-yl)ethyl)-2-oxopyridin-1(2H)-yl)propanoic acid

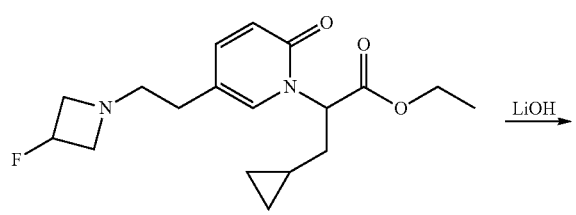

Ethyl 3-cyclopropyl-2-(5-(2-(3-fluoroazetidin-1-yl)ethyl)-2-oxopyridin-1(2H)-yl)propanoate (400 mg, 1.20 mmol) was treated with LiOH—$H_2O$ (201 mg, 4.80 mmol) in EtOH (4 mL) and $H_2O$ (1 mL) at room temperature for 2 hours. The mixture was acidified to pH 4~5 with 1N HCl. The mixture was concentrated in vacuo and the residue was purified by silica gel column (DCM:MeOH 10:1) to provide 3-cyclopropyl-2-(5-(2-(3-fluoroazetidin-1-yl)ethyl)-2-oxopyridin-1(2H)-yl)propanoic acid as a white solid (310 mg). Yield 85% (ESI 309.15 $(M+H)^+$).

186

Preparation of 2-(5-(2-((R)-3-fluoropyrrolidin-1-yl)ethyl)-2-oxopyridin-1(2H)-yl)-4-methylpentanoic acid Step 1: ethyl 2-(5-bromo-2-oxopyridin-1(2H)-yl)-4-methylpentanoate

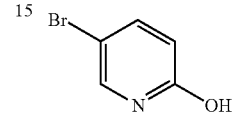

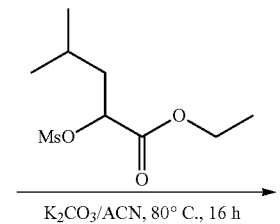

A mixture of 5-bromopyridin-2-ol (12.0 g, 69.0 mmol), $K_2CO_3$ (19.1 g, 138.0 mmol) and ethyl 4-methyl-2-(methylsulfonyloxy)pentanoate (18.5 g, 77.7 mmol) in $CH_3CN$ (230 mL) was stirred at 80° C. overnight. The solvent was concentrated in vacuo and the residue was purified by silica gel column (pet ether: EtOAc 1:2) to provide ethyl 2-(5-bromo-2-oxopyridin-1(2H)-yl)-4-methylpentanoate as a yellow oil (13.0 g). Yield 60% (ESI 316.0 $(M+H)^+$).

Step 2: ethyl 2-(5-allyl-2-oxopyridin-1(2H)-yl-4-methylpentanoate

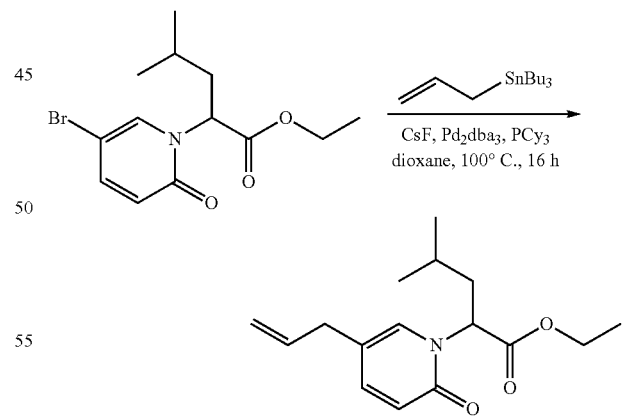

A mixture of ethyl 2-(5-bromo-2-oxopyridin-1(2H)-yl)-4-methylpentanoate (13.0 g, 41.1 mmol), allyltributylstannane (14.9 g, 45.1 mmol), $Pd_2dba_3$ (1.8 g, 2.06 mmol), tricyclohexyl phosphine (1.1 g, 4.11 mmol) and CsF (12.5 g, 82.2 mmol) in anhydrous dioxane (50 mL) was stirred under $N_2$ at 100° C. for 16 h. The mixture was cooled to room temperature and quenched with saturated $NH_4Cl$ solution (100 mL) and extracted with EtOAc (100 mL). The aqueous layer was extracted with EtOAc (200 mL×2). The combined organic layers were washed with brine (100 mL), dried over anhydrous Na₂SO₄, filtered and concentrated in vacuo. The residue was purified by silica gel column (pet ether: EtOAc 19:1) to provide ethyl 2-(5-allyl-2-oxopyridin-1(2H)-yl)-4-methylpentanoate as a yellow solid (7.1 g). Yield 62% (ESI 278.1 (M+H)⁺).

Step 3: ethyl 4-methyl-2-(2-oxo-5-(2-oxoethyl)pyridin-1(2H)-yl)pentanoate

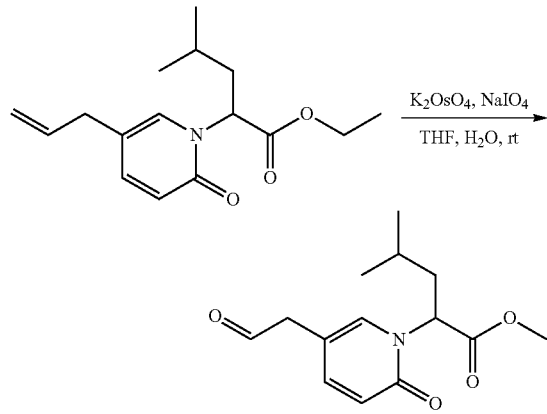

To a solution of ethyl 2-(5-allyl-2-oxopyridin-1(2H)-yl)-4-methylpentanoate (7.1 g, 25.6 mmol) in THF/H₂O (80 mL/30 mL) was added a solution of K₂OsO₄-2H₂O (94.0 mg, 0.26 mmol) in H₂O (4 mL) and stirred at room temperature for 1 h. A solution of NaIO₄ (10.8 g, 51.2 mmol) in H₂O (20 mL) was added and stirred at room temperature for 2 h. LCMS showed the reaction was completed. The reaction mixture was diluted with 100 mL of water and extracted with EtOAc (120 mL×3). The combined organic phase was dried over anhydrous Na₂SO₄, filtered and concentrated in vacuo to give the crude product ethyl 4-methyl-2-(2-oxo-5-(2-oxoethyl)pyridin-1(2H)-yl)pentanoate as a yellow oil (7.0 g, crude) used directly in the next reaction without further purification. (ESI 280.3 (M+H)⁺).

Step 4: ethyl 2-(5-(2-((R)-3-fluoropyrrolidin-1-yl)ethyl)-2-oxopyridin-1(2H)-yl)-4-methylpentanoate

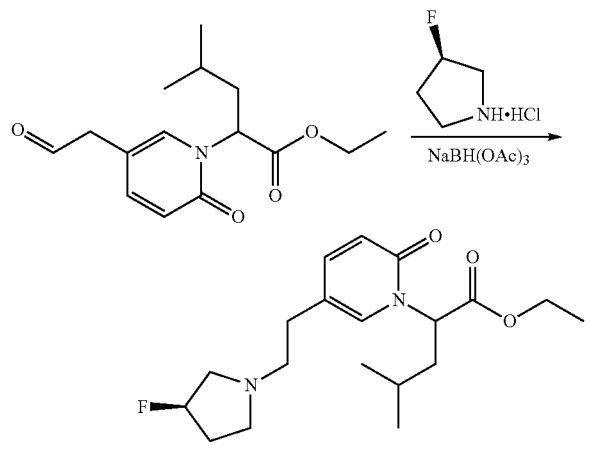

To a mixture of ethyl 4-methyl-2-(2-oxo-5-(2-oxoethyl)pyridin-1(2H)-yl)pentanoate (7.0 g, 25.0 mmol) in DCE (70 mL) at 25° C. was added (R)-3-fluoropyrrolidine hydrochloride (2.7 g, 25.0 mmol) and stirred at 25° C. for 30 mins. Then NaBH(OAc)₃ (10.6 g, 50.0 mmol) was added at 5° C. and stirred at 25° C. for 16 hours. The mixture was concentrated in vacuo and the residue was purified by silica gel column (DCM:MeOH 19:1) to give compound ethyl 2-(5-(2-((R)-3-fluoropyrrolidin-1-yl)ethyl)-2-oxopyridin-1(2H)-yl)-4-methylpentanoate (1.3 g) as a yellow oil. Yield: 15% (ESI 353.2 (M+H)⁺).

Step 5: 2-(5-(2-((R)-3-fluoropyrrolidin-1-yl)ethyl)-2-oxopyridin-1(2H)-yl)-4-methylpentanoic acid

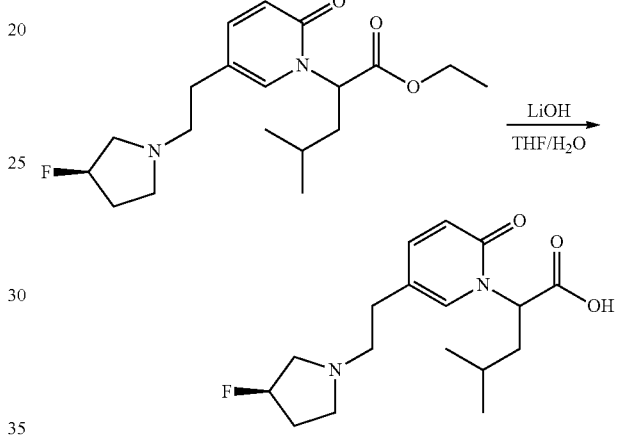

Ethyl 2-(5-(2-((R)-3-fluoropyrrolidin-1-yl)ethyl)-2-oxopyridin-1(2H)-yl)-4-methylpentanoate (1.3 g, 3.69 mmol) was treated with LiOH—H₂O (775.0 mg, 18.4 mmol) in MeOH (12 mL) and water (5 mL) at room temperature for 2 hours. The MeOH was removed in vacuo, acidified with 1N HCl to pH=5. The residue was purified by reverse phase HPLC on a C18/120 g column (A: water, B: MeOH, 0~100%) to provide 2-(5-(2-((R)-3-fluoropyrrolidin-1-yl)ethyl)-2-oxopyridin-1(2H)-yl)-4-methylpentanoic acid as a white solid (1.03 g). Yield 86% (ESI 325.1 (M+H)⁺).

Preparation of 2-(5-(2-(dimethylamino)ethyl)-4-methyl-2-oxopyridin-1(2H)-yl)-4-methylpentanoic acid Step 1: (E)-2-methoxy-5-(2-methoxyvinyl)-4-methylpyridine

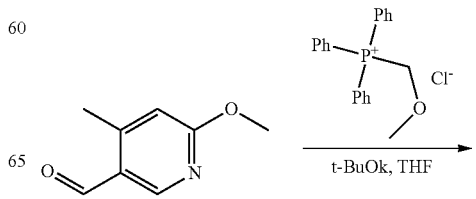

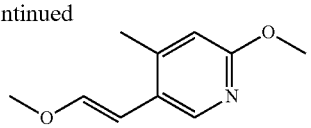

A mixture of (methoxymethyl)triphenyl phosphonium chloride (8.5 g, 24.8 mmol) and t-BuOK (4.6 g, 41.3 mmol) in THF (40 mL) was stirred at room temperature for 20 mins. 6-methoxy-4-methylnicotinaldehyde (2.5 g, 16.5 mmol) in 10 mL of THF was added and the mixture stirred at room temperature for 2 hours. The reaction mixture was poured into 40 mL of water and extracted with EtOAc (50 mL×2). The organic phase was concentrated in vacuo and the residue purified by reverse phase HPLC on a C18/40 g column (A: water 10 mM $NH_4HCO_3$, B: MeOH, 0~100%) to provide (E)-2-methoxy-5-(2-methoxyvinyl)-4-methylpyridine as a colorless oil (1.8 g). Yield 61% (ESI 180.1 $(M+H)^+$).

Step 2:
2-(6-methoxy-4-methylpyridin-3-yl)acetaldehyde

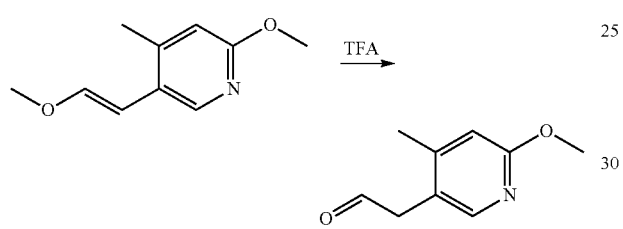

(E)-2-methoxy-5-(2-methoxyvinyl)-4-methylpyridine (1.8 g, 10 mmol) was treated with TFA (20 mL) at room temperature for 4 hours. The solvent was removed in vacuo to provide 2-(6-methoxy-4-methylpyridin-3-yl)acetaldehyde as a red oil (1.5 g, crude) used without further purification. (ESI 166.1 $(M+H)^+$).

Step 3: 2-(6-methoxy-4-methylpyridin-3-yl)-N,N-dimethlyethanamine

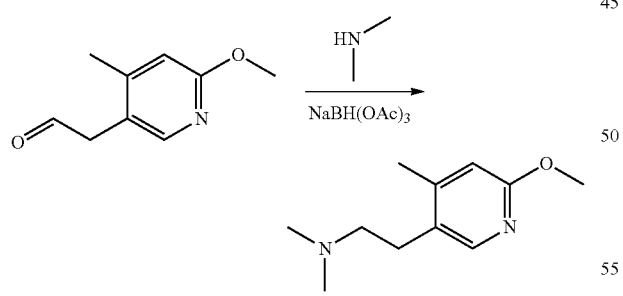

A mixture of 2-(6-methoxy-4-methylpyridin-3-yl)acetaldehyde (1.45 g, 8.78 mmol), dimethylamine (2M in THF, 17.5 mL, 35.72 mmol) and AcOH (0.8 g, 13.2 mmol) in DCE (30 mL) was stirred at room temperature for 15 mins. $NaBH(OAc)_3$ (3.71 g, 17.5 mmol) was added and stirred at room temperature for 3 hours. The solvent was removed in vacuo and the residue purified by silica gel column (DCM: MeOH 10:1) to provide 2-(6-methoxy-4-methylpyridin-3-yl)-N,N-dimethylethanamine as a yellow oil (850 mg). Yield 50% (ESI 195.1 $(M+H)^+$).

Step 4:
5-(2-(dimethylamino)ethyl)-4-methylpyridin-2-ol

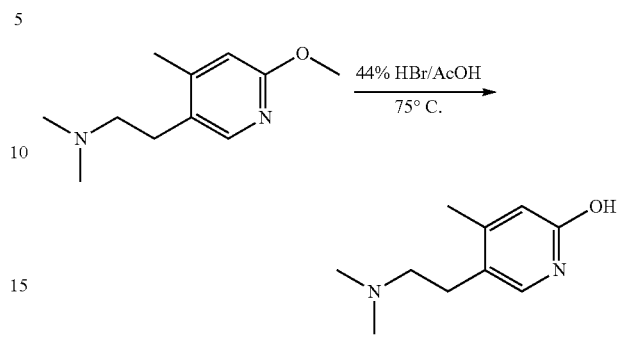

A mixture of 2-(6-methoxy-4-methylpyridin-3-yl)-N,N-dimethylethylamine (850 mg, 4.38 mmol) in HBr/AcOH (20 mL) was heated at 75° C. for 16 h. The solvent was removed in vacuo and the residue purified by reverse phase HPLC on a C18/40 g column (A: water 10 mM $NH_4HCO_3$, B: MeOH, 0~100%) to provide 5-(2-(dimethylamino)ethyl)-4-methylpyridin-2-ol as a red solid (650 mg). Yield 82% (ESI 181.1 $(M+H)^+$).

Step 5: ethyl 2-(5-(2-(dimethylamino)ethyl)-4-methyl-2-oxopyridin-1(2H)-yl)-4-methylpentanoate

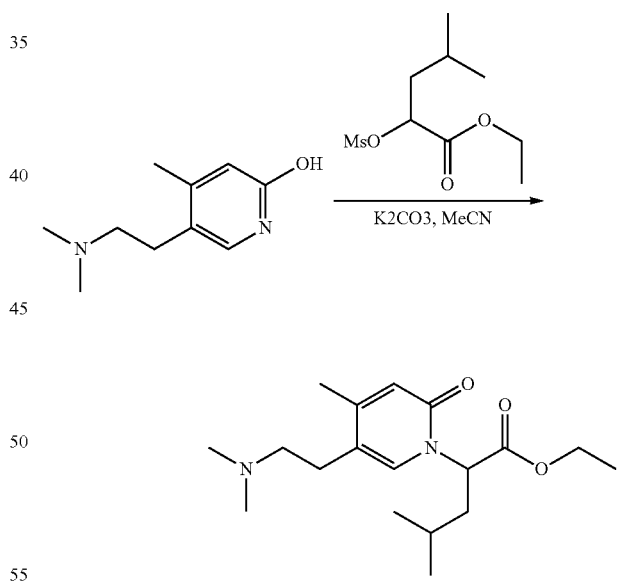

A mixture of 5-(2-(dimethylamino)ethyl)-4-methylpyridin-2-ol (650 g, 3.6 mmol), ethyl 4-methyl-2-(methylsulfonyloxy)pentanoate (1.71 g, 7.2 mmol) and $K_2CO_3$ (1.49 g, 10.8 mmol) in MeCN (20 mL) was stirred at 80° C. overnight. The solvent was removed in vacuo and the residue purified by reverse phase IPLC on a C18/40 g column (A: water 10 mM $NH_4HCO_3$, B: MeOH, 0~100%) to provide ethyl 2-(5-(2-(dimethylamino)ethyl)-4-methyl-2-oxopyridin-1(2H)-yl)-4-methylpentanoate (500 mg). Yield 43% (ESI 323.2 $(M+H)^+$).

Step 6: 2-(5-(2-(dimethylamino)ethyl)-4-methyl-2-oxopyridin-1(2H)-yl)-4-methylpentanoic acid

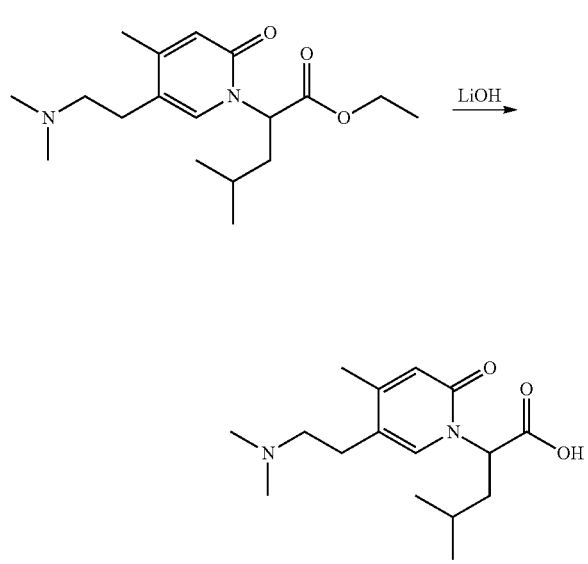

Ethyl 2-(5-(2-(dimethylamino)ethyl)-4-methyl-2-oxopyridin-1(2H)-yl)-4-methylpentanoate (500 mg, 1.55 mmol) was treated with LiOH—H$_2$O (260 mg, 6.2 mmol) in MeOH (10 mL) and H$_2$O (2 mL) at room temperature for 2 hours. The mixture was acidified to pH 4~5 with 1N HCl and purified by reverse phase HPLC on a C18/40 g column (A: water 10 mM NH$_4$HCO$_3$, B: MeOH, 0~100%) to provide 2-(5-(2-(dimethylamino)ethyl)-4-methyl-2-oxopyridin-1(2H)-yl)-4-methylpentanoic acid as a white solid (420 mg). Yield 92% (ESI 295.2 (M+H)$^+$).

Preparation of 2-(5-(2-(dimethylamino)ethyl)-4-methyl-2-oxopyridin-1(2H)-yl)-5-methylhexanoic acid Step 1: (R)-2-bromo-5-methylhexanoic acid

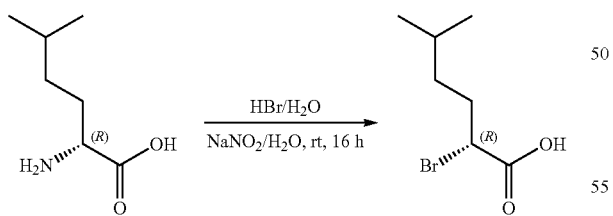

To a mixture of (R)-2-amino-5-methylhexanoic acid (30 g, 207 mmol) in 40% HBr (200 mL) and H$_2$O (200 mL) at 0° C. was added a solution of NaNO$_2$ (17 g, 248 mmol) in H$_2$O (15 mL) dropwise. The mixture was stirred at room temperature overnight. The mixture was extracted with DCM (200 mL). The organic phase was washed with brine (200 mL), dried over Na$_2$SO$_4$, concentrated in vacuo to provide (R)-2-bromo-5-methylhexanoic acid as a yellow oil (30 g). Yield 70% (ESI 211.1 (M+H)$^+$).

Step 2: ethyl 2-bromo-5-methylhexanoate

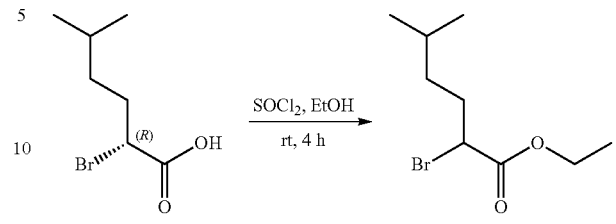

To a mixture of (R)-2-bromo-5-methylhexanoic acid (30 g, 144 mmol) in EtOH (200 mL) at 0° C. was added SOCl$_2$ (86 g, 720 mmol). The mixture was stirred for 4 h at room temperature. The solvent was removed in vacuo to provide ethyl 2-bromo-5-methylhexanoate as a colorless oil (35 g, crude). (ESI 239.1 (M+H)$^+$).

Step 3: ethyl 2-(5-bromo-4-methyl-2-oxopyridin-1(2H)-yl)-5-methylhexanoate

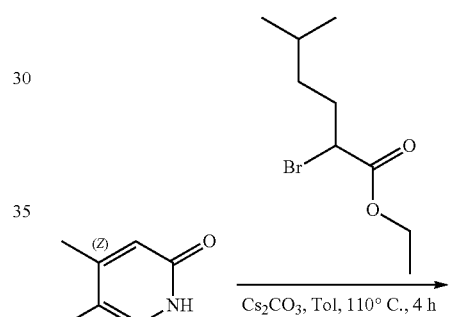

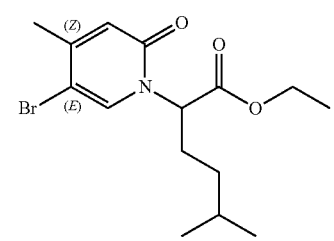

A mixture of 5-bromo-4-methylpyridin-2(1H)-one (8 g, 42.78 mmol), Cs$_2$CO$_3$ (27.9 g, 85.56 mmol) and ethyl 2-bromo-5-methylhexanoate (15 g, 64.17 mmol) in toluene (160 mL) was stirred at 110° C. for 4 hours. The solvent was concentrated in vacuo and the residue was purified by silica gel column (pet ether: EtOAc 4:1) to provide ethyl 2-(5-bromo-4-methyl-2-oxopyridin-1(2H)-yl)-5-methylhexanoateas a colorless oil (6.5 g). Yield 44% (ESI 346.1 (M+H)$^+$).

Step 4: (E)-ethyl 2-(5-(2-ethoxyvinyl)-4-methyl-2-oxopyridin-1(2H)-yl)-5-methylhexanoate

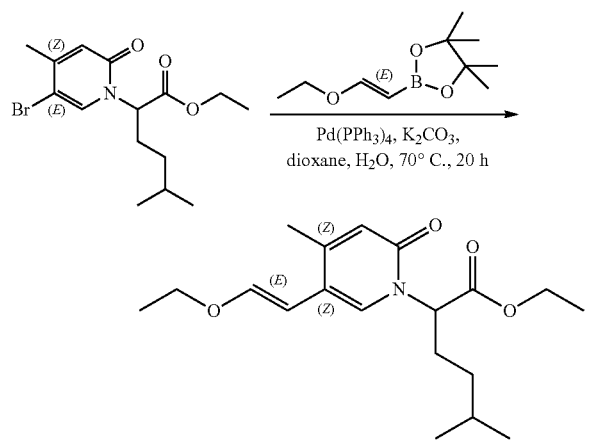

A mixture of ethyl 2-(5-bromo-4-methyl-2-oxopyridin-1(2H)-yl)-5-methylhexanoate (5.4 g, 15.7 mmol), (E)-2-(2-ethoxyvinyl)-4,4,5,5-tetramethyl-1,3,2-dioxaborolane (6.22 g, 31.4 mmol), Pd(PPh$_3$)$_4$ (912 mg, 0.79 mmol) and K$_2$CO$_3$ (4.33 g, 31.4 mmol) in 1,4-dioxane (70 mL) and water (7 mL) was stirred at 70° C. under N$_2$ for 20 h. The reaction mixture was diluted with 100 mL of water, extracted with EtOAc (100 mL×2). The combined organic phase was washed with brine (150 mL), dried over anhydrous Na$_2$SO$_4$, filtered and concentrated in vacuo. The residue was purified by silica gel column (pet ether: EtOAc 1:1) to provide (E)-ethyl 2-(5-(2-ethoxyvinyl)-4-methyl-2-oxopyridin-1(2H)-yl)-5-methylhexanoate (3.8 g) as a yellow oil. Yield 72% (ESI 336.2 (M+H)$^+$).

Step 5: ethyl 5-methyl-2-(4-methyl-2-oxo-5-(2-oxoethyl)pyridin-1(2H)-yl)hexanoate

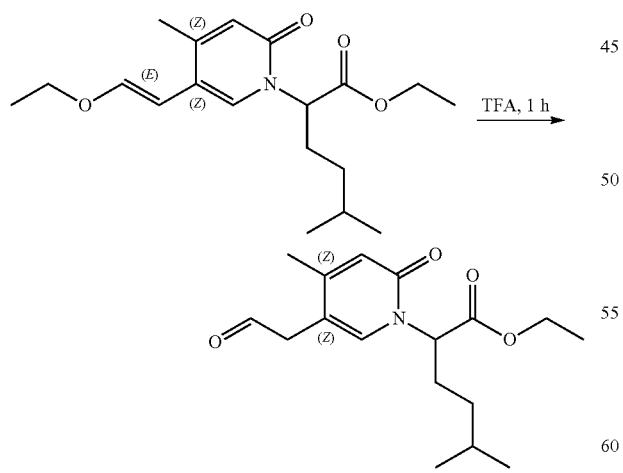

(E)-ethyl 2-(5-(2-ethoxyvinyl)-4-methyl-2-oxopyridin-1(2H)-yl)-5-methylhexanoate (3.8 g, 11.34 mmol) was treated with TFA (40 mL) at room temperature for 1 hour. The solvent was removed in vacuo and the residue was purified by silica gel column (EtOAc) to provide ethyl 5-methyl-2-(4-methyl-2-oxo-5-(2-oxoethyl)pyridin-1(2H)-yl)hexanoate as a colorless oil (2 g). Yield 57% (ESI 308.2 (M+H)$^+$).

Step 6: ethyl 2-(5-(2-(dimethylamino)ethyl)-4-methyl-2-oxopyridin-1(2H)-yl)-5-methylhexanoate

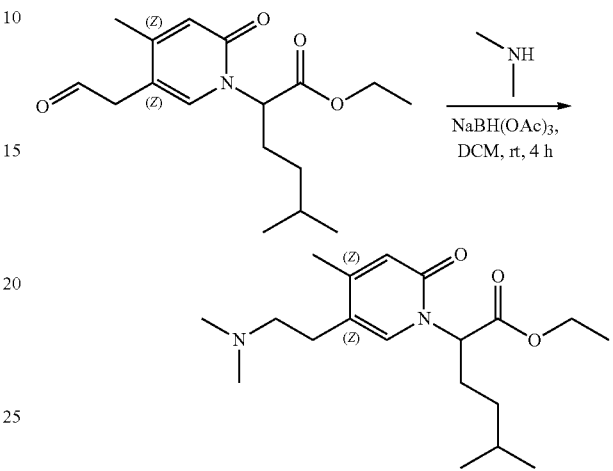

To a mixture of ethyl 5-methyl-2-(4-methyl-2-oxo-5-(2-oxoethyl)pyridin-1(2H)-yl)hexanoate (2 g, 6.51 mmol) in DCM (30 mL) was added dimethylamine (2 M) (6.5 mL, 13.02 mmol) and stirred at room temperature for 20 minutes. Then NaBH(OAc)$_3$ (2.76 g, 13.02 mmol) was added and stirred at room temperature for 4 h. The solvent was removed in vacuo and the residue was purified by silica gel column (DCM:MeOH 10:1) to provide ethyl 2-(5-(2-(dimethylamino)ethyl)-4-methyl-2-oxopyridin-1(2H)-yl)-5-methylhexanoate as a colorless oil (1.4 g). Yield 64% (ESI 337.3 (M+H)$^+$).

Step 7: 2-(5-(2-(dimethylamino)ethyl)-4-methyl-2-oxopyridin-1(2H)-yl)-5-methylhexanoic acid

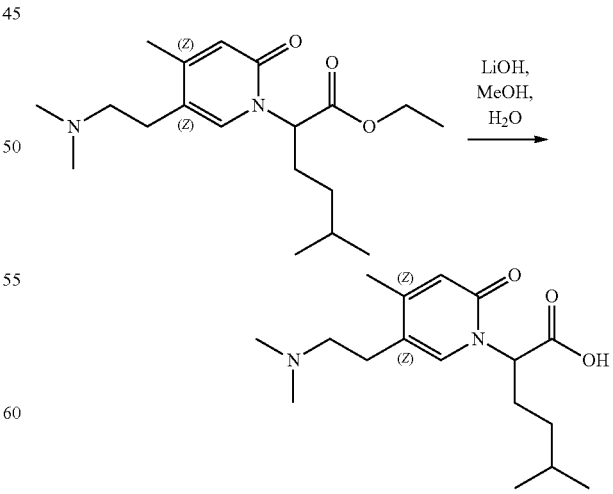

Ethyl 2-(5-(2-(dimethylamino)ethyl)-4-methyl-2-oxopyridin-1(2H)-yl)-5-methylhexanoate (1.4 g, 4.17 mmol) was treated with LiOH—H$_2$O (700 mg, 16.68 mmol)

in MeOH (20 mL) and H₂O (4 mL) at room temperature for 2 hours. The reaction mixture was acidified to pH 4~5 with 1 N HCl. The solvent was removed in vacuo and the residue was purified by reverse phase HPLC on a C18/40 g column (A: water 10 mM NH₄HCO₃, B: MeOH, 0~100%) to provide 2-(5-(2-(dimethylamino)ethyl)-4-methyl-2-oxopyridin-1(2H)-yl)-5-methylhexanoic acid (900 mg) as a white solid. Yield 70% (ESI 309.2 (M+H)⁺).

Preparation of 2-(5-(2-(3-fluoroazetidin-1-yl)ethyl)-4-methyl-2-oxopyridin-1(2H)-yl)-4-methylpentanoic acid Step 1: 5-(2-(3-fluoroazetidin-1-yl)ethyl)-4-methylpyridin-2-ol

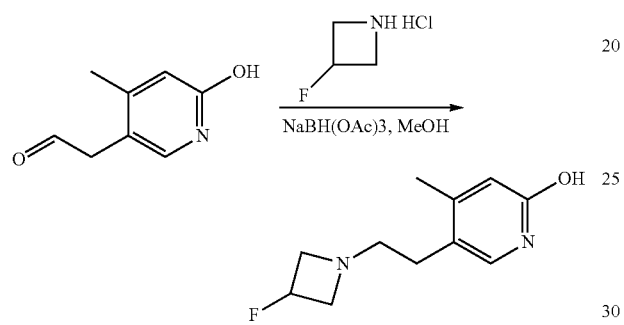

A mixture of 2-(6-hydroxy-4-methylpyridin-3-yl)acetaldehyde (2 g, 13.2 mmol), 3-fluoroazetidine hydrochloride (2.2 g, 19.8 mmol) in MeOH (20 mL) was stirred at room temperature for 30 mins. NaBH(OAc)₃ (5.6 g, 26.4 mmol) was added and stirred at room temperature for 2 hours. The solvent was removed in vacuo and the residue was purified by silica gel column (DCM:MeOH 2:1) to provide 5-(2-(3-fluoroazetidin-1-yl)ethyl)-4-methylpyridin-2-ol as a yellow oil (1 g). Yield 36% (ESI 211.1 (M+H)⁺).

Step 2: ethyl 2-(5-(2-(3-fluoroazetidin-1-yl)ethyl)-4-methyl-2-oxopyridin-1(2H)-yl)-4-methylpentanoate

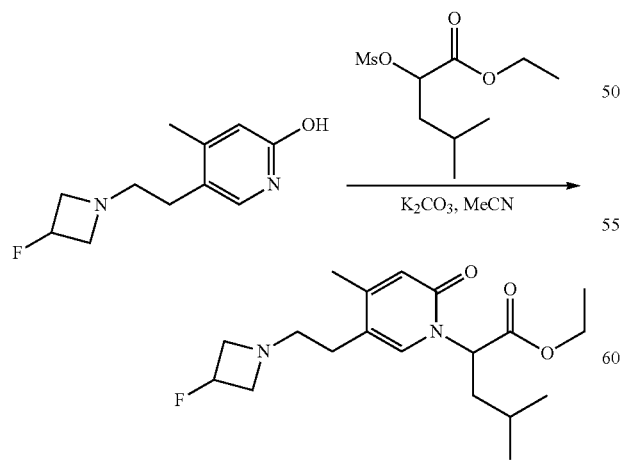

A mixture of methyl 5-(2-(dimethylamino)ethyl)pyridin-2(1H)-one (1 g, 4.76 mmol), ethyl 4-methyl-2-(methylsulfonyloxy)pentanoate (1.36 g, 5.71 mmol) and K₂CO₃ (1.97 g, 14.28 mmol) in MeCN (20 mL) was stirred at 85° C. overnight. The solvent was removed in vacuo and the residue purified by silica gel column (DCM:MeOH 1:2) to provide ethyl 2-(5-(2-(3-fluoroazetidin-1-yl)ethyl)-4-methyl-2-oxopyridin-1(2H)-yl)-4-methylpentanoate as a white solid (500 mg). Yield 30% (ESI 353.2 (M+H)⁺).

Step 3: 2-(5-(2-(3-fluoroazetidin-1-yl)ethyl)-4-methyl-2-oxopyridin-1(2H)-yl)-4-methylpentanoic acid

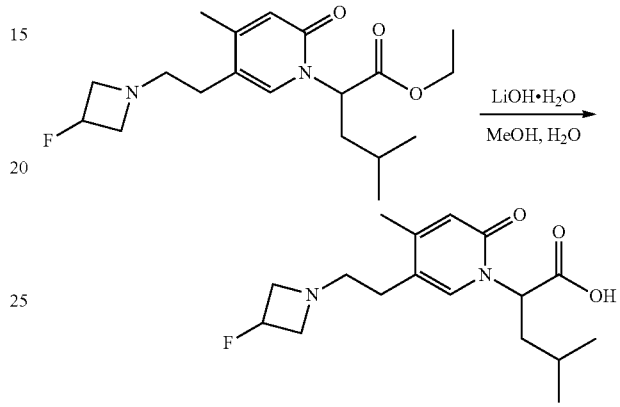

Ethyl 2-(5-(2-(3-fluoroazetidin-1-yl)ethyl)-4-methyl-2-oxopyridin-1(2H)-yl)-4-methylpentanoate (500 mg, 1.42 mmol) was treated with LiOH—H₂O (298 mg, 7.1 mmol) in MeOH (10 mL) and H₂O (2.5 mL) at room temperature for 2 hours. The mixture was acidified to pH 4~5 with 1N HCl, purified by reverse phase HPLC on a C18/40 g column (A: water 10 mM NH₄HCO₃, B: MeOH, 0~100%) to give 2-(5-(2-(3-fluoroazetidin-1-yl)ethyl)-4-methyl-2-oxopyridin-1(2H)-yl)-4-methylpentanoic acid as a white solid (360 mg). Yield 78% (ESI 325.1 (M+H)⁺).

Preparation of 2-(5-(2-((R)-3-fluoropyrrolidin-1-yl)ethyl)-4-methyl-2-oxopyridin-1(2H)-yl)-4-methylpentanoic acid Step 1: ethyl 2-(5-allyl-4-methy-2-oxopyridin-2)-yl)-4-methylpentanoate

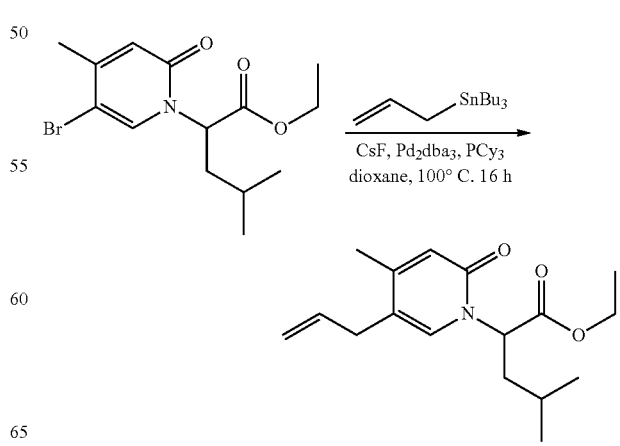

A mixture of ethyl 2-(5-bromo-4-methyl-2-oxopyridin-1(2H)-yl)-4-methylpentanoate (2.9 g, 8.78 mmol), allyltributylstannane (3.5 g, 10.54 mmol), Pd$_2$dba$_3$ (402 mg, 0.44 mmol), tricyclohexyl phosphine (247 mg, 0.88 mmol) and CsF (2.7 g, 17.56 mmol) in anhydrous dioxane (100 mL) was stirred at 100° C. for 16 h. The mixture was cooled to room temperature. The mixture was filtered and washed with dioxane (20 mL). The filtrate was concentrated in vacuo and the residue was purified by silica gel column (pet ether: EtOAc 3:1) to provide ethyl 2-(5-allyl-4-methyl-2-oxopyridin-1(2H)-yl)-4-methylpentanoate as a yellow oil (1.6 g). Yield 60% (ESI 292 (M+H)$^+$).

Step 2: ethyl 4-methyl-2-(4-methyl-2-oxo-5-(2-oxoethyl)pyridin-1(2H)-yl)pentanoate

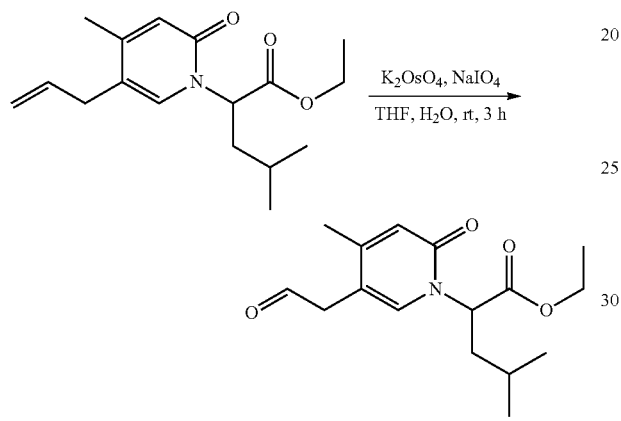

To a solution of ethyl 2-(5-allyl-4-methyl-2-oxopyridin-1(2H)-yl)-4-methylpentanoate (1.6 g, 5.49 mmol) in THF/H$_2$O (20 mL/10 mL) was added a solution of K$_2$OsO$_4$·2H$_2$O (20 mg, 0.055 mmol) in H$_2$O (1 mL) dropwise and stirred at room temperature for 1 h. A solution of NaIO$_4$ (2.3 g, 10.98 mmol) in H$_2$O (5 mL) was added dropwise and stirred at room temperature for 3 h. LCMS showed the reaction was completed. The reaction mixture was diluted with water (40 mL) and extracted with EtOAc (50 mL×3). The combined organic phase was dried over anhydrous Na$_2$SO$_4$, filtered and concentrated in vacuo to provide ethyl 4-methyl-2-(4-methyl-2-oxo-5-(2-oxoethyl)pyridin-1(2H)-yl)pentanoate as a brown oil which was used in next step without further purification. (ESI 294 (M+H)$^+$).

Step 3: ethyl 2-(5-(2-((R)-3-fluoropyrrolidin-1-yl)ethyl)-4-methyl-2-oxopyridin-1(2H)-yl)-4-methylpentanoate

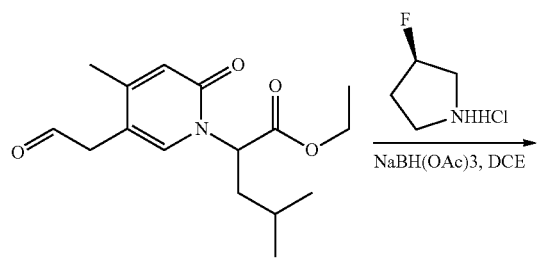

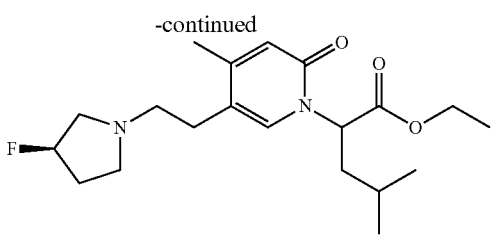

A mixture of ethyl 4-methyl-2-(4-methyl-2-oxo-5-(2-oxoethyl)pyridin-1(2H)-yl)pentanoate (950 mg, 3.24 mmol) and (R)-3-fluoropyrrolidine hydrochloride (814 mg, 6.48 mmol) in DCE (20 mL) was stirred at room temperature for 1 h. Then NaBH(OAc)$_3$ (2.1 g, 9.72 mmol) was added and stirred at room temperature for 2 h. The mixture was concentrated in vacuo and the residue was purified by reverse phase HPLC on a C18/40 g column (A: water/10 mM NH$_4$HCO$_3$, B: MeOH, 0~100%) to provide ethyl 2-(5-(2-((R)-3-fluoropyrrolidin-1-yl)ethyl)-4-methyl-2-oxopyridin-1(2H)-yl)-4-methylpentanoate as a yellow oil (550 mg). Yield 46% (ESI 367 (M+H)$^+$).

Step 4: 2-(5-(2-((R)-3-fluoropyrrolidin-1-yl)ethyl)-4-methyl-2-oxopyridin-1(2H)-yl)-4-methylpentanoic acid

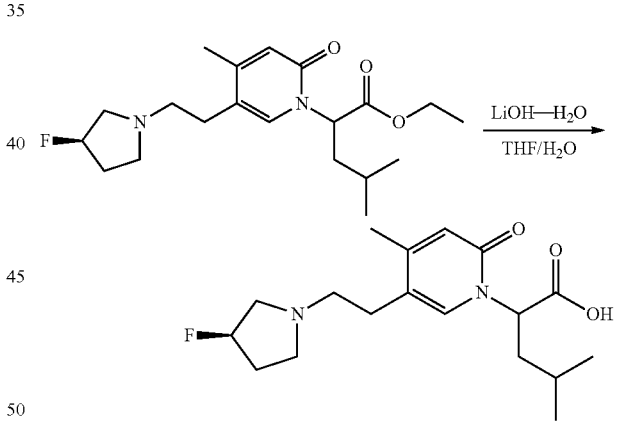

Ethyl 2-(5-(2-((R)-3-fluoropyrrolidin-1-yl)ethyl)-4-methyl-2-oxopyridin-1(2H)-yl)-4-methylpentanoate (550 mg, 1.50 mmol) was treated with LiOH—H$_2$O (120 mg, 4.50 mmol) in THF (6 mL) and water (2 mL) at room temperature for 2 hours. The reaction was acidified with 1N HCl to pH=8. The solvent was removed in vacuo and the residue was purified by reverse phase HPLC on a C18/40 g column (A: water/10 mM NH$_4$HCO$_3$, B: MeOH, 0~100%) to provide 2-(5-(2-((R)-3-fluoropyrrolidin-1-yl)ethyl)-4-methyl-2-oxopyridin-1(2H)-yl)-4-methylpentanoic acid as a white solid (270 mg). Yield 53% (ESI 339 (M+H)$^+$).

Preparation of 2-(5-(2-(azetidin-1-yl)ethyl)-2-oxo-4-(trifluoromethyl)pyridin-1(2H)-yl)-4-methylpentanoic acid Step 1: (E)-2-methoxy-5-(2-methoxyvinyl)-4-(trifluoromethyl)pyridine

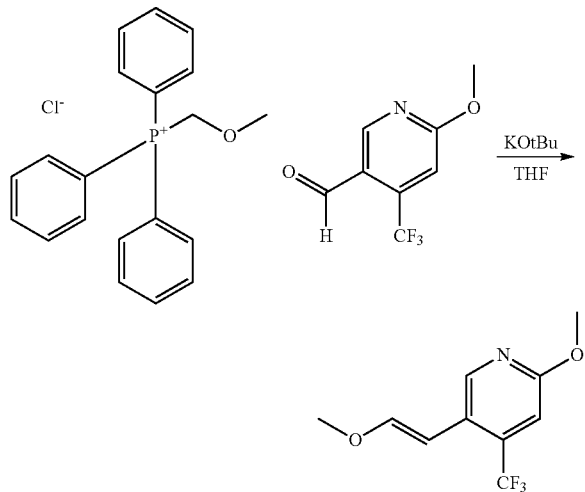

To a solution of (methoxymethyl)triphenylphosphonium chloride (1.0 g, 2.95 mmol) in THF (13.406 mL) at 0° C. was added potassium tert-butoxide (376 mg, 3.35 mmol). After stirring for 1 hour at 0° C., a solution of 6-methoxy-4-(trifluoromethyl)nicotinaldehyde (550 mg, 2.68 mmol) in THF (6.5 mL) was added. The reaction was allowed to stir overnight at room temperature and quenched with a NH$_4$Cl solution. The mixture was extracted (EtOAc×3), concentrated and purified by silica gel chromatography (0-100 Ethyl acetate: Hexanes) to provide (E)-2-methoxy-5-(2-methoxyvinyl)-4-(trifluoromethyl)pyridine (450 mgs). Yield 72% (ESI 234.2 (M+H)$^+$).

Step 2: 2-(6-methoxy-4-(trifluoromethyl)pyridin-3-yl)acetaldehyde

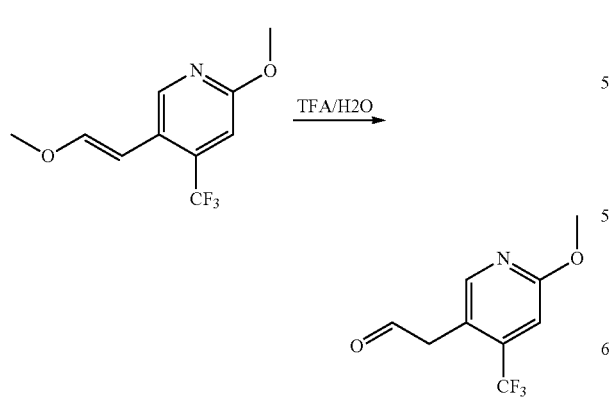

To a solution of (E)-2-methoxy-5-(2-methoxyvinyl)-4-(trifluoromethyl)pyridine (450 mg, 1.930 mmol) in DCM (29.689 mL) was added TFA (0.595 mL, 7.72 mmol) and water (0.591 mL, 32.8 mmol). The reaction was stirred for 18 hrs at 45° C. The reaction was diluted with DCM and quenched with NaHCO$_3$. The mixture was washed with water, dried with Na$_2$SO$_4$, filtered and concentrated to provide 2-(6-methoxy-4-(trifluoromethyl)pyridin-3-yl)acetaldehyde (343 mgs) used without further purification. Yield 81% (ESI 220.18 (M+H)$^+$).

Step 3: 5-(2-(azetidin-1-yl)ethyl)-2-methoxy-4-(trifluoromethyl)pyridine

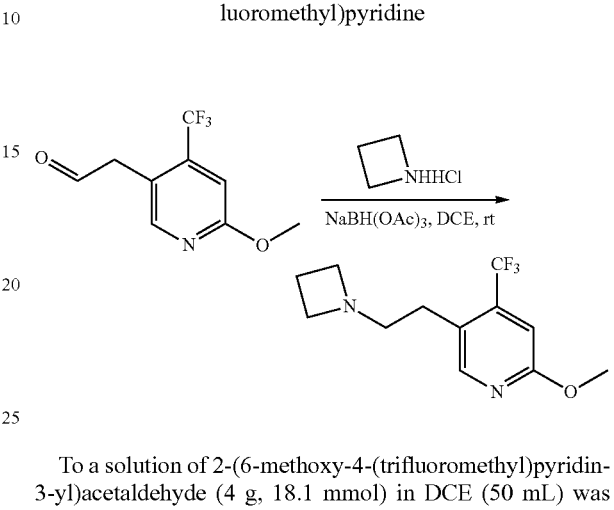

To a solution of 2-(6-methoxy-4-(trifluoromethyl)pyridin-3-yl)acetaldehyde (4 g, 18.1 mmol) in DCE (50 mL) was added azetidine hydrochloride (3.4 g, 36.2 mmol). The reaction mixture was stirred at room temperature for 20 mins. NaBH(OAc)$_3$ (7.7 g, 36.2 mmol) was added and stirred at room temperature for 16 hours. The reaction mixture was quenched by addition of MeOH (20 mL) and filtered. The filtrate was concentrated in vacuo and the residue was purified by reverse phase HPLC on a C18/80 g column (A: water 10 mM NH$_4$HCO$_3$, B: MeOH, 0~100%) to provide 5-(2-(azetidin-1-yl)ethyl)-2-methoxy-4-(trifluoromethyl)pyridine as a yellow oil (3 g). Yield 63% (ESI 261.2 (M+H)$^+$).

Step 4: 5-(2-(azetidin-1-yl)ethyl)-4-(trifluoromethyl)pyridin-2(1H)-one

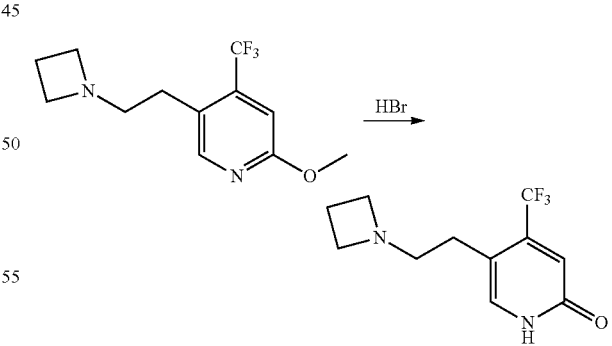

A mixture of 5-(2-(azetidin-1-yl)ethyl)-2-methoxy-4-(trifluoromethyl)pyridine (2.95 g, 11.3 mmol) in HBr/AcOH (20 mL) was stirred at 50° C. for 5 h. The reaction mixture was concentrated in vacuo and the residue was purified by reverse phase HPLC on a C18/80 g column (A: water 10 mM NH$_4$HCO$_3$, B: MeOH, 0~100%) to provide 5-(2-(azetidin-1-yl)ethyl)-4-(trifluoromethyl)pyridin-2(1H)-one as a yellow oil (710 mg). Yield 25% (ESI 247.1 (M+H)$^+$).

Step 5: ethyl 2-(5-(2-(azetidin-1-yl)ethyl)-2-oxo-4-(trifluoromethyl)pyridin-1(2H)-yl)-4-methylpentanoate

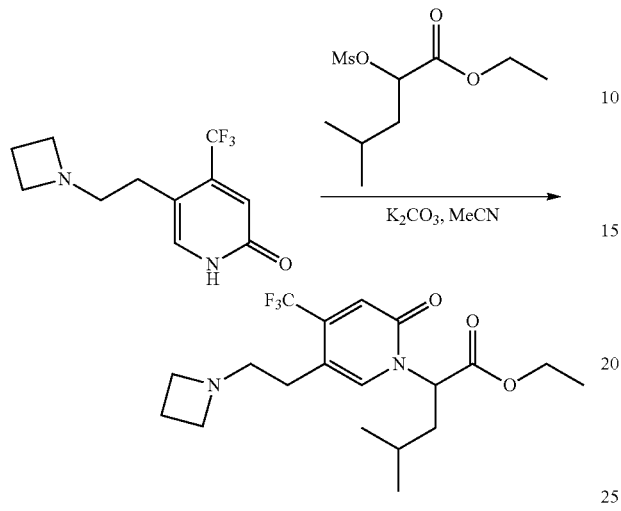

To a solution of 5-(2-(azetidin-1-yl)ethyl)-4-(trifluoromethyl)pyridin-2(1H)-one (710 mg, 2.9 mmol) in MeCN (10 mL) was added ethyl 4-methyl-2-(methylsulfonyloxy)pentanoate (1.1 g, 4.4 mmol) and K$_2$CO$_3$ (1.2 g, 8.7 mmol). The reaction mixture was stirred at 80° C. for 16 hours. The reaction mixture was concentrated in vacuo and the residue was purified by reverse phase HPLC on a C18/40 g column (A: water 10 mM NH$_4$HCO$_3$, B: MeOH, 0~100%) to provide ethyl 2-(5-(2-(azetidin-1-yl)ethyl)-2-oxo-4-(trifluoromethyl)pyridin-1(2H)-yl)-4-methylpentanoate as a yellow oil (500 mg). Yield 44% (ESI 389.2 (M+H)$^+$).

Step 6: 2-(5-(2-(azetidin-1-yl)ethyl)-2-oxo-4-(trifluoromethyl)pyridin-1(2H)-yl)-4-methylpentanoic acid

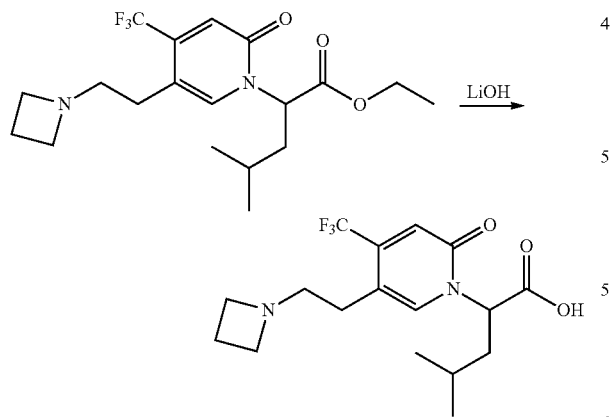

Ethyl 2-(5-(2-(azetidin-1-yl)ethyl)-2-oxo-4-(trifluoromethyl)pyridin-1(2H)-yl)-4-methylpentanoate (500 mg, 1.3 mmol) was treated with LiOH—H$_2$O (270 mg, 6.5 mmol) in EtOH (5 mL) and water (1 mL) at room temperature for 2 hours. The reaction mixture was neutralized with 2 N HCl and concentrated in vacuo. The residue was purified by reverse phase HPLC on a C18/40 g column (A: water 10 mM NH$_4$HCO$_3$, B: MeOH, 0~100%) to provide 2-(5-(2-(azetidin-1-yl)ethyl)-2-oxo-4-(trifluoromethyl)pyridin-1 (2H)-yl)-4-methylpentanoic acid as a yellow oil (410 mg). Yield 88% (ESI 361.2 (M+H)$^+$).

Preparation of 2-(5-(2-(dimethylamino)ethyl)-2-oxo-4-(trifluoromethyl)pyridin-1(2H)-yl)-4-methylpentanoic acid

Step 1: 2-(6-methoxy-4-(trifluoromethyl)pyridin-3-yl)-N,N-dimethylethan-1-amine

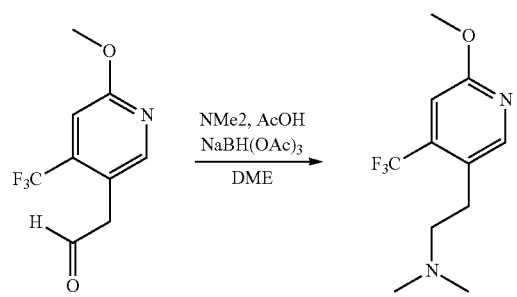 [SMILES: COc1cc(C(F)(F)F)c(CC=O)cn1 ; COc1cc(C(F)(F)F)c(CCN(C)C)cn1]

To a solution of 2-(6-methoxy-4-(trifluoromethyl)pyridin-3-yl)acetaldehyde (0.34 g, 1.6 mmol) in DCE (7.8 mL) was added dimethylamine (3.9 mL, 7.8 mmol) and acetic acid (0.05 mL, 0.78 mmol) and stirred for 1 hour. To the solution was added sodium triacetoxyborohydride (0.6 g, 3.1 mmol). The reaction was allowed to stir for 12 hours then concentrated and purified by silica gel chromatography (0-35% DCM (1% TEA):MeOH 0-30%) to provide 2-(6-methoxy-4-(trifluoromethyl)pyridin-3-yl)-N,N-dimethylethan-1-amine (305 mg). Yield 79% (ESI 249.27 (M+H)$^+$).

Step 2: 5-(2-(dimethylamino)ethyl)-4-(trifluoromethyl)pyridin-2(1H)-one

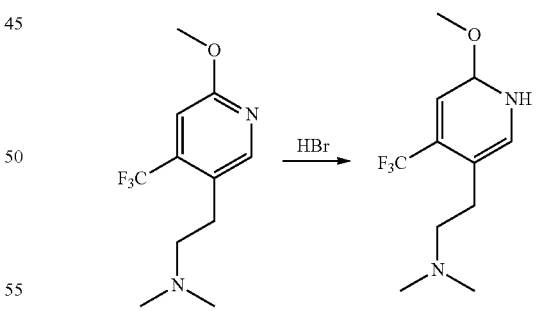

HBr (33% in Acetic Acid) (4.04 mL, 24.57 mmol) was added to 2-(6-methoxy-4-(trifluoromethyl)pyridin-3-yl)-N,N-dimethylethan-1-amine (0.305 g, 1.229 mmol) and heated to 75° C. in a pressure vessel. After 4 hours, the solvent was removed and the residue purify by silica gel chromatography (0-25% DCM:MeOH with 1% TEA as a modifier) to provide 5-(2-(dimethylamino)ethyl)-4-(trifluoromethyl)pyridin-2 (1H)-one (219 mg). Yield 76% (ESI 235.15 (M+H)$^+$). $^1$H NMR (400 MHz, MeOD) δ 7.56 (s, 1H), 6.85 (s, 1H), 2.76 (m, 2H), 2.61 (m, 1H), 2.37 (m, 6H)

Step 3: ethyl 2-(5-(2-(dimethylamino)ethyl)-2-oxo-4-(trifluoromethyl)pyridin-1(2H)-yl)-4-methylpentanoate

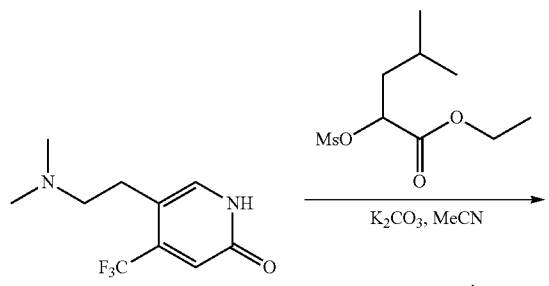

A mixture of 5-(2-(dimethylamino)ethyl)-4-(trifluoromethyl)pyridin-2(1H)-one (685 mg, 2.92 mmol), K$_2$CO$_3$ (1.60 g, 11.55 mmol) and ethyl 4-methyl-2-(methylsulfonyloxy) pentanoate (1.60 g, 6.70 mmol) in CH$_3$CN (60 mL) was stirred at 85° C. overnight. The solvent was concentrated in vacuo and the residue was purified by silica gel column (DCM:MeOH 2:1) to give ethyl 2-(5-(2-(dimethylamino)ethyl)-2-oxo-4-(trifluoromethyl)pyridin-1(2H)-yl)-4-methylpentanoate as brown oil (390 mg). Yield 35% (ESI 377.2 (M+H)$^+$). $^1$H NMR (500 MHz, MeOD) δ 7.84 (s, 1H), 6.68 (s, 1H), 5.51 (dd, J=11.0, 5.0 Hz, 1H), 4.23 (q, J=7.0 Hz, 2H), 2.77 (t, J=8.0 Hz, 2H), 2.53 (t, J=8.0 Hz, 2H), 2.33 (s, 6H), 2.18-2.12 (m, 1H), 2.08-2.02 (m, 1H), 1.46-1.38 (m, 1H), 1.27 (t, J=7.0 Hz, 3H), 0.97 (t, J=7.0 Hz, 6H).

Step 4: 2-(5-(2-(dimethylamino)ethyl)-2-oxo-4-(trifluoromethyl)pyridin-1(2H)-yl)-4-methylpentanoic acid

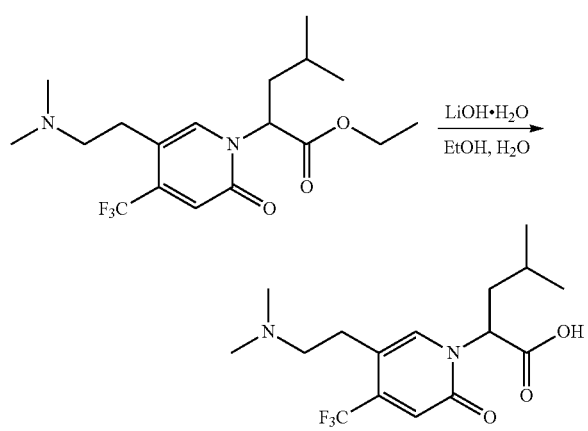

Ethyl 2-(5-(2-(dimethylamino)ethyl)-2-oxo-4-(trifluoromethyl)pyridin-1(2H)-yl)-4-methylpentanoate (390 mg, 1.0 mmol) was treated with LiOH monohydrate (435 mg, 10.36 mmol) in EtOH (10 mL) and H$_2$O (1 mL) at room temperature for 1 hour. The mixture was acidified to pH 4~5 with 1N HCl aqueous solution. The mixture was concentrated in vacuo and purified by silica gel column (MeOH: EtOAc 1:2) to give 2-(5-(2-(dimethylamino)ethyl)-2-oxo-4-(trifluoromethyl)pyridin-1(2H)-yl)-4-methylpentanoic acid as an oil (358 mg). Yield 99% (ESI 349.1 (M+H)$^+$).

Preparation of 2-(5-(2-(dimethylamino)ethyl)-2-oxo-4-(trifluoromethyl)pyridin-1(2H)-yl)-3-methylbutanoic acid

Step 1: ethyl 2-(5-(2-(dimethylamino)ethyl)-2-oxo-4-(trifluoromethyl)pyridin-1(2H)-yl)-3-methylbutanoate

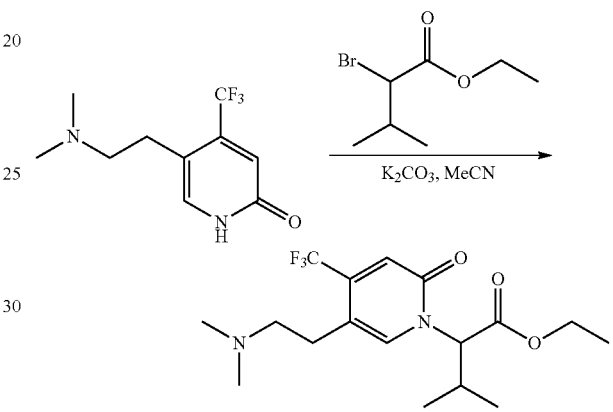

To a solution of 5-(2-(dimethylamino)ethyl)-4-(trifluoromethyl)pyridin-2(1H)-one (2.4 g, 10.2 mmol) in MeCN (40 mL) was added ethyl 2-bromo-3-methylbutanoate (4.3 g, 20.4 mmol) and K$_2$CO$_3$ (2.8 g, 20.4 mmol). The reaction mixture was stirred at 80° C. for 16 h. The reaction mixture was concentrated in vacuo and the residue was purified by reverse phase HPLC on a C18/40 g column (A: water 10 mM NH$_4$HCO$_3$, B: MeOH, 0~100%) to provide ethyl 2-(5-(2-(dimethylamino)ethyl)-2-oxo-4-(trifluoromethyl)pyridin-1(2H)-yl)-3-methylbutanoate as a yellow oil (2.6 g). Yield 69% (ESI 363.2 (M+H)$^+$).

Step 2: 2-(5-(2-(dimethylamino)ethyl)-2-oxo-4-(trifluoromethyl)pyridin-1(2H)-yl)-3-methylbutanoic acid

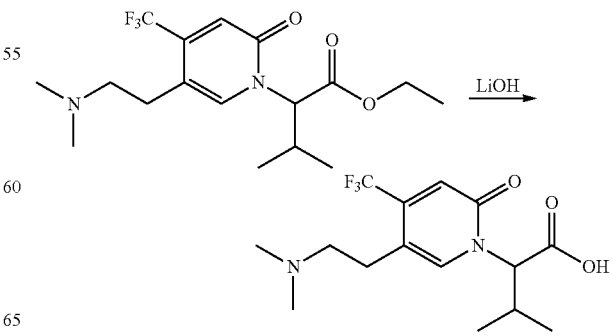

Ethyl 2-(5-(2-(dimethylamino)ethyl)-2-oxo-4-(trifluoromethyl)pyridin-1(2H)-yl)-3-methylbutanoate (2.6 g, 7.1 mmol) was treated with LiOH—H₂O (1.47 g, 35 mmol) in EtOH (15 mL) and water (3 mL) at room temperature for 2 h. The reaction mixture was neutralized with 2 N HCl, concentrated in vacuo and the residue was purified by reverse phase HPLC on a C18/40 g column (A: water 10 mM NH₄HCO₃, B: MeOH, 0~100%) to provide 2-(5-(2-(dimethylamino)ethyl)-2-oxo-4-(trifluoromethyl)pyridin-1 (2H)-yl)-3-methylbutanoic acid as a yellow oil (1.8 g). Yield 75% (ESI 335.2 (M+H)⁺).

Preparation of 3-cyclopropyl-2-(5-(2-(dimethylamino)ethyl)-2-oxo-4-(trifluoromethyl)pyridin-1(2H)-yl)propanoic acid Step 1: ethyl 2-(5-bromo-2-oxo-4-(trifluoromethyl)pyridin-1(2H)-yl)-3-cyclopropylpropanoate

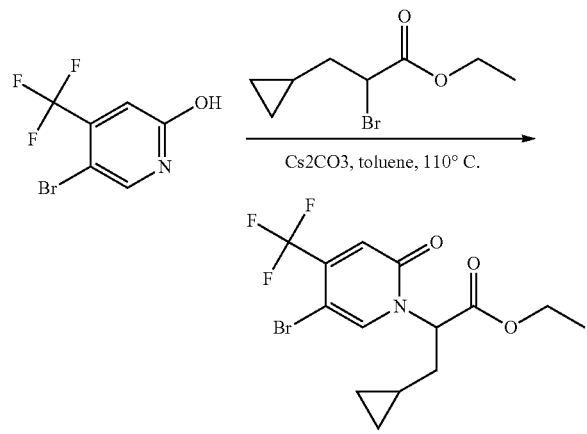

A mixture of 5-bromo-4-(trifluoromethyl)pyridin-2-ol (2.5 g, 10.33 mmol), Cs₂CO₃ (6.7 g, 20.66 mmol) and ethyl 2-bromo-3-cyclopropylpropanoate (3.4 g, 15.50 mmol) in toluene (100 mL) was stirred at 110° C. for 16 h. LCMS showed the reaction was completed. The mixture was filtered and washed with EtOAc (20 mL). The filtrate was concentrated in vacuo and the residue was purified by silica gel column (pet ether: EtOAc 10:1) to provide ethyl 2-(5-bromo-2-oxo-4-(trifluoromethyl)pyridin-1(2H)-yl)-3-cyclopropylpropanoate as a colorless oil (1.5 g). Yield 38% (ESI 384.0 (M+H)⁺).

Step 2: ethyl 2-(5-allyl-2-oxo-4-(trifluoromethyl)pyridin-1(2)-yl)-3-cyclopropylpropanoate

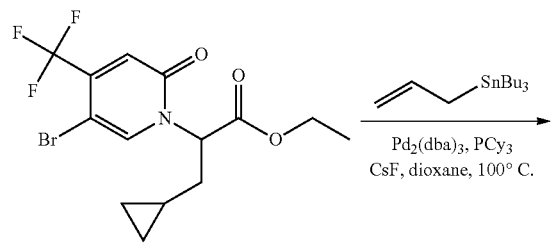

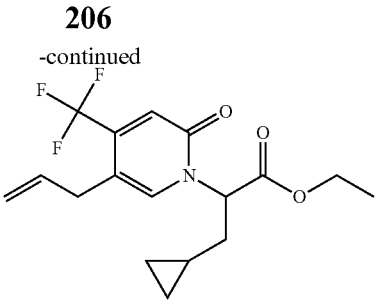

To a solution of ethyl 2-(5-bromo-2-oxo-4-(trifluoromethyl)pyridin-1(2)-yl)-3-cyclopropylpropanoate (2.3 g, 6.02 mmol) and allyltributylstannane (2.4 g, 7.22 mmol) under nitrogen atmosphere in dioxane (50 mL) was added Pd₂dba₃ (348 mg, 0.30 mmol), tricyclohexyl phosphine (168 mg, 0.60 mmol), CsF (1.8 g, 12.04 mmol) and stirred at 100° C. for 16 h. The mixture was cooled to room temperature. A saturation NH₄Cl solution (100 mL) and EtOAc (100 mL) was added to the mixture and the aqueous layer was extracted with EtOAc (100 mL×2). The combined organic phase was washed with brine (100 mL), dried over anhydrous Na₂SO₄, filtered and concentrated in vacuo. The residue was purified by silica gel column (pet ether: EtOAc 10:1) to provide ethyl 2-(5-allyl-2-oxo-4-(trifluoromethyl)pyridin-1(2H)-yl)-3-cyclopropylpropanoate as a colorless oil (1.5 g). Yield 72% (ESI 344.0 (M+H)⁺).

Step 3: ethyl 3-cyclopropyl-2-(2-oxo-5-(2-oxoethyl)-4-(trifluoromethyl)pyridin-1(2H)-yl)propanoate

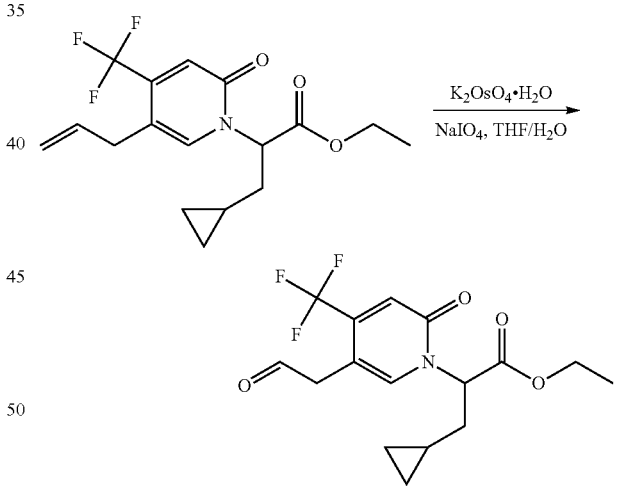

To a solution of ethyl 2-(5-allyl-2-oxo-4-(trifluoromethyl)pyridin-1(2)-yl)-3-cyclopropylpropanoate (1.5 g, 4.37 mmol) in THF/H₂O (20 mL/20 mL) was added a solution of K₂OsO₄-2H₂O (16.0 mg, 0.0437 mmol) in H₂O (3 mL) and stirred at room temperature for 1 hour. A solution of NaIO₄ (1.8 g, 8.74 mmol) in H₂O (10 mL) was added dropwise and the mixture was stirred at room temperature for another hour. LCMS showed the reaction was completed. The reaction mixture was diluted with water (40 mL) and extracted with EtOAc (50 mL×3). The combined organic phase was dried over anhydrous Na₂SO₄, filtered and concentrated in vacuo to provide ethyl 3-cyclopropyl-2-(2-oxo-5-(2-oxoethyl)-4-(trifluoromethyl)pyridin-1(2H)-yl)propanoate as a brown oil used directly in the next reaction without further purification (1.5 g, crude). (ESI 346.1 (M+H)+).

Step 4: ethyl 3-cyclopropyl-2-(5-(2-(dimethylamino)ethyl)-2-oxo-4-(trifluoromethyl)pyridin-1(2H)-yl)propanoate

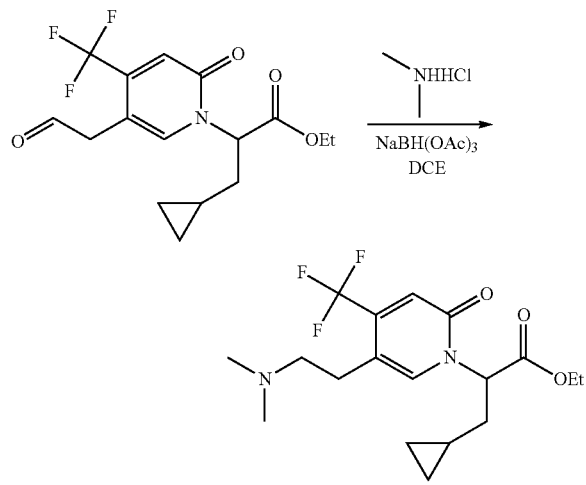

To a mixture of ethyl 3-cyclopropyl-2-(2-oxo-5-(2-oxoethyl)-4-(trifluoromethyl)pyridin-1(2)-yl)propanoate (1.5 g, 4.34 mmol) in DCE (20 mL) at 25° C. was added dimethylamine hydrochloride (708 mg, 8.68 mmol) and stirred for 1 hour. NaBH(OAc)₃ (2.8 g, 13.02 mmol) was added at 5° C. and stirred at 25° C. for 16 hours. The mixture was concentrated in vacuo and the residue was purified by silica gel column (DCM:MeOH 10:1) to give the desired ethyl 3-cyclopropyl-2-(5-(2-(dimethylamino)ethyl)-2-oxo-4-(trifluoromethyl)pyridin-1(2H)-yl)propanoate as a colorless oil (400 mg) Yield 25% (ESI 375.1 [M+H]+).

Step 5: 3-cyclopropyl-2-(5-(2-(dimethylamino)ethyl)-2-oxo-4-(trifluoromethyl)pyridin-1(2H)-yl)propanoic acid

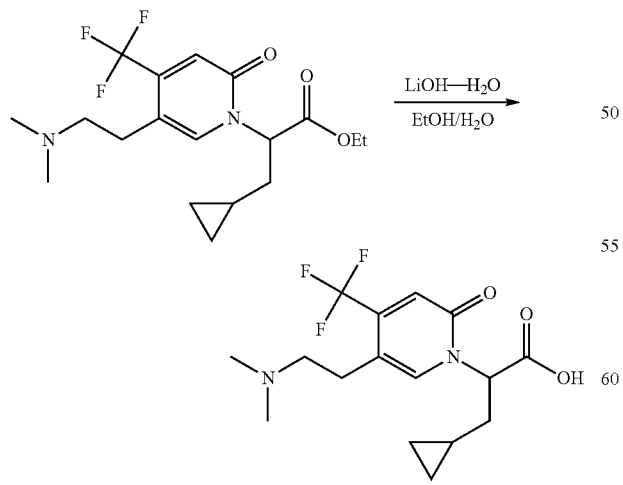

Ethyl 3-cyclopropyl-2-(5-(2-(dimethylamino)ethyl)-2-oxo-4-(trifluoromethyl)pyridin-1(2H)-yl)propanoate (400 mg, 1.07 mmol) was treated with LiOH—H₂O (224 mg, 5.35 mmol) in EtOH (5 mL) and water (2 mL) and the mixture was stirred at room temperature for 30 minutes. The mixture was acidified with 1N HCl to pH 5~6 and purified by reverse phase HPLC on a C18/120 g column (A: water/10 mM NH₄HCO₃, B: MeOH, 0~100%) to provide 3-cyclopropyl-2-(5-(2-(dimethylamino)ethyl)-2-oxo-4-(trifluoromethyl)pyridin-1(2H)-yl)propanoic acid as a white solid (150 mg). Yield 41% (ESI 347.0 (M+H)+).

Preparation of 2-(5-(2-(dimethylamino)ethyl)-2-oxo-4-(trifluoromethyl)pyridin-1(2H)-yl)-5-methylhexanoic acid Step 1: ethyl 2-(5-bromo-2-oxo-4-(trifluoromethyl)pyridin-1(2H)-yl)-5-methylhexanoate

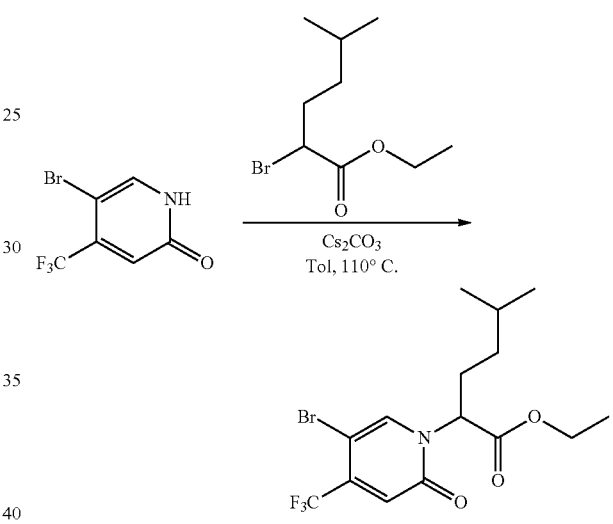

A mixture of 5-bromo-2-hydroxy-4-(trifluoromethyl)pyridine (6.00 g, 24.79 mmol), ethyl 2-bromo-5-methylhexanoate (8.82 g, 37.19 mmol) and Cs₂CO₃ (24.24 g, 74.38 mmol) in anhydrous toluene (120 mL) was heated at 110° C. under nitrogen atmosphere for 3 h. The solvent was removed in vacuo and the residue was purified by silica gel column (petroleum ether: EtOAc 23:1) to provide ethyl 2-(5-bromo-2-oxo-4-(trifluoromethyl)pyridin-1(2H)-yl)-5-methylhexanoate as brown oil (5.9 g). Yield 59%. (ESI 400.0 (M+H)+, ESI 422.0 (M+Na)*).

Step 2: (E)-ethyl 2-(5-(2-ethoxyvinyl)-2-oxo-4-(trifluoromethyl)pyridin-1(2H)-yl)-5-methylhexanoate

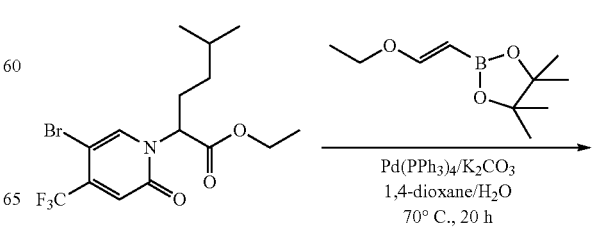

-continued

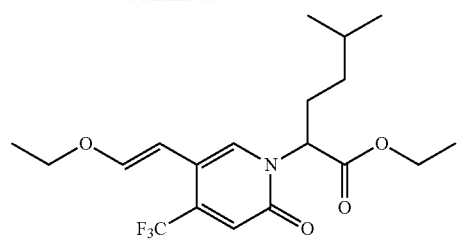

A mixture of ethyl 2-(5-bromo-2-oxo-4-(trifluoromethyl)pyridin-1(2H)-yl)-5-methylhexanoate (5.56 g, 13.97 mmol), (E)-1-ethoxyethene-2-boronic acid pinacol ester (4.15 g, 20.95 mmol), tetrakis(triphenylphosphine)palladium(0) (2.42 g, 2.10 mmol) and $K_2CO_3$ (5.79 g, 41.91 mmol) in co-solvent of anhydrous 1,4-dioxane (140 mL) and water (14 mL) was heated at 70° C. under nitrogen atmosphere for 20 h. The solvent was removed in vacuo and the residue was purified by silica gel column (petroleum ether: EtOAc 10:1) to provide (E)-ethyl 2-(5-(2-ethoxyvinyl)-2-oxo-4-(trifluoromethyl)pyridin-1(2H)-yl)-5-methylhexanoate as brown oil (3.4 g). Yield 63%. (ESI 390.1 $(M+H)^+$).

Step 3: ethyl 5-methyl-2-(2-oxo-5-(2-oxoethyl)-4-(trifluoromethyl)pyridin-1(2H)-yl)hexanoate

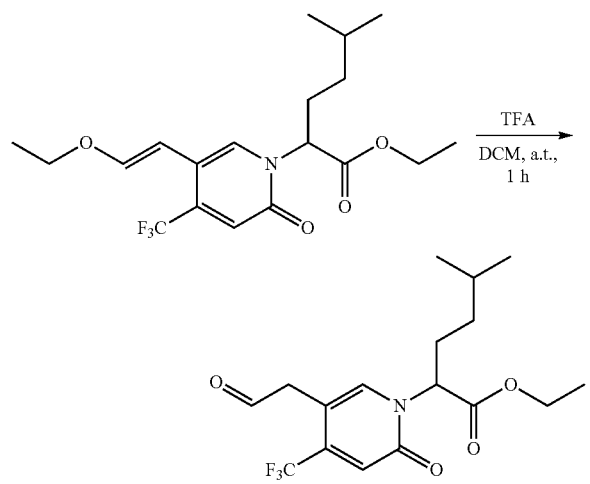

Trifluoroacetic acid (32 mL, 430.80 mmol) was added to a stirring solution of (E)-ethyl 2-(5-(2-ethoxyvinyl)-2-oxo-4-(trifluoromethyl)pyridin-1(2H)-yl)-5-methylhexanoate (5.2 g, 13.35 mmol) in DCM (64 mL) and the reaction mixture was stirred at room temperature for 1 h. The solvent was removed in vacuo to provide ethyl 5-methyl-2-(2-oxo-5-(2-oxoethyl)-4-(trifluoromethyl)pyridin-1(2H)-yl)hexanoate as brown oil (5.2 g, crude). (ESI 362.1 $(M+H)^+$).

Step 4: ethyl 2-(5-(2-(dimethylamino)ethyl)-2-oxo-4-(trifluoromethyl)pyridin-1(2H)-yl)-5-methyl-hexanoate

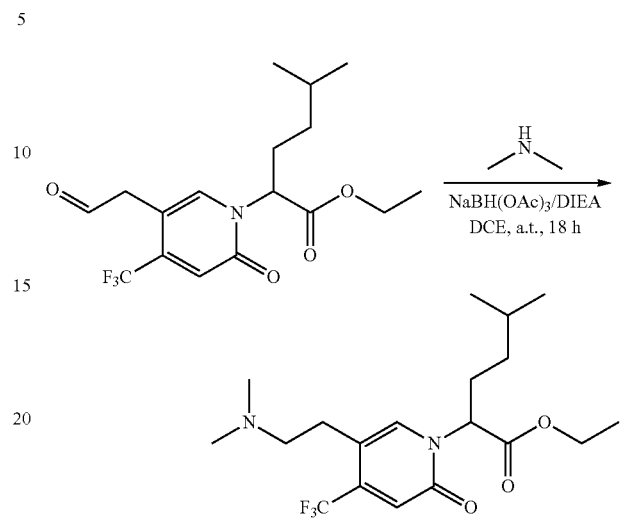

The mixture of ethyl 5-methyl-2-(2-oxo-5-(2-oxoethyl)-4-(trifluoromethyl)pyridin-1(2H)-yl)hexanoate (1.6 g, 4.45 mmol) and dimethylamine (60 mL, 2M in THF, 120 mmol) in 1,2-dichloroethane (43 mL) was stirred at ambient temperature for 1 h. Sodium triacetoxyborohydride (14.91 g, 70.34 mmol) was added in one portion and stirred at ambient temperature for 18 h. The solvent was removed in vacuo and the residue was purified by silica gel column (DCM:MeOH 3:1) to provide ethyl 2-(5-(2-(dimethylamino)ethyl)-2-oxo-4-(trifluoromethyl)pyridin-1(2H)-yl)-5-methylhexanoate as brown oil (1.2 g). Yield 72%. (ESI 391.1 $(M+H)^+$).

Step 5: 2-(5-(2-(dimethylamino)ethyl)-2-oxo-4-(trifluoromethyl)pyridin-1(2H)-yl)-5-methylhexanoic acid

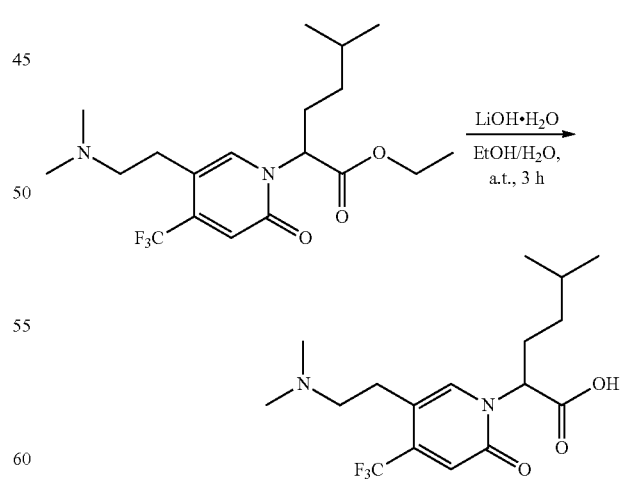

Ethyl 2-(5-(2-(dimethylamino)ethyl)-2-oxo-4-(trifluoromethyl)pyridin-1(2H)-yl)-5-methylhexanoate (925 mg, 2.37 mmol) was treated with LiOH monohydrate (298 mg, 7.11 mmol) in EtOH (10 mL) and $H_2O$ (0.7 mL) at room temperature for 3 h. The reaction mixture was acidified to pH 4~5 with 1N HCl. The solvent was removed in vacuo and the residue was purified by reverse phase HPLC on a C18/40 g column (A: water 10 mM NH₄HCO₃, B: MeOH, 0~80%) to provide 2-(5-(2-(dimethylamino)ethyl)-2-oxo-4-(trifluoromethyl)pyridin-1(2H)-yl)-5-methylhexanoic acid as a yellow solid (617 mg). Yield 72% (ESI 363.1 (M+H)⁺).

Preparation of (3R)-2-(5-(2-(dimethylamino)ethyl)-2-oxo-4-(trifluoromethyl)pyridin-1(2H)-yl)-3-methylpentanoic acid Step 1: ethyl (3R)-2-bromo-3-methylpentanoate

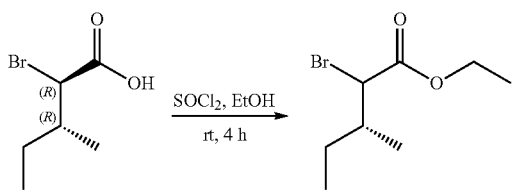

To a mixture of (2R,3R)-2-bromo-3-methylpentanoic acid (5 g, 25.6 mmol) in EtOH (50 mL) at 0° C. was added SOCl₂(6.1 g, 51.2 mmol). The mixture was stirred for 4 h at room temperature.

The solvent was removed in vacuo to provide ethyl (3R)-2-bromo-3-methylpentanoate as a yellow oil (5.3, crude). (ESI 223 (M+H)⁺).

Step 2: ethyl(3R)-2-(5-bromo-2-oxo-4-(trifluoromethyl)pyridin-1(2H)-yl)-3-methylpentanoate

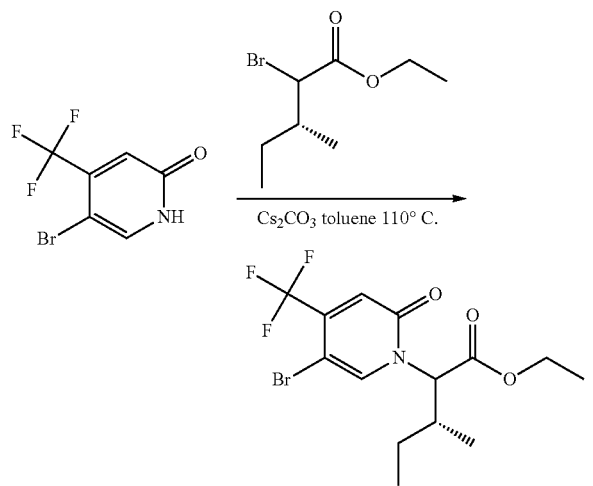

To a stirred solution of 5-bromo-4-(trifluoromethyl)pyridin-2(1H)-one (3.50 g, 14.52 mmol) and ethyl (3R)-2-bromo-3-methylpentanoate (3.54 g, 15.97 mmol) in toluene (50 mL) was added Cs₂CO₃ (5.38 g, 16.58 mmol) and stirred at 110° C. for 2 hours. The reaction was cooled to room temperature, filtered and washed with 20 mL of EtOAc. The filtrate was concentrated in vacuo and the residue was purified by silica gel column (pet ether: EtOAc 20:1) to provide ethyl (3R)-2-(5-bromo-2-oxo-4-(trifluoromethyl)pyridin-1(2H)-yl)-3-methylpentanoate as a white solid (2.2 g). Yield 40% (ESI 384.0 (M+H)⁺).

Step 3: ethyl (3R)-2-(5-allyl-2-oxo-4-(trifluoromethyl)pyridin-1(2H)-yl)-3-methylpentanoate

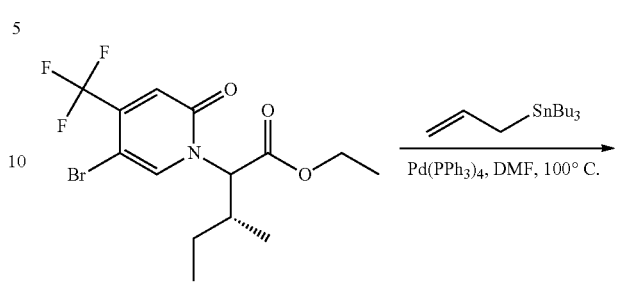

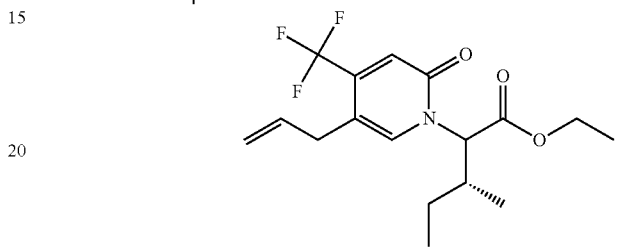

To a solution of ethyl (3R)-2-(5-bromo-2-oxo-4-(trifluoromethyl)pyridin-1(2H)-yl)-3-methylpentanoate (2.2 g, 5.74 mmol) and allyltributylstannane (2.28 g, 6.89 mmol) under N₂ atmosphere in DMF (15 mL) was added Pd(PPh₃)₄ (0.67 g, 0.58 mmol) and stirred at 100° C. for 16 hours. The reaction mixture was concentrated in vacuo. The residue was diluted with 50 mL of EtOAc, poured into 20% aq. KF (100 mL), stirred at 20° C. for 1 hour and then filtered and washed with 100 mL of EtOAc. The filtrate was extracted with EA (100 mL×3). The combined organic phase was washed with brine (200 mL), dried over anhydrous Na₂SO₄, filtered and concentrated in vacuo and the residue was purified by silica gel column (pet ether: EtOAc 20:1) to provide ethyl (3R)-2-(5-allyl-2-oxo-4-(trifluoromethyl)pyridin-1(2H)-yl)-3-methylpentanoate as a colorless oil (1.51 g). Yield 76% (ESI 346(M+H)⁺).

Step 4: ethyl (3R)-3-methyl-2-(2-oxo-5-(2-oxoethyl)-4-(trifluoromethyl)pyridin-1(2H)-yl)pentanoate

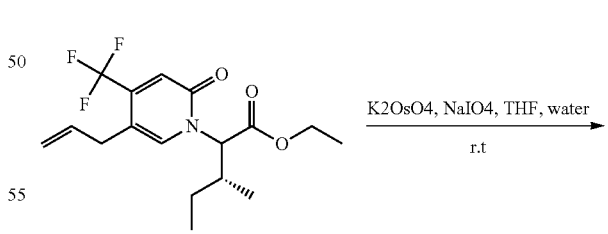

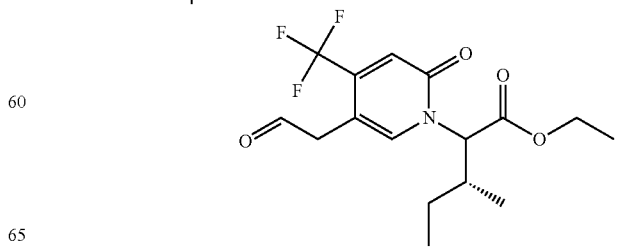

To a mixture of ethyl (3R)-2-(5-allyl-2-oxo-4-(trifluoromethyl)pyridin-1(2H)-yl)-3-methylpentanoate (1.51 g, 4.36 mmol) in THF (15 mL) and H₂O (10 mL) at 0° C. was added K₂OsO₄·2H₂O (130 mg, 0.345 mmol) and stirred at 0° C. for 5 mins. Then a solution of NaIO₄ (2.80 g, 13.08 mmol) in H₂O (5 mL) was added dropwise and stirred at 0° C. for 2 hours and then at 25° C. for 2 hours. The mixture was quenched with a saturated Na₂S₂O₃ solution (50 mL) and the mixture was extracted with EA (60 mL×3). The combined organics were washed with brine (30 mL×3), dried over anhydrous Na₂SO₄, filtered and concentrated in vacuo to give the desired crude product ethyl (3R)-3-methyl-2-(2-oxo-5-(2-oxoethyl)-4-(trifluoromethyl)pyridin-1(2H)-yl)pentanoate (1.5 g, crude) as yellow oil. (ESI 348(M+H)⁺).

Step 5: ethyl (3R)-2-(5-(2-(dimethylamino)ethyl)-2-oxo-4-(trifluoromethyl)pyridin-1(2H)-yl)-3-methylpentanoate

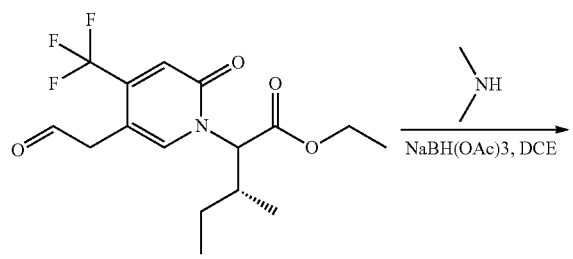

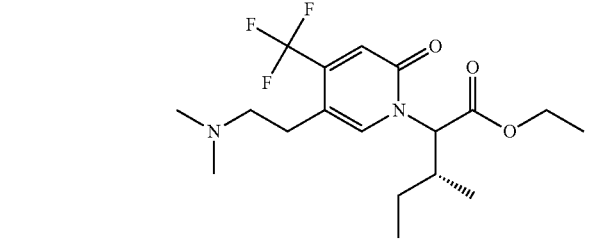

To a mixture of ethyl (3R)-3-methyl-2-(2-oxo-5-(2-oxoethyl)-4-(trifluoromethyl)pyridin-1(2H)-yl)pentanoate (1 g, 2.87 mmol) in DCE (10 mL) at 25° C. was added dimethylamine hydrochloride (700 mg, 8.62 mmol) and stirred at 25° C. for 10 min. Then NaBH(OAc)₃ (1.22 g, 5.74 mmol) was added and stirred at 25° C. for 2 hours. The mixture was concentrated in vacuo and the residue was purified by silica gel column (DCM:MeOH 10:1) to provide ethyl (3R)-2-(5-(2-(dimethylamino)ethyl)-2-oxo-4-(trifluoromethyl)pyridin-1(2H)-yl)-3-methylpentanoate as a yellow oil (550 mg). Yield 51% (ESI 377 (M+H)⁺).

Step 6: (3R)-2-(5-(2-(dimethylamino)ethyl)-2-oxo-4-(trifluoromethyl)pyridin-1(2H)-yl)-3-methylpentanoic acid

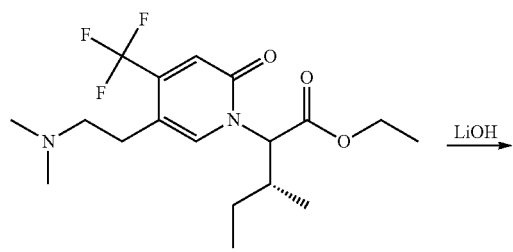

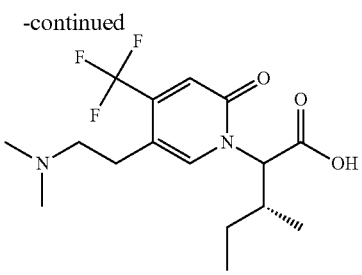

Ethyl(3R)-2-(5-(2-(dimethylamino)ethyl)-2-oxo-4-(trifluoromethyl)pyridin-1(2H)-yl)-3-methylpentanoate (550 mg, 1.46 mmol) was treated with LiOH—H₂O (240 mg, 5.84 mmol) in MeOH (5 mL) and water (1 mL) at room temperature for 1 hour. The MeOH was removed and the aqueous material acidified with 1N HCl to pH 4. The mixture was purified by reverse phase HPLC on a C18/40 g column (A: water 10 mM NH₄HCO₃, B: MeOH, 0~100%) to provide (3R)-2-(5-(2-(dimethylamino)ethyl)-2-oxo-4-(trifluoromethyl)pyridin-1(2H)-yl)-3-methylpentanoic acid as a yellow oil (400 mg). Yield 78.5% (ESI 349 (M+H)⁺).

Preparation of 2-(5-(2-(dimethylamino)ethyl)-2-oxo-4-(trifluoromethyl)pyridin-1(2H)-yl)pentanoic acid Step 1: ethyl 2-(5-bromo-2-oxo-4-(trifluoromethyl)pyridin-1(2H)-yl)pentanoate

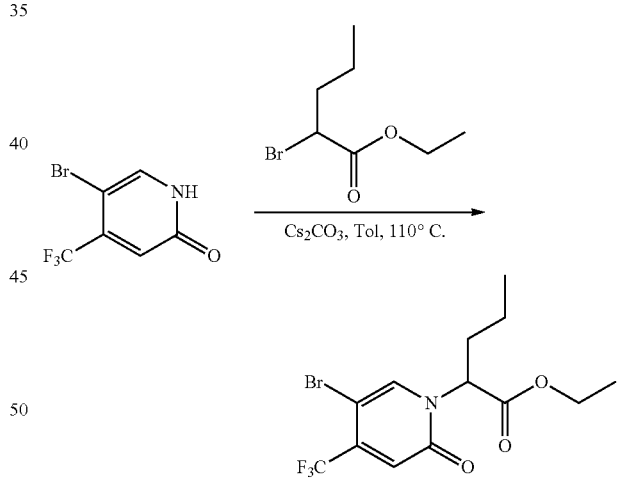

To a stirred solution of 5-bromo-4-(trifluoromethyl)pyridin-2(1H)-one (2 g, 8.29 mmol) and methyl 2-bromo-4-methylpentanoate (2.24 g, 10.78 mmol) in toluene (40 mL) was added Cs₂CO₃ (5.38 g, 16.58 mmol) portion wise and stirred at 110° C. for 2 hours. The reaction mixture was diluted with 50 mL of EtOAc, filtered and washed with 20 mL of EtOAc. The filtrate was concentrated in vacuo and the residue was purified by silica gel column (pet ether: EtOAc 20:1) to provide ethyl 2-(5-bromo-2-oxo-4-(trifluoromethyl)pyridin-1(2H)-yl)pentanoate as a white solid (2.3 g). Yield 65% (ESI 372.0 (M+H)⁺).

Step 2: ethyl (E)-2-(5-(2-ethoxyvinyl)-2-oxo-4-(trifluoromethyl)pyridin-1(2H)-yl)pentanoate

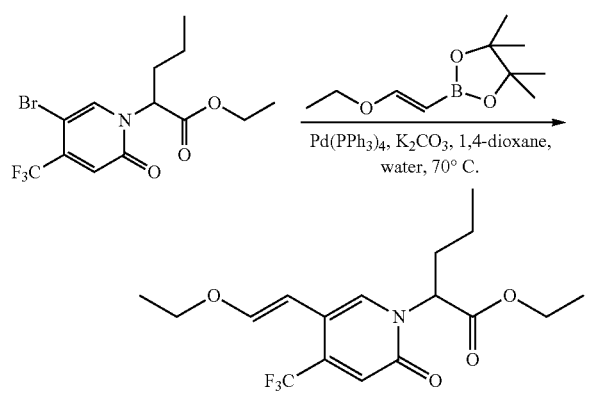

A mixture of ethyl 2-(5-bromo-2-oxo-4-(trifluoromethyl)pyridin-1(2H)-yl)pentanoate (2.2 g, 5.96 mmol), (E)-2-(2-ethoxyvinyl)-4,4,5,5-tetramethyl-1,3,2-dioxaborolane (1.35 g, 6.85 mmol), Pd(PPh$_3$)$_4$ (206 mg, 0.17 mmol) and K$_2$CO$_3$ (1.64 g, 11.92 mmol) in 1,4-dioxane (30 mL) and water (3 mL) was stirred at 70° C. under N$_2$ for 20 h. The reaction mixture was poured into 100 mL of water, extracted with EA (50 mL×3). The combined organic phase was washed with brine (150 mL), dried over anhydrous Na$_2$SO$_4$, filtered and concentrated in vacuo, purified by silica gel column (pet ether: EtOAc 10:1) to provide ethyl (E)-2-(5-(2-ethoxyvinyl)-2-oxo-4-(trifluoromethyl)pyridin-1(2H)-yl)pentanoate as a white solid (1 g). Yield 46% (ESI 362.1 (M+H)$^+$).

Step 3: ethyl 2-(2-oxo-5-(2-oxoethyl)-4-(trifluoromethyl)pyridin-1(2H)-yl)pentanoate

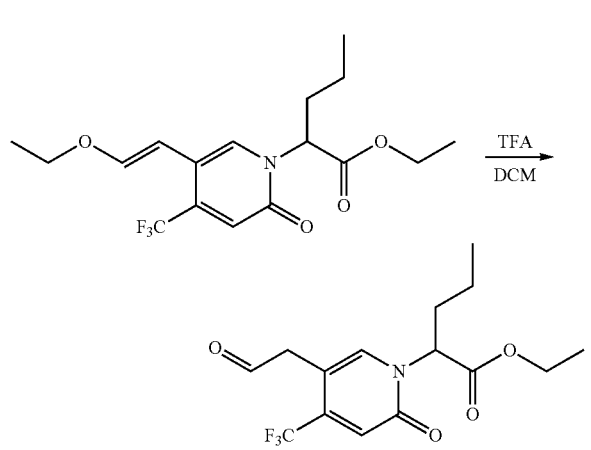

To a mixture of (E)-2-(5-(2-ethoxyvinyl)-2-oxo-4-(trifluoromethyl)pyridin-1(2H)-yl)pentanoate (920 mg, 2.55 mmol) in DCM (20 mL) was added TFA (10 mL). The mixture was stirred at room temperature for 4 hours. LCMS showed that the reaction was completed. The mixture was concentrated in vacuo to give crude product ethyl 2-(2-oxo-5-(2-oxoethyl)-4-(trifluoromethyl)pyridin-1(2H)-yl)pentanoate as a yellow oil (800 mg) used directly in the next reaction without further purification. Yield 94% (ESI 334.1 [M+H]$^+$).

Step 4: ethyl 2-(5-(2-(dimethylamino)ethyl)-2-oxo-4-(trifluoromethyl)pyridin-1(2H)-yl)pentanoate

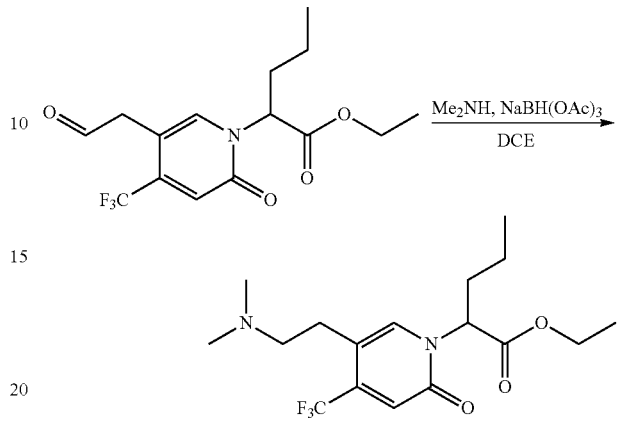

To a mixture of ethyl 2-(2-oxo-5-(2-oxoethyl)-4-(trifluoromethyl)pyridin-1(2H)-yl)pentanoate (750 mg, 2.25 mmol) in DCE (10 mL) at 25° C. was added dimethylamine (2M in THF, 1.7 mL, 3.4 mmol) and stirred at 25° C. for 10 min. NaBH(OAc)$_3$ (950 mg, 4.5 mmol) was added and stirred at 25° C. for 2 hours. The mixture was concentrated in vacuo and the residue was purified by silica gel column (DCM: MeOH 10:1) to provide ethyl 2-(5-(2-(dimethylamino)ethyl)-2-oxo-4-(trifluoromethyl)pyridin-1(2H)-yl)pentanoate as a yellow oil (630 mg). Yield 77% (ESI 363.1 (M+H)$^+$).

Step 5: 2-(5-(2-(dimethylamino)ethyl)-2-oxo-4-(trifluoromethyl)pyridin-1(2H)-yl)pentanoic acid

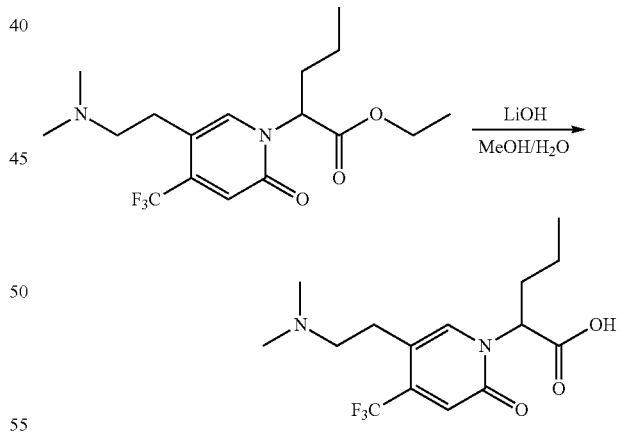

Ethyl 2-(5-(2-(dimethylamino)ethyl)-2-oxo-4-(trifluoromethyl)pyridin-1(2H)-yl)pentanoate (630 g, 1.74 mmol) was treated with LiOH—H$_2$O (142 mg, 3.48 mmol) in MeOH (6 mL) and water (3 mL) at 20° C. for 1 hour. The MeOH was removed and the remaining aqueous acidified with 1N HCl to pH=4. The mixture was purified by reverse phase HPLC on a C18/40 g column (A: water 10 mM NH$_4$HCO$_3$, B: MeOH, 0~100%) to provide 2-(5-(2-(dimethylamino)ethyl)-2-oxo-4-(trifluoromethyl)pyridin-1(2H)-yl)pentanoic acid as a yellow oil (430 mg). Yield 73% (ESI 335.1 (M+H)$^+$).

217

Preparation of 2-(5-(2-(3-methoxyazetidin-1-yl)ethyl)-2-oxo-4-(trifluoromethyl)pyridin-1(2H)-yl)-4-methylpentanoic acid Step 1: 2 (E)-ethyl 2-(5-(2-ethoxyvinyl)-2-oxo-4-(trifluoromethyl)pyridin-1(2H)-yl)-4-_methylpentanoate

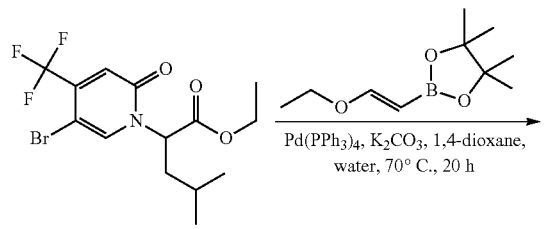

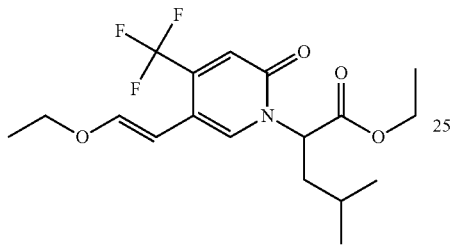

To a solution of ethyl 2-(5-bromo-2-oxo-4-(trifluoromethyl)pyridin-1(2H)-yl)-4-methylpentanoate (12 g, 31 mmol) in 1,4-dioxane (150 mL) and water (15 mL) was added (E)-2-(2-ethoxyvinyl)-4,4,5,5-tetramethyl-1,3,2-dioxaborolane (9.3 g, 45.5 mmol), $K_2CO_3$ (12.8 g, 93 mmol) and $Pd(PPh_3)_4$ (1.8 g, 1.55 mmol). The reaction mixture was stirred at 70° C. for 20 h. The reaction mixture was cooled to room temperature, diluted with EtOAc (300 mL) and washed with brine, dried over $Na_2SO_4$, concentrated in vacuo. The residue was purified by silica gel column (pet. Ether: EtOAc 1:2) to provide (E)-ethyl 2-(5-(2-ethoxyvinyl)-2-oxo-4-(trifluoromethyl)pyridin-1(2H)-yl)-4-methylpentanoate as a yellow oil (9 g). Yield 76% (ESI 376.1 (M+H)$^+$).

Step 2: ethyl 4-methyl-2-(2-oxo-5-(2-oxoethyl)-4-(trifluoromethyl)pyridin-1(2H)-yl)pentanoate

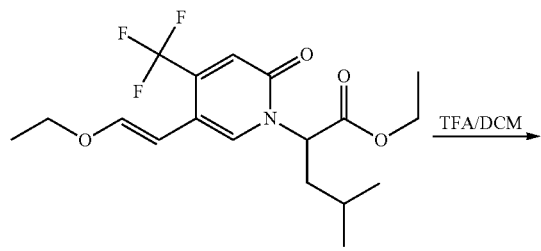

218

-continued

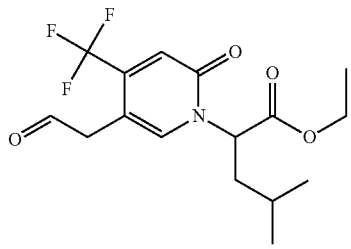

A mixture of (E)-ethyl 2-(5-(2-ethoxyvinyl)-2-oxo-4-(trifluoromethyl)pyridin-1(2H)-yl)-4-methylpentanoate (9 g, 24 mmol) in TFA (25 mL) and DCM (25 mL) was stirred at room temperature for 16 h. The reaction mixture was concentrated in vacuo to give crude ethyl 4-methyl-2-(2-oxo-5-(2-oxoethyl)-4-(trifluoromethyl)pyridin-1(2H)-yl) pentanoate as a yellow oil (9 g). Yield 100% (crude) (ESI 348.1 (M+H)$^+$).

Step 3: ethyl 2-(5-(2-(3-methoxyazetidin-1-yl)ethyl)-2-oxo-4-(trifluoromethyl)pyridin-1(2H)-yl)-4-methylpentanoate

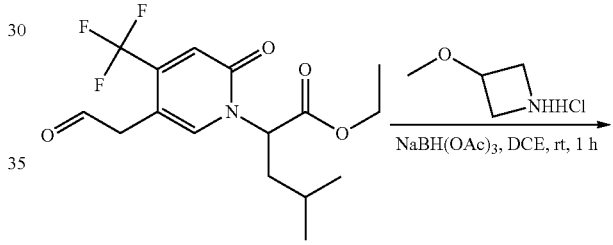

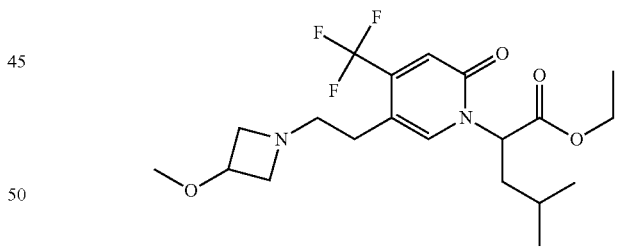

To a solution of ethyl 4-methyl-2-(2-oxo-5-(2-oxoethyl)-4-(trifluoromethyl)pyridin-1(2H)-yl)pentanoate (10 g crude, 24 mmol) in DCE (100 mL) was added 3-methoxyazetidine hydrochloride (5.9 g, 48 mmol) and stirred at room temperature for 20 min. $NaBH(OAc)_3$ (10.1 g, 48 mmol) was added and stirred at room temperature for 1 h. The reaction was quenched with MeOH (30 mL) and filtered. The filtrate was concentrated in vacuo and the residue was purified by reverse phase HPLC on a C18/120 g column (A: water 10 mM $NH_4HCO_3$, B: MeOH, 0~100%) to provide ethyl 2-(5-(2-(3-methoxyazetidin-1-yl)ethyl)-2-oxo-4-(trifluoromethyl)pyridin-1(2H)-yl)-4-methylpentanoate as a yellow oil (8 g). Yield 79% (ESI 419.2 (M+H)$^+$).

Step 4: 2-(5-(2-(3-methoxyazetidin-1-yl)ethyl)-2-oxo-4-(trifluoromethyl)pyridin-1(2H)-yl)-4-methylpentanoic acid

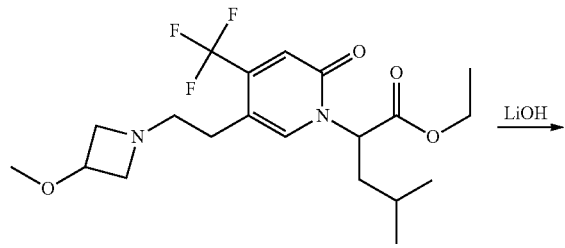

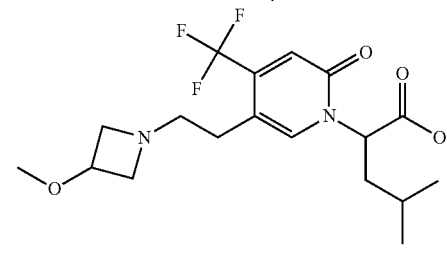

Ethyl 2-(5-(2-(3-methoxyazetidin-1-yl)ethyl)-2-oxo-4-(trifluoromethyl)pyridin-1(2H)-yl)-4-methylpentanoate (8 g, 19 mmol) was treated with LiOH—H$_2$O (2.4 g, 57 mmol) in EtOH (60 mL) and water (12 mL) at room temperature for 2 h. The reaction mixture was neutralized by 2 N HCl and concentrated in vacuo. The residue was purified by reverse phase HPLC on a C18/120 g column (A: water 10 mM NH$_4$HCO$_3$, B: MeOH, 0~100%) to provide 2-(5-(2-(3-methoxyazetidin-1-yl)ethyl)-2-oxo-4-(trifluoromethyl)pyridin-1(2H)-yl)-4-methylpentanoic acid as a yellow solid (6 g). Yield 80% (ESI 391.1 (M+H)$^+$).

Preparation of 2-(5-(2-(dimethylamino)ethyl)-3-methyl-2-oxopyridin-1(2H)-yl)-4-methylpentanoic acid

Step 1: ethyl 2-(5-bromo-3-methyl-2-oxopyridin-1(2H)-yl)-4-methylpentanoate

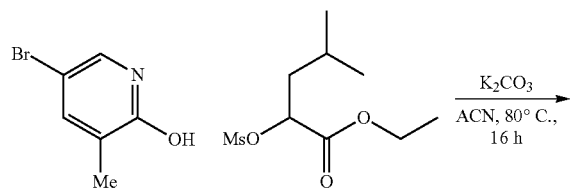

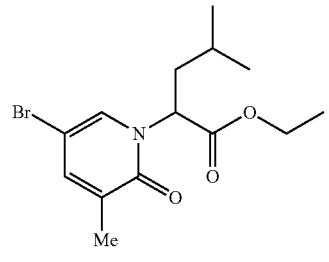

A mixture of 5-((dimethylamino)methyl)pyridin-2(1H)-one (500 mg, 3.28 mmol), K$_2$CO$_3$ (1.36 g, 9.86 mmol) and ethyl 4-methyl-2-(methylsulfonyloxy)pentanoate (1.17 g, 4.93 mmol) in CH$_3$CN (20 mL) was stirred at 80° C. overnight. The solvent was removed in vacuo and the residue was purified by silica gel column (pet ether: EtOAc 1:2) to provide ethyl 2-(5-((dimethylamino)methyl)-2-oxopyridin-1(2H)-yl)-4-methylpentanoate as a yellow oil (300 mg). Yield 31% (ESI 330 (M+H)$^+$).

Step 2: ethyl 2-(5-allyl-3-methyl-2-oxopyridin-1(2H)-yl)-4-methylpentanoate

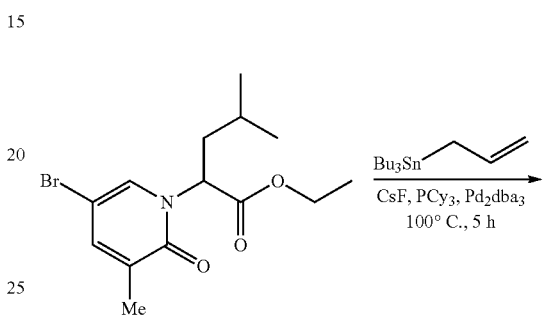

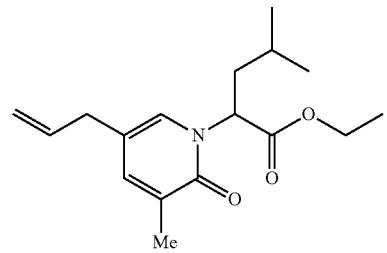

To a solution of ethyl 2-(5-bromo-3-methyl-2-oxopyridin-1(2H)-yl)-4-methylpentanoate (2.5 g, 7.57 mmol) and allyltributylstannane (2.5 g, 7.57 mmol) under N$_2$ atmosphere in dioxane (25 mL) was added Pd$_2$(dba)$_3$ (0.3 g, 0.38 mmol) and CsF (2.3 g, 15.1 mmol) and tricyclohexyl phosphine (212.0 mg, 0.76 mmol) and stirred at 100° C. for 5 hours. The mixture was cooled to room temperature, filtered and washed with EtOAc. The filtrate was concentrated in vacuo and the residue was purified by silica gel column (pet ether: EtOAc 20:1) to provide ethyl 2-(5-allyl-3-methyl-2-oxopyridin-1(2H)-yl)-4-methylpentanoate as a colorless oil (1.61 g). Yield 73% (ESI 292 (M+H)$^+$).

Step 3: ethyl 4-methyl-2-(3-methyl-2-oxo-5-(2-oxoethyl)pyridin-1(2H)-yl)pentanoate

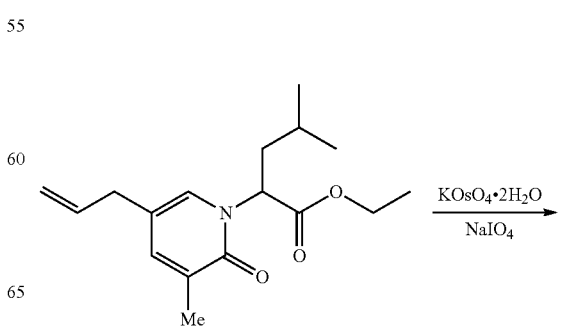

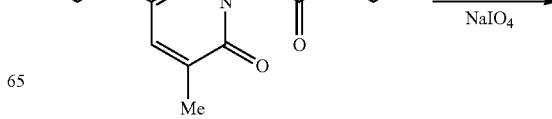

-continued

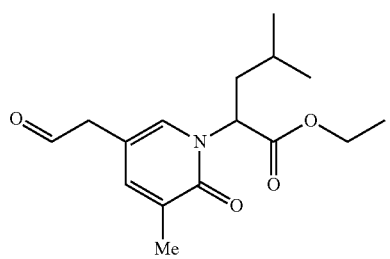

To a solution of ethyl 2-(5-allyl-3-methyl-2-oxopyridin-1(2H)-yl)-4-methylpentanoate (1.61 g, 5.53 mmol) in THF/H$_2$O (24 mL/12 mL) was added a solution of K$_2$OsO$_4$·2H$_2$O (21 mg, 0.058 mmol) in H$_2$O (4 mL) and stirred at room temperature for 1 h. A solution of NaIO$_4$ (2.37 g, 11.1 mmol) in H$_2$O (20 mL) was added and stirred at room temperature for 2 h. LCMS showed the reaction was completed. The reaction mixture was diluted with 100 mL of water and extracted with EtOAc (100 mL×3). The combined organic phase was dried over anhydrous Na$_2$SO$_4$, filtered and concentrated in vacuo to give the crude product ethyl 4-methyl-2-(3-methyl-2-oxo-5-(2-oxoethyl)pyridin-1(2H)-yl)pentanoate as a yellow oil (1.6 g, crude) used directly in the next reaction. (ESI 294.1 (M+H)$^+$).

Step 4: ethyl 2-(5-(2-(dimethylamino)ethyl)-3-methyl-2-oxopyridin-1(2H)-yl)-4-methylpentanoate

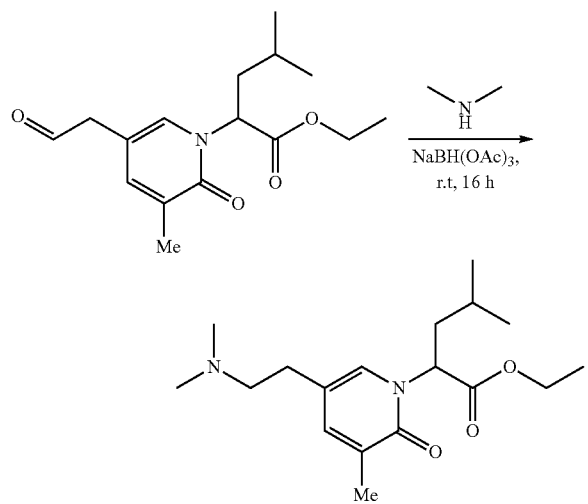

A mixture of ethyl 4-methyl-2-(3-methyl-2-oxo-5-(2-oxoethyl)pyridin-1(2H)-yl)pentanoate (2 g, 16.2 mmol), dimethylamine (2M in THF) (41 mL) in DCE (10 mL) was stirred at room temperature for 30 mins. Then NaBH(OAc)$_3$ (5.2 g, 24.39 mmol) was added and stirred at room temperature overnight. The reaction mixture was concentrated in vacuo and the residue was purified by reverse phase HPLC on a C18/40 g column (A: water 10 mM NH$_4$HCO$_3$, B: MeOH, 0~100%) to provide ethyl 2-(5-(2-(dimethylamino)ethyl)-3-methyl-2-oxopyridin-1(2H)-yl)-4-methylpentanoate as a yellow oil (1 g). Yield 46% (ESI 323.2 (M+H)$^+$).

Step 5: 2-(5-(2-(dimethylamino)ethyl)-3-methyl-2-oxopyridin-1(2H)-yl)-4-methylpentanoic acid

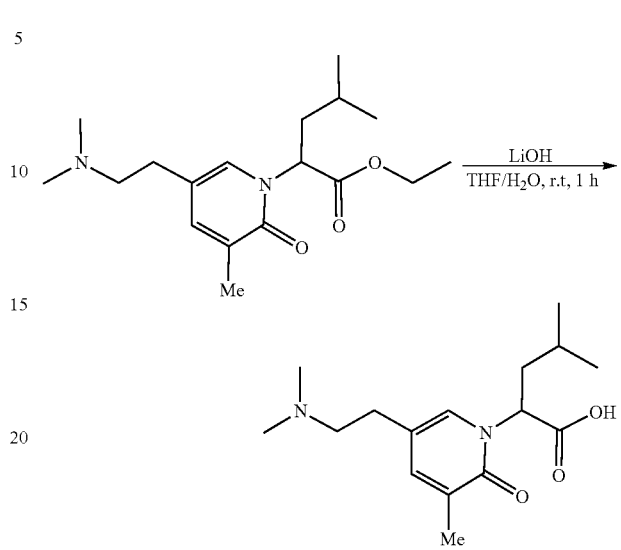

Ethyl 2-(5-((dimethylamino)methyl)-2-oxopyridin-1(2H)-yl)-4-methylpentanoate (606 mg, 1.88 mmol) was treated with LiOH—H$_2$O (395 mg, 9.4 mmol) in THF (8 mL) and water (3 mL) at room temperature for 2 hours. The reaction was acidified with 1N HCl to pH=3~4. The solvent was removed in vacuo and the residue was purified by preparatory-HPLC A (30-80% MeCN) to provide 2-(5-(2-(dimethylamino)ethyl)-3-methyl-2-oxopyridin-1(2H)-yl)-4-methylpentanoic acid as a white solid (480 mg). Yield 87% (ESI 295(M+H)$^+$).

Preparation of 2-(3-(difluoromethyl)-5-(2-(dimethylamino)ethyl)-2-oxopyridin-1(2H)-yl)-4-methylpentanoic acid Step 1:5-bromo-3-(difluoromethyl)-2-methoxypyridine

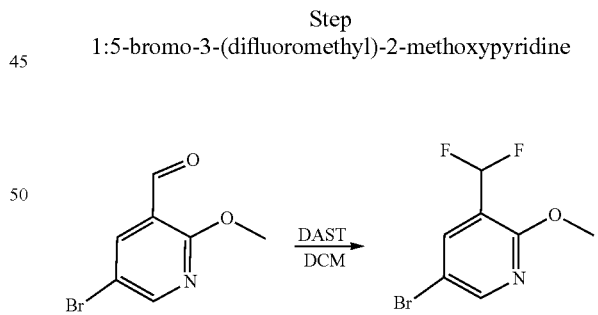

To a mixture of 5-bromo-2-methoxynicotinaldehyde (10.0 g, 46.3 mmol) in dry DCM (100 mL) under N$_2$ at 0° C. was added DAST (29.8 g, 185.2 mmol) and stirred at 0° C. for 2 days. The reaction was quenched with 100 mL of a saturated NaHCO$_3$ solution. The aqueous layer was extracted with DCM (100 mL×3). The combined organic layers were washed with NaHCO$_3$(sat, 100 mL) and brine (100 mL), dried over anhydrous Na$_2$SO$_4$, filtered and concentrated in vacuo to give 5-bromo-3-(difluoromethyl)-2-methoxypyridine as a yellow oil (11.0 g). Yield 100% (ESI 238.1 (M+H)$^+$).

Step 2: 5-bromo-3-(difluoromethyl)pyridin-2-ol

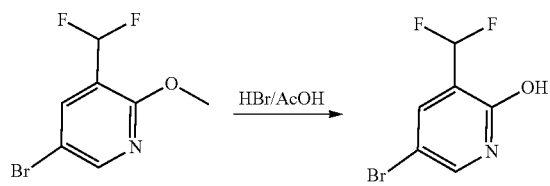

A mixture of 5-bromo-3-(difluoromethyl)-2-methoxypyridine (11.0 g, 46.2 mmol) in HBr (33% in acetic acid, 100 mL) was stirred at room temperature for 5 hours and then at 40° C. for 75 mins. The mixture was concentrated and poured into 100 mL of saturated NaHCO$_3$ solution and extracted with DCM. The combined organic layers dried over Na$_2$SO$_4$ and concentrated in vacuo to give 5-bromo-3-(difluoromethyl)pyridin-2-ol as a white solid (8.5 g) used without further purification. Yield 73.2% (ESI 226.0 (M+H)$^+$).

Step 3: ethyl 2-(5-bromo-3-(difluoromethyl)-2-oxopyridin-1(2H)-yl)-4

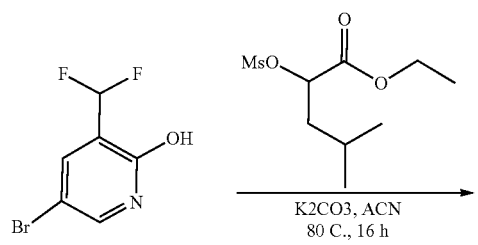

A mixture of 5-bromo-3-(difluoromethyl)pyridin-2-ol (7.0 g, 31.2 mmol), ethyl 4-methyl-2-((methylsulfonyl)oxy) pentanoate (14.0 g, 37.4 mmol) and K$_2$CO$_3$ (14.0 g, 62.5 mmol) in ACN (100 mL) was stirred at 80° C. overnight. The mixture was filtered and washed with ACN (20 mL). The filtrate was concentrated in vacuo and the residue purified by silica gel column (pet ether: EtOAc 4:1) to provide ethyl 2-(5-bromo-3-(difluoromethyl)-2-oxopyridin-1(2H)-yl)-4 as a white solid (10.0 g). Yield 80.3% (ESI 366.0 (M+H)$^+$).

Step 4: ethyl 2-(5-allyl-3-(difluoromethyl)-2-oxopyridin-1(2H)-yl)-4-methylpentanoate

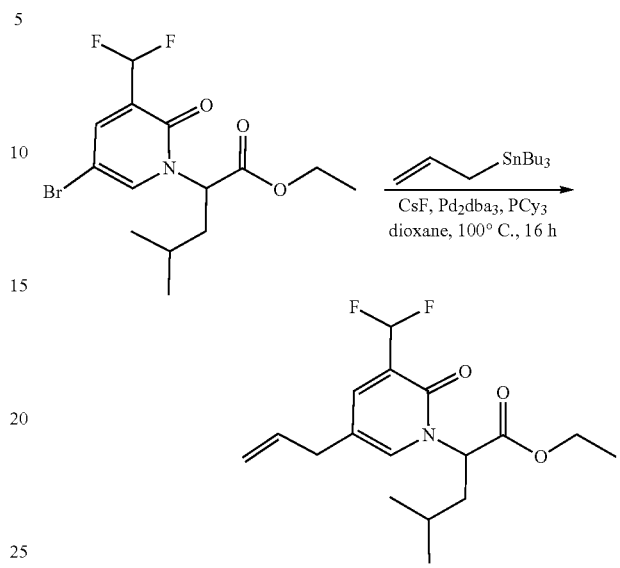

A mixture of ethyl 2-(5-bromo-3-(difluoromethyl)-2-oxopyridin-1(2H)-yl)-4 (6.0 g, 16.2 mmol), allyltributylstannane (7.0 g, 19.2 mmol), CsF (5.0 g, 32.4 mmol), Pd(dba)$_3$ (720 mg, 1.62 mmol) and PCy$_3$ (450 mg, 0.135 mmol) in dioxane (100 mL) was stirred at 100° C. overnight. The mixture was poured into water (200 mL), extracted with EtOAc (100 mL×3). The combined organic layers were washed with brine (200 mL), dried over Na$_2$SO$_4$, filtered and concentrated in vacuo. The residue was purified by silica gel column (pet ether: EtOAc 4:1) to give ethyl 2-(5-allyl-3-(difluoromethyl)-2-oxopyridin-1(2H)-yl)-4 as a white solid (3.0 g). Yield 71.6% (ESI 328.1 (M+H)$^+$).

Step 5: ethyl 2-(3-(difluoromethyl)-2-oxo-5-(2-oxoethyl)pyridin-1(2H)-yl)-4-methylpentanoate

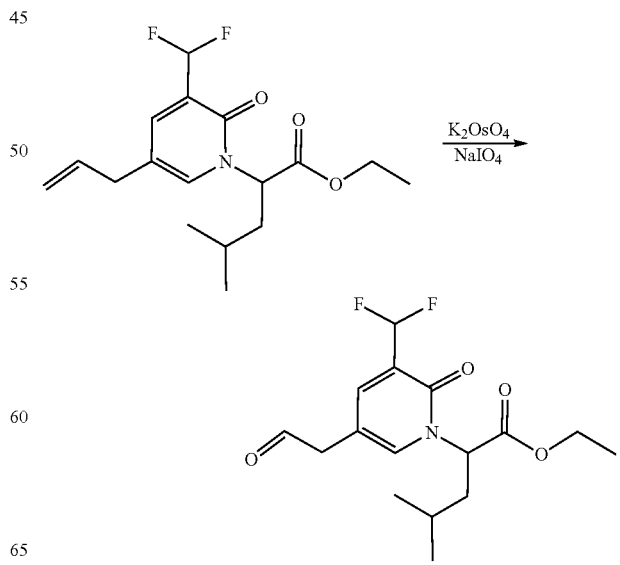

225

To a mixture of ethyl 2-(5-allyl-3-(difluoromethyl)-2-oxopyridin-1(2H)-yl)-4 (3.0 g, 9.1 mmol) in THF/H$_2$O (2/1, 100 mL) was added K$_2$OsO$_4$ (33.7 mg, 0.09 mmol) and stirred at room temperature for 1 hour. NaIO$_4$ (3.9, 18.3 mmol) was added and the mixture was stirred for 2 hours. The mixture was poured into water (200 mL) and extracted with EtOAc (100 mL×3). The combined organic layers were washed brine (200 mL) and dried over Na$_2$SO$_4$, filtered and concentrated in vacuo to give ethyl 2-(3-(difluoromethyl)-2-oxo-5-(2-oxoethyl)pyridin-1(2H)-yl)-4-methylpentanoate as a yellow oil (3.0 g, crude) used without further purification. (ESI 330.1 (M+H)$^+$).

Step 6: ethyl 2-(3-(difluoromethyl)-5-(2-(dimethylamino)ethyl)-2-oxopyridin-1(2H)-yl)-4-methylpentanoate

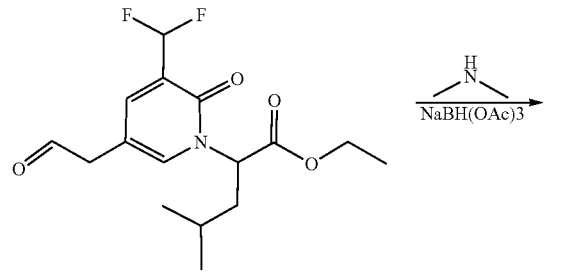

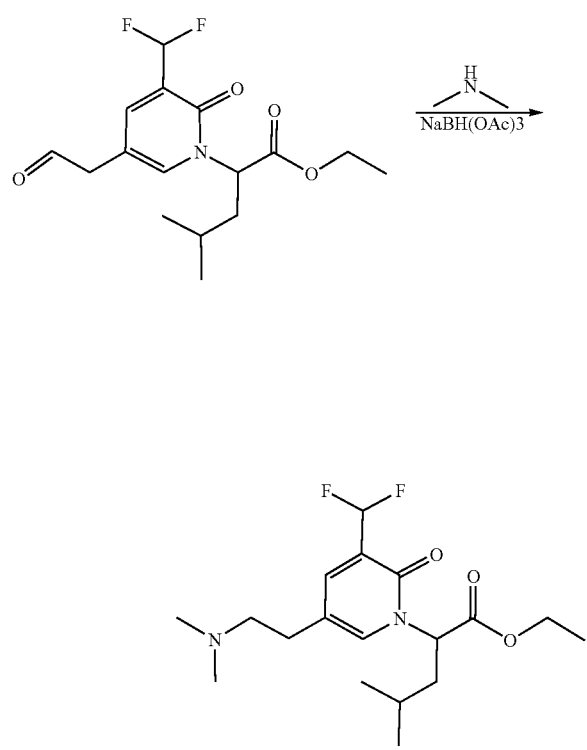

A mixture of ethyl 2-(3-(difluoromethyl)-2-oxo-5-(2-oxoethyl)pyridin-1(2H)-yl)-4-methylpentanoate (3.0 g, 9.1 mmol), dimethylamine (2M in THF, 14 mL, 28 mmol) in DCE (50 mL) was stirred at room temperature for 30 mins. NaBH(OAc)$_3$ (3.8 g, 18.2 mmol) was added portion-wise and the reaction was stirred at room temperature overnight. The solvent was concentrated in vacuo and the residue purified by reverse phase HPLC on a C18/120 g column (A: water 10 mM NH$_4$HCO$_3$, B: MeOH, 0~100%) to give ethyl 2-(3-(difluoromethyl)-5-(2-(dimethylamino)ethyl)-2-oxopyridin-1(2H)-yl)-4-methylpentanoate as a yellow oil (2.0 g). Yield 33.6% (ESI 359.2 (M+H)$^+$).

226

Step 7: 2-(3-(difluoromethyl)-5-(2-(dimethylamino)ethyl)-2-oxopyridin-1(2H)-yl)-4-methylpentanoic acid

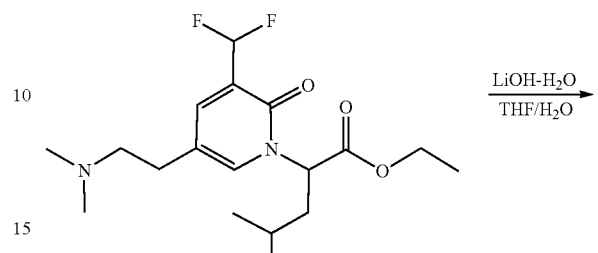

A mixture of ethyl 2-(3-(difluoromethyl)-5-(2-(dimethylamino)ethyl)-2-oxopyridin-1(2H)-yl)-4-methylpentanoate (2.0 g, 5.5 mmol) was treated with LiOH—H$_2$O (40 mg, 1.01 mmol) in THF (20 mL) and water (10 mL) at room temperature for 2 hours. The solvent was removed in vacuo and the residue purified by reverse phase HPLC on a C18/120 g column (A: water 10 mM NH$_4$HCO$_3$, B: MeOH, 0~100%) to give 2-(3-(difluoromethyl)-5-(2-(dimethylamino)ethyl)-2-oxopyridin-1(2H)-yl)-4-methylpentanoic acid as a white solid (1.2 g). Yield 85.6% (ESI 331.1 (M+H)$^+$).

Preparation of 2-(5-(2-(dimethylamino)ethyl)-3-fluoro-2-oxopyridin-1(2H)-yl)-4-methylpentanoic acid Step 1: ethyl 2-(5-bromo-3-fluoro-2-oxopyridin-1(2H)-yl)-4-methylpentanoate

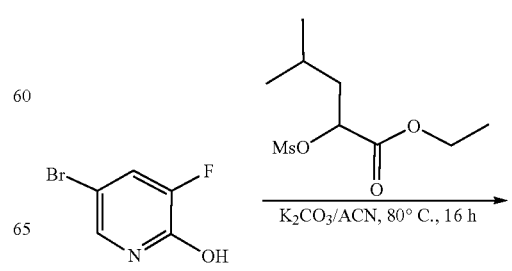

227
-continued

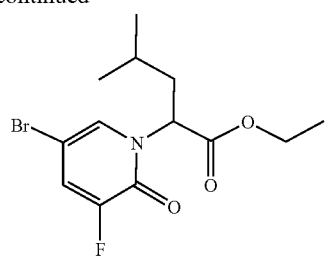

A mixture of 5-bromo-3-fluoropyridin-2-ol (5.0 g, 15.6 mmol), K₂CO₃ (7.36 g, 53.3 mmol) and ethyl 4-methyl-2-(methylsulfonyloxy)pentanoate (9.9 g, 23.4 mmol) in CH₃CN (180 mL) was stirred at 80° C. overnight. The solvent was concentrated in vacuo and the residue was purified by silica gel column (pet ether: EtOAc 1:2) to give ethyl 2-(5-bromo-3-fluoro-2-oxopyridin-1(2H)-yl)-4-methylpentanoate as a yellow oil (6.5 g). Yield 81% (ESI 334.0 (M+H)⁺).

Step 2: ethyl 2-(5-allyl-3-fluoro-2-oxopyridin-1 (2H)-yl)-4-methylpentanoate

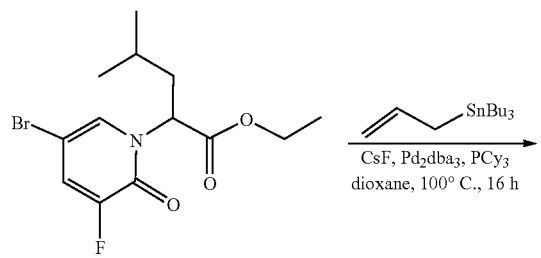

A mixture of ethyl 2-(5-bromo-3-fluoro-2-oxopyridin-1 (2H)-yl)-4-methylpentanoate (5.0 g, 7.6 mmol), allyltributylstannane (6.0 g, 9.1 mmol), Pd₂dba₃ (240.0 mg, 0.76 mmol), tricyclohexyl phosphine (450 mg, 0.76 mmo), CsF (4.6 g, 15.1 mmol) in anhydrous dioxane (100 mL) was stirred under N₂ at 100° C. for 16 h. The mixture was cooled to room temperature and diluted with a saturated NH₄Cl solution (100 mL) and EtOAc (100 mL). Separated the mixture and the aqueous layer was extracted with EtOAc (100 mL×2). The combined organic phase was washed with brine (100 mL), dried over anhydrous Na₂SO₄, filtered and concentrated in vacuo. The residue was purified by silica gel column (pet ether: EtOAc 4:1) to provide ethyl 2-(5-allyl-3-fluoro-4-methyl-2-oxopyridin-1(2H)-yl)-4-methylpentanoate as a yellow solid (3.0 g). Yield 69% (ESI 296.2 (M+H)⁺).

228

Step 3: ethyl 2-(3-fluoro-2-oxo-5-(2-oxoethyl)pyridin-1(2H)-yl)-4-methylpentanoate

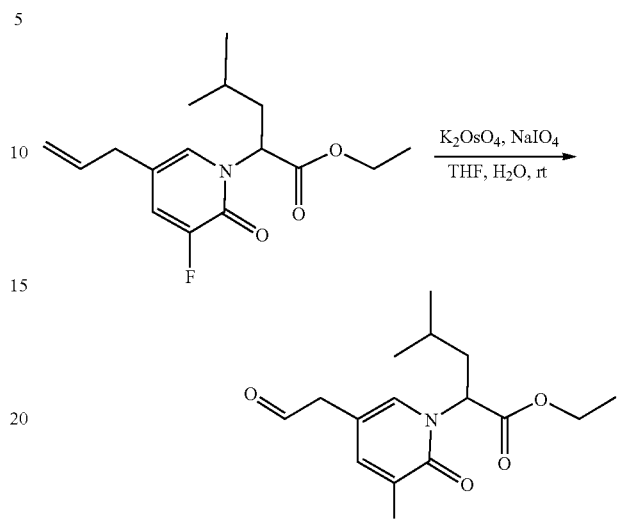

To a solution of ethyl 2-(5-allyl-3-fluoro-4-methyl-2-oxopyridin-1(2H)-yl)-4-methylpentanoate (5.5 g, 18.6 mmol) in THF/H₂O (60 mL/20 mL) was added a solution of K₂OsO₄·2H₂O (60.0 mg, 0.16 mmol) in H₂O (4 mL) and stirred at room temperature for 1 h. A solution of NaIO₄ (7.8 g, 37.2 mmol) in H₂O (20 mL) was added and stirred at room temperature for 2 h. LCMS showed the reaction was completed. The reaction mixture was diluted with 100 mL of water and extracted with EtOAc (120 mL×3). The combined organic phase was dried over anhydrous Na₂SO₄, filtered and concentrated in vacuo to give the crude product ethyl 2-(3-fluoro-2-oxo-5-(2-oxoethyl)pyridin-1(2H)-yl)-4-methylpentanoate as a yellow oil (5.0 g, crude) used directly in the next reaction without further purification. (ESI 298.1 (M+H)⁺).

Step 4: ethyl 2-(5-(2-(dimethylamino)ethyl)-3-fluoro-2-oxopyridin-1(2H)-yl)-4-methylpentanoate

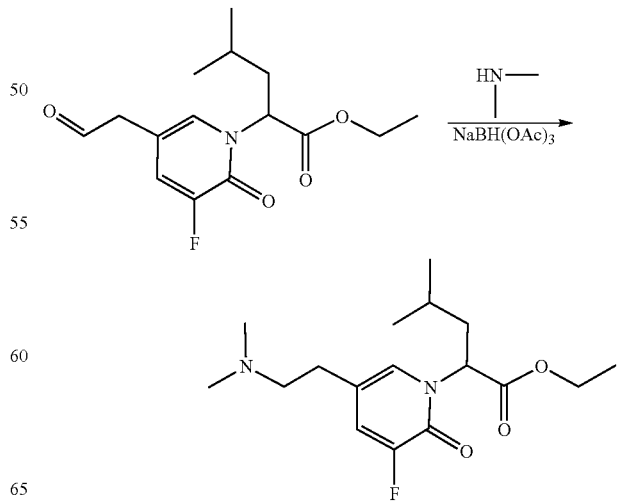

To a mixture of ethyl 2-(3-fluoro-2-oxo-5-(2-oxoethyl)pyridin-1(2H)-yl)-4-methylpentanoate (1.2 g, 4.0 mmol) in DCE (50 mL) at 25° C. was added dimethylamine (2.0 M in THF, 8.0 mL, 16.0 mmol) and stirred at 25° C. for 30 mins. NaBH(OAc)₃ (1.7 g, 8.0 mmol) was added at 5° C. and stirred at 25° C. for 16 hours. The mixture was concentrated in vacuo and the residue was purified by silica gel column (DCM:MeOH 10:1) to provide ethyl 2-(5-(2-(dimethylamino)ethyl)-3-fluoro-2-oxopyridin-1(2H)-yl)-4-methylpentanoate (800 mg) as a colorless oil. Yield 60% (ESI 327.1 (M+H)⁺).

Step 5: 2-(5-(2-(dimethylamino)ethyl)-3-fluoro-2-oxopyridin-1(2H)-yl)-4-methylpentanoic acid

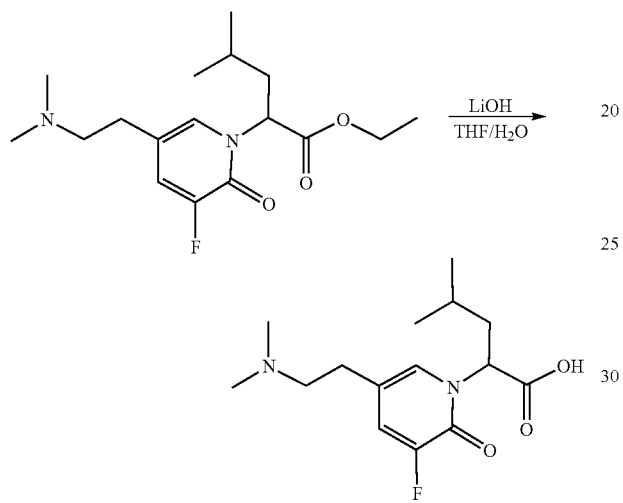

Ethyl 2-(5-(2-(dimethylamino)ethyl)-3-fluoro-2-oxopyridin-1(2H)-yl)-4-methylpentanoate (800 mg, 2.45 mmol) was treated with LiOH—H₂O (310.0 mg, 7.35 mmol) in THF (4 mL) and water (1 mL) at room temperature for 2 hours. The THF was removed and the aqueous acidified with 1N HCl to pH 5~6. The residue was purified by reverse phase HPLC on a C18/120 g column (A: water 10 mM NH₄HCO₃, B: MeOH, 0~100%) to provide 2-(5-(2-(dimethylamino)ethyl)-3-fluoro-2-oxopyridin-1(2H)-yl)-4-methylpentanoic acid as a white solid (700 mg). Yield 88% (ESI 299.2 (M+H)⁺).

Preparation of 2-(3-fluoro-5-(2-(3-fluoroazetidin-1-yl)ethyl)-2-oxopyridin-1(2H)-yl)-4-methylpentanoic acid Step 1: ethyl 2-(3-fluoro-5-(2-(3-fluoroazetidin-1-yl)ethyl)-2-oxopyridin-1(2H)-yl)-4-methylpentanoate

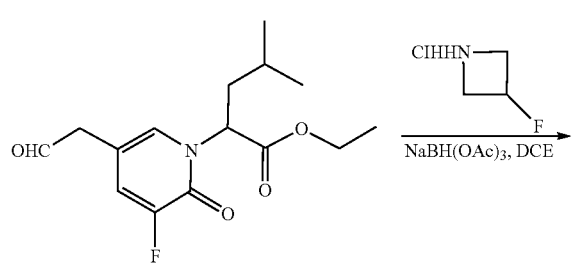

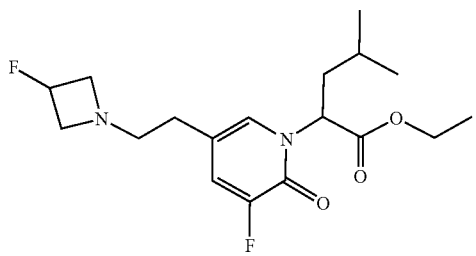

To a mixture of ethyl 2-(3-fluoro-2-oxo-5-(2-oxoethyl)pyridin-1(2H)-yl)-4-methylpentanoate (5 g, 15 mmol) in DCE (70 mL) at 25° C. was added 3-fluoroazetidine hydrochloride (1.8 g, 22.5 mmol) and stirred at 25° C. for 10 min. NaBH(OAc)₃ (6.4 g, 30 mmol) was added at 5° C. and stirred at 25° C. for 2 hours. The mixture was concentrated in vacuo and the residue was purified by silica gel column (DCM:MeOH 10:1) to provide ethyl 2-(3-fluoro-5-(2-(3-fluoroazetidin-1-yl)ethyl)-2-oxopyridin-1(2H)-yl)-4-methylpentanoate (3.8 g) as yellow oil. Yield: 63% (ESI 357.2 (M+H)⁺).

Step 2: 2-(3-fluoro-5-(2-(3-fluoroazetidin-1-yl)ethyl)-2-oxopyridin-1(2H)-yl)-4-methylpentanoic acid

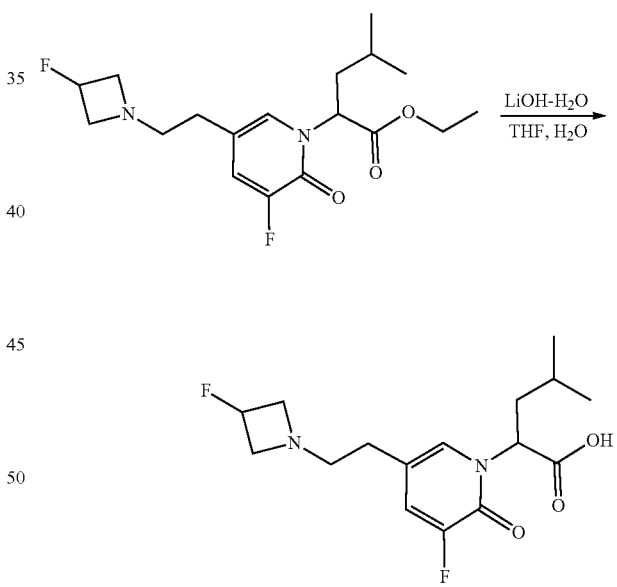

Methyl ethyl 2-(3-fluoro-5-(2-(3-fluoroazetidin-1-yl)ethyl)-2-oxopyridin-1(2H)-yl)-4-methylpentanoate (86 mg, 0.24 mmol) was treated with LiOH monohydrate (50 mg, 1.2 mmol) in THF (3 mL) and H₂O (0.5 mL) at room temperature for 1 hour. The reaction mixture was acidified to pH 4~5 with 1N HCl. The residue was purified by reverse phase HPLC on a C18/120 g column (A: water 10 mM NH₄HCO₃, B: MeOH, 0~100%) to provide 2-(3-fluoro-5-(2-(3-fluoroazetidin-1-yl)ethyl)-2-oxopyridin-1(2H)-yl)-4-methylpentanoic acid as a white solid (55 mg). Yield 70% (ESI 329.1 (M+H)⁺).

Preparation of 2-(3-fluoro-5-(2-(3-fluoroazetidin-1-yl)ethyl)-2-oxopyridin-1(2H)-yl)pentanoic acid Step 1: ethyl 2-(5-bromo-3-fluoro-2-oxopyridin-1(2H)-yl)pentanoate

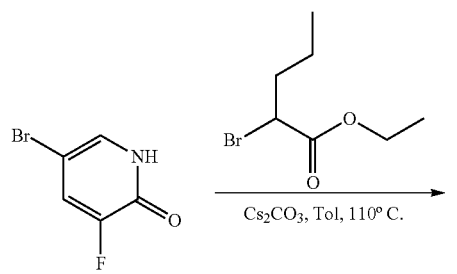

A mixture of 5-bromo-3-fluoropyridin-2(1H)-one (2.1 g, 11.0 mmol), ethyl 2-bromopentanoate (3.43 g, 16.5 mmol) and Cs₂CO₃ (7.17 g, 22.0 mmol) in Toluene (50 mL) was stirred at 110° C. overnight. The reaction mixture was filtered, washed with EtOAc, concentrated in vacuo. The residue was purified by silica gel column (pet ether: EtOAc 2:1) to provide ethyl 2-(5-bromo-3-fluoro-2-oxopyridin-1(2H)-yl)pentanoate as a white oil (2.9 g). Yield 82% (ESI 320.02 (M+H)$^+$).

Step 2: ethyl 2-(5-allyl-3-fluoro-2-oxopyridin-1(2H)-yl)pentanoate

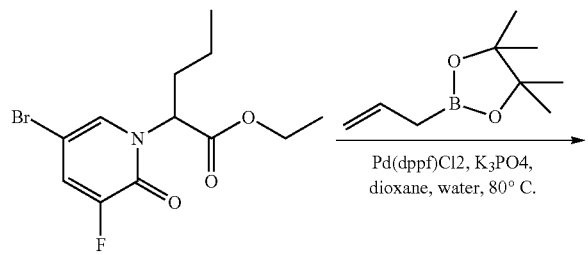

A mixture of ethyl 2-(5-bromo-3-fluoro-2-oxopyridin-1(2H)-yl)pentanoate (2.9 g, 13.2 mmol), 2-allyl-4,4,5,5-tetramethyl-1,3,2-dioxaborolane (2.66 g, 15.8 mmol), Pd(dppf)Cl₂ (482.5 mg, 0.66 mmol), and K₃PO₄ (5.60 g, 26.4 mmol) in 1,4-dioxane (30 mL) and H₂O (5 mL) was stirred at 80° C. for 2 hours. The reaction mixture was diluted with 50 mL of water, extracted with EA (60 mL×2). The combined organic phase was washed with brine (100 mL), dried over anhydrous Na₂SO₄, filtered and concentrated in vacuo and the residue purified by silica gel column (pet ether: EtOAc 1:2) to provide ethyl 2-(5-allyl-3-fluoro-2-oxopyridin-1(2H)-yl)pentanoate as a white oil (1.9 g). Yield 75% (ESI 282.24 (M+H)$^+$).

Step 3: ethyl 2-(3-fluoro-2-oxo-5-(2-oxoethyl)pyridin-1(2H)-yl)pentanoate

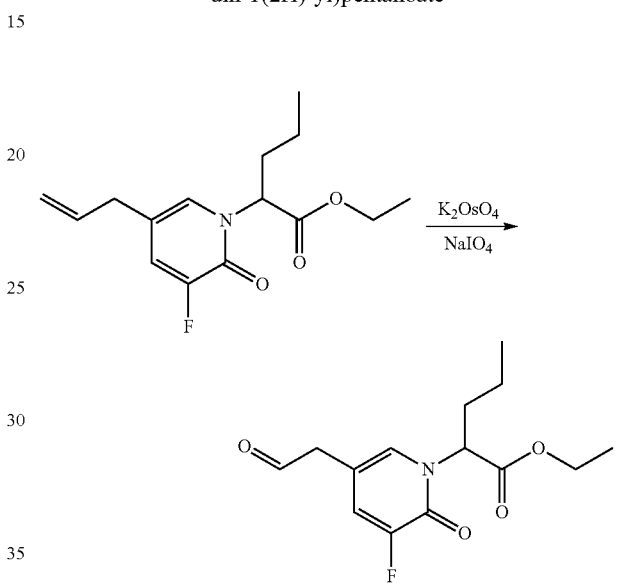

To a mixture of ethyl ethyl 2-(5-allyl-3-fluoro-2-oxopyridin-1(2H)-yl)pentanoate (1.9 g, 6.7 mmol) in THF (20 mL) and H₂O (30 mL) was added K₂OsO₄ (25.8 mg, 0.07 mmol) and stirred at room temperature for 1 hour. NaIO₄ (3.9, 13.4 mmol) was added and the mixture was stirred at room temperature for 2 hours. The mixture was poured into water (100 mL) and extracted with EtOAc (50 mL×3). The combined organic layers were washed brine (100 mL), dried over Na₂SO₄, filtered and concentrated in vacuo to provide ethyl 2-(3-fluoro-2-oxo-5-(2-oxoethyl)pyridin-1(2H)-yl)pentanoate as a yellow oil (1.7 g, crude) used directly in the next reaction. (ESI 284.12 (M+H)$^+$).

Step 4: ethyl 2-(3-fluoro-5-(2-(3-fluoroazetidin-1-yl)ethyl)-2-oxopyridin-1(2H)-yl)pentanoate

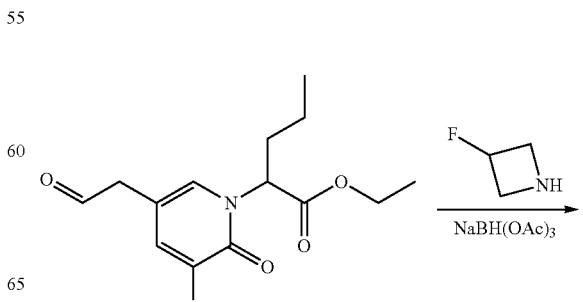

233

-continued

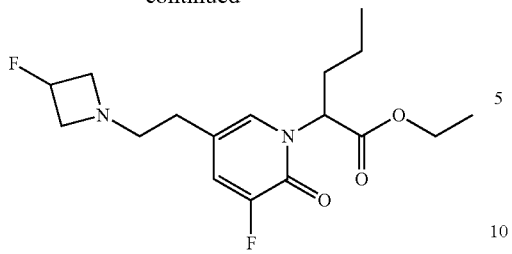

A mixture of ethyl 2-(3-fluoro-2-oxo-5-(2-oxoethyl)pyridin-1(2H)-yl)pentanoate (1.7 g, 6 mmol), AcOH (0.44 g, 7.2 mmol) and 3-fluoroazetidine hydrochloride (1.0 g, 9.0 mmol) in MeOH (30 mL) was stirred at room temperature for 30 mins. NaBH(OAc)$_3$ (2.54 g, 12 mmol) was added and stirred at room temperature for 2 hours. The solvent was concentrated in vacuo and the residue was purified by silica gel column (pet ether: EtOAc 4:1) to provide ethyl 2-(3-fluoro-5-(2-(3-fluoroazetidin-1-yl)ethyl)-2-oxopyridin-1(2H)-yl)pentanoate as a yellow oil (700 mg). Yield 40% (ESI 343.18 (M+H)$^+$).

Step 5: 2-(3-fluoro-5-(2-(3-fluoroazetidin-1-yl) ethyl)-2-oxopyridin-1(2H)-yl)pentanoic acid

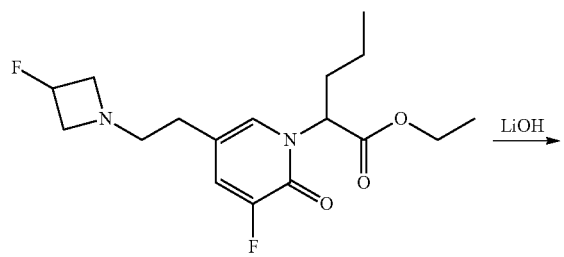

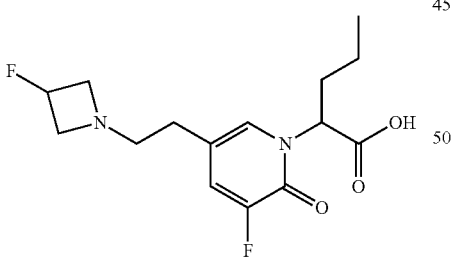

Ethyl 2-(3-fluoro-5-(2-(3-fluoroazetidin-1-yl)ethyl)-2-oxopyridin-1(2H)-yl)pentanoate (700 mg, 2.05 mmol) was treated with LiOH—H$_2$O (344 mg, 8.2 mmol) in EtOH (4 mL) and H$_2$O (1 mL) at room temperature for 2 hours. The mixture was acidified to pH 4~5 with 1N HCl. The reaction mixture was concentrated in vacuo and the residue was purified by reverse phase HPLC on a C18/40 g column (A: water 10 mM NH$_4$HCO$_3$, B: MeOH, 20%) to provide 2-(3-fluoro-5-(2-(3-fluoroazetidin-1-yl)ethyl)-2-oxopyridin-1(2H)-yl)pentanoic acid as a yellow solid (500 mg). Yield 78% (ESI 315.14 (M+H)$^+$).

234

Preparation of (3R)-2-(3-fluoro-5-(2-(3-fluoroazetidin-1-yl)ethyl)-2-oxopyridin-1(2)-yl)-3-methylpentanoic acid Step 1: (2R, 3R-2-bromo-3-methylpentanoic acid

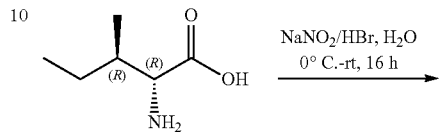

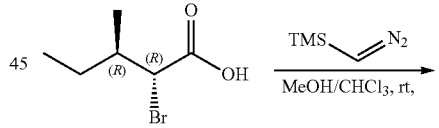

To a solution of D-isoleucine (10.0 g, 76.23 mmol) in H$_2$O (50 mL) was added 40% HBr in water (100 mL). The reaction mixture was cooled to 0° C. A solution of sodium nitrite (7.9 g, 114.35 mmol) in H$_2$O (10 mL) was added dropwise. Then the reaction mixture was stirred at room temperature for 3 hours. The reaction mixture was extracted with EtOAc (100 mL×3). The organic layer was washed with brine (50 mL) and dried over anhydrous Na$_2$SO$_4$, filtered and concentrated in vacuo to provide (2R, 3R)-2-bromo-3-methylpentanoic acid as a brown oil used directly in the next reaction without further purification (14.0 g). Yield 95% (ESI 195.1 (M+H)$^+$).

Step 2: methyl (3R)-2-bromo-3-methylpentanoate

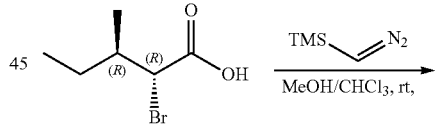

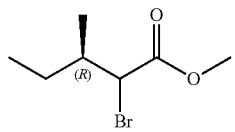

A mixture of (2R, 3R)-2-bromo-3-methylpentanoic acid (12.6 g, 64.60 mmol) in MeOH/CHCl$_3$ (30 mL/90 mL) was cooled to 0° C. (Diazomethyl)trimethylsilane (2.0 M in hexane; 64.6 m L, 129.20 mmol) was added dropwise. The mixture was stirred at room temperature for 1 hour. LCMS showed that the reaction was completed. The mixture was concentrated in vacuo to provide methyl (3R)-2-bromo-3-methylpentanoate as a yellow oil used directly in the next reaction without further purification (12.0 g). Yield 89% (ESI 209.1 (M+H)$^+$).

Step 3: methyl (3R)-2-(5-bromo-3-fluoro-2-oxopyridin-1(2H)-yl)-3-methylpentanoate

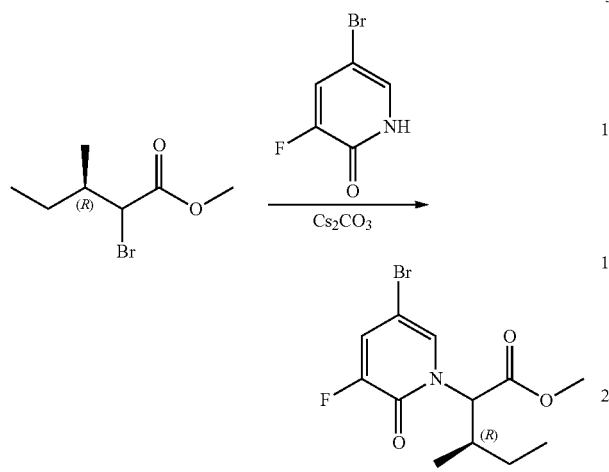

A mixture of 5-bromo-3-fluoropyridin-2(1H)-one (3.1 g, 16.15 mmol), Cs$_2$CO$_3$ (10.5 g, 32.3 mmol) and methyl (3R)-2-bromo-3-methylpentanoate (5.06 g, 24.23 mmol) in dioxane (100 mL) was stirred at 110° C. for 16 h. LCMS showed the reaction was completed. The mixture was filtered and washed with EtOAc (20 mL). The filtrate was concentrated in vacuo and the residue was purified by silica gel column (pet ether: EtOAc 10:1) to provide methyl (3R)-2-(5-bromo-3-fluoro-2-oxopyridin-1(2H)-yl)-3-methylpentanoate as a colorless oil (2.2 g). Yield 43% (ESI 322.0 (M+H)$^+$).

Step 4: methyl(3R)-2-(5-allyl-3-fluoro-2-oxopyridin-1(2)-yl)-3-methylpentanoate

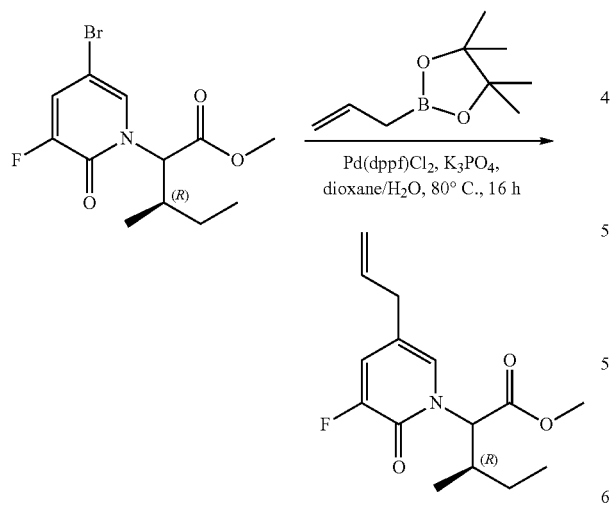

A mixture of methyl (3R)-2-(5-bromo-3-fluoro-2-oxopyridin-1(2H)-yl)-3-methylpentanoate (2.2 g, 6.87 mmol), 2-allyl-4,4,5,5-tetramethyl-1,3,2-dioxaborolane (3.5 g, 20.61 mmol), Pd(dppf)Cl$_2$ (251 mg, 0.34 mmol) and K$_3$PO$_4$ (2.9 g, 13.74 mmol, 2.0 eq) in dioxane (100 mL) and H$_2$O (10 mL) was stirred under nitrogen atmosphere at 80° C. for 16 hours. The mixture was concentrated in vacuo and the residue was purified by silica gel column (pet ether: EtOAc 10:1) to provide methyl (3R)-2-(5-allyl-3-fluoro-2-oxopyridin-1(2H)-yl)-3-methylpentanoate as a yellow oil (1.2 g). Yield 55% (ESI 282.1 (M+H)$^+$).

Step 5: methyl (3R)-2-(3-fluoro-2-oxo-5-(2-oxoethyl)pyridin-1(2H)-yl)-3-methylpentanoate

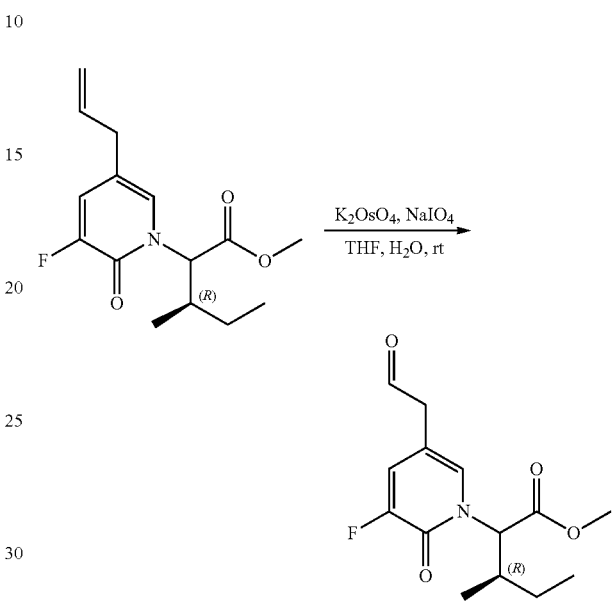

To a solution of methyl (3R)-2-(5-allyl-3-fluoro-2-oxopyridin-1(2H)-yl)-3-methylpentanoate (1.2 g, 4.27 mmol) in THF/H$_2$O (20 mL/20 mL) was added a solution of K$_2$OsO$_4$·2H$_2$O (15.7 mg, 0.043 mmol) in H$_2$O (3 mL) and stirred at room temperature for 1 hour. Then a solution of NaIO$_4$ (1.8 g, 8.54 mmol) in H$_2$O (10 mL) was added dropwise and the mixture was stirred at room temperature for 2 hours. LCMS showed the reaction was completed. The reaction mixture was diluted with H$_2$O (50 mL), extracted with EtOAc (50 mL×3). The combined organic phase was dried over anhydrous Na$_2$SO$_4$, filtered and concentrated in vacuo to provide methyl (3R)-2-(3-fluoro-2-oxo-5-(2-oxoethyl)pyridin-1(2H)-yl)-3-methylpentanoate as a colorless oil used directly in the next reaction without further purification (1.3 g, crude). (ESI 284.1 (M+H)$^+$).

Step 6: methyl (3R)-2-(3-fluoro-5-(2-(3-fluoroazetidin-1-yl)ethyl)-2-oxopyridin-1(2H)-yl)-3-methylpentanoate

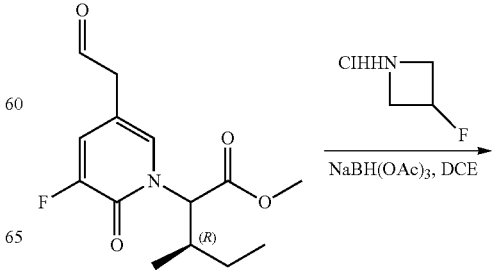

237
-continued

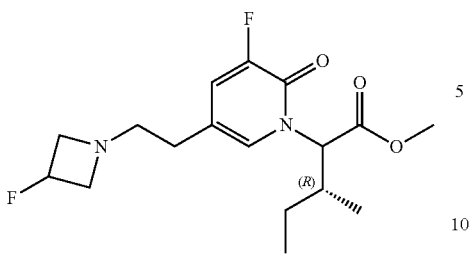

To a mixture of methyl (3R)-2-(3-fluoro-2-oxo-5-(2-oxo-ethyl)pyridin-1(2H)-yl)-3-methylpentanoate (1.3 g, 4.59 mmol) in DCE (20 mL) at 25° C. was added 3-fluoroazetidine hydrochloride (768 mg, 6.89 mmol) and stirred at 25° C. for 1 hour. NaBH(OAc)$_3$ (2.9 g, 13.77 mmol) was added at 5° C. and stirred at 25° C. for 16 hours. The mixture was concentrated in vacuo and the residue was purified by silica gel column (DCM:MeOH 20:1) to provide methyl (3R)-2-(3-fluoro-5-(2-(3-fluoroazetidin-1-yl)ethyl)-2-oxopyridin-1(2H)-yl)-3-methylpentanoate as a brown oil (800 mg). Yield 51% (ESI 343.1 [M+H]$^+$).

Step 7: (3R)-2-(3-fluoro-5-(2-(3-fluoroazetidin-1-yl)ethyl)-2-oxopyridin-1(2H)-yl)-3-methylpentanoic acid

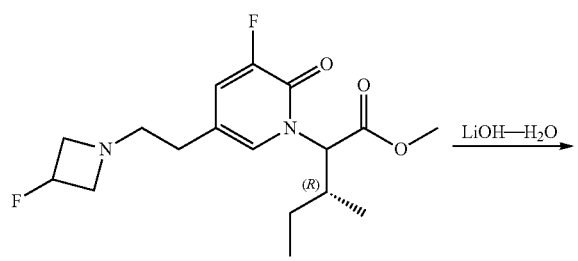

Methyl (3R)-2-(3-fluoro-5-(2-(3-fluoroazetidin-1-yl)ethyl)-2-oxopyridin-1(2H)-yl)-3-methylpentanoate (800 mg, 2.34 mmol) was treated with LiOH—H$_2$O (491 mg, 11.7 mmol) in EtOH (5 mL) and water (2 mL) and the mixture was stirred at room temperature for 30 minutes. The mixture was acidified with 1N HCl to pH 5~6, concentrated and purified by reverse phase HPLC on a C18/40 g column (A: water/0.01% TFA, B: MeOH, 0~100%) to provide (3R)-2-(3-fluoro-5-(2-(3-fluoroazetidin-1-yl)ethyl)-2-oxopyridin-1(2H)-yl)-3-methylpentanoic acid as a white solid (600 mg). Yield 78% (ESI 329.2 (M+H)$^+$).

238
Preparation of 3-cyclopropyl-2-(3-fluoro-5-(2-(3-fluoroazetidin-1-yl)ethyl)-2-oxopyridin-1(2H)-yl) propanoic acid Step 1: ethyl 2-(5-bromo-3-fluoro-2-oxopyridin-1 (2H)-yl)-3-cyclopropylpropanoate

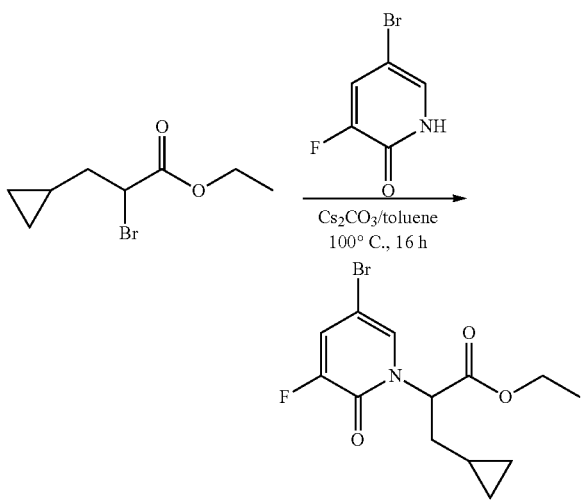

A mixture of 5-bromo-3-fluoropyridin-2(1H)-one (2.0 g, 10.4 mmol), Cs$_2$CO$_3$ (6.5 g, 20.8 mmol) and ethyl 2-bromo-3-cyclopropylpropanoate (2.7 g, 12.4 mmol) in toluene (50 mL) was stirred at 110° C. for 16 hours. LCMS showed the reaction was completed. The mixture was filtered and washed with EtOAc (20 mL). The filtrate was concentrated in vacuo and the residue was purified by silica gel column (pet ether: EtOAc 4:1) to provide ethyl 2-(5-bromo-3-fluoro-2-oxopyridin-1(2H)-yl)-3-cyclopropylpropanoate as a yellow oil (2.0 g). Yield 58% (ESI 333 (M+H)$^+$).

Step 2: ethyl 2-(5-allyl-3-fluoro-2-oxopyridin-1 (2H)-yl)-3-cyclopropylpropanoate

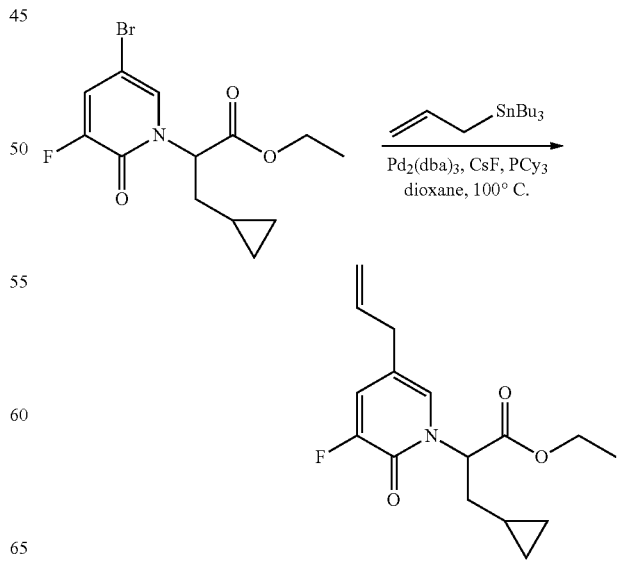

A mixture of ethyl 2-(5-bromo-3-fluoro-2-oxopyridin-1 (2H)-yl)-3-cyclopropylpropanoate (1.5 g, 4.5 mmol), allyl-tributylstannane (1.5 g, 5.4 mmol), CsF (1.4 g, 9 mmol), Pd(dba)$_3$ (126 mg, 0.45 mmol) and PCy$_3$ (206 mg, 0.225 mmol) in dioxane (100 mL) was stirred at 100° C. overnight. The mixture was poured into water (200 mL) and extracted with EtOAc (100 mL×3). The combined organic layers were washed with brine (100 mL), dried over Na$_2$SO$_4$, filtered and concentrated in vacuo. The residue was purified by silica gel column (pet ether: EtOAc 4:1) to provide ethyl 2-(5-allyl-3-fluoro-2-oxopyridin-1(2H)-yl)-3-cyclopropylpropanoate as a yellow oil (1.0 g). Yield 83% (ESI 294(M+H)$^+$).

Step 3: ethyl 3-cyclopropyl-2-(3-fluoro-2-oxo-5-(2-oxoethyl)pyridin-1(2H)-yl)propanoate

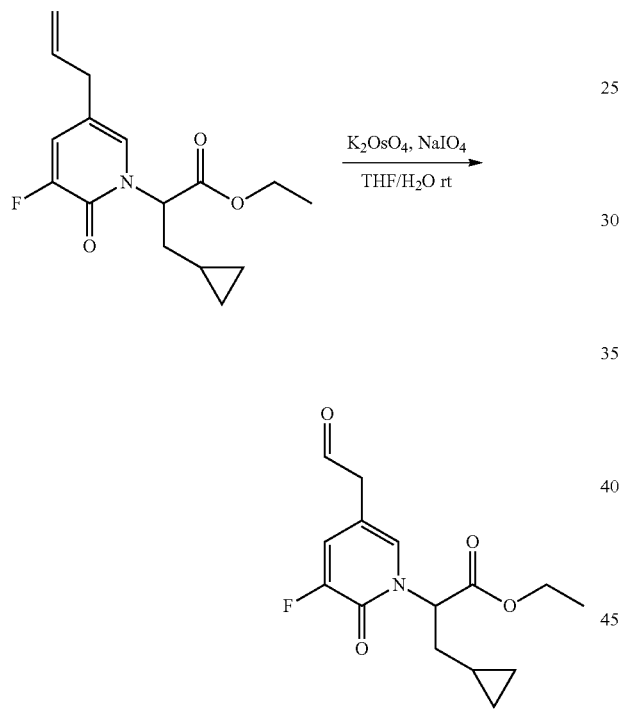

To a solution of ethyl 2-(5-allyl-3-fluoro-2-oxopyridin-1 (2H)-yl)-3-cyclopropylpropanoate (800 mg, 2.7 mmol) in THF/H$_2$O (60 mL/20 mL) was added a solution of K$_2$OsO$_4$·2H$_2$O (10 mg, 0.027 mmol) in H$_2$O (4 mL) and stirred at room temperature for 1 h. Then a solution of NaIO$_4$ (1.1 g, 5.4 mmol) in H$_2$O (20 mL) was added and stirred at room temperature for 2 h. LCMS showed the reaction was completed. The reaction mixture was diluted with 100 mL of water and extracted with EtOAc (100 mL×3). The combined organic phase was dried over anhydrous Na$_2$SO$_4$, filtered and concentrated in vacuo to provide ethyl 3-cyclopropyl-2-(3-fluoro-2-oxo-5-(2-oxoethyl)pyridin-1(2H)-yl)propanoate as a yellow oil used directly in the next reaction without further purification (820 mg, crude). (ESI 296 (M+H)$^+$).

Step 4: ethyl 3-cyclopropyl-2-(3-fluoro-5-(2-(3-fluoroazetidin-1-yl)ethyl)-2-oxopyridin-1(2H)-yl) propanoate

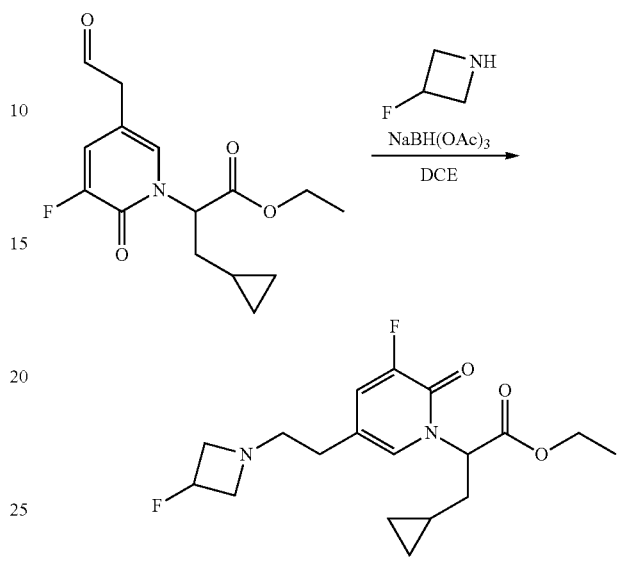

A mixture of ethyl 3-cyclopropyl-2-(3-fluoro-2-oxo-5-(2-oxoethyl)pyridin-1(2H)-yl)propanoate (500 mg, 1.7 mmol) and 3-fluoroazetidine hydrochloride (188 mg, 1.7 mmol) in DCE (20 mL) was stirred at room temperature for 10 minutes. NaBH(OAc)$_3$ (530 g, 1.5 mmol) was added and stirred at room temperature for 2 h. The mixture was diluted with water (50 mL) and extracted with DCM (50 mL×3). The combined organic phase was dried over anhydrous Na$_2$SO$_4$, filtered and concentrated in vacuo and the residue was purified by reverse phase HPLC on a C18/40 g column (A: water 10 mM NH$_4$HCO$_3$, B: MeOH, 0~100%) to provide ethyl 3-cyclopropyl-2-(3-fluoro-5-(2-(3-fluoroazetidin-1-yl)ethyl)-2-oxopyridin-1(2H)-yl)propanoate as a yellow oil (300 mg). Yield 31% (ESI 355 (M+H)$^+$).

Step 5: 3-cyclopropyl-2-(3-fluoro-5-(2-(3-fluoroazetidin-1-yl)ethyl)-2-oxopyridin-1(2H)-yl)propanoic acid

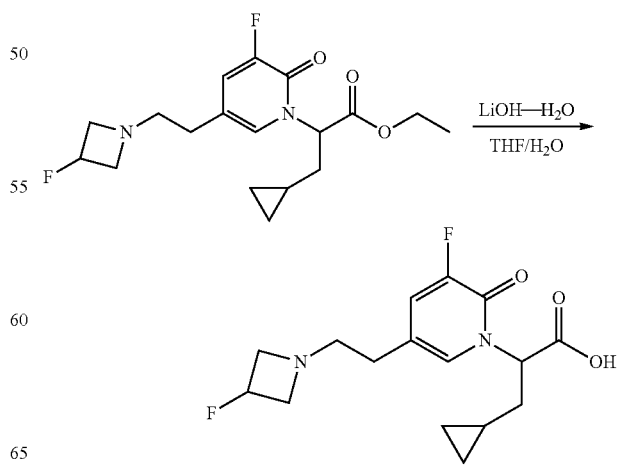

Ethyl 3-cyclopropyl-2-(3-fluoro-5-(2-(3-fluoroazetidin-1-yl)ethyl)-2-oxopyridin-1(2H)-yl)propanoate (300 mg, 0.84 mmol) was treated with LiOH—H$_2$O (178 mg, 4.20 mmol) in THF (10 mL) and water (5 mL) at room temperature for 2 hours. The reaction mixture was acidified to pH 5 with 1N HCl and concentrated. The mixture was purified by reverse phase HPLC on a C18/40 g column (A: water, B: MeOH, 0~100%) to provide 2-(3-fluoro-5-(2-(3-fluoroazetidin-1-yl)ethyl)-4-methyl-2-oxopyridin-1(2H)-yl)-4-methylpentanoic acid as a white solid (200 mg). Yield 86% (ESI 327 (M+H)$^+$).

Preparation of 2-(3-fluoro-5-(2-(3-fluoroazetidin-1-yl)ethyl)-2-oxopyridin-1(2H)-yl)-3-methylbutanoic acid Step 1: ethyl 2-(5-bromo-3-fluoro-2-oxopyridin-1(2H)-yl)-3-methylbutanoate

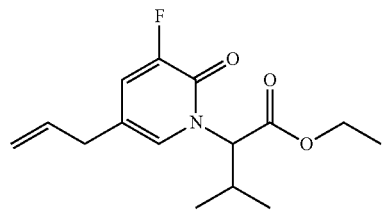

A mixture of 5-bromo-3-fluoropyridin-2(1H)-one (5.0 g, 26.2 mmol, 1.0 eq), K$_2$CO$_3$ (7.2 g, 52.4 mmol, 2.0 eq) and ethyl 2-bromo-3-methylbutanoate (6.5 g, 31.4 mmol, 1.2 eq) in ACN (100 mL) was stirred at 80° C. for 16 hours. LCMS showed the reaction was completed. The mixture was filtered and washed with EtOAc (20 mL). The filtrate was concentrated in vacuo and the residue was purified by silica gel column (pet ether: EtOAc 4:1) to provide ethyl 2-(5-bromo-3-fluoro-2-oxopyridin-1(2H)-yl)-3-methylbutanoate as a yellow oil (3.0 g). Yield 36% (ESI 320.1 (M+H)$^+$).

Step 2: ethyl 2-(5-allyl-3-fluoro-2-oxopyridin-1(2H)-yl)-3-methylbutanoate

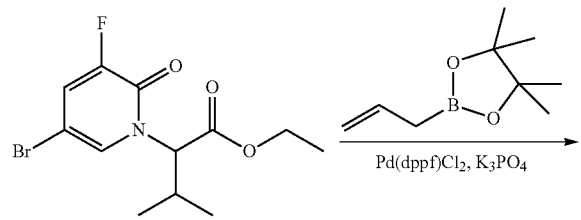

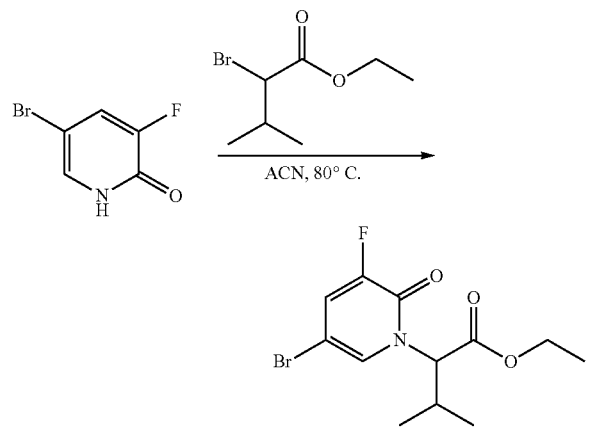

A mixture of ethyl 2-(5-bromo-3-fluoro-2-oxopyridin-1(2H)-yl)-3-methylbutanoate (3.0 g, 9.4 mmol, 1 eq), 2-allyl-4,4,5,5-tetramethyl-1,3,2-dioxaborolane (1.9 g, 11.3 mmol, 1.2 eq), Pd(dppf)Cl$_2$ (343.6 mg, 0.47 mmol, 0.05 eq) and K$_3$PO$_4$ (4.0 g, 18.8 mmol, 2.0 eq) in dioxane (100 mL) and H$_2$O (10 mL) was stirred at 100° C. overnight. Water (200 mL) was added and the solution was extracted with EtOAc (100 mL×3). The combined organic phases were washed with brine (100 mL), dried over anhydrous Na$_2$SO$_4$, filtered and concentrated in vacuo. The residue was purified by silica gel column (pet ether: EtOAc 4:1) to provide ethyl 2-(5-allyl-3-fluoro-2-oxopyridin-1(2H)-yl)-3-methylbutanoate as a yellow oil (2.4 g). Yield 92% (ESI 282.0 (M+H)$^+$).

Step 3: ethyl 2-(3-fluoro-2-oxo-5-(2-oxoethyl)pyridin-1(2H)-yl)-3-methylbutanoate

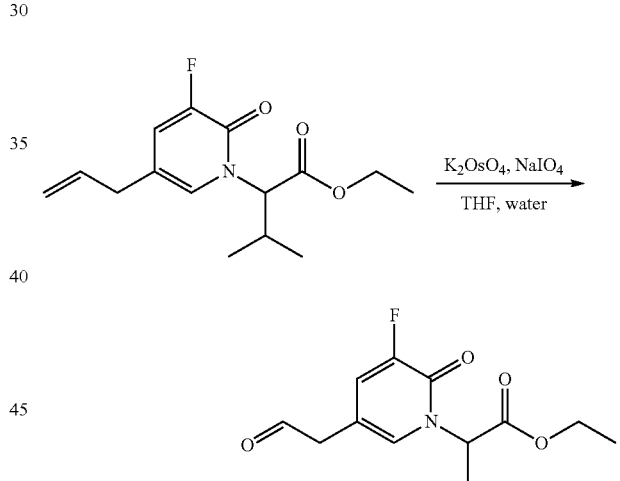

To a solution of ethyl 2-(5-allyl-3-fluoro-2-oxopyridin-1(2H)-yl)-3-methylbutanoate (2.4 g, 8.6 mmol, 1.0 eq) in THF (100 mL) and H$_2$O (30 mL) was added a solution of K$_2$OsO$_4$·2H$_2$O (32 mg, 0.086 mmol, 0.01 eq) in H$_2$O (4 mL). The mixture was stirred at room temperature for 1 hour. Then a solution of NaIO$_4$ (3.7 g, 17.2 mmol, 2.0 eq) in H$_2$O (20 mL) was added and stirred at room temperature for 2 hours. LCMS showed the reaction was completed. Water (100 mL) was added and the solution was extracted with EtOAc (100 mL×3). The combined organic phases were washed with brine (50 mL), dried over anhydrous Na$_2$SO$_4$, filtered and concentrated in vacuo to provide ethyl 2-(3-fluoro-2-oxo-5-(2-oxoethyl)pyridin-1(2H)-yl)-3-methylbutanoate as a yellow oil used directly in the next reaction without further purification (1.6 g, crude). (ESI 284.1 (M+H)$^+$).

Step 4: ethyl 2-(3-fluoro-5-(2-(3-fluoroazetidin-1-yl)ethyl)-2-oxopyridin-1(2H)-yl)-3-methylbutanoate

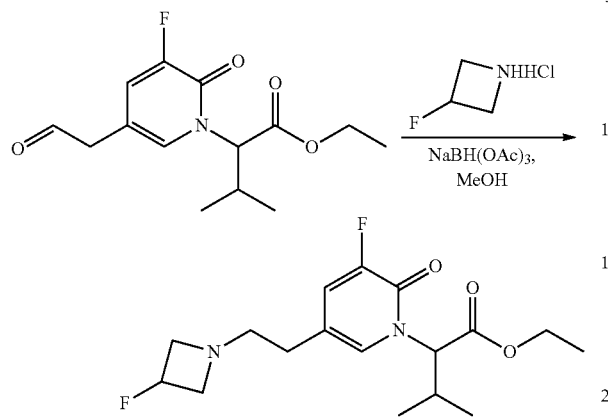

A mixture of ethyl 2-(3-fluoro-2-oxo-5-(2-oxoethyl)pyridin-1(2H)-yl)-3-methylbutanoate (1.6 g, 5.7 mmol, 1.0 eq) and 3-fluoroazetidine hydrochloride (427.5 mg, 5.7 mmol, 1.0 eq) in MeOH (20 mL) was stirred at room temperature for 10 minutes. NaBH(OAc)$_3$ (1.8 g, 8.6 mmol, 1.5 eq) was added and stirred at room temperature for 2 hours. LCMS showed the reaction was completed. The solvent was concentrated in vacuo and the residue was purified by silica gel column (pet ether: EtOAc 1:1) to provide ethyl 2-(3-fluoro-5-(2-(3-fluoroazetidin-1-yl)ethyl)-2-oxopyridin-1(2H)-yl)-3-methylbutanoate as a yellow oil (700 mg). Yield 24% for two steps (ESI 343.1 (M+H)$^+$).

Step 5: 2-(3-fluoro-5-(2-(3-fluoroazetidin-1-yl)ethyl)-2-oxopyridin-1(2H)-yl)-3-methylbutanoic acid

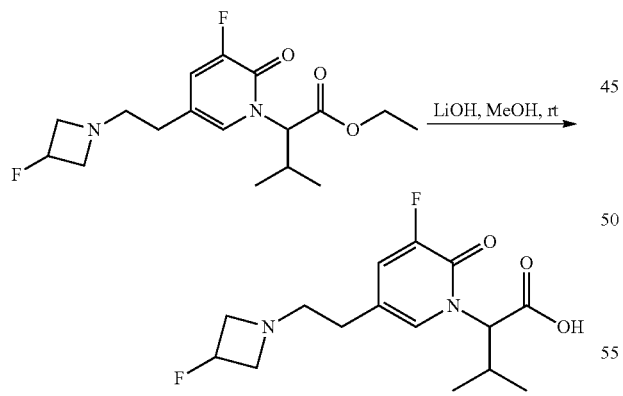

Ethyl 2-(3-fluoro-5-(2-(3-fluoroazetidin-1-yl)ethyl)-2-oxopyridin-1(2H)-yl)-3-methylbutanoate (700 mg, 2.0 mmol, 1.0 eq) was treated with LiOH—H$_2$O (336 mg, 8.0 mmol, 4.0 eq) in MeOH (10 mL) and water (5 mL) at room temperature for 2 hours. The reaction mixture was acidified to pH 5 with 1N HCl and concentrated. The mixture was purified by reverse phase HPLC on a C18/40 g column (A: water 10 mM NH$_4$HCO$_3$, B: MeOH, 0~100%) to provide 2-(3-fluoro-5-(2-(3-fluoroazetidin-1-yl)ethyl)-2-oxopyridin-1(2H)-yl)-3-methylbutanoic acid as a white solid (500 mg). Yield 78% (ESI 315.1 (M+H)$^+$).

Preparation of 2-(3-fluoro-5-(2-((R)-3-fluoropyrrolidin-1-yl)ethyl)-2-oxopyridin-1(2H)-yl)-4-methylpentanoic acid

Step 1: ethyl 2-(3-fluoro-5-(2-((R)-3-fluoropyrrolidin-1-yl)ethyl)-2-oxopyridin-1(2H)-yl)-4-methylpentanoate

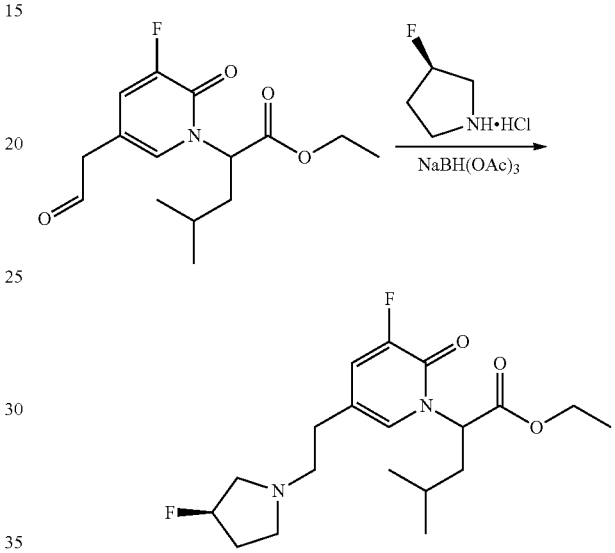

To a mixture of ethyl 2-(3-fluoro-2-oxo-5-(2-oxoethyl)pyridin-1(2)-yl)-4-methylpentanoate (3.3 g, 11.2 mmol) in DCE (70 mL) at 25° C. was added (R)-3-fluoropyrrolidine hydrochloride (1.4 g, 11.2 mmol) and stirred at 25° C. for 30 mins. NaBH(OAc)$_3$ (4.6 g, 22.4 mmol) was added at 5° C. and stirred at 25° C. for 16 hours. The mixture was concentrated in vacuo and the residue was purified by silica gel column (DCM:MeOH 10:1) to give compound ethyl 2-(3-fluoro-5-(2-((R)-3-fluoropyrrolidin-1-yl)ethyl)-2-oxopyridin-1(2H)-yl)-4-methylpentanoate (1.7 g) as a yellow oil. Yield 41% (ESI 371.2 (M+H)$^+$).

Step 2: 2-(3-fluoro-5-(2-((R)-3-fluoropyrrolidin-1-yl)ethyl)-2-oxopyridin-1(2H)-yl)-4-methylpentanoic acid

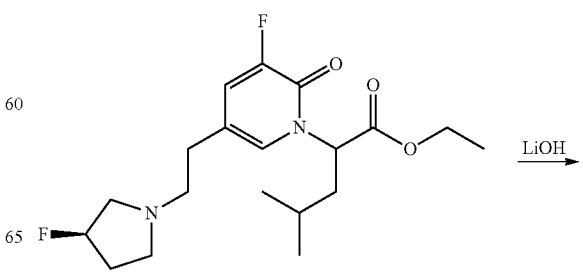

-continued

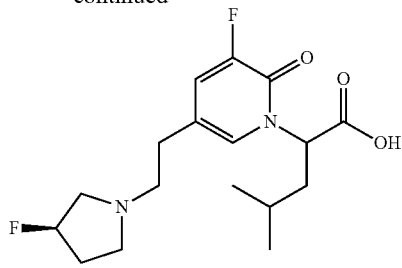

Ethyl 2-(3-fluoro-5-(2-((R)-3-fluoropyrrolidin-1-yl)ethyl)-2-oxopyridin-1(2H)-yl)-4-methylpentanoate (1.7 g, 4.59 mmol) was treated with LiOH—H$_2$O (960.0 mg, 23.0 mmol, 5.0 eq) in MeOH (12 mL) and water (5 mL) at room temperature for 2 hours. The MeOH was removed and the aqueous acidified with 1N HCl to pH=5. The residue was purified by reverse phase HPLC on a C18/40 g column (A: water 10 mM NH$_4$HCO$_3$, B: MeOH, 0~100%) to provide 2-(3-fluoro-5-(2-((R)-3-fluoropyrrolidin-1-yl)ethyl)-2-oxopyridin-1(2H)-yl)-4-methylpentanoic acid as a white solid (1.1 g). Yield 70% (ESI 343.1 (M+H)$^+$).

Preparation of 2-(5-(2-(dimethylamino)ethyl)-3-fluoro-4-methyl-2-oxopyridin-1(2H)-yl)-4-methylpentanoic acid Step 1: 3-fluoro-4-methylpyridin-2(1H)-one

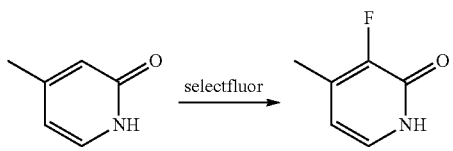

A mixture of 4-methylpyridin-2(1H)-one (10 g, 92 mmol, 1.0 eq) and selectfluor (16 g, 46 mmol, 0.5 eq) in CHCl$_3$ (100 mL) and water (100 mL) was stirred at 35° C. for 16 h. The reaction mixture was diluted with a saturated NaCl solution (100 mL) and extracted with DCM (100 mL×3). The combined organic phase was dried over anhydrous Na$_2$SO$_4$, filtered and concentrated in vacuo. The residue was purified by silica gel column (EtOAc: DCM:MeOH 100:10:6) to provide 3-fluoro-4-methylpyridin-2(1H)-one as a white solid (2.4 g). Yield 21% (ESI 128 (M+H)$^+$). $^1$H NMR (400 MHz, CDCl$_3$) δ 13.53 (s, 1H), 7.20 (dd, J=6.6, 0.6 Hz, 1H), 6.14 (t, J=6.1 Hz, 1H), 2.24 (d, J=2.5 Hz, 3H). $^{19}$F NMR (376 MHz, CDCl$_3$) δ −140.20.

Step 2:
5-bromo-3-fluoro-4-methylpyridin-2(1H)-one

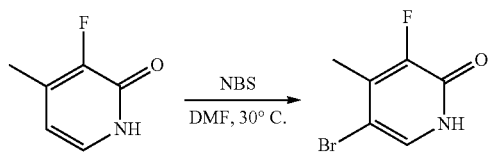

To a solution of 3-fluoro-4-methylpyridin-2(1H)-one (2.4 g, 18.9 mmol, 1.0 eq) in DMF (20 mL) was added NBS (3.7 g, 20.8 mmol, 1.1 eq) and stirred at 30° C. for 1 h. The reaction mixture was purified by reverse phase HPLC (A: water (0.01% TFA); B ACN, 45% of B) to provide 5-bromo-3-fluoro-4-methylpyridin-2(1H)-one as a white solid (3 g). Yield 77% (ESI 206 (M+H)$^+$). $^1$H NMR (500 MHz, CDCl$_3$) δ 7.42 (d, J=1.3 Hz, 1H), 2.31 (d, J=3.0 Hz, 3H).

Step 3: ethyl 2-(5-bromo-3-fluoro-4-methyl-2-oxopyridin-1(2H)-yl)-4-methylpentanoate

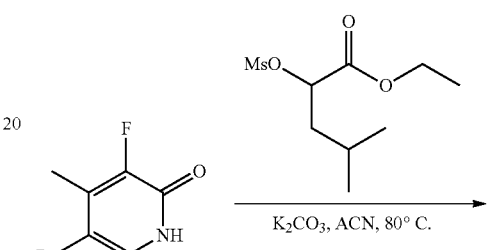

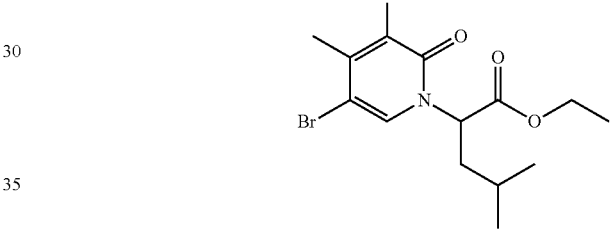

A mixture of 5-bromo-3-fluoro-4-methylpyridin-2(1H)-one (3.0 g, 14.6 mmol, 1.0 eq), K$_2$CO$_3$ (4 g, 29.3 mmol, 2.0 eq) and ethyl 4-methyl-2-((methylsulfonyl)oxy)pentanoate (7 g, 29.3 mmol, 2 eq) in CH$_3$CN (50 mL) was stirred at 80° C. for 16 h. LCMS showed the reaction was completed. The mixture was filtered and washed with CH$_3$CN (20 mL). The filtrate was concentrated in vacuo and the residue was purified by silica gel column (pet ether: EtOAc 4:1) to provide ethyl 2-(5-bromo-3-fluoro-4-methyl-2-oxopyridin-1(2H)-yl)-4-methylpentanoate as a yellow oil (4.5 g). Yield 89% (ESI 348 (M+H)$^+$).

Step 4: ethyl 2-(5-allyl-3-fluoro-4-methyl-2-oxopyridin-1(2H)-yl)-4-methylpentanoate

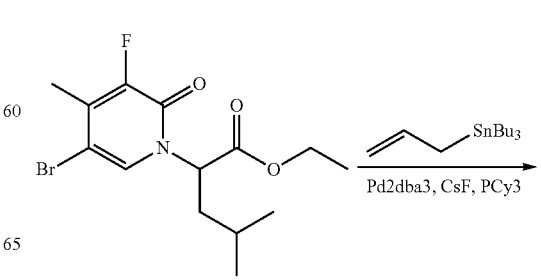

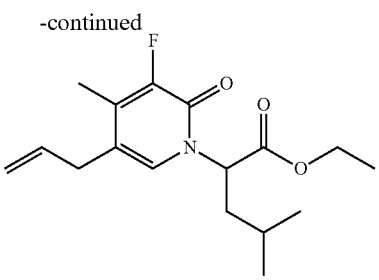

A mixture of ethyl 2-(5-bromo-3-fluoro-4-methyl-2-oxopyridin-1(2H)-yl)-4-methylpentanoate (4.5 g, 13 mmol, 1.0 eq), allyltributylstannane (35.6 g, 16.9 mmol, 1.3 eq), Pd$_2$dba$_3$ (595 mg, 0.65 mmol, 0.05 eq), tricyclohexyl phosphine (364 mg, 1.3 mmol, 0.1 eq) and CsF (4 g, 26 mmol, 2.0 eq) in anhydrous dioxane (100 mL) was stirred under N$_2$ at 100° C. for 16 hours. The mixture was cooled to room temperature. A saturated NH$_4$Cl solution (100 mL) was added and the solution was extracted with EtOAc (100 mL×3). The combined organic layers were washed with brine (100 mL), dried over anhydrous Na$_2$SO$_4$, filtered and concentrated in vacuo. The residue was purified by silica gel column (pet ether: EtOAc 4:1) to provide ethyl 2-(5-allyl-3-fluoro-4-methyl-2-oxopyridin-1(2H)-yl)-4-methylpentanoate as a yellow solid (2 g). Yield 50% (ESI 310 (M+H)$^+$). $^1$H NMR (400 MHz, CDCl$_3$) δ 6.86 (s, 1H), 5.93-5.84 (m, 1H), 5.77-5.73 (m, 1H), 5.18-5.03 (m, 2H), 4.20 (q, J=8 Hz, 2H), 3.18-3.14 (m, 2H), 2.13 (d, J=2.8 Hz, 3H), 2.01-1.94 (m, 1H), 1.90-1.84 (m, 1H), 1.45-1.37 (m, 1H), 1.26 (t, J=8 Hz, 2H), 0.98-0.91 (m, 6H).

Step 5: ethyl 2-(3-fluoro-4-methyl-2-oxo-5-(2-oxoethyl)pyridin-1(2H)-yl)-4-methylpentanoate

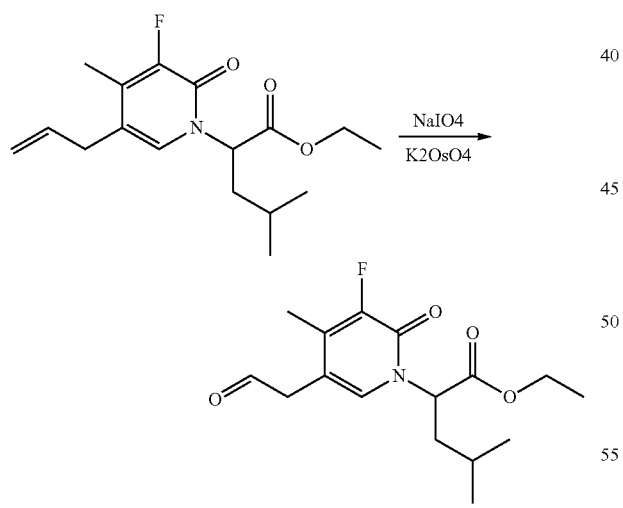

To a solution of ethyl 2-(5-allyl-3-fluoro-4-methyl-2-oxopyridin-1(2H)-yl)-4-methylpentanoate (1.8 g, 5.8 mmol, 1.0 eq) in THF/H$_2$O (60 mL/20 mL) was added a solution of K$_2$OsO$_4$·2H$_2$O (21 mg, 0.058 mmol, 0.01 eq) in H$_2$O (4 mL) and stirred at room temperature for 1 h. Then a solution of NaIO$_4$ (1.25 g, 11.7 mmol, 2.0 eq) in H$_2$O (20 mL) was added and stirred at room temperature for 2 h. LCMS showed the reaction was completed. The reaction mixture was diluted with 100 mL of water and extracted with EtOAc (100 mL×3). The combined organic phase was dried over anhydrous Na$_2$SO$_4$, filtered and concentrated in vacuo to provide ethyl 2-(3-fluoro-4-methyl-2-oxo-5-(2-oxoethyl)pyridin-1(2H)-yl)-4-methylpentanoate as a yellow oil used directly in the next reaction without further purification (2 g, crude). (ESI 312 (M+H)$^+$).

Step 6: ethyl 2-(5-(2-(dimethylamino)ethyl)-3-fluoro-4-methyl-2-oxopyridin-1(2H)-yl)-4-methylpentanoate

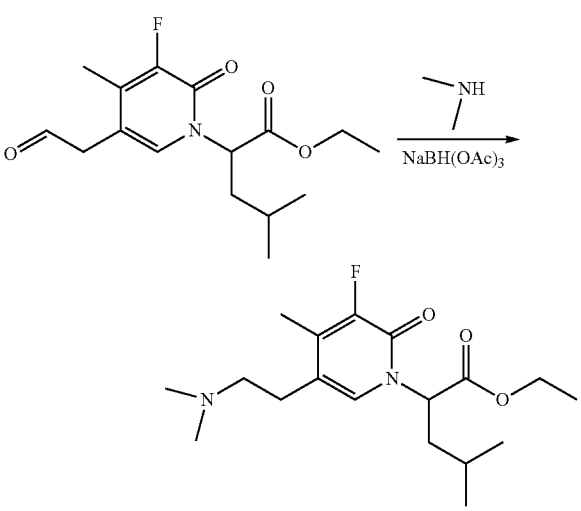

A mixture of ethyl 2-(3-fluoro-4-methyl-2-oxo-5-(2-oxoethyl)pyridin-1(2H)-yl)-4-methylpentanoate (2.0 g, 6.42 mmol) and dimethylamine (9.64 mL, 19.27 mmol) (2.0 M) in THF was added in DCE (32.1 mL) and stirred at room temperature for 10 mins. NaBH(OAc)$_3$ (4.08 g, 19.3 mmol, 3.0 eq) was added to the reaction mixture and stirred at room temperature for 2 h. The mixture was diluted with water (50 mL) and extracted with DCM (50 mL×3). The combined organic phase was dried over anhydrous Na$_2$SO$_4$. The solvent was removed in vacuo and the residue was purified by reverse phase HPLC in NH$_4$HCO$_3$ condition (A: water 10 mM NH$_4$HCO$_3$, B: MeOH, 0~100%) to provide ethyl 2-(5-(2-(dimethylamino)ethyl)-3-fluoro-4-methyl-2-oxopyridin-1(2H)-yl)-4-methylpentanoate (1.41 g, 4.14 mmol, 64.5% yield) as yellow oil. (ESI 341 (M+H)$^+$).

Step 7: 2-(5-(2-(dimethylamino)ethyl)-3-fluoro-4-methyl-2-oxopyridin-1(2H)-yl)-4-methylpentanoic acid

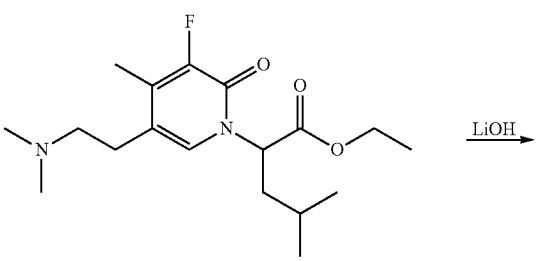

249

-continued

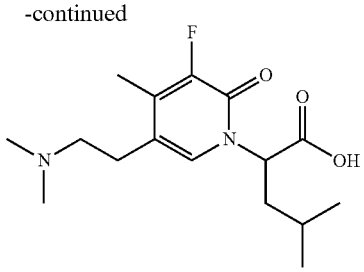

Ethyl 2-(5-(2-(dimethylamino)ethyl)-3-fluoro-4-methyl-2-oxopyridin-1(2H)-yl)-4-methylpentanoate (1.41 g, 4.14 mmol) was treated with lithium hydroxide (0.496 g, 20.71 mmol) in MeOH (10 mL) and water (5 mL) at room temperature for 2 hours. The MeOH was removed and the aqueous acidified with 1N HCl to pH=5. The residue was purified by reverse phase HPLC in neutral condition (A: water, B: MeOH, 0~100%) to provide 2-(5-(2-(dimethylamino)ethyl)-3-fluoro-4-methyl-2-oxopyridin-1(2H)-yl)-4-methylpentanoic acid (1.21 g, 3.87 mmol, 94% yield) (ESI 313 (M+H)$^+$).

Preparation of 2-(3-fluoro-5-(2-(3-fluoroazetidin-1-yl)ethyl)-4-methyl-2-oxopyridin-1(2H)-yl)-4-methylpentanoic acid Step 1: ethyl 2-(3-fluoro-5-(2-(3-fluoroazetidin-1-yl)ethyl)-4-methyl-2-oxopyridin-1(2H)-yl)-4-methylpentanoate

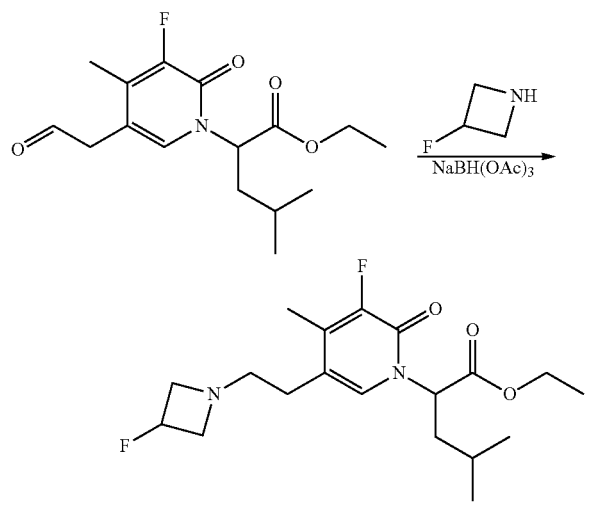

A mixture of ethyl 2-(3-fluoro-4-methyl-2-oxo-5-(2-oxoethyl)pyridin-1(2H)-yl)-4-methylpentanoate (2 g, 6.4 mmol) and 3-fluoroazetidine hydrochloride (2.1 g, 19.3 mmol, 3.0 eq) in DCE (20 mL) was stirred at room temperature for 10 minutes. NaBH(OAc)$_3$ (4.2 g, 19.3 mmol, 3.0 eq) was added to the reaction mixture and stirred at room temperature for 2 h. The mixture was diluted with water (50 mL) and extracted with DCM (50 mL×3). The combined organic phase was dried over anhydrous Na$_2$SO$_4$, filtered and concentrated in vacuo and the residue was purified by reverse phase HPLC (A: water 10 mM NH$_4$HCO$_3$, B: MeOH, 70% B) to provide ethyl 2-(3-fluoro-5-(2-(3-fluoroazetidin-1-yl)ethyl)-4-methyl-2-oxopyridin-1(2H)-yl)-4-methylpentanoate as a yellow oil (1 g). Yield 42% (ESI 371 (M+H)$^+$).

250

Step 2: 2-(3-fluoro-5-(2-(3-fluoroazetidin-1-yl)ethyl)-4-methyl-2-oxopyridin-1(2H)-yl)-4-methylpentanoic acid

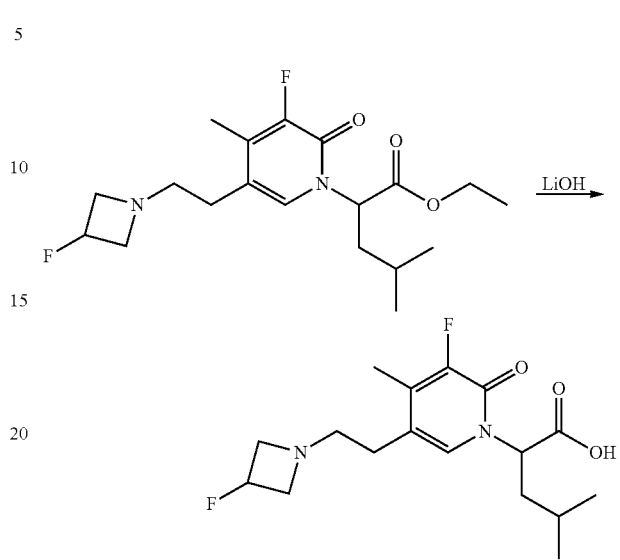

Ethyl 2-(3-fluoro-5-(2-(3-fluoroazetidin-1-yl)ethyl)-4-methyl-2-oxopyridin-1(2H)-yl)-4-methylpentanoate (1 g, 2.7 mmol, 1.0 eq) was treated with LiOH—H$_2$O (567 mg, 13.5 mmol, 5.0 eq) in MeOH (10 mL) and water (5 mL) at room temperature for 2 hours. The reaction mixture was acidified to pH 5 with 1N HCl and concentrated. The mixture was purified by reverse phase HPLC in neutral condition (A: water, B: MeOH, 60% B) to provide 2-(3-fluoro-5-(2-(3-fluoroazetidin-1-yl)ethyl)-4-methyl-2-oxopyridin-1(2H)-yl)-4-methylpentanoic acid as a white solid (800 mg). Yield 86% (ESI 343 (M+H)$^+$).

Preparation of 2-(3-fluoro-5-(2-(3-methoxyazetidin-1-yl)ethyl)-4-methyl-2-oxopyridin-1(2H)-yl)-4-methylpentanoic acid Step 1: ethyl 2-(3-fluoro-5-(2-(3-methoxyazetidin-1-yl)ethyl)-4-methyl-2-oxopyridin-1(2H)-yl)-4-methylpentanoate

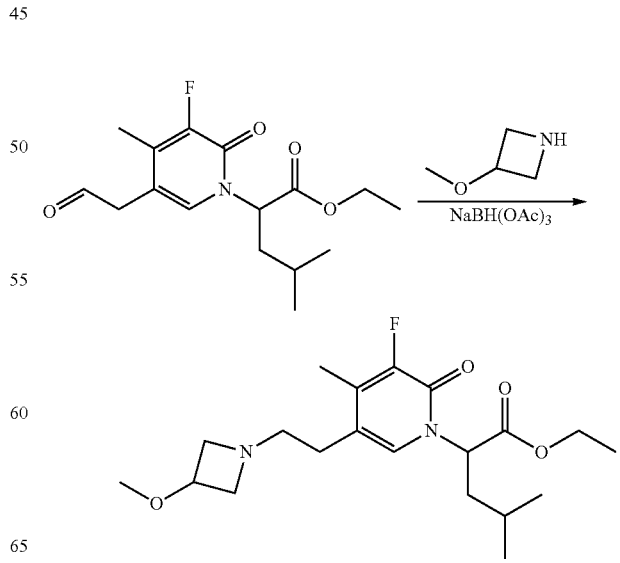

A mixture of ethyl 2-(3-fluoro-4-methyl-2-oxo-5-(2-oxo-ethyl)pyridin-1(2H)-yl)-4-methylpentanoate (4.5 g, 14.4 mmol) and 3-methoxyazetidine hydrochloride (2.7 g, 21.7 mmol) in DCE (20 mL) was stirred at room temperature for 1 h. NaBH(OAc)$_3$ (6.2 g, 29.2 mmol) was added and stirred at room temperature for 2 h. The mixture was diluted with water (50 mL) and extracted with DCM (50 mL×3). The combined organic phase was dried over anhydrous Na$_2$SO$_4$, filtered and concentrated in vacuo and the residue was purified by reverse phase HPLC on a C18/120 g column (A: water 10 mM NH$_4$HCO$_3$, B: MeOH, 0~100%) to provide ethyl 2-(3-fluoro-5-(2-(3-methoxyazetidin-1-yl)ethyl)-4-methyl-2-oxopyridin-1(2H)-yl)-4-methylpentanoate as a yellow oil (2.7 g). Yield 49% (ESI 383.1 (M+H)$^+$).

Step 2: 2-(3-fluoro-5-(2-(3-methoxyazetidin-1-yl)ethyl)-4-methyl-2-oxopyridin-1(2H)-yl)-4-methyl-pentanoic acid

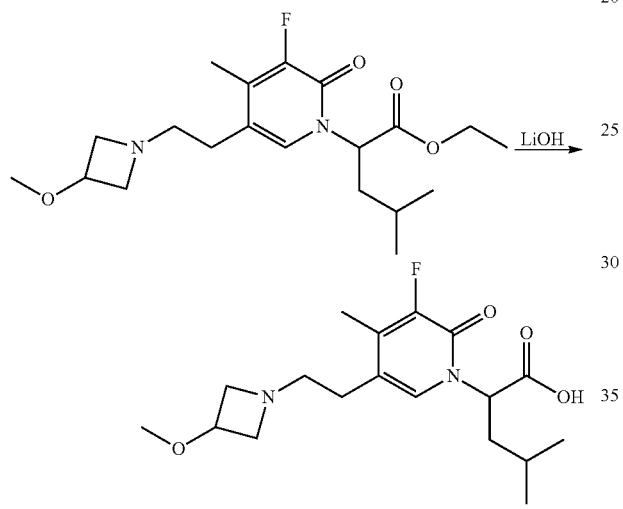

Ethyl 2-(3-fluoro-5-(2-(3-methoxyazetidin-1-yl)ethyl)-4-methyl-2-oxopyridin-1(2H)-yl)-4-methylpentanoate (3.0 g, 7.9 mmol) was treated with LiOH—H$_2$O (1.6 g, 39.3 mmol) in EtOH (20 mL) and water (5 mL) at room temperature for 2 hours. The EtOH was removed and the aqueous acidified with 1N HCl to pH 5 and concentrated. The mixture was purified by reverse phase HPLC on a C18/120 g column (A: water, B: MeOH, 0~100%) to provide 2-(3-fluoro-5-(2-(3-fluoroazetidin-1-yl)ethyl)-4-methyl-2-oxopyridin-1(2H)-yl)-4-methylpentanoic acid as a white solid (2.4 g). Yield 86% (ESI 355.3 (M+H)$^+$).

Preparation of 2-(5-(2-(dimethylamino)ethyl)-3-fluoro-2-oxo-4-(trifluoromethyl)pyridin-1(2H)-yl)-4-methylpentanoic acid Step 1: 5-bromo-3-fluoro-4-(trifluoromethyl)pyridin-2-ol

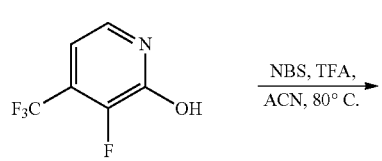

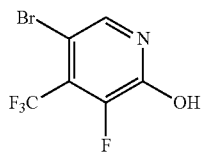

A mixture of 3-fluoro-4-(trifluoromethyl)pyridin-2-ol (16.0 g, 88.35 mmol) and NBS (23.5 g, 132.53 mmol) in TFA (32 mL) and MeCN (320 mL) was stirred at 80° C. for 24 hours. LCMS showed the reaction was completed. The reaction was concentrated in vacuo and the residue was purified by silica gel column (petroleum ether: EtOAc 1:1) to provide 5-bromo-3-fluoro-4-(trifluoromethyl)pyridin-2-ol as a white solid (19.7 g). Yield 86% (ESI 259.9 (M+H)$^+$).

Step 2: ethyl 2-(5-bromo-3-fluoro-2-oxo-4-(trifluoromethyl)pyridin-1(2H)-yl)-4-methylpentanoate

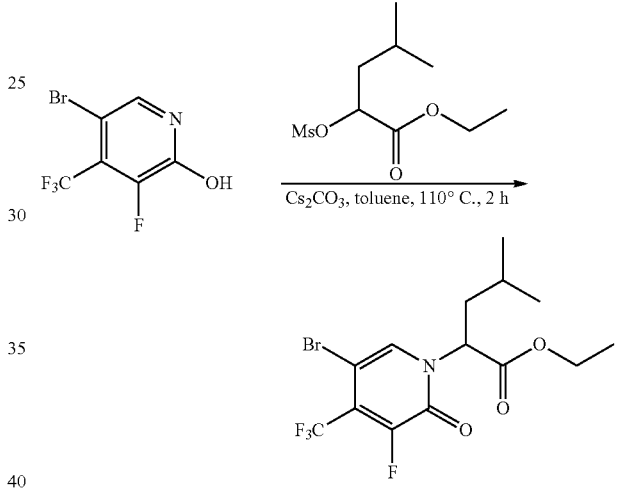

A mixture of 5-bromo-3-fluoro-4-(trifluoromethyl)pyridin-2-ol (19.7 g, 75.77 mmol), Cs$_2$CO$_3$ (49.3 g, 151.54 mmol) and ethyl 4-methyl-2-((methylsulfonyl)oxy)pentanoate (23.5 g, 98.5 mmol) in toluene (100 mL) was stirred at 110° C. for 2 h. LCMS showed the reaction was completed. The mixture was filtered and washed with EtOAc (20 mL). The filtrate was concentrated in vacuo and the residue was purified by silica gel column (pet ether: EtOAc 10:1) to provide ethyl 2-(5-bromo-3-fluoro-2-oxo-4-(trifluoromethyl)pyridin-1(2H)-yl)-4-methylpentanoate as a white solid (12.4 g). Yield 41% (ESI 402.0 (M+H)$^+$).

Step 3: ethyl (E)-2-(5-(2-ethoxyvinyl)-3-fluoro-2-oxo-4-(trifluoromethyl)pyridin-1(2H)-yl)-4-methylpentanoate

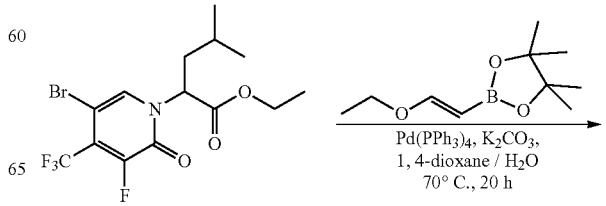

253

-continued

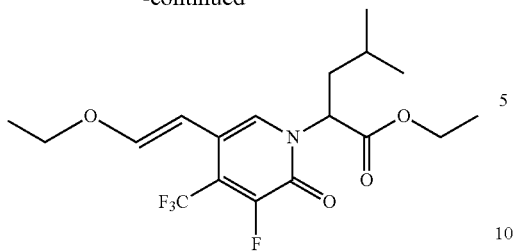

A mixture of ethyl 2-(5-bromo-3-fluoro-2-oxo-4-(trifluoromethyl)pyridin-1(2H)-yl)-4-methylpentanoate (9.7 g, 24.12 mmol), (E)-2-(2-ethoxyvinyl)-4,4,5,5-tetramethyl-1,3,2-dioxaborolane (5.7 g, 28.94 mmol), Pd(PPh$_3$)$_4$ (832 mg, 0.72 mmol,) and K$_2$CO$_3$ (6.7 g, 48.24 mmol) in 1,4-dioxane (100 mL) and water (10 mL) was stirred at 70° C. under N$_2$ for 20 h. The reaction mixture was poured into 100 mL of water and extracted with EtOAc (100 mL×2). The combined organic phase was washed with brine (30 mL), dried over anhydrous Na$_2$SO$_4$, filtered and concentrated in vacuo. The residue was purified by silica gel column (pet ether: EtOAc 10:1) to provide ethyl (E)-2-(5-(2-ethoxyvinyl)-3-fluoro-2-oxo-4-(trifluoromethyl)pyridin-1(2H)-yl)-4-methylpentanoate (6.0 g). Yield 63% (ESI 394.1 (M+H)$^+$).

Step 4: ethyl 2-(3-fluoro-2-oxo-5-(2-oxoethyl)-4-(trifluoromethyl)pyridin-1(2H)-yl)-4-methylpentanoate

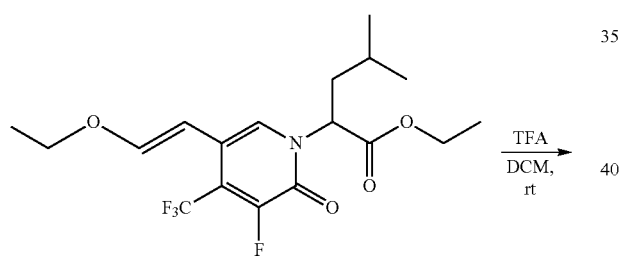

To a mixture of ethyl (E)-2-(5-(2-ethoxyvinyl)-3-fluoro-2-oxo-4-(trifluoromethyl)pyridin-1(2H)-yl)-4-methylpentanoate (6.0 g, 15.25 mmol) in DCM (50 mL) was added TFA (5 mL). The mixture was stirred at room temperature for 3 hours. LCMS showed that the reaction was completed. The mixture was concentrated in vacuo. The residue was dissolved in EtOAc (100 mL), washed with saturated NaHCO$_3$(30 mL) and brine (30 mL), dried over anhydrous Na$_2$SO$_4$, filtered and concentrated in vacuo to give crude product ethyl 2-(3-fluoro-2-oxo-5-(2-oxoethyl)-4-(trifluoromethyl)pyridin-1(2H)-yl)-4-methylpentanoate as a colorless oil (5.5 g) used directly in the next reaction without further purification. Yield 99% (ESI 366.1 [M+H]$^+$).

254

Step 5: ethyl 2-(5-(2-(dimethylamino)ethyl)-3-fluoro-2-oxo-4-(trifluoromethyl)pyridin-1(2H)-yl)-4-methylpentanoate

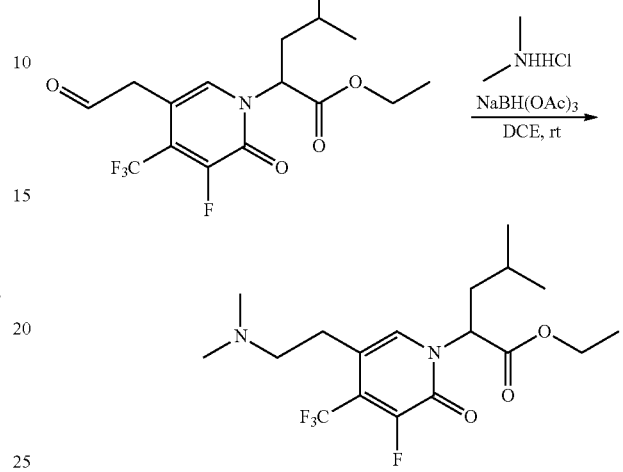

To a mixture of ethyl 2-(3-fluoro-2-oxo-5-(2-oxoethyl)-4-(trifluoromethyl)pyridin-1(2H)-yl)-4-methylpentanoate (5.5 g, 15.06 mmol) in DCE (100 mL) at 25° C. was added dimethylamine hydrochloride (2.5 g, 30.12 mmol) and stirred for 1 hour. NaBH(OAc)$_3$ (6.4 g, 30.12 mmol) was added at 5° C. and stirred at 25° C. for 16 hours. The mixture was concentrated in vacuo and the residue was purified by silica gel column (DCM:MeOH 10:1) to provide ethyl 2-(5-(2-(dimethylamino)ethyl)-3-fluoro-2-oxo-4-(trifluoromethyl)pyridin-1(2H)-yl)-4-methylpentanoate as a brown oil (4.5 g) Yield 76% (ESI 395.1 [M+H]$^+$).

Step 6: 2-(5-(2-(dimethylamino)ethyl)-3-fluoro-2-oxo-4-(trifluoromethyl)pyridin-1(2H)-yl)-4-methylpentanoic acid

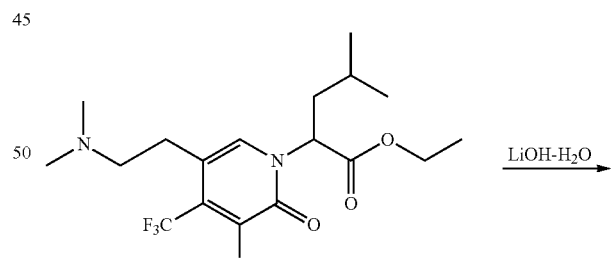

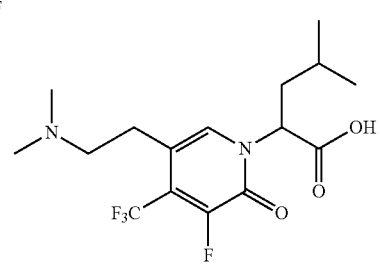

Ethyl 2-(5-(2-(dimethylamino)ethyl)-3-fluoro-2-oxo-4-(trifluoromethyl)pyridin-1(2H)-yl)-4-methylpentanoate (4.5 g, 11.41 mmol) was treated with LiOH—H$_2$O (2.4 g, 57.05 mmol) in EtOH (10 mL) and water (2 mL) and the mixture was stirred at room temperature for 1 hour. The mixture was acidified with 1N HCl to pH=5~6, concentrated and purified by reverse phase HPLC on a C18/40 g column (A: water 10 mM NH$_4$HCO$_3$, B: MeOH, 0~100%) to provide 2-(5-(2-(dimethylamino)ethyl)-3-fluoro-2-oxo-4-(trifluoromethyl)pyridin-1(2H)-yl)-4-methylpentanoic acid as a white solid (3.7 g). Yield 89% (ESI 367.1 (M+H)$^+$).

Example 3: Synthesis of Exemplary Compounds of the Invention

Prep-HPLC Methods

Crude samples were dissolved in MeOH and purified by prep HPLC using a Gilson 215 instrument, detection wavelength 214 nm:

Prep HPLC A: column: Xtimate C18, 21.2*250 mm, 10 μm; mobile phase: A water (10 mM ammonium hydrogen carbonate), B CH$_3$CN; gradient elution as in text; flow rate: 30 mL/min.

Prep HPLC B: column: Xtimate C18, 21.2*250 mm, 10 μm; mobile phase: A water (0.1% formic acid), B CH$_3$CN; gradient elution as in text; flow rate: 30 mL/min.

3-1. Preparation of (3S)-3-(4,5-difluoro-2',6'-dimethylbiphenyl-3-yl)-3-(2-(5-(2-(3-fluoroazetidin-1-yl)ethyl)-4-methyl-2-oxopyridin-1(2H)-yl)-4-methylpentanamido)propanoic acid (compounds D-P1 and D-P2)

Step 1: (3S)-ethyl 3-(4,5-difluoro-2',6'-dimethylbiphenyl-3-yl)-3-(2-(5-(2-(3-fluoroazetidin-1-yl)ethyl)-4-methyl-2-oxopyridin-1(2H)-yl)-4-methylpentanamido)propanoate

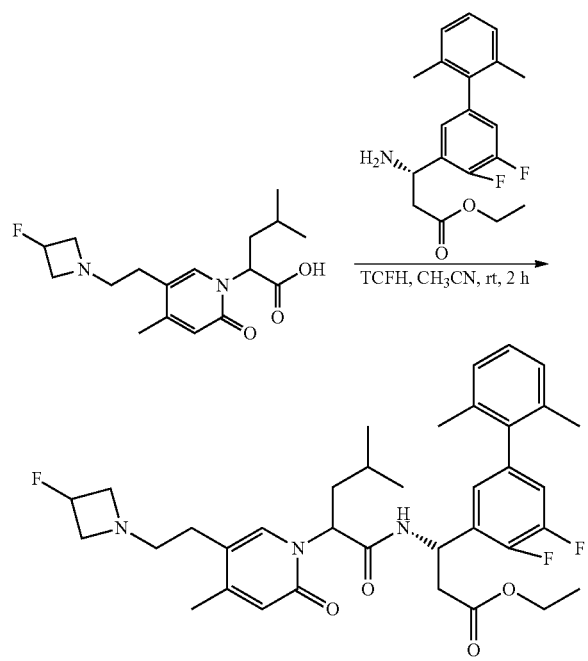

A mixture of 2-(5-(2-(3-fluoroazetidin-1-yl)ethyl)-4-methyl-2-oxopyridin-1(2H)-yl)-4-methylpentanoic acid (84 mg, 0.26 mmol), (S)-ethyl 3-amino-3-(4,5-difluoro-2',6'-dimethylbiphenyl-3-yl)propanoate (173 mg, 0.52 mmol), TCFH (94 mg, 0.34 mmol), and NMI (0.30 mL, 3.76 mmol) in acetonitrile (5 mL) was stirred at room temperature for 2 hours. The reaction mixture was poured into 100 mL of EtOAc, washed with water (30 mL), brine (30 mL), dried over Na$_2$SO$_4$, filtered and concentrated in vacuo. The reaction mixture was concentrated in vacuo and purified by reverse phase HPLC on a C18/40 g column (A: water/0.01% TFA, B: MeOH, 0~64%) to provide (3S)-ethyl 3-(4,5-difluoro-2',6'-dimethylbiphenyl-3-yl)-3-(2-(5-(2-(3-fluoroazetidin-1-yl)ethyl)-4-methyl-2-oxopyridin-1(2H)-yl)-4-methylpentanamido)propanoate as a white solid (131 mg). Yield 79% (ESI 640.2 (M+H)$^+$).

Step 2: (3S)-3-(4,5-difluoro-2',6'-dimethylbiphenyl-3-yl)-3-(2-(5-(2-(3-fluoroazetidin-1-yl)ethyl)-4-methyl-2-oxopyridin-1(2H)-yl)-4-methylpentanamido)propanoic acid

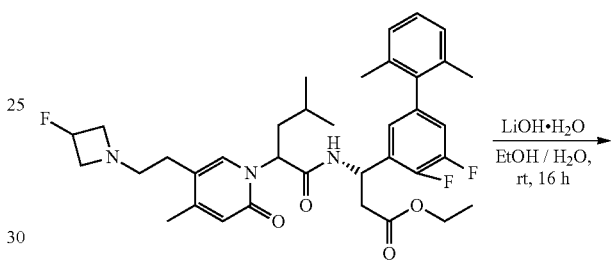

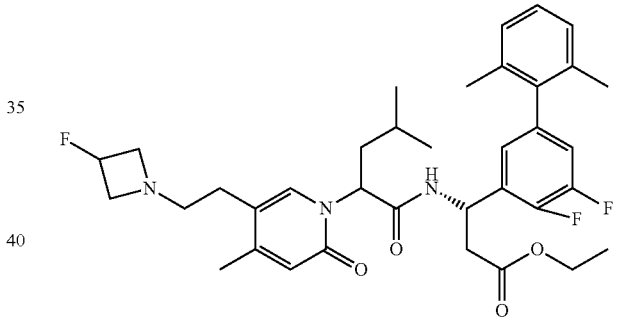

(3S)-ethyl 3-(4,5-difluoro-2',6'-dimethylbiphenyl-3-yl)-3-(2-(5-(2-(3-fluoroazetidin-1-yl)ethyl)-4-methyl-2-oxopyridin-1(2H)-yl)-4-methylpentanamido)propanoate (131 mg, 0.20 mmol) was treated with LiOH monohydrate (72 mg, 1.71 mmol) in EtOH (12.5 mL) and H$_2$O (0.25 mL) at room temperature for 16 hours. The reaction mixture was acidified to pH 4~5 with concentrated HCl. The reaction mixture was concentrated in vacuo and purified by prep-HPLC A (30-60% MeCN) to give the diastereomeric products D-P1 (23 mg) and D-P2 (23 mg) as a white solid.

D-P1 ESI 612.2 (M+H)$^+$. $^1$H NMR (500 MHz, MeOD) δ 7.46 (s, 1H), 7.14 (t, J=8.0 Hz, 1H), 7.07 (t, J=6.0 Hz, 2H), 6.93-6.89 (m, 1H), 6.81 (d, J=5.5 Hz, 1H), 6.27 (s, 1H), 5.59-5.54 (m, 2H), 5.28-5.12 (m, 1H), 4.07-3.94 (m, 2H), 3.74-3.60 (m, 2H), 3.05-2.99 (m, 2H), 2.79-2.69 (m, 2H), 2.65-2.59 (m, 2H), 2.20 (s, 3H), 1.99 (s, 3H), 1.92 (t, J=7.0 Hz, 2H), 1.85 (s, 3H), 1.44-1.36 (m, 1H), 0.93 (d, J=6.5 Hz, 3H), 0.90 (d, J=6.5 Hz, 3H).

D-P2 ESI 612.2 (M+H)$^+$. $^1$H NMR (500 MHz, MeOD) δ 7.46 (s, 1H), 7.14 (t, J=8.0 Hz, 1H), 7.07 (t, J=6.0 Hz, 2H), 6.93-6.89 (m, 1H), 6.81 (d, J=5.5 Hz, 1H), 6.27 (s, 1H), 5.59-5.54 (m, 2H), 5.28-5.12 (m, 1H), 4.07-3.94 (m, 2H), 3.75-3.60 (m, 2H), 3.06-2.98 (m, 2H), 2.79-2.69 (m, 2H), 2.65-2.59 (m, 2H), 2.20 (s, 3H), 1.99 (s, 3H), 1.92 (t, J=7.0 Hz, 2H), 1.85 (s, 3H), 1.44-1.36 (m, 1H), 0.93 (d, J=6.5 Hz, 3H), 0.90 (d, J=6.5 Hz, 3H).

3-2. Preparation of (3S)-3-(3-cyclopropyl-2-(5-(2-(3-fluoroazetidin-1-yl)ethyl)-2-oxopyridin-1(2H)-yl) propanamido)-3-(4,5-difluoro-2',6'-dimethyl-[1,1'-biphenyl]-3-yl)propanoic acid (compounds E-P1 and E-P2)

Step 1: ethyl(3S)-3-(3-cyclopropyl-2-(5-(2-(3-fluoroazetidin-1-yl)ethyl)-2-oxopyridin-1(2H)-yl)propanamido)-3-(4,5-difluoro-2',6'-dimethyl-[1,1'-biphenyl]-3-yl)propanoate

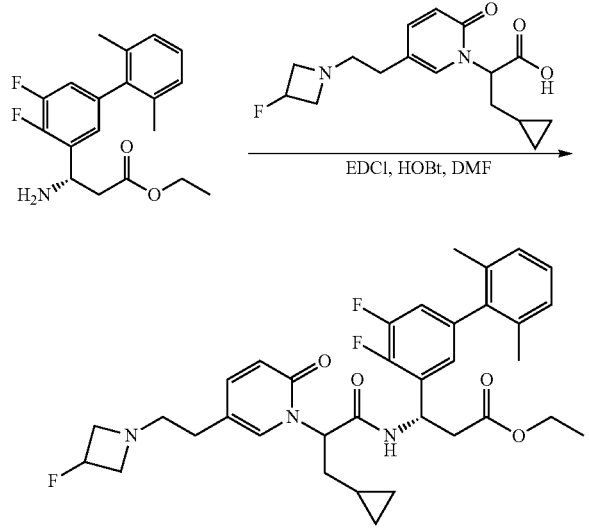

A mixture of ethyl (S)-3-amino-3-(4,5-difluoro-2',6'-dimethyl-[1,1'-biphenyl]-3-yl)propanoate (90 mg, 0.27 mmol), 3-cyclopropyl-2-(5-(2-(3-fluoroazetidin-1-yl)ethyl)-2-oxopyridin-1(2H)-yl)propanoic acid (125 mg, 0.40 mmol), HOBT (73 mg, 0.54 mmol), EDCI (104 mg, 0.54 mmol) and TEA (120 mg, 0.81 mmol) in DMF (2 mL) was stirred at 50° C. for 4 hours. The reaction mixture was concentrated in vacuo and purified by reverse phase HPLC on a C18/40 g column (A: water 10 mM NH$_4$HCO$_3$, B: MeOH, 0~100%) to provide ethyl (3S)-3-(3-cyclopropyl-2-(5-(2-(3-fluoroazetidin-1-yl)ethyl)-2-oxopyridin-1(2H)-yl)propanamido)-3-(4,5-difluoro-2',6'-dimethyl-[1,1'-biphenyl]-3-yl)propanoate as a yellow oil (60 mg). Yield 35% (ESI 624.2 (M+H)$^+$).

Step 2: (3S)-3-(3-cyclopropyl-2-(5-(2-(3-fluoroazetidin-1-yl)ethyl)-2-oxopyridin-1(2H)-yl)propanamido)-3-(4,5-difluoro-2',6'-dimethyl-[1,1'-biphenyl]-3-yl)propanoic acid

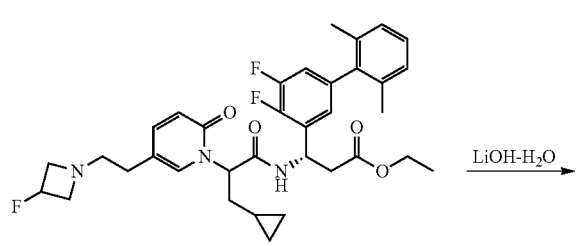

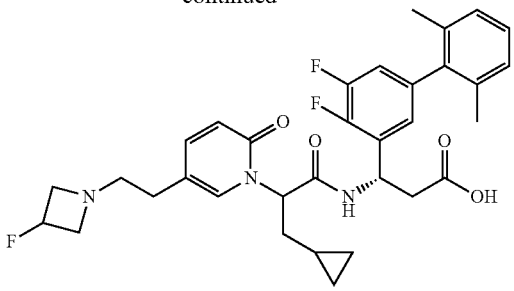

Ethyl (3S)-3-(3-cyclopropyl-2-(5-(2-(3-fluoroazetidin-1-yl)ethyl)-2-oxopyridin-1(2H)-yl)propanamido)-3-(4,5-difluoro-2',6'-dimethyl-[1,1'-biphenyl]-3-yl)propanoate (50 mg, 0.08 mmol) was treated with LiOH—H$_2$O (13 mg, 0.32 mmol) in MeOH (2 mL) and H$_2$O (0.5 mL) at room temperature for 1 hour. The reaction mixture was acidified to pH 4~5 with 1N HCl. The solvent was removed in vacuo and the residue was purified by prep-HPLC A (30-60% MeCN) to give the diastereomeric products E-P1 (1 mg) and E-P2 (1 mg) as a white solid.

E-P1 ESI 596.2 (M+H)$^+$. $^1$H NMR (500 MHz, MeOD) δ 7.47 (s, 1H), 7.33 (d, J=7.2 Hz, 1H), 7.07-6.99 (m, 3H), 6.88-6.80 (m, 1H), 6.71-6.70 (m, 1H), 6.34 (d, J=9.2 Hz, 1H), 5.45 (s, 2H), 5.19-5.03 (m, 1H), 3.96-3.84 (m, 2H), 3.57 (s, 2H), 2.97-2.96 (m, 2H), 2.67 (s, 2H), 2.50 (s, 2H), 1.91 (s, 5H), 1.79 (s, 3H), 0.55 (s, 1H), 0.35-0.34 (m, 2H), 0.07-0.00 (m, 2H).

E-P2 ESI 596.2 (M+H)$^+$. $^1$H NMR (500 MHz, MeOD) δ 7.49 (s, 1H), 7.41 (d, J=9.0 Hz, 1H), 7.15-6.84 (m, 5H), 6.50 (d, J=9.3 Hz, 1H), 5.57-5.44 (m, 2H), 5.19-5.07 (m, 1H), 3.95-3.59 (m, 3H), 2.99 (s, 2H), 2.59-2.54 (m, 4H), 2.15-2.12 (m, 1H), 1.99-1.95 (m, 8H), 0.52-0.47 (m, 1H), 0.25-0.23 (m, 2H), 0.01-0.05 (m, 2H).

3-3. Preparation of (3S)-3-(2-(5-(2-(dimethylamino)ethyl)-2-oxo-4-(trifluoromethyl)pyridin-1(2H)-yl)-3-methylbutanamido)-3-(4-fluoro-2',4',5,6'-tetramethylbiphenyl-3-yl)propanoic acid (compounds F-P1 and F-P2)

Step 1: (3S)-ethyl 3-(2-(5-(2-(dimethylamino)ethyl)-2-oxo-4-(trifluoromethyl)pyridin-1(2H)-yl)-3-methylbutanamido)-3-(4-fluoro-2',4',5,6'-tetramethylbiphenyl-3-yl)propanoate

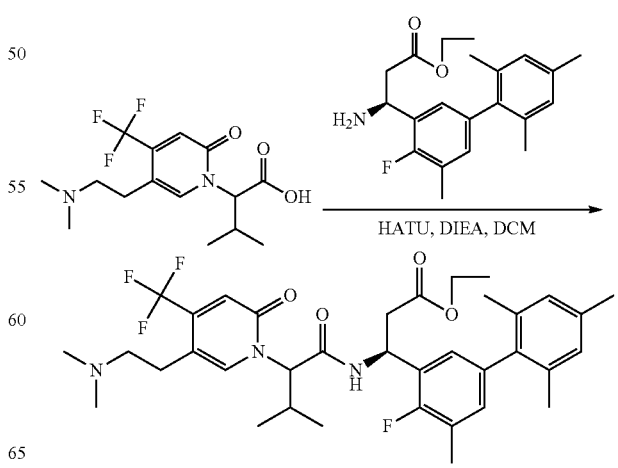

A mixture of 2-(5-(2-(dimethylamino)ethyl)-2-oxo-4-(trifluoromethyl)pyridin-1(2H)-yl)-3-methylbutanoic acid (150 mg, 0.45 mmol), (S)-ethyl 3-amino-3-(4-fluoro-2',4',5,6'-tetramethylbiphenyl-3-yl)propanoate (154 mg, 0.45 mmol), HATU (205 mg, 0.54 mmol) and DIEA (175 mg, 1.35 mmol) in DCM (5 mL) was stirred at room temperature for 1 hour. The solvent was removed in vacuo and the residue was purified by silica gel column (DCM:MeOH 4:1) to provide (3S)-ethyl 3-(2-(5-(2-(dimethylamino)ethyl)-2-oxo-4-(trifluoromethyl)pyridin-1(2H)-yl)-3-methylbutanamido)-3-(4-fluoro-2',4',5,6'-tetramethylbiphenyl-3-yl)propanoate as a brown oil (100 mg). Yield 33% (ESI 660.3 (M+H)$^+$).

Step 2: (3S)-3-(2-(5-(2-(dimethylamino)ethyl)-2-oxo-4-(trifluoromethyl)pyridin-1(2H)-yl)-3-methylbutanamido)-3-(4-fluoro-2',4',5,6'-tetramethylbiphenyl-3-yl)propanoic acid

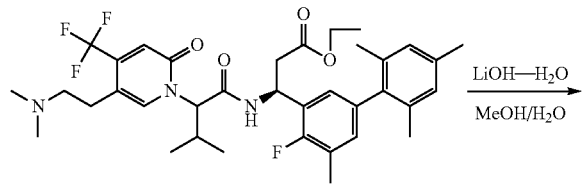

(3S)-ethyl 3-(2-(5-(2-(dimethylamino)ethyl)-2-oxo-4-(trifluoromethyl)pyridin-1(2H)-yl)-3-methylbutanamido)-3-(4-fluoro-2',4',5,6'-tetramethylbiphenyl-3-yl)propanoate (100 mg, 0.15 mmol) was treated with LiOH—H$_2$O (32 mg, 0.75 mmol) in MeOH (3 mL) and H$_2$O (1 mL) at room temperature for 3 hours. The reaction mixture was acidified to pH 4~5 with 1N HCl. The solvent was removed in vacuo and the residue was purified by prep-HPLC A (30-60% MeCN) to give the diastereomeric products F-P1 (30.0 mg) and F-P2 (32.0 mg) as a white solid.

F-P1 ESI 632.2 (M+H)$^+$. $^1$H NMR (400 MHz, MeOD) δ 7.95 (s, 1H), 6.89 (s, 1H), 6.84-6.76 (m, 3H), 6.67 (s, 1H), 5.65-5.54 (m, 1H), 5.26 (d, J=11.3 Hz, 1H), 3.06-2.85 (m, 4H), 2.80-2.63 (m, 8H), 2.53-2.38 (m, 1H), 2.34-2.23 (m, 6H), 1.95 (s, 3H), 1.63 (s, 3H), 1.17 (d, J=6.5 Hz, 3H), 0.80 (d, J=6.5 Hz, 3H).

F-P2 ESI 632.2 (M+H)$^+$. $^1$H NMR (400 MHz, MeOD) δ 8.11-7.95 (m, 1H), 7.02-6.83 (m, 5H), 5.76 (s, 1H), 5.24 (d, J=10.9 Hz, 1H), 3.27-2.90 (m, 4H), 2.81 (d, J=3.7 Hz, 6H), 2.66-2.36 (m, 3H), 2.31 (d, J=5.7 Hz, 6H), 1.95 (t, J=5.8 Hz, 6H), 0.95 (s, 3H), 0.82-0.66 (m, 3H).

3-4. Preparation of (3S)-3-(2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)biphenyl-3-yl)propanoic acid (compounds G-P1 and G-P2)

Step 1: (3S)-ethyl 3-(2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)biphenyl-3-yl)propanoate

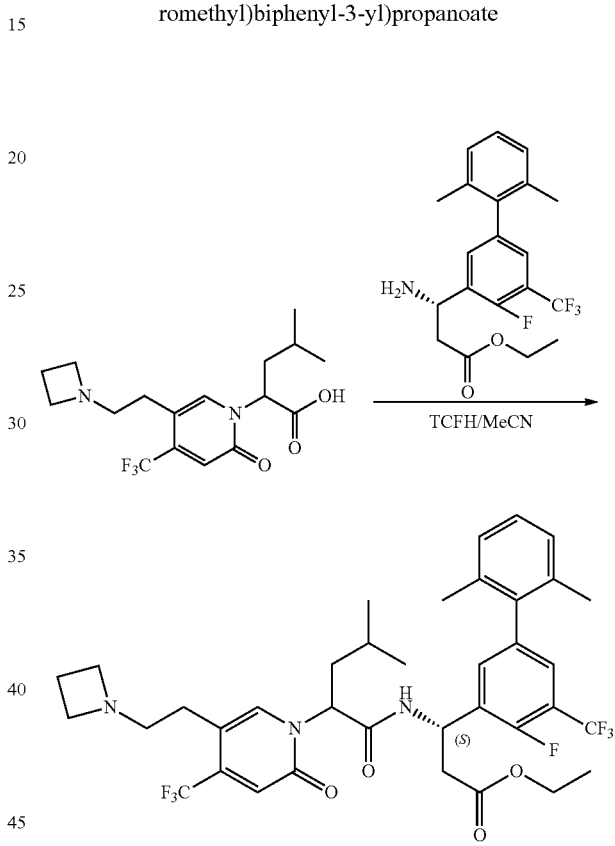

A mixture of 2-(5-(2-(azetidin-1-yl)ethyl)-2-oxo-4-(trifluoromethyl)pyridin-1(2H)-yl)-4-methylpentanoic acid (150 mg, 0.42 mmol), (S)-ethyl 3-amino-3-(4-fluoro-2',6'-dimethyl-5-(trifluoromethyl)biphenyl-3-yl)propanoate (161 mg, 0.42 mmol), TCFH (235 mg, 0.84 mmol), and NMI (138 mg, 1.68 mmol) in acetonitrile (4 mL) was stirred at room temperature for 2 hours. The reaction mixture was concentrated in vacuo and purified by reverse phase HPLC on a C18/40 g column (A: water 10 mM NH$_4$HCO$_3$, B: MeOH, 0~100%) to provide (3S)-ethyl 3-(2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)biphenyl-3-yl)propanoate as colorless oil (155 mg). Yield 51% (ESI 726.1 (M+H)$^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)biphenyl-3-yl)propanoic acid 3-5. Preparation of ((3S)-3-(2-(3-(difluoromethyl)-5-(2-(dimethylamino)ethyl)-2-oxopyridin-1(2H)-yl)-4-methylpentanamido)-3-(4-fluoro-2',4',5',6'-tetramethyl-[1,1'-biphenyl]-3-yl)propanoic acid (compounds H-P1 and H-P2)

Step 1: ethyl (3S)-3-(2-(3-(difluoromethyl)-5-(2-(dimethylamino)ethyl)-2-oxopyridin-1(2H)-yl)-4-methylpentanamido)-3-(4-fluoro-2',4',5',6'-tetramethyl-[1,1'-biphenyl]-3-yl)propanoate

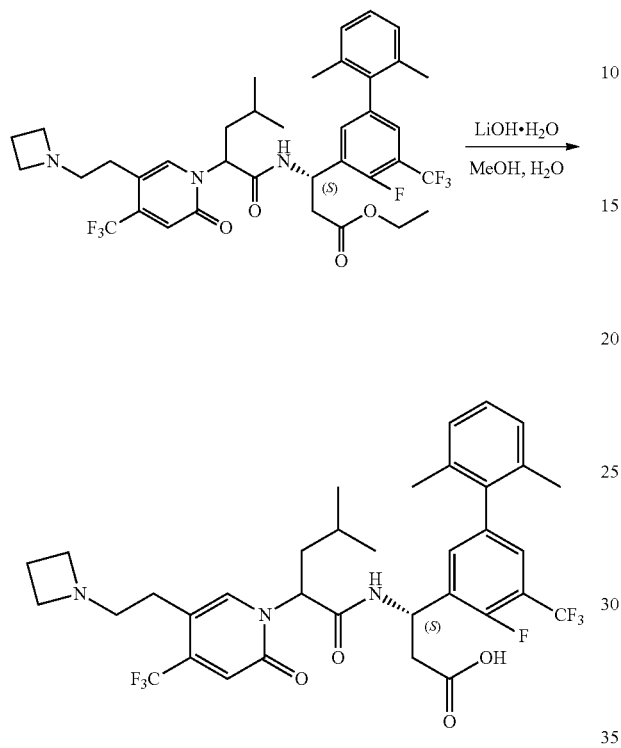

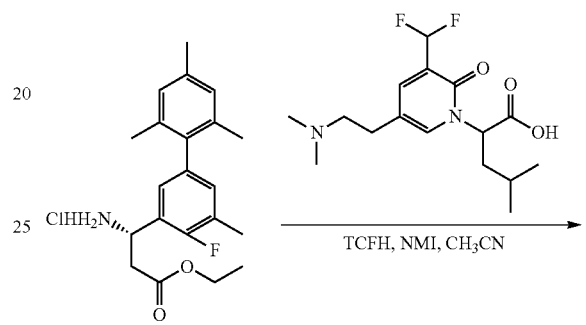

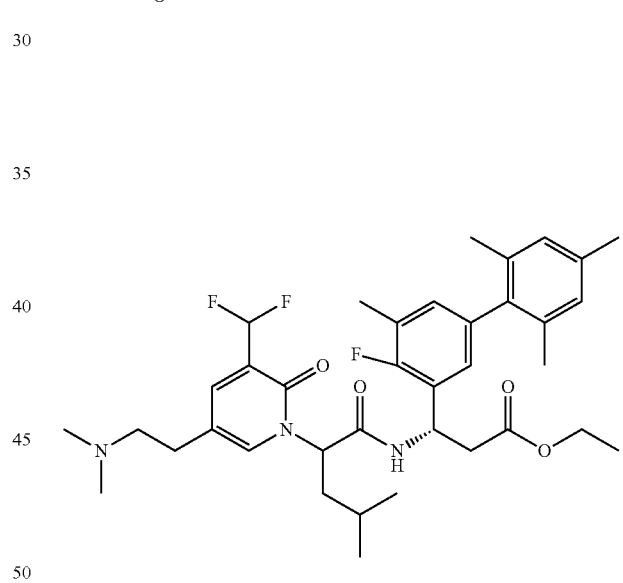

(3S)-ethyl 3-(2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)biphenyl-3-yl)propanoate (155 mg, 0.21 mmol) was treated with LiOH monohydrate (35 mg, 0.84 mmol) in MeOH (4 mL) and H$_2$O (1 mL) at room temperature for 2 hours. The reaction mixture was acidified to pH 4~5 with 1N HCl. The mixture was concentrated in vacuo and the residue was purified by prep-HPLC A (30-65% MeCN) to give the diastereomeric products G-P1 (37.8 mg) and G-P2 (49.6 mg) as a white solid.

G-P1 ESI 698.2 (M+H)$^+$. $^1$H NMR (400 MHz, MeOD) δ 7.85 (s, 1H), 7.41 (d, J=5.0 Hz, 1H), 7.36-7.27 (m, 1H), 7.21-7.09 (m, 3H), 6.74 (s, 1H), 5.71-5.54 (m, 2H), 4.04 (t, J=8.1 Hz, 4H), 3.29 (t, J=6.7 Hz, 2H), 2.86-2.82 (m, 2H), 2.78-2.68 (m, 2H), 2.50-2.36 (m, 2H), 2.08-1.93 (m, 5H), 1.86 (s, 3H), 1.44-1.41 (m, 1H), 1.13-0.79 (m, 6H).

G-P2 ESI 698.2 (M+H)$^+$. $^1$H NMR (400 MHz, MeOD) δ 7.76 (s, 1H), 7.50-7.44 (m, 1H), 7.41-7.33 (m, 1H), 7.22-7.18 (m, 1H), 7.14 (d, J=7.4 Hz, 2H), 6.90 (s, 1H), 5.813-5.80 (m, 1H), 5.64 (t, J=7.7 Hz, 1H), 4.13 (t, J=8.0 Hz, 4H), 3.55-3.34 (m, 2H), 2.99-2.88 (m, 1H), 2.85-2.81 (m, 1H), 2.71-2.66 (m, 1H), 2.60-2.54 (m, 1H), 2.53-2.43 (m, 2H), 2.07-1.93 (m, 7H), 1.76-1.61 (m, 1H), 1.42-1.37 (m, 1H), 0.95-0.83 (m, 6H).

A mixture of ethyl (S)-3-amino-3-(4-fluoro-2',4',5',6'-tetramethyl-[1,1'-biphenyl]-3-yl)propanoate hydrochloride (120 mg, 0.35 mmol), 2-(3-(difluoromethyl)-5-(2-(dimethylamino)ethyl)-2-oxopyridin-1(2H)-yl)-4-methylpentanoic acid (138 mg, 0.42 mmol), TCFH (147 mg, 0.52 mmol) and NMI (86 mg, 1.05 mmol) in acetonitrile (5 mL) was stirred at room temperature for 1 hour. The solvent was removed in vacuo and the residue was purified by silica gel column (DCM:MeOH 4:1) to provide ethyl (3S)-3-(2-(3-(difluoromethyl)-5-(2-(dimethylamino)ethyl)-2-oxopyridin-1(2H)-yl)-4-methylpentanamido)-3-(4-fluoro-2',4',5',6'-tetramethyl-[1,1'-biphenyl]-3-yl)propanoate as a brown solid (150 mg). Yield 65.2% (ESI 656.2 (M+H)$^+$).

Step 2: (3S)-3-(2-(3-(difluoromethyl)-5-(2-(dimethylamino)ethyl)-2-oxopyridin-1(2H)-yl)-4-methylpentanamido)-3-(4-fluoro-2',4',5',6'-tetramethyl-[1,1'-biphenyl]-3-yl)propanoic acid

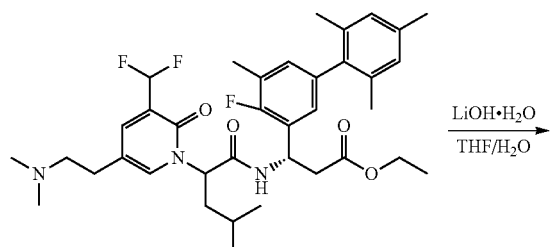

3-6. Preparation of (3S)-3-(4,4'-difluoro-2',5,6'-trimethyl-[1,1'-biphenyl]-3-yl)-3-(2-(3-(difluoromethyl)-5-(2-(dimethylamino)ethyl)-2-oxopyridin-1(2H)-yl)-4-methylpentanamido)propanoic acid (compounds I-P1 and I-P2)

Step 1: ethyl (3S)-3-(4,4'-difluoro-2',5,6'-trimethyl-[1,1'-biphenyl]-3-yl)-3-(2-(3-(difluoromethyl)-5-(2-(dimethylamino)ethyl)-2-oxopyridin-1(2H)-yl)-4-methylpentanamido)propanoate

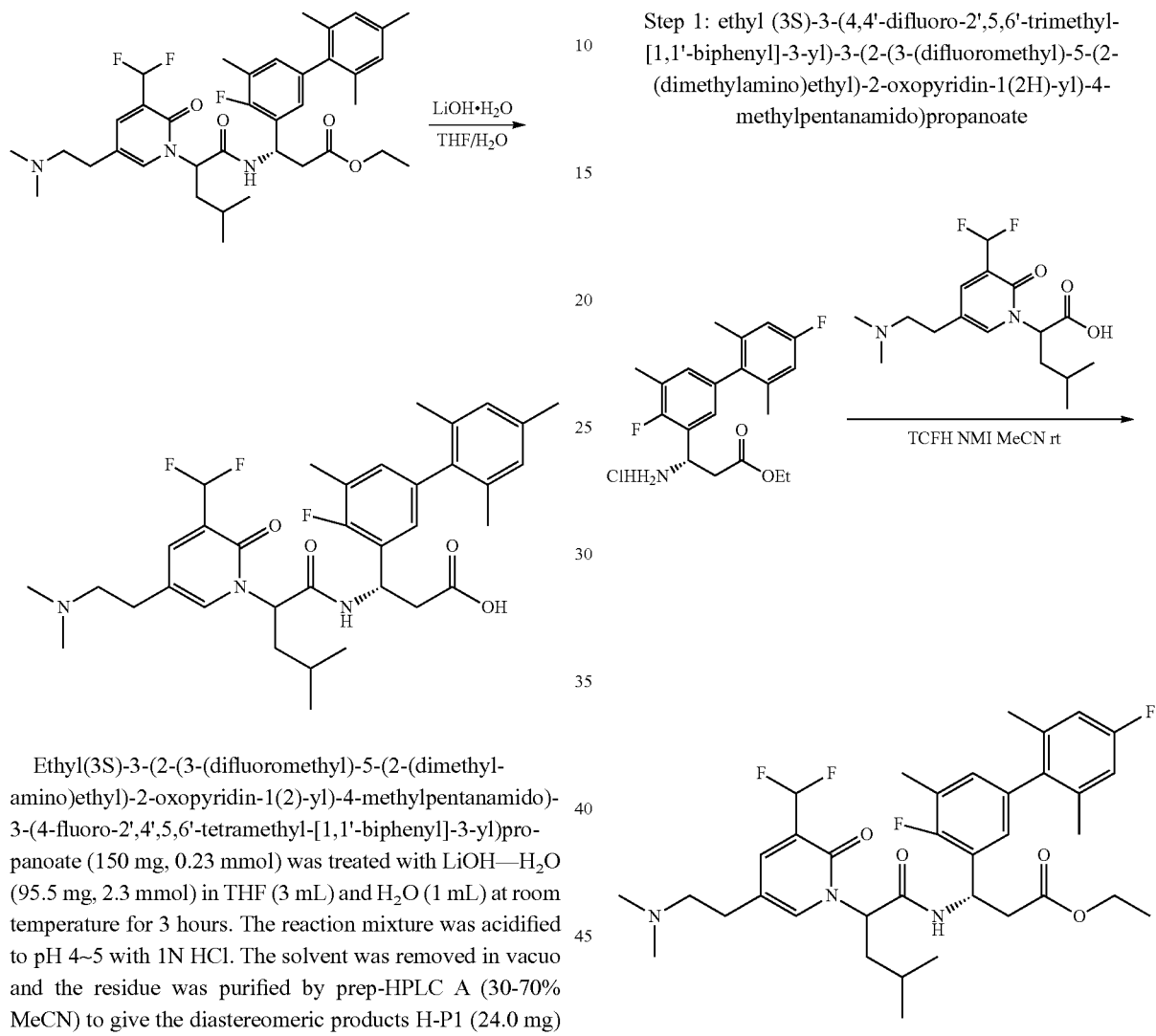

Ethyl(3S)-3-(2-(3-(difluoromethyl)-5-(2-(dimethylamino)ethyl)-2-oxopyridin-1(2)-yl)-4-methylpentanamido)-3-(4-fluoro-2',4',5',6'-tetramethyl-[1,1'-biphenyl]-3-yl)propanoate (150 mg, 0.23 mmol) was treated with LiOH—H₂O (95.5 mg, 2.3 mmol) in THF (3 mL) and H₂O (1 mL) at room temperature for 3 hours. The reaction mixture was acidified to pH 4~5 with 1N HCl. The solvent was removed in vacuo and the residue was purified by prep-HPLC A (30-70% MeCN) to give the diastereomeric products H-P1 (24.0 mg) and H-P2 (33.0 mg) as a white solid.

H-P1 ESI 628.3 (M+H)⁺. ¹H NMR (400 MHz, MeOD) δ 7.71 (s, 2H), 6.78 (s, 2H), 6.76-6.62 (m, 2H), 6.42 (t, J=55.1 Hz, 1H), 5.49-5.45 (m, 1H), 5.30 (t, J=5.7 Hz, 1H), 3.20-3.10 (m, 1H), 3.09-3.02 (m, 1H), 2.83-2.70 (m, 2H), 2.61 (s, 6H), 2.58-2.50 (m, 1H), 2.48-2.39 (m, 1H), 2.22-2.10 (m, 6H), 1.94-1.84 (m, 2H), 1.83 (s, 3H), 1.73 (s, 3H), 1.36-1.29 (m, 1H), 0.89-0.78 (m, 6H).

H-P2 ESI 628.3 (M+H)⁺. ¹H NMR (400 MHz, MeOD) δ 7.70 (s, 2H), 6.79-6.71 (m, 4H), 6.49 (t, J=55.1 Hz, 1H), 5.50-5.45 (m, 2H), 3.30-3.23 (m, 1H), 3.18-3.13 (m, 1H), 2.85-2.74 (m, 2H), 2.70 (s, 6H), 2.54-2.43 (m, 1H), 2.39-2.29 (m, 1H), 2.18 (s, 6H), 1.93-1.85 (m, 1H), 1.83 (d, J=5.9 Hz, 6H), 1.76-1.62 (m, 1H), 1.33-1.30 (m, 1H), 0.80-0.77 (m, 6H).

A mixture of 2-(3-(difluoromethyl)-5-(2-(dimethylamino)ethyl)-2-oxopyridin-1(2H)-yl)-4-methylpentanoic acid (120 mg, 0.39 mmol), ethyl (S)-3-amino-3-(4,4'-difluoro-2',5,6'-trimethyl-[1,1'-biphenyl]-3-yl)propanoate hydrochloride (120 mg, 0.36 mmol), TCFH (120 mg, 0.54 mmol), and NMI (75 mg, 1.08 mmol) in acetonitrile (5 mL) was stirred at room temperature for 20 hours. The reaction mixture was concentrated in vacuo and purified by reverse phase HPLC on a C18/40 g column (A: water 10 mM NH₄HCO₃, B: MeOH, 0~100%) to provide ethyl (3S)-3-(4,4'-difluoro-2',5,6'-trimethyl-[1,1'-biphenyl]-3-yl)-3-(2-(3-(difluoromethyl)-5-(2-(dimethylamino)ethyl)-2-oxopyridin-1(2H)-yl)-4-methylpentanamido)propanoate as brown solid (150 mg). Yield 63.2% (ESI 660.3 (M+H)⁺).

265

Step 2: (3S)-3-(4,4'-difluoro-2',5,6'-trimethyl-[1,1'-biphenyl]-3-yl)-3-(2-(3-(difluoromethyl)-5-(2-(dimethylamino)ethyl)-2-oxopyridin-1(2H)-yl)-4-methylpentanamido)propanoic acid

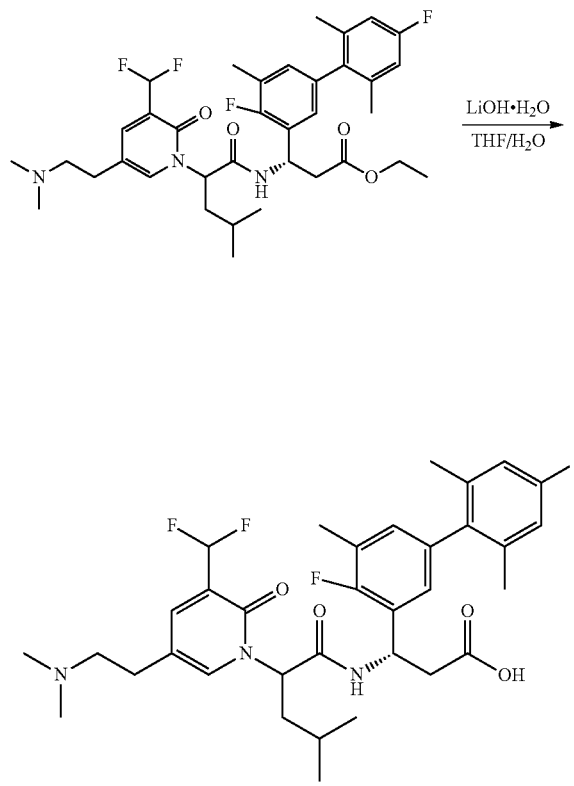

Ethyl(3S)-3-(4,4'-difluoro-2',5,6'-trimethyl-[1,1'-biphenyl]-3-yl)-3-(2-(3-(difluoromethyl)-5-(2-(dimethylamino)ethyl)-2-oxopyridin-1(2H)-yl)-4-methylpentanamido)propanoate (150 mg, 0.23 mmol) was treated with LiOH monohydrate (100 mg, 2.3 mmol) in EtOH (6 mL) and H₂O (0.8 mL) at 36° C. for 1 hour. The reaction mixture was acidified to pH 4~5 with 1N HCl. The solvent was removed in vacuo and the residue was purified by prep-HPLC A (30-60% MeCN) to provide the diastereomeric products I-P1 (20 mg) and I-P2 (22 mg) as a white solid.

I-P1 ESI 632.2 (M+H)⁺. ¹H NMR (400 MHz, MeOD) δ 7.72 (s, 2H), 6.74-6.67 (m, 4H), 6.46 (t, J=55.2 Hz, 1H), 5.48-5.44 (m, 1H), 5.33-5.30 (m, 1H), 3.20-3.16 (m, 1H), 3.12-3.04 (m, 1H), 2.84-2.73 (m, 2H), 2.65 (s, 6H), 2.59-2.42 (m, 2H), 2.17 (s, 3H), 1.95-1.83 (m, 5H), 1.78 (s, 3H), 1.39-1.29 (m, 1H), 0.85-0.75 (m, 6H).

I-P2 ESI 632.2 (M+H)⁺. ¹H NMR (400 MHz, MeOD) δ 7.84 (s, 1H), 7.81 (s, 1H), 6.90-6.78 (m, 4H), 6.65 (t, J=55.2 Hz, 1H), 5.63-5.57 (m, 2H), 3.48-3.38 (m, 1H), 3.32-3.23 (m, 1H), 3.02-2.87 (m, 2H), 2.83 (s, 6H), 2.67-2.54 (m, 1H), 2.50-2.41 (m, 1H), 2.32 (d, J=1.6 Hz, 3H), 2.07-2.01 (m, 1H), 2.00 (d, J=6.2 Hz, 6H), 1.88-1.76 (m, 1H), 1.50-1.39 (m, 1H), 0.96-0.86 (m, 6H).

266

3-7. Preparation of (3S)-3-(2-(5-(2-(dimethylamino)ethyl)-4-methyl-2-oxopyridin-1(2H)-yl)-5-methylhexanamido)-3-(4-fluoro-2',5,6'-trimethylbiphenyl-3-yl)propanoic acid (compounds J-P1 and J-P2)

Step 1: (3S)-ethyl 3-(2-(5-(2-(dimethylamino)ethyl)-4-methyl-2-oxopyridin-1(2H)-yl)-5-methylhexanamido)-3-(4-fluoro-2',5,6'-trimethylbiphenyl-3-yl)propanoate

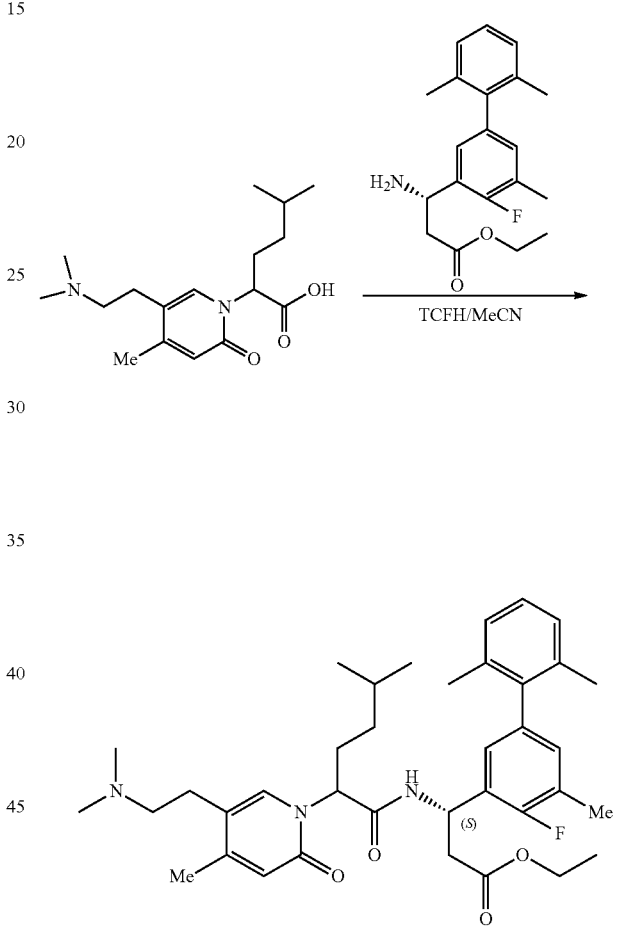

A mixture of 2-(5-(2-(dimethylamino)ethyl)-4-methyl-2-oxopyridin-1(2H)-yl)-5-methylhexanoic acid (150 mg, 0.49 mmol), (S)-ethyl 3-amino-3-(4-fluoro-2',5,6'-trimethylbiphenyl-3-yl)propanoate (161 mg, 0.49 mmol), TCFH (274 mg, 0.98 mmol), and NMI (201 mg, 2.45 mmol) in acetonitrile (5 mL) was stirred at room temperature for 2 hours. The reaction mixture was concentrated in vacuo and purified by reverse phase HPLC on a C18/40 g column (A: water 10 mM NH₄HCO₃, B: MeOH, 0~100%) to provide (3S)-ethyl 3-(2-(5-(2-(dimethylamino)ethyl)-4-methyl-2-oxopyridin-1 (2H)-yl)-5-methylhexanamido)-3-(4-fluoro-2',5,6'-trimethylbiphenyl-3-yl)propanoate as colorless oil (170 mg). Yield 56% (ESI 620.2 (M+H)⁺).

Step 2: (3S)-3-(2-(5-(2-(dimethylamino)ethyl)-4-methyl-2-oxopyridin-1(2H)-yl)-5-methylhexanamido)-3-(4-fluoro-2',5,6'-trimethylbiphenyl-3-yl)propanoic acid

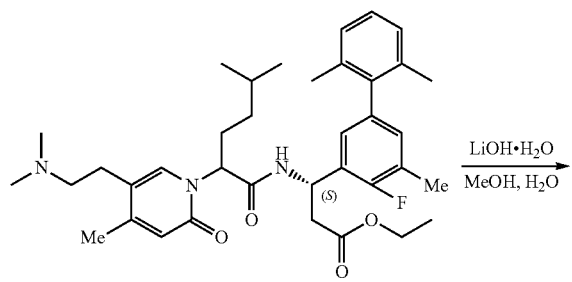

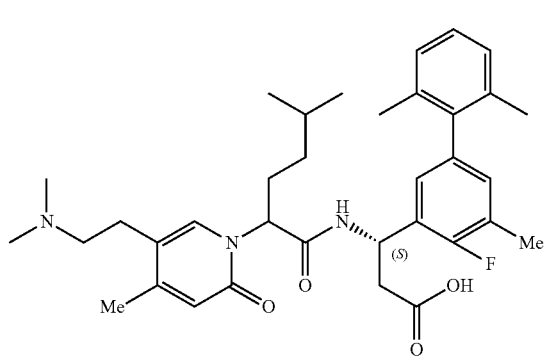

(3S)-ethyl 3-(2-(5-(2-(dimethylamino)ethyl)-4-methyl-2-oxopyridin-1(2H)-yl)-5-methylhexanamido)-3-(4-fluoro-2',5,6'-trimethylbiphenyl-3-yl)propanoate (170 mg, 0.27 mmol) was treated with LiOH monohydrate (57 mg, 1.35 mmol) in MeOH (4 mL) and H$_2$O (1 mL) at room temperature for 2 hours. The reaction mixture was acidified to pH 4~5 with 1N HCl. The reaction mixture was concentrated in vacuo and purified by prep-HPLC A (30-60% MeCN) to provide the diastereomeric products J-P1 (50 mg) and J-P2 (60.4 mg) as a white solid.

J-P1 ESI 592.3 (M+H)$^+$. 1H NMR (400 MHz, MeOD) δ 7.57 (s, 1H), 7.17-7.10 (m, 1H), 7.07 (d, J=8.1 Hz, 2H), 6.87-6.82 (m, 2H), 6.33 (s, 1H), 5.49 (t, J=5.7 Hz, 1H), 5.39 (s, 1H), 3.26-3.05 (m, 2H), 2.88 (d, J=7.9 Hz, 2H), 2.82-2.69 (m, 6H), 2.69-2.58 (m, 2H), 2.26 (t, J=15.5 Hz, 6H), 2.22-2.10 (m, 1H), 1.97 (d, J=16.6 Hz, 4H), 1.91 (s, 3H), 1.60-1.53 (m, 1H), 1.29-1.14 (m, 1H), 1.09-1.04 (m, 1H), 0.89-0.87 (m, 6H).

J-P2 ESI 592.3 (M+H)+. $^1$H NMR (400 MHz, MeOD) δ 7.55 (s, 1H), 7.15-7.07 (m, 3H), 6.91 (d, J=6.9 Hz, 2H), 6.43 (s, 1H), 5.67-5.64 (m, 1H), 5.42 (t, J=7.7 Hz, 1H), 3.31-3.25 (m, 1H), 3.25-3.14 (m, 1H), 2.99-2.88 (m, 2H), 2.86 (d, J=17.8 Hz, 6H), 2.65-2.60 (m, 1H), 2.51-2.45 (m, 1H), 2.38-2.19 (m, 6H), 2.19-2.06 (m, 1H), 2.00 (s, 6H), 1.86-1.77 (m, 1H), 1.57-1.50 (m, 1H), 1.17-1.09 (m, 1H), 1.07-1.01 (m, 1H), 0.84 (t, J=6.4 Hz, 6H).

3-8. Preparation of (3S)-3-(2-(5-(2-(dimethylamino)ethyl)-3-fluoro-2-oxopyridin-1(2H)-yl)-4-methylpentanamido)-3-(4-fluoro-2',6'-dimethyl-5-(trifluoromethyl)biphenyl-3-yl)propanoic acid (compounds K-P1 and K-P2)

Step 1: (3S)-ethyl 3-(2-(5-(2-(dimethylamino)ethyl)-3-fluoro-2-oxopyridin-1(2H)-yl)-4-methylpentanamido)-3-(4-fluoro-2',6'-dimethyl-5-(trifluoromethyl)biphenyl-3-yl)propanoate

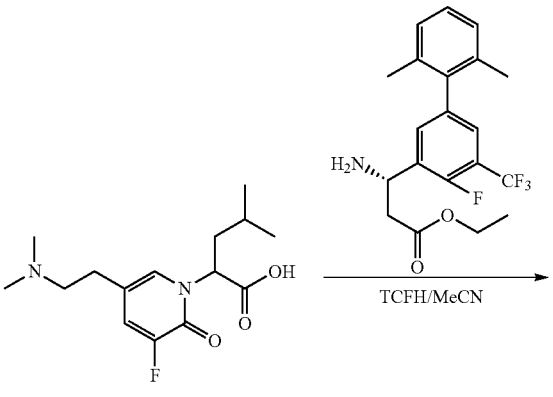

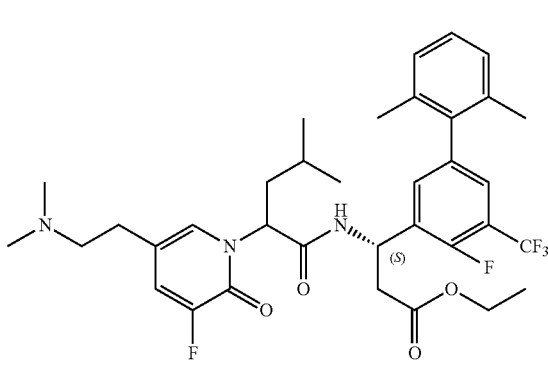

A mixture of 2-(5-(2-(dimethylamino)ethyl)-3-fluoro-2-oxopyridin-1(2H)-yl)-4-methylpentanoic acid (130 mg, 0.44 mmol), (S)-ethyl 3-amino-3-(4-fluoro-2',6'-dimethyl-5-(trifluoromethyl)biphenyl-3-yl)propanoate (169 mg, 0.44 mmol), TCFH (246 mg, 0.88 mmol), and NMI (144 mg, 1.76 mmol) in acetonitrile (4 mL) was stirred at room temperature for 2 hours. The reaction mixture was concentrated in vacuo and purified by reverse phase HPLC on a C18/40 g column (A: water 10 mM NH$_4$HCO$_3$, B: MeOH, 0~100%) to provide (3S)-ethyl 3-(2-(5-(2-(dimethylamino)ethyl)-3-fluoro-2-oxopyridin-1(2H)-yl)-4-methylpentanamido)-3-(4-fluoro-2',6'-dimethyl-5-(trifluoromethyl)biphenyl-3-yl)propanoate as yellow oil (150 mg). Yield 51% (ESI 664.2 (M+H)$^+$).

Step 2: (3S)-3-(2-(5-(2-(dimethylamino)ethyl)-3-fluoro-2-oxopyridin-1(2H)-yl)-4-methylpentanamido)-3-(4-fluoro-2',6'-dimethyl-5-(trifluoromethyl)biphenyl-3-yl)propanoic acid 3-9. Preparation of (3S)-3-(4,5-difluoro-2',6'-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid (compounds L-P1 and L-P2)

Step 1: ethyl (3S)-3-(4,5-difluoro-2',6'-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate

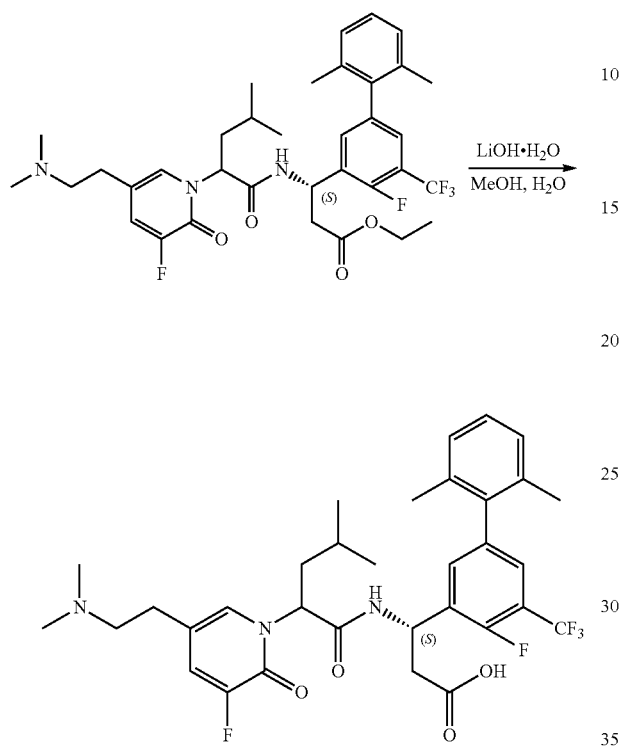

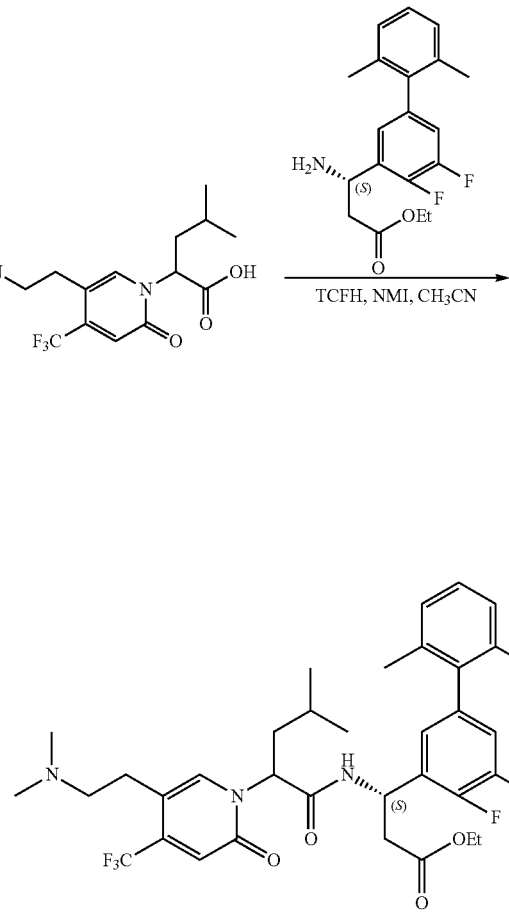

(3S)-ethyl 3-(2-(5-(2-(dimethylamino)ethyl)-3-fluoro-2-oxopyridin-1(2H)-yl)-4-methylpentanamido)-3-(4-fluoro-2',6'-dimethyl-5-(trifluoromethyl)biphenyl-3-yl)propanoate (150 mg, 0.23 mmol) was treated with LiOH monohydrate (39 mg, 0.92 mmol) in MeOH (4 mL) and H$_2$O (1 mL) at 36° C. for 2 hours. The reaction mixture was acidified to pH 4~5 with 1N HCl. The reaction mixture was concentrated in vacuo and purified by prep-HPLC A (30-60% MeCN) to give the diastereomeric products K-P1 (41 mg) and K-P2 (46.8 mg) as a white solid.

K-P1 ESI 636.2 (M+H)+. $^1$H NMR (400 MHz, MeOD) δ 7.53 (s, 1H), 7.47-7.44 (m, 1H), 7.33-7.28 (m, 2H), 7.23-7.17 (m, 1H), 7.16-7.08 (m, 2H), 5.65-5.61 (m, 1H), 5.46 (t, J=5.7 Hz, 1H), 3.38 (d, J=7.8 Hz, 1H), 3.24-3.17 (m, 1H), 2.95-2.84 (m, 2H), 2.82-2.64 (m, 7H), 2.60-2.54 (m, 1H), 2.08-1.97 (m, 5H), 1.94 (s, 3H), 1.43 (s, 1H), 0.96-0.91 (m, 6H).

K-P2 ESI 636.2 (M+H)+. $^1$H NMR (400 MHz, MeOD) δ 7.38 (s, 1H), 7.33-7.28 (m, 2H), 7.24 (d, J=6.3 Hz, 1H), 7.12-6.99 (m, 3H), 5.55-5.49 (m, 2H), 3.36-3.25 (m, 1H), 3.18-3.12 (m, 1H), 2.91-2.79 (m, 1H), 2.73 (d, J=11.7 Hz, 7H), 2.52-2.48 (m, 1H), 2.39-2.32 (m, 1H), 2.00-1.79 (m, 7H), 1.75-1.68 (m, 1H), 1.29-1.24 (m, 1H), 0.81-0.78 (m, 6H).

A mixture of 2-(5-(2-(dimethylamino)ethyl)-2-oxo-4-(trifluoromethyl)pyridin-1(2H)-yl)-4-methylpentanoic acid (100 mg, 0.29 mmol), ethyl (S)-3-amino-3-(4,5-difluoro-2',6'-dimethyl-[1,1'-biphenyl]-3-yl)propanoate (96 mg, 0.29 mmol), TCFH (100 mg, 0.34 mmol) and NMI (96.0 mg, 1.14 mmol) in CH$_3$CN (3 mL) was stirred at room temperature for 1.5 hours. The reaction mixture was concentrated in vacuo and purified by reverse phase HPLC on a C18/40 g column (A: water 10 mM NH$_4$HCO$_3$, B: MeOH, 0~100%) to provide ethyl (3S)-3-(4,5-difluoro-2',6'-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate as a yellow solid (131 mg). Yield 68.1% (ESI 664.2 [M+H]+).

Step 2: (3S)-3-(4,5-difluoro-2',6'-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid

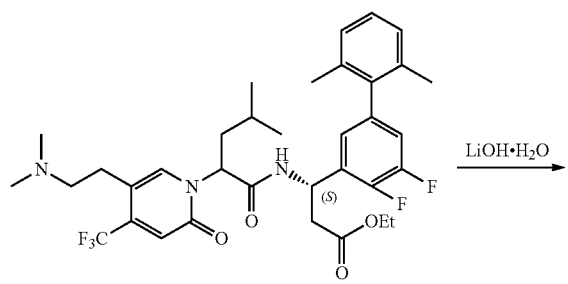

Ethyl (3S)-3-(4,5-difluoro-2',6'-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate (131.0 mg, 0.19 mmol) was treated with LiOH—H₂O (100.0 mg, 2.38 mmol) in THF (2 mL) and water (0.5 mL) at 30° C. for 1 hour. The reaction mixture was acidified to pH 4~5 with 2N HCl. The solvent was removed in vacuo and the residue was purified by prep-HPLC A (30-60% MeCN) to give the diastereomeric product L-P1 (11.1 mg) and L-P2 (19.0 mg) as a white solid.

L-P1 ESI 636.1 (M+H)¹H NMR (400 MHz, MeOD) δ 7.77 (s, 1H), 7.05-6.92 (m, 3H), 6.83-6.76 (m, 2H), 6.63 (s, 1H), 5.58-5.45 (m, 2H), 3.03-2.96 (m, 2H), 2.84-2.81 (m, 2H), 2.65 (s, 6H), 2.62-2.60 (m, 2H), 1.92-1.79 (m, 5H), 1.72 (s, 3H), 1.33-1.30 (m, 1H), 0.86-0.81 (m, 6H).

L-P2 ESI 636.1 (M+H)⁺. ¹H NMR (400 MHz, MeOD) δ 7.72 (s, 1H), 7.07-6.97 (m, 3H), 6.90-6.80 (m, 3H), 6.77 (s, 1H), 5.63-5.59 (m, 1H), 5.49 (t, J=7.6 Hz, 1H), 3.22-3.08 (m, 2H), 2.88 (t, J=6.9 Hz, 2H), 2.72 (s, 6H), 2.58-2.38 (m, 2H), 1.92-1.83 (m, 7H), 1.64-1.56 (m, 1H), 1.33-1.24 (m, 1H), 0.77 (d, J=6.5 Hz, 6H).

3-10. Preparation of (3S)-3-(4,4'-difluoro-2',6'-dimethyl-5-(trifluoromethyl)-[1,1'-biphenyl]-3-yl)-3-(2-(5-(2-(dimethylamino)ethyl)-3-methyl-2-oxopyridin-1(2H)-yl)-4-methylpentanamido)propanoic acid (compounds M-P1 and M-P2)

Step 1: ethyl (3S)-3-(4,4'-difluoro-2',6'-dimethyl-5-(trifluoromethyl)-[1,1'-biphenyl]-3-yl)-3-(2-(5-(2-(dimethylamino)ethyl)-3-methyl-2-oxopyridin-1(2H)-yl)-4-methylpentanamido)propanoate

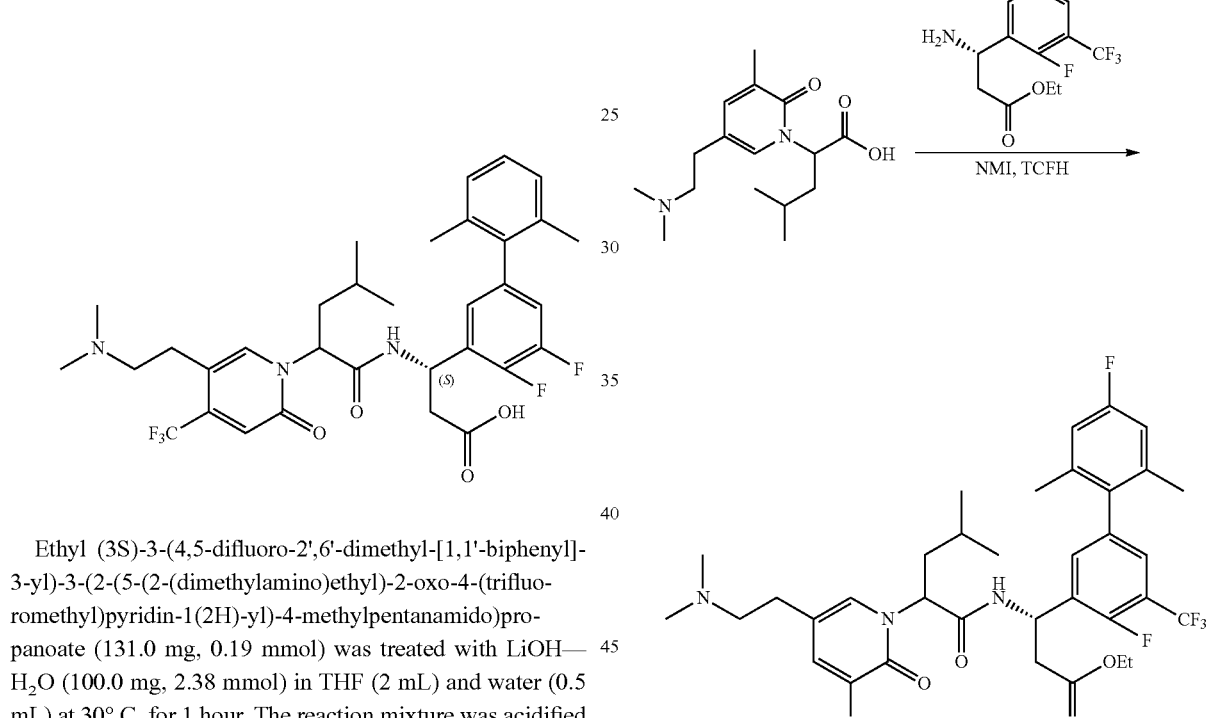

A mixture of 2-(5-(2-(dimethylamino)ethyl)-3-methyl-2-oxopyridin-1(2H)-yl)-4-methylpentanoic acid (160 mg, 0.54 mmol), ethyl (S)-3-amino-3-(4,4'-difluoro-2',6'-dimethyl-5-(trifluoromethyl)-[1,1'-biphenyl]-3-yl)propanoate (260 mg, 0.64 mmol), TCFH (226 mg, 0.81 mmol), NMI (221.4 mg, 2.7 mmol) and CH₃CN (5 mL) was stirred at room temperature for 1 hour. The reaction mixture was concentrated in vacuo and purified by reverse phase HPLC on a C18/40 g column (A: water 10 mM NH₄HCO₃, B: MeOH, 0~100%) to provide ethyl (3S)-3-(4,4'-difluoro-2',6'-dimethyl-5-(trifluoromethyl)-[1,1'-biphenyl]-3-yl)-3-(2-(5-(2-(dimethylamino)ethyl)-3-methyl-2-oxopyridin-1(2H)-yl)-4-methylpentanamido)propanoate as a colorless oil (180 mg). Yield 50% (ESI 678.3 (M+H)⁺).

Step 2: (3S)-3-(4,4'-difluoro-2',6'-dimethyl-5-(trifluoromethyl)-[1,1'-biphenyl]-3-yl)-3-(2-(5-(2-(dimethylamino)ethyl)-3-methyl-2-oxopyridin-1(2H)-yl)-4-methylpentanamido)propanoic acid

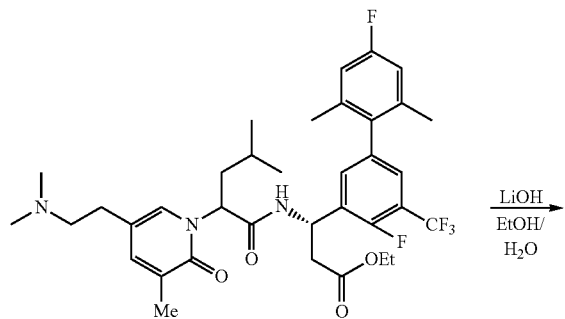

Ethyl (3S)-3-(4,4'-difluoro-2',6'-dimethyl-5-(trifluoromethyl)-[1,1'-biphenyl]-3-yl)-3-(2-(5-(2-(dimethylamino)ethyl)-3-methyl-2-oxopyridin-1(2H)-yl)-4-methylpentanamido)propanoate (180 mg, 0.26 mmol) was treated with LiOH—H$_2$O (39 mg, 0.92 mmol) in EtOH (3 mL) and H$_2$O (1 mL) at room temperature for 1 hour. The reaction mixture was acidified to pH 4~5 with 1N HCl. The solvent was removed in vacuo and the residue was purified by prep-HPLC A (30-60% MeCN) to give the diastereomeric products M-P1 (50 mg) and M-P2 (53.0 mg) as a white solid.

M-P1 ESI 650.3 (M+H)$^+$. $^1$H NMR (400 MHz, MeOD) δ 7.52 (s, 1H), 7.39 (s, 1H), 7.33-7.18 (m, 2H), 6.88 (d, J=9.6 Hz, 2H), 5.56-5.47 (m, 2H), 3.28-3.17 (m, 2H), 2.84-2.69 (m, 9H), 2.63-2.57 (m, 1H), 2.06-1.92 (m, 8H), 1.86 (s, 3H), 1.48-1.38 (m, 1H), 0.95-0.90 (m, 6H).

M-P2 ESI 650.3 (M+H)$^+$. $^1$H NMR (400 MHz, MeOD) δ 7.56 (s, 1H), 7.43 (s, 1H), 7.38-7.22 (m, 2H), 6.92-6.87 (m, 2H), 5.65-5.54 (m, 2H), 3.46-3.39 (m, 1H), 3.29-3.24 (m, 1H), 2.97-2.75 (m, 8H), 2.67-2.61 (m, 1H), 2.51-2.45 (m, 1H), 2.05-1.90 (m, 11H), 1.45-1.38 (m, 1H), 0.94-0.88 (m, 6H).

3-11. Preparation of (3S)-3-(2-(5-(2-(dimethylamino)ethyl)-3-fluoro-2-oxo-4-(trifluoromethyl)pyridin-1(2H)-yl)-4-methylpentanamido)-3-(4-fluoro-4'-methoxy-2',5,6'-trimethyl-[1,1'-biphenyl]-3-yl)propanoic acid (compounds P-P1 and P-P2)

Step 1: ethyl (3S)-3-(2-(5-(2-(dimethylamino)ethyl)-3-fluoro-2-oxo-4-(trifluoromethyl)pyridin-1(2H)-yl)-4-methylpentanamido)-3-(4-fluoro-4'-methoxy-2',5,6'-trimethyl-[1,1'-biphenyl]-3-yl)propanoate

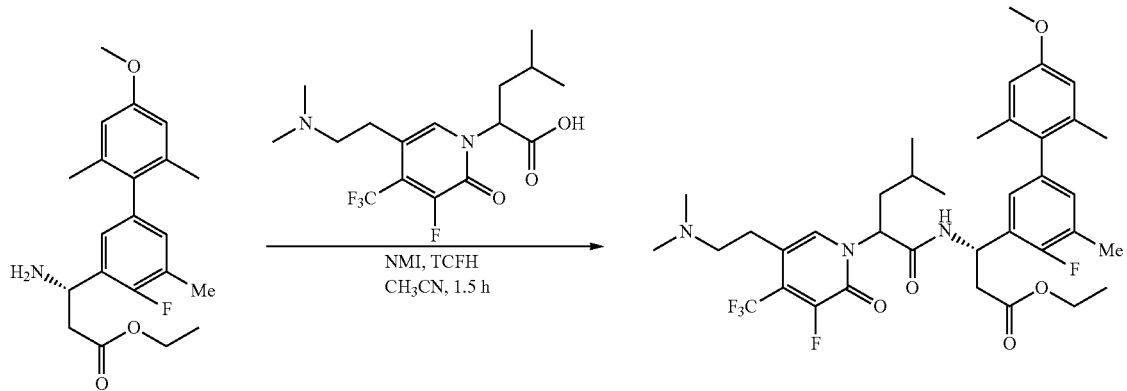

A mixture of ethyl (S)-3-amino-3-(4-fluoro-4'-methoxy-2',5,6'-trimethyl-[1,1'-biphenyl]-3-yl)propanoate (220 mg, 0.60 mmol), 2-(5-(2-(dimethylamino)ethyl)-3-fluoro-2-oxo-4-(trifluoromethyl)pyridin-1(2H)-yl)-4-methylpentanoic acid (100 mg, 0.55 mmol), TCFH (230 mg, 0.82 mmol), and NMI (177 mg, 2.18 mmol) in acetonitrile (10 mL) was stirred at room temperature for 20 hours. The reaction mixture was concentrated in vacuo and purified by reverse phase HPLC on a C18/40 g column (A: water 10 mM NH$_4$HCO$_3$, B: MeOH, 0~100%) to provide ethyl (3S)-3-(2-(5-(2-(dimethylamino)ethyl)-3-fluoro-2-oxo-4-(trifluoromethyl)pyridin-1(2H)-yl)-4-methylpentanamido)-3-(4-fluoro-4'-methoxy-2',5,6'-trimethyl-[1,1'-biphenyl]-3-yl)propanoate (214 mg) as a white solid. Yield 56% (ESI 708.3 (M+H)$^+$).

Step 2: (3S)-3-(2-(5-(2-(dimethylamino)ethyl)-3-fluoro-2-oxo-4-(trifluoromethyl)pyridin-1(2H)-yl)-4-methylpentanamido)-3-(4-fluoro-4'-methoxy-2',5,6'-trimethyl-[1,1'-biphenyl]-3-yl)propanoic acid

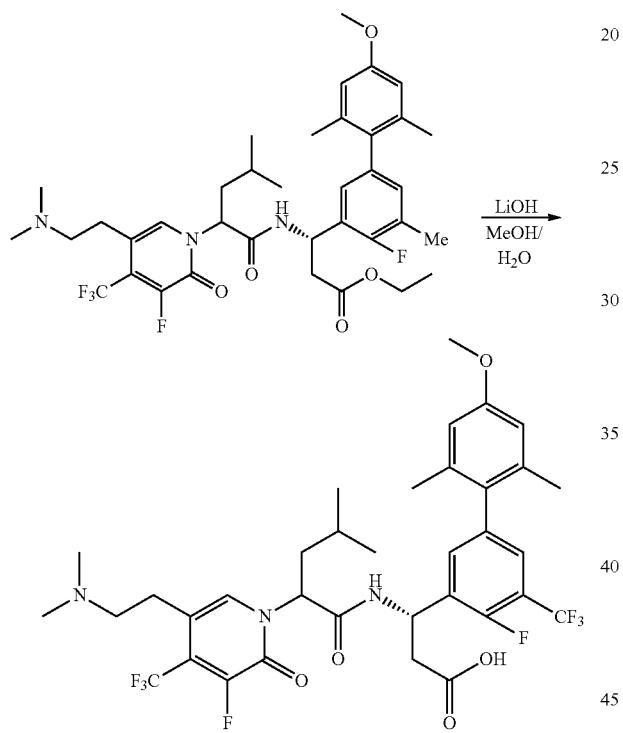

Ethyl (3S)-3-(2-(5-(2-(dimethylamino)ethyl)-3-fluoro-2-oxo-4-(trifluoromethyl)pyridin-1(2H)-yl)-4-methylpentanamido)-3-(4-fluoro-4'-methoxy-2',5,6'-trimethyl-[1,1'-biphenyl]-3-yl)propanoate (214 mg, 0.30 mmol) was treated with LiOH—H$_2$O (52 mg, 1.24 mmol) in MeOH (3 mL) and H$_2$O (1 mL) at room temperature for 2 hours. The reaction mixture was acidified to pH 4~5 with 1N HCl. The solvent was removed in vacuo and the residue was purified by prep-HPLC A (30-60% CH$_3$CN) to give the diastereomeric products P-P1 (39.8 mg) and P-P2 (48.6 mg) as a white solid.

P-P1 ESI 680.4 (M+H)$^+$. $^1$H NMR (500 MHz, MeOD) δ 7.69 (s, 1H), 6.88-6.85 (m, 2H), 6.64 (d, J=10.6 Hz, 2H), 5.73-5.65 (m, 1H), 5.55 (t, J=6.8 Hz, 1H), 4.92 (s, 3H), 3.79 (s, 3H), 3.17-2.92 (m, 4H), 2.82-2.69 (m, 7H), 2.29 (s, 3H), 2.10-1.94 (m, 5H), 1.83 (s, 1H), 1.51-1.41 (m, 1H), 0.97-0.93 (m, 6H).

P-P2 ESI 680.3 (M+H)$^+$. $^1$H NMR (500 MHz, MeOD) δ 7.60 (s, 1H), 6.91 (t, J=7.1 Hz, 2H), 6.67 (s, 2H), 5.73-5.70 (m, 1H), 5.61 (t, J=7.5 Hz, 1H), 3.80 (s, 3H), 3.23-3.18 (m, 2H), 3.18-2.95 (m, 2H), 2.83 (s, 6H), 2.65-2.61 (m, 1H), 2.52-2.47 (m, 1H), 2.32 (s, 3H), 2.11-1.95 (m, 7H), 1.72-1.66 (m, 1H), 1.45-1.41 (m, 1H), 0.94-0.85 (m, 6H).

3-12. Preparation of (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',6'-dimethyl-5-(trifluoromethyl)-[1,1'-biphenyl]-3-yl)propanoic acid (compounds R-P1 and R-P2)

Step 1: ethyl (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',6'-dimethyl-5-(trifluoromethyl)-[1,1'-biphenyl]-3-yl)propanoate

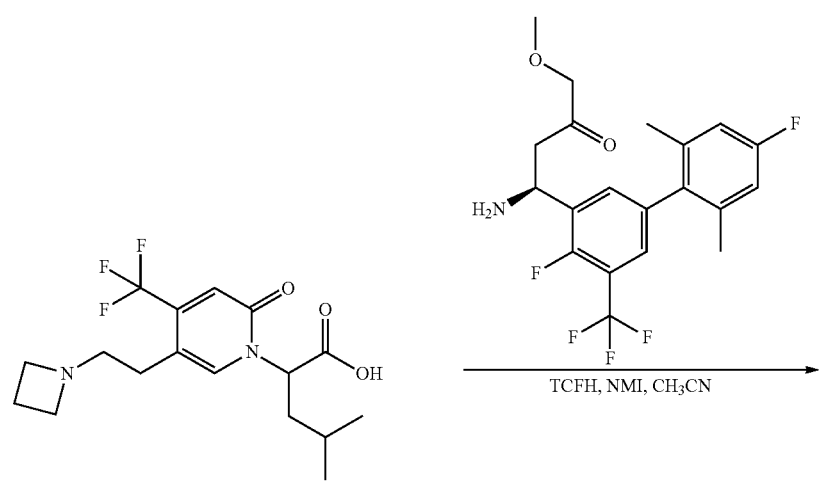

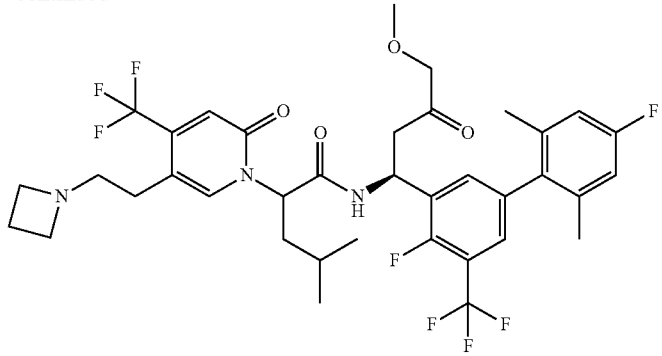

A mixture of 2-(5-(2-(azetidin-1-yl)ethyl)-2-oxo-4-(trifluoromethyl)pyridin-1(2H)-yl)-4-methylpentanoic acid (100 mg, 0.28 mmol), ethyl (S)-3-amino-3-(4,4'-difluoro-2',6'-dimethyl-5-(trifluoromethyl)-[1,1'-biphenyl]-3-yl)propanoate (112 mg, 0.28 mmol), NMI (69 mg, 0.84 mmol) and TCFH (95 mg, 0.34 mmol) in CH$_3$CN (5 mL) was stirred at room temperature for 2 hours. The solvent was removed in vacuo and the residue was purified by silica gel column (MeOH/DCM 7%) to provide ethyl (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',6'-dimethyl-5-(trifluoromethyl)-[1,1'-biphenyl]-3-yl)propanoate as a yellow oil (180 mg). Yield 87% (ESI 744.1 [M+H]$^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',6'-dimethyl-5-(trifluoromethyl)-[1,1'-biphenyl]-3-yl)propanoic acid LiOH—H$_2$O (50 mg, 1.20 mmol) in THF (3 mL), MeOH (2 mL) and H$_2$O (1 mL) at room temperature for 16 hours. The reaction mixture was acidified to pH 4~5 with 1N HCl. The solvent was removed in vacuo and the residue was purified by prep-HPLC A (30-60% MeCN) to give the diastereomeric products R-P1 (65.0 mg) and R-P2 (35.0 mg) as a white solid.

R-P1 ESI 716.2 (M+H)$^+$ $^1$H NMR (400 MHz, MeOD) δ 7.85 (s, 1H), 7.40-7.32 (m, 2H), 6.90-6.86 (m, 2H), 6.75 (s, 1H), 5.64-5.60 (m, 2H), 4.07 (t, J=8.1 Hz, 4H), 3.36-3.33 (m, 1H), 3.31-3.27 (m, 1H), 2.91-2.69 (m, 4H), 2.49-2.44 (m, 2H), 2.06-1.97 (m, 5H), 1.89 (s, 3H), 1.48-1.36 (m, 1H), 0.99-0.91 (m, 6H).

R-P2 ESI 716.2 (M+H)$^+$ $^1$H NMR (400 MHz, MeOD) δ 7.75 (s, 1H), 7.45-7.38 (m, 2H), 6.92 (s, 1H), 6.90 (s, 2H),

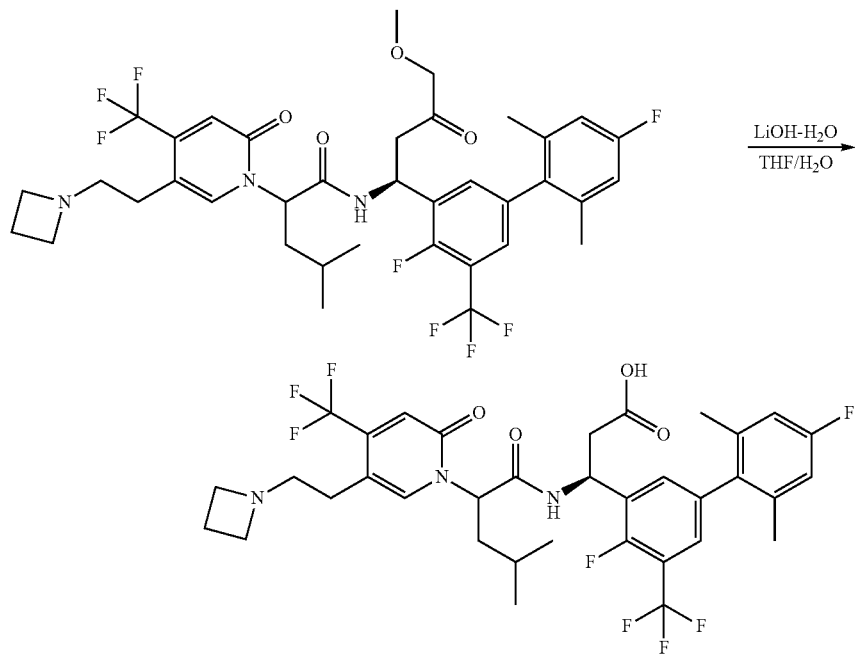

Ethyl (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',6'-dimethyl-5-(trifluoromethyl)-[1,1'-biphenyl]-3-yl)propanoate (180 mg, 0.24 mmol) was treated with 5.82-5.78 (m, 1H), 5.63 (t, J=7.7 Hz, 1H), 4.15 (t, J=7.9 Hz, 4H), 3.45-3.35 (m, 2H), 2.99-2.80 (m, 2H), 2.69-2.42 (m, 4H), 2.03-1.92 (m, 7H), 1.76-1.63 (m, 1H), 1.44-1.37 (m, 1H), 0.92-0.89 (m, 6H).

3-13. Preparation of (S)-3-(4,5-difluoro-2',6'-dimethyl-[1,1'-biphenyl]-3-yl)-3-((S)-2-(5-(2-(dimethylamino)ethyl)-4-methyl-2-oxopyridin-1(2H)-yl)-4-methylpentanamido)propanoic acid (compounds S-P1 and S-P2)

Step 1: ethyl (S)-3-(4,5-difluoro-2',6'-dimethyl-[1,1'-biphenyl]-3-yl)-3-((S)-2-(5-(2-(dimethylamino)ethyl)-4-methyl-2-oxopyridin-1(2H)-yl)-4-methylpentanamido)propanoate

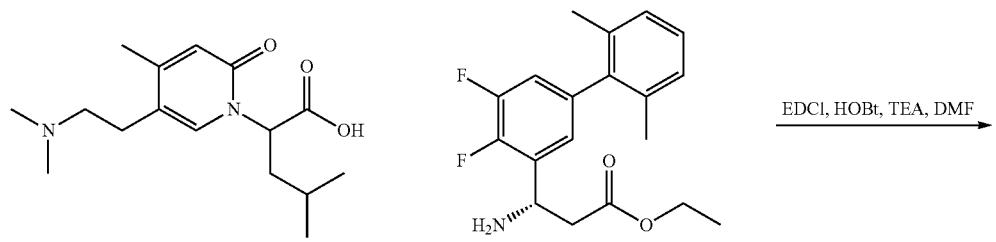

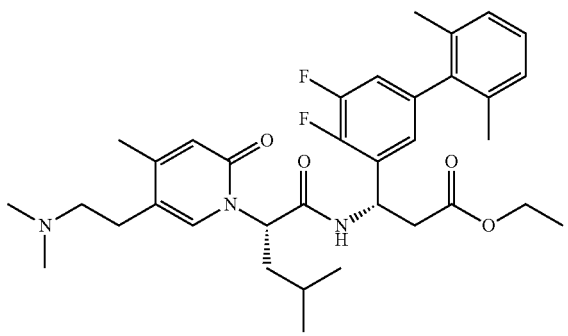

A mixture of 2-(5-(2-(dimethylamino)ethyl)-4-methyl-2-oxopyridin-1(2H)-yl)-4-methylpentanoic acid (80 mg, 0.27 mmol), ethyl (S)-3-amino-3-(4,5-difluoro-2',6'-dimethyl-[1,1'-biphenyl]-3-yl)propanoate (100 mg, 0.30 mmol), EDCI (77 mg, 0.41 mmol), TEA (0.2 mL) and HOBt (36 mg, 0.27 mmol) in acetonitrile (10 mL) was stirred at room temperature for 20 hours. The reaction mixture was concentrated in vacuo and purified by reverse phase HPLC on a C18/40 g column (A: water 10 mM NH₄HCO₃, B: MeOH, 0~100%) to provide ethyl (S)-3-(4,5-difluoro-2',6'-dimethyl-[1,1'-biphenyl]-3-yl)-3-((S)-2-(5-(2-(dimethylamino)ethyl)-4-methyl-2-oxopyridin-1(2H)-yl)-4-methylpentanamido)propanoate as yellow oil (75 mg). Yield 45% (ESI 610.3 (M+H)$^+$).

Step 2: (S)-3-(4,5-difluoro-2',6'-dimethyl-[1,1'-biphenyl]-3-yl)-3-((S)-2-(5-(2-(dimethylamino)ethyl)-4-methyl-2-oxopyridin-1(2H)-yl)-4-methylpentanamido)propanoic acid

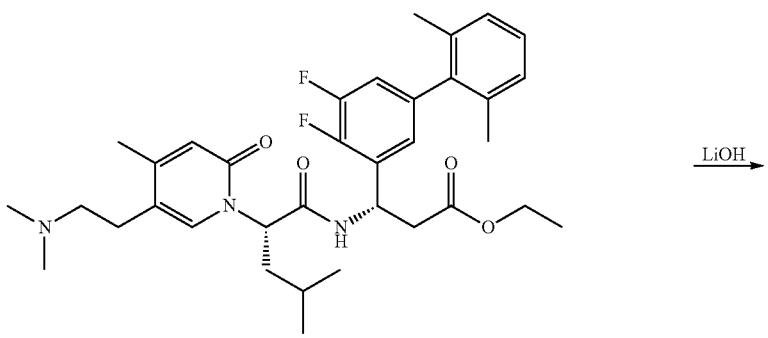

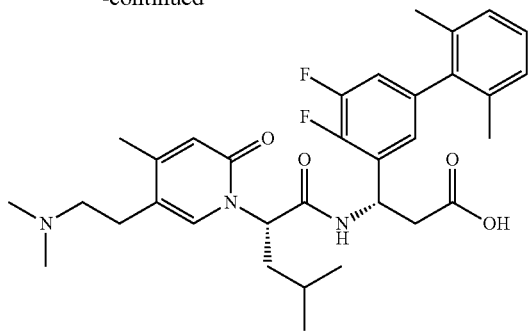

Ethyl (S)-3-(4,5-difluoro-2',6'-dimethyl-[1,1'-biphenyl]-3-yl)-3-((S)-2-(5-(2-(dimethylamino)ethyl)-4-methyl-2-oxopyridin-1(2H)-yl)-4-methylpentanamido)propanoate (75 mg, 0.12 mmol) was treated with LiOH monohydrate (26 mg, 0.62 mmol) in MeOH (2 mL) and H₂O (1 mL) at room temperature for 2 h. The reaction mixture was acidified to pH 4~5 with 1N HCl. The mixture was concentrated in vacuo and the residue was purified by prep-HPLC A (30-60% MeCN) to give the diastereomeric products S-P1 (28 mg) and S-P2 (38 mg) as a white solid.

S-P1 ESI 582.2 (M+H)⁺. ¹H NMR (500 MHz, MeOD) δ 7.58 (s, 1H), 7.19-7.14 (m, 1H), 7.10 (d, J=8.6 Hz, 2H), 6.96-6.90 (m, 1H), 6.83 (d, J=5.8 Hz, 1H), 6.33 (s, 1H), 5.57 (s, 1H), 5.52-5.47 (m, 1H), 3.33-3.13 (m, 2H), 2.88 (t, J=7.3 Hz, 2H), 2.79 (s, 6H), 2.72-2.60 (m, 2H), 2.26 (s, 3H), 2.03-1.90 (m, 8H), 1.40 (d, J=7.3 Hz, 1H), 0.95-0.91 (m, 6H).

S-P2 ESI 582.2 (M+H)⁺. ¹H NMR (500 MHz, MeOD) δ 7.54 (s, 1H), 7.19-7.15 (m, 1H), 7.11 (d, J=7.8 Hz, 2H), 7.01-6.95 (m, 1H), 6.90 (d, J=5.9 Hz, 1H), 6.42 (s, 1H), 5.67-5.64 (m, 1H), 5.61-5.55 (m, 1H), 3.24-3.18 (m, 1H), 2.97-2.84 (m, 8H), 2.63 (dd, J=15.2, 4.2 Hz, 1H), 2.49 (dd, J=15.2, 9.9 Hz, 1H), 2.27 (s, 3H), 2.02 (s, 6H), 1.99-1.93 (m, 1H), 1.81-1.73 (m, 1H), 1.41-1.37 (m, 1H), 0.90-0.88 (m, 6H).

3-14. Preparation of (3S)-3-(2-(5-(2-(dimethylamino)ethyl)-4-methyl-2-oxopyridin-1(2H)-yl)-4-methylpentanamido)-3-(4-fluoro-2',4',5,6'-tetramethyl-[1,1'-biphenyl]-3-yl)propanoic acid (compounds T-P1 and T-P2)

Step 1: ethyl(3S)-3-(2-(5-(2-(dimethylamino)ethyl)-4-methyl-2-oxopyridin-1(2H)-yl)-4-methylpentanamido)-3-(4-fluoro-2',4',5,6'-tetramethyl-[1,1'-biphenyl]-3-yl)propanoate

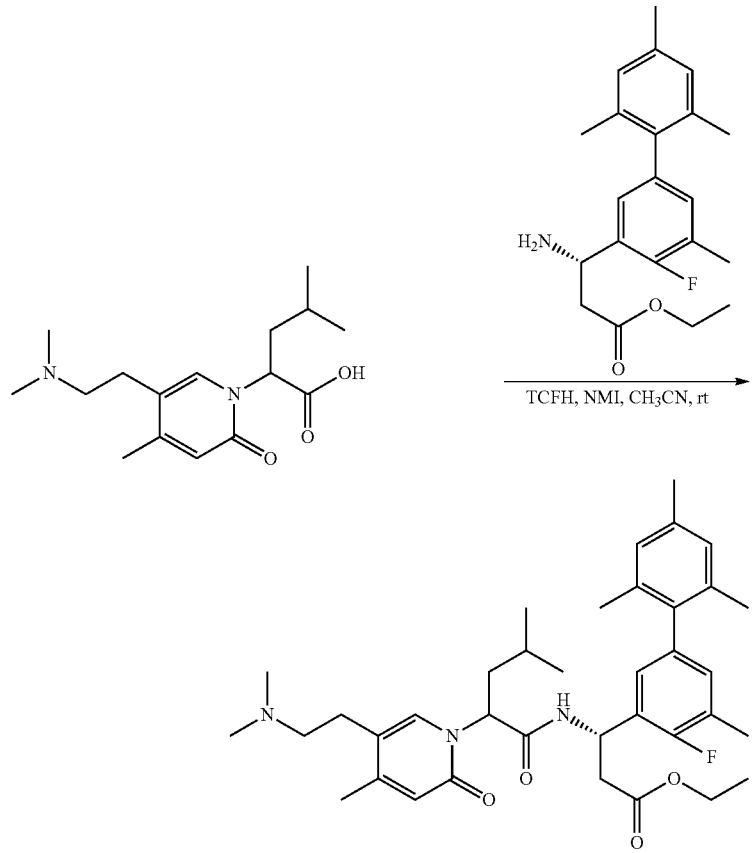 [SMILES: Cc1cc(=O)n(C(CC(C)C)C(=O)O)cc1CCN(C)C ; CCOC(=O)C[C@H](N)c1cc(-c2c(C)cc(C)cc2C)cc(C)c1F ; CCOC(=O)C[C@H](NC(=O)C(CC(C)C)n1cc(CCN(C)C)c(C)cc1=O)c1cc(-c2c(C)cc(C)cc2C)cc(C)c1F]

A mixture of 2-(5-(2-(dimethylamino)ethyl)-4-methyl-2-oxopyridin-1(2H)-yl)-4-methylpentanoic acid (100.0 mg, 0.34 mmol), ethyl (S)-3-amino-3-(4-fluoro-2',4',5,6'-tetramethyl-[1,1'-biphenyl]-3-yl)propanoate (117.0 mg, 0.34 mmol), TCFH (190.4 mg, 0.68 mmol), NMI (115.5 mg, 1.36 mmol) in CH₃CN (5 mL) was stirred at room temperature for 2 hours. The reaction mixture was concentrated in vacuo and purified by reverse phase HPLC on a C18/40 g column (A: water 10 mM NH₄HCO₃, B: MeOH, 0~100%) to provide ethyl (3S)-3-(2-(5-(2-(dimethylamino)ethyl)-4-methyl-2-oxopyridin-1(2H)-yl)-4-methylpentanamido)-3-(4-fluoro-2',4',5,6'-tetramethyl-[1,1'-biphenyl]-3-yl)propanoate as a white oil (95.0 mg). Yield 45% (ESI 620.3 (M+H)⁺).

Step 2: (3S)-3-(2-(5-(2-(dimethylamino)ethyl)-4-methyl-2-oxopyridin-1(2H)-yl)-4-methylpentanamido)-3-(4-fluoro-2',4',5,6'-tetramethyl-[1,1'-biphenyl]-3-yl)propanoic acid

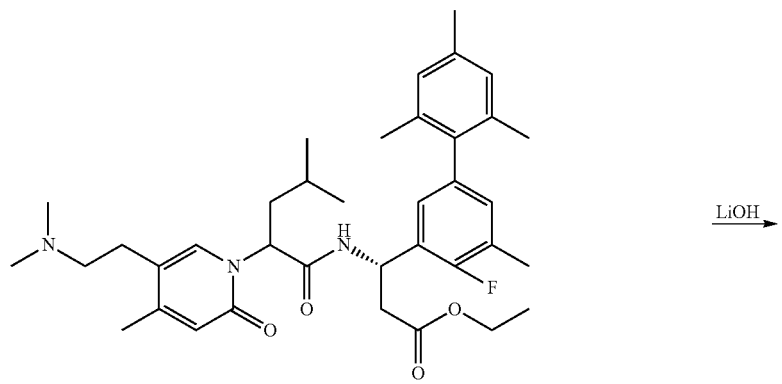

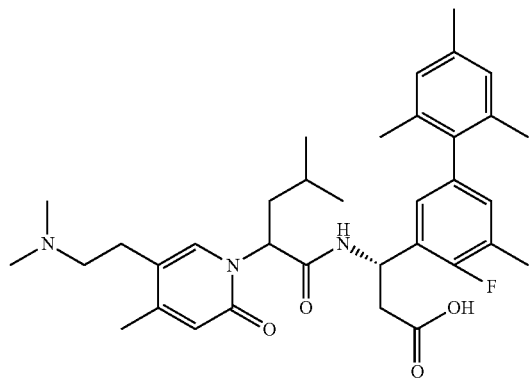

Ethyl (3S)-3-(2-(5-(2-(dimethylamino)ethyl)-4-methyl-2-oxopyridin-1(2H)-yl)-4-methylpentanamido)-3-(4-fluoro-2',4',5,6'-tetramethyl-[1,1'-biphenyl]-3-yl)propanoate (95.0 mg, 0.15 mmol) was treated with LiOH—H₂O (25.2 mg, 0.60 mmol) in MeOH (4 mL) and H₂O (1 mL) at room temperature for 2 hours. The reaction mixture was acidified to pH 4~5 with 1N HCl. The solvent was removed in vacuo and the residue was purified by prep-HPLC A (30-60% MeCN) to give the diastereomeric products T-P1 (26.2 mg) and T-P2 (58.3 mg) as a white solid.

T-P1 ESI 592.3 (M+H)⁺. ¹H NMR (400 MHz, MeOD) δ 7.54 (s, 1H), 6.89 (d, J=3.6 Hz, 2H), 6.85-6.72 (m, 2H), 6.32 (s, 1H), 5.69-5.56 (m, 1H), 5.53-5.41 (m, 1H), 3.04-2.84 (m, 2H), 2.79 (t, J=7.3 Hz, 2H), 2.71-2.51 (m, 8H), 2.36-2.17 (m, 9H), 2.06-1.88 (m, 5H), 1.83 (s, 3H), 1.51-1.30 (m, 1H), 1.02-0.82 (m, 6H).
T-P2 ESI 592.3 (M+H)⁺. ¹H NMR (400 MHz, MeOD) δ 7.56 (s, 1H), 6.98-6.82 (m, 4H), 6.44 (s, 1H), 5.69-5.50 (m, 2H), 3.20 (d, J=38.2 Hz, 2H), 2.85 (d, J=33.5 Hz, 8H), 2.70-2.40 (m, 2H), 2.38-2.19 (m, 9H), 2.04-1.87 (m, 7H), 1.85-1.70 (m, 1H), 1.47-1.26 (m, 1H), 0.99-0.78 (m, 6H).

3-15. Preparation of (3S)-3-(4-fluoro-3'-methoxy-2', 5,6'-trimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido) propanoic acid (compounds N-P1 and N-P2)

Step 1: ethyl(3S)-3-(4-fluoro-3'-methoxy-2',5,6'-trimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido) propanoate

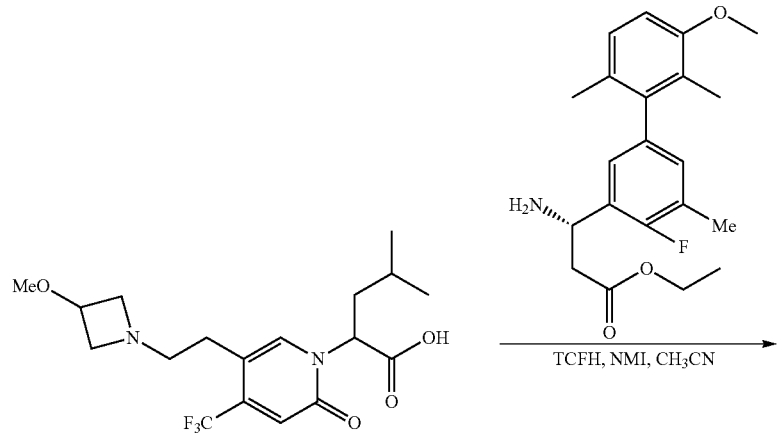

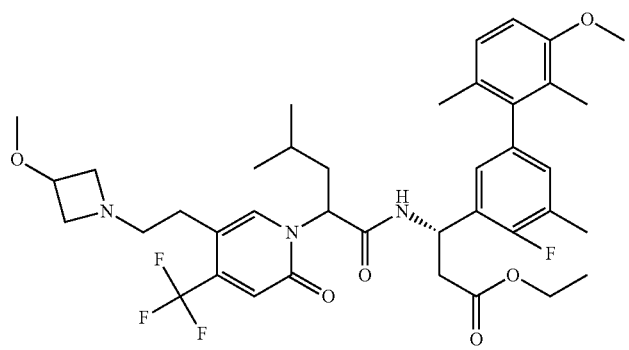

A mixture of 2-(5-(2-(3-methoxyazetidin-1-yl)ethyl)-2-oxo-4-(trifluoromethyl)pyridin-1(2H)-yl)-4-methylpentanoic acid (272 mg, 0.70 mmol, 1.25 eq), ethyl (S)-3-amino-3-(4-fluoro-3'-methoxy-2',5,6'-trimethyl-[1,1'-biphenyl]-3-yl)propanoate (200 mg, 0.56 mmol, 1.00 eq), NMI (0.5 mL) and TCFH (232 mg, 0.83 mmol, 1.50 eq) in $CH_3CN$ (5 mL) was stirred at room temperature for 1 hour. The solvent was concentrated in vacuo and the residue was purified by prep-HPLC A (30-60% $CH_3CN$) to provide ethyl (3S)-3-(4-fluoro-3'-methoxy-2',5,6'-trimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate (201 mg). Yield 49% (ESI 732.2 [M+H]$^+$).

Step 2: (3S)-3-(4-fluoro-3'-methoxy-2',5,6'-trimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid

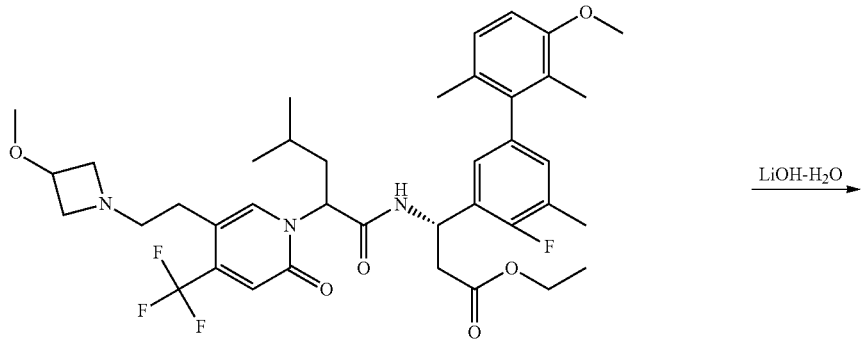

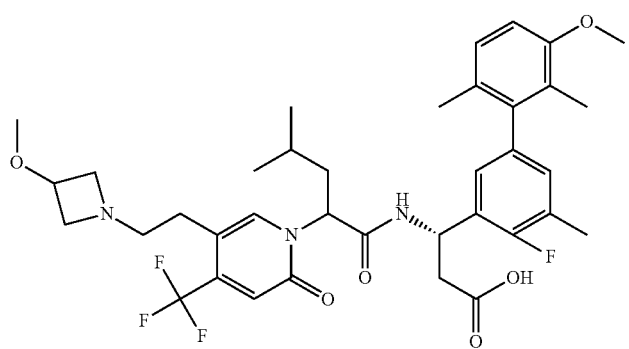

Ethyl (3S)-3-(4-fluoro-3'-methoxy-2',5,6'-trimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate (201 mg, 0.27 mmol, 1.00 eq) was treated with LiOH—H$_2$O (44 mg, 1.08 mmol, 4.00 eq) in MeOH (10 mL) and H$_2$O (5 mL) at room temperature for 2 hours. The reaction mixture was acidified to pH 4~5 with 1N HCl. The solvent was removed in vacuo and the residue was purified by prep-HPLC A (30-60% CH$_3$CN) to give the diastereomeric products N-P1 (31 mg) and N-P2 (41 mg) as a white solid.

N-P1 ESI 704.4 (M+H)$^+$. $^1$H NMR (400 MHz, MeOD) δ 7.84 (s, 1H), 7.03-6.79 (m, 5H), 5.69-5.58 (m, 2H), 4.21-4.18 (m, 3H), 3.83 (s, 3H), 3.76-3.70 (m, 2H), 3.31 (s, 3H), 3.24-3.20 (m, 2H), 2.84-2.72 (m, 4H), 2.29 (s, 3H), 1.98 (t, J=7.6 Hz, 2H), 1.92-1.68 (m, 6H), 1.48-1.41 (m, 1H), 0.98-0.93 (m, 6H).

N-P2 ESI 704.4 (M+H)$^+$. $^1$H NMR (400 MHz, MeOD) δ 7.76 (s, 1H), 7.05 (d, J=8.4 Hz, 1H), 7.01-6.80 (m, 4H), 5.74-5.62 (m, 2H), 4.24 (s, 3H), 3.84 (s, 3H), 3.75-3.66 (m, 2H), 3.31 (s, 3H), 3.30-3.15 (m, 2H), 2.85-2.63 (m, 4H), 2.33 (s, 3H), 2.09-1.89 (m, 4H), 1.86 (d, J=3.1 Hz, 3H), 1.74-1.67 (m, 1H), 1.42-1.39 (m, 1H), 0.90 (d, J=6.3 Hz, 6H).

3-16. Preparation of (3S)-3-(2-(5-(2-(dimethyl-amino)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic acid (compounds U-P1 and U-P2)

Step 1: ethyl (3S)-3-(2-(5-(2-(dimethylamino)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoate

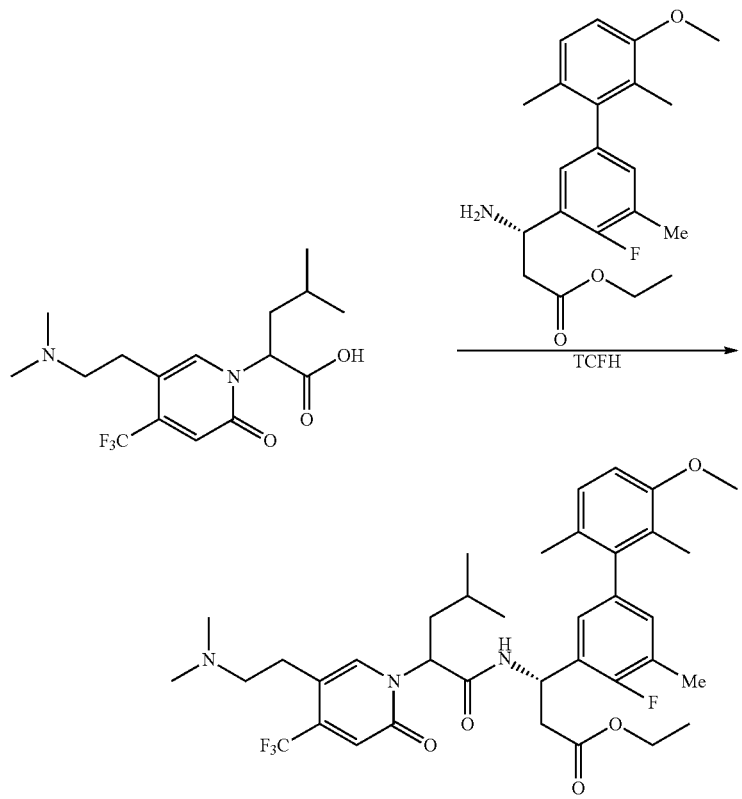

A mixture of 2-(5-(2-(dimethylamino)ethyl)-2-oxo-4-(trifluoromethyl)pyridin-1(2H)-yl)-4-methylpentanoic acid (232 mg, 0.67 mmol, 1.20 eq), ethyl (S)-3-amino-3-(4-fluoro-3'-methoxy-2',5,6'-trimethyl-[1,1'-biphenyl]-3-yl)propanoate (200 mg, 0.56 mmol, 1.00 eq), NMI (0.5 mL) and TCFH (233 mg, 0.83 mmol, 1.50 eq) in CH$_3$CN (5 mL) was stirred at room temperature for 1 hour. The solvent was concentrated in vacuo and the residue was purified by prep-HPLC A (30-60% CH$_3$CN) to provide ethyl (3S)-3-(2-(5-(2-(dimethylamino)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoate as a white solid (250 mg). Yield 65% (ESI 690.2 [M+H]$^+$).

Step 2: (3S)-3-(2-(5-(2-(dimethylamino)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic acid

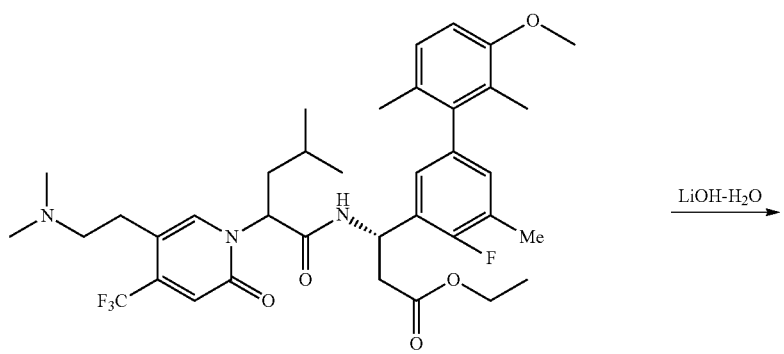

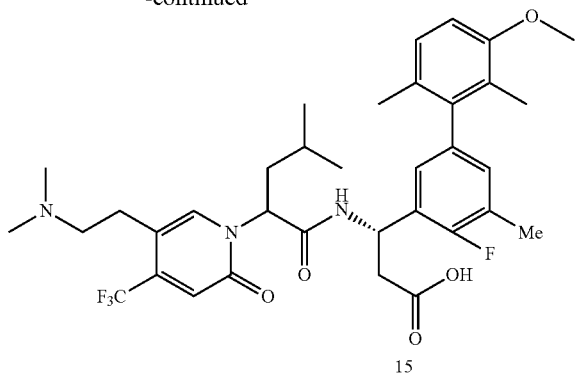

15

Ethyl (3S)-3-(2-(5-(2-(dimethylamino)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoate (250 mg, 0.32 mmol, 1.00 eq) was treated with LiOH—H$_2$O (19 mg, 0.81 mmol, 2.50 eq) in MeOH (5 mL) and H$_2$O (0.5 mL) at room temperature for 2 hours. The reaction mixture was acidified to pH 4~5 with 1N HCl. The solvent was removed in vacuo and the residue was purified by prep-HPLC A (30-60% CH$_3$CN) to give the diastereomeric products U-P1 (40.0 mg) and U-P2 (55.0 mg) as a white solid.

U-P1 ESI 662.3 (M+H)$^+$. $^1$H NMR (400 MHz, MeOD) δ 7.90 (s, 1H), 7.04-6.99 (m, 1H), 6.86-6.76 (m, 4H), 5.70-5.66 (m, 1H), 5.58-5.55 (m, 1H), 3.83 (s, 3H), 3.15-3.03 (m, 2H), 2.97-2.93 (m, 2H), 2.74-2.69 (m, 8H), 2.29 (s, 3H), 2.00-1.96 (m, 2H), 1.92-1.67 (m, 6H), 1.48-1.41 (m, 1H), 0.97-0.93 (m, 6H).

U-P2 ESI 662.3 (M+H)$^+$. $^1$H NMR (400 MHz, MeOD) δ 7.84 (s, 1H), 7.05 (d, J=8.5 Hz, 1H), 7.03-6.79 (m, 4H), 5.73-5.69 (m, 1H), 5.61 (t, J=7.7 Hz, 1H), 3.84 (s, 3H), 3.33-3.22 (m, 2H), 3.01-2.98 (m, 2H), 2.82 (s, 6H), 2.67-2.62 (m, 1H), 2.55-2.49 (m, 1H), 2.32 (s, 3H), 2.24-1.88 (m, 4H), 1.86 (d, J=3.1 Hz, 3H), 1.81-1.60 (m, 1H), 1.45-1.37 (m, 1H), 0.90-0.88 (m, 6H).

3-17. Preparation of (3S)-3-(2-(5-(2-(dimethylamino)ethyl)-2-oxo-4-(trifluoromethyl)pyridin-1(2H)-yl)-4-methylpentanamido)-3-(4-fluoro-4'-methoxy-2',5,6'-trimethyl-[1,1'-biphenyl]-3-yl)propanoic acid (compounds V-P1 and V-P2)

Step 1: ethyl (3S)-3-(2-(5-(2-(dimethylamino)ethyl)-2-oxo-4-(trifluoromethyl)pyridin-1(2H)-yl)-4-methylpentanamido)-3-(4-fluoro-4'-methoxy-2',5,6'-trimethyl-[1,1'-biphenyl]-3-yl)propanoate

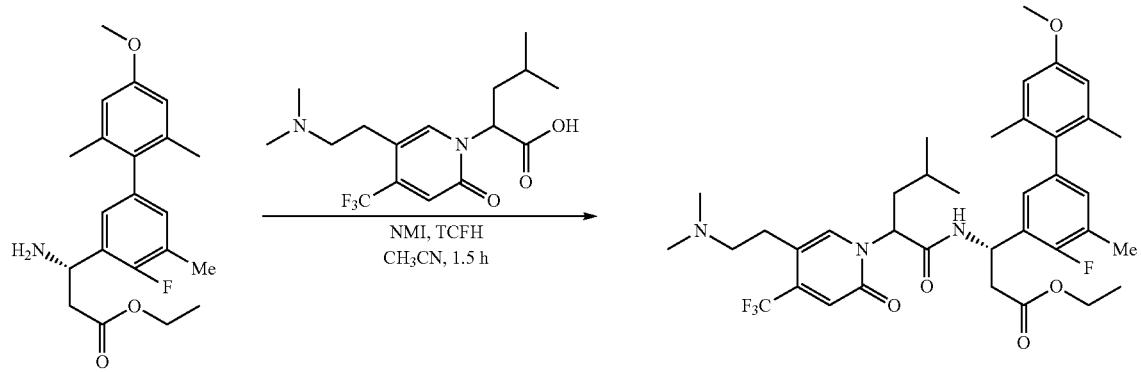

A mixture of 2-(5-(2-(dimethylamino)ethyl)-2-oxo-4-(trifluoromethyl)pyridin-1(2H)-yl)-4-methylpentanoic acid (170 mg, 0.49 mmol), ethyl (S)-3-amino-3-(4-fluoro-4'-methoxy-2',5,6'-trimethyl-[1,1'-biphenyl]-3-yl)propanoate (176 mg, 0.49 mmol), NMI (160 mg, 1.96 mmol) and TCFH (205.8 mg, 0.74 mmol) in CH$_3$CN (10 mL) was stirred at room temperature for 1.5 hours. The solvent was concentrated in vacuo and the residue was purified by silica gel column (DCM:MeOH 9:1) to provide ethyl (3S)-3-(2-(5-(2-(dimethylamino)ethyl)-2-oxo-4-(trifluoromethyl)pyridin-1(2H)-yl)-4-methylpentanamido)-3-(4-fluoro-4'-methoxy-2',5,6'-trimethyl-[1,1'-biphenyl]-3-yl)propanoate as a yellow solid (131 mg). Yield 39% (ESI 690.3 [M+H]$^+$).

Step 2: (3S)-3-(2-(5-(2-(dimethylamino)ethyl)-2-oxo-4-(trifluoromethyl)pyridin-1(2H)-yl)-4-methylpentanamido)-3-(4-fluoro-4'-methoxy-2',5,6'-trimethyl-[1,1'-biphenyl]-3-yl)propanoic acid yl)propanoate (131 mg, 0.19 mmol) was treated with LiOH—H$_2$O (32 mg, 0.76 mmol) in MeOH (10 mL) and H$_2$O (5 mL) at room temperature for 2 hours. The reaction mixture was acidified to pH 4~5 with 1N HCl. The solvent was removed in vacuo and the residue was purified by prep-HPLC A (30-60% CH$_3$CN) to give the diastereomeric products V-P1 (24 mg) and V-P2 (15 mg) as a white solid.

V-P1 ESI 662.3 (M+H)$^+$. $^1$H NMR (500 MHz, MeOD) δ 7.90 (s, 1H), 6.85 (t, J=7.6 Hz, 2H), 6.76 (s, 1H), 6.63 (d, J=18.7 Hz, 2H), 5.68 (t, J=7.9 Hz, 1H), 5.57-5.54 (m, 1H), 3.80 (s, 3H), 3.12-3.02 (m, 2H), 2.98-2.90 (m, 2H), 2.90-2.46 (m, 8H), 2.28 (s, 3H), 2.06-1.94 (m, 5H), 1.80 (s, 3H), 1.48-1.41 (m, 1H), 0.97-0.93 (m, 6H).

V-P2 ESI 662.3 (M+H)$^+$. $^1$H NMR (500 MHz, MeOD) δ 7.87 (s, 1H), 6.92-6.90 (m, 3H), 6.67 (s, 2H), 5.73-5.70 (m, 1H), 5.62 (t, J=7.6 Hz, 1H), 3.80 (s, 3H), 3.30-3.20 (m, 2H),

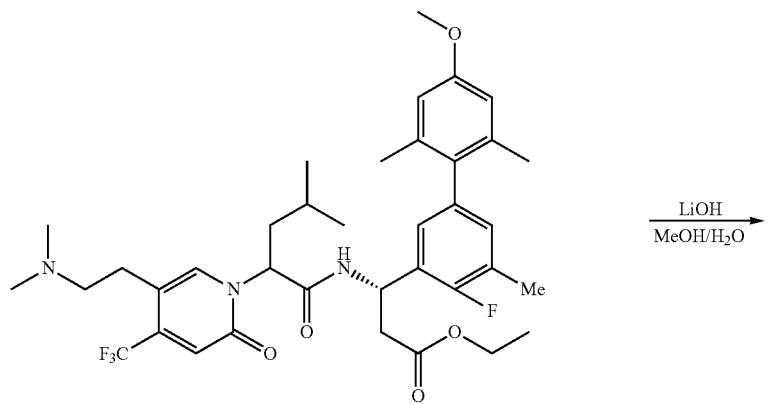

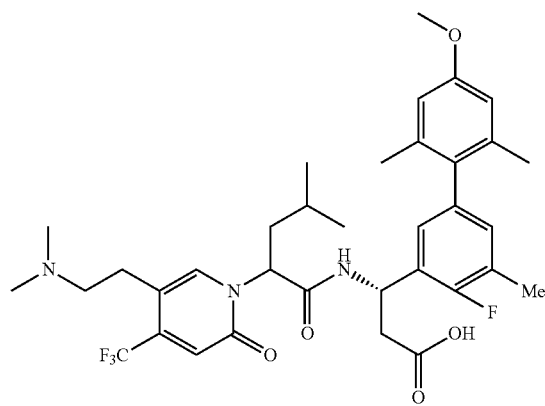

Ethyl (3S)-3-(2-(5-(2-(dimethylamino)ethyl)-2-oxo-4-(trifluoromethyl)pyridin-1(2H)-yl)-4-methylpentanamido)-3-(4-fluoro-4'-methoxy-2',5,6'-trimethyl-[1,1'-biphenyl]-3-

3.01-2.97 (m, 2H), 2.83 (s, 6H), 2.70-2.59 (m, 1H), 2.55-2.50 (m, 1H), 2.32 (s, 3H), 1.98 (d, J=4.0 Hz, 7H), 1.73-1.68 (m, 1H), 1.43-1.36 (m, 1H), 0.90-0.88 (m, 6H).

3-18. Preparation of (3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid (compounds W-P1 and W-P2)

Step 1: ethyl (3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate

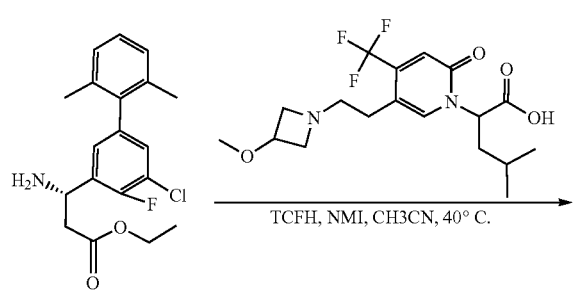

A mixture of 2-(5-(2-(3-methoxyazetidin-1-yl)ethyl)-2-oxo-4-(trifluoromethyl)pyridin-1(2H)-yl)-4-methylpentanoic acid (167 mg, 0.43 mmol), ethyl (S)-3-amino-3-(5-chloro-4-fluoro-2',6'-dimethyl-[1,1'-biphenyl]-3-yl)propanoate (150 mg, 0.43 mmol), TCFH (182 mg, 0.65 mmol) and NMI (176 mg, 2.15 mmol) in CH₃CN (4 mL) was stirred at 40° C. for 2 hours. The reaction mixture was concentrated in vacuo and purified by reverse phase HPLC on a C18/40 g column (A: water 10 mM NH₄HCO₃, B: MeOH, 0~100%) to provide ethyl (3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate as a yellow oil (150 mg). Yield 48% (ESI 722.2 (M+H)⁺).

Step 2: (3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid

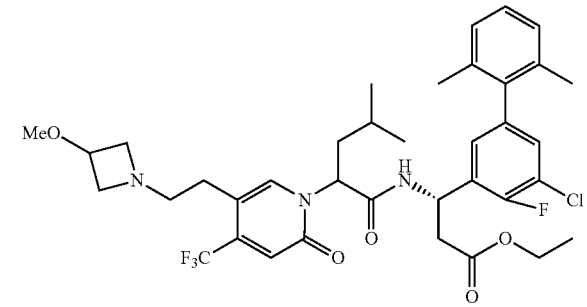

Ethyl (3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate (150 mg, 0.21 mmol) was treated with LiOH—H₂O (42 mg, 1 mmol) in MeOH (3 mL) and H₂O (1 mL) at room temperature for 2 hours. The reaction mixture was acidified to pH 4~5 with 1N HCl. The solvent was removed in vacuo and the residue was purified by prep-HPLC A (30-60% CH₃CN) to give the diastereomeric products W-P1 (46 mg) and W-P2 (57 mg) as a white solid.

W-P1 ESI 694.2 (M+H)⁺. ¹H NMR (400 MHz, MeOD) δ 7.85 (s, 1H), 7.21-7.00 (m, 5H), 6.74 (s, 1H), 5.72-5.50 (m, 2H), 4.27-4.08 (m, 3H), 3.80-3.61 (m, 2H), 3.31 (s, 3H), 3.26-3.09 (m, 2H), 2.86-2.70 (m, 4H), 2.09-1.93 (m, 5H), 1.84 (s, 3H), 1.50-1.37 (m, 1H), 1.04-0.83 (m, 6H).

W-P2 ESI 694.2 (M+H)⁺. ¹H NMR (400 MHz, MeOD) δ 7.75 (s, 1H), 7.26-7.06 (m, 5H), 6.90 (s, 1H), 5.79-5.70 (m, 1H), 5.63 (t, J=7.7 Hz, 1H), 4.44-4.22 (m, 3H), 3.98-3.76 (m, 2H), 3.41-3.34 (m, 5H), 2.99-2.74 (m, 2H), 2.70-2.49 (m, 2H), 2.08-1.89 (m, 7H), 1.77-1.62 (m, 1H), 1.48-1.32 (m, 1H), 0.90 (d, J=6.4 Hz, 6H).

3-19. Preparation of (3S)-3-(5-chloro-4,4'-difluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid (compounds X-P1 and X-P2)

Step 1: (3S)-3-(5-chloro-4,4'-difluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate ethyl

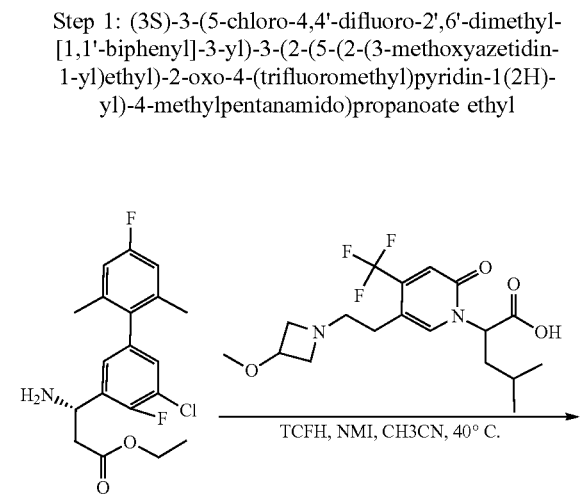

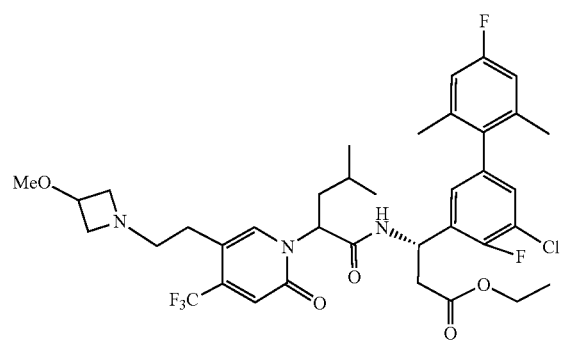

A mixture of 2-(5-(2-(3-methoxyazetidin-1-yl)ethyl)-2-oxo-4-(trifluoromethyl)pyridin-1(2H)-yl)-4-methylpentanoic acid (160 mg, 0.41 mmol), ethyl (S)-3-amino-3-(5-chloro-4,4'-difluoro-2',6'-dimethyl-[1,1'-biphenyl]-3-yl)propanoate (150 mg, 0.41 mmol), TCFH (174 mg, 0.62 mmol) and NMI (168 mg, 2.05 mmol) in CH$_3$CN (4 mL) was stirred at 40° C. for 2 hours. The reaction mixture was concentrated in vacuo and purified by reverse phase HPLC on a C18/40 g column (A: water 10 mM NH$_4$HCO$_3$, B: MeOH, 0~100%) to provide ethyl (3S)-3-(5-chloro-4,4'-difluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoateas a yellow oil (150 mg). Yield 49% (ESI 740.2 (M+H)$^+$).

Step 2: (3S)-3-(5-chloro-4,4'-difluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid

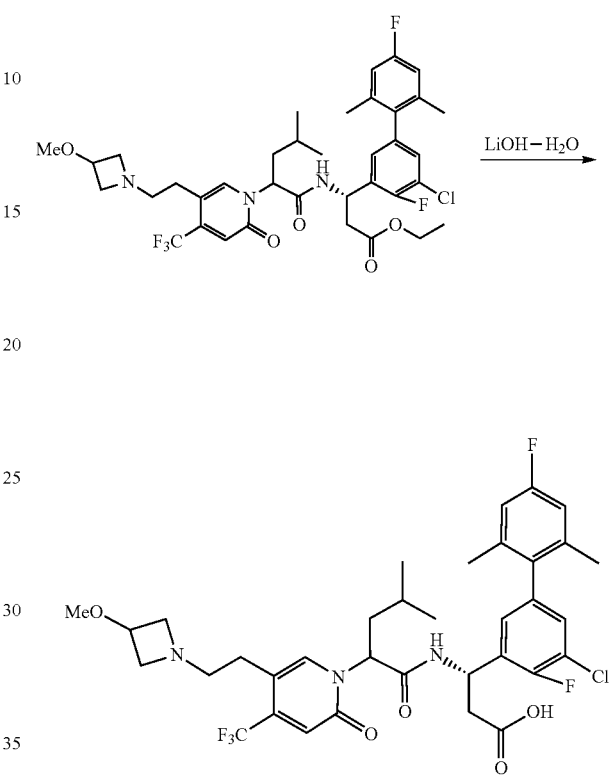

Ethyl (3S)-3-(5-chloro-4,4'-difluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate (150 mg, 0.20 mmol) was treated with LiOH—H$_2$O (42 mg, 1 mmol) in MeOH (3 mL) and H$_2$O (1 mL) at room temperature for 2 hours. The reaction mixture was acidified to pH 4~5 with 1N HCl. The solvent was removed in vacuo and the residue was purified by prep-HPLC A (30-60% CH$_3$CN) to give the diastereomeric products X-P1 (35 mg) and X-P2 (49 mg) as a white solid.

X-P1 ESI 712.2 (M+H)$^+$. $^1$H NMR (400 MHz, MeOD) δ 7.85 (s, 1H), 7.13 (d, J=6.6 Hz, 1H), 7.07-7.00 (m, 1H), 6.90-6.79 (m, 2H), 6.74 (s, 1H), 5.72-5.48 (m, 2H), 4.26-4.07 (m, 3H), 3.80-3.64 (m, 2H), 3.32 (s, 3H), 3.19 (t, J=6.2 Hz, 2H), 2.86-2.71 (m, 4H), 2.08-1.95 (m, 5H), 1.86 (d, J=4.4 Hz, 3H), 1.51-1.36 (m, 1H), 1.01-0.88 (m, 6H).

X-P2 ESI 712.2 (M+H)$^+$. $^1$H NMR (400 MHz, MeOD) δ 7.74 (s, 1H), 7.25-7.16 (m, 1H), 7.15-7.05 (m, 1H), 6.93-6.83 (m, 3H), 5.81-5.68 (m, 1H), 5.63 (t, J=7.7 Hz, 1H), 4.44-4.23 (m, 3H), 3.95-3.78 (m, 2H), 3.40-3.34 (m, 5H), 3.00-2.75 (m, 2H), 2.70-2.47 (m, 2H), 2.08-1.93 (m, 7H), 1.76-1.64 (m, 1H), 1.47-1.33 (m, 1H), 0.96-0.84 (m, 6H).

3-20. Preparation of (3S)-3-(4,4'-difluoro-2',5,6'-trimethylbiphenyl-3-yl)-3-(2-(5-(2-(dimethylamino)ethyl)-2-oxo-4-(trifluoromethyl)pyridin-1(2H)-yl)-5-methylhexanamido)propanoic acid (compounds Y-P1 and Y-P2)

Step 1: (3S)-ethyl 3-(4,4'-difluoro-2',5,6'-trimethylbiphenyl-3-yl)-3-(2-(5-(2-(dimethylamino)ethyl)-2-oxo-4-(trifluoromethyl)pyridin-1(2H)-yl)-5-methylhexanamido)propanoate

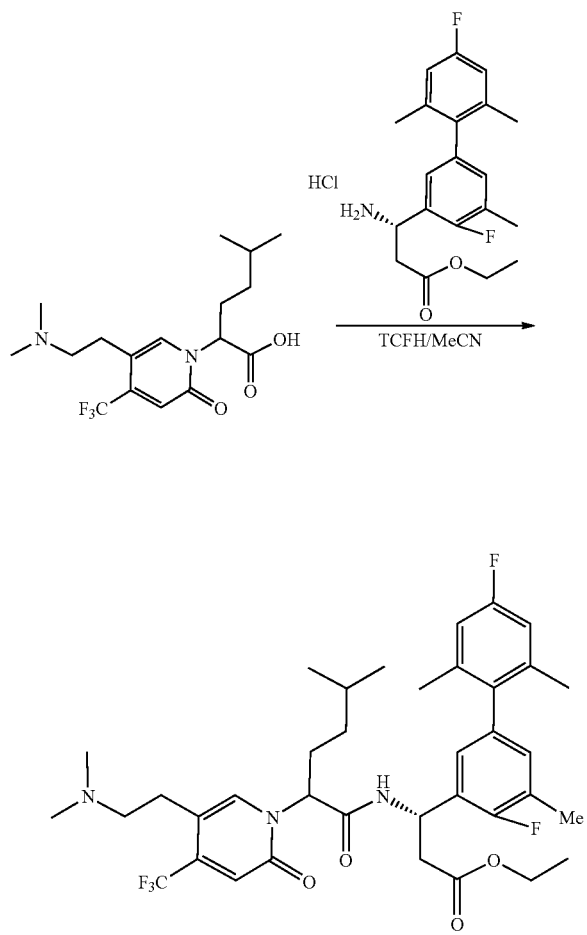

A mixture of 2-(5-(2-(dimethylamino)ethyl)-2-oxo-4-(trifluoromethyl)pyridin-1(2H)-yl)-5-methylhexanoic acid (273 mg, 0.75 mmol), (S)-ethyl 3-amino-3-(4,4'-difluoro-2',5,6'-trimethylbiphenyl-3-yl)propanoate hydrochloride (164 mg, 0.39 mmol), TCFH (211 mg, 0.75 mmol), and NMI (0.45 mL, 5.70 mmol) in acetonitrile (9 mL) was stirred at room temperature for 16 hours. The reaction mixture was concentrated in vacuo and purified by reverse phase HPLC on a C18/40 g column (A: water 10 mM $NH_4HCO_3$, B: MeOH, 0~80%) to provide (3S)-ethyl 3-(4,4'-difluoro-2',5,6'-trimethylbiphenyl-3-yl)-3-(2-(5-(2-(dimethylamino)ethyl)-2-oxo-4-(trifluoromethyl)pyridin-1(2H)-yl)-5-methylhexanamido)propanoate as brown solid (262 mg). Yield 97% (ESI 692.3 (M+H)$^+$).

Step 2: (3S)-3-(4,4'-difluoro-2',5,6'-trimethylbiphenyl-3-yl)-3-(2-(5-(2 (dimethylamino)ethyl)-2-oxo-4-(trifluoromethyl)pyridin-1(2H)-yl)-5-methylhexanamido)propanoic acid

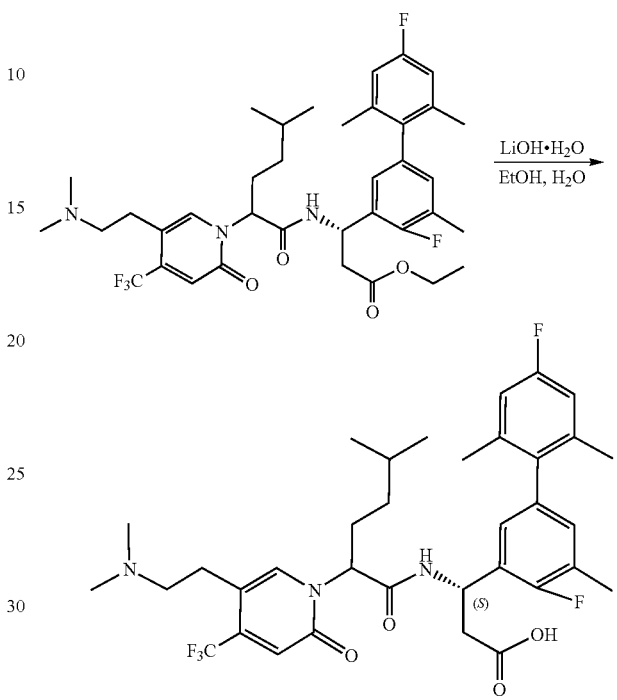

(3S)-ethyl 3-(4,4'-difluoro-2',5,6'-trimethylbiphenyl-3-yl)-3-(2-(5-(2-(dimethylamino)ethyl)-2-oxo-4-(trifluoromethyl)pyridin-1(2H)-yl)-5-methylhexanamido)propanoate (262 mg, 0.38 mmol) was treated with LiOH monohydrate (80 mg, 1.90 mmol) in EtOH (6 mL) and $H_2O$ (0.10 mL) at 36° C. for 1 hour. The reaction mixture was acidified to pH 4~5 with 1N HCl. The reaction mixture was concentrated in vacuo and purified by prep-HPLC A (30-60% MeCN) to give the diastereomeric products Y-P1 (68 mg) and Y-P2 (66 mg) as a white solid.

Y-P1 ESI 664.2 (M+H). $^1$H NMR (400 MHz, MeOD) δ 7.89 (s, 1H), 6.87-6.85 (m, 1H), 6.83-6.78 (m, 2H), 6.76-6.73 (m, 1H), 6.70 (s, 1H), 5.56-5.52 (m, 1H), 5.50-5.46 (m, 1H), 3.10-3.03 (m, 2H), 2.95-2.91 (m, 2H), 2.75-2.66 (m, 8H), 2.26 (d, J=1.2 Hz, 3H), 2.22-2.14 (m, 1H), 2.00-1.92 (m, 4H), 1.78 (s, 3H), 1.60-1.53 (m, 1H), 1.29-1.18 (m, 1H), 1.13-1.04 (m, 1H), 0.88 (d, J=2.8 Hz, 3H), 0.86 (d, J=2.8 Hz, 3H).

Y-P2 ESI 664.2 (M+H)$^+$. $^1$H NMR (400 MHz, MeOD) δ 7.92 (s, 1H), 6.95-6.93 (m, 1H), 6.91-6.88 (m, 1H), 6.87 (s, 1H), 6.82 (s, 1H), 6.80 (s, 1H), 5.72-5.68 (m, 1H), 5.47 (t, J=7.6 Hz, 1H), 3.24-3.12 (m, 2H), 3.02-2.93 (m, 2H), 2.78 (t, J=5.8 Hz, 6H), 2.67-2.62 (m, 1H), 2.58-2.52 (m, 1H), 2.30 (d, J=1.6 Hz, 3H), 2.13-2.04 (m, 1H), 2.00 (s, 3H), 1.99 (s, 3H), 1.84-1.75 (m, 1H), 1.52-1.44 (m, 1H), 1.15-0.99 (m, 2H), 0.80 (d, J=4.0 Hz, 3H), 0.77 (d, J=4.5 Hz, 3H).

3-21. Preparation of (3S)-3-(2-(5-(2-(dimethylamino)ethyl)-2-oxo-4-(trifluoromethyl)pyridin-1(2H)-yl)-5-methylhexanamido)-3-(4-fluoro-2',5,6'-trimethyl-[1,1'-biphenyl]-3-yl)propanoic acid (compounds Z-P1 and Z-P2)

Step 1: (3S)-ethyl 3-(2-(5-(2-(dimethylamino)ethyl)-2-oxo-4-(trifluoromethyl)pyridin-1(2H)-yl)-5-methylhexanamido)-3-(4-fluoro-2',5,6'-trimethylbiphenyl-3-yl)propanoate

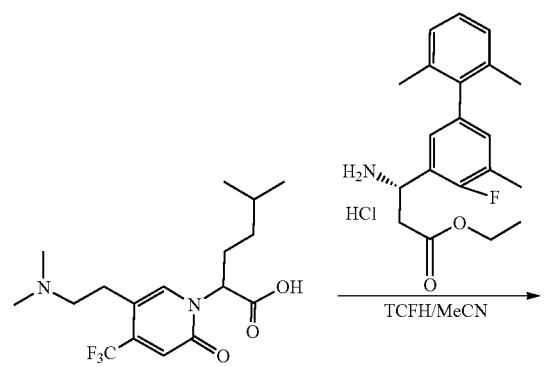

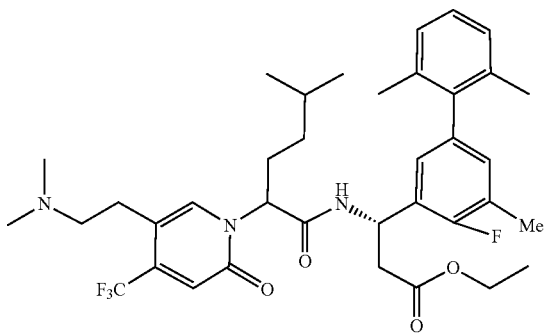

A mixture of 2-(5-(2-(dimethylamino)ethyl)-2-oxo-4-(trifluoromethyl)pyridin-1(2H)-yl)-5-methylhexanoic acid (283 mg, 0.78 mmol), (S)-ethyl 3-amino-3-(4-fluoro-2',5,6'-trimethylbiphenyl-3-yl)propanoate hydrochloride (170 mg, 0.46 mmol), TCFH (248 mg, 0.88 mmol), and NMI (0.21 mL, 2.63 mmol) in acetonitrile (10 mL) was stirred at room temperature for 20 hours. The reaction mixture was concentrated in vacuo and purified by reverse phase HPLC on a C18/40 g column (A: water 10 mM $NH_4HCO_3$, B: MeOH, 0~100%) to provide (3S)-ethyl 3-(2-(5-(2-(dimethylamino)ethyl)-2-oxo-4-(trifluoromethyl)pyridin-1(2H)-yl)-5-methylhexanamido)-3-(4-fluoro-2',5,6'-trimethylbiphenyl-3-yl)propanoate as a brown solid (223 mg). Yield 71% (ESI 674.3 $(M+H)^+$).

Step 2: (3S)-3-(2-(5-(2-(dimethylamino)ethyl)-2-oxo-4-(trifluoromethyl)pyridin-1(2H)-yl)-5-methylhexanamido)-3-(4-fluoro-2',5,6'-trimethyl-[1,1'-biphenyl]-3-yl)propanoic acid

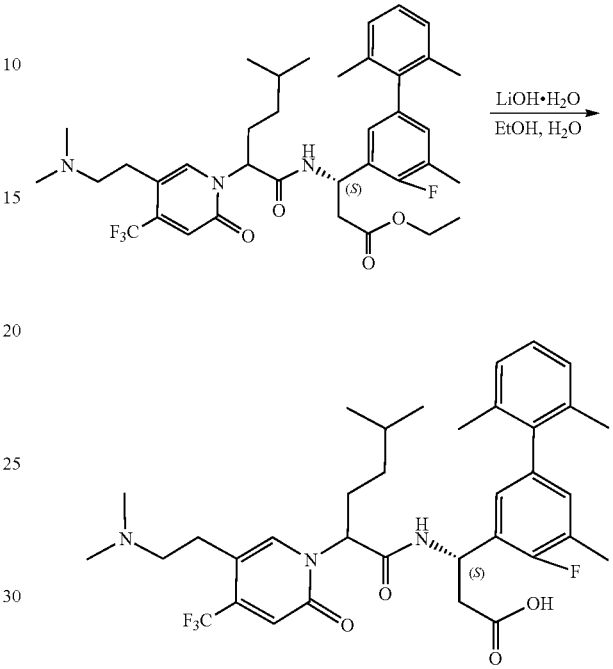

(3S)-ethyl 3-(2-(5-(2-(dimethylamino)ethyl)-2-oxo-4-(trifluoromethyl)pyridin-1(2H)-yl)-5-methylhexanamido)-3-(4-fluoro-2',5,6'-trimethylbiphenyl-3-yl)propanoate (223 mg, 0.33 mmol) was treated with LiOH monohydrate (35 mg, 0.82 mmol) in EtOH (6 mL) and $H_2O$ (0.08 mL) at 36° C. for 1 h. The reaction mixture was acidified to pH 4~5 with 1N HCl. The reaction mixture was concentrated in vacuo and purified by prep-HPLC A (30-60% MeCN) to give the diastereomeric products Z-P1(60 mg) and Z-P2 (59 mg) as a white solid.

Z-P1 ESI 646.3 $(M+H)^+$. $^1$H NMR (400 MHz, MeOD) δ 7.89 (s, 1H), 7.09 (t, J=7.4 Hz, 1H), 7.04 (d, J=6.8 Hz, 1H), 7.00 (d, J=7.2 Hz, 1H), 6.89-6.87 (m, 1H), 6.84 (d, J=7.0 Hz, 1H), 6.71 (s, 1H), 5.57-5.54 (m, 1H), 5.51-5.47 (m, 1H), 3.12-3.02 (m, 2H), 2.93 (t, J=7.9 Hz, 2H), 2.74 (s, 6H), 2.73-2.69 (m, 2H), 2.27 (d, J=1.4 Hz, 3H), 2.24-2.14 (m, 1H), 2.02-1.90 (m, 4H), 1.79 (s, 3H), 1.61-1.51 (m, 1H), 1.27-1.18 (m, 1H), 1.13-1.03 (m, 1H), 0.88 (d, J=2.4 Hz, 3H), 0.86 (d, J=2.4 Hz, 3H).

Z-P2 ESI 646.3 $(M+H)^+$. $^1$H NMR (400 MHz, MeOD) δ 7.87 (s, 1H), 7.13-7.05 (m, 3H), 6.94-6.88 (m, 3H), 5.73-5.69 (m, 1H), 5.45 (t, J=7.6 Hz, 1H), 3.27-3.15 (m, 2H), 2.98 (t, J=6.8 Hz, 2H), 2.80 (s, 6H), 2.66-2.61 (m, 1H), 2.55-2.49 (m, 1H), 2.31 (d, J=1.2 Hz, 3H), 2.14-2.05 (m, 1H), 1.99 (d, J=2.6 Hz, 6H), 1.82-1.73 (m, 1H), 1.56-1.46 (m, 1H), 1.16-0.99 (m, 2H), 0.81 (t, J=6.5 Hz, 6H).

3-22. Preparation of (3S)-3-(4-fluoro-2',4',5,6'-tetramethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid (compounds AA-P1 and AA-P2)

Step 1: ethyl (3S)-3-(4-fluoro-2',4',5,6'-tetramethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate

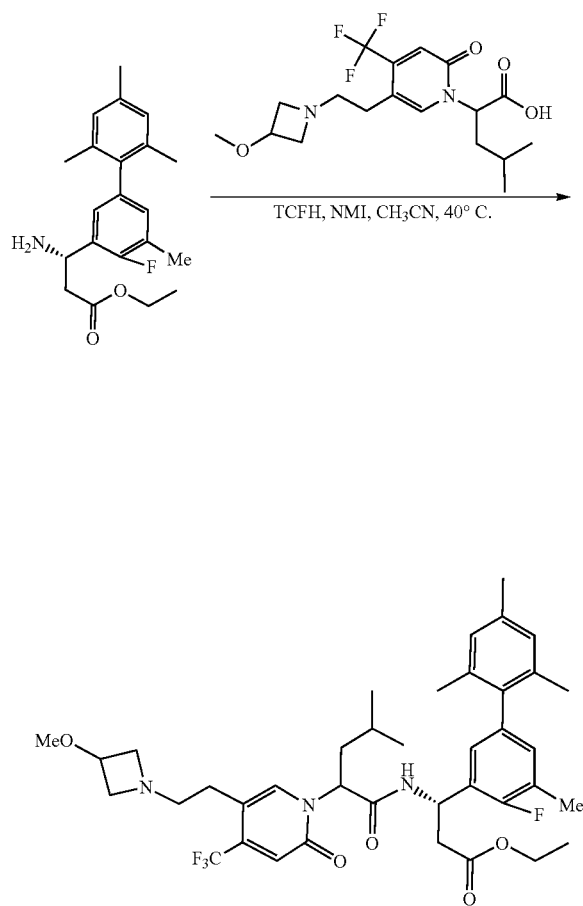

A mixture of 2-(5-(2-(3-methoxyazetidin-1-yl)ethyl)-2-oxo-4-(trifluoromethyl)pyridin-1(2H)-yl)-4-methylpentanoic acid (168 mg, 0.43 mmol), ethyl (S)-3-amino-3-(4-fluoro-2',4',5,6'-tetramethyl-[1,1'-biphenyl]-3-yl)propanoate (150 mg, 0.43 mmol), TCFH (182 mg, 0.65 mmol) and NMI (177 mg, 2.2 mmol) in CH$_3$CN (4 mL) was stirred at 40° C. for 2 hours. The reaction mixture was concentrated in vacuo and purified by reverse phase HPLC on a C18/40 g column (A: water 10 mM NH$_4$HCO$_3$, B: MeOH, 0~100%) to provide ethyl (3S)-3-(4-fluoro-2',4',5,6'-tetramethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate as a yellow oil (160 mg). Yield 51% (ESI 716.2 (M+H)$^+$).

Step 2: (3S)-3-(4-fluoro-2',4',5,6'-tetramethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid

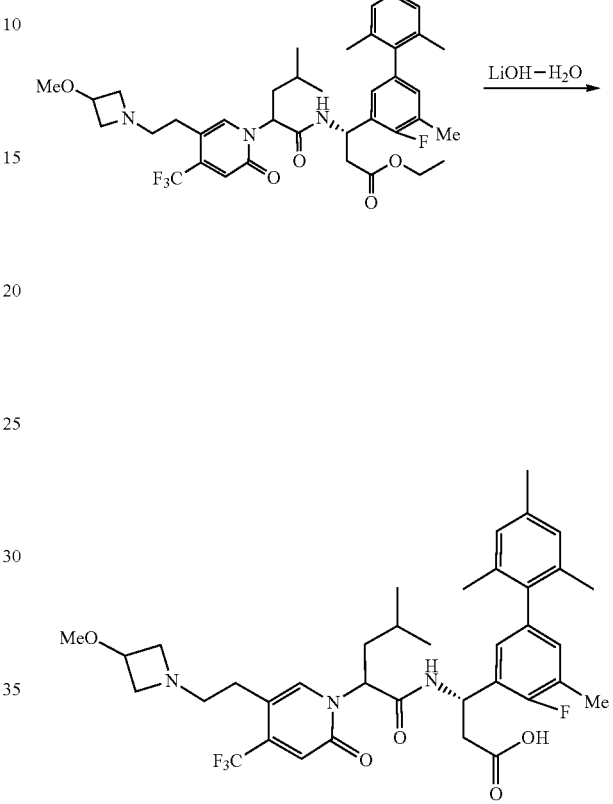

Ethyl (3S)-3-(4-fluoro-2',4',5,6'-tetramethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate (160 mg, 0.22 mmol) was treated with LiOH—H$_2$O (42 mg, 1 mmol) in MeOH (3 mL) and H$_2$O (1 mL) at room temperature for 2 hours. The reaction mixture was acidified to pH 4~5 with 1N HCl. The solvent was removed in vacuo and the residue was purified by prep-HPLC A (30-60% CH$_3$CN) to give the diastereomeric products AA-P1 (46 mg) and AA-P2 (61 mg) as a white solid.

AA-P1 ESI 688.3 (M+H)$^+$. $^1$H NMR (400 MHz, MeOD) δ 7.83 (s, 1H), 6.97-6.81 (m, 4H), 6.75 (s, 1H), 5.75-5.52 (m, 2H), 4.20-4.00 (m, 3H), 3.61 (d, J=11.2 Hz, 2H), 3.30 (s, 3H), 3.14 (t, J=6.9 Hz, 2H), 2.87-2.66 (m, 4H), 2.29 (s, 6H), 2.04-1.90 (m, 5H), 1.80 (s, 3H), 1.50-1.38 (m, 1H), 1.05-0.88 (m, 6H).

AA-P2 ESI 688.3 (M+H)$^+$. $^1$H NMR (400 MHz, MeOD) δ 7.74 (s, 1H), 6.97-6.84 (m, 5H), 5.80-5.69 (m, 1H), 5.62 (t, J=7.7 Hz, 1H), 4.46-4.21 (m, 3H), 3.93-3.76 (m, 2H), 3.40-3.34 (m, 5H), 3.04-2.76 (m, 2H), 2.70-2.45 (m, 2H), 2.38-2.21 (m, 6H), 2.07-1.88 (m, 7H), 1.75-1.61 (m, 1H), 1.49-1.33 (m, 1H), 1.03-0.83 (m, 6H).

3-23. Preparation of (3S)-3-(4-fluoro-2',5,6'-trimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid (compounds AB-P1 and AB-P2)

Step 1: ethyl (3S)-3-(4-fluoro-2',5,6'-trimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate

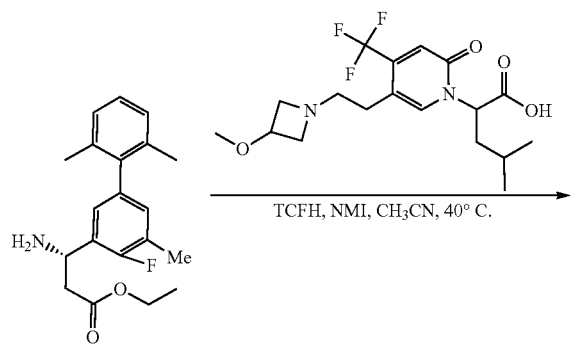

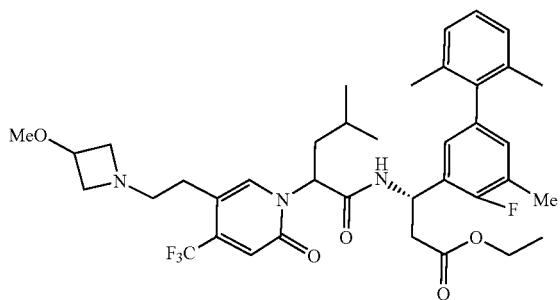

A mixture of 2-(5-(2-(3-methoxyazetidin-1-yl)ethyl)-2-oxo-4-(trifluoromethyl)pyridin-1(2H)-yl)-4-methylpentanoic acid (180 mg, 0.46 mmol), ethyl (S)-3-amino-3-(4-fluoro-2',5,6'-trimethyl-[1,1'-biphenyl]-3-yl)propanoate (150 mg, 0.46 mmol), TCFH (193 mg, 0.69 mmol) and NMI (188 mg, 2.3 mmol) in CH$_3$CN (4 mL) was stirred at 40° C. for 2 hours. The reaction mixture was concentrated in vacuo and purified by reverse phase HPLC on a C18/40 g column (A: water 10 mM NH$_4$HCO$_3$, B: MeOH, 0~100%) to provide ethyl (3S)-3-(4-fluoro-2',5,6'-trimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate as a yellow oil (140 mg). Yield 43% (ESI 702.1 (M+H)$^+$).

Step 2: (3S)-3-(4-fluoro-2',5,6'-trimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid

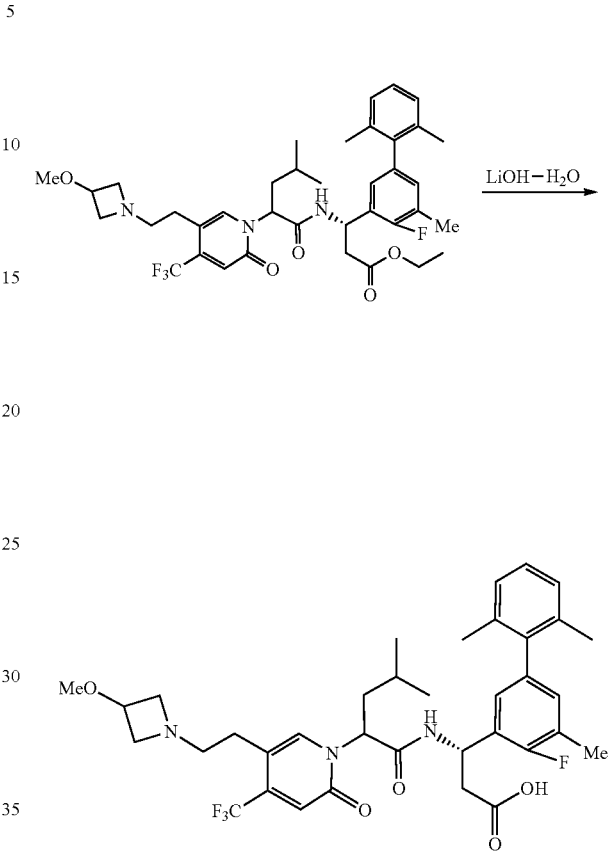

Ethyl (3S)-3-(4-fluoro-2',5,6'-trimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate (140 mg, 0.20 mmol) was treated with LiOH—H$_2$O (42 mg, 1 mmol) in MeOH (3 mL) and H$_2$O (1 mL) at room temperature for 2 hours. The reaction mixture was acidified to pH 4~5 with 1N HCl. The solvent was removed in vacuo and the residue was purified by prep-HPLC A (30-60% CH$_3$CN) to give the diastereomeric products AB-P1 (34 mg) and AB-P2 (46 mg) as a white solid.

AB-P1 ESI 674.3 (M+H)$^+$. $^1$H NMR (400 MHz, MeOD) δ 7.84 (s, 1H), 7.16-6.98 (m, 3H), 6.88 (t, J=7.5 Hz, 2H), 6.76 (s, 1H), 5.74-5.53 (m, 2H), 4.24-4.04 (m, 3H), 3.70-3.53 (m, 2H), 3.30 (s, 3H), 3.14 (t, J=7.1 Hz, 2H), 2.84-2.66 (m, 4H), 2.30 (s, 3H), 2.03-1.91 (m, 5H), 1.84 (s, 3H), 1.52-1.34 (m, 1H), 1.14-0.86 (m, 6H).

AB-P2 ESI 674.3 (M+H)$^+$. $^1$H NMR (400 MHz, MeOD) δ 7.75 (s, 1H), 7.20-7.06 (m, 3H), 7.00-6.86 (m, 3H), 5.84-5.71 (m, 1H), 5.62 (t, J=7.7 Hz, 1H), 4.46-4.22 (m, 3H), 3.97-3.75 (m, 2H), 3.42-3.34 (m, 5H), 3.00-2.76 (m, 2H), 2.69-2.45 (m, 2H), 2.34 (d, J=1.7 Hz, 3H), 2.09-1.92 (m, 7H), 1.71-1.59 (m, 1H), 1.49-1.35 (m, 1H), 1.04-0.83 (m, 6H).

3-24. Preparation of (3S)-3-(2-(5-(2-(dimethylamino)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoic acid (compounds AC-P1 and AC-P2)

Step 1: (3S)-ethyl 3-(2-(5-(2-(dimethylamino)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoate

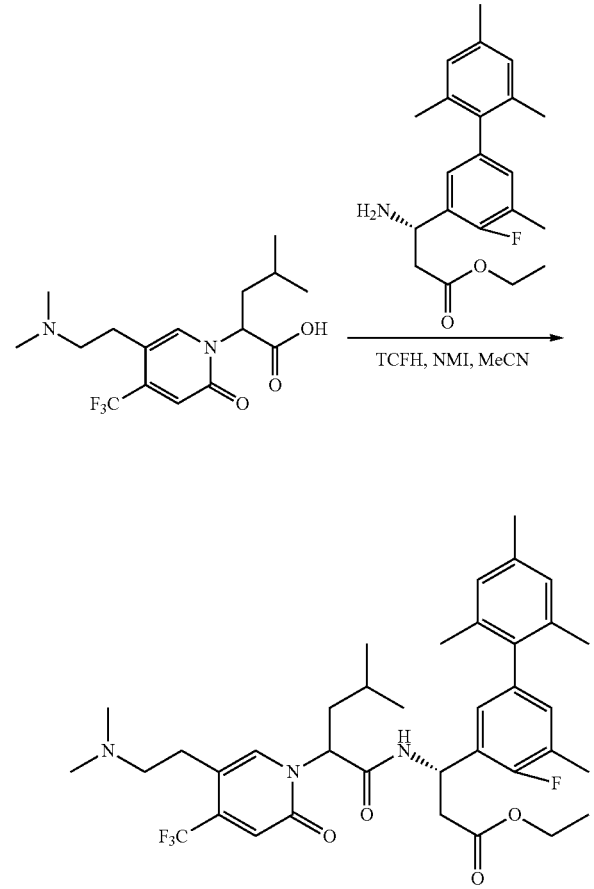

A mixture of 2-(5-(2-(dimethylamino)ethyl)-2-oxo-4-(trifluoromethyl)pyridin-1(2H)-yl)-4-methylpentanoic acid (150 mg, 0.43 mmol, 1.0 eq), (S)-ethyl 3-amino-3-(4-fluoro-2',4',5,6'-tetramethylbiphenyl-3-yl)propanoate (148 mg, 0.361 mg, 1.29 mmol, 3 eq), TCFH (361 mg, 1.29 mmol, 3 eq) and 1-methyl-1H-imidazole (176 mg, 2.15 mmol, 5.0 eq) in CH$_3$CN (5 mL) was stirred at room temperature for 16 hours. LCMS showed that the reaction was completed. The solvent was concentrated in vacuo and the residue was purified by reverse phase HPLC on a C18/40 g column (A: water 10 mM NH$_4$HCO$_3$, B: MeOH, 0~100%) to provide (3S)-ethyl 3-(2-(5-(2-(dimethylamino)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoate as a yellow solid (130 mg). Yield 45% (ESI 674.2 [M+H]$^+$).

Step 2: (3S)-3-(2-(5-(2-(dimethylamino)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoic acid

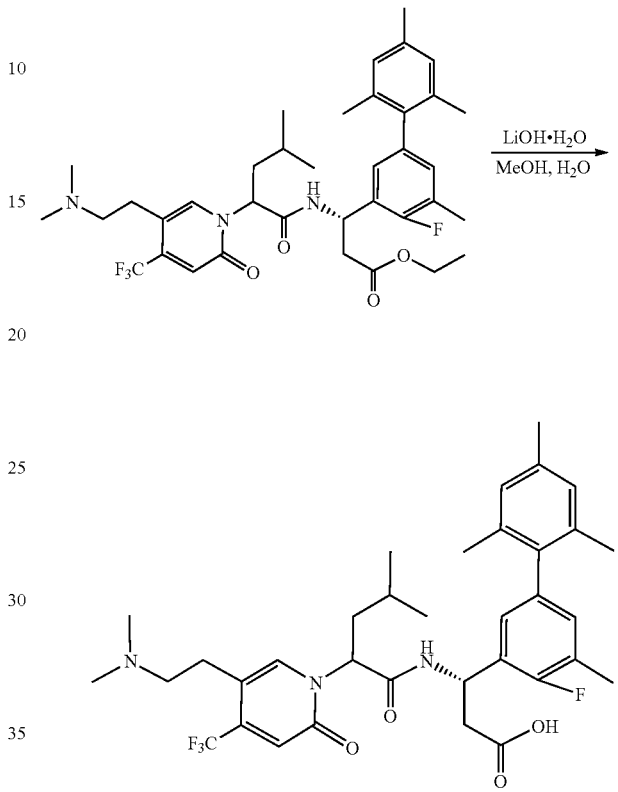

(3S)-ethyl 3-(2-(5-(2-(dimethylamino)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoate (130 mg, 0.19 mmol, 1.0 eq) was treated with LiOH—H$_2$O (40 mg, 0.95 mmol, 5.0 eq) in MeOH (4 mL) and water (1 mL) at 28° C. for 1 hour. LCMS showed that the reaction was completed. The reaction mixture was acidified to pH 5~6 with 1N HCl. The solvent was removed in vacuo and the residue was purified by prep-HPLC A (30-60% MeCN) to give the diastereomeric products AC-P1 (42 mg) and AC-P2 (34 mg) as a white solid.

AC-P1 ESI 646.3 (M+H)$^+$. $^1$H NMR (400 MHz, MeOD) δ 7.90 (s, 1H), 6.89 (s, 1H), 6.84 (d, J=8.0 Hz, 3H), 6.74 (s, 1H), 5.68 (t, J=8.0 Hz, 1H), 5.57-5.54 (m, 1H), 3.12-3.06 (m, 2H), 2.95 (d, J=7.4 Hz, 2H), 2.78-2.67 (m, 8H), 2.29 (d, J=4.2 Hz, 6H), 2.02-1.93 (m, 5H), 1.77 (s, 3H), 1.47-1.41 (m, 1H), 0.97-0.93 (m, 6H).

AC-P2 ESI 646.3 (M+H)$^+$. $^1$H NMR (400 MHz, MeOD) δ 7.87 (s, 1H), 6.90 (d, J=5.8 Hz, 5H), 5.73-5.70 (m, 1H), 5.62 (t, J=7.6 Hz, 1H), 3.30-3.17 (m, 2H), 3.00 (t, J=6.5 Hz, 2H), 2.82 (s, 6H), 2.66-2.60 (m, 1H), 2.55-2.49 (m, 1H), 2.31 (d, J=7.7 Hz, 6H), 2.01-1.96 (m, 7H), 1.76-1.66 (m, 1H), 1.43-1.36 (m, 1H), 0.93-0.84 (m, 6H).

3-25. Preparation of (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)pentanamido)propanoic acid (compounds AD-P1 and AD-P2)

Step 1: ethyl(3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)pentanamido)propanoate

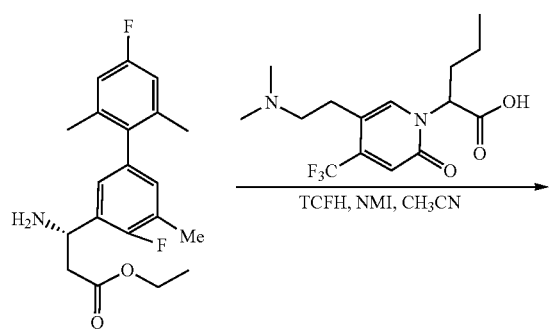

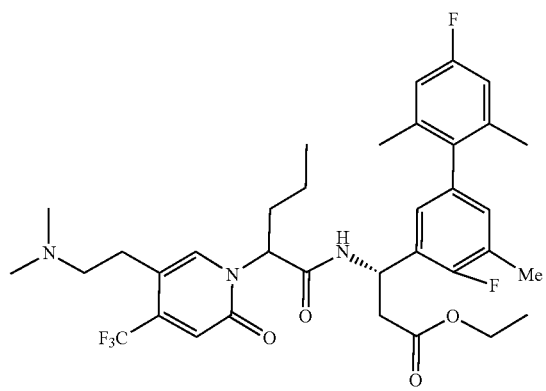

A mixture of ethyl (S)-3-amino-3-(4,4'-difluoro-2',5,6'-trimethyl-[1,1'-biphenyl]-3-yl)propanoate (150 mg, 0.43 mmol), 2-(5-(2-(dimethylamino)ethyl)-2-oxo-4-(trifluoromethyl)pyridin-1(2H)-yl)-4-methylpentanoic acid (174 mg, 0.52 mmol), TCFH (180 mg, 0.64 mmol) and NMI (70 mg, 0.86 mmol) in $CH_3CN$ (5 mL) was stirred at 20° C. for 2 hours. The reaction mixture was concentrated in vacuo and purified by reverse phase HPLC on a C18/40 g column (A: water 10 mM $NH_4HCO_3$, B: MeOH, 0~100%) to provide ethyl (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)pentanamido)propanoate as a yellow oil (200 mg). Yield 70% (ESI 664.3 (M+H)$^+$).

Step 2: (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)pentanamido)propanoic acid

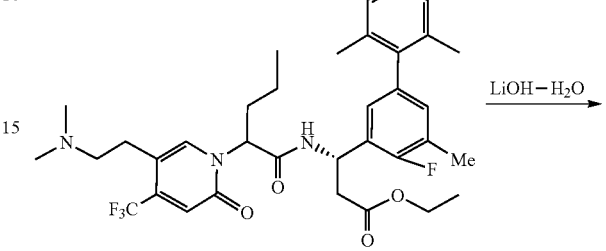

Ethyl (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)pentanamido)propanoate (200 mg, 0.3 mmol) was treated with LiOH—$H_2O$ (37 mg, 0.9 mmol) in MeOH (2 mL) and $H_2O$ (1 mL) at room temperature for 2 hours. The reaction mixture was acidified to pH 4~5 with 1N HCl. The solvent was removed in vacuo and the residue was purified by prep-HPLC A (30-60% MeCN) to give the diastereomeric products AD-P1 (57 mg) and AD-P2 (51 mg) as a white solid.

AD-P1 ESI 636.2 (M+H)$^+$. $^1$H NMR (500 MHz, MeOD) δ 7.90 (s, 1H), 6.89-6.77 (m, 4H), 6.74 (s, 1H), 5.58-5.55 (m, 2H), 3.16-3.13 (m, 2H), 2.98-2.95 (m, 2H), 2.81 (s, 6H), 2.75-2.72 (m, 2H), 2.29 (s, 3H), 2.18-2.12 (m, 1H), 2.01-2.00 (m, 4H), 1.82 (m, 3H), 1.36-1.31 (m, 2H), 0.97 (t, J=7.4 Hz, 3H).

AD-P2 ESI 636.2 (M+H)$^+$. $^1$H NMR (500 MHz, MeOD) δ 7.84 (s, 1H), 6.93-6.89 (m, 3H), 6.84 (d, J=9.6 Hz, 2H), 5.72-5.69 (m, 1H), 5.52 (t, J=7.6 Hz, 1H), 3.28-3.22 (m, 2H), 3.02-2.99 (m, 2H), 2.83 (s, 6H), 2.65-2.61 (m, 1H), 2.55-2.50 (m, 1H), 2.32 (t, J=6.4 Hz, 3H), 2.10-2.05 (m, 1H), 2.01 (s, 6H), 1.84-1.79 (m, 1H), 1.25-1.23 (m, 2H), 0.90 (t, J=7.4 Hz, 3H).

3-26. Preparation of (3S)-3-(2',6'-dichloro-4,4'-difluoro-5-methyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid (compounds AE-P1 and AE-P2)

Step 1: ethyl (3S)-3-(2',6'-dichloro-4,4'-difluoro-5-methyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate

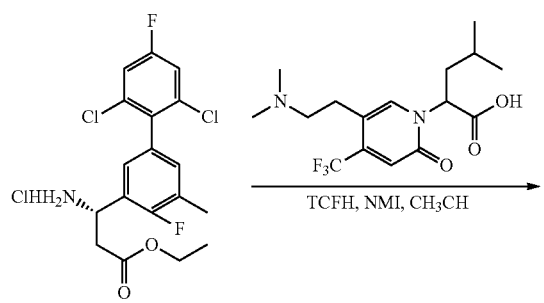

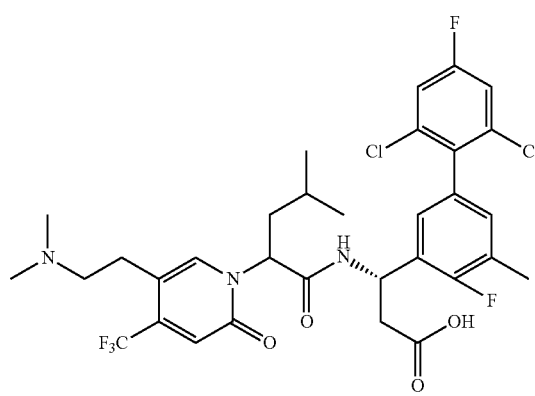

A mixture of ethyl (S)-3-amino-3-(2',6'-dichloro-4,4'-difluoro-5-methyl-[1,1'-biphenyl]-3-yl)propanoate hydrochloride (450 mg, 1.06 mmol), 2-(5-(2-(dimethylamino)ethyl)-2-oxo-4-(trifluoromethyl)pyridin-1(2H)-yl)-4-methylpentanoic acid (370 mg, 1.06 mmol), TCFH (356 mg, 1.27 mmol) and NMI (261 mg, 3.18 mmol) in $CH_3CN$ (10 mL) was stirred at room temperature for 1 hour. The solvent was removed in vacuo and the residue was purified by silica gel column (DCM:MeOH 4:1) to provide ethyl (3S)-3-(2',6'-dichloro-4,4'-difluoro-5-methyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate as a brown solid (610 mg). Yield 80% (ESI 718.0 $(M+H)^+$).

Step 2: (3S)-3-(2',6'-dichloro-4,4'-difluoro-5-methyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid

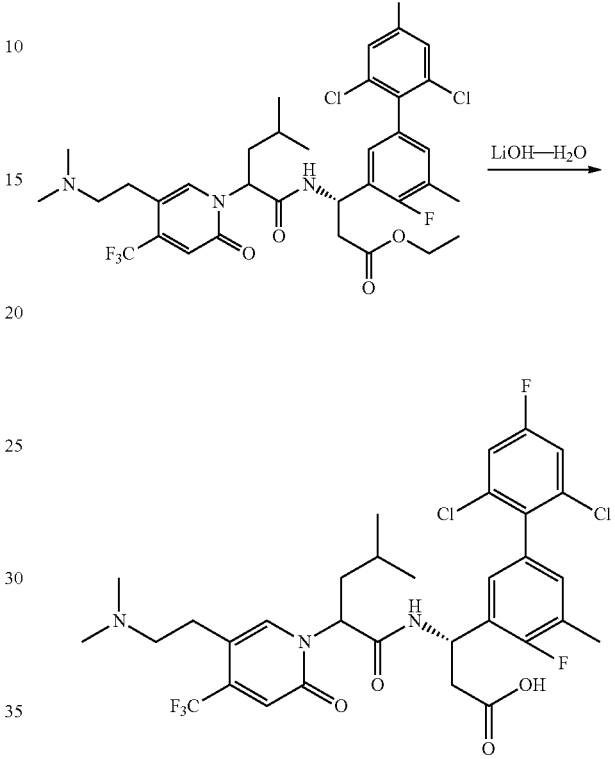

Ethyl (3S)-3-(2',6'-dichloro-4,4'-difluoro-5-methyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate (110 mg, 0.15 mmol) was treated with LiOH—$H_2O$ (32 mg, 0.75 mmol) in THF (3 mL) and $H_2O$ (1 mL) at room temperature for 3 hours. The reaction mixture was acidified to pH 4~5 with 1N HCl. The solvent was removed in vacuo and the residue was purified by prep-HPLC A (30-60% MeCN) to provide the diastereomeric products AE-P1 (29.0 mg) and AE-P2 (31.0 mg) as a white solid.

AE-P1 ESI 690.0 $(M+H)^+$. $^1H$ NMR (400 MHz, MeOD) δ 7.89 (s, 1H), 7.38-7.5 (m, 1H), 7.29-7.25 (m, 1H), 6.99 (t, J=7.5 Hz, 2H), 6.77 (s, 1H), 5.71 (t, J=8.0 Hz, 1H), 5.60-5.56 (m, 1H), 3.05-2.91 (m, 4H), 2.80-2.60 (m, 8H), 2.29 (t, J=0.8 Hz, 3H), 1.99 (t, J=7.5 Hz, 2H), 1.49-1.42 (m, 1H), 0.98-0.93 (m, 6H).

AE-P2 ESI 690.0 $(M+H)^+$. $^1H$ NMR (400 MHz, MeOD) δ 7.88 (s, 1H), 7.37 (t, J=9.0 Hz, 2H), 7.09-7.03 (m, 2H), 6.92 (s, 1H), 5.76-5.72 (m, 1H), 5.65 (t, J=7.7 Hz, 1H), 3.29-3.10 (m, 2H), 3.00 (t, J=6.6 Hz, 2H), 2.80 (s, 6H), 2.66-2.61 (m, 1H), 2.56-2.50 (m, 1H), 2.34 (d, J=1.4 Hz, 3H), 2.01-1.94 (m, 1H), 1.77-1.61 (m, 1H), 1.43-1.37 (m, 1H), 0.90-0.87 (m, 6H).

3-27. Preparation of (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic acid (compounds AF-P1 and AF-P2)

Step 1: ethyl(3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoate

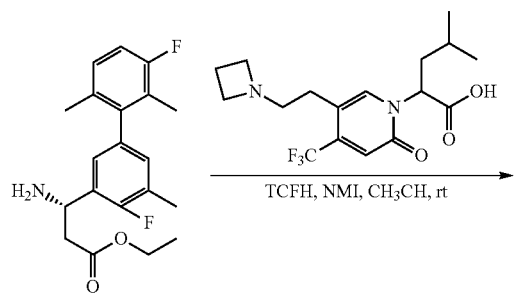

A mixture of ethyl (S)-3-amino-3-(3',4-difluoro-2',5,6'-trimethyl-[1,1'-biphenyl]-3-yl)propanoate (120.0 mg, 0.34 mmol), 2-(5-(2-(azetidin-1-yl)ethyl)-2-oxo-4-(trifluoromethyl)pyridin-1(2H)-yl)-4-methylpentanoic acid (122.4 mg, 0.34 mmol), TCFH (190.4 mg, 0.68 mmol), NMI (115.5 mg, 1.36 mmol) in CH₃CN (5 mL) was stirred at room temperature for 2 hours. The solvent was concentrated in vacuo and the residue was purified by reverse phase IPLC on a C18/40 g column (A: water 10 mM NH₄HCO₃, B: MeOH, 0~100%) to provide ethyl (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoate as a white oil (90.0 mg). Yield 38% (ESI 690.3 (M+H)⁺).

Step 2: (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic acid

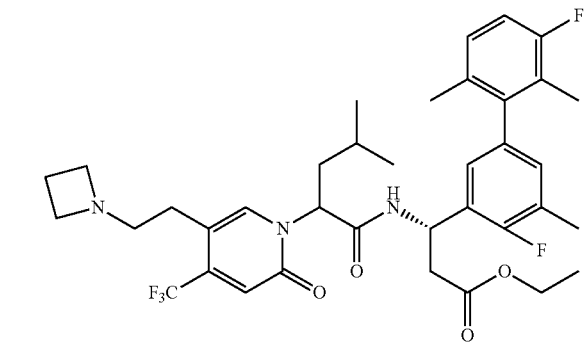

Ethyl(3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoate (90 mg, 0.13 mmol) was treated with LiOH—H₂O (22 mg, 0.52 mmol) in MeOH (4 mL) and H₂O (1 mL) at room temperature for 2 hours. The reaction mixture was acidified to pH 4~5 with 1N HCl. The solvent was removed in vacuo and the residue was purified by prep-HPLC A (30-60% MeCN) to provide the diastereomeric products AF-P1 (15 mg) and AF-P2 (15 mg) as a white solid.

AF-P1 ESI 662.2 (M+H)⁺. ¹H NMR (400 MHz, MeOD) δ 7.84 (s, 1H), 7.14-7.01 (m, 1H), 7.00-6.84 (m, 3H), 6.79 (d, J=7.3 Hz, 1H), 5.70-5.51 (m, 2H), 4.13-3.94 (m, 4H), 3.28-3.18 (m, 2H), 2.86 (t, J=6.9 Hz, 2H), 2.72 (d, J=6.5 Hz, 2H), 2.54-2.37 (m, 2H), 2.31 (s, 3H), 2.06-1.95 (m, 3H), 1.96-1.70 (m, 5H), 1.50-1.32 (m, 1H), 1.01-0.83 (m, 6H).

AF-P2 ESI 662.2 (M+H)⁺. ¹H NMR (400 MHz, MeOD) δ 7.74 (s, 1H), 7.19-7.04 (m, 1H), 7.03-6.82 (m, 4H), 5.85-5.70 (m, 1H), 5.61 (t, J=7.6 Hz, 1H), 4.13 (t, J=7.5 Hz, 4H), 3.41 (s, 2H), 2.94 (d, J=15.8 Hz, 1H), 2.87-2.73 (m, 1H), 2.70-2.58 (m, 1H), 2.56-2.40 (m, 3H), 2.35 (d, J=1.5 Hz, 3H), 2.00 (t, J=7.6 Hz, 4H), 1.94-1.85 (m, 3H), 1.73-1.57 (m, 1H), 1.48-1.36 (m, 1H), 0.91 (d, J=6.6 Hz, 6H).

3-28. Preparation of (3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic acid (compounds AG-P1 and AG-P2)

Step 1: ethyl (3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoate

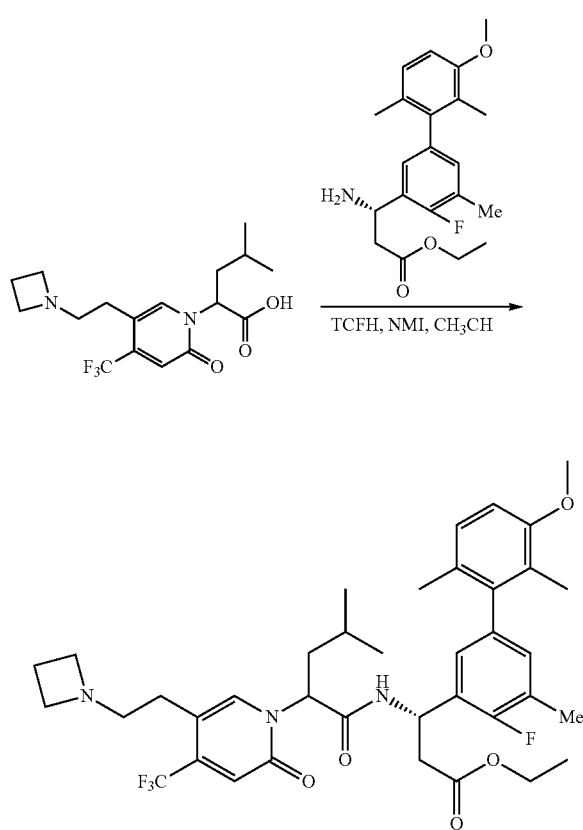

A mixture of 2-(5-(2-(azetidin-1-yl)ethyl)-2-oxo-4-(trifluoromethyl)pyridin-1(2H)-yl)-4-methylpentanoic acid (160 mg, 0.44 mmol, 1.0 eq), ethyl (S)-3-amino-3-(4-fluoro-3'-methoxy-2',5,6'-trimethyl-[1,1'-biphenyl]-3-yl)propanoate (158 mg, 0.44 mmol, 1.0 eq), N,N,N,N-Tetramethylchloroformamidinium hexafluorophosphate (246 mg, 0.88 mmol, 2 eq) and 1-methyl-1H-imidazole (144 mg, 1.76 mmol, 4.0 eq) in CH$_3$CN (5 mL) was stirred at room temperature for 2 hours. LCMS showed that the reaction was completed. The solvent was concentrated in vacuo and the residue was purified by reverse phase HPLC on a C18/40 g column (A: water 10 mM NH$_4$HCO$_3$, B: MeOH, 0~100%) to provide ethyl (3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoate as a yellow solid (170 mg). Yield 55% (ESI 702.1 [M+H]$^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic acid

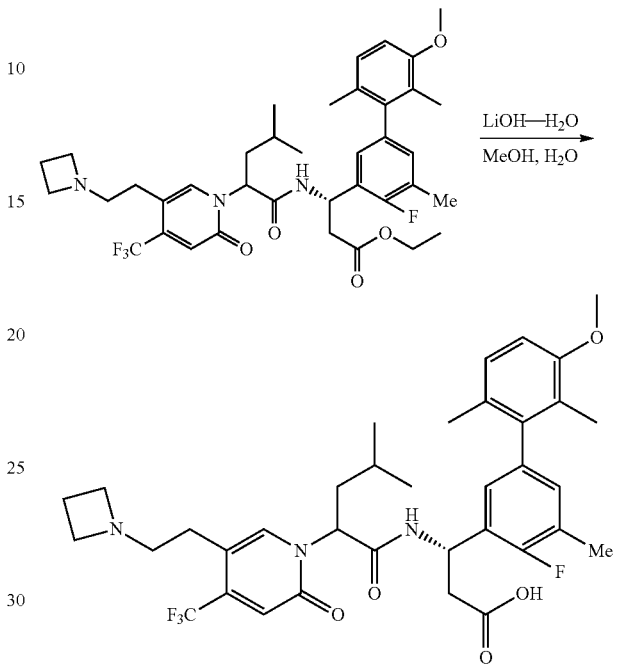

Ethyl (3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoate (170 mg, 0.24 mmol, 1.0 eq) was treated with LiOH—H$_2$O (40 mg, 0.96 mmol, 4.0 eq) in MeOH (4 mL) and water (1 mL) at 30° C. for 1 hour. LCMS showed that the reaction was completed. The reaction mixture was acidified to pH 5~6 with 1N HCl. The solvent was removed in vacuo and the residue was purified by prep-HPLC A (30-60% MeCN) to provide the diastereomeric products AG-P1 (50.8 mg) and AG-P2 (60 mg) as a white solid.

AG-P1 ESI 674.3 (M+H)$^+$. $^1$H NMR (500 MHz, MeOD) δ 7.83 (s, 1H), 7.03 (t, J=7.8 Hz, 1H), 6.92-6.76 (m, 4H), 5.63-5.59 (m, 2H), 4.03-3.97 (m, 4H), 3.83 (s, 3H), 3.32-3.24 (m, 2H), 2.86 (t, J=6.7 Hz, 2H), 2.72-2.70 (m, 2H), 2.49-2.37 (m, 2H), 2.30 (s, 3H), 1.99 (t, J=7.6 Hz, 2H), 1.89 (d, J=37.2 Hz, 3H), 1.78 (d, J=34.9 Hz, 3H), 1.49-1.34 (m, 1H), 0.96-0.92 (m, 6H).

AG-P2 ESI 674.2 (M+H)$^+$. $^1$H NMR (500 MHz, MeOD) δ 7.74 (s, 1H), 7.06 (d, J=8.3 Hz, 1H), 6.94-6.89 (m, 3H), 6.84 (d, J=8.4 Hz, 1H), 5.79-5.76 (m, 1H), 5.60 (t, J=7.6 Hz, 1H), 4.14 (t, J=8.0 Hz, 4H), 3.84 (d, J=1.1 Hz, 3H), 3.50-3.40 (m, 1H), 3.36 (d, J=9.5 Hz, 1H), 2.94 (d, J=16.2 Hz, 1H), 2.86-2.76 (m, 1H), 2.69-2.61 (m, 1H), 2.57-2.44 (m, 3H), 2.34 (d, J=1.3 Hz, 3H), 2.05-1.96 (m, 1H), 1.93 (d, J=6.2 Hz, 3H), 1.86 (d, J=4.9 Hz, 3H), 1.68-1.63 (m, 1H), 1.45-1.40 (m, 1H), 0.90 (d, J=6.3 Hz, 6H).

3-29. Preparation of (3S)-3-(2-(5-(2-(dimethylamino)ethyl)-2-oxo-4-(trifluoromethyl)pyridin-1(2H)-yl)-4-methylpentanamido)-3-(2'-ethyl-4-fluoro-5,6'-dimethyl-[1,1'-biphenyl]-3-yl)propanoic acid (compounds AH-P1 and AH-P2)

Step 1: ethyl (3S)-3-(2-(5-(2-(dimethylamino)ethyl)-2-oxo-4-(trifluoromethyl)pyridin-1(2H)-yl)-4-methylpentanamido)-3-(2'-ethyl-4-fluoro-5,6'-dimethyl-[1,1'-biphenyl]-3-yl)propanoate

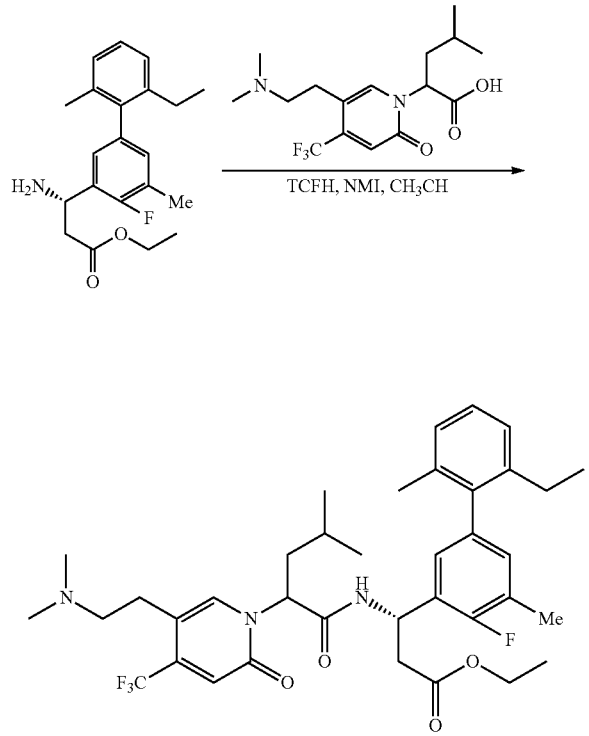

A mixture of ethyl (S)-3-amino-3-(2'-ethyl-4-fluoro-5,6'-dimethyl-[1,1'-biphenyl]-3-yl)propanoate (150 mg, 0.43 mmol), 2-(5-(2-(dimethylamino)ethyl)-2-oxo-4-(trifluoromethyl)pyridin-1(2H)-yl)-4-methylpentanoic acid (101 mg, 0.52 mmol), TCFH (180 mg, 0.64 mmol) and NMI (70 mg, 0.86 mmol) in CH$_3$CN (5 mL) was stirred at 20° C. for 2 hours. The solvent was concentrated in vacuo and the residue was purified by reverse phase IPLC on a C18/40 g column (A: water 10 mM NH$_4$HCO$_3$, B: MeOH, 0~100%) to provide ethyl (3S)-3-(2-(5-(2-(dimethylamino)ethyl)-2-oxo-4-(trifluoromethyl)pyridin-1(2H)-yl)-4-methylpentanamido)-3-(2'-ethyl-4-fluoro-5,6'-dimethyl-[1,1'-biphenyl]-3-yl)propanoate as a yellow oil (180 mg). Yield 62% (ESI 674.2 (M+H)$^+$).

Step 2: (3S)-3-(2-(5-(2-(dimethylamino)ethyl)-2-oxo-4-(trifluoromethyl)pyridin-1(2H)-yl)-4-methylpentanamido)-3-(2'-ethyl-4-fluoro-5,6'-dimethyl-[1,1'-biphenyl]-3-yl)propanoic acid

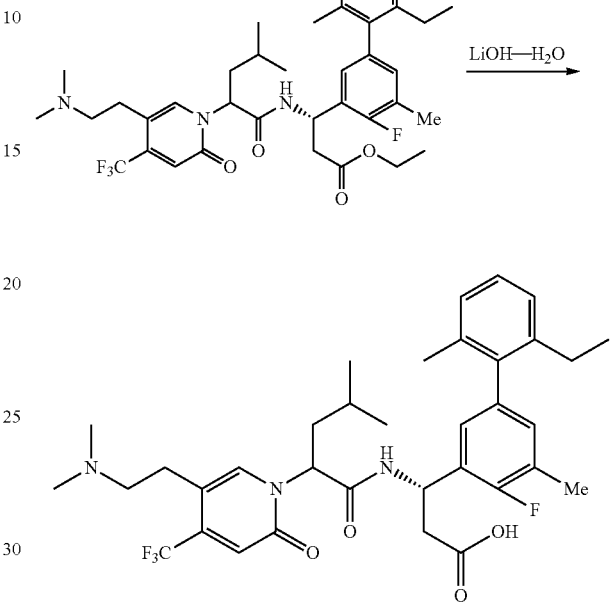

Ethyl (3S)-3-(2-(5-(2-(dimethylamino)ethyl)-2-oxo-4-(trifluoromethyl)pyridin-1(2H)-yl)-4-methylpentanamido)-3-(2'-ethyl-4-fluoro-5,6'-dimethyl-[1,1'-biphenyl]-3-yl)propanoate (150 mg, 0.22 mmol) was treated with LiOH—H$_2$O (28 mg, 0.66 mmol) in MeOH (2 mL) and H$_2$O (1 mL) at room temperature for 2 hours. The reaction mixture was acidified to pH 4~5 with 1N HCl. The solvent was removed in vacuo and the residue was purified by prep-HPLC A (30-60% MeCN) to give the diastereomeric products AH-P1 (66 mg) and AH-P2 (46 mg) as a white solid.

AH-P1 ESI 646.3 (M+H)$^+$. $^1$H NMR (400 MHz, MeOD) δ 7.90 (s, 1H), 7.16-7.05 (m, 3H), 6.90-6.86 (m, 2H), 6.76 (d, J=7.9 Hz, 1H), 5.70-5.57 (m, 2H), 3.09 (d, J=7.1 Hz, 2H), 2.95 (d, J=7.2 Hz, 2H), 2.75-2.70 (m, 8H), 2.34-2.29 (m, 4H), 2.20-2.18 (m, 1H), 2.00-1.96 (m, 3H), 1.79 (s, 1H), 1.47-1.39 (m, 1H), 1.02-0.92 (m, 8H), 0.83 (t, J=7.5 Hz, 2H).

AH-P2 ESI 646.3 (M+H)$^+$. $^1$H NMR (400 MHz, MeOD) δ 7.84 (d, J=6.6 Hz, 1H), 7.18 (t, J=7.5 Hz, 1H), 7.12-7.07 (m, 2H), 6.96-6.89 (m, 3H), 5.74-5.70 (m, 1H), 5.61 (t, J=7.6 Hz, 1H), 3.31-3.14 (m, 2H), 3.00 (t, J=6.7 Hz, 2H), 2.81 (d, J=1.2 Hz, 6H), 2.62-2.61 (m, 1H), 2.57-2.44 (m, 1H), 2.36-2.31 (m, 5H), 2.00-1.97 (m, 4H), 1.71-1.65 (m, 1H), 1.42-1.37 (m, 1H), 1.02-0.98 (m, 3H), 0.88 (d, J=6.5 Hz, 6H).

3-30. Preparation of (3S)-3-(5-chloro-4-fluoro-2',4',6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid (compounds AI-P1 and AI-P2)

Step 1: ethyl (3S)-3-(5-chloro-4-fluoro-2',4',6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate

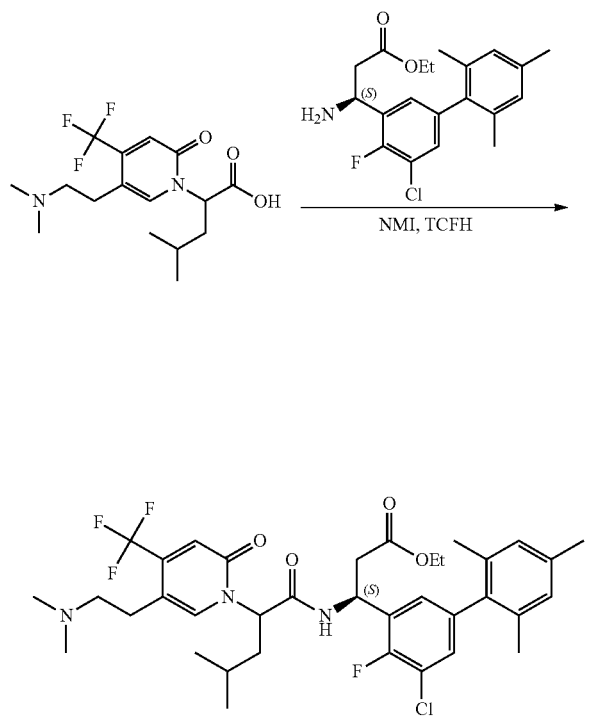

A mixture of 2-(5-(2-(dimethylamino)ethyl)-2-oxo-4-(trifluoromethyl)pyridin-1(2H)-yl)-4-methylpentanoic acid (120 mg, 0.34 mmol), ethyl (S)-3-amino-3-(5-chloro-4-fluoro-2',4',6'-trimethyl-[1,1'-biphenyl]-3-yl)propanoate (145 mg, 0.40 mmol), TCFH (142 mg, 0.51 mmol), NMI (139.4 mg, 1.7 mmol) in CH$_3$CN (4 mL) was stirred at room temperature for 1 hour. The solvent was concentrated in vacuo and the residue was by reverse phase HPLC on a C18/40 g column (A: water 10 mM NH$_4$HCO$_3$, B: MeOH, 0~100%) to provide ethyl (3S)-3-(5-chloro-4-fluoro-2',4',6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate as a red oil (175 mg). Yield 74% (ESI 694.2 (M+H)$^+$).

Step 2: (3S)-3-(5-chloro-4-fluoro-2',4',6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid

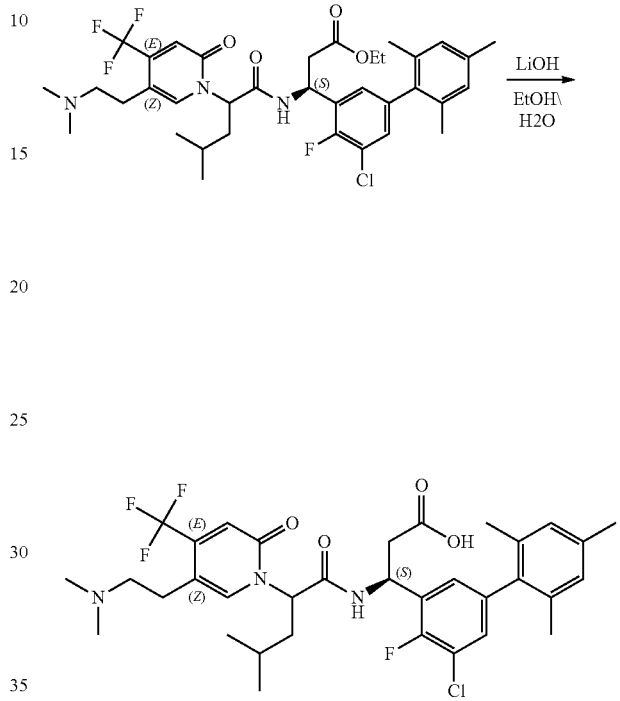

Ethyl(3S)-3-(5-chloro-4-fluoro-2',4',6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate (175 mg, 0.25 mmol) was treated with LiOH—H$_2$O (52.5 mg, 1.25 mmol) in EtOH (3 mL) and H$_2$O (1 mL) at room temperature for 2 hours. The reaction mixture was acidified to pH 4~5 with 1N HCl. The solvent was removed in vacuo and the residue was purified by prep-HPLC A (30-60% MeCN) to give the diastereomeric products AI-P1 (29 mg) and AI-P2 (23 mg) as a white solid.

AI-P1 ESI 666.2 (M+H)$^+$. $^1$H NMR (400 MHz, MeOD) δ 7.90 (s, 1H), 7.08-7.06 (m, 1H), 7.01-6.98 (m, 1H), 6.92 (s, 1H), 6.87 (s, 1H), 6.71 (s, 1H), 5.70-5.65 (m, 1H), 5.56-5.62 (m, 1H), 3.17-2.89 (m, 4H), 2.82-2.63 (m, 8H), 2.30 (s, 3H), 2.08-1.91 (m, 5H), 1.76 (s, 3H), 1.52-1.38 (m, 1H), 1.03-0.83 (m, 6H).

AI-P2 ESI 666.2 (M+H)$^+$. $^1$H NMR (400 MHz, MeOD) δ 7.89 (s, 1H), 7.16-7.13 (m, 1H), 7.08-67.05 (m, 1H), 6.93 (s, 2H), 6.89 (s, 1H), 5.77-5.54 (m, 2H), 3.28-3.17 (m, 2H), 3.02-2.98 (m, 2H), 2.83 (s, 6H), 2.71-2.47 (m, 2H), 2.31 (s, 3H), 2.11-1.87 (m, 7H), 1.83-1.64 (m, 1H), 1.46-1.23 (m, 1H), 1.06-0.62 (m, 6H).

3-31. Preparation of (3S)-3-(2-(5-(2-(azetidin-1-yl)ethyl)-2-oxo-4-(trifluoromethyl)pyridin-1(2H)-yl)-4-methylpentanamido)-3-(2',4-difluoro-4',5,6'-trimethylbiphenyl-3-yl)propanoic acid (compounds AJ-P1 and AJ-P2)

Step 1: ethyl (3S)-3-(2-(5-(2-(azetidin-1-yl)ethyl)-2-oxo-4-(trifluoromethyl)pyridin-1(2H)-yl)-4-methylpentanamido)-3-(2',4-difluoro-4',5,6'-trimethyl-[1,1'-biphenyl]-3-yl)propanoate

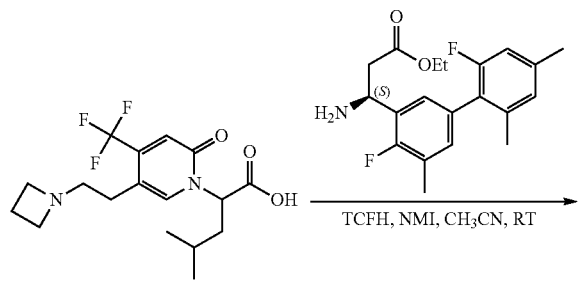

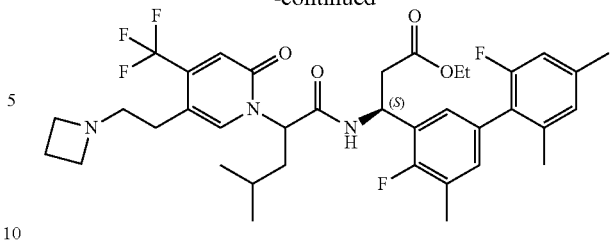

A mixture of 2-(5-(2-(azetidin-1-yl)ethyl)-2-oxo-4-(trifluoromethyl)pyridin-1(2H)-yl)-4-methylpentanoic acid (150 mg, 0.42 mmol), ethyl (S)-3-amino-3-(2',4-difluoro-4',5,6'-trimethyl-[1,1'-biphenyl]-3-yl)propanoate (145 mg, 0.42 mmol), TCFH (141 mg, 0.50 mmol) and NMI (104 mg, 1.26 mmol) in CH$_3$CN (5 mL) was stirred at room temperature for 1 hour. The solvent was removed in vacuo and the residue was purified by silica gel column (DCM:MeOH 4:1) to provide ethyl (3S)-3-(2-(5-(2-(azetidin-1-yl)ethyl)-2-oxo-4-(trifluoromethyl)pyridin-1(2H)-yl)-4-methylpentanamido)-3-(2',4-difluoro-4',5,6'-trimethyl-[1,1'-biphenyl]-3-yl)propanoate as a white solid (130 mg). Yield 45% (ESI 690.3 (M+H)$^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(2',4-difluoro-4',5,6'-trimethylbiphenyl-3-yl)propanoic acid

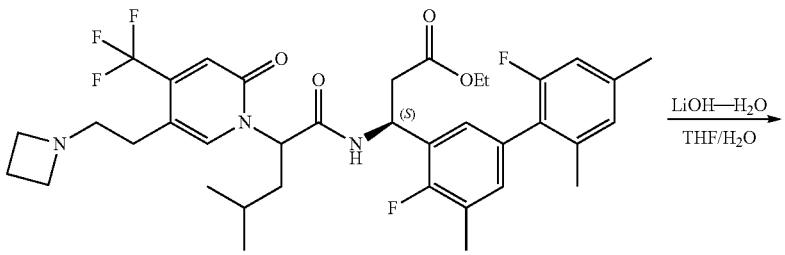

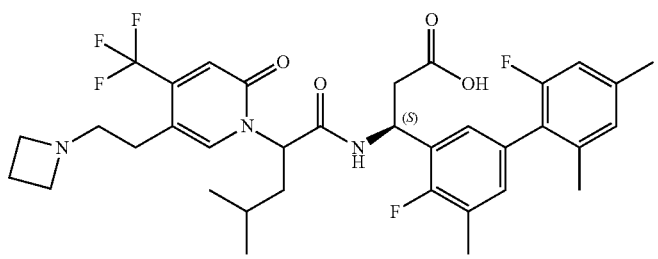

Ethyl(3S)-3-(2-(5-(2-(azetidin-1-yl)ethyl)-2-oxo-4-(trifluoromethyl)pyridin-1(2H)-yl)-4-methylpentanamido)-3-(2',4-difluoro-4',5,6'-trimethyl-[1,1'-biphenyl]-3-yl)propanoate (130 mg, 0.19 mmol) was treated with LiOH—H$_2$O (40 mg, 0.95 mmol) in THF (3 mL) and H$_2$O (1 mL) at room temperature for 3 hours. The reaction mixture was acidified to pH 4~5 with 1N HCl. The solvent was removed in vacuo and the residue was purified by prep-HPLC A (30-60% MeCN) to give the diastereomeric products AJ-P1 (30.0 mg) and AJ-P2 (29.7 mg) as a white solid.

AJ-P1 ESI 662.2 (M+H)$^+$. $^1$H NMR (400 MHz, MeOD) δ 7.83 (s, 1H), 6.99 (t, J=6.3 Hz, 2H), 6.92 (s, 1H), 6.79 (t, J=4.9 Hz, 2H), 5.68 (t, J=8.0 Hz, 1H), 5.59 (t, J=6.6 Hz, 1H), 4.00-3.96 (m, 4H), 3.30-3.25 (m, 2H), 2.85 (t, J=6.9 Hz, 2H), 2.72-2.70 (m, 2H), 2.44-2.37 (m, 2H), 2.35 (s, 3H), 2.29 (d, J=1.2 Hz, 3H), 2.05 (s, 3H), 2.00 (t, J=7.6 Hz, 2H), 1.45-1.40 (m, 1H), 0.95 (t, J=7.1 Hz, 6H).

AJ-P2 ESI 662.2 (M+H)$^+$. $^1$H NMR (400 MHz, MeOD) δ 7.76 (s, 1H), 7.08 (d, J=6.5 Hz, 1H), 7.04 (d, J=6.9 Hz, 1H), 6.93 (d, J=8.1 Hz, 2H), 6.82 (d, J=10.4 Hz, 1H), 5.78-5.74 (m, 1H), 5.64 (t, J=7.7 Hz, 1H), 4.11 (t, J=8.0 Hz, 4H), 3.44-3.38 (m, 1H), 2.96-2.89 (m, 1H), 2.84-2.76 (m, 1H), 2.67-2.62 (m, 1H), 2.57-2.43 (m, 3H), 2.35-2.33 (m, 6H), 2.11 (s, 3H), 2.02-1.94 (m, 1H), 1.71-1.64 (m, 1H), 1.44-1.30 (m, 2H), 0.91-0.88 (m, 6H).

3-32. Preparation of (3S)-3-(4,4'-difluoro-2',5,6'-trimethyl-[1,1'-biphenyl]-3-yl)-3-(2-(5-(2-(dimethyl-amino)ethyl)-2-oxo-4-(trifluoromethyl)pyridin-1(2H)-yl)-4-methylpentanamido)propanoic acid (compounds AK-P1 and AK-P2)

Step 1: ethyl (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate

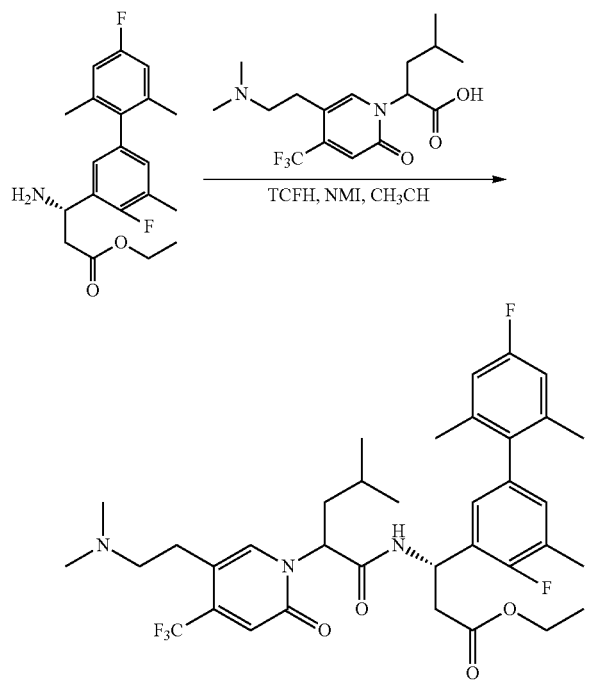

A mixture of ethyl (S)-3-amino-3-(4,4'-difluoro-2',5,6'-trimethyl-[1,1'-biphenyl]-3-yl)propanoate (150 mg, 0.43 mmol), 2-(5-(2-(dimethylamino)ethyl)-2-oxo-4-(trifluoromethyl)pyridin-1(2H)-yl)-4-methylpentanoic acid (180 mg, 0.51 mmol), TCFH (240 mg, 0.86 mmol) and NMI (106 mg, 1.29 mmol) in CH$_3$CN (5 mL) was stirred at 20° C. for 2 hours. The solvent was concentrated in vacuo and the residue was purified by reverse phase HPLC on a C18/40 g column (A: water 10 mM NH$_4$HCO$_3$, B: MeOH, 0~100%) to provide ethyl (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate as a yellow oil (120 mg). Yield 41% (ESI 678.1 (M+H)$^+$).

Step 2: (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)-4-methyl-pentanamido)propanoic acid

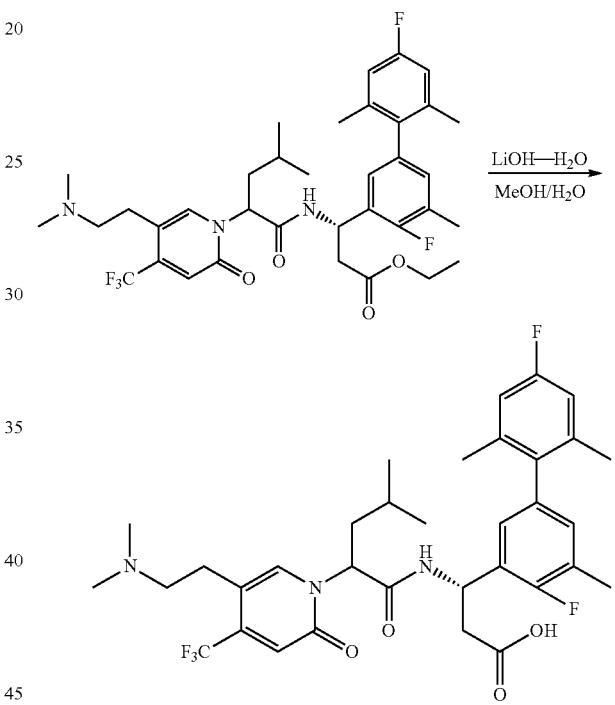

Ethyl (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate (100 mg, 0.14 mmol) was treated with LiOH—H$_2$O (18 mg, 0.44 mmol) in MeOH (2 mL) and H$_2$O (1 mL) at room temperature for 2 hours. The reaction mixture was acidified to pH 4~5 with 1N HCl. The solvent was removed in vacuo and the residue was purified by prep-HPLC A (30-60% MeCN) to provide the diastereomeric products AK-P1 (36 mg) and AK-P2 (32 mg) as a white solid.

AK-P1 ESI 650.3 (M+H)$^+$. $^1$H NMR (400 MHz, MeOD) δ 7.91 (s, 1H), 6.88-6.74 (m, 5H), 5.69 (t, J=8.1 Hz, 1H), 5.58-5.54 (m, 1H), 3.19-3.07 (m, 2H), 3.02-2.95 (m, 2H), 2.84-2.67 (m, 8H), 2.30 (t, J=8.2 Hz, 3H), 2.03-1.94 (m, 5H), 1.80 (d, J=9.4 Hz, 3H), 1.48-1.39 (m, 1H), 0.97-0.88 (m, 6H).

AK-P2 ESI 650.2 (M+H)$^+$. $^1$H NMR (400 MHz, MeOD) δ 7.88 (s, 1H), 6.93-6.83 (m, 5H), 5.71-5.62 (m, 2H), 3.19 (s, 2H), 3.00-2.97 (m, 2H), 2.80 (s, 6H), 2.67-2.57 (m, 2H), 2.32 (d, J=1.5 Hz, 3H), 2.01-1.93 (m, 7H), 1.79-1.74 (m, 1H), 1.42-1.35 (m, 1H), 0.90-0.87 (m, 6H).

3-33. Preparation of (3S)-3-(4,4'-difluoro-2',5,6'-trimethyl-[1,1'-biphenyl]-3-yl)-3-(2-(5-(2-(dimethylamino)ethyl)-3-fluoro-4-methyl-2-oxopyridin-1(2H)-yl)-4-methylpentanamido)propanoic acid (compounds AL-P1 and AL-P2)

Step 1: ethyl (S)-3-(4,4'-difluoro-2',5,6'-trimethyl-[1,1'-biphenyl]-3-yl)-3-((S)-2-(5-(2-(dimethylamino)ethyl)-3-fluoro-4-methyl-2-oxopyridin-1(2H)-yl)-4-methylpentanamido)propanoate

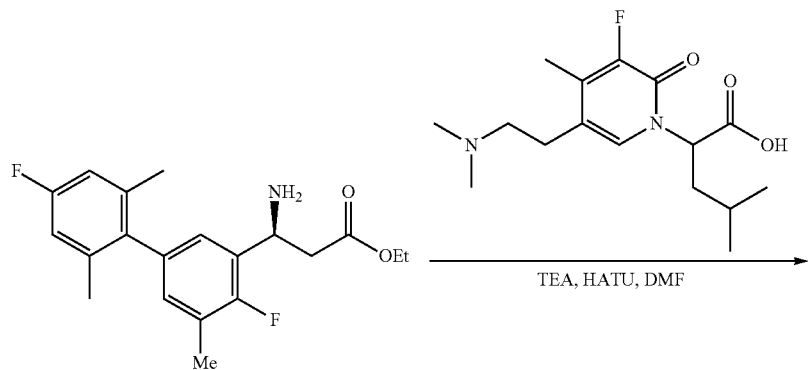

To a solution of 2-(5-(2-(dimethylamino)ethyl)-3-fluoro-4-methyl-2-oxopyridin-1(2H)-yl)-4-methylpentanoic acid (1 g, 3.20 mmol) and HATU (2.434 g, 6.40 mmol) in DMF (16.01 mL) was added TEA (0.892 mL, 6.40 mmol) at room temperature. After stirring for 5 minutes, ethyl (S)-3-amino-3-(4,4'-difluoro-2',5,6'-trimethyl-[1,1'-biphenyl]-3-yl)propanoate (1.668 g, 4.80 mmol) in 5.0 mL DMF was added to the solution. The reaction mixture was dilluted with 200 mL of water and 10 mL of brine. The mixture was washed (EtOAc; 200 mL×3). The combined organic phase was dried over Na$_2$SO$_4$, concentrated and purified by silica gel column (DCM:MeOH 10:1) to provide ethyl (S)-3-(4,4'-difluoro-2',5,6'-trimethyl-[1,1'-biphenyl]-3-yl)-3-((S)-2-(5-(2-(dimethylamino)ethyl)-3-fluoro-4-methyl-2-oxopyridin-1(2H)-yl)-4-methylpentanamido)propanoate (1.76 g, 86% yield) as pinkish oil. (ESI 642 (M+H)$^+$)

Step 2: (3S)-3-(4,4'-difluoro-2',5,6'-trimethyl-[1,1'-biphenyl]-3-yl)-3-(2-(5-(2-(dimethylamino)ethyl)-3-fluoro-4-methyl-2-oxopyridin-1(2H)-yl)-4-methylpentanamido)propanoic acid

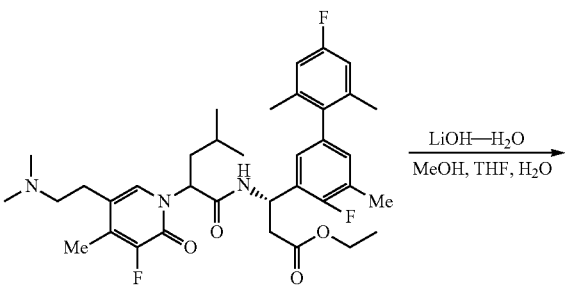

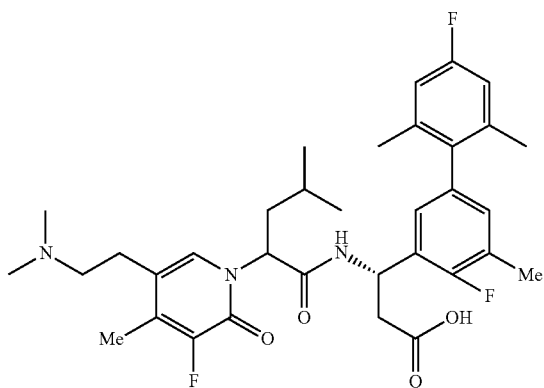

Ethyl (3S)-3-(4,4'-difluoro-2',5,6'-trimethyl-[1,1'-biphenyl]-3-yl)-3-(2-(5-(2-(dimethylamino)ethyl)-3-fluoro-4-methyl-2-oxopyridin-1(2H)-yl)-4-methylpentanamido)propanoate (1.65 g, 2.6 mmol, 1.0 eq) was treated with LiOH monohydrate (391 mg, 9.3 mmol, 4.0 eq) in methanol (5 mL), THF (5 mL) and H₂O (5 mL) at room temperature for 2 hours. The reaction mixture was acidified to pH 4~5 with 1N HCl aqueous solution, concentrated in vacuo and the residue was purified by prep HPLC A to provide the diastereomeric products AL-P1 (383 mg) and AL-P2 (239 mg) as a white solid.

AL-P1 ESI 614.2 (M+H)⁺. ¹H NMR (400 MHz, MeOD) δ 7.48 (s, 1H), 6.86-6.81 (m, 4H), 5.66-5.60 (m, 1H), 5.50-5.47 (m, 1H), 3.22-3.12 (m, 2H), 2.93-2.89 (m, 2H), 2.77 (s, 6H), 2.72-2.61 (m, 2H), 2.29 (d, J=1.6 Hz, 3H), 2.25 (d, J=2.8 Hz, 3H), 2.00-1.93 (m, 5H), 1.88 (s, 3H), 1.46-1.36 (m, 1H), 0.95-0.90 (m, 6H).

AL-P2 ESI 614.2 (M+H)⁺. ¹H NMR (400 MHz, MeOD) δ 7.43 (s, 1H), 6.88 (dd, J=24.6, 8.2 Hz, 4H), 5.66-5.57 (m, 2H), 3.27-3.13 (m, 2H), 2.97-2.93 (m, 2H), 2.86 (s, 6H), 2.62-2.57 (m, 1H), 2.51-2.39 (m, 1H), 2.33 (d, J=1.7 Hz, 3H), 2.25 (d, J=2.7 Hz, 3H), 2.05-1.93 (m, 7H), 1.80-1.73 (m, 1H), 1.41-1.34 (m, 1H), 0.91-0.89 (m, 6H).

3-34. Preparation of (3S)-3-(2-(5-(2-(dimethylamino)ethyl)-3-fluoro-4-methyl-2-oxopyridin-1(2H)-yl)-4-methylpentanamido)-3-(4-fluoro-2',5,6'-trimethyl-[1,1'-biphenyl]-3-yl)propanoic acid (compounds AM-P1 and AM-P2)

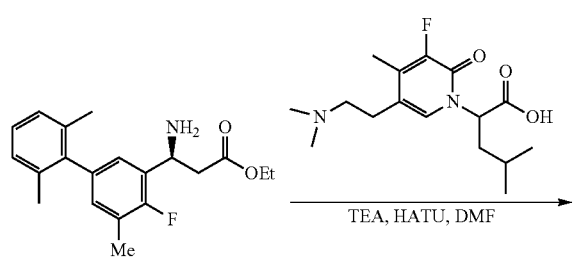

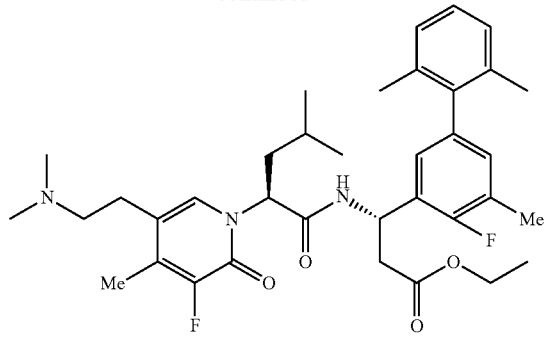

To a solution of 2-(5-(2-(dimethylamino)ethyl)-3-fluoro-4-methyl-2-oxopyridin-1(2H)-yl)-4-methylpentanoic acid (1 g, 3.20 mmol) and HATU (2.434 g, 6.40 mmol) in DMF (16.01 mL) was added TEA (0.892 mL, 6.40 mmol) at room temperature. After stirring for 5 minutes, ethyl (S)-3-amino-3-(4,4'-difluoro-2',5,6'-trimethyl-[1,1'-biphenyl]-3-yl)propanoate (1.668 g, 4.80 mmol) in 5.0 mL DMF was added to the solution. The reaction mixture was dilluted with 200 mL of water and 10 mL of brine. The mixture was washed (EtOAc; 200 mL×3). The combined organic phase was dried over Na₂SO₄, concentrated and purified by silica gel column (DCM:MeOH 10:1) to provide ethyl (S)-3-(4,4'-difluoro-2',5,6'-trimethyl-[1,1'-biphenyl]-3-yl)-3-((S)-2-(5-(2-(dimethylamino)ethyl)-3-fluoro-4-methyl-2-oxopyridin-1(2H)-yl)-4-methylpentanamido)propanoate (1.76 g, 86% yield) as pinkish oil. (ESI 642 (M+H)⁺)

Step 2: (3S)-3-(4,4'-difluoro-2',5,6'-trimethyl-[1,1'-biphenyl]-3-yl)-3-(2-(5-(2-(dimethylamino)ethyl)-3-fluoro-4-methyl-2-oxopyridin-1(2H)-yl)-4-methylpentanamido)propanoic acid

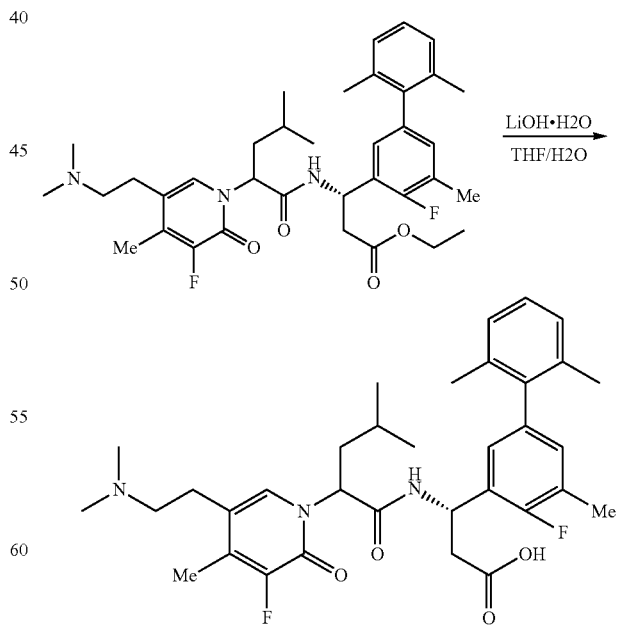

Ethyl (3S)-3-(2-(5-(2-(dimethylamino)ethyl)-3-fluoro-4-methyl-2-oxopyridin-1(2H)-yl)-4-methylpentanamido)-3-(4-fluoro-2',5,6'-trimethyl-[1,1'-biphenyl]-3-yl)propanoate (1.2 g, 1.93 mmol) was treated with LiOH—H₂O (162 mg, 3.85 mmol) in THF (12 mL) and H₂O (2 mL) at room temperature for 30 mins. The reaction mixture was acidified to pH 4~5 with 2N HCl. The solvent was removed in vacuo and the residue was purified by prep-HPLC A (30-60% MeCN) to give the diastereomeric products AM-P1 (482 mg) and AM-P2 (237 mg) as a white solid.

AM-P1 ESI 596.3 (M+H)⁺. ¹H NMR (400 MHz, MeOD) δ 7.47 (s, 1H), 7.16-7.01 (m, 3H), 6.90-6.79 (m, 2H), 5.68-5.64 (m, 1H), 5.51-5.48 (m, 1H), 3.17-3.08 (m, 2H), 2.92-2.88 (m, 2H), 2.76 (s, 6H), 2.72-2.44 (m, 2H), 2.29 (s, 3H), 2.23 (d, J=2.6 Hz, 3H), 1.99-1.94 (m, 5H), 1.87 (s, 3H), 1.42-1.38 (m, 1H), 0.94-0.90 (m, 6H).

AM-P2 ESI 596.2 (M+H)⁺. ¹H NMR (400 MHz, MeOD) δ 7.39 (s, 1H), 7.15-7.08 (m, 3H), 6.93-6.90 (m, 2H), 5.67-5.60 (m, 2H), 3.32-3.28 (m, 1H), 3.22-3.16 (m, 1H), 2.96-2.92 (m, 2H), 2.84 (s, 6H), 2.63-2.58 (m, 1H), 2.50-2.43 (m, 1H), 2.32 (d, J=1.6 Hz, 3H), 2.24 (d, J=2.8 Hz, 3H), 2.01-1.93 (m, 7H), 1.78-1.71 (m, 1H), 1.41-1.34 (m, 1H), 0.90 (d, J=6.8 Hz, 6H).

3-35. Preparation of (3S)-3-(2-(5-(2-(azetidin-1-yl)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoic acid (compounds AN-P1 and AN-P2)

Step 1: ethyl(3S)-3-(2-(5-(2-(azetidin-1-yl)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoate A mixture of 2-(5-(2-(azetidin-1-yl)ethyl)-2-oxo-4-(trifluoromethyl)pyridin-1(2H)-yl)-4-methylpentanoic acid (150 mg, 0.41 mmol), ethyl (S)-3-amino-3-(4-fluoro-2',4',5,6'-tetramethyl-[1,1'-biphenyl]-3-yl)propanoate (141 mg, 0.41 mmol), TCFH (230 mg, 0.82 mmol), NMI (135 mg, 1.64 mmol) in CH₃CN (5 mL) was stirred at room temperature for 2 hours. The solvent was concentrated in vacuo and the residue was purified by reverse phase IPLC on a C18/40 g column (A: water 10 mM NH₄HCO₃, B: MeOH, 0~100%) to provide ethyl (3S)-3-(2-(5-(2-(azetidin-1-yl)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoate as a white oil (90 mg). Yield 32% (ESI 686.3 (M+H)⁺).

Step 2: (3S)-3-(2-(5-(2-(azetidin-1-yl)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoic acid

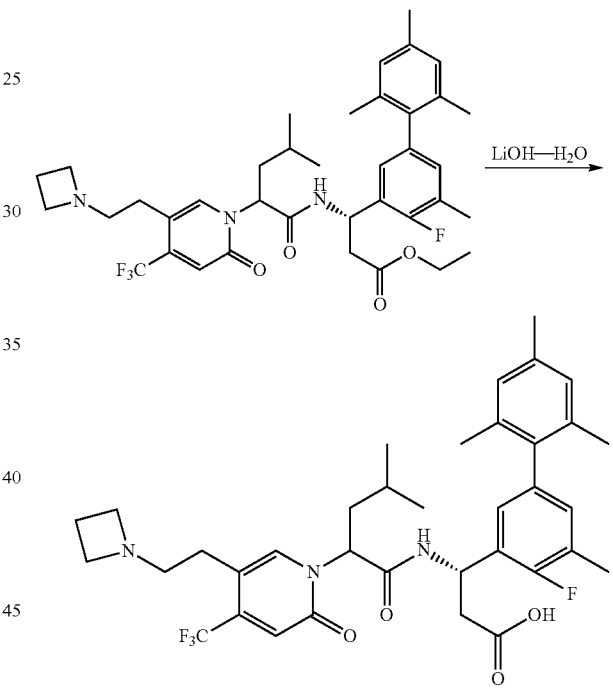

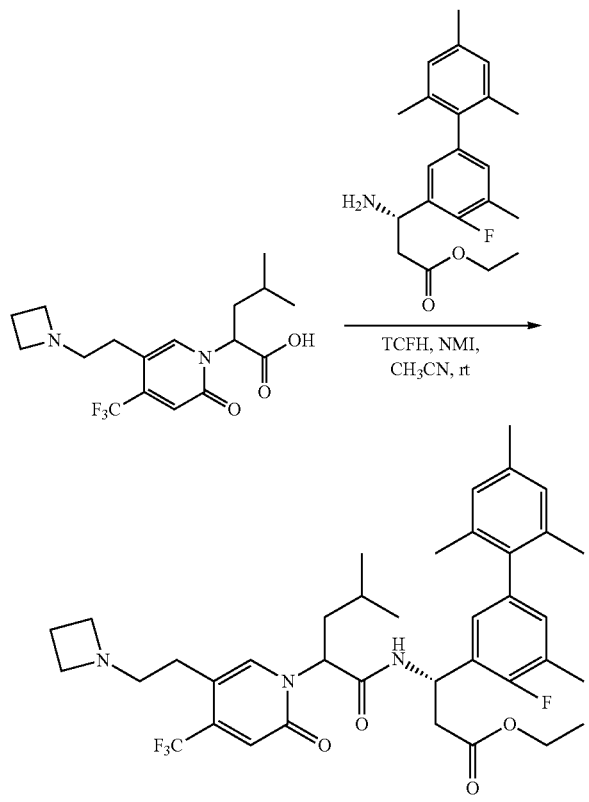

Ethyl (3S)-3-(2-(5-(2-(azetidin-1-yl)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoate (90 mg, 0.14 mmol) was treated with LiOH—H₂O (24 mg, 0.56 mmol) in MeOH (4 mL) and H₂O (1 mL) at room temperature for 2 hours. The reaction mixture was acidified to pH 4~5 with 1N HCl. The solvent was removed in vacuo and the residue was purified by prep-HPLC A (30-60% MeCN) to give the diastereomeric products AN-P1 (22 mg) and AN-P2 (22 mg) as a white solid.

AN-P1 ESI 658.3 (M+H)⁺. ¹H NMR (400 MHz, MeOD) δ 7.84 (s, 1H), 6.96-6.83 (m, 4H), 6.80 (s, 1H), 5.73-5.50 (m, 2H), 4.03 (s, 4H), 3.15 (s, 2H), 2.86 (t, J=6.7 Hz, 2H), 2.77-2.62 (m, 2H), 2.51-2.38 (m, 2H), 2.30 (s, 6H), 2.09-1.91 (m, 5H), 1.85 (s, 3H), 1.49-1.30 (m, 1H), 1.04-0.83 (m, 6H).

AN-P2 ESI 658.3 (M+H)⁺. ¹H NMR (400 MHz, MeOD) δ 7.75 (s, 1H), 6.92 (t, J=7.5 Hz, 5H), 5.84-5.72 (m, 1H), 5.61 (t, J=7.6 Hz, 1H), 4.14 (s, 4H), 3.42 (s, 2H), 2.94 (d, J=16.0 Hz, 2H), 2.87-2.59 (m, 2H), 2.56-2.41 (m, 2H), 2.37-2.25 (m, 6H), 2.05-1.88 (m, 7H), 1.72-1.59 (m, 1H), 1.47-1.34 (m, 1H), 0.96-0.82 (m, 6H).

3-36. Preparation of (3S)-3-(2-(5-(2-(azetidin-1-yl)ethyl)-2-oxo-4-(trifluoromethyl)pyridin-1(2H)-yl)-4-methylpentanamido)-3-(5-chloro-4-fluoro-2',6'-dimethyl-[1,1'-biphenyl]-3-yl)propanoic acid (compounds AO-P1 and AO-P2)

Step 1: ethyl (3S)-3-(2-(5-(2-(azetidin-1-yl)ethyl)-2-oxo-4-(trifluoromethyl)pyridin-1(2H)-yl)-4-methylpentanamido)-3-(5-chloro-4-fluoro-2',6'-dimethyl-[1,1'-biphenyl]-3-yl)propanoate

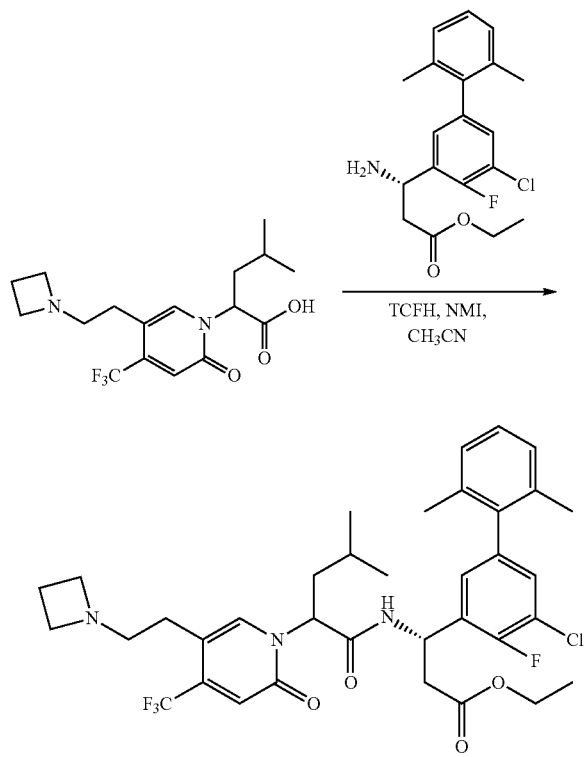

A mixture of 2-(5-(2-(azetidin-1-yl)ethyl)-2-oxo-4-(trifluoromethyl)pyridin-1(2H)-yl)-4-methylpentanoic acid (150 mg, 0.42 mmol), ethyl (S)-3-amino-3-(5-chloro-4-fluoro-2',6'-dimethyl-[1,1'-biphenyl]-3-yl)propanoate (154 mg, 0.42 mmol), TCFH (180 mg, 0.63 mmol) and NMI (100 mg, 1.26 mmol) in CH$_3$CN (5 mL) was stirred at 40° C. for 2 hours. The solvent was concentrated in vacuo and the residue was purified by reverse phase IPLC on a C18/40 g column (A: water 10 mM NH$_4$HCO$_3$, B: MeOH, 0~100%) to provide ethyl (3S)-3-(2-(5-(2-(azetidin-1-yl)ethyl)-2-oxo-4-(trifluoromethyl)pyridin-1(2H)-yl)-4-methylpentanamido)-3-(5-chloro-4-fluoro-2',6'-dimethyl-[1,1'-biphenyl]-3-yl)propanoate as a yellow oil (150 mg). Yield 52.8% (ESI 692.0 (M+H)$^+$).

Step 2: ethyl (3S)-3-(2-(5-(2-(azetidin-1-yl)ethyl)-2-oxo-4-(trifluoromethyl)pyridin-1(2H)-yl)-4-methylpentanamido)-3-(5-chloro-4-fluoro-2',6'-dimethyl-[1,1'-biphenyl]-3-yl)propanoate

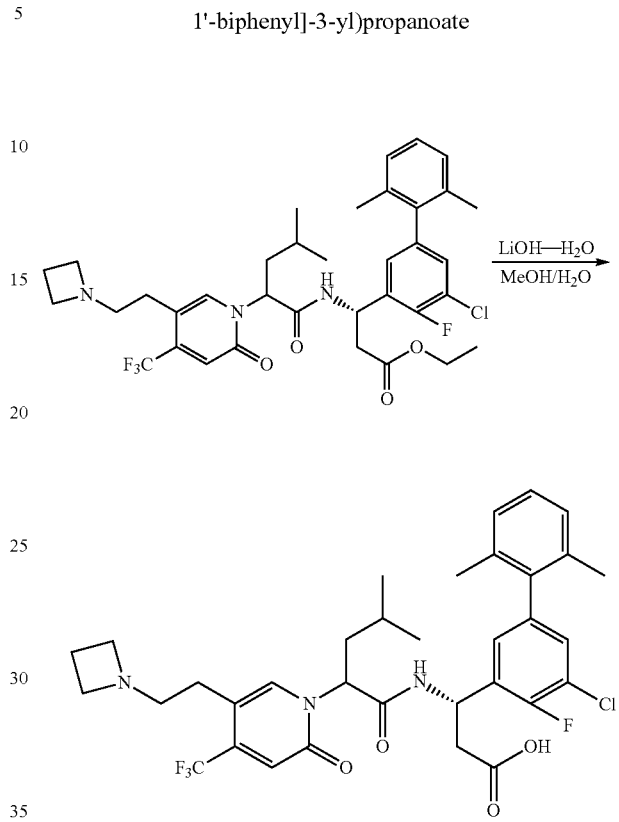

Ethyl (3S)-3-(2-(5-(2-(azetidin-1-yl)ethyl)-2-oxo-4-(trifluoromethyl)pyridin-1(2H)-yl)-4-methylpentanamido)-3-(5-chloro-4-fluoro-2',6'-dimethyl-[1,1'-biphenyl]-3-yl)propanoate (150 mg, 0.22 mmol) was treated with LiOH—H$_2$O (95.5 mg, 2.3 mmol) in MeOH (4 mL) and H$_2$O (4 mL) at room temperature for 2 hours. The reaction mixture was acidified to pH 4~5 with 1N HCl. The solvent was removed in vacuo and the residue was purified by prep-HPLC A (30-60% CH$_3$CN) to give the diastereomeric products AO-P1 (29 mg) and AO-P2 (34 mg) as a white solid.

AO-P1 ESI 664.2 (M+H)$^+$. $^1$H NMR (400 MHz, MeOD) δ 7.72 (s, 1H), 7.11-6.90 (m, 5H), 6.65 (s, 1H), 5.60-5.40 (m, 2H), 3.91 (t, J=8.2 Hz, 4H), 3.21-3.11 (m, 2H), 2.73 (t, J=7.0 Hz, 2H), 2.67-2.55 (m, 2H), 2.41-2.25 (m, 2H), 1.96-1.83 (m, 5H), 1.77 (s, 3H), 1.36-1.24 (m, 1H), 0.88-0.77 (m, 6H).

AO-P2 ESI 664.2 (M+H)$^+$. $^1$H NMR (400 MHz, MeOD) δ 7.75 (s, 1H), 7.26-7.07 (m, 5H), 6.90 (s, 1H), 5.86-5.74 (m, 1H), 5.62 (t, J=7.6 Hz, 1H), 4.14 (t, J=7.9 Hz, 4H), 3.49-3.36 (m, 2H), 3.01-2.74 (m, 2H), 2.71-2.62 (m, 1H), 2.59-2.43 (m, 3H), 2.12-1.91 (m, 7H), 1.77-1.58 (m, 1H), 1.49-1.32 (m, 1H), 0.90 (d, J=6.6 Hz, 6H).

3-37. Preparation of (3S)-3-(2-(5-(2-(azetidin-1-yl)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoic acid (compounds AP-P1 and AP-P2)

Step 1: ethyl (3S)-3-(2-(5-(2-(azetidin-1-yl)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoate

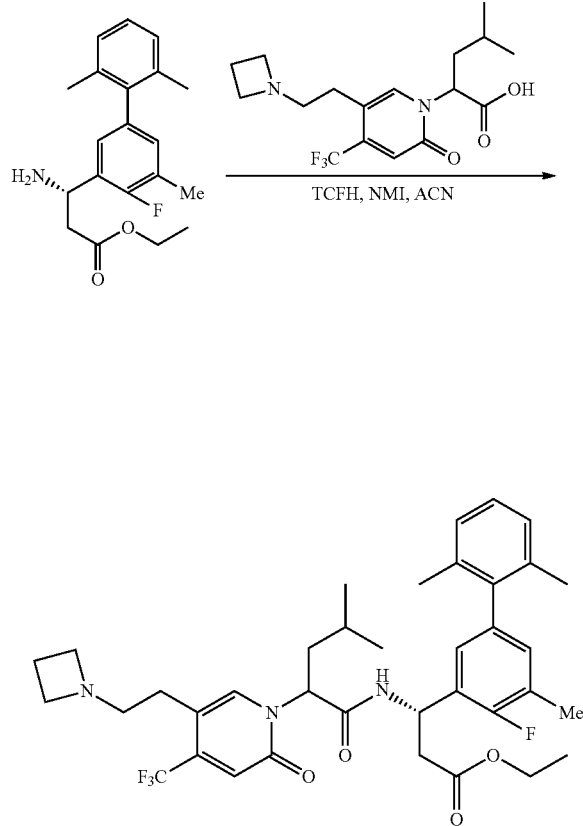

A mixture of 2-(5-(2-(azetidin-1-yl)ethyl)-2-oxo-4-(trifluoromethyl)pyridin-1(2H)-yl)-4-methylpentanoic acid (262 mg, 0.73 mmol, 1.20 eq), ethyl (S)-3-amino-3-(4-fluoro-2',5,6'-trimethyl-[1,1'-biphenyl]-3-yl)propanoate (200 mg, 0.61 mmol, 1.00 eq), NMI (0.5 mL) and TCFH (255 mg, 0.91 mmol, 1.50 eq) in CH$_3$CN (5 mL) was stirred at room temperature for 1 hour. The solvent was concentrated in vacuo and the residue was purified reverse phase HPLC on a C18/40 g column (A: water 10 mM NH$_4$HCO$_3$, B: MeOH, 0~100%) to provide ethyl (3S)-3-(2-(5-(2-(azetidin-1-yl)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoate as a white solid (300 mg). Yield 73.5% (ESI 672.3 [M+H]$^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoic acid

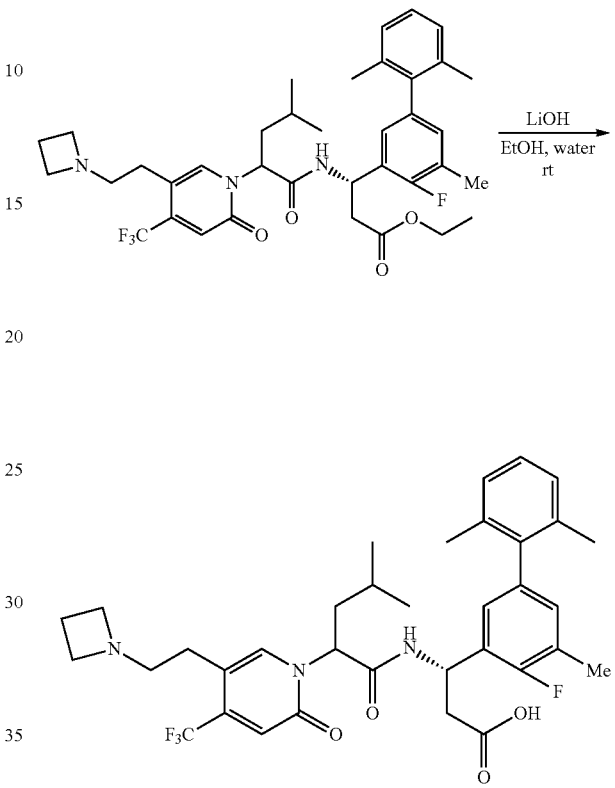

Ethyl (3S)-3-(2-(5-(2-(azetidin-1-yl)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoate (300 mg, 0.45 mmol, 1.00 eq) was treated with LiOH—H$_2$O (100 mg, 2.38 mmol, 5.00 eq) in MeOH (5 mL) and H$_2$O (1 mL) at room temperature for 1 hour. The reaction mixture was acidified to pH 4~5 with 1N HCl. The solvent was removed in vacuo and the residue was purified by prep-HPLC A (30-60% MeCN) to give AP-P1 (30 mg) and AP-P2 (50 mg) as a white solid.

AP-P1 ESI 644.2 (M+H)$^+$. $^1$H NMR (400 MHz, MeOD) δ 7.84 (s, 1H), 7.17-7.02 (m, 3H), 6.96-6.85 (m, 2H), 6.80 (s, 1H), 5.71-5.56 (m, 2H), 4.13-3.94 (m, 4H), 3.33-3.29 (m, 2H), 2.86 (t, J=6.7 Hz, 2H), 2.71 (d, J=6.1 Hz, 2H), 2.48-2.40 (m, 2H), 2.31 (d, J=1.7 Hz, 3H), 2.07-1.92 (m, 5H), 1.89 (s, 3H), 1.45-1.39 (m, 1H), 0.99-0.84 (m, 6H).

AP-P2 ESI 644.2 (M+H)$^+$. $^1$H NMR (400 MHz, MeOD) δ 7.75 (s, 1H), 7.12-7.08 (m, 3H), 6.97-6.91 (m, 3H), 5.79-5.76 (m, 1H), 5.61 (t, J=7.6 Hz, 1H), 4.14 (t, J=7.5 Hz, 4H), 3.53-3.34 (m, 2H), 2.94 (d, J=15.6 Hz, 1H), 2.88-2.71 (m, 1H), 2.68-2.63 (m, 1H), 2.54-2.44 (m, 3H), 2.34 (s, 3H), 2.02-1.96 (m, 7H), 1.75-1.54 (m, 1H), 1.45-1.39 (m, 1H), 0.90 (d, J=6.4 Hz, 6H).

3-38. Preparation of (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',5,6'-trimethyl-[1,1'-biphenyl]-3-yl)propanoic acid (compounds AQ-P1 and AQ-P2)

Step 1: ethyl (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',5,6'-trimethyl-[1,1'-biphenyl]-3-yl)propanoate Step 2: (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',5,6'-trimethyl-[1,1'-biphenyl]-3-yl)propanoic acid

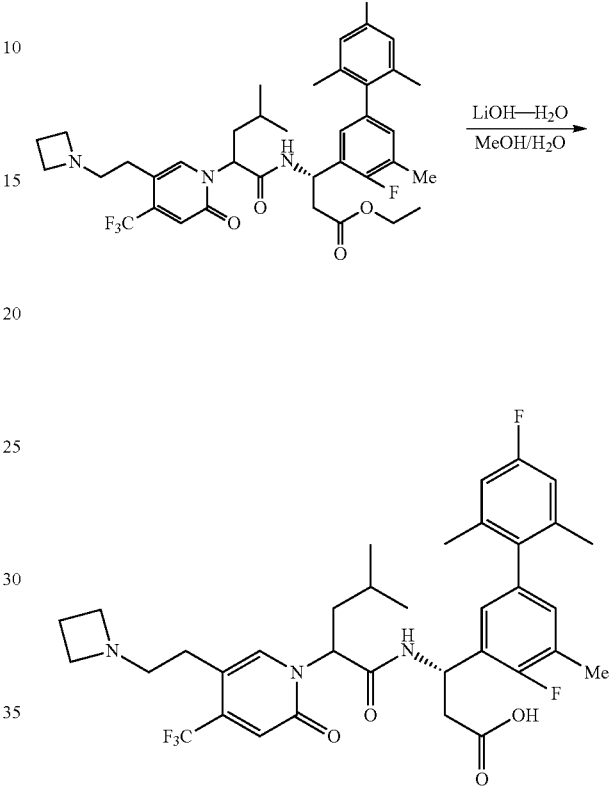

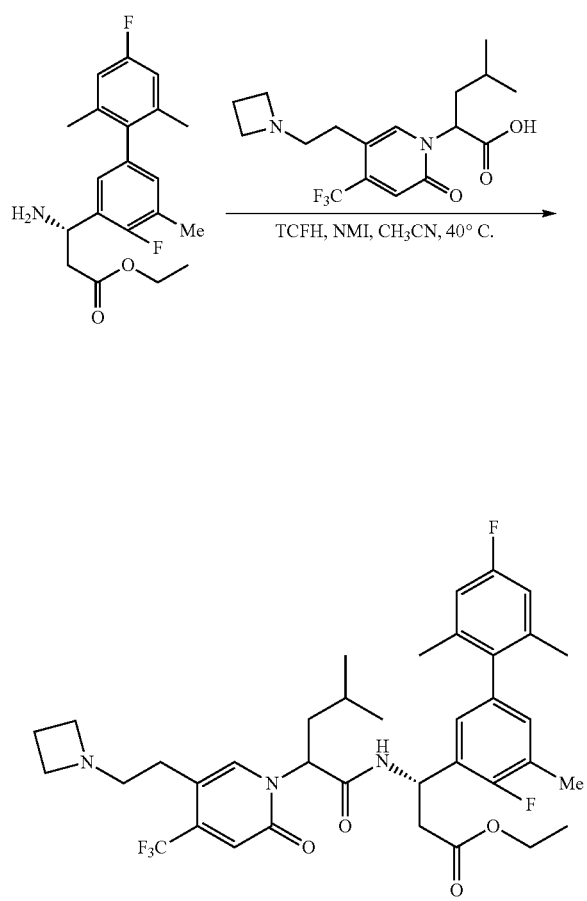

A mixture of 2-(5-(2-(azetidin-1-yl)ethyl)-2-oxo-4-(trifluoromethyl)pyridin-1(2H)-yl)-4-methylpentanoic acid (165 mg, 0.46 mmol), ethyl (S)-3-amino-3-(4,4'-difluoro-2',5,6'-trimethyl-[1,1'-biphenyl]-3-yl)propanoate (160 mg, 0.46 mmol), TCFH (193 mg, 0.69 mmol) and NMI (188 mg, 2.3 mmol) in $CH_3CN$ (4 mL) was stirred at 40° C. for 2 hours. The solvent was concentrated in vacuo and the residue was purified by reverse phase HPLC on a C18/40 g column (A: water 10 mM $NH_4HCO_3$, B: MeOH, 0~100%) to provide ethyl (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',5,6'-trimethyl-[1,1'-biphenyl]-3-yl)propanoate as a yellow oil (200 mg). Yield 62% (ESI 690.2 $(M+H)^+$).

Ethyl (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',5,6'-trimethyl-[1,1'-biphenyl]-3-yl)propanoate (200 mg, 0.29 mmol) was treated with LiOH—$H_2O$ (42 mg, 1 mmol) in MeOH (3 mL) and $H_2O$ (1 mL) at room temperature for 2 hours. The reaction mixture was acidified to pH 4~5 with 1N HCl. The solvent was removed in vacuo and the residue was purified by prep-HPLC A (30-60% $CH_3CN$) to give the diastereomeric products AQ-P1 (54 mg) and AQ-1-P2 (53 mg) as a white solid.

AQ-P1 ESI 662.2 $(M+H)^+$. $^1H$ NMR (400 MHz, MeOD) δ 7.86 (s, 1H), 6.94-6.74 (m, 5H), 5.72-5.55 (m, 2H), 4.05 (t, J=8.0 Hz, 4H), 3.33-3.25 (m, 2H), 2.86 (t, J=7.1 Hz, 2H), 2.77-2.64 (m, 2H), 2.55-2.38 (m, 2H), 2.30 (s, 3H), 2.06-1.94 (m, 5H), 1.87 (s, 3H), 1.53-1.34 (m, 1H), 1.01-0.86 (m, 6H).

AQ-P2 ESI 662.2 $(M+H)^+$. $^1H$ NMR (400 MHz, MeOD) δ 7.78 (s, 1H), 6.98-6.89 (m, 3H), 6.85 (d, J=9.6 Hz, 2H), 5.80-5.70 (m, 1H), 5.63 (t, J=7.6 Hz, 1H), 4.14 (s, 4H), 3.52-3.36 (m, 2H), 2.97-2.43 (m, 6H), 2.33 (s, 3H), 2.06-1.93 (m, 7H), 1.77-1.63 (m, 1H), 1.49-1.29 (m, 1H), 0.96-0.84 (m, 6H).

3-39. Preparation of (3S)-3-(4,4'-difluoro-2',5,6'-trimethyl-[1,1'-biphenyl]-3-yl)-3-(2-(5-(2-(3-fluoroazetidin-1-yl)ethyl)-4-methyl-2-oxopyridin-1(2H)-yl)-4-methylpentanamido)propanoic acid (compounds AR-P1 and AR-P2)

Step 1: ethyl(3S)-3-(4,4'-difluoro-2',5,6'-trimethyl-[1,1'-biphenyl]-3-yl)-3-(2-(5-(2-(3-fluoroazetidin-1-yl)ethyl)-4-methyl-2-oxopyridin-1(2H)-yl)-4-methylpentanamido)propanoate

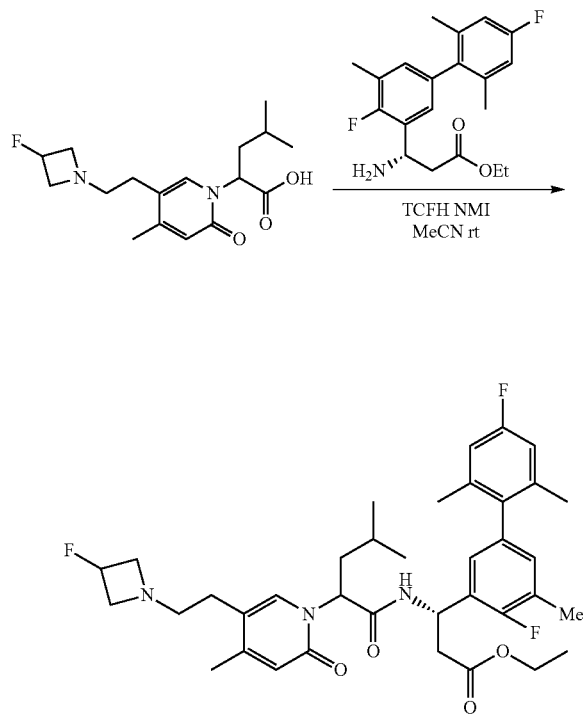

A mixture of 2-(5-(2-(3-fluoroazetidin-1-yl)ethyl)-4-methyl-2-oxopyridin-1(2H)-yl)-4-methylpentanoic acid (112 mg, 0.34 mmol), ethyl (S)-3-amino-3-(4,4'-difluoro-2',5,6'-trimethyl-[1,1'-biphenyl]-3-yl)propanoate (100 mg, 0.29 mmol), TCFH (120 mg, 0.43 mmol) and NMI (71 mg, 0.87 mmol) in CH$_3$CN (5 mL) was stirred at room temperature for 2 hours. The solvent was concentrated in vacuo and the residue was purified by reverse phase HPLC on a C18/40 g column (A: water 10 mM NH$_4$HCO$_3$, B: MeOH, 0~100%) to provide ethyl (3S)-3-(4,4'-difluoro-2',5,6'-trimethyl-[1,1'-biphenyl]-3-yl)-3-(2-(5-(2-(3-fluoroazetidin-1-yl)ethyl)-4-methyl-2-oxopyridin-1(2H)-yl)-4-methylpentanamido)propanoate as a yellow oil (150 mg). Yield 79.7% (ESI 654.3 (M+H)$^+$).

Step 2: (3S)-3-(4,4'-difluoro-2',5,6'-trimethyl-[1,1'-biphenyl]-3-yl)-3-(2-(5-(2-(3-fluoroazetidin-1-yl)ethyl)-4-methyl-2-oxopyridin-1(2H)-yl)-4-methylpentanamido)propanoic acid

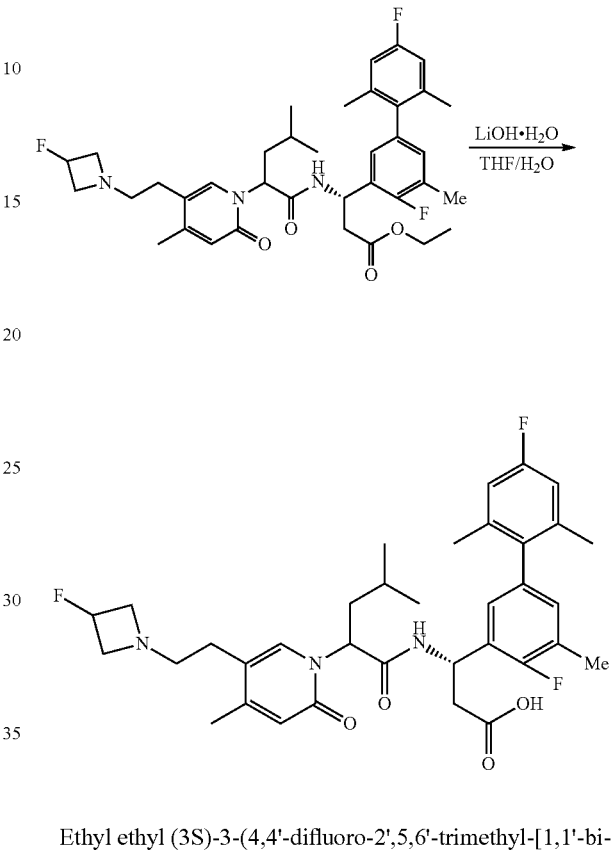

Ethyl ethyl (3S)-3-(4,4'-difluoro-2',5,6'-biphenyl]-3-yl)-3-(2-(5-(2-(3-fluoroazetidin-1-yl)ethyl)-4-methyl-2-oxopyridin-1(2H)-yl)-4-methylpentanamido)propanoate (150 mg, 0.23 mmol) was treated with LiOH—H$_2$O (100 mg, 2.3 mmol) in THF (3 mL) and H$_2$O (3 mL) at room temperature for 2 hours. The reaction mixture was acidified to pH 4~5 with 1N HCl. The solvent was removed in vacuo and the residue was purified by prep-HPLC A (30-60% CH$_3$CN) to give the diastereomeric products AR-P1 (43 mg) and AR-P2 (36 mg) as a white solid.

AR-P1 ESI 626.3 (M+H)$^+$. $^1$H NMR (400 MHz, MeOD) δ 7.49 (s, 1H), 6.92-6.68 (m, 4H), 6.30 (s, 1H), 5.74-5.52 (m, 2H), 5.30-5.12 (m, 1H), 4.15-3.90 (m, 2H), 3.75-3.57 (m, 2H), 3.05-3.00 (m, 2H), 2.85-2.62 (m, 3H), 2.32-2.27 (m, 4H), 2.22 (d, J=1.2 Hz, 3H), 1.99 (s, 3H), 1.96-1.92 (m, 2H), 1.85 (s, 3H), 1.45-1.35 (m, 1H), 0.96-0.91 (m, 6H).

AR-P2 ESI 626.2 (M+H)$^+$. $^1$H NMR (400 MHz, MeOD) δ 7.33 (s, 1H), 6.87-6.81 (m, 4H), 6.30 (s, 1H), 5.62-5.43 (m, 2H), 5.34-5.08 (m, 1H), 4.37-4.12 (m, 2H), 4.00-3.76 (m, 2H), 3.19-3.11 (m, 2H), 2.79-2.67 (m, 1H), 2.62-2.36 (m, 3H), 2.20 (d, J=1.6 Hz, 3H), 2.12 (s, 3H), 1.89 (s, 6H), 1.85-1.75 (m, 1H), 1.69-1.58 (m, 1H), 1.32-1.21 (m, 1H), 0.82-0.72 (m, 6H).

3-40. Preparation of (3S)-3-(4,4'-difluoro-2',5,6'-trimethylbiphenyl-3-yl)-3-(2-(5-(2-((R)-3-fluoropyrrolidin-1-yl)ethyl)-4-methyl-2-oxopyridin-1(2H)-yl)-4-methylpentanamido)propanoic acid (compounds AS-P1 and AS-P2)

Step 1: (3S)-ethyl 3-(4,4'-difluoro-2',5,6'-trimethylbiphenyl-3-yl)-3-(2-(5-(2-((R)-3-fluoropyrrolidin-1-yl)ethyl)-4-methyl-2-oxopyridin-1(2H)-yl)-4-methylpentanamido)propanoate

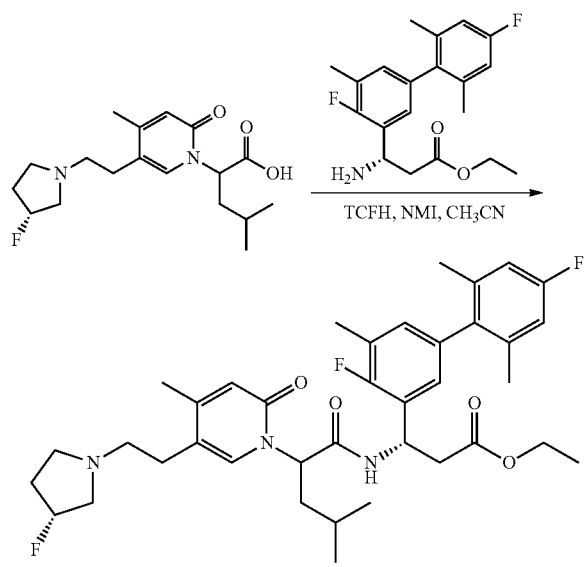

A mixture of 2-(5-(2-((R)-3-fluoropyrrolidin-1-yl)ethyl)-4-methyl-2-oxopyridin-1(2H)-yl)-4-methylpentanoic acid (120 mg, 0.36 mmol), (S)-ethyl 3-amino-3-(4,4'-difluoro-2',5,6'-trimethylbiphenyl-3-yl)propanoate (123 mg, 0.36 mmol), TCFH (114 mg, 0.41 mmol) and NMI (84 mg, 1.02 mmol) in CH₃CN (5 mL) was stirred at room temperature for 1 hour. The solvent was removed in vacuo and the residue was purified by silica gel column (DCM:MeOH 4:1) to provide (3S)-ethyl 3-(4,4'-difluoro-2',5,6'-trimethylbiphenyl-3-yl)-3-(2-(5-(2-((R)-3-fluoropyrrolidin-1-yl)ethyl)-4-methyl-2-oxopyridin-1(2H)-yl)-4-methylpentanamido)propanoate as a white solid (120 mg). Yield 51% (ESI 668.2 (M+H)$^+$).

Step 2: (3S)-3-(4,4'-difluoro-2',5,6'-trimethylbiphenyl-3-yl)-3-(2-(5-(2-((R)-3-fluoropyrrolidin-1-yl)ethyl)-4-methyl-2-oxopyridin-1(2H)-yl)-4-methylpentanamido)propanoic acid

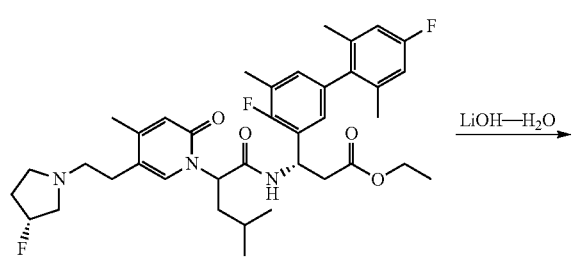

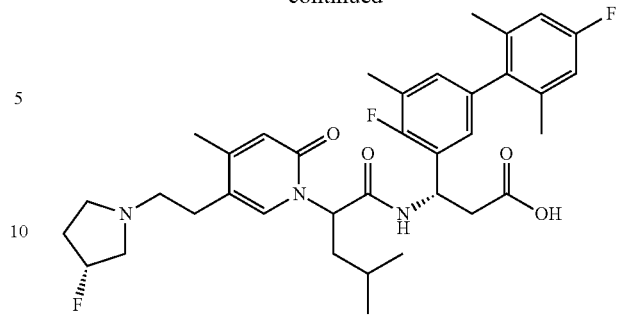

(3S)-ethyl 3-(4,4'-difluoro-2',5,6'-trimethylbiphenyl-3-yl)-3-(2-(5-(2-((R)-3-fluoropyrrolidin-1-yl)ethyl)-4-methyl-2-oxopyridin-1(2H)-yl)-4-methylpentanamido)propanoate (120 mg, 0.18 mmol)) was treated with LiOH—H₂O (32 mg, 0.75 mmol) in THF (3 mL) and H₂O (1 mL) at room temperature for 3 hours. The reaction mixture was acidified to pH 4~5 with 1N HCl. The solvent was removed in vacuo and the residue was purified by prep-HPLC A (30-60% CH₃CN) to give the diastereomeric products AS-P1 (28.0 mg) and AS-P2 (43.0 mg) as a white solid.

AS-P1 ESI 640.3 (M+H)$^+$. $^1$H NMR (400 MHz, MeOD) δ 7.56 (s, 1H), 6.84-6.79 (m, 4H), 6.26 (s, 1H), 5.65-5.60 (m, 1H), 5.55-5.50 (m, 1H), 5.35-5.52 (m, 1H), 3.38-3.33 (m, 1H), 3.32-2.66 (m, 9H), 2.39-2.11 (m, 8H), 1.98-1.92 (m, 5H), 1.81 (s, 3H), 1.46-1.39 (m, 1H), 0.96-0.91 (m, 6H).

AS-P2 ESI 640.3 (M+H)+. $^1$H NMR (400 MHz, MeOD) δ 7.57 (s, 1H), 6.90-6.82 (m, 4H), 6.42 (s, 1H), 5.64-5.58 (m, 2H), 5.40-5.24 (m, 1H), 3.51-3.37 (m, 3H), 3.32-3.10 (m, 3H), 2.92-2.76 (m, 2H), 2.68-2.55 (m, 2H), 2.40-2.21 (m, 8H), 2.05-1.88 (m, 7H), 1.80-1.73 (m, 1H), 1.41-1.34 (m, 1H), 0.96-0.87 (m, 6H).

3-41. Preparation of (3S)-3-(4,4'-difluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic acid (compounds AT-P1 and AT-P2)

Step 1: ethyl (3S)-3-(4,4'-difluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoate

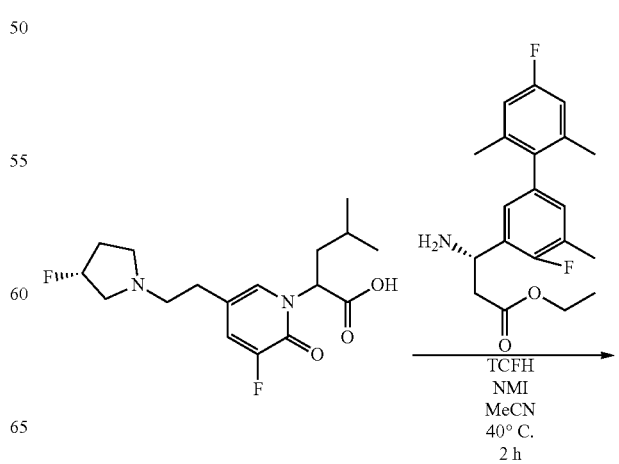

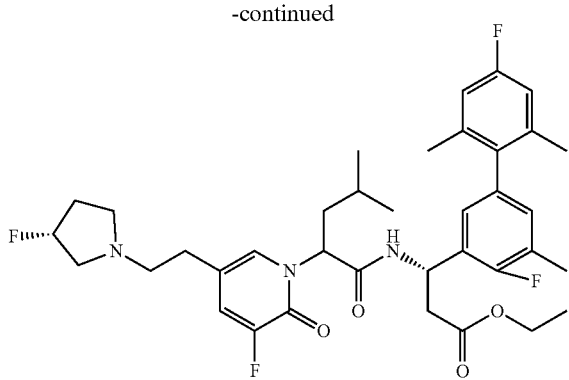

A mixture of 2-(3-fluoro-5-(2-((R)-3-fluoropyrrolidin-1-yl)ethyl)-2-oxopyridin-1(2H)-yl)-4-methylpentanoic acid (120 mg, 0.35 mmol), ethyl (S)-3-amino-3-(4,4'-difluoro-2',5,6'-trimethyl-[1,1'-biphenyl]-3-yl)propanoate (140 mg, 0.42 mmol), TCFH (117 mg, 0.42 mmol) and NMI (86 mg, 1.05 mmol) in CH₃CN (5 mL) was stirred at 40° C. for 2 hours. The solvent was concentrated in vacuo and the residue was purified by reverse phase IPLC on a C18/40 g column (A: water 10 mM NH₄HCO₃, B: MeOH, 0~100%) to provide ethyl (3S)-3-(4,4'-difluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoate as a yellow oil (150 mg). Yield 63.8% (ESI 672.3 (M+H)⁺).

Step 2: ethyl (3S)-3-(4,4'-difluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoate

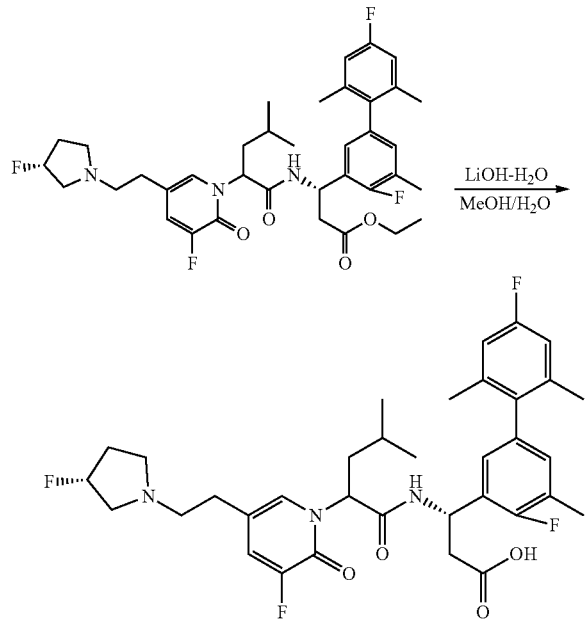

Ethyl (3S)-3-(4,4'-difluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoate (150 mg, 0.22 mmol) was treated with LiOH—H₂O (94 mg, 2.2 mmol) in MeOH (5 mL) and H₂O (5 mL) at room temperature for 2 hours. The reaction mixture was acidified to pH 4~5 with 1N HCl. The solvent was removed in vacuo and the residue was purified by prep-HPLC A (30-60% CH₃CN) to give the diastereomeric products AT-P1 (28 mg) and AT-P2 (37 mg) as a white solid.

AT-P1 ESI 644.2 (M+H)⁺. ¹H NMR (400 MHz, MeOD) δ 7.50 (s, 1H), 7.37 (d, J=10.1 Hz, 1H), 6.92-6.77 (m, 4H), 5.74-5.62 (m, 1H), 5.57-5.46 (m, 1H), 5.27 (d, J=53.4 Hz, 1H), 3.29-2.96 (m, 6H), 2.84-2.56 (m, 4H), 2.40-2.10 (m, 5H), 2.07-1.90 (m, 5H), 1.87 (s, 3H), 1.49-1.38 (m, 1H), 1.03-0.89 (m, 6H).

AT-P2 ESI 644.2 (M+H)⁺. ¹H NMR (400 MHz, MeOD) δ 7.49 (s, 1H), 7.41 (d, J=10.3 Hz, 1H), 6.97-6.76 (m, 4H), 5.67 (t, J=7.7 Hz, 1H), 5.62-5.52 (m, 1H), 5.33 (d, J=55.0 Hz, 1H), 3.69-3.34 (m, 6H), 2.92-2.77 (m, 2H), 2.65-2.43 (m, 2H), 2.30 (d, J=17.3 Hz, 5H), 2.10-1.89 (m, 7H), 1.86-1.74 (m, 1H), 1.48-1.34 (m, 1H), 0.95-0.86 (m, 6H).

3-42. Preparation of (3S)-3-(4-fluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic acid (compounds AU-P1 and AU-P2)

Step 1: ethyl(3S)-3-(4-fluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoate

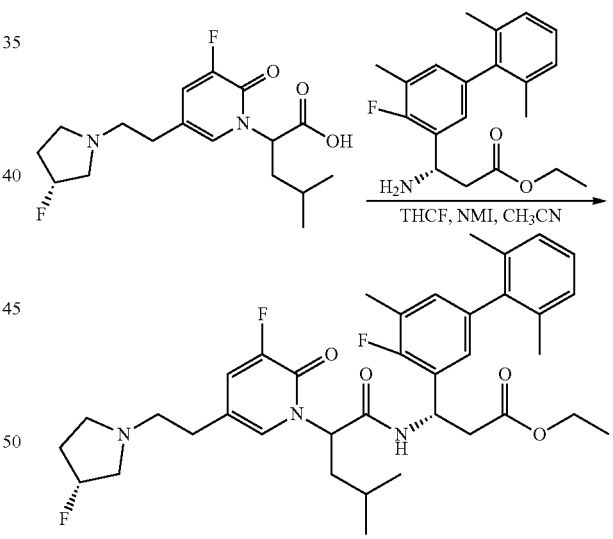

A mixture of 2-(3-fluoro-5-(2-((R)-3-fluoropyrrolidin-1-yl)ethyl)-2-oxopyridin-1(2H)-yl)-4-methylpentanoic acid (150 mg, 0.44 mmol), ethyl (S)-3-amino-3-(4-fluoro-2',5,6'-trimethyl-[1,1'-biphenyl]-3-yl)propanoate (144 mg, 0.44 mmol), TCFH (148 mg, 0.53 mmol), NMI (108 mg, 1.32 mmol) in CH₃CN (4 mL) was stirred at room temperature for 1 hour. LCMS showed that the reaction was completed. The solvent was concentrated in vacuo and the residue was purified by reverse phase HPLC on a C18/120 g column (A: water 10 mM NH₄HCO₃, B: CH₃CN, 0~100%) to provide ethyl (3S)-3-(4-fluoro-2',5,6'-trimethyl-[1,1'-biphenyl]-3-yl)-3-(2-(3-fluoro-5-(2-((R)-3-fluoropyrrolidin-1-yl)ethyl)-

2-oxopyridin-1(2H)-yl)-4-methylpentanamido)propanoate as a colorless oil (130 mg). Yield 45% (ESI 654.2 (M+H)+).

Step 2: (3S)-3-(4-fluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic acid

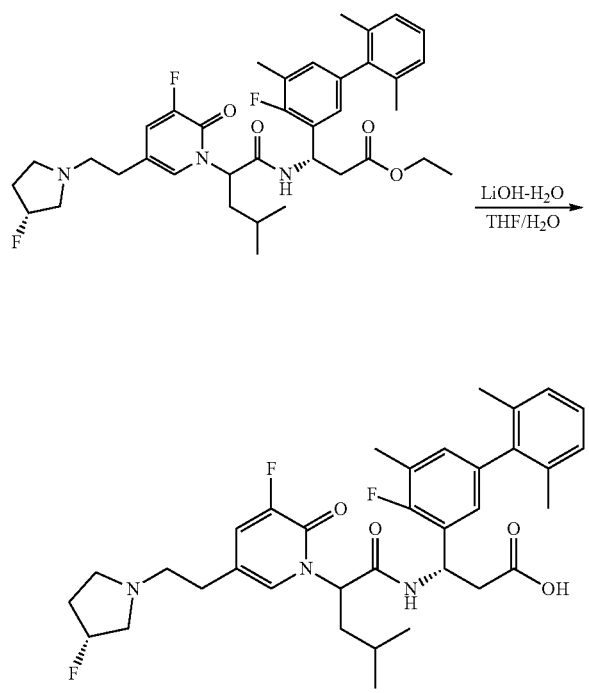

Ethyl(3S)-3-(4-fluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoate (130 mg, 0.20 mmol) was treated with LiOH—H$_2$O (83 mg, 2.0 mmol) in THF (2 mL) and H$_2$O (1 mL) at 35° C. for 1 hour. The reaction mixture was acidified to pH 4~5 with 1N HCl. The solvent was removed in vacuo and the residue was purified by prep-HPLC A (30-60% MeCN) to give the diastereomeric products AU-P1(33 mg) and AU-P2 (53 mg) as a white solid.

AU-P1 ESI 626.2 (M+H)+. $^1$H NMR (400 MHz, MeOD) δ 7.51 (s, 1H), 7.38-7.35 (m, 1H), 7.15-7.06 (m, 3H), 6.88-6.81 (m, 2H), 5.73-5.68 (m, 1H), 5.53-5.50 (m, 1H), 5.35-5.19 (m, 1H), 3.44-3.35 (m, 1H), 3.30-3.08 (m, 5H), 2.80-2.65 (m, 4H), 2.37-2.18 (m, 5H), 1.98-1.95 (m, 5H), 1.88 (s, 3H), 1.47-1.40 (m, 1H), 097-0.93 (m, 6H).

AU-P2 ESI 626.2 (M+H)+. $^1$H NMR (400 MHz, MeOD) δ 7.50 (s, 1H), 7.41-7.38 (m, 1H), 7.14-7.07 (m, 3H), 6.93-6.90 (m, 2H), 5.70-5.66 (m, 1H), 5.61-5.58 (m, 1H), 5.40-5.25 (m, 1H), 3.65-3.37 (m, 5H), 3.30-3.25 (m, 1H), 2.91-2.79 (m, 2H), 2.64-2.48 (m, 2H), 2.39-2.25 (m, 5H), 2.00-1.94 (m, 7H), 1.84-1.75 (m, 1H), 1.43-1.35 (m, 1H), 0.92-0.89 (m, 6H).

3-43. Preparation of (3S)-3-(4-fluoro-2',5,6'-trimethyl-[1,1'-biphenyl]-3-yl)-3-(2-(3-fluoro-5-(2-(3-fluoroazetidin-1-yl)ethyl)-2-oxopyridin-1(2H)-yl)-4-methylpentanamido)propanoic acid (compounds AV-P1 and AV-P2)

Step 1: ethyl (3S)-3-(4-fluoro-2',5,6'-trimethyl-[1,1'-biphenyl]-3-yl)-3-(2-(3-fluoro-5-(2-(3-fluoroazetidin-1-yl)ethyl)-2-oxopyridin-1(2H)-yl)-4-methylpentanamido)propanoate

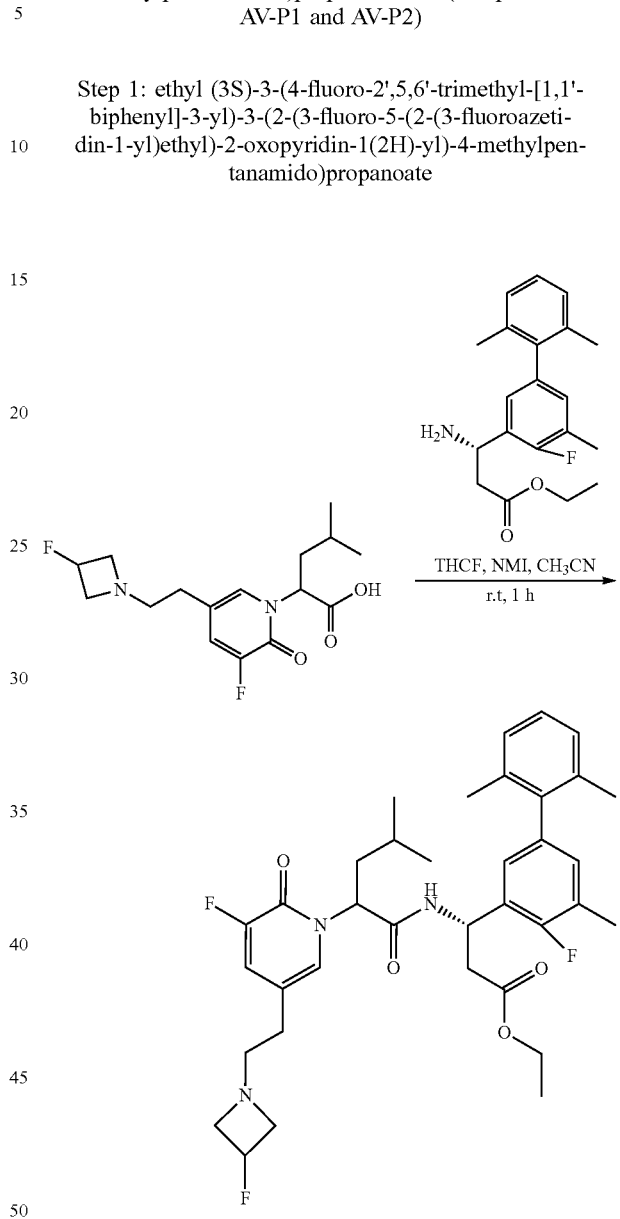

A mixture of ethyl (S)-3-amino-3-(4-fluoro-2',5,6'-trimethyl-[1,1'-biphenyl]-3-yl)propanoate (142 mg, 0.43 mmol), 2-(3-fluoro-5-(2-(3-fluoroazetidin-1-yl)ethyl)-2-oxopyridin-1(2H)-yl)-4-methylpentanoic acid (120 mg, 0.36 mmol), N,N,N,N-Tetramethylchloroformamidinium hexafluorophosphate (151 mg, 0.54 mmol) and 1-methyl-1H-imidazole (147.6 mg, 1.8 mmol) in CH$_3$CN (4 mL) was stirred at room temperature for 1 hour. The solvent was removed in vacuo and the residue was purified by reverse phase HPLC on a C18/40 g column (A: water 10 mM NH$_4$HCO$_3$, B: MeOH, 0~100%) to provide ethyl (3S)-3-(4-fluoro-2',5,6'-trimethyl-[1,1'-biphenyl]-3-yl)-3-(2-(3-fluoro-5-(2-(3-fluoroazetidin-1-yl)ethyl)-2-oxopyridin-1(2H)-yl)-4-methylpentanamido)propanoate as a yellow solid (110 mg). Yield 48% (ESI 640.2 [M+H]+).

Step 2: (3S)-3-(4-fluoro-2',5,6'-trimethyl-[1,1'-biphenyl]-3-yl)-3-(2-(3-fluoro-5-(2-(3-fluoroazetidin-1-yl)ethyl)-2-oxopyridin-1(2H)-yl)-4-methylpentanamido)propanoic acid

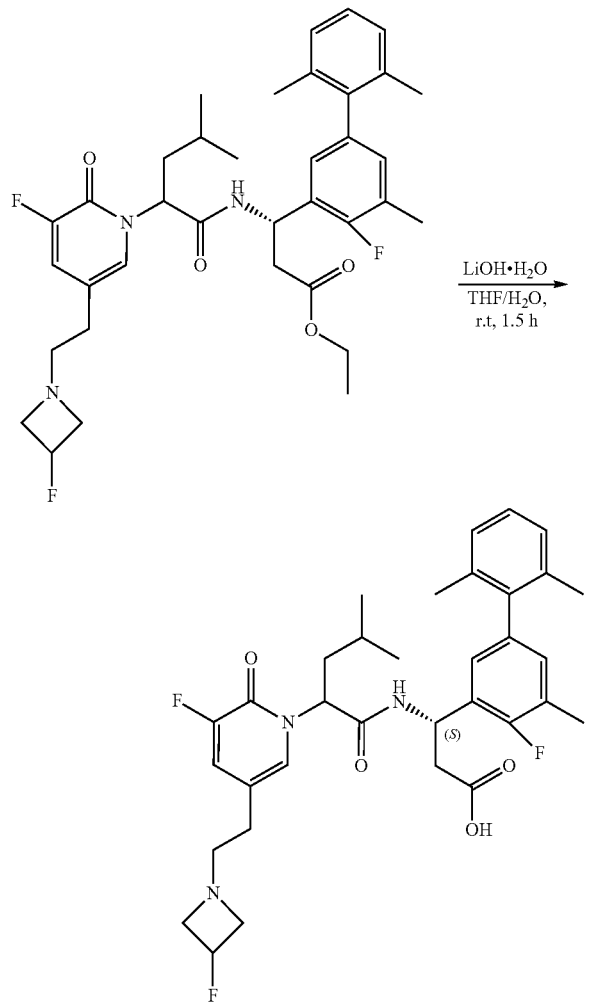

Ethyl (3S)-3-(4-fluoro-2',5,6'-trimethyl-[1,1'-biphenyl]-3-yl)-3-(2-(3-fluoro-5-(2-(3-fluoroazetidin-1-yl)ethyl)-2-oxopyridin-1(2H)-yl)-4-methylpentanamido)propanoate (110 mg, 0.17 mmol) was treated with LiOH—H$_2$O (36 mg, 0.86 mmol) in THF (20 mL) and water (8 mL) at 30° C. for 1 hour. The reaction mixture was acidified to pH 4~5 with 2N HCl. The solvent was removed in vacuo and the residue was purified by preparatory HPLC B to give the diastereomeric product AV-P1 (40 mg) and AV-P2 (39 mg) as a white solid.

AV-P1 ESI 612.3 (M+H)$^+$. $^1$H NMR (400 MHz, MeOD) δ 7.76 (s, 0.18H, FA), 7.50-7.27 (m, 2H), 7.23-7.02 (m, 3H), 6.96-6.75 (m, 2H), 5.69 (t, J=8.0 Hz, 1H), 5.50 (t, J=6.1 Hz, 1H), 5.20 (d, J=57.4 Hz, 1H), 4.11 (s, 1H), 3.95 (s, 1H), 3.75-3.53 (m, 2H), 3.21-3.05 (m, 2H), 2.85-2.52 (m, 4H), 2.30 (s, 3H), 2.05-1.82 (m, 8H), 1.56-1.32 (m, 1H), 1.06-0.83 (m, 6H).

AV-P2 ESI 612.3 (M+H)$^+$. $^1$H NMR (400 MHz, MeOD) δ 8.36 (s, 0.27H, FA), 7.51-7.29 (m, 2H), 7.09 (t, J=7.6 Hz, 3H), 6.94 (t, J=7.0 Hz, 2H), 5.80-5.58 (m, 2H), 5.57-5.18 (m, 1H), 4.54-4.21 (m, 2H), 4.16-3.93 (m, 2H), 3.39 (d, J=5.5 Hz, 2H), 2.83-2.48 (m, 4H), 2.33 (d, J=1.6 Hz, 3H), 2.00 (s, 7H), 1.88-1.66 (m, 1H), 1.54-1.26 (m, 1H), 1.23-0.69 (m, 6H).

3-44. Preparation of (3S)-3-(2-(5-(2-(dimethylamino)ethyl)-3-methyl-2-oxopyridin-1(2H)-yl)-4-methylpentanamido)-3-(4-fluoro-2',5,6'-trimethyl-[1,1'-biphenyl]-3-yl)propanoic acid (compounds AW-P1 and AW-P2)

Step 1: ethyl (3S)-3-(2-(5-(2-(dimethylamino)ethyl)-3-methyl-2-oxopyridin-1(2H)-yl)-4-methylpentanamido)-3-(4-fluoro-2',5,6'-trimethyl-[1,1'-biphenyl]-3-yl)propanoate

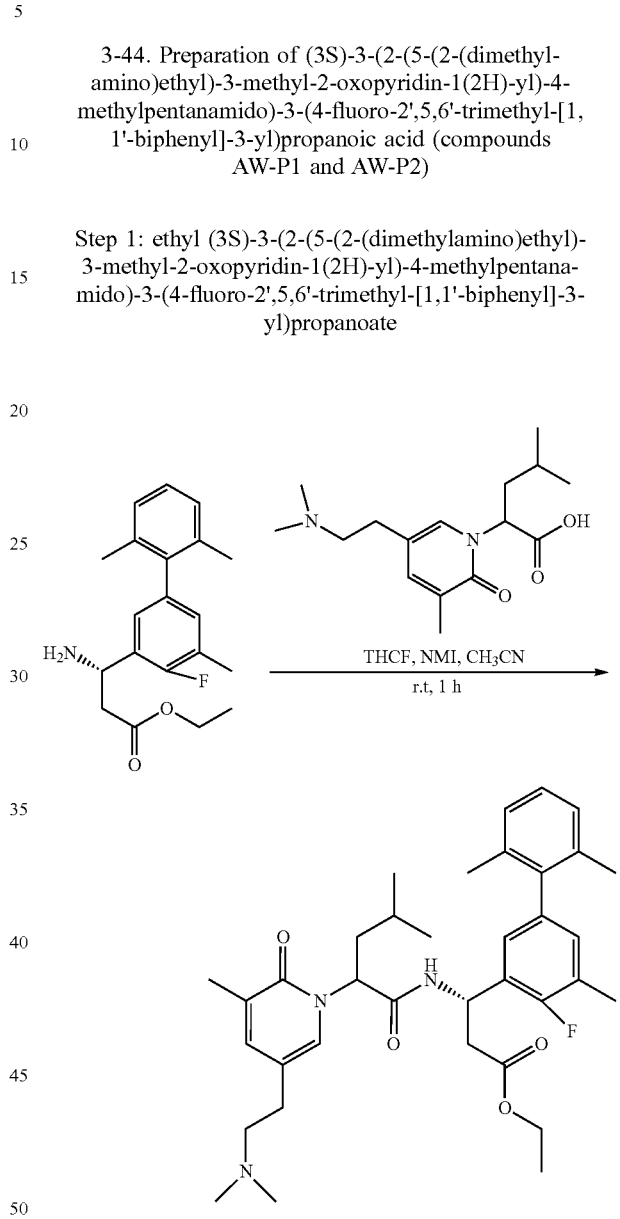

A mixture of ethyl (S)-3-amino-3-(4-fluoro-2',5,6'-trimethyl-[1,1'-biphenyl]-3-yl)propanoate (130.0 mg, 0.44 mmol), 2-(5-(2-(dimethylamino)ethyl)-3-methyl-2-oxopyridin-1(2H)-yl)-4-methylpentanoic acid (145.0 mg, 0.44 mmol), N,N,N,N-Tetramethylchloroformamidinium hexafluorophosphate (131 mg, 0.47 mmol) and 1-methyl-1H-imidazole (96.0 mg, 1.17 mmol) in CH$_3$CN (4 mL) was stirred at room temperature for 1 hour. The solvent was removed in vacuo and the residue was purified by reverse phase HPLC on a C18/40 g column (A: water 10 mM NH$_4$HCO$_3$, B: MeOH, 0~100%) to provide ethyl (3S)-3-(2-(5-(2-(dimethylamino)ethyl)-3-methyl-2-oxopyridin-1(2H)-yl)-4-methylpentanamido)-3-(4-fluoro-2',5,6'-trimethyl-[1,1'-biphenyl]-3-yl)propanoate as a yellow solid (130 mg). Yield 48.6% (ESI 606.2 [M+H]$^+$).

Step 2: (3S)-3-(2-(5-(2-(dimethylamino)ethyl)-3-methyl-2-oxopyridin-1(2H)-yl)-4-methylpentanamido)-3-(4-fluoro-2',5,6'-trimethyl-[1,1'-biphenyl]-3-yl)propanoic acid 3-45. Preparation of (3S)-3-(2-(5-(2-(dimethylamino)ethyl)-3-fluoro-2-oxopyridin-1(2H)-yl)-4-methylpentanamido)-3-(4-fluoro-2',5,6'-trimethylbiphenyl-3-yl)propanoic acid (compounds AX-P1 and AX-P2)

Step 1: (3S)-ethyl 3-(2-(5-(2-(dimethylamino)ethyl)-3-fluoro-2-oxopyridin-1(2H)-yl)-4-methylpentanamido)-3-(4-fluoro-2',5,6'-trimethylbiphenyl-3-yl)propanoate

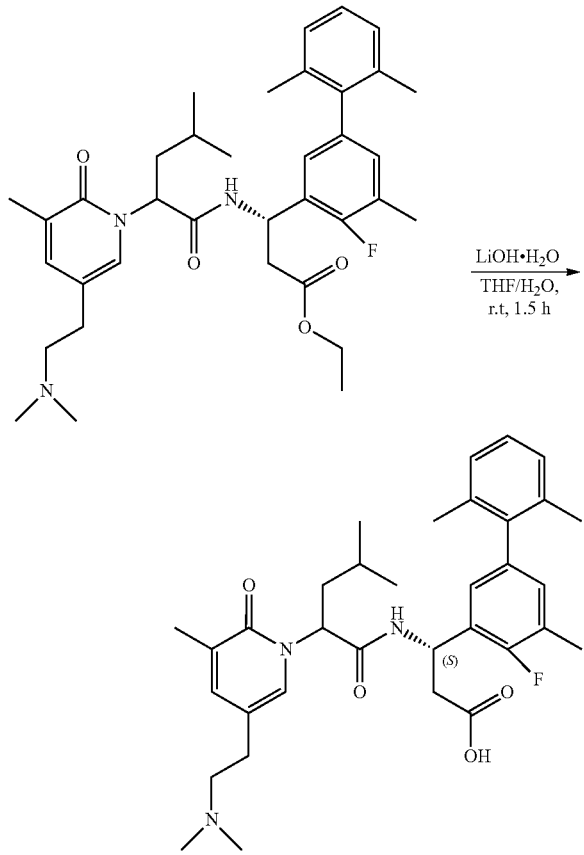

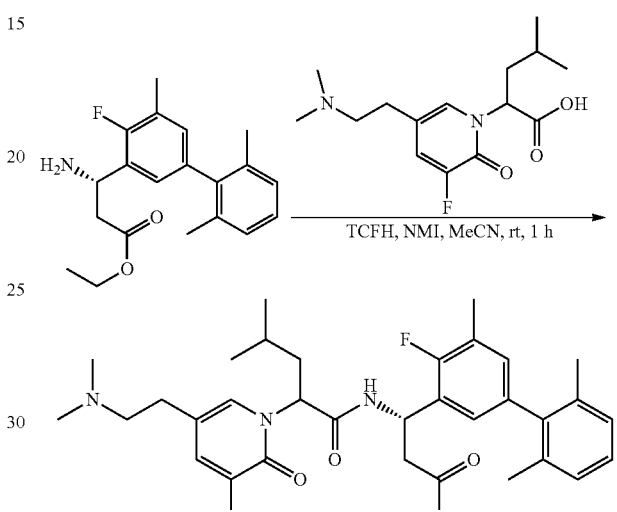

A mixture of 2-(5-(2-(dimethylamino)ethyl)-3-fluoro-2-oxopyridin-1(2H)-yl)-4-methylpentanoic acid (109 mg, 0.36 mmol), (S)-ethyl 3-amino-3-(4-fluoro-2',5,6'-trimethylbiphenyl-3-yl)propanoate (120 mg, 0.36 mmol), TCFH (114 mg, 0.41 mmol) and NMI (84 mg, 1.02 mmol) in CH$_3$CN (5 mL) was stirred at room temperature for 1 hour. The solvent was removed in vacuo and the residue was purified by silica gel column (DCM:MeOH 4:1) to provide (3S)-ethyl 3-(2-(5-(2-(dimethylamino)ethyl)-3-fluoro-2-oxopyridin-1(2H)-yl)-4-methylpentanamido)-3-(4-fluoro-2',5,6'-trimethylbiphenyl-3-yl)propanoate as a white solid (130 mg). Yield 59% (ESI 610.2 (M+H)$^+$).

Ethyl (3S)-3-(2-(5-(2-(dimethylamino)ethyl)-3-methyl-2-oxopyridin-1(2H)-yl)-4-methylpentanamido)-3-(4-fluoro-2',5,6'-trimethyl-[1,1'-biphenyl]-3-yl)propanoate (130.0 mg, 0.21 mmol) was treated with LiOH—H$_2$O (46.0 mg, 1.0 mmol) in THF (6 mL) and water (3 mL) at 30° C. for 1 hour. The reaction mixture was acidified to pH 4~5 with 1 N HCl. The solvent was removed in vacuo and the residue was purified by Prep HPLC A (30-60% MeCN) to give the diastereomeric products AW-P1 (30.3 mg) and AW-P2 (46.0 mg) as a white solid.

AW-P1 ESI 578.3 (M+H)$^+$. $^1$H NMR (400 MHz, MeOD) δ 7.46 (s, 1H), 7.43 (s, 1H), 7.17-7.07 (m, 3H), 6.88-6.86 (m, 1H), 6.74-6.71 (m, 1H), 5.57-5.54 (m, 1H), 5.36 (t, J=5.0 Hz, 1H), 3.38-3.5 (m, 1H), 3.19-3.06 (m, 1H), 2.83-2.77 (m, 2H), 2.67 (s, 6H), 2.64-2.59 (m, 1H), 2.53-2.47 (m, 1H), 2.30 (d, J=1.7 Hz, 3H), 2.05 (s, 3H), 1.98-1.93 (m, 8H), 1.48-1.39 (m, 1H), 0.95-0.89 (m, 6H).

AW-P2 ESI 578.3 (M+H)$^+$. $^1$H NMR (400 MHz, MeOD) δ 7.51 (s, 1H), 7.41 (s, 1H), 7.17-7.02 (m, 3H), 6.89-6.87 (m, 1H), 6.81-6.79 (m, 1H), 5.64-5.60 (m, 1H), 5.55-5.51 (m, 1H), 3.45-3.38 (m, 1H), 3.30-3.23 (m, 1H), 2.97-2.72 (m, 8H), 2.61-2.56 (m, 1H), 2.45-2.39 (m, 1H), 2.31 (d, J=1.8 Hz, 3H), 2.06-1.80 (m, 11H), 1.46-1.39 (m, 1H), 0.94-0.88 (m, 6H).

Step 2: (3S)-3-(2-(5-(2-(dimethylamino)ethyl)-3-fluoro-2-oxopyridin-1(2H)-yl)-4-methylpentanamido)-3-(4-fluoro-2',5,6'-trimethylbiphenyl-3-yl)propanoic acid

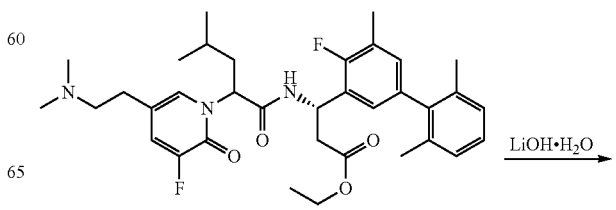

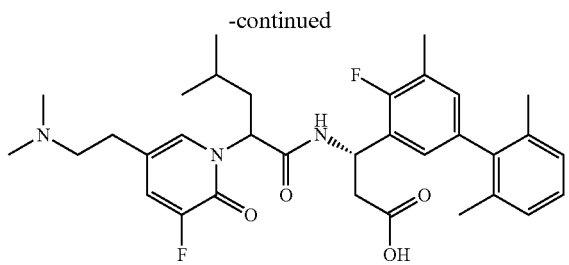

(3S)-ethyl 3-(2-(5-(2-(dimethylamino)ethyl)-3-fluoro-2-oxopyridin-1(2H)-yl)-4-methylpentanamido)-3-(4-fluoro-2',5,6'-trimethylbiphenyl-3-yl)propanoate (130 mg, 0.21 mmol)) was treated with LiOH—H₂O (32 mg, 0.75 mmol) in THF (3 mL) and H₂O (1 mL) at room temperature for 3 hours. The reaction mixture was acidified to pH 4~5 with 1N HCl. The solvent was removed in vacuo and the residue was purified by pre-HPLC A (30-60% MeCN) to give the diastereomeric products AX-P1 (32.0 mg) and AX-P2 (35.0 mg) as a white solid.

AX-P1 ESI 582.1 (M+H)⁺. ¹H NMR (400 MHz, MeOD) δ 7.48 (s, 1H), 7.40 (d, J=10.2 Hz, 1H), 7.15-7.08 (m, 3H), 6.86 (d, J=6.8 Hz, 1H), 6.78 (d, J=6.4 Hz, 1H), 5.67 (t, J=8.1 Hz, 1H), 5.43 (t, J=5.5 Hz, 1H), 3.18-3.13 (m, 1H), 3.03-2.99 (m, 1H), 2.81-2.77 (m, 2H), 2.68-2.53 (m, 8H), 2.29 (s, 3H), 2.00-1.94 (m, 5H), 1.92 (s, 3H), 1.45-1.39 (m, 1H), 0.96-0.90 (m, 6H).

AX-P2 ESI 582.1 (M+H)⁺. ¹H NMR (400 MHz, MeOD) δ 7.50 (s, 1H), 7.43-7.40 (m, 1H), 7.15-7.07 (m, 3H), 6.91 (d, J=6.9 Hz, 2H), 5.66-5.58 (m, 2H), 3.41-3.34 (m, 1H), 3.28-3.22 (m, 1H), 2.99-2.91 (m, 1H), 2.85-2.81 (m, 7H), 2.61-2.55 (m, 1H), 2.47-2.41 (m, 1H), 2.32 (d, J=1.8 Hz, 3H), 2.04-1.97 (m, 7H), 1.85-1.77 (m, 1H), 1.44-1.36 (m, 1H), 0.92-0.89 (m, 6H).

3-46. Preparation of (3S)-3-(2-(5-(2-(dimethylamino)ethyl)-4-methyl-2-oxopyridin-1(2H)-yl)-4-methylpentanamido)-3-(4-fluoro-2',5,6'-trimethylbiphenyl-3-yl)propanoic acid (compounds AZ-P1 and AZ-P2)

Step 1: ethyl (3S)-3-(2-(5-(2-(dimethylamino)ethyl)-4-methyl-2-oxopyridin-1(2H)-yl)-4-methylpentanamido)-3-(4-fluoro-2',5,6'-trimethyl-[1,1'-biphenyl]-3-yl)propanoate

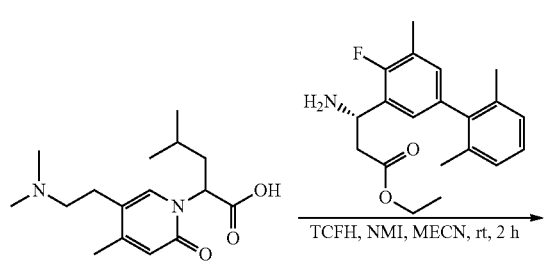

A mixture of 2-(5-(2-(dimethylamino)ethyl)-4-methyl-2-oxopyridin-1(2H)-yl)-4-methylpentanoic acid (100 mg, 0.34 mmol), ethyl (S)-3-amino-3-(4-fluoro-2',5,6'-trimethyl-[1,1'-biphenyl]-3-yl)propanoate (112 mg, 0.34 mmol), TCFH (115 mg, 0.41 mmol), NMI (84 mg, 1.02 mmol) in CH₃CN (5 mL) was stirred at room temperature for 1 hour. The solvent was removed in vacuo and the residue was purified by silica gel column (DCM:MeOH 4:1) to provide ethyl (3S)-3-(2-(5-(2-(dimethylamino)ethyl)-4-methyl-2-oxopyridin-1(2H)-yl)-4-methylpentanamido)-3-(4-fluoro-2',5,6'-trimethyl-[1,1'-biphenyl]-3-yl)propanoate as a white solid (90 mg). Yield 44% (ESI 606.2 (M+H)⁺).

Step 2: (3S)-3-(2-(5-(2-(dimethylamino)ethyl)-4-methyl-2-oxopyridin-1(2H)-yl)-4-methylpentanamido)-3-(4-fluoro-2',5,6'-trimethylbiphenyl-3-yl)propanoic acid

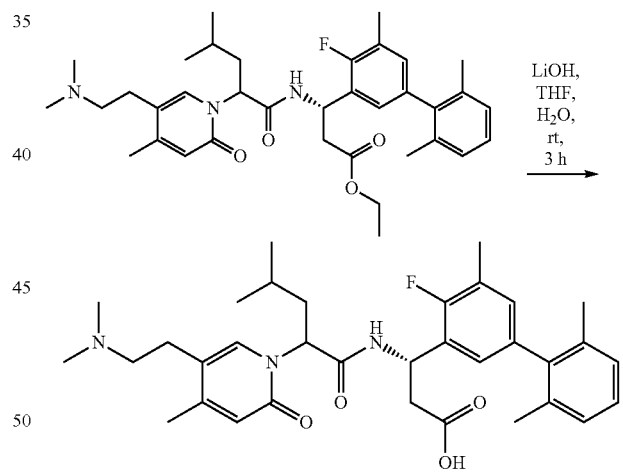

Ethyl(3S)-3-(2-(5-(2-(dimethylamino)ethyl)-4-methyl-2-oxopyridin-1(2H)-yl)-4-methylpentanamido)-3-(4-fluoro-2',5,6'-trimethyl-[1,1'-biphenyl]-3-yl)propanoate (90 mg, 0.15 mmol)) was treated with LiOH—H₂O (32 mg, 0.75 mmol) in THF (3 mL) and H₂O (1 mL) at room temperature for 3 hours. The reaction mixture was acidified to pH 4~5 with 1N HCl. The solvent was removed in vacuo and the residue was purified by prep-HPLC A (30-60% MeCN) to give the diastereomeric products AZ-P1 (30.0 mg) and AZ-P2 (26.0 mg) as a white solid.

AZ-P1 ESI 578.2 (M+H)⁺. ¹H NMR (500 MHz, MeOD) δ 7.57 (s, 1H), 7.18-7.03 (m, 3H), 6.86-6.81 (m, 2H), 6.35 (s, 1H), 5.59-5.55 (m, 1H), 5.49-5.46 (m, 1H), 3.25-3.16 (m, 1H), 3.13-3.108 (m, 1H), 2.87 (t, J=7.2 Hz, 2H), 2.75 (s,

6H), 2.70-2.59 (m, 2H), 2.29 (d, J=1.5 Hz, 3H), 2.26 (s, 3H), 1.99-1.94 (m, 5H), 1.90 (s, 3H), 1.46-1.37 (m, 1H), 0.94-0.89 (m, 6H).

AZ-P2 ESI 578.2 (M+H)+. $^1$H NMR (500 MHz, MeOD) δ 7.55 (s, 1H), 7.15-7.07 (m, 3H), 6.90 (d, J=6.9 Hz, 2H), 6.43 (s, 1H), 5.65-5.56 (m, 2H), 3.31-3.28 (m, 1H), 3.22-3.15 (m, 1H), 2.98-2.88 (m, 2H), 2.84 (s, 6H), 2.63-2.59 (m, 1H), 2.50-2.44 (m, 1H), 2.32 (d, J=1.5 Hz, 3H), 2.26 (s, 3H), 2.03-1.91 (m, 7H), 1.80-1.72 (m, 1H), 1.42-1.32 (m, 1H), 0.90-0.88 (m, 6H).

3-47. Preparation of (3S)-3-(2-(5-(2-(dimethyl-amino)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoic acid (compounds BA-P1 and BA-P2)

Step 1: ethyl (3S)-3-(2-(5-(2-(dimethylamino)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoate

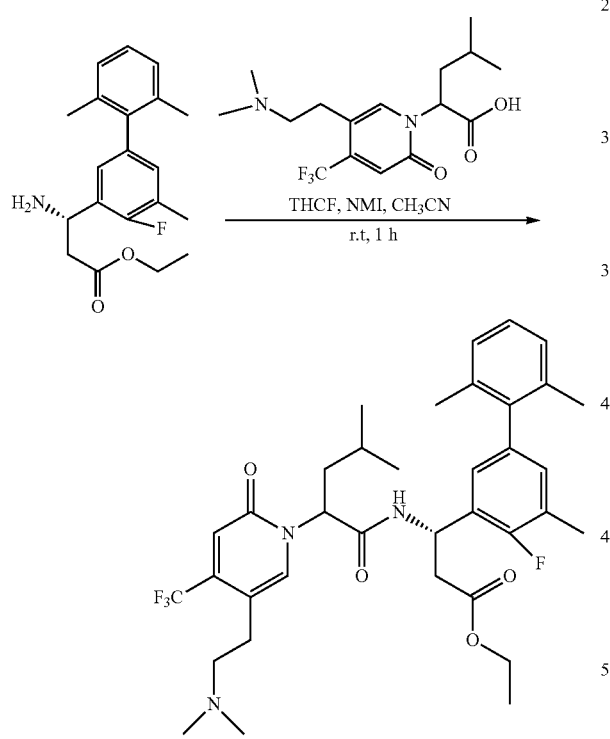

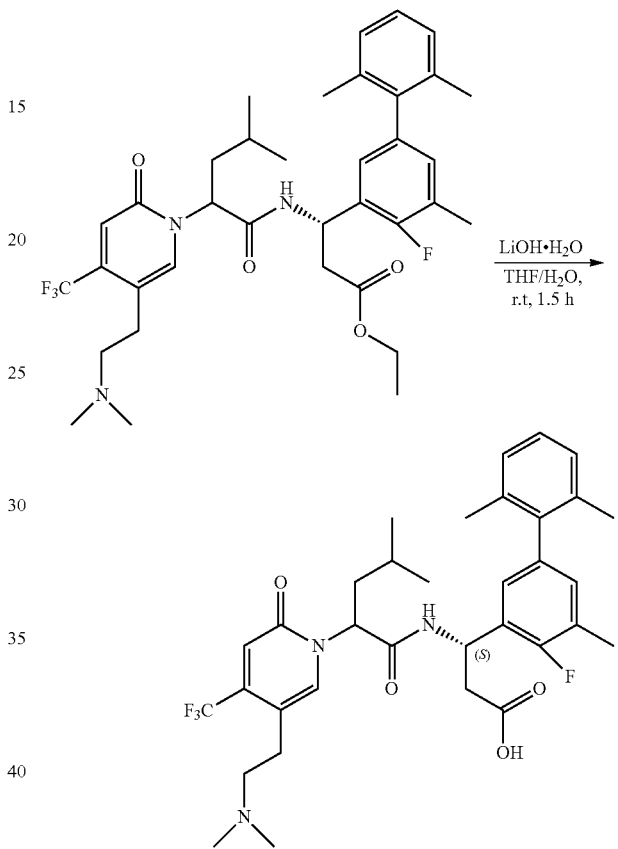

A mixture of ethyl (S)-3-amino-3-(4-fluoro-2',5,6'-trimethyl-[1,1'-biphenyl]-3-yl)propanoate (95.0 mg, 0.29 mmol), 2-(5-(2-(dimethylamino)ethyl)-2-oxo-4-(trifluoromethyl)pyridin-1(2H)-yl)-4-methylpentanoic acid (100.0 mg, 0.29 mmol), N,N,N,N-Tetramethylchloroformamidinium hexafluorophosphate (97.0 mg, 0.35 mmol) and 1-methyl-1H-imidazole (71.0 mg, 0.87 mmol) in CH$_3$CN (4 mL) was stirred at room temperature for 1 hour. The solvent was removed in vacuo and the residue was purified by reverse phase HPLC on a C18/40 g column (A: water 10 mM NH$_4$HCO$_3$, B: MeOH, 0~100%) to provide ethyl (3S)-3-(2-(5-(2-(dimethylamino)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoate as a yellow solid (100.0 mg). Yield 52.3% (ESI 660.2 [M+H]+).

Step 2: (3S)-3-(2-(5-(2-(dimethylamino)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoic acid Ethyl (3S)-3-(2-(5-(2-(dimethylamino)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoate (100.0 mg, 0.15 mmol) was treated with LiOH—H$_2$O (32.0 mg, 0.75 mmol) in THF (3 mL) and water (1 mL) at 30° C. for 1 hour. The reaction mixture was acidified to pH 4~5 with 2N HCl. The solvent was removed in vacuo and the residue was purified by prep-HPLC A (30-60% MeCN) to give the diastereomeric products BA-P1 (16.4 mg) and BA-P2 (12.5 mg) as a white solid.

BA-P1 ESI 632.2 (M+H)+. $^1$H NMR (500 MHz, MeOD) δ 7.77 (s, 1H), 7.03-6.86 (m, 3H), 6.79-6.70 (m, 2H), 6.64 (s, 1H), 5.56 (t, J=8.0 Hz, 1H), 5.48-5.38 (m, 1H), 2.98-2.92 (m, 2H), 2.83-2.78 (m, 2H), 2.62-2.59 (m, 8H), 2.17 (s, 3H), 1.87 (d, J=11.3 Hz, 5H), 1.71 (s, 3H), 1.34-1.30 (m, 1H), 0.85-0.81 (m, 6H).

BA-P2 ESI 632.2 (M+H)+. $^1$H NMR (500 MHz, MeOD) δ 7.71 (s, 1H), 7.03-6.95 (m, 3H), 6.82-6.77 (m, 3H), 5.60-5.57 (m, 1H), 5.49 (t, J=7.7 Hz, 1H), 3.15-3.06 (m, 2H), 2.88 (t, J=6.6 Hz, 2H), 2.70 (s, 6H), 2.54-2.50 (m, 1H), 2.42-2.37 (m, 1H), 2.21 (s, 3H), 1.90-1.85 (m, 7H), 1.62-1.52 (m, 1H), 1.33-1.22 (m, 1H), 0.79-0.77 (m, 6H).

Example 4: Characterization of Exemplary Compounds of the Invention

The following compounds were synthesized using procedures similar to the ones used in example 3.

4-1. (3S)-3-(4,5-difluoro-2',6'-dimethylbiphenyl-3-yl)-3-(2-(5-(((R)-3-fluoropyrrolidin-1-yl)methyl)-2-oxopyridin-1(2H)-yl)-4-methylpentanamido)propanoic acid (Diastereomeric Compounds BB-P1 and BB-P2)

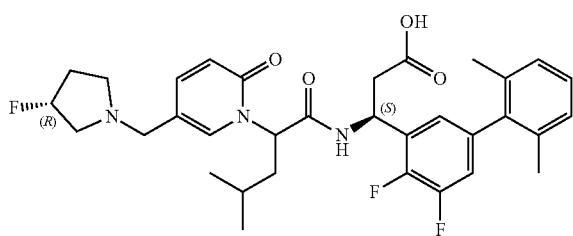

BB-P1 ESI 598.2 (M+H)+. 1H NMR (500 MHz, MeOD) δ 7.74 (d, J=2.1 Hz, 1H), 7.53-7.42 (m, 1H), 7.16-7.00 (m, 3H), 6.93-6.80 (m, 2H), 6.42 (d, J=9.3 Hz, 1H), 5.71 (t, J=8.1 Hz, 1H), 5.55 (t, J=7.1 Hz, 1H), 5.34-5.13 (m, 1H), 3.80-3.61 (m, 2H), 3.17-2.93 (m, 3H), 2.83-2.63 (m, 3H), 2.33-2.16 (m, 1H), 2.16-2.02 (m, 1H), 1.98 (s, 3H), 1.92 (t, J=7.6 Hz, 2H), 1.83 (s, 3H), 1.47-1.33 (m, 1H), 0.99-0.87 (m, 6H).

BB-P2 ESI 598.2 (M+H)+. 1H NMR (500 MHz, MeOD) δ 7.69 (d, J=2.2 Hz, 1H), 7.62-7.51 (m, 1H), 7.16-7.01 (m, 3H), 6.99-6.84 (m, 2H), 6.54 (d, J=9.3 Hz, 1H), 5.80-5.69 (m, 1H), 5.51-5.45 (m, 1H), 5.33 (d, J=54.4 Hz, 1H), 4.18 (d, J=13.2 Hz, 1H), 3.83 (d, J=13.2 Hz, 1H), 3.55-3.31 (m, 4H), 2.73-2.64 (m, 1H), 2.58-2.46 (m, 1H), 2.42-2.18 (m, 2H), 2.03-1.86 (m, 7H), 1.58-1.36 (m, 2H), 0.84 (s, 6H).

4-2. (3S)-3-(4,5-difluoro-2',6'-dimethylbiphenyl-3-yl)-3-(2-(5-(2-((R)-3-fluoropyrrolidin-1-yl)ethyl)-2-oxopyridin-1(2H)-yl)-4-methylpentanamido)propanoic acid (Diastereomeric Compounds BC-P1 and BC-P2)

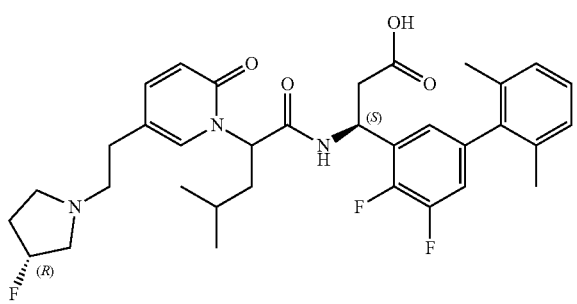

BC-P1 ESI 612.2 (M+H)+. 1H NMR (500 MHz, MeOD) δ 7.63 (s, 1H), 7.45 (d, J=9.3 Hz, 1H), 7.22-7.04 (m, 3H), 6.98-6.87 (m, 1H), 6.80 (d, J=5.1 Hz, 1H), 6.43 (d, J=9.3 Hz, 1H), 5.68-5.57 (m, 1H), 5.50 (d, J=5.7 Hz, 1H), 5.29 (d, J=53.5 Hz, 1H), 3.48-3.33 (m, 1H), 3.31-3.02 (m, 5H), 2.83-2.57 (m, 4H), 2.42-2.10 (m, 2H), 2.05-1.81 (m, 8H), 1.51-1.35 (m, 1H), 0.98-0.79 (m, 6H).

BC-P2 ESI 612.2 (M+H)+. 1H NMR (500 MHz, MeOD) δ 7.61 (s, 1H), 7.47 (d, J=9.3 Hz, 1H), 7.19-7.00 (m, 3H), 6.97-6.90 (m, 1H), 6.86 (d, J=4.7 Hz, 1H), 6.51 (d, J=9.2 Hz, 1H), 5.66-5.52 (m, 2H), 5.36 (s, 1H), 3.66-3.32 (m, 5H), 3.16 (s, 1H), 2.83 (s, 2H), 2.63-2.42 (m, 2H), 2.30 (d, J=29.3 Hz, 2H), 2.05-1.85 (m, 8H), 1.45-1.30 (m, 1H), 0.88 (t, J=6.1 Hz, 6H).

4-3. (3S)-3-(4,5-difluoro-2'-methyl-6'-(trifluoromethyl)-[1,1'-biphenyl]-3-yl)-3-(2-(5-(2-(dimethylamino)ethyl)-4-methyl-2-oxopyridin-1(2H)-yl)-4-methylpentanamido)propanoic acid (diastereomeric compounds BD-P1 and BD-P2)

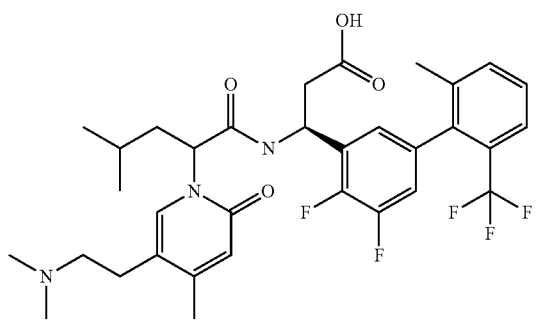

BD-P1 ESI 636.2 (M+H)+. 1H NMR (500 MHz, MeOD) δ 7.65-7.46 (m, 4H), 7.03-6.87 (m, 2H), 6.30 (d, J=21.6 Hz, 1H), 5.55-5.52 (m, 2H), 3.18-3.02 (m, 2H), 2.88-2.84 (m, 2H), 2.78 (s, 3H)), 2.75 (S, 3H), 2.67-2.64 (m, 2H), 2.25 (s, 3H), 2.06 (s, 2H), 1.97-1.85 (m, 3H), 1.45-1.35 (m, 1H), 0.94-0.90 (m, 6H).

BD-P2 ESI 636.2 (M+H)+. 1H NMR (500 MHz, MeOD) δ 7.67-7.44 (m, 4H), 7.08-6.91 (m, 2H), 6.42 (d, J=20.9 Hz, 1H), 5.70-5.51 (m, 2H), 3.32-3.23 (m, 1H), 3.20-3.18 (m, 1H), 2.99-2.74 (m, 8H), 2.64-2.59 (m, 1H), 2.52-2.47 (m, 1H), 2.28-2.26 (d, J=10.0 Hz, 3H), 2.07-2.06 (d, J=6.6 Hz, 3H), 2.00-1.88 (m, 1H), 1.81-1.65 (m, 1H), 1.43-1.32 (m, 1H), 0.90-0.87 (m, 6H).

4-4. (3S)-3-(4-fluoro-2',5',6'-trimethylbiphenyl-3-yl)-3-(2-(5-(2-(3-fluoroazetidin-1-yl)ethyl)-2-oxopyridin-1(2H)-yl)-4-methylpentanamido)propanoic acid (Diastereomeric Compounds BE-P1 and BE-P2)

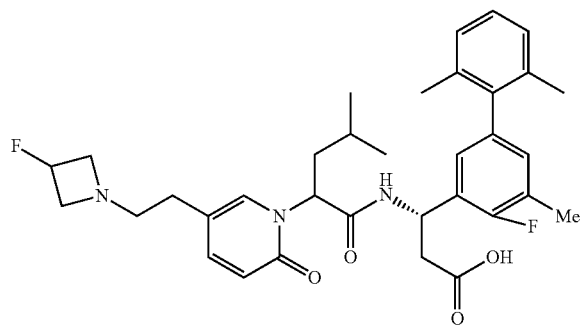 [SMILES: Cc1cc(-c2c(C)cccc2C)cc([C@H](CC(=O)O)NC(=O)C(CC(C)C)n2cc(CCN3CC(F)C3)ccc2=O)c1F]

BE-P1 ESI 594.2 (M+H)+. 1H NMR (500 MHz, MeOD) δ 7.52 (d, J=2.1 Hz, 1H), 7.47-7.39 (m, 1H), 7.19-7.02 (m, 3H), 6.89 (d, J=5.6 Hz, 1H), 6.83-6.73 (m, 1H), 6.48 (d, J=9.3 Hz, 1H), 5.69-5.57 (m, 1H), 5.54-5.43 (m, 1H), 5.33-5.09 (m, 1H), 4.20-4.06 (m, 1H), 4.03-3.87 (m, 1H), 3.78-3.63 (m, 2H), 3.27-3.06 (m, 2H), 2.77-2.53 (m, 4H), 2.31 (d, J=1.3 Hz, 3H), 2.03-1.85 (m, 8H), 1.58-1.34 (m, 1H), 1.03-0.84 (m, 6H).

BE-P2 ESI 594.2 (M+H)+. 1H NMR (500 MHz, MeOD) δ 7.57-7.41 (m, 2H), 7.23-7.05 (m, 3H), 6.92 (d, J=6.9 Hz, 2H), 6.56 (d, J=9.3 Hz, 1H), 5.67-5.57 (m, 2H), 5.46-5.17 (m, 1H), 4.50-4.24 (m, 2H), 4.08-3.89 (m, 2H), 3.42-3.35 (m, 2H), 2.86-2.60 (m, 3H), 2.57-2.45 (m, 1H), 2.33 (s, 3H), 2.05-1.91 (m, 7H), 1.86-1.71 (m, 1H), 1.48-1.32 (m, 1H), 0.91 (t, J=6.3 Hz, 6H).

4-5. (3S)-3-(5-chloro-4-fluoro-2',6'-dimethyl-[1,1'-biphenyl]-3-yl)-3-(2-(3-fluoro-5-(2-(3-fluoroazetidin-1-yl)ethyl)-2-oxopyridin-1(2H)-yl)-4-methylpentanamido)propanoic acid (diastereomeric compounds BD2-P1 and BD2-P2)

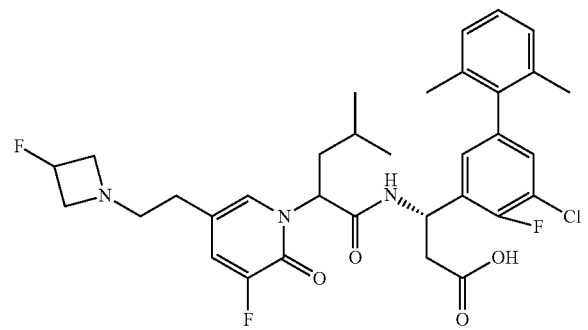 [SMILES: Cc1cccc(C)c1-c1cc(Cl)c(F)c([C@H](CC(=O)O)NC(=O)C(CC(C)C)n2cc(CCN3CC(F)C3)cc(F)c2=O)c1]

BD2-P1 ESI 632.1 (M+H)+. 1H NMR (400 MHz, MeOD) δ 7.69-7.28 (m, 2H), 7.23-7.05 (m, 4H), 6.97 (dd, J=6.3, 1.9 Hz, 1H), 5.69 (dd, J=9.4, 6.8 Hz, 1H), 5.52 (t, J=6.4 Hz, 1H), 5.25 (dt, J=57.2, 4.2 Hz, 1H), 4.15 (dt, J=44.5, 9.1 Hz, 2H), 3.96-3.70 (m, 2H), 3.23 (dt, J=11.3, 5.6 Hz, 2H), 2.94-2.45 (m, 4H), 2.13-1.80 (m, 8H), 1.59-1.25 (m, 1H), 1.15-0.78 (m, 6H).

BD2-P2 ESI 632.1 (M+H)+. 1H NMR (400 MHz, MeOD) δ 7.54-7.27 (m, 2H), 7.14 (dt, J=12.8, 6.1 Hz, 5H), 5.87-5.52 (m, 2H), 5.30 (dt, J=57.3, 4.4 Hz, 1H), 4.43-4.14 (m, 2H), 4.06-3.75 (m, 2H), 3.33-3.25 (m, 2H), 2.87-2.40 (m, 4H), 2.17-1.85 (m, 7H), 1.88-1.67 (m, 1H), 1.50-1.22 (m, 1H), 0.91 (d, J=6.6 Hz, 6H).

4-6. (3S)-3-(5-chloro-4-fluoro-2',6'-dimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic acid (diastereomeric compounds BE2-P1 and BE2-P2)

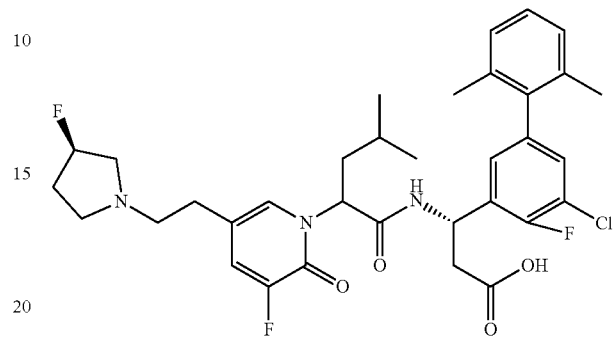

BE2-P1 ESI 646.2 (M+H)+. 1H NMR (400 MHz, MeOD) δ 7.51 (s, 1H), 7.37 (d, J=10.2 Hz, 1H), 7.16-7.08 (m, 4H), 6.98-6.97 (m, 1H), 5.71-5.67 (m, 1H), 5.52-5.49 (m, 1H), 5.35-5.21 (m, 1H), 3.41-3.12 (m, 6H), 2.81-2.69 (m, 4H), 2.37-2.20 (m, 2H), 2.05-1.88 (m, 8H), 1.44-1.40 (m, 1H), 0.96-0.92 (m, 6H).

BE2-P2 ESI 646.2 (M+H)+. 1H NMR (400 MHz, MeOD) δ 7.51 (s, 1H), 7.40 (d, J=10.2 Hz, 1H), 7.18-7.06 (m, 5H), 5.70-5.58 (m, 2H), 5.41-5.27 (m, 1H), 3.67-3.21 (m, 6H), 2.88-2.83 (m, 2H), 2.60-2.53 (m, 2H), 2.39-2.27 (m, 2H), 1.97-1.83 (m, 7H), 1.83-1.76 (m, 1H), 1.40-1.35 (m, 1H), 0.91-0.89 (m, 6H).

4-7. (3S)-3-(5-chloro-4-fluoro-2',6'-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid (diastereomeric compounds BF-P1 and BF-P2)

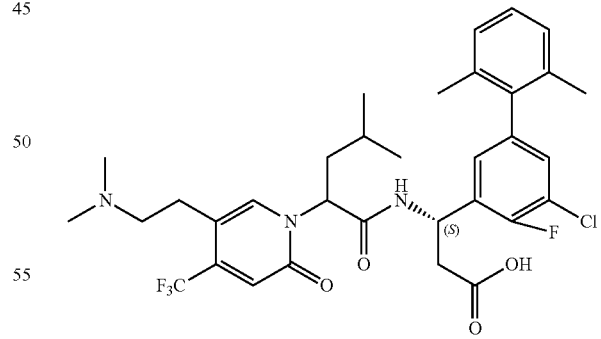

BF-P1 ESI 652.2 (M+H)+. 1H NMR (400 MHz, MeOD) δ 7.91 (s, 1H), 7.11-7.03 (m, 5H), 6.75 (s, 1H), 5.82-5.62 (m, 1H), 5.62-5.46 (m, 1H), 3.21-2.89 (m, 4H), 2.83 (s, 6H), 2.77-2.72 (m, 2H), 2.05-1.89 (m, 5H), 1.83 (s, 3H), 1.46-1.40 (m, 1H), 0.98-0.93 (m, 6H).

BF-P2 ESI 652.2 (M+H)+. 1H NMR (400 MHz, MeOD) δ 7.91 (s, 1H), 7.24-7.04 (m, 5H), 6.89 (s, 1H), 5.75-5.70 (m, 1H), 5.66-5.62 (m, 1H), 3.29-3.21 (m, 2H), 3.09-2.98 (m,

2H), 2.84 (d, J=5.9 Hz, 6H), 2.68-2.53 (m, 2H), 2.03-1.86 (m, 7H), 1.76-1.69 (m, 1H), 1.42-1.33 (m, 1H), 0.88-0.86 (m, 6H).

4-8. (3S)-3-(2-(5-(2-(dimethylamino)ethyl)-2-oxo-4-(trifluoromethyl)pyridin-1(2H)-yl)-4-methylpentanamido)-3-(4-fluoro-2',6'-dimethyl-5-(trifluoromethyl)biphenyl-3-yl)propanoic acid (diastereomeric compounds BG-P1 and BG-P2)

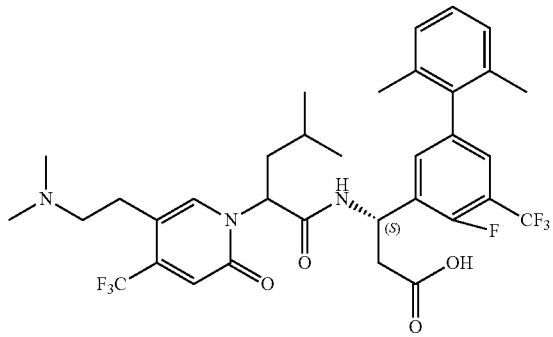

BG-P1 ESI 686.2 (M+H)⁺. ¹H NMR (400 MHz, MeOD) δ 7.90 (s, 1H), 7.39 (d, J=4.8 Hz, 1H), 7.31 (d, J=6.3 Hz, 1H), 7.19 (t, J=7.5 Hz, 1H), 7.13 (d, J=7.1 Hz, 1H), 7.09 (d, J=7.4 Hz, 1H), 6.73 (s, 1H), 5.73-5.64 (m, 1H), 5.62-5.59 (m, 1H), 3.17-3.12 (m, 2H), 2.97 (d, J=8.4 Hz, 2H), 2.80 (d, J=11.1 Hz, 6H), 2.76-2.73 (m, 2H), 2.11-1.89 (m, 5H), 1.82 (s, 3H), 1.47-1.41 (m, 1H), 0.98-0.93 (m, 6H).

BG-P2 ESI 686.2 (M+H)⁺. ¹H NMR (400 MHz, MeOD) δ 7.85 (s, 1H), 7.44 (d, J=5.4 Hz, 1H), 7.38 (d, J=6.6 Hz, 1H), 7.22-7.18 (m, 1H), 7.14 (d, J=7.3 Hz, 2H), 6.90 (s, 1H), 5.76-5.72 (m, 1H), 5.64 (t, J=7.7 Hz, 1H), 3.25 (d, J=8.1 Hz, 2H), 3.00 (t, J=7.0 Hz, 2H), 2.85 (s, 6H), 2.71-2.66 (m, 1H), 2.61-2.54 (m, 1H), 2.02 (d, J=2.4 Hz, 6H), 1.99-1.94 (m, 1H), 1.78-1.68 (m, 1H), 1.46-1.30 (m, 1H), 0.91-0.89 (m, 6H).

4-9. (3S)-3-(2-(5-(2-(dimethylamino)ethyl)-3-methyl-2-oxopyridin-1(2H)-yl)-4-methylpentanamido)-3-(4-fluoro-2',6'-dimethyl-5-(trifluoromethyl)biphenyl-3-yl)propanoic acid (diastereomeric compounds BH-P1 and BH-P2)

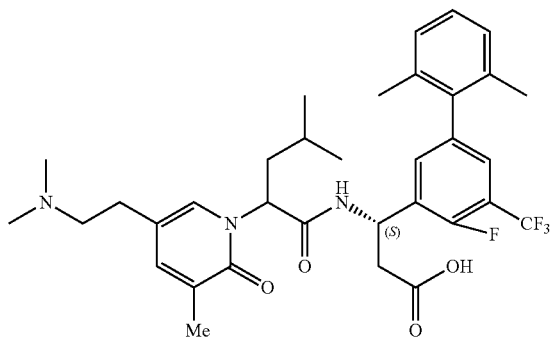

BH-P1 ESI 632.2 (M+H)⁺. ¹H NMR (400 MHz, MeOD) δ 7.52 (s, 1H), 7.42 (s, 1H), 7.32 (d, J=4.9 Hz, 1H), 7.24-7.18 (m, 2H), 7.17-7.10 (m, 2H), 5.52 (s, 1H), 5.45 (t, J=5.3 Hz, 1H), 3.37 (d, J=7.6 Hz, 1H), 3.32-3.29 (m, 1H), 3.27-3.17 (m, 1H), 2.82 (t, J=6.5 Hz, 2H), 2.74 (s, 6H), 2.71-2.66 (m, 1H), 2.56-2.51 (m, 1H), 2.03 (d, J=14.9 Hz, 1H), 1.97 (d, J=7.2 Hz, 6H), 1.94 (s, 3H), 1.44-1.39 (m, 1H), 0.95-0.90 (m, 6H).

BH-P2 ESI 632.2 (M+H)⁺. ¹H NMR (400 MHz, MeOD) δ 7.86 (s, 1H), 7.44 (d, J=4.8 Hz, 1H), 7.38 (d, J=6.5 Hz, 1H), 7.22-7.18 (m, 1H), 7.14 (d, J=7.2 Hz, 2H), 6.90 (s, 1H), 5.76-5.72 (m, 1H), 5.64 (t, J=7.6 Hz, 1H), 3.35 (s, 3H), 3.25 (s, 2H), 3.00 (t, J=7.1 Hz, 2H), 2.86 (s, 6H), 2.70-2.54 (m, 2H), 2.02 (d, J=2.4 Hz, 6H), 1.99-1.92 (m, 1H), 1.77-1.72 (m, 1H), 1.46-1.30 (m, 1H), 0.91-0.89 (m, 6H).

4-10. (3S)-3-(2',6'-dichloro-4,4'-difluoro-5-methylbiphenyl-3-yl)-3-(2-(3-fluoro-5-(2-(3-fluoroazetidin-1-yl)ethyl)-2-oxopyridin-1(2H)-yl)-4-methylpentanamido)propanoic acid (diastereomeric compounds BI-P1 and BI-P2)

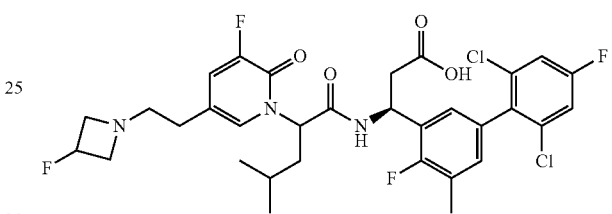

GI-P1 ESI 670.1 (M+H)⁺. ¹H NMR (400 MHz, MeOD) δ 7.42 (s, 1H), 7.40-7.32 (m, 3H), 7.01 (d, J=6.7 Hz, 1H), 6.96 (d, J=6.6 Hz, 1H), 5.70 (t, J=8.1 Hz, 1H), 5.59-5.46 (m, 1H), 5.32-5.08 (m, 1H), 4.18-3.92 (m, 2H), 3.82-3.57 (m, 2H), 3.22-3.03 (m, 2H), 2.79-2.53 (m, 4H), 2.31 (d, J=1.3 Hz, 3H), 1.97 (t, J=7.6 Hz, 2H), 1.51-1.33 (m, 1H), 1.01-0.86 (m, 6H).

GI-P2 ESI 670.1 (M+H)⁺. ¹H NMR (400 MHz, MeOD) δ 7.45-7.31 (m, 4H), 7.14-6.99 (m, 2H), 5.75-5.61 (m, 2H), 5.42-5.18 (m, 1H), 4.44-4.21 (m, 2H), 4.11-3.85 (m, 2H), 3.36-3.34 (m, 2H), 2.80-2.44 (m, 4H), 2.34 (d, J=1.3 Hz, 3H), 2.03-1.90 (m, 1H), 1.83-1.70 (m, 1H), 1.47-1.30 (m, 1H), 0.99-0.86 (m, 6H).

4-11. (3S)-3-(3-cyclopropyl-2-(3-fluoro-5-(2-(3-fluoroazetidin-1-yl)ethyl)-2-oxopyridin-1(2H)-yl)propanamido)-3-(4,4'-difluoro-2',5,6'-trimethyl-[1,1'-biphenyl]-3-yl)propanoic acid (diastereomeric compounds BJ-P1 and BJ-P2)

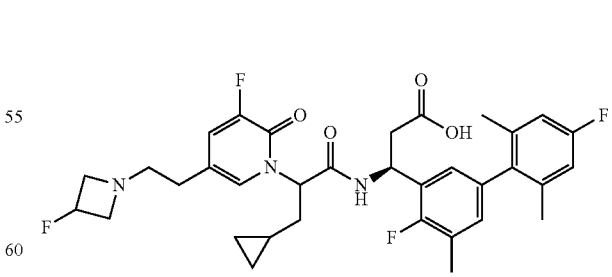

BJ-P1 ESI 628.2 (M+H)⁺. ¹H NMR (400 MHz, MeOD) δ 7.37 (s, 1H), 7.26 (d, J=10.2 Hz, 1H), 6.91-6.64 (m, 4H), 5.55 (t, J=7.6 Hz, 1H), 5.48-5.40 (m, 1H), 5.13 (d, J=57.3 Hz, 1H), 3.98 (d, J=16.3 Hz, 2H), 3.63 (s, 2H), 3.03 (d, J=6.5 Hz, 2H), 2.74-2.59 (m, 2H), 2.59-2.50 (m, 3H), 1.99-1.85

(m, 5H), 1.81 (d, J=9.0 Hz, 3H), 0.56 (d, J=7.3 Hz, 1H), 0.36 (d, J=8.0 Hz, 2H), 0.13--0.07 (m, 2H).

BJ-P2 ESI 628.2 (M+H)+. 1H NMR (400 MHz, MeOD) δ 7.50-7.28 (m, 2H), 7.03-6.71 (m, 4H), 5.75-5.55 (m, 2H), 5.30 (d, J=57.3 Hz, 1H), 4.47-4.17 (m, 2H), 4.12-3.75 (m, 2H), 3.44-3.32 (m, 2H), 2.82-2.46 (m, 4H), 2.32 (s, 3H), 2.18-1.91 (m, 7H), 1.77-1.60 (m, 1H), 0.58 (s, 1H), 0.42-0.23 (m, 2H), 0.15--0.07 (m, 2H).

4-12. (3S)-3-(4,4'-difluoro-2',5,6'-trimethyl-[1,1'-biphenyl]-3-yl)-3-(((3R)-2-(3-fluoro-5-(2-(3-fluoro-azetidin-1-yl)ethyl)-2-oxopyridin-1(2H)-yl)-3-methylpentanamido)propanoic acid (diastereomeric compounds BK-P1 and BK-P2)

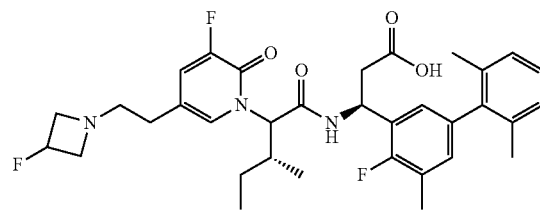

BK-P1 ESI 630.2 (M+H)+. 1H NMR (400 MHz, MeOD) δ 7.52 (s, 1H), 7.31-7.28 (m, 1H), 6.86-6.76 (m, 4H), 5.66-5.55 (m, 1H), 5.35-5.33 (d, J=11.2 Hz, 1H), 5.23.5.09 (m, 1H), 3.85-3.80 (m, 2H), 3.52-3.49 (m, 2H), 2.91-2.88 (t, J=6.7 Hz, 2H), 2.80-2.78 (m, 2H), 2.55-2.52 (t, J=7.1 Hz, 2H), 2.28 (d, J=1.5 Hz, 4H), 1.98 (s, 3H), 1.75 (s, 3H), 1.69-1.68 (m, 1H), 1.30-1.26 (m, 1H), 1.03-0.99 (t, J=7.4 Hz, 3H), 0.75-0.74 (d, J=6.6 Hz, 3H).

BK-P2 ESI 630.2 (M+H)+. 1H NMR (400 MHz, MeOD) δ 7.46 (s, 1H), 7.36-7.34 (d, J=10.3 Hz, 1H), 7.00-6.93 (dd, J=20.7, 6.6 Hz, 2H), 6.86-6.84 (d, J=9.6 Hz, 2H), 5.75-5.72 (dd, J=10.3, 4.1 Hz, 1H), 5.39-5.23 (m, 2H), 4.47-4.22 (m, 2H), 4.09-3.85 (m, 2H), 3.30-3.28 (m, 2H), 2.75-2.72 (m, 2H), 2.67-2.47 (m, 2H), 2.41-2.20 (m, 4H), 2.02 (s, 6H), 1.17-1.10 (m, 1H), 1.08-0.88 (m, 4H), 0.85-0.81 (t, J=7.2 Hz, 3H).

4-13. (3S)-3-(4,4'-difluoro-2',5,6'-trimethyl-[1,1'-biphenyl]-3-yl)-3-(2-(3-fluoro-5-(2-(3-fluoroazetidin-1-yl)ethyl)-2-oxopyridin-1(2H)-yl)-3-methylbutanamido)propanoic acid (diastereomeric compounds BL-P1 and BL-P2)

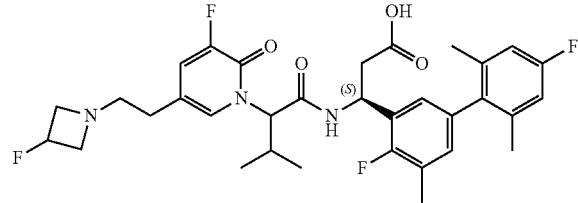

BL-P1 ESI 616.2 (M+H)+. 1H NMR (400 MHz, MeOD) δ 7.52 (s, 1H), 7.29 (d, J=10.9 Hz, 1H), 6.94-6.65 (m, 4H), 5.62 (s, 1H), 5.26 (d, J=11.1 Hz, 1H), 5.07 (s, 1H), 3.75 (s, 2H), 3.15 (s, 1H), 2.78 (s, 5H), 2.48 (d, J=31.1 Hz, 3H), 2.28 (s, 3H), 1.98 (s, 3H), 1.74 (s, 3H), 1.14 (d, J=6.4 Hz, 3H), 0.78 (d, J=6.6 Hz, 3H).

BL-P2 ESI 616.2 (M+H)+. 1H NMR (400 MHz, MeOD) δ 7.44 (s, 1H), 7.40-7.28 (m, 1H), 7.02-6.72 (m, 4H), 5.88-5.62 (m, 1H), 5.38 (s, 2H), 5.24 (d, J=11.0 Hz, 2H), 4.32 (s, 2H), 3.97 (s, 2H), 2.74 (d, J=5.1 Hz, 2H), 2.66-2.39 (m, 3H), 2.33 (d, J=1.6 Hz, 3H), 2.01 (d, J=3.3 Hz, 6H), 1.00 (d, J=6.4 Hz, 3H), 0.75 (d, J=6.7 Hz, 3H).

4-14. (3S)-3-(2'-cyclopropyl-4-fluoro-5,6'-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid (diastereomeric compounds BM-P1 and BM-P2)

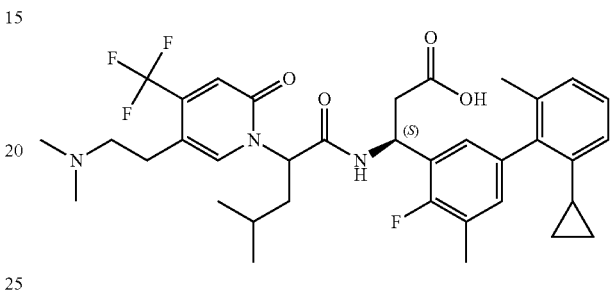

BM-P1 ESI 658.3 (M+H)+. 1H NMR (400 MHz, MeOD) 7.91 (d, J=5.9 Hz, 1H), 7.13 (t, J=7.7 Hz, 1H), 7.07-6.87 (m, 3H), 6.76 (d, J=11.4 Hz, 2H), 5.83-5.64 (m, 1H), 5.57 (t, J=5.9 Hz, 1H), 3.18-2.98 (m, 2H), 2.94 (d, J=7.1 Hz, 2H), 2.82 (d, J=4.7 Hz, 1H), 2.80-2.48 (m, 8H), 2.32 (d, J=17.2 Hz, 3H), 2.12-1.89 (m, 3H), 1.81 (s, 1H), 1.57-1.26 (m, 2H), 1.02-0.83 (m, 6H), 0.75-0.61 (m, 1H), 0.60-0.22 (m, 3H).

BM-P2 ESI 658.3 (M+H)+. 1H NMR (400 MHz, MeOD) δ 7.83 (d, J=11.7 Hz, 1H), 7.28-6.65 (m, 6H), 5.82-5.43 (m, 2H), 3.30-3.09 (m, 2H), 2.99 (t, J=6.9 Hz, 2H), 2.80 (d, J=2.6 Hz, 6H), 2.70-2.42 (m, 2H), 2.33 (d, J=1.6 Hz, 3H), 2.10-1.90 (m, 4H), 1.80-1.60 (m, 1H), 1.55-1.28 (m, 2H), 1.00-0.80 (m, 6H), 0.79-0.45 (m, 4H).

4-15. (3S)-3-(5-chloro-4,4'-difluoro-2',6'-dimethyl-[1,1'-biphenyl]-3-yl)-3-(2-(3-fluoro-5-(2-(3-fluoro-azetidin-1-yl)ethyl)-2-oxopyridin-1(2H)-yl)-4-methylpentanamido)propanoic acid (diastereomeric compounds BN-P1 and BN-P2)

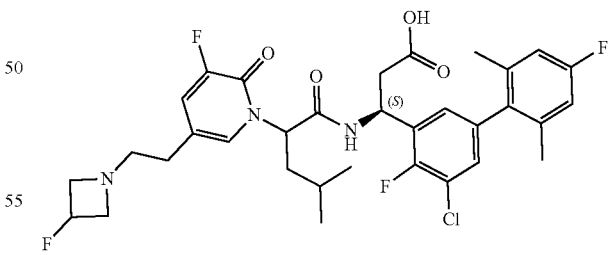

BN-P1 ESI 650.2 (M+H)+. 1H NMR (400 MHz, MeOD) δ 7.38 (s, 1H), 7.34-7.27 (m, 1H), 7.12-7.06 (m, 1H), 6.96-6.88 (m, 1H), 6.81 (d, J=9.6 Hz, 2H), 5.65-5.52 (m, 1H), 5.45 (t, J=6.3 Hz, 1H), 5.18 (d, J=57.7 Hz, 1H), 4.14-3.88 (m, 2H), 3.72 (s, 2H), 3.10 (s, 2H), 2.78-2.52 (m, 4H), 2.02-1.75 (m, 8H), 1.46-1.28 (m, 1H), 0.98-0.76 (m, 6H).

BN-P2 ESI 650.2 (M+H)+. 1H NMR (400 MHz, MeOD) δ 7.33 (d, J=8.4 Hz, 2H), 7.19-7.09 (m, 1H), 7.06-6.94 (m,

1H), 6.83 (d, J=9.6 Hz, 2H), 5.70-5.51 (m, 2H), 5.27 (d, J=57.4 Hz, 1H), 4.32 (s, 2H), 4.00 (s, 2H), 2.76-2.35 (m, 4H), 1.96 (d, J=13.7 Hz, 6H), 1.94-1.85 (m, 1H), 1.80-1.67 (m, 1H), 1.39-1.24 (m, 1H), 0.96-0.63 (m, 6H).

4-16. (3S)-3-(2-(5-(2-(azetidin-1-yl)ethyl)-2-oxo-4-(trifluoromethyl)pyridin-1(2H)-yl)-4-methylpentanamido)-3-(4-fluoro-2'-methoxy-5-methyl-6'-(trifluoromethyl)biphenyl-3-yl)propanoic acid (diastereomeric compounds BO-P1 and BO-P2)

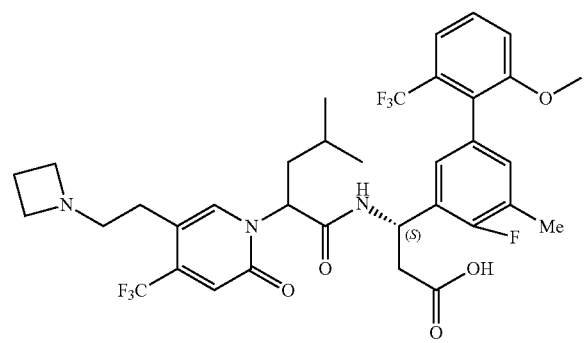

BO-P1 ESI 714.2 (M+H)+. 1H NMR (500 MHz, MeOD) δ 7.83 (d, J=6.8 Hz, 1H), 7.57-7.48 (m, 1H), 7.41-7.25 (m, 2H), 7.04-6.96 (m, 1H), 6.93 (t, J=7.0 Hz, 1H), 6.82 (d, J=10.1 Hz, 1H), 5.74-5.60 (m, 2H), 4.09-3.89 (m, 4H), 3.72 (d, J=21.5 Hz, 3H), 3.32-3.19 (m, 2H), 2.94-2.81 (m, 2H), 2.77-2.62 (m, 2H), 2.50-2.34 (m, 2H), 2.29 (s, 3H), 2.06-1.89 (m, 2H), 1.53-1.32 (m, 1H), 0.96-0.92 (m, 6H).
BO-P2 ESI 714.1 (M+H)+. 1H NMR (500 MHz, MeOD) δ 7.71 (d, J=4.3 Hz, 1H), 7.54 (t, J=8.2 Hz, 1H), 7.37 (d, J=8.0 Hz, 1H), 7.33 (d, J=8.3 Hz, 1H), 7.07-7.00 (m, 1H), 6.97 (d, J=6.6 Hz, 1H), 6.91 (d, J=4.9 Hz, 1H), 5.85-5.72 (m, 1H), 5.63-5.59 (m, 1H), 4.14 (s, 4H), 3.75 (d, J=2.7 Hz, 3H), 3.40 (d, J=25.2 Hz, 2H), 2.94 (d, J=16.0 Hz, 1H), 2.82 (d, J=9.4 Hz, 1H), 2.70-2.57 (m, 1H), 2.54-2.42 (m, 3H), 2.32 (s, 3H), 2.08-1.91 (m, 1H), 1.70-1.57 (m, 1H), 1.46-1.41 (m, 1H), 0.91 (t, J=4.9 Hz, 6H).

4-17. (3S)-3-(3',4-difluoro-2',5,6'-trimethyl-[1,1'-biphenyl]-3-yl)-3-(2-(3-fluoro-5-(2-(3-fluoroazetidin-1-yl)ethyl)-2-oxopyridin-1(2H)-yl)-4-methylpentanamido)propanoic acid (diastereomeric compounds BP-P1 and BP-P2)

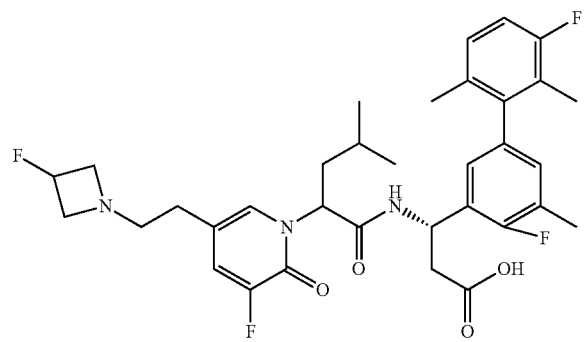 [SMILES: Cc1cc(-c2c(C)ccc(F)c2C)cc([C@H](CC(=O)O)NC(=O)C(CC(C)C)n2cc(CCN3CC(F)C3)cc(F)c2=O)c1F]

BP-P1 ESI 630.3 (M+H)+. 1H NMR (400 MHz, MeOD) δ 7.42 (s, 1H), 7.34 (d, J=10.6 Hz, 1H), 7.15-7.02 (m, 1H), 7.01-6.76 (m, 3H), 5.67 (t, J=7.6 Hz, 1H), 5.51 (s, 1H), 5.20 (d, J=57.8 Hz, 1H), 4.00 (d, J=43.3 Hz, 2H), 3.76-3.45 (m, 2H), 3.09 (d, J=5.7 Hz, 2H), 2.84-2.50 (m, 4H), 2.31 (s, 3H), 2.02-1.64 (m, 8H), 1.48-1.18 (m, 1H), 1.06-0.77 (m, 6H).
BP-P2 ESI 630.3 (M+H)+. 1H NMR (400 MHz, MeOD) δ 7.37 (d, J=10.7 Hz, 2H), 7.16-7.03 (m, 1H), 6.95 (t, J=8.9 Hz, 3H), 5.75-5.52 (m, 2H), 5.30 (d, J=57.4 Hz, 1H), 4.30 (d, J=18.4 Hz, 2H), 3.97 (s, 2H), 3.31-3.14 (m, 2H), 2.84-2.42 (m, 4H), 2.34 (d, J=1.3 Hz, 3H), 2.03-1.84 (m, 7H), 1.83-1.66 (m, 1H), 1.50-1.21 (m, 1H), 0.99-0.75 (m, 6H).

4-18. (3S)-3-(4-fluoro-2',5,6'-trimethyl-[1,1'-biphenyl]-3-yl)-3-(2-(3-fluoro-5-(2-(3-methoxyazetidin-1-yl)ethyl)-4-methyl-2-oxopyridin-1(2H)-yl)-4-methylpentanamido)propanoic acid (compounds BQ-P1 and BQ-P2)

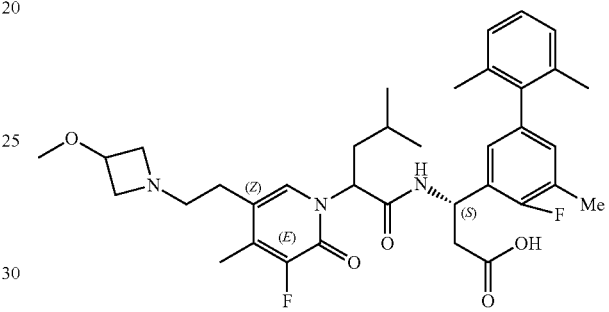

BQ-P1 ESI 638.3 (M+H)+. 1H NMR (400 MHz, MeOD) δ 7.39 (s, 1H), 7.16-7.04 (m, 3H), 6.88 (t, J=7.3 Hz, 2H), 5.64-5.53 (m, 2H), 4.24-4.08 (m, 3H), 3.73-3.61 (m, 2H), 3.30-3.26 (m, 5H), 2.83-2.67 (m, 4H), 2.31 (s, 3H), 2.24 (t, J=6.7 Hz, 3H), 2.02-1.92 (m, 8H), 1.40-1.35 (m, 1H), 0.96-0.90 (m, 6H).
BQ-P2 ESI 638.3 (M+H)+. 1H NMR (400 MHz, MeOD) δ 7.20 (s, 1H), 7.04-6.94 (m, 3H), 6.84-6.80 (t, J=7.6 Hz, 2H), 5.61-5.42 (m, 2H), 4.37-4.09 (m, 3H), 3.83-3.70 (m, 2H), 3.38-3.22 (m, 5H), 2.83-2.32 (m, 4H), 2.22 (d, J=1.6 Hz, 3H), 2.10 (d, J=2.8 Hz, 3H), 1.96-1.80 (m, 7H), 1.63-1.52 (m, 1H), 1.32-1.19 (m, 1H), 0.79-0.78 (m, 6H).

4-19. (3S)-3-(4-fluoro-2',5,6'-trimethyl-[1,1'-biphenyl]-3-yl)-3-(2-(3-fluoro-5-(2-(3-fluoroazetidin-1-yl)ethyl)-2-oxopyridin-1(2H)-yl)pentanamido)propanoic acid (diastereomeric compounds BR-P1 and BR-P2)

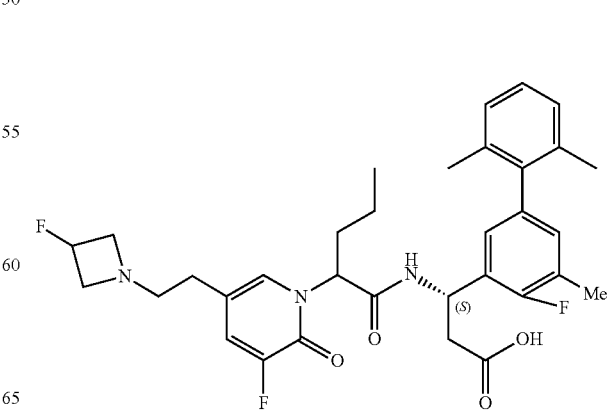

BR-P1 ESI 598.3 (M+H)⁺. ¹H NMR (400 MHz, MeOD) δ 7.49-7.23 (m, 2H), 7.19-7.00 (m, 3H), 6.96-6.66 (m, 2H), 5.74-5.44 (m, 2H), 5.19 (d, J=57.3 Hz, 1H), 3.94 (s, 2H), 3.77-3.41 (m, 2H), 3.18-3.00 (m, 2H), 2.87-2.47 (m, 4H), 2.38-2.22 (m, 3H), 2.22-2.06 (m, 1H), 2.06-1.73 (m 7H), 1.44-1.20 (m, 2H), 1.06-0.78 (m, 3H).

BR-P2 ESI 598.3 (M+H)⁺. ¹H NMR (400 MHz, MeOD) δ 7.44-7.29 (m, 2H), 7.18-7.01 (m, 3H), 6.99-6.79 (m, 2H), 5.73-5.49 (m, 2H), 5.24 (d, J=57.6 Hz, 1H), 4.11 (s, 2H), 3.73 (d, J=9.2 Hz, 2H), 3.14 (d, J=6.1 Hz, 2H), 2.75-2.48 (m, 4H), 2.33 (d, J=1.7 Hz, 3H), 2.16-2.04 (m, 1H), 2.02 (t, J=8.9 Hz, 6H), 1.91-1.76 (m, 1H), 1.35-1.12 (m, 2H), 0.91 (t, J=7.4 Hz, 3H).

4-20. (3S)-3-(2-(5-(2-(azetidin-1-yl)ethyl)-2-oxo-4-(trifluoromethyl)pyridin-1(2H)-yl)-4-methylpentanamido)-3-(5'-cyano-4-fluoro-2',5-dimethyl-[1,1'-biphenyl]-3-yl)propanoic acid (diastereomeric compounds BS-P1 and BS-P2)

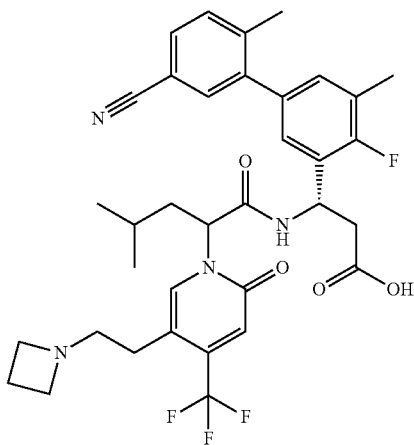 [SMILES: Cc1ccc(C#N)cc1-c1cc(C)c(F)c([C@H](CC(=O)O)NC(=O)C(CC(C)C)n2cc(CCN3CCC3)c(C(F)(F)F)cc2=O)c1]

BS-P1 ESI 655.3 (M+H)⁺. ¹H NMR (400 MHz, MeOD) δ 7.84 (s, 1H), 7.69-7.57 (m, 1H), 7.54 (s, 1H), 7.47 (d, J=8.0 Hz, 1H), 7.17-7.01 (m, 2H), 6.82 (s, 1H), 5.75-5.43 (m, 2H), 4.04 (t, J=8.1 Hz, 4H), 3.15 (s, 2H), 2.85 (t, J=6.9 Hz, 2H), 2.78-2.61 (m, 2H), 2.52-2.37 (m, 2H), 2.31 (d, J=7.7 Hz, 6H), 2.11-1.90 (m, 2H), 1.42 (d, J=7.2 Hz, 1H), 0.96 (t, J=6.4 Hz, 6H).

BS-P2 ESI 655.3 (M+H)⁺. ¹H NMR (400 MHz, MeOD) δ 7.74 (s, 1H), 7.68-7.60 (m, 1H), 7.56 (d, J=1.6 Hz, 1H), 7.49 (d, J=7.9 Hz, 1H), 7.16 (d, J=6.7 Hz, 2H), 6.93 (s, 1H), 5.83-5.71 (m, 1H), 5.64 (t, J=7.7 Hz, 1H), 4.15 (t, J=8.0 Hz, 4H), 3.42 (d, J=15.1 Hz, 2H), 3.01-2.75 (m, 2H), 2.70-2.42 (m, 4H), 2.41-2.26 (m, 6H), 2.10-1.93 (m, 1H), 1.79-1.63 (m, 1H), 1.55-1.29 (m, 1H), 0.93 (t, J=6.4 Hz, 6H).

4-21. (3S)-3-(2-(5-(2-(azetidin-1-yl)ethyl)-2-oxo-4-(trifluoromethyl)pyridin-1(2H)-yl)-4-methylpentanamido)-3-(2'-cyano-4-fluoro-4',5-dimethyl-[1,1'-biphenyl]-3-yl)propanoic acid (diastereomeric compounds BT-P1 and BT-P2)

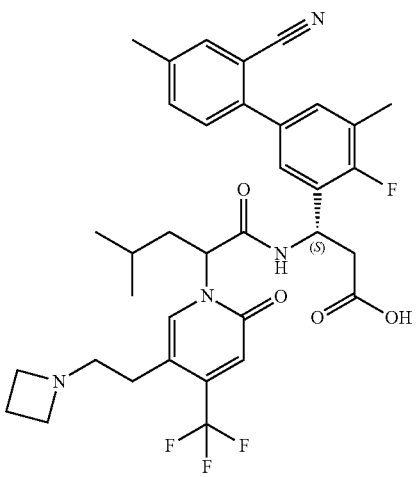

BT-P1 ESI 655.3 (M+H)⁺. ¹H NMR (400 MHz, MeOD) δ 7.85 (s, 1H), 7.60 (s, 1H), 7.47 (s, 1H), 7.36-7.30 (s, 3H), 6.74 (s, 1H), 5.78-5.59 (m, 2H), 3.84-3.80 (m, 4H), 3.15-3.10 (m, 2H), 2.75-2.72 (m, 4H), 2.43 (s, 3H), 2.34-2.30 (m, 5H), 2.06-2.01 (m, 2H), 1.40-1.37 (m, 1H), 0.99-0.96 (m, 6H).

BT-P2 ESI 655.3 (M+H)⁺. ¹H NMR (400 MHz, MeOD) δ 7.72 (s, 1H), 7.66 (s, 1H), 7.57 (d, J=8.1 Hz, 1H), 7.51-7.34 (m, 3H), 6.92 (s, 1H), 5.75-5.69 (m, 2H), 4.05-4.01 (m, 4H), 2.95-2.55 (m, 5H), 2.46-2.37 (m, 9H), 2.06-1.96 (m, 1H), 1.85-1.75 (m, 1H), 1.49-1.37 (m, 1H),), 0.94-0.92 (m, 6H).

4-22. (3S)-3-(2-(5-(2-(azetidin-1-yl)ethyl)-2-oxo-4-(trifluoromethyl)pyridin-1(2H)-yl)-4-methylpentanamido)-3-(6'-cyano-3',4-difluoro-2',5-dimethyl-[1,1'-biphenyl]-3-yl)propanoic acid (diastereomeric compounds BU-P1 and BU-P2)

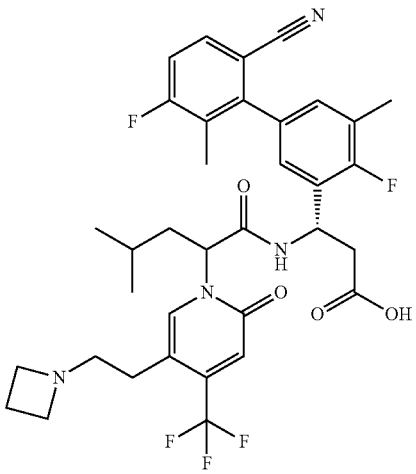 [SMILES: Cc1cc(-c2c(C#N)ccc(F)c2C)cc([C@H](CC(=O)O)NC(=O)C(CC(C)C)n2cc(CCN3CCC3)c(C(F)(F)F)cc2=O)c1F]

BU-P1 ESI 673.3 (M+H)⁺. ¹H NMR (400 MHz, MeOD) δ 7.83 (s, 1H), 7.71-7.62 (m, 1H), 7.31-7.27 (t, J=8.8 Hz, 1H), 7.14-7.10 (m, 2H), 6.80-6.75 (d, J=22.1 Hz, 1H), 5.76-5.62 (m, 2H), 4.02-3.97 (m, 4H), 3.32-3.15 (m, 2H), 2.95-2.60 (m, 4H), 2.51-2.25 (m, 5H), 2.11-1.93 (m, 5H), 1.45-1.44 (m, 1H), 0.97-0.96 (m, 6H).

BU-P2 ESI 673.3 (M+H)⁺. ¹H NMR (400 MHz, MeOD) δ 7.81-7.66 (m, 2H), 7.37-7.08 (m, 3H), 6.92 (s, 1H), 5.85-5.56 (m, 2H), 4.16-4.10 (m, 4H), 3.43-3.42 (m, 2H), 3.02-2.75 (m, 2H), 2.66 (d, J=12.1 Hz, 1H), 2.62-2.30 (m, 6H), 2.18-1.95 (m, 4H), 1.80-1.64 (m, 1H), 1.45-1.38 (m, 1H), 0.92-0.91 (m, 6H).

4-23. (3S)-3-(2-(5-(2-(azetidin-1-yl)ethyl)-2-oxo-4-(trifluoromethyl)pyridin-1(2H)-yl)-4-methylpentanamido)-3-(2'-cyano-4,5'-difluoro-4',5-dimethylbiphenyl-3-yl)propanoic acid (diastereomeric compounds BV-P1 and BV-P2)

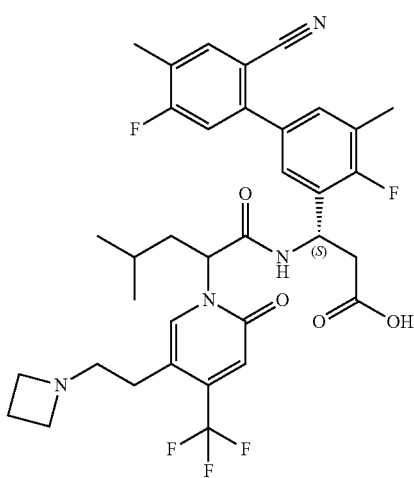

BV-P1 ESI 673.2 (M+H)⁺. ¹H NMR (400 MHz, MeOD) δ 7.96 (s, 1H), 7.73-7.46 (m, 2H), 7.31 (d, J=4.5 Hz, 1H), 7.07-6.69 (m, 1H), 5.75 (s, 1H), 5.62 (t, J=6.8 Hz, 1H), 3.96 (s, 4H), 3.27-3.11 (m, 2H), 2.92-2.58 (m, 4H), 2.45-2.21 (m, 8H), 2.12-1.91 (m, 2H), 1.41 (s, 1H), 1.04-0.88 (m, 6H).

BV-P2 ESI 673.2 (M+H)⁺. ¹H NMR (400 MHz, MeOD) δ 7.78 (d, J=7.6 Hz, 1H), 7.72 (s, 1H), 7.47-7.38 (m, 2H), 7.32 (d, J=10.2 Hz, 1H), 6.93 (s, 1H), 5.78-5.65 (m, 2H), 4.13 (t, J=8.0 Hz, 4H), 3.48-3.35 (m, 2H), 2.99-2.75 (m, 2H), 2.70-2.42 (m, 4H), 2.37 (s, 6H), 2.11-1.93 (m, 1H), 1.85-1.71 (m, 1H), 1.51-1.30 (m, 1H), 1.05-0.85 (m, 6H).

4-24. (3S)-3-(2-(5-(2-(azetidin-1-yl)ethyl)-2-oxo-4-(trifluoromethyl)pyridin-1(2H)-yl)-4-methylpentanamido)-3-(2'-cyano-4-fluoro-4'-methoxy-5-methyl-[1,1'-biphenyl]-3-yl)propanoic acid (diastereomeric compounds BW-P1 and BW-P2)

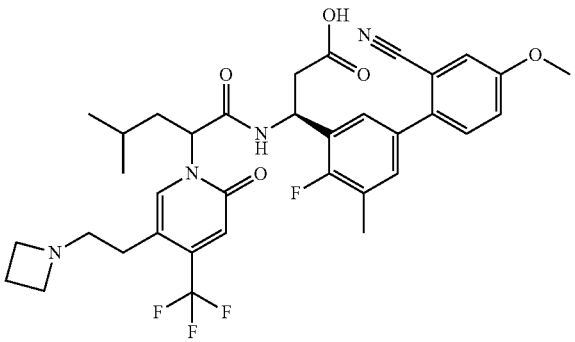 [SMILES: COc1ccc(-c2cc(C)c(F)c([C@H](CC(=O)O)NC(=O)C(CC(C)C)n3cc(CCN4CCC4)c(C(F)(F)F)cc3=O)c2)c(C#N)c1]

BW-P1 ESI 671.2 (M+H)⁺. ¹H NMR (500 MHz, MeOD) δ 7.93 (s, 1H), 7.44 (s, 1H), 7.26 (s, 2H), 7.15 (d, J=52.3 Hz, 2H), 6.75 (s, 1H), 5.80-5.70 (m, 1H), 5.68-5.60 (m, 1H), 3.95 (d, J=7.9 Hz, 4H), 3.90 (d, J=10.4 Hz, 3H), 3.24 (m, 2H), 2.81 (m, 1H), 2.75 (m, 3H), 2.46-2.35 (m, 2H), 2.31 (s, 3H), 2.04 (m, 2H), 1.48-1.38 (m, 2H), 0.98 (m, 6H).

BW-P2 ESI 671.2 (M+H)⁺. ¹H NMR (500 MHz, MeOD) δ 7.72 (s, 1H), 7.50 (d, J=8.7 Hz, 1H), 7.38 (ddm, 2H), 7.35-7.29 (m, 2H), 6.93 (s, 1H), 5.75 (m, 1H), 5.70 (t, J=7.7 Hz, 1H), 4.11 (m, 4H), 3.91 (s, 3H), 3.39 (m, 2H), 2.94 (d, J=16.7 Hz, 1H), 2.86-2.77 (m, 1H), 2.66 (m, 1H), 2.55 (m, 1H), 2.50-2.41 (m, 2H), 2.37 (s, 3H), 2.02 (m, 1H), 1.83-1.74 (m, 1H), 1.41 (m, 2H), 0.93 (m, 6H).

4-25. (3S)-3-(2-(5-(2-(azetidin-1-yl)ethyl)-2-oxo-4-(trifluoromethyl)pyridin-1(2H)-yl)-4-methylpentanamido)-3-(2'-cyano-5'-ethyl-4-fluoro-5-methyl-[1,1'-biphenyl]-3-yl)propanoic acid (diastereomeric compounds BX-P1 and BX-P2)

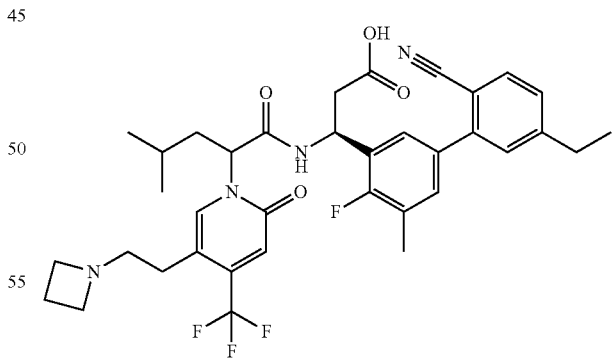

BX-P1 ESI 669.2 (M+H)⁺. ¹H NMR (400 MHz, MeOD) δ 7.96-7.83 (m, 1H), 7.70 (d, J=7.9 Hz, 1H), 7.46-7.16 (m, 4H), 6.76 (s, 1H), 5.82-5.48 (m, 2H), 4.07-3.90 (m, 4H), 3.31-3.14 (m, 2H), 2.88-2.66 (m, 6H), 2.49-2.30 (m, 5H), 2.13-1.99 (m, 2H), 1.52-1.21 (m, 4H), 0.97 (d, J=6.6 Hz, 6H).

BX-P2 ESI 669.3 (M+H)⁺. ¹H NMR (400 MHz, MeOD) δ 7.84-7.66 (m, 2H), 7.47-7.28 (m, 4H), 6.93 (s, 1H), 5.73

(t, J=7.7 Hz, 2H), 4.16 (t, J=8.0 Hz, 4H), 3.53-3.34 (m, 2H), 3.04-2.30 (m, 11H), 2.10-1.93 (m, 1H), 1.89-1.77 (m, 1H), 1.46-1.23 (m, 4H), 1.01-0.83 (m, 6H).

4-26. (3S)-3-(4,4'-difluoro-2',5,6'-trimethyl-[1,1'-biphenyl]-3-yl)-3-(2-(3-fluoro-5-(2-(3-fluoroazetidin-1-yl)ethyl)-2-oxopyridin-1(2H)-yl)pentanamido) propanoic acid (diastereomeric compounds BY-P1 and BY-P2)

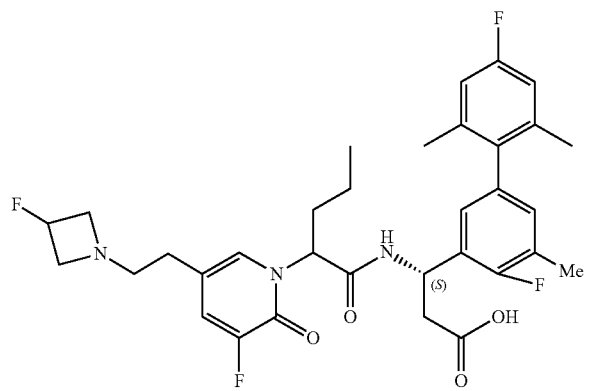

BY-P1 ESI 616.3 (M+H)⁺. ¹H NMR (400 MHz, MeOD) δ 7.43 (s, 1H), 7.38-7.27 (m, 1H), 6.91-6.68 (m, 4H), 5.67-5.44 (m, 2H), 5.21 (d, J=57.3 Hz, 1H), 4.02 (d, J=35.4 Hz, 2H), 3.83-3.54 (m, 2H), 3.20-2.99 (m, 2H), 2.82-2.53 (m, 4H), 2.29 (d, J=1.6 Hz, 3H), 2.24-2.08 (m, 1H), 2.05-1.92 (m, 4H), 1.88 (s, 3H), 1.42-1.21 (m, 2H), 0.96 (t, J=7.4 Hz, 3H).

BY-P2 ESI 616.3 (M+H)⁺. ¹H NMR (400 MHz, MeOD) δ 7.44-7.28 (m, 2H), 7.01-6.76 (m, 4H), 5.69-5.49 (m, 2H), 5.29 (d, J=57.4 Hz, 1H), 4.38-4.13 (m, 2H), 4.02-3.74 (m, 2H), 3.37-3.20 (m, 2H), 2.81-2.43 (m, 4H), 2.33 (d, J=1.7 Hz, 3H), 2.16-2.04 (m, 1H), 2.01 (s, 6H), 1.90-1.77 (m, 1H), 1.35-1.09 (m, 2H), 0.92 (t, J=7.4 Hz, 3H).

4-27. (3S)-3-(2-(5-(2-(dimethylamino)ethyl)-2-oxo-4-(trifluoromethyl)pyridin-1(2H)-yl)pentanamido)-3-(4-fluoro-2',5,6'-trimethyl-[1,1'-biphenyl]-3-yl)propanoic acid (diastereomeric compounds BZ-P1 and BZ-P2)

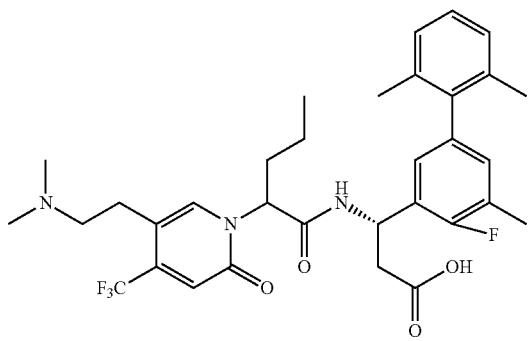

BZ-P1 ESI 618.3 (M+H)⁺. ¹H NMR (500 MHz, MeOD) δ 7.90 (s, 1H), 7.11-7.02 (m, 3H), 6.90-6.86 (m, 2H), 6.74 (s, 1H), 5.59-5.56 (m, 2H), 3.18-3.14 (m, 2H), 2.99 (d, J=22.6 Hz, 2H), 2.81 (s, 6H), 2.76-2.73 (m, 2H), 2.29 (s, 3H), 2.19-2.12 (m, 1H), 2.02-1.95 (m, 4H), 1.80 (s, 3H), 1.37-1.30 (m, 2H), 0.96 (t, J=7.3 Hz, 3H).

BZ-P2 ESI 618.3 (M+H)⁺. ¹H NMR (500 MHz, MeOD) δ 7.86 (s, 1H), 7.14-7.65 (m, 3H), 6.95-6.89 (m, 3H), 5.73 (d, J=7.3 Hz, 1H), 5.53 (t, J=7.6 Hz, 1H), 3.33-3.20 (m, 2H), 3.01 (t, J=6.8 Hz, 2H), 2.82 (s, 6H), 2.68-2.62 (m, 1H), 2.56-2.51 (m, 1H), 2.32 (s, 3H), 2.07-2.00 (m, 7H), 1.82-1.72 (m, 1H), 1.23 (s, 2H), 0.89 (d, J=3.5 Hz, 3H).

4-28. (3S)-3-(5-chloro-4-fluoro-2',6'-dimethyl-[1,1'-biphenyl]-3-yl)-3-(2-(5-(2-(dimethylamino)ethyl)-2-oxo-4-(trifluoromethyl)pyridin-1(2H)-yl)-5-methyl-hexanamido)propanoic acid (diastereomeric compounds CA-P1 and CA-P2)

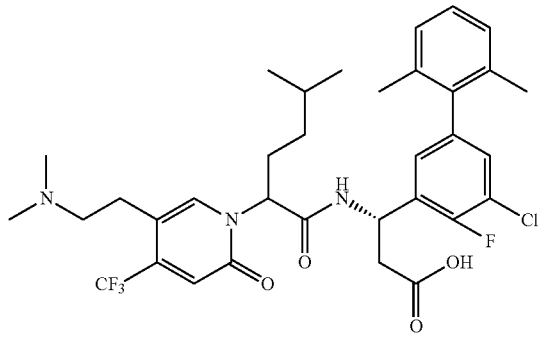 [SMILES: Cc1cccc(C)c1-c1cc(Cl)c(F)c([C@H](CC(=O)O)NC(=O)C(CCC(C)C)n2cc(CCN(C)C)c(C(F)(F)F)cc2=O)c1]

CA-P1 ESI 666.3 (M+H)⁺. ¹H NMR (400 MHz, MeOD) δ 7.88 (s, 1H), 7.13 (t, J=7.6 Hz, 1H), 7.09-7.06 (m, 2H), 7.04 (s, 1H), 7.02 (s, 1H), 6.69 (s, 1H), 5.53 (t, J=7.2 Hz, 1H), 5.49-5.45 (m, 1H), 3.16-3.04 (m, 2H), 2.94 (t, J=8.0 Hz, 2H), 2.76 (s, 6H), 2.73-2.71 (m, 2H), 2.23-2.14 (m, 1H), 1.99 (s, 3H), 1.97-1.91 (m, 1H), 1.79 (s, 3H), 1.63-1.51 (m, 1H), 1.27-1.18 (m, 1H), 1.13-1.04 (m, 1H), 0.88 (d, J=3.2 Hz, 3H), 0.86 (d, J=3.6 Hz, 3H).

CA-P2 ESI 666.2 (M+H)⁺. ¹H NMR (400 MHz, MeOD) δ 7.86 (s, 1H), 7.17-7.13 (m, 2H), 7.10-7.08 (m, 3H), 6.88 (s, 1H), 5.71-5.68 (m, 1H), 5.46 (t, J=7.4 Hz, 1H), 3.28-3.15 (m, 2H), 2.98 (t, J=7.0 Hz, 2H), 2.81 (s, 6H), 2.68-2.63 (m, 1H), 2.58-2.52 (m, 1H), 2.16-2.05 (m, 1H), 2.01 (s, 3H), 2.00 (s, 3H), 1.83-1.74 (m, 1H), 1.56-1.46 (m, 1H), 1.16-0.99 (m, 2H), 0.82 (d, J=5.2 Hz, 3H), 0.80 (d, J=4.8 Hz, 3H).

4-29. (3S)-3-(2-(5-(2-(dimethylamino)ethyl)-2-oxo-4-(trifluoromethyl)pyridin-1(2H)-yl)-4-methylpentanamido)-3-(2-fluoro-3-methyl-5-((S)-2-methylpiperidin-1-yl)phenyl)propanoic acid (diastereomeric compounds CB-P1 and CB-P2)

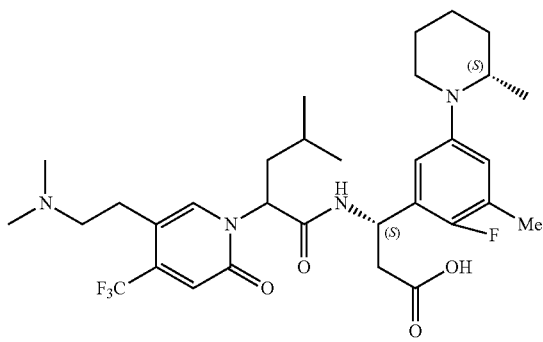

CB-P1 ESI 625.4 (M+H)+. ¹H NMR (400 MHz, MeOD) δ 7.92 (s, 1H), 6.91-6.74 (m, 3H), 5.74 (t, J=8.0 Hz, 1H), 5.49 (t, J=7.0 Hz, 1H), 3.49-3.38 (m, 1H), 3.13-2.82 (m, 6H), 2.77-2.62 (m, 8H), 2.21 (s, 3H), 2.01 (t, J=7.6 Hz, 2H), 1.91-1.36 (m, 7H), 0.98 (d, J=6.5 Hz, 6H), 0.79 (d, J=6.4 Hz, 3H).

CB-P2 ESI 625.4 (M+H)+. ¹H NMR (400 MHz, MeOD) δ 7.89 (s, 1H), 7.01-6.78 (m, 3H), 5.74-5.55 (m, 2H), 3.59-3.44 (m, 1H), 3.30-3.14 (m, 2H), 3.08-2.90 (m, 4H), 2.82 (s, 6H), 2.62-2.42 (m, 2H), 2.25 (d, J=1.7 Hz, 3H), 2.04-1.35 (m, 9H), 0.99-0.86 (m, 9H).

4-30. (3S)-3-(2-(5-(2-(azetidin-1-yl)ethyl)-2-oxo-4-(trifluoromethyl)pyridin-1(2H)-yl)-4-methylpentanamido)-3-(2'-cyclopropyl-4,5'-difluoro-5-methyl-[1,1'-biphenyl]-3-yl)propanoic acid (diastereomeric compounds CC-P1 and CC-P2)

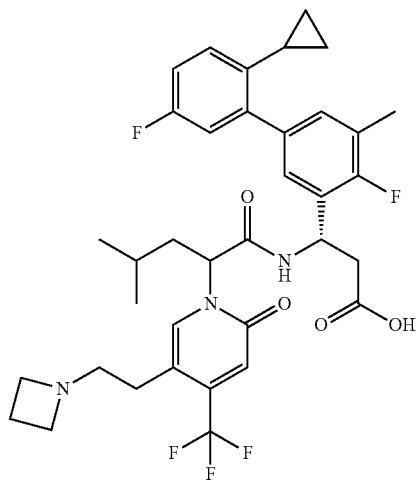 [SMILES: Cc1cc(-c2cc(F)ccc2C2CC2)cc([C@H](CC(=O)O)NC(=O)C(CC(C)C)n2cc(CCN3CCC3)c(C(F)(F)F)cc2=O)c1F]

CC-P1 ESI 674.4 (M+H)+. ¹H NMR (400 MHz, MeOD) δ 7.87 (s, 1H), 7.23-7.17 (m, 2H), 7.03-6.98 (m, 2H), 6.89-6.82 (m, 2H), 5.73-5.56 (m, 2H), 4.09 (t, J=8.1 Hz, 4H), 3.35-3.32 (m, 2H), 2.87-2.84 (m, 2H), 2.76-2.75 (m, 2H), 2.48-2.43 (m, 2H), 2.31 (d, J=1.6 Hz, 3H), 2.05-1.97 (m, 2H), 1.81-1.74 (m, 1H), 1.16-1.39 (m, 1H), 0.97-0.91 (m, 6H), 0.79-0.74 (m, 2H), 0.57-0.53 (m, 2H).

CC-P2 ESI 674.3 (M+H)+. ¹H NMR (400 MHz, MeOD) δ 7.74 (s, 1H), 7.27-7.21 (m, 2H), 7.05-6.91 (m, 4H), 5.77-5.74 (m, 1H), 5.64 (t, J=7.6 Hz, 1H), 4.14 (t, J=8.1 Hz, 4H), 3.42-3.32 (m, 2H), 2.96-2.81 (m, 2H), 2.67-2.45 (m, 4H), 2.35 (t, J=8.8 Hz, 3H), 2.03-1.96 (m, 1H), 1.83-1.66 (m, 2H), 1.42-1.38 (m, 1H), 0.92-0.89 (m, 6H), 0.84-0.79 (m, 2H), 0.63-0.59 (m, 2H).

4-31. (3S)-3-(2-(5-(2-(azetidin-1-yl)ethyl)-2-oxo-4-(trifluoromethyl)pyridin-1(2H)-yl)-4-methylpentanamido)-3-(6'-cyano-4-fluoro-2',3',5-trimethyl-[1,1'-biphenyl]-3-yl)propanoic acid (diastereomeric compounds CD-P1 and CD-P2)

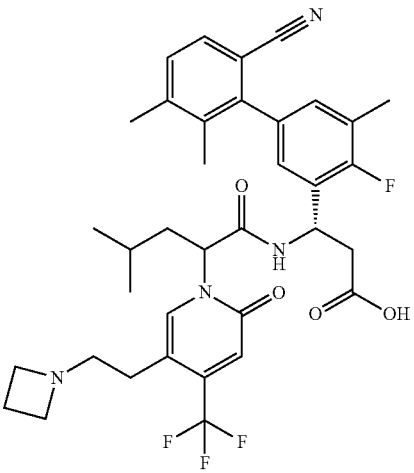 [SMILES: Cc1ccc(C#N)c(-c2cc(C)c(F)c([C@H](CC(=O)O)NC(=O)C(CC(C)C)n3cc(CCN4CCC4)c(C(F)(F)F)cc3=O)c2)c1C]

CD-P1 ESI 669.4 (M+H)+. ¹H NMR (400 MHz, MeOD) δ 7.85 (d, J=8.9 Hz, 1H), 7.61-7.27 (m, 2H), 7.16-6.95 (m, 2H), 6.77 (d, J=35.8 Hz, 1H), 5.80-5.43 (m, 2H), 4.11-3.86 (m, 4H), 3.31-3.15 (m, 2H), 2.94-2.60 (m, 4H), 2.51-2.24 (m, 8H), 2.15-1.89 (m, 5H), 1.56-1.38 (m, 1H), 1.09-0.83 (m, 6H).

CD-P2 ESI 669.4 (M+H)+. ¹H NMR (400 MHz, MeOD) δ 7.72 (d, J=6.8 Hz, 1H), 7.54 (d, J=7.9 Hz, 1H), 7.36 (d, J=7.9 Hz, 1H), 7.22-7.05 (m, 2H), 6.91 (s, 1H), 5.90-5.53 (m, 2H), 4.32-3.89 (m, 4H), 3.54-3.33 (m, 2H), 3.11-2.29 (m, 12H), 2.07-1.92 (m, 4H), 1.83-1.64 (m, 1H), 1.52-1.30 (m, 1H), 0.97-0.81 (m, 6H).

4-32. (3S)-3-(2-(5-(2-(azetidin-1-yl)ethyl)-2-oxo-4-(trifluoromethyl)pyridin-1(2H)-yl)-4-methylpentanamido)-3-(5'-cyano-4-fluoro-2',4',5-trimethyl-[1,1'-biphenyl]-3-yl)propanoic acid (diastereomeric compounds CE-P1 and CE-P2)

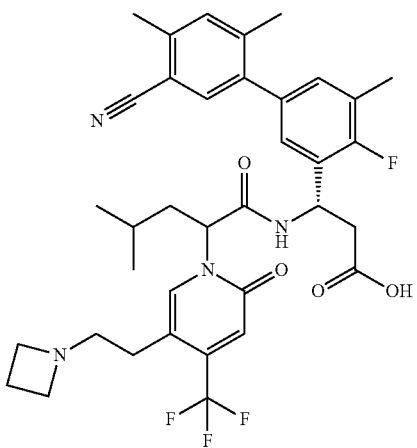 [SMILES: Cc1cc(C)c(-c2cc(C)c(F)c([C@H](CC(=O)O)NC(=O)C(CC(C)C)n3cc(CCN4CCC4)c(C(F)(F)F)cc3=O)c2)cc1C#N]

CE-P1 ESI 669.2 (M+H)+. 1H NMR (400 MHz, MeOD) δ 7.74 (s, 1H), 7.26 (d, J=40.1 Hz, 2H), 6.96 (t, J=7.5 Hz, 2H), 6.65 (s, 1H), 5.74-5.22 (m, 2H), 3.92 (t, J=8.1 Hz, 4H), 3.21-3.09 (m, 2H), 2.66 (dt, J=11.9, 7.1 Hz, 4H), 2.49-2.19 (m, 5H), 2.15 (d, J=20.6 Hz, 6H), 1.90 (m, J=13.4, 6.1 Hz, 2H), 1.47-1.10 (m, 1H), 0.83 (t, J=6.2 Hz, 6H).

CE-P2 ESI 669.2 (M+H)+. 1H NMR (400 MHz, MeOD) δ 7.75 (s, 1H), 7.42 (d, J=42.0 Hz, 2H), 7.13 (d, J=6.4 Hz, 2H), 6.92 (s, 1H), 5.92-5.45 (m, 2H), 4.14 (t, J=8.0 Hz, 4H), 3.40 (d, J=16.8 Hz, 2H), 2.92 (s, 2H), 2.75-2.55 (m, 1H), 2.52-2.41 (m, 6H), 2.40-2.18 (m, 6H), 2.12-1.88 (m, 1H), 1.82-1.53 (m, 1H), 1.53-1.20 (m, 1H), 0.92 (t, J=6.6 Hz, 6H).

4-33. (3S)-3-(4,5-difluoro-2',6'-dimethyl-[1,1'-biphenyl]-3-yl)-3-(2-(5-(2-(dimethylamino)ethyl)-2-oxopyridin-1(2H)-yl)-4-methylpentanamido)propanoic acid (diastereomeric compounds CF-P1 and CF-P2)

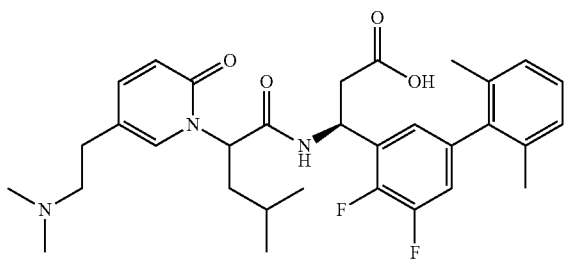 [SMILES: Cc1cccc(C)c1-c1cc(F)c(F)c([C@H](CC(=O)O)NC(=O)C(CC(C)C)n2cc(CCN(C)C)ccc2=O)c1]

CF-P1 ESI 568.2 (M+H)+. 1H NMR (500 MHz, MeOD) δ 7.64 (d, J=2.0 Hz, 1H), 7.54-7.51 (m, 1H), 7.18 (t, J=7.5 Hz, 1H), 7.11 (t, J=6.8 Hz, 2H), 6.99-6.90 (m, 1H), 6.78 (d, J=5.9 Hz, 1H), 6.52 (d, J=9.3 Hz, 1H), 5.61-5.56 (m, 1H), 5.42 (t, J=5.6 Hz, 1H), 3.32-3.19 (s, 1H), 3.24-3.10 (m, 1H), 2.88-2.80 (m, 2H), 2.73 (s, 6H), 2.70-2.64 (m, 1H), 2.59-2.53 (m, 1H), 2.06-1.89 (m, 8H), 1.50-1.36 (m, 1H), 0.97-0.90 (m, 6H).

CF-P2 ESI 568.2 (M+H)+. 1H NMR (500 MHz, MeOD) δ 1H NMR (500 MHz, MeOD) δ 7.65 (d, J=2.1 Hz, 1H), 7.54-7.50 (m, 1H), 7.22-7.13 (m, 1H), 7.14-7.07 (m, 2H), 7.01-6.90 (m, 1H), 6.88 (d, J=5.8 Hz, 1H), 6.54 (d, J=9.3 Hz, 1H), 5.66-5.52 (m, 2H), 3.38-3.34 (m, 1H), 3.28-3.21 (m, 1H), 2.98-2.86 (m, 1H), 2.86-2.73 (m, 7H), 2.64-2.59 (m, 1H), 2.51-2.44 (m, 1H), 2.08-1.91 (m, 7H), 1.92-1.81 (m, 1H), 1.49-1.35 (m, 1H), 0.93-0.88 (m, 6H).

4-34. (3S)-3-(2-(5-(2-(dimethylamino)ethyl)-2-oxopyridin-1(2H)-yl)-4-methylpentanamido)-3-(4,4',5-trifluoro-2',6'-dimethyl-[1,1'-biphenyl]-3-yl)propanoic acid (diastereomeric compounds CG-P1 and CG-P2)

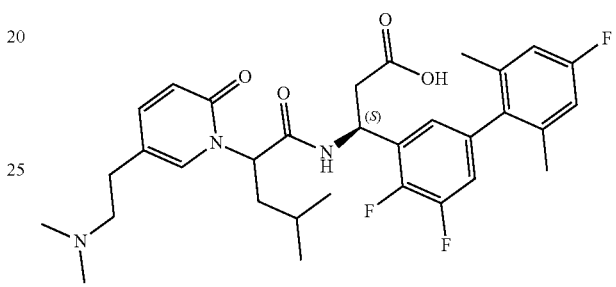

CG-P1 ESI 586.2 (M+H)+. 1H NMR (500 MHz, MeOD) δ 7.65 (s, 1H), 7.57-7.48 (m, 1H), 6.99-6.90 (m, 1H), 6.87 (d, J=8.8 Hz, 2H), 6.79 (d, J=5.8 Hz, 1H), 6.52 (d, J=9.4 Hz, 1H), 5.56 (s, 1H), 5.42 (t, J=5.6 Hz, 1H), 3.32-3.27 (m, 1H), 3.23-3.16 (m, 1H), 2.93-2.80 (m, 2H), 2.75 (s, 6H), 2.70-2.62 (m, 1H), 2.59-2.52 (m, 1H), 2.10-1.91 (m, 8H), 1.44 (s, 1H), 0.98-0.87 (m, 6H).

CG-P2 ESI 586.2 (M+H)+. 1H NMR (500 MHz, MeOD) δ 7.65 (d, J=2.1 Hz, 1H), 7.56-7.50 ((m, 1H), 7.01-6.94 (m, 1H), 6.90-6.81 (m, 3H), 6.55 (d, J=9.3 Hz, 1H), 5.64-5.54 (m, 2H), 3.45-3.36 (m, 1H), 3.31-3.24 (m, 1H), 2.99-2.90 (m, 1H), 2.90-2.78 (m, 7H), 2.64-2.55 (m, 1H), 2.51-2.41 (m, 1H), 2.07-1.95 (m, 7H), 1.92-1.83 (m, 1H), 1.46-1.36 (m, 1H), 0.96-0.86 (m, 6H).

4-35. (3S)-3-(4,5-difluoro-2',6'-dimethyl-[1,1'-biphenyl]-3-yl)-3-(2-(5-(2-(3-fluoroazetidin-1-yl)ethyl)-2-oxopyridin-1(2H)-yl)-4-methylpentanamido)propanoic acid (diastereomeric compounds CH-P1 and CH-P2)

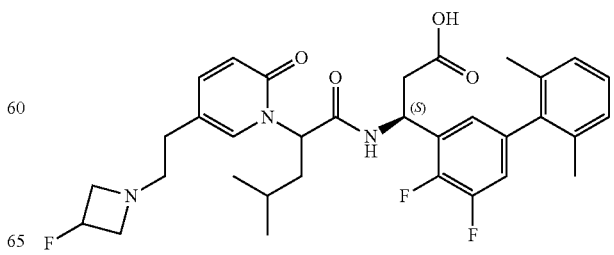

CH-P1 ESI 598.2 (M+H)⁺. ¹H NMR (500 MHz, MeOD) δ 7.54 (d, J=1.9 Hz, 1H), 7.46-7.40 (m, 1H), 7.21-7.14 (m, 1H), 7.11 (d, J=7.3 Hz, 2H), 6.99-6.90 (m, 1H), 6.81 (d, J=5.9 Hz, 1H), 6.47 (d, J=9.3 Hz, 1H), 5.62 (t, J=8.1 Hz, 1H), 5.51 (t, J=6.1 Hz, 1H), 5.31-5.14 (m, 1H), 4.17-3.96 (m, 2H), 3.82-3.67 (m, 2H), 3.21-3.11 (m, 2H), 2.78-2.58 (m, 4H), 2.03-1.89 (m, 8H), 1.47-1.40 (m, 1H), 0.97-0.88 (m, 6H).

CH-P2 ESI 598.2 (M+H)⁺. ¹H NMR (500 MHz, MeOD) δ 7.53 (d, J=2.0 Hz, 1H), 7.49-7.42 (m, 1H), 7.16 (d, J=7.4 Hz, 1H), 7.11 (d, J=7.7 Hz, 2H), 7.03-6.94 (m, 1H), 6.92 (d, J=5.9 Hz, 1H), 6.55 (d, J=9.3 Hz, 1H), 5.68-5.60 (m, 2H), 5.41-5.22 (m, 1H), 4.47-4.27 (m, 2H), 4.09-3.94 (m, 2H), 3.37 (s, 2H), 2.79-2.62 (m, 3H), 2.60-2.50 (m, 1H), 2.03 (d, J=2.2 Hz, 6H), 1.98-1.91 (m, 1H), 1.84-1.76 (m, 1H), 1.47-1.37 (m, 1H), 0.91 (t, J=6.1 Hz, 6H).

4-36. (3S)-3-(4-fluoro-2',5,6'-trimethyl-[1,1'-biphenyl]-3-yl)-3-(2-(5-(2-(3-fluoroazetidin-1-yl)ethyl)-4-methyl-2-oxopyridin-1(2H)-yl)-4-methylpentanamido)propanoic acid (Diastereomeric Compounds CI-P1 and CI-P2)

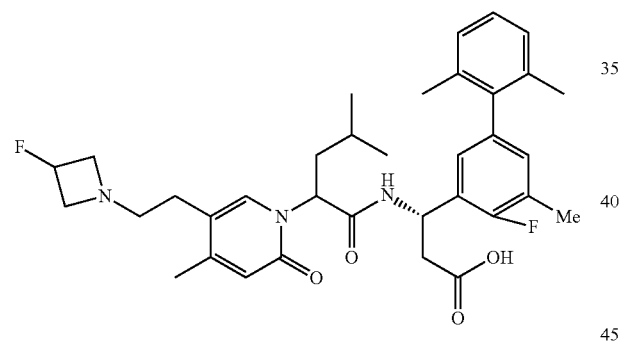

CI-P1 ESI 608.2 (M+H)⁺. ¹H NMR (500 MHz, MeOD) δ 8.45 (s, 0.47 HCOOH), 7.54 (s, 1H), 7.15-7.05 (m, 3H), 6.89-6.81 (m, 2H), 6.30 (s, 1H), 5.68-5.48 (m, 2H), 5.40-5.14 (m, 1H), 4.35-4.13 (m, 2H), 4.06-3.86 (m, 2H), 3.26-3.20 (m, 2H), 2.88-2.65 (m, 4H), 2.29 (s, 3H), 2.23 (s, 3H), 2.01-1.89 (m, 5H), 1.85 (s, 3H), 1.48-1.38 (m, 1H), 0.98-0.91 (m, 6H).

CI-P2 ESI 608.2 (M+H)⁺. ¹H NMR (500 MHz, MeOD) δ 8.45 (s, 0.23 HCOOH), 7.46 (s, 1H), 7.20-7.02 (m, 3H), 6.93 (d, J=5.0 Hz, 2H), 6.44 (s, 1H), 5.75-5.54 (m, 2H), 5.34 (d, J=57.3 Hz, 1H), 4.48-4.35 (m, 2H), 4.16-3.96 (m, 2H), 3.42-3.34 (m, 2H), 2.90-2.82 (m, 1H), 2.74-2.63 (m, 2H), 2.60-2.52 (m, 1H), 2.33 (s, 3H), 2.25 (s, 3H), 2.07-1.85 (m, 7H), 1.82-1.70 (m, 1H), 1.44-1.34 (m, 1H), 0.91-0.87 (m, 6H).

4-37. (3S)-3-(2-(5-((dimethylamino)methyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoic acid (diastereomeric compounds CJ-P1 and CJ-P2)

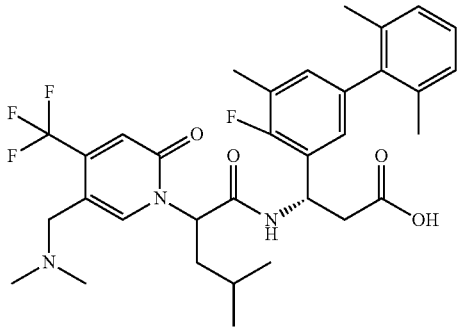 [SMILES: Cc1cc(-c2c(C)cccc2C)cc([C@H](CC(=O)O)NC(=O)C(CC(C)C)n2cc(CN(C)C)c(C(F)(F)F)cc2=O)c1F]

CJ-P1 ESI 618.2 (M+H)⁺. ¹H NMR (400 MHz, MeOD) δ 8.07 (s, 1H), 7.15-7.00 (m, 3H), 6.94-6.83 (m, 2H), 6.77 (s, 1H), 5.75 (t, J=8.1 Hz, 1H), 5.63-5.52 (m, 1H), 3.83-3.59 (m, 2H), 2.82-2.72 (m, 2H), 2.52 (s, 6H), 2.29 (d, J=1.3 Hz, 3H), 2.05-1.95 (m, 5H), 1.80 (s, 3H), 1.49-1.37 (m, 1H), 1.01-0.91 (m, 6H).

CJ-P2 ESI 618.2 (M+H)⁺. ¹H NMR (400 MHz, MeOD) δ 8.09 (s, 1H), 7.18-7.00 (m, 3H), 7.00-6.84 (m, 3H), 5.81-5.70 (m, 1H), 5.63-5.46 (m, 1H), 4.10 (d, J=14.4 Hz, 1H), 3.87 (d, J=14.4 Hz, 1H), 2.79-2.55 (m, 8H), 2.34 (d, J=1.5 Hz, 3H), 2.05-1.93 (m, 7H), 1.71-1.61 (m, 1H), 1.48-1.39 (m, 1H), 0.93-0.82 (m, 6H).

4-38. (3S)-3-(4,4'-difluoro-2',5,6'-trimethyl-[1,1'-biphenyl]-3-yl)-3-(2-(5-((dimethylamino)methyl)-2-oxo-4-(trifluoromethyl)pyridin-1(2H)-yl)-4-methylpentanamido)propanoic acid (Diastereomeric Compounds CK-P1 and CK-P2)

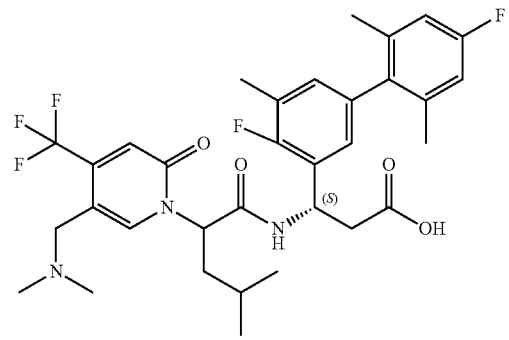

CK-P1 ESI 636.1 (M+H)⁺. ¹H NMR (400 MHz, MeOD) δ 8.06 (s, 1H), 6.95-6.72 (m, 5H), 5.75 (t, J=8.1 Hz, 1H), 5.62-5.56 (m, 1H), 3.79-3.65 (m, 2H), 2.86-2.65 (m, 2H), 2.52 (s, 6H), 2.29 (s, 3H), 2.04-1.93 (m, 5H), 1.81 (s, 3H), 1.50-1.38 (m, 1H), 0.96 (t, J=7.4 Hz, 6H).

CK-P2 ESI 636.1 (M+H)⁺. ¹H NMR (400 MHz, MeOD) δ 8.08 (s, 1H), 6.95-6.88 (m, 3H), 6.85 (d, J=9.6 Hz, 2H), 5.76-5.70 (m, 1H), 5.55 (t, J=7.5 Hz, 1H), 4.08 (d, J=14.4

Hz, 1H), 3.85 (d, J=14.4 Hz, 1H), 2.79-2.52 (m, 8H), 2.34 (s, 3H), 2.03-1.93 (m, 7H), 1.70-1.61 (m, 1H), 1.50-1.38 (m, 1H), 0.95-0.80 (m, 6H).

4-39. (3S)-3-(2-(5-((dimethylamino)methyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoic acid (diastereomeric compounds CL-P1 and CL-P2)

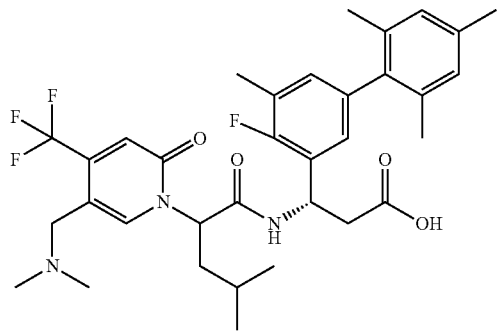 [SMILES: Cc1cc(C)c(-c2cc(C)c(F)c([C@H](CC(=O)O)NC(=O)C(CC(C)C)n3cc(CN(C)C)c(C(F)(F)F)cc3=O)c2)c(C)c1]

CL-P1 ESI 632.2 (M+H)$^+$. $^1$H NMR (400 MHz, MeOD) δ 8.05 (s, 1H), 6.92-6.82 (m, 4H), 6.76 (s, 1H), 5.75 (t, J=8.1 Hz, 1H), 5.63-5.50 (m, 1H), 3.78-3.62 (m, 2H), 2.88-2.65 (m, 2H), 2.50 (s, 6H), 2.29 (d, J=3.7 Hz, 6H), 2.03-1.89 (m, 5H), 1.76 (s, 3H), 1.52-1.36 (m, 1H), 0.96 (t, J=7.2 Hz, 6H).

CL-P2 ESI 632.2 (M+H)$^+$. $^1$H NMR (400 MHz, MeOD) δ 8.09 (s, 1H), 6.95-6.83 (m, 5H), 5.81-5.68 (m, 1H), 5.54 (t, J=7.4 Hz, 1H), 4.09 (d, J=14.4 Hz, 1H), 3.85 (d, J=14.3 Hz, 1H), 2.81-2.52 (m, 8H), 2.32 (d, J=9.8 Hz, 6H), 1.97 (t, J=9.1 Hz, 7H), 1.71-1.58 (m, 1H), 1.50-1.34 (m, 1H), 0.88 (d, J=6.4 Hz, 6H).

4-40. (3S)-3-(4,5-difluoro-2',4',6'-trimethyl-[1,1'-biphenyl]-3-yl)-3-(2-(5-((dimethylamino)methyl)-2-oxo-4-(trifluoromethyl)pyridin-1(2H)-yl)-4-methyl-pentanamido)propanoic acid (Diastereomeric Compounds CM-P1 and CM-P2)

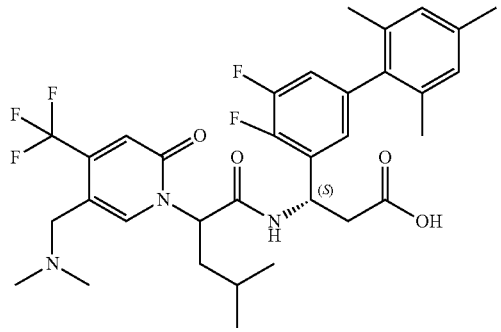

CM-P1 ESI 636.2 (M+H)$^+$. $^1$H NMR (400 MHz, MeOD) δ 7.99 (s, 1H), 6.92-6.84 (m, 4H), 6.72 (s, 1H), 5.82-5.68 (m, 1H), 5.61-5.55 (m, 1H), 3.61-3.48 (m, 2H), 2.83-2.65 (m, 2H), 2.38 (s, 6H), 2.30 (s, 3H), 2.03-1.92 (m, 5H), 1.73 (s, 3H), 1.49-1.37 (m, 1H), 0.99-0.93 (m, 6H).

CM-P2 ESI 636.2 (M+H)$^+$. $^1$H NMR (400 MHz, MeOD) δ 8.08 (s, 1H), 7.02-6.84 (m, 5H), 5.77-5.72 (m, 1H), 5.59-5.52 (m, 1H), 4.08 (d, J=14.4 Hz, 1H), 3.85 (d, J=14.4 Hz, 1H), 2.79-2.75 (m, 1H), 2.70-2.54 (m, 7H), 2.31 (s, 3H), 2.02-1.87 (m, 7H), 1.74-1.57 (m, 1H), 1.49-1.37 (m, 1H), 0.91-0.86 (m, 6H).

4-41. (3S)-3-(2-(5-(2-(dimethylamino)ethyl)-3-fluoro-2-oxopyridin-1(2H)-yl)-4-methylpentanamido)-3-(4,4',5-trifluoro-2',6'-dimethyl-[1,1'-biphenyl]-3-yl)propanoic acid (diastereomeric compounds CN-P1 and CN-P2)

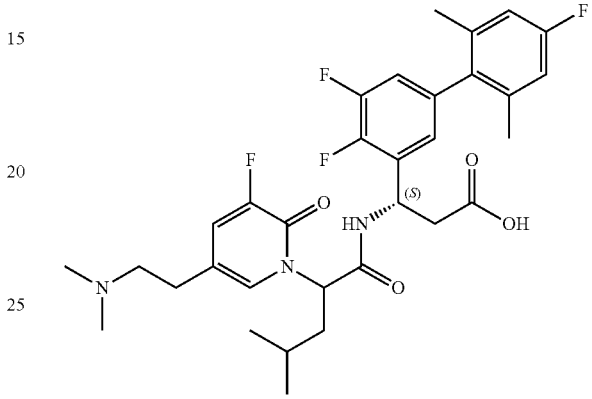

CN-P1 ESI 604.2 (M+H)$^+$. $^1$H NMR (400 MHz, MeOD) δ 7.44 (s, 1H), 7.34-7.30 (m, 1H), 6.96-6.75 (m, 4H), 5.76-5.71 (m, 1H), 5.60-5.48 (m, 1H), 2.76-2.55 (m, 6H), 2.39 (s, 6H), 2.07-1.90 (m, 5H), 1.84 (s, 3H), 1.49-1.33 (m, 1H), 0.98-0.92 (m, 6H).

CN-P2 ESI 604.2 (M+H)$^+$. $^1$H NMR (400 MHz, MeOD) δ 7.50 (s, 1H), 7.46-7.10 (m, 1H), 7.04-6.93 (m, 1H), 6.91-6.84 (m, 3H), 5.67-5.57 (m, 2H), 3.47-3.37 (m, 1H), 3.31-3.21 (m, 1H), 3.02-2.91 (m, 1H), 2.90-2.79 (m, 7H), 2.64-2.57 (m, 1H), 2.50-2.42 (m, 1H), 2.07-1.92 (m, 7H), 1.90-1.78 (m, 1H), 1.47-1.31 (m, 1H), 0.94-0.89 (m, 6H).

4-42. (3S)-3-(4,5-difluoro-2',4',6'-trimethyl-[1,1'-biphenyl]-3-yl)-3-(2-(5-(2-(dimethylamino)ethyl)-3-fluoro-2-oxopyridin-1(2H)-yl)-4-methylpentanamido)propa-noic acid (Diastereomeric Compounds CO-P1 and CO-P2)

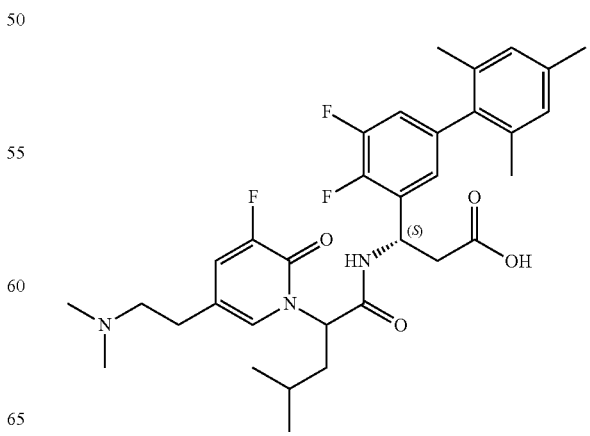

377

CO-P1 ESI 600.2 (M+H)⁺. ¹H NMR (400 MHz, MeOD) δ 7.49-7.44 (m, 2H), 6.92 (t, J=8.2 Hz, 3H), 6.76 (d, J=6.0 Hz, 1H), 5.65-5.61 (m, 1H), 5.40 (t, J=5.6 Hz, 1H), 3.19-3.15 (m, 2H), 2.90-2.84 (m, 3H), 2.75-2.63 (m, 7H), 2.57-2.52 (m, 1H), 2.31 (s, 3H), 2.03-1.87 (m, 9H), 1.46-1.40 (m, 1H), 0.98-0.91 (m, 6H).

CO-P2 ESI 600.2 (M+H)⁺. ¹H NMR (400 MHz, MeOD) δ 7.37-7.29 (m, 2H), 6.87-6.71 (m, 4H), 5.57-5.42 (m, 2H), 3.34-3.24 (m, 1H), 3.18-3.07 (m, 1H), 2.87-2.81 (m, 1H), 2.73-2.70 (m, 7H), 2.50-2.45 (m, 1H), 2.36-2.30 (m, 1H), 2.19 (s, 3H), 1.96-1.80 (m, 7H), 1.74-1.63 (m, 1H), 1.30-1.25 (m, 1H), 0.81-0.79 (m, 6H).

4-43. (3S)-3-(2-(5-(2-(3-fluoroazetidin-1-yl)ethyl)-4-methyl-2-oxopyridin-1(2H)-yl)-4-methylpentanamido)-3-(4,4',5-trifluoro-2',6'-dimethylbiphenyl-3-yl)propanoic acid (Diastereomeric Compounds CP-P1 and CP-P2)

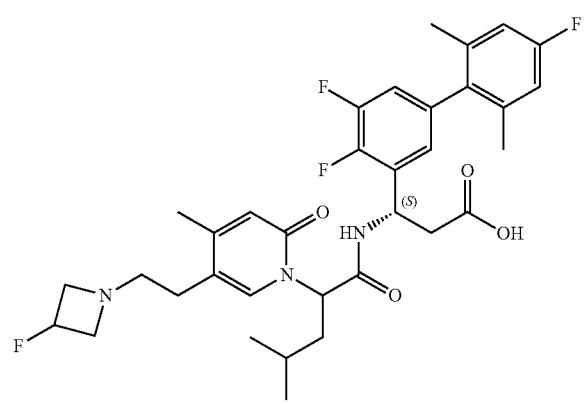

CP-P1 ESI 630.2 (M+H)⁺. 1H NMR (400 MHz, MeOD) δ 7.49 (s, 1H), 6.99-6.89 (m, 1H), 6.89-6.76 (m, 3H), 6.29 (s, 1H), 5.66-5.50 (m, 2H), 5.40-5.10 (m, 1H), 4.14-3.90 (m, 2H), 3.86-3.55 (m, 2H), 3.03 (s, 2H), 2.86-2.53 (m, 4H), 2.23 (s, 3H), 2.06-1.90 (m, 5H), 1.86 (s, 3H), 1.49-1.32 (m, 1H), 1.02-0.84 (m, 6H).

CP-P2 ESI 630.2 (M+H)⁺. 1H NMR (400 MHz, MeOD) δ 7.49 (s, 1H), 7.09-6.86 (m, 4H), 6.44 (s, 1H), 5.72-5.55 (m, 2H), 5.30 (d, J=57.8 Hz, 1H), 4.28 (s, 2H), 3.93 (s, 2H), 3.19 (s, 2H), 2.87-2.50 (m, 4H), 2.25 (s, 3H), 2.04 (s, 6H), 1.93-1.73 (m, 2H), 1.47-1.28 (m, 1H), 0.91-0.85 (m, 6H).

378

4-44. (3S)-3-(5-chloro-4,4'-difluoro-2',6'-dimethylbiphenyl-3-yl)-3-(2-(5-(2-(dimethylamino)ethyl)-2-oxo-4-(trifluoromethyl)pyridin-1(2H)-yl)-4-methylpentanamido)propanoic acid (Diastereomeric Compounds CQ-P1 and CQ-P2)

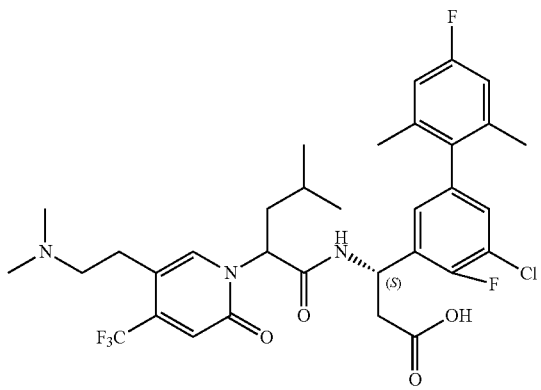

CQ-P1 ESI 670.2 (M+H)⁺. 1H NMR (400 MHz, MeOD) δ 7.90 (s, 1H), 7.13-7.11 (m, 1H), 7.04-7.02 (m, 1H), 6.88-6.81 (m, 2H), 6.74 (s, 1H), 5.69-5.65 (m, 1H), 5.57-5.53 (m, 1H), 3.16-3.10 (m, 2H), 2.97-2.94 (m, 2H), 2.80 (s, 6H), 2.74-2.71 (m, 2H), 2.02-1.98 (m, 5H), 1.84 (s, 3H), 1.47-1.40 (m, 1H), 0.98-0.93 (m, 6H).

CQ-P2 ESI 670.2 (M+H)⁺. 1H NMR (400 MHz, MeOD) δ 7.86 (s, 1H), 7.20-7.18 (m, 1H), 7.07 (d, J=6.1 Hz, 1H), 6.88 (d, J=11.2 Hz, 3H), 5.73-5.67 (m, 1H), 5.63 (t, J=7.6 Hz, 1H), 3.30-3.18 (m, 2H), 3.01 (t, J=6.9 Hz, 2H), 2.85 (s, 6H), 2.69-2.60 (m, 1H), 2.58-2.52 (m, 1H), 2.03-1.95 (m, 7H), 1.77-1.70 (m, 1H), 1.41-1.36 (m, 1H), 0.91-0.89 (m, 6H).

4-45. (3S)-3-(5-chloro-4,4'-difluoro-2',6'-dimethylbiphenyl-3-yl)-3-(2-(5-(2-(3-fluoroazetidin-1-yl)ethyl)-4-methyl-2-oxopyridin-1(2H)-yl)-4-methylpentanamido)propanoic acid (Diastereomeric Compounds CR-P1 and CR-P2)

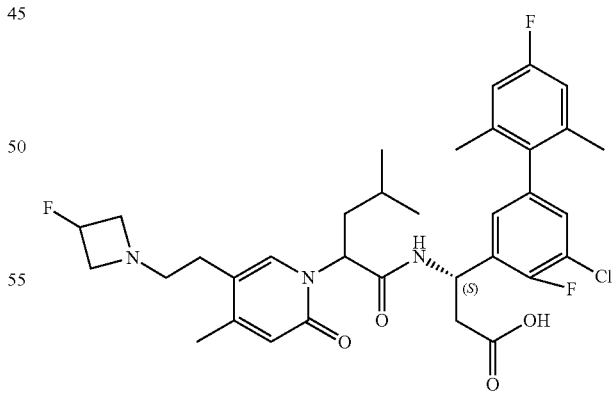

CR-P1 ESI 646.2 (M+H)⁺. 1H NMR (400 MHz, MeOD) δ 7.50 (s, 1H), 7.15-7.13 (m, 1H), 6.99-6.97 (m, 1H), 6.88-6.85 (m, 2H), 6.29 (s, 1H), 5.64-5.49 (m, 2H), 5.32-5.18 (m, 1H), 4.11-4.07 (m, 2H), 3.85-3.72 (m, 2H), 3.10 (t, J=6.9 Hz, 2H), 2.82-2.62 (m, 4H), 2.24 (s, 3H), 2.09-1.90 (m, 5H), 1.89 (d, J=8.2 Hz, 3H), 1.43-1.38 (m, 1H), 0.96-0.92 (m, 6H).

CR-P2 ESI 646.2 (M+H)⁺. 1H NMR (400 MHz, MeOD) δ 7.45 (s, 1H), 7.21-7.18 (m, 1H), 7.08-7.06 (m, 1H), 6.89 (d, J=9.6 Hz, 2H), 6.43 (s, 1H), 5.73-5.53 (m, 2H), 5.43-5.25 (m, 1H), 4.44-4.41 (m, 2H), 4.16-4.01 (m, 2H), 3.39-3.36 (m, 2H), 2.91-2.87 (m, 1H), 2.73-2.62 (m, 2H), 2.52-2.49 (m, 1H), 2.25 (s, 3H), 2.03 (s, 6H), 1.98-1.88 (m, 1H), 1.81-1.72 (m, 1H), 1.44-1.33 (m, 1H), 0.91-0.89 (m, 6H).

4-46. (3S)-3-(2-(5-(2-(dimethylamino)ethyl)-2-oxo-4-(trifluoromethyl)pyridin-1(2H)-yl)-4-methylpentanamido)-3-(4,4',5-trifluoro-2',6'-dimethylbiphenyl-3-yl)propanoic acid (Diastereomeric Compounds CS-P1 and CS-P2)

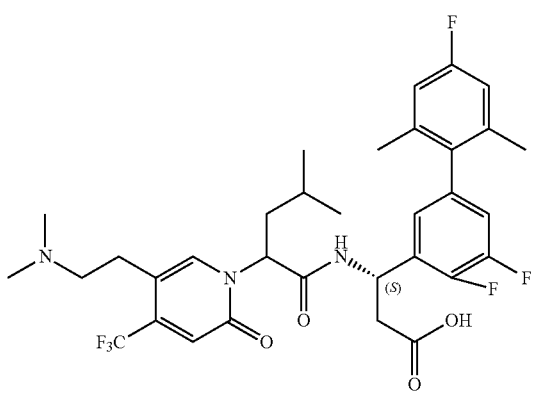

CS-P1 ESI 654.2 (M+H)⁺. 1H NMR (400 MHz, MeOD) δ 7.89 (s, 1H), 6.98-6.78 (m, 4H), 6.75 (s, 1H), 5.69-5.65 (m, 1H), 5.59-5.56 (m, 1H), 3.15-3.06 (m, 2H), 2.95 (d, J=6.2 Hz, 2H), 2.77 (s, 6H), 2.74-2.71 (m, 2H), 2.13-1.91 (m, 5H), 1.85 (s, 3H), 1.50-1.40 (m, 1H), 0.98-0.94 (m, 6H).

CS-P2 ESI 654.2 (M+H)⁺. 1H NMR (400 MHz, MeOD) δ 7.86 (s, 1H), 7.05-6.96 (m, 1H), 6.95-6.83 (m, 4H), 5.73-5.69 (m, 1H), 5.63 (t, J=7.7 Hz, 1H), 3.28-3.14 (m, 2H), 2.99 (t, J=7.0 Hz, 2H), 2.82 (s, 6H), 2.69-2.64 (m, 1H), 2.62-2.52 (m, 1H), 2.03 (d, J=2.1 Hz, 6H), 1.99-1.94 (m, 1H), 1.77-1.72 (m, 1H), 1.45-1.31 (m, 1H), 0.91-0.89 (m, 6H).

4-47. (3S)-3-(5-chloro-4,4'-difluoro-2',6'-dimethylbiphenyl-3-yl)-3-(2-(5-(2-(3-fluoroazetidin-1-yl)ethyl)-2-oxopyridin-1(2H)-yl)-4-methylpentanamido)propanoic acid (diastereomeric compounds CT-P1 and CT-P2)

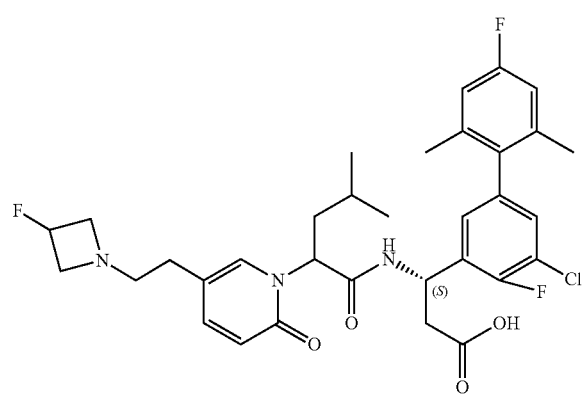

CT-P1 ESI 632.2 (M+H)⁺. 1H NMR (400 MHz, MeOD) δ 7.59 (s, 1H), 7.46-7.43 (m, 1H), 7.15-7.13 (m, 1H), 7.00-6.92 (m, 1H), 6.87 (d, J=9.6 Hz, 2H), 6.45 (d, J=9.3 Hz, 1H), 5.68-5.57 (m, 1H), 5.51 (t, J=6.2 Hz, 1H), 5.38-5.16 (m, 1H), 4.25-4.04 (m, 2H), 3.96-3.76 (m, 2H), 3.25-3.13 (m, 2H), 2.83-2.58 (m, 4H), 2.08-1.92 (m, 5H), 1.88 (s, 3H), 1.47-1.40 (m, 1H), 0.97-0.92 (m, 6H).

CT-P2 ESI 632.2 (M+H)⁺. 1H NMR (400 MHz, MeOD) δ 7.54 (s, 1H), 7.49 (d, J=8.8 Hz, 1H), 7.20-7.18 (m, 1H), 7.04 (d, J=4.5 Hz, 1H), 6.88 (d, J=9.6 Hz, 2H), 6.56 (d, J=9.1 Hz, 1H), 5.71-5.57 (m, 2H), 5.34 (d, J=59.0 Hz, 1H), 4.40 (s, 2H), 4.08 (s, 2H), 3.42 (s, 1H), 2.70 (d, J=52.7 Hz, 3H), 2.52 (s, 1H), 2.03 (d, J=3.5 Hz, 6H), 1.99-1.93 (m, 2H), 1.88-1.76 (m, 1H), 1.49-1.31 (m, 1H), 0.91 (t, J=6.7 Hz, 6H).

4-48. (3S)-3-(4,4'-difluoro-2',5,6'-trimethylbiphenyl-3-yl)-3-(2-(5-(2-(dimethylamino)ethyl)-3-fluoro-2-oxopyridin-1(2H)-yl)-4-methylpentanamido)propanoic acid (diastereomeric compounds CU-P1 and CU-P2)

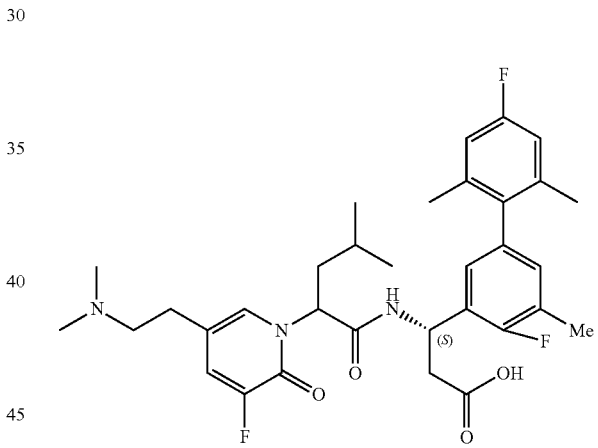

CU-P1 ESI 600.3 (M+H)⁺. 1H NMR (400 MHz, MeOD) δ 7.52 (s, 1H), 7.47-7.44 (m, 1H), 6.91-6.81 (m, 3H), 6.78 (d, J=6.8 Hz, 1H), 5.64-5.60 (m, 1H), 5.40 (t, J=5.6 Hz, 1H), 3.36 (d, J=6.1 Hz, 1H), 3.24-3.12 (m, 1H), 2.97-2.77 (m, 2H), 2.73 (s, 6H), 2.70-2.61 (m, 1H), 2.57-2.52 (m, 1H), 2.30 (d, J=1.6 Hz, 3H), 2.12-1.96 (m, 5H), 1.95 (s, 3H), 1.52-1.37 (m, 1H), 0.97-0.91 (m, 6H).

CU-P2 ESI 600.2 (M+H)⁺. 1H NMR (400 MHz, MeOD) δ 7.50 (s, 1H), 7.45-7.42 (m, 1H), 6.89 (t, J=6.1 Hz, 2H), 6.84 (d, J=9.6 Hz, 2H), 5.66-5.62 (m, 1H), 5.59-5.56 (m, 1H), 3.47-3.36 (m, 1H), 3.30-3.25 (m, 1H), 3.00-2.94 (m, 1H), 2.90-2.77 (m, 7H), 2.61-2.56 (m, 1H), 2.46-2.40 (m, 1H), 2.32 (d, J=1.8 Hz, 3H), 2.09-1.94 (m, 7H), 1.87-1.79 (m, 1H), 1.48-1.37 (m, 1H), 0.93-0.90 (m, 6H).

4-49. (3S)-3-(5-chloro-4,4'-difluoro-2',6'-dimethylbiphenyl-3-yl)-3-(2-(5-(2-(dimethylamino)ethyl)-3-fluoro-2-oxopyridin-1(2H)-yl)-4-methylpentanamido)propanoic acid (diastereomeric compounds CV-P1 and CV-P2)

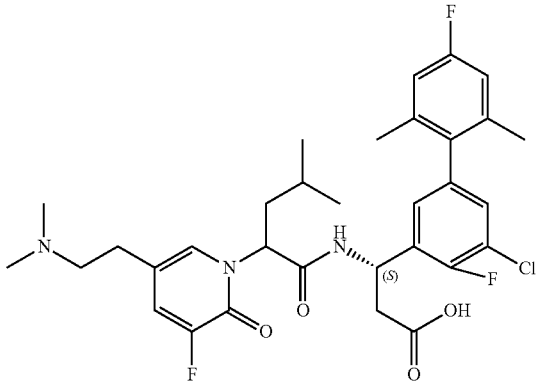

CV-P1 ESI 620.2 (M+H)⁺. 1H NMR (400 MHz, MeOD) δ 7.53 (s, 1H), 7.46-7.43 (m, 1H), 7.15-7.12 (m, 1H), 6.95-6.93 (m, 1H), 6.87 (d, J=9.6 Hz, 2H), 5.65-5.61 (m, 1H), 5.42 (t, J=5.8 Hz, 1H), 3.31-3.26 (m, 1H), 3.20-3.15 (m, 1H), 2.96-2.81 (m, 2H), 2.75 (s, 6H), 2.70-2.65 (m, 1H), 2.59-2.54 (m, 1H), 2.19-1.78 (m, 8H), 1.46-1.40 (m, 1H), 0.97-0.91 (m, 6H).

CV-P2 ESI 620.2 (M+H)⁺. 1H NMR (400 MHz, MeOD) δ 7.50 (s, 1H), 7.45-7.42 (m, 1H), 7.18-7.16 (m, 1H), 7.04-7.02 (m, 1H), 6.88 (d, J=9.6 Hz, 2H), 5.67-5.63 (m, 1H), 5.59-5.56 (m, 1H), 3.46-3.36 (m, 1H), 3.29-3.22 (m, 1H), 2.98-2.92 (m, 1H), 2.86-2.84 (m, 1H), 2.82 (s, 6H), 2.62-2.58 (m, 1H), 2.51-2.41 (m, 1H), 2.03 (d, J=1.5 Hz, 6H), 1.97 (t, J=7.1 Hz, 1H), 1.90-1.78 (m, 1H), 1.41-1.36 (m, 1H), 0.97-0.74 (m, 6H).

4-50. (3S)-3-(4,4'-difluoro-2',5,6'-trimethylbiphenyl-3-yl)-3-(2-(5-(2-(dimethylamino)ethyl)-4-methyl-2-oxopyridin-1(2H)-yl)-4-methylpentanamido)propanoic acid (diastereomeric compounds CW-P1 and CW-P2)

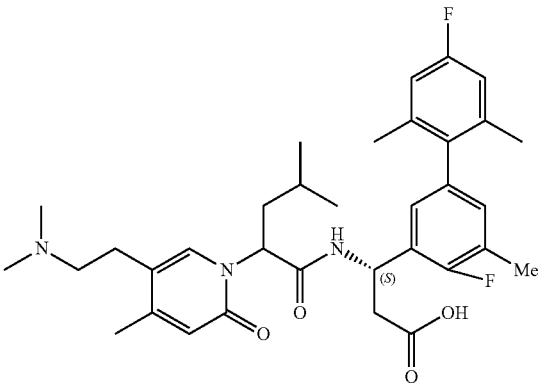

CW-P1 ESI 596.3 (M+H)⁺. 1H NMR (400 MHz, MeOD) δ 7.59 (s, 1H), 6.83 (t, J=7.2 Hz, 4H), 6.32 (s, 1H), 5.70-5.56 (m, 1H), 5.54-5.47 (m, 1H), 3.21-3.06 (m, 2H), 2.95-2.83 (m, 2H), 2.79 (s, 6H), 2.73-2.55 (m, 2H), 2.35-2.20 (m, 6H), 2.07-1.91 (m, 5H), 1.85 (s, 3H), 1.50-1.29 (m, 1H), 1.02-0.83 (m, 6H).

CW-P2 ESI 596.3 (M+H)⁺. 1H NMR (400 MHz, MeOD) δ 7.57 (s, 1H), 6.99-6.78 (m, 4H), 6.43 (s, 1H), 5.71-5.53 (m, 2H), 3.28-3.06 (m, 2H), 2.97-2.85 (m, 2H), 2.81 (s, 6H), 2.66-2.56 (m, 1H), 2.56-2.40 (m, 1H), 2.36-2.24 (m, 6H), 2.05-1.89 (m, 7H), 1.86-1.72 (m, 1H), 1.43-1.28 (m, 1H), 0.89 (t, J=5.2 Hz, 6H).

4-51. (3S)-3-(4'-chloro-4-fluoro-2',5,6'-trimethylbiphenyl-3-yl)-3-(2-(5-(2-(dimethylamino)ethyl)-4-methyl-2-oxopyridin-1(2H)-yl)-4-methylpentanamido)propanoic acid (diastereomeric compounds CX-P1 and CX-P2)

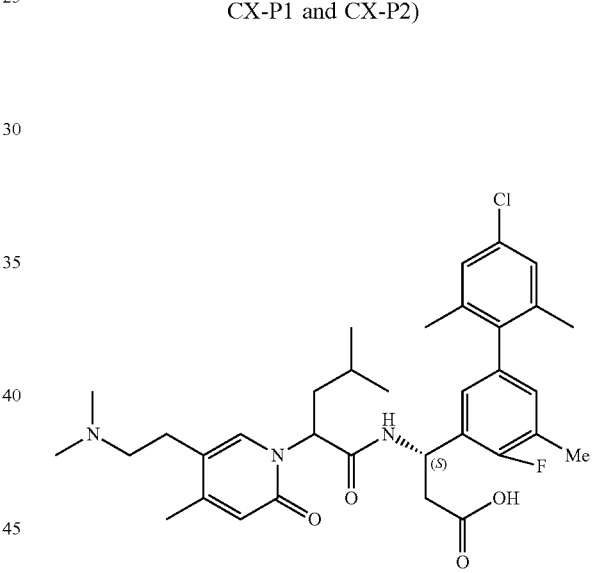

CX-P1 ESI 612.2 (M+H)⁺. 1H NMR (400 MHz, MeOD) δ 7.58 (s, 1H), 7.11 (d, J=2.5 Hz, 2H), 6.92-6.76 (m, 2H), 6.32 (s, 1H), 5.61-5.41 (m, 2H), 3.25-3.05 (m, 2H), 2.88 (t, J=7.3 Hz, 2H), 2.78 (s, 6H), 2.71-2.54 (m, 2H), 2.28 (d, J=13.0 Hz, 6H), 2.05-1.92 (m, 5H), 1.88 (s, 3H), 1.48-1.32 (m, 1H), 1.04-0.85 (m, 6H).

CX-P2 ESI 612.2 (M+H)⁺. 1H NMR (400 MHz, MeOD) δ 7.55 (s, 1H), 7.13 (s, 2H), 6.93-6.84 (m, 2H), 6.42 (s, 1H), 5.70-5.54 (m, 2H), 3.24-3.11 (m, 2H), 2.99-2.76 (m, 8H), 2.64-2.42 (m, 2H), 2.36-2.20 (m, 6H), 2.03-1.90 (m, 7H), 1.83-1.72 (m, 1H), 1.47-1.28 (m, 1H), 0.90 (t, J=6.2 Hz, 6H).

4-52. (3S)-3-(2-(5-(2-(dimethylamino)ethyl)-3-fluoro-2-oxopyridin-1(2H)-yl)-4-methylpentanamido)-3-(4-fluoro-2',4',5',6'-tetramethyl-[1,1'-biphenyl]-3-yl)propanoic acid (diastereomeric compounds CY-P1 and CY-P2)

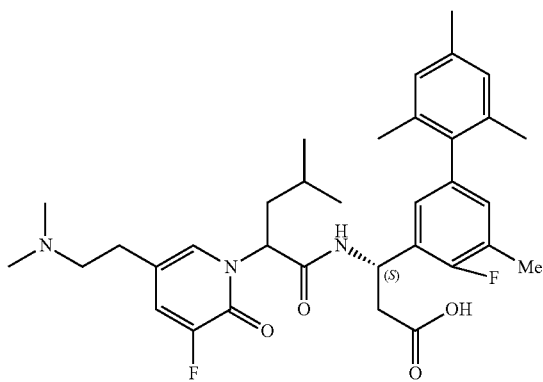

CY-P1 ESI 596.3 (M+H)⁺. ¹H NMR (400 MHz, MeOD) δ 7.59-7.37 (m, 2H), 6.96-6.64 (m, 4H), 5.76-5.58 (m, 1H), 5.39 (t, J=5.5 Hz, 1H), 3.42-3.25 (m, 1H), 3.23-3.06 (m, 1H), 2.96-2.76 (m, 2H), 2.73-2.46 (m, 8H), 2.41-2.22 (m, 6H), 2.05-1.88 (m, 8H), 1.44 (m, J=13.7, 6.7 Hz, 1H), 0.93 (m, J=17.3, 6.6 Hz, 6H).

CY-P2 ESI 596.3 (M+H)⁺. ¹H NMR (400 MHz, MeOD) δ 7.51 (s, 1H), 7.42 (m, J=10.3, 2.1 Hz, 1H), 6.89 (m, J=7.0, 4.6 Hz, 4H), 5.62 (m, J=14.0, 9.4, 5.4 Hz, 2H), 3.43-3.30 (m, 1H), 3.23 (s, 1H), 2.93 (m, J=9.6, 4.9 Hz, 1H), 2.87-2.75 (m, 7H), 2.59 (m, J=14.9, 4.0 Hz, 1H), 2.44 (m, J=14.8, 10.1 Hz, 1H), 2.34-2.22 (m, 6H), 2.05-1.91 (m, 7H), 1.84-1.72 (m, 1H), 1.46-1.22 (m, 1H), 0.91 (m, J=6.6, 3.1 Hz, 6H).

4-53. (3S)-3-(4-fluoro-2',4',5',6'-tetramethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic acid (diastereomeric compounds CZ-P1 and CZ-P2)

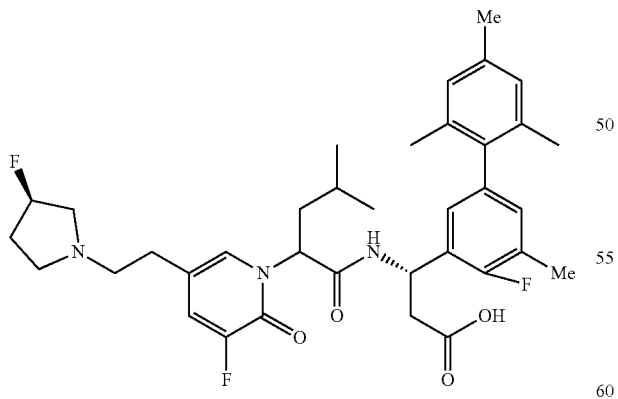

CZ-P1 ESI 640.2 (M+H)⁺. 1H NMR (400 MHz, MeOD) δ 7.50 (s, 1H), 7.41-7.31 (m, 1H), 6.95 (s, 2H), 6.85 (d, J=7.0 Hz, 1H), 6.79 (d, J=6.7 Hz, 1H), 5.70 (s, 1H), 5.49 (s, 1H), 5.24 (d, J=53.7 Hz, 1H), 3.26-3.00 (m, 5H), 2.88-2.56 (m, 4H), 2.41-2.13 (m, 9H), 2.07-1.90 (m, 5H), 1.85 (s, 3H), 1.53-1.26 (m, 1H), 1.05-0.80 (m, 6H).

CZ-P2 ESI 640.2 (M+H)⁺. 1H NMR (500 MHz, MeOD) δ 7.49 (s, 1H), 7.47-7.36 (m, 1H), 6.90 (d, J=8.8 Hz, 4H), 5.67 (t, J=7.7 Hz, 1H), 5.61-5.52 (m, 1H), 5.33 (d, J=54.6 Hz, 1H), 3.73-3.38 (m, 5H), 3.28 (s, 1H), 2.97-2.76 (m, 2H), 2.65-2.43 (m, 2H), 2.41-2.19 (m, 6H), 2.07-1.88 (m, 7H), 1.84-1.73 (m, 1H), 1.51-1.20 (m, 1H), 0.91 (d, J=6.5 Hz, 6H).

4-54. (3S)-3-(2-(5-(2-(dimethylamino)ethyl)-3-methyl-2-oxopyridin-1(2H)-yl)-4-methylpentanamido)-3-(4-fluoro-2',4',5',6'-tetramethyl-[1,1'-biphenyl]-3-yl)propanoic acid (diastereomeric compounds DA-P1 and DA-P2)

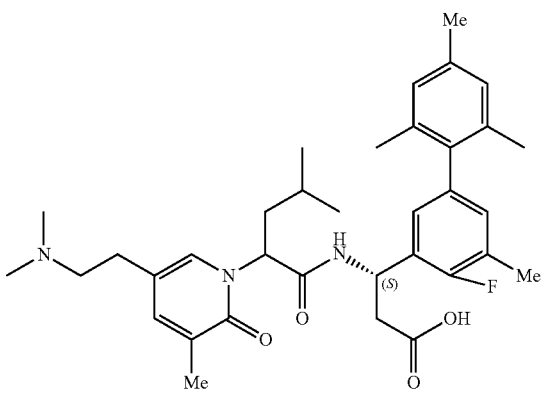

DA-P1 ESI 592.3 (M+H)⁺. ¹H NMR (400 MHz, MeOD) δ 7.35 (S, 1H), 7.32 (S, 1H), 6.80 (d, J=8.4 Hz, 2H), 6.73 (d, J=5.5 Hz, 1H), 6.59 (d, J=6.7 Hz, 1H), 5.48-5.46 (m, 1H), 5.23 (t, J=5.1 Hz, 1H), 3.08-2.98 (m, 1H), 2.68-2.67 (m, 2H), 2.56 (s, 6H), 2.51-2.35 (m, 3H), 2.25-2.11 (m, 6H), 1.97-1.74 (m, 11H), 1.36-1.24 (m, 1H), 0.88-0.76 (m, 6H).

DA-P2 ESI 592.3 (M+H)⁺. ¹H NMR (400 MHz, MeOD) δ 7.40 (s, 1H), 7.29 (s, 1H), 6.78-6.74 (m, 3H), 6.67 (d, J=7.0 Hz, 1H), 5.52-5.48 (m, 1H), 5.42-5.39 (m, 1H), 3.33-3.27 (m, 1H), 3.20-3.14 (m, 1H), 2.85-2.61 (m, 8H), 2.49-2.44 (m, 1H), 2.33-2.27 (m, 1H), 2.18 (s, 6H), 1.97-1.67 (m, 11H), 1.38-1.24 (m, 1H), 0.82-0.77 (m, 6H).

4-55. (3S)-3-(4,4'-difluoro-2',6'-dimethyl-5-(trifluoromethyl)-[1,1'-biphenyl]-3-yl)-3-(2-(5-(2-(dimethylamino)ethyl)-3-fluoro-2-oxopyridin-1(2H)-yl)-4-methylpentanamido)propanoic acid (diastereomeric compounds DB-P1 and DB-P2)

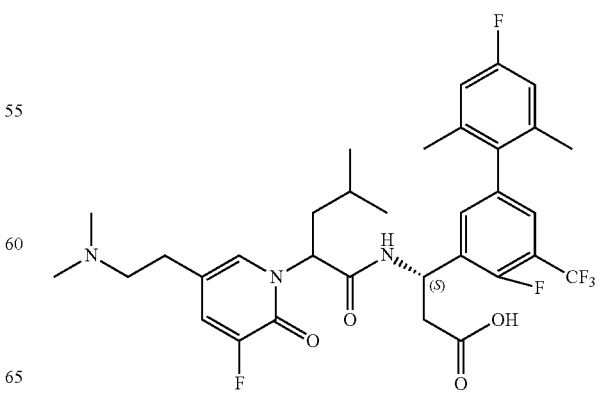

DB-P1 ESI 654.3 (M+H)+. 1H NMR (400 MHz, MeOD) δ 7.55 (s, 1H), 7.50-7.37 (m, 1H), 7.40-7.25 (m, 2H), 6.89 (d, J=9.6 Hz, 2H), 5.73-5.55 (m, 1H), 5.47 (t, J=5.9 Hz, 1H), 3.27-3.13 (m, 1H), 2.98-2.82 (m, 3H), 2.78 (s, 6H), 2.73-2.64 (m, 1H), 2.63-2.50 (m, 1H), 2.13-1.97 (m, 5H), 1.93 (s, 3H), 1.42 (s, 1H), 1.11-0.79 (m, 6H).

DB-P2 ESI 654.3 (M+H)+. 1H NMR (400 MHz, MeOD) δ 7.51 (s, 1H), 7.48-7.41 (m, 1H), 7.38 (t, J=6.0 Hz, 2H), 6.90 (d, J=9.6 Hz, 2H), 5.76-5.43 (m, 2H), 3.42 (d, J=10.1 Hz, 1H), 3.28 (d, J=12.8 Hz, 1H), 2.96 (d, J=9.5 Hz, 1H), 2.85 (d, J=7.2 Hz, 6H), 2.74-2.54 (m, 1H), 2.55-2.34 (m, 1H), 2.15-1.93 (m, 6H), 1.93-1.72 (m, 1H), 1.52-1.27 (m, 1H), 0.92 (t, J=6.5 Hz, 6H).

4-56. (3S)-3-(4-fluoro-2',4',5,6'-tetramethylbiphenyl-3-yl)-3-(2-(3-fluoro-5-(2-(3-fluoroazetidin-1-yl)ethyl)-2-oxopyridin-1(2H)-yl)-4-methylpentanamido)propanoic acid (diastereomeric compounds DC-P1 and DC-P2)

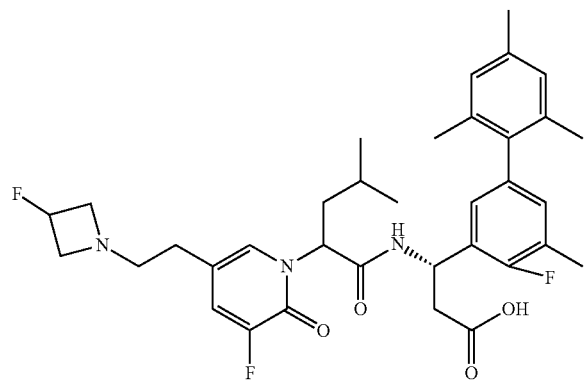 [SMILES: Cc1cc(C)c(-c2cc(C)c(F)c([C@H](CC(=O)O)NC(=O)C(CC(C)C)n3cc(CCN4CC(F)C4)cc(F)c3=O)c2)c(C)c1]

DC-P1 ESI 626.3 (M+H)+. 1H NMR (400 MHz, MeOD) δ 7.45-7.33 (m, 2H), 6.96-6.85 (m, 3H), 6.83-6.75 (m, 1H), 5.69 (t, J=8.1 Hz, 1H), 5.52-5.45 (m, 1H), 5.30-5.10 (m, 1H), 4.23-4.09 (m, 1H), 4.02-3.89 (m, 1H), 3.78-3.62 (m, 2H), 3.26-3.16 (m, 2H), 2.78-2.56 (m, 4H), 2.36-2.25 (m, 6H), 2.00-1.92 (m, 5H), 1.88 (s, 3H), 1.48-1.39 (m, 1H), 0.98-0.86 (m, 6H).

DC-P2 ESI 626.3 (M+H)+. 1H NMR (400 MHz, MeOD) δ 7.45-7.35 (m, 2H), 6.97-6.86 (m, 4H), 5.76-5.62 (m, 2H), 5.42-5.20 (m, 1H), 4.49-4.28 (m, 2H), 4.12-3.95 (m, 2H), 3.44-3.36 (m, 2H), 2.78-2.63 (m, 2H), 2.67-2.52 (m, 1H), 2.61-2.52 (m, 1H), 2.37-2.25 (m, 6H), 2.01-1.91 (m, 7H), 1.85-1.69 (m, 1H), 1.43-1.36 (m, 1H), 0.96-0.85 (m, 6H).

4-57. (3S)-3-(2'-chloro-4,4'-difluoro-5,6'-dimethyl-[1,1'-biphenyl]-3-yl)-3-(2-(3-fluoro-5-(2-(3-fluoroazetidin-1-yl)ethyl)-2-oxopyridin-1(2H)-yl)-4-methylpentanamido)propanoic acid (diastereomeric compounds DD-P1 and DD-P2)

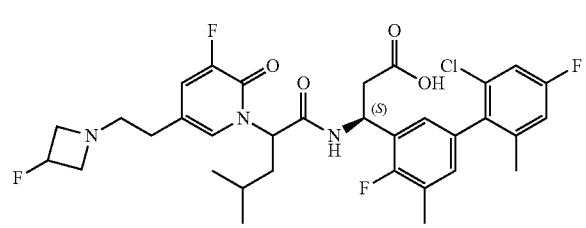

DD-P1 ESI 650.2 (M+H)+. 1H NMR (400 MHz, MeOD) δ 7.43-7.34 (m, 2H), 7.17-7.13 (m, 1H), 7.06-7.01 (m, 1H), 6.89-6.85 (m, 1H), 5.72-5.67 (m, 1H), 5.54-5.49 (m, 1H), 5.32-5.09 (m, 1H), 4.15-3.65 (m, 4H), 3.19-3.10 (m, 2H), 2.78-2.60 (m, 4H), 2.31 (s, 3H), 2.08-1.92 (m, 5H), 1.49-1.39 (m, 1H), 0.97-0.93 (m, 6H).

DD-P2 ESI 650.2 (M+H)+. 1H NMR (400 MHz, MeOD) δ 7.39-7.36 (m, 2H), 7.15 (d, J=8.5 Hz, 1H), 7.08-6.96 (m, 3H), 5.73-5.61 (m, 2H), 5.41-5.22 (m, 1H), 4.48-4.28 (m, 2H), 4.11-3.94 (m, 2H), 3.42-3.33 (m, 2H), 2.80-2.47 (m, 4H), 2.34 (d, J=1.8 Hz, 3H), 2.09 (d, J=2.7 Hz, 3H), 2.03-1.90 (m, 1H), 1.83-1.72 (m, 1H), 1.44-1.30 (m, 1H), 0.94-0.89 (m, 6H).

4-58. (3S)-3-(2-(3-fluoro-5-(2-(3-fluoroazetidin-1-yl)ethyl)-2-oxopyridin-1(2H)-yl)-4-methylpentanamido)-3-(2',4,4'-trifluoro-5,6'-dimethylbiphenyl-3-yl)propanoic acid (Diastereomeric Compounds DE-P1 and DE-P2)

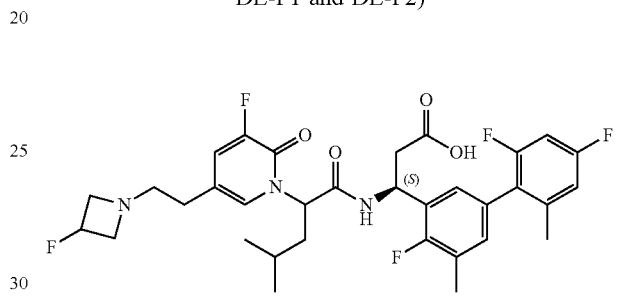

DE-P1 ESI 634.2 (M+H)+. 1H NMR (400 MHz, MeOD) δ 7.43 (s, 1H), 7.36 (d, J=10.3 Hz, 1H), 7.02 (d, J=6.8 Hz, 1H), 6.98-6.89 (m, 2H), 6.85 (t, J=9.2 Hz, 1H), 5.69 (t, J=8.1 Hz, 1H), 5.53-5.50 (m, 1H), 5.30-5.08 (m, 1H), 4.09-3.99 (m, 2H), 3.77-3.63 (m, 2H), 3.15-3.12 (m, 2H), 2.79-2.69 (m, 2H), 2.66-2.62 (m, 2H), 2.31 (s, 3H), 2.09 (s, 3H), 1.97 (t, J=7.6 Hz, 2H), 1.51-1.37 (m, 1H), 0.98-0.93 (m, 6H).

DE-P2 ESI 634.2 (M+H)+. 1H NMR (400 MHz, MeOD) δ 7.43-7.32 (m, 2H), 7.06 (d, J=6.7 Hz, 2H), 6.93 (d, J=9.3 Hz, 1H), 6.88-6.83 (m, 1H), 5.74-5.59 (m, 2H), 5.39-5.24 (m, 1H), 4.42-4.32 (m, 2H), 4.10-3.88 (m, 2H), 3.40-3.37 (m, 2H), 2.81-2.71 (m, 2H), 2.65-2.60 (m, 1H), 2.55-2.48 (m, 1H), 2.34 (d, J=1.6 Hz, 3H), 2.16 (s, 3H), 2.03-1.93 (m, 1H), 1.86-1.75 (m, 1H), 1.45-1.33 (m, 1H), 0.93-0.91 (m, 6H).

4-59. (3S)-3-(2-(5-(2-(azetidin-1-yl)ethyl)-2-oxo-4-(trifluoromethyl)pyridin-1(2H)-yl)-4-methylpentanamido)-3-(2'-cyclopropyl-4,4'-difluoro-5,6'-dimethyl-[1,1'-biphenyl]-3-yl)propanoic acid (diastereomeric compounds DF-P1 and DF-P2)

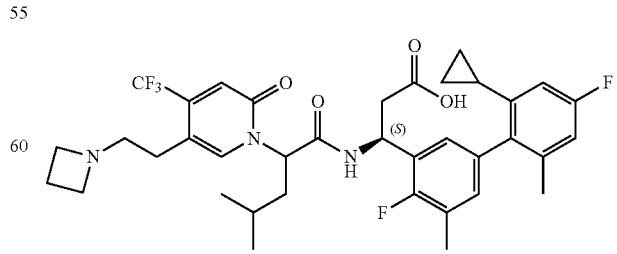

DF-P1 ESI 688.2 (M+H)+. 1H NMR (400 MHz, MeOD) δ 7.84 (s, 1H), 6.95 (dd, J=19.9, 7.2 Hz, 2H), 6.86-6.64 (m,

2H), 6.55-6.23 (m, 1H), 5.75-5.49 (m, 2H), 3.85 (t, J=7.7 Hz, 4H), 3.33 (m, J=3.2, 1.6 Hz, 2H), 3.13 (m, J=6.8 Hz, 2H), 2.90-2.58 (m, 2H), 2.51-2.21 (m, 5H), 2.01 (d, J=5.3 Hz, 4H), 1.87 (s, 1H), 1.40 (s, 2H), 1.07-0.85 (m, 6H), 0.75 (m, J=8.6, 3.5 Hz, 1H), 0.66-0.43 (m, 3H).

DF-P2 ESI 688.2 (M+H)$^+$. $^1$H NMR (400 MHz, MeOD) δ 7.74 (d, J=11.5 Hz, 1H), 6.94 (m, J=46.9, 28.6, 8.1 Hz, 4H), 6.50 (d, J=10.4 Hz, 1H), 5.78 (m, J=11.0, 3.1 Hz, 1H), 5.62 (m, J=7.3 Hz, 1H), 4.13 (m, J=8.0 Hz, 4H), 3.50-3.32 (m, 2H), 2.94 (d, J=16.3 Hz, 1H), 2.81 (d, J=7.7 Hz, 2H), 2.68-2.61 (m, 1H), 2.57-2.42 (m, 3H), 2.34 (d, J=1.1 Hz, 3H), 2.05-1.79 (m, 4H), 1.65 (m, J=13.9, 7.1 Hz, 1H), 1.50-1.30 (m, 2H), 0.88 (d, J=6.6 Hz, 6H), 0.74 (m, J=14.0, 7.3 Hz, 2H), 0.60 (m, J=6.4, 5.0 Hz, 2H).

4-60. (3S)-3-((3R)-2-(5-(2-(dimethylamino)ethyl)-2-oxo-4-(trifluoromethyl)pyridin-1(2H)-yl)-3-methylpentanamido)-3-(4-fluoro-2',4',5,6'-tetramethylbiphenyl-3-yl)propanoic acid (Diastereomeric Compounds DG-P1 and DG-P2)

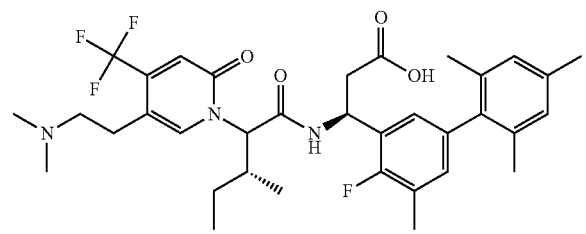

DG-P1 ESI 646.2 (M+H)$^+$. 1H NMR (400 MHz, MeOD) δ 7.94 (s, 1H), 6.89 (s, 1H), 6.82-6.75 (m, 3H), 6.66 (s, 1H), 5.65-5.53 (m, 1H), 5.33 (d, J=11.3 Hz, 1H), 3.05-2.83 (m, 5H), 2.82-2.62 (m, 6H), 2.40-2.18 (m, 8H), 2.03-1.88 (m, 3H), 1.78-1.67 (m, 1H), 1.63 (s, 3H), 1.38-1.21 (m, 1H), 1.07-0.96 (m, 3H), 0.75 (d, J=6.5 Hz, 3H).

DG-P2 ESI 646.2 (M+H)$^+$. 1H NMR (400 MHz, MeOD) δ 7.92 (s, 1H), 6.91-6.72 (m, 5H), 5.69-5.52 (m, 1H), 5.21 (d, J=10.9 Hz, 1H), 3.14-2.79 (m, 3H), 2.68 (s, 6H), 2.55-2.36 (m, 2H), 2.22-2.06 (m, H), 1.84 (d, J=3.6 Hz, 4H), 1.32-0.99 (m, 3H), 0.93-0.61 (m, 7H).

4-61. (3S)-3-(2',6'-dichloro-4-fluoro-4',5-dimethylbiphenyl-3-yl)-3-(2-(5-(2-(dimethylamino)ethyl)-2-oxo-4-(trifluoromethyl)pyridin-1(2H)-yl)-3-methylbutanamido)propanoic acid (Diastereomeric Compounds DH-P1 and DH-P2)

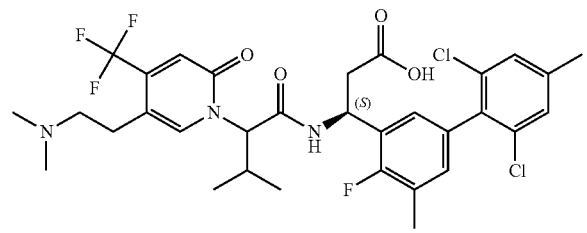

DH-P1 ESI 672.1 (M+H)$^+$. 1H NMR (400 MHz, MeOD) δ: 7.91 (s, 1H), 7.27 (d, J=6.0 Hz, 1H), 7.14 (d, J=5.2 Hz, 1H), 6.90 (t, J=6.0 Hz, 2H), 6.67 (d, J=5.6 Hz, 1H), 5.64-5.60 (m, 1H), 5.29 (d, J=11.2 Hz, 1H), 2.97-2.85 (m, 4H), 2.78-2.61 (m, 8H), 2.46-2.40 (m, 1H), 2.36 (s, 3H), 2.27 (s, 3H), 1.16 (d, J=6.4 Hz, 3H), 0.78 (d, J=6.4 Hz, 3H).

DH-P2 ESI 672.2 (M+H)$^+$. 1H NMR (400 MHz, MeOD) δ: 8.01 (s, 1H), 7.30 (s, 2H), 7.09-7.07 (m, 1H), 7.00 (d, J=7.2 Hz, 1H), 6.90 (s, 1H), 5.78-5.74 (m, 1H), 5.23 (d, J=11.2 Hz, 1H), 3.27-3.20 (m, 1H), 3.17-3.11 (m, 1H), 3.09-3.01 (m, 1H), 2.99-2.93 (m, 1H), 2.78 (s, 6H), 2.61-2.50 (m, 2H), 2.47-2.37 (m, 4H), 2.31 (d, J=1.2 Hz, 3H), 0.94 (d, J=6.4 Hz, 3H), 0.71 (d, J=6.8 Hz, 3H).

4-62. (3S)-3-(2-(5-(2-(azetidin-1-yl)ethyl)-2-oxo-4-(trifluoromethyl)pyridin-1(2H)-yl)-4-methylpentanamido)-3-(2'-cyclopropyl-4-fluoro-4',5,6'-trimethyl-[1,1'-biphenyl]-3-yl)propanoic acid (diastereomeric compounds DI-P1 and DI-P2)

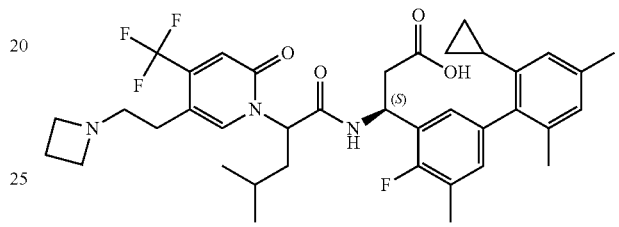

DI-P1 ESI 684.3 (M+H)$^+$. $^1$H NMR (400 MHz, MeOD) δ 7.84 (s, 1H), 6.97-6.78 (m, 4H), 6.58 (s, 1H), 5.69-5.59 (m, 2H), 3.97-3.94 (m, 4H), 3.26-3.21 (m, 2H), 2.86-2.81 (m, 2H), 2.72-2.68 (m, 2H), 2.46-2.38 (m, 2H), 2.29 (d, J=4.9 Hz, 6H), 2.03-1.97 (m, 3H), 1.85 (s, 2H), 1.48-1.31 (m, 2H), 0.98-0.91 (m, 6H), 0.67 (d, J=8.4 Hz, 1H), 0.59-0.44 (m, 3H).

DI-P2 ESI 684.3 (M+H)$^+$. $^1$H NMR (400 MHz, MeOD) δ 7.73 (d, J=10.5 Hz, 1H), 7.02-6.96 (m, 2H), 6.91 (s, 1H), 6.90 (s, 1H), 6.59 (s, 1H), 5.78-5.75 (m, 1H), 5.64-5.59 (m, 1H), 4.14-4.10 (m, 4H), 3.47-3.38 (m, 2H), 2.97-2.92 (m, 1H), 2.85-2.75 (m, 1H), 2.69-2.60 (m, 1H), 2.55-2.45 (m, 3H), 2.34 (s, 3H), 2.29 (s, 3H), 2.05-1.96 (m, 4H), 1.71-1.61 (m, 1H), 1.49-1.39 (m, 2H), 0.90 (d, J=6.6 Hz, 6H), 0.70-0.66 (m, 2H), 0.58-0.55 (m, 2H).

4-63. (3S)-3-(2',6'-dichloro-4-fluoro-5-methylbiphenyl-3-yl)-3-(2-(5-(2-(dimethylamino)ethyl)-2-oxo-4-(trifluoromethyl)pyridin-1(2H)-yl)-4-methylpentanamido)propanoic acid (Diastereomeric Compounds DJ-P1 and DJ-P2)

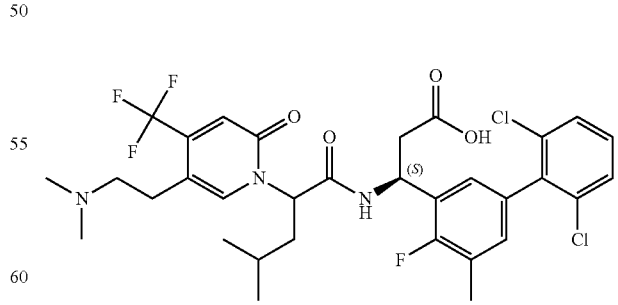

DJ-P1 ESI 672.2 (M+H)$^+$. 1H NMR (400 MHz, MeOD) δ: 7.89 (s, 1H), 7.46 (d, J=8.0 Hz, 1H), 7.39 (d, J=7.2 Hz, 1H), 7.32 (t, J=8.0 Hz, 1H), 7.00-6.96 (m, 2H), 6.75 (s, 1H), 5.72-5.68 (m, 1H), 5.60-5.56 (m, 1H), 3.10-3.01 (m, 2H), 2.94-2.92 (m, 2H), 2.74-2.65 (m, 8H), 2.27 (d, J=1.2 Hz,

3H), 2.01-1.93 (m, 2H), 1.47-1.41 (m, 1H), 0.95 (d, J=6.4 Hz, 3H), 0.93 (d, J=6.4 Hz, 3H).

DJ-P2 ESI 672.2 (M+H)⁺. 1H NMR (400 MHz, MeOD) δ: 7.91-5.88 (m, 1H), 7.47 (d, J=8.0 Hz, 2H), 7.35-7.31 (m, 1H), 7.08-7.02 (m, 2H), 6.89 (s, 1H), 5.78-5.74 (m, 1H), 5.64 (t, J=7.6 Hz, 1H), 3.27-3.15 (m, 2H), 3.06-2.95 (m, 2H), 2.80 (s, 6H), 2.65-2.60 (m, 1H), 2.55-2.49 (m, 1H), 2.32 (s, 3H), 1.99-1.92 (m, 1H), 1.71-1.64 (m, 1H), 1.41-1.34 (m, 1H), 0.86-0.84 (m, 6H).

4-64. (3S)-3-(2-(5-(2-(azetidin-1-yl)ethyl)-2-oxo-4-(trifluoromethyl)pyridin-1(2H)-yl)-4-methylpentanamido)-3-(4-fluoro-2',5,6'-trimethyl-4'-(trifluoromethyl)biphenyl-3-yl)propanoic acid (diastereomeric compounds DK-P1 and DK-P2)

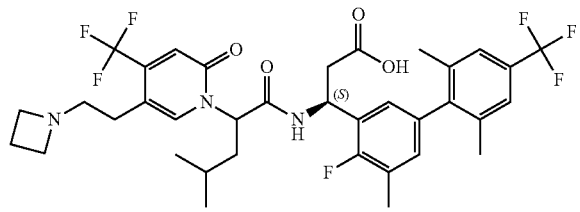

DK-P1 ESI 712.2 (M+H)⁺. 1H NMR (400 MHz, MeOD) δ: 7.88 (s, 1H), 7.39 (s, 1H), 7.35 (s, 1H), 6.91 (t, J=6.2 Hz, 2H), 6.70 (s, 1H), 5.66-5.57 (m, 2H), 4.04 (t, J=8.2 Hz, 4H), 3.29 (t, J=7.4 Hz, 2H), 2.84 (t, J=7.2 Hz, 2H), 2.78-2.67 (m, 2H), 2.48-2.40 (m, 2H), 2.30 (d, J=1.2 Hz, 3H), 2.08 (s, 3H), 2.03-1.99 (m, 2H), 1.91 (s, 3H), 1.47-1.40 (m, 1H),), 0.95 (d, J=6.8 Hz, 3H), 0.93 (d, J=6.4 Hz, 3H).

DK-P2 ESI 712.2 (M+H)⁺. 1H NMR (400 MHz, MeOD) δ: 7.74 (s, 1H), 7.41 (s, 2H), 6.98 (s, 1H), 6.96 (s, 1H), 6.90 (s, 1H), 5.79-5.76 (m, 1H), 5.60 (t, J=8.0 Hz, 1H), 4.15 (t, J=8.0 Hz, 4H), 3.48-3.42 (m, 1H), 3.38-3.33 (m, 1H), 2.98-2.91 (m, 1H), 2.84-2.77 (m, 1H), 2.69-2.64 (m, 1H), 2.55-2.45 (m, 3H), 2.35 (d, J=1.6 Hz, 3H), 2.09 (s, 3H), 2.08 (s, 3H), 2.03-1.96 (m, 1H), 1.69-1.62 (m, 1H), 1.46-1.36 (m, 1H), 0.89 (d, J=1.6 Hz, 3H), 0.87 (d, J=2.0 Hz, 3H).

4-65. (3S)-3-(2'-chloro-4-fluoro-5,6'-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid (diastereomeric compounds DL-P1 and DL-P2)

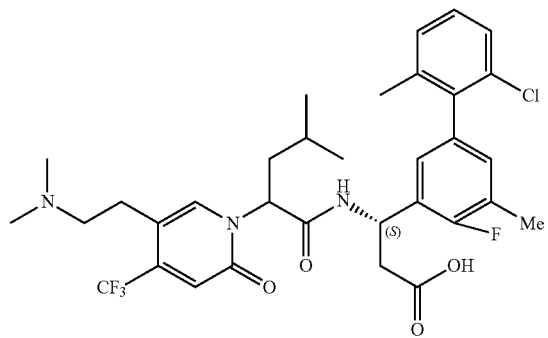

DL-P1 ESI 652.2 (M+H)⁺. 1H NMR (400 MHz, MeOD) δ 7.90 (d, J=4.5 Hz, 1H), 7.37-7.09 (m, 3H), 6.93 (m, J=10.9, 4.9 Hz, 2H), 6.75 (d, J=6.5 Hz, 1H), 5.68 (m, J=30.2, 23.4 Hz, 2H), 3.00 (d, J=50.0 Hz, 4H), 2.73 (d, J=14.3 Hz, 8H), 2.30 (s, 3H), 2.13-1.83 (m, 5H), 1.45 (d, J=6.4 Hz, 1H), 0.96 (m, J=12.9, 6.6, 2.5 Hz, 6H).

DL-P2 ESI 652.2 (M+H)⁺. 1H NMR (400 MHz, MeOD) δ 7.88 (s, 1H), 7.34-7.09 (m, 3H), 7.11-6.51 (m, 3H), 5.69 (m, J=21.6, 10.6, 4.3 Hz, 2H), 3.15 (s, 2H), 2.98 (s, 2H), 2.88-2.53 (m, 8H), 2.34 (s, 3H), 2.08 (d, J=5.6 Hz, 3H), 1.98-1.81 (m, 1H), 1.78 (s, 1H), 1.40 (s, 1H), 0.89 (m, J=6.4, 4.6 Hz, 6H).

4-66. (3S)-3-(2-(5-(2-(azetidin-1-yl)ethyl)-2-oxo-4-(trifluoromethyl)pyridin-1(2H)-yl)-4-methylpentanamido)-3-(2',4-difluoro-5,6'-dimethylbiphenyl-3-yl)propanoic acid (Diastereomeric Compounds DM-P1 and DM-P2)

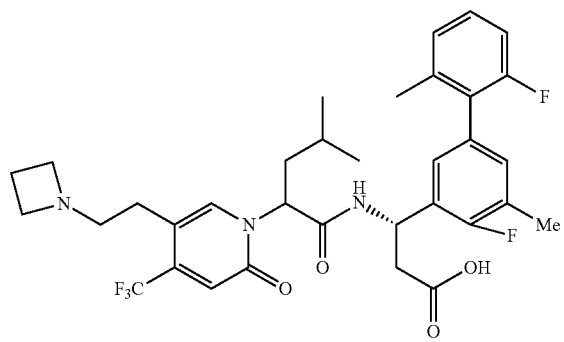 [SMILES: Cc1cc(-c2c(C)cccc2F)cc([C@H](CC(=O)O)NC(=O)C(CC(C)C)n2cc(CCN3CCC3)c(C(F)(F)F)cc2=O)c1F]

DM-P1 ESI 648.2 (M+H)⁺. 1H NMR (400 MHz, MeOD) δ 7.84 (s, 1H), 7.30-7.23 (m, 1H), 7.16-7.09 (m, 1H), 7.06-6.92 (m, 3H), 6.81 (s, 1H), 5.71-5.60 (m, 2H), 4.01 (t, J=8.1 Hz, 4H), 3.29 (s, 2H), 2.86 (t, J=6.8 Hz, 2H), 2.72 (d, J=6.6 Hz, 2H), 2.46-2.36 (m, 2H), 2.36-2.31 (m, 3H), 2.10 (s, 3H), 2.00 (t, J=7.6 Hz, 2H), 1.51-1.42 (m, 1H), 0.98-0.93 (m, 6H).

DM-P2 ESI 648.2 (M+H)⁺. 1H NMR (400 MHz, MeOD) δ 7.75 (s, 1H), 7.31-7.19 (m, 1H), 7.15-7.04 (m, 3H), 6.99 (t, J=8.8 Hz, 1H), 6.92 (s, 1H), 5.81-5.75 (m, 1H), 5.64 (t, J=7.6 Hz, 1H), 4.14 (t, J=8.0 Hz, 4H), 3.49-3.35 (m, 2H), 2.94 (d, J=15.7 Hz, 1H), 2.87-2.75 (m, 1H), 2.69-2.56 (m, 1H), 2.57-2.43 (m, 3H), 2.35 (d, J=1.5 Hz, 3H), 2.17 (d, J=8.1 Hz, 3H), 2.04-1.95 (m, 1H), 1.72-1.62 (m, 1H), 1.46-1.32 (m, 1H), 0.97-0.91 (m, 6H).

4-67. (3S)-3-(3',4-difluoro-2',4',5,6'-tetramethylbiphenyl-3-yl)-3-(2-(5-(2-(dimethylamino)ethyl)-2-oxo-4-(trifluoromethyl)pyridin-1(2H)-yl)-4-methylpentanamido)propanoic acid (Diastereomeric Compounds DN-P1 and DN-P2)

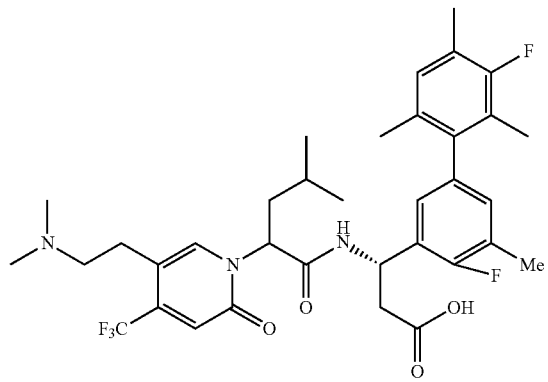 [SMILES: Cc1cc(-c2c(C)cc(C)c(F)c2C)cc([C@H](CC(=O)O)NC(=O)C(CC(C)C)n2cc(CCN(C)C)c(C(F)(F)F)cc2=O)c1F]

DN-P1 ESI 664.2 (M+H)⁺. ¹H NMR (400 MHz, MeOD) δ 7.85 (s, 1H), 7.01-6.79 (m, 4H), 5.78-5.58 (m, 2H), 3.29-3.07 (m, 2H), 3.04-2.89 (m, 2H), 2.81 (s, 6H), 2.70-2.42 (m, 2H), 2.33 (s, 3H), 2.26 (s, 3H), 2.13-1.83 (m, 7H), 1.81-1.60 (m, 1H), 1.52-1.30 (m, 1H), 1.02-0.81 (m, 6H).

DN-P2 ESI 664.2 (M+H)⁺. ¹H NMR (400 MHz, MeOD) δ 7.91 (s, 1H), 6.99-6.68 (m, 4H), 5.82-5.50 (m, 2H), 3.19-2.89 (m, 4H), 2.83-2.54 (m, 8H), 2.38-2.22 (m, 6H), 2.13-1.80 (m, 5H), 1.72 (d, J=14.7 Hz, 3H), 1.51-1.36 (m, 1H), 1.06-0.84 (m, 6H).

4-68. (3S)-3-(2-(5-(2-(azetidin-1-yl)ethyl)-2-oxo-4-(trifluoromethyl)pyridin-1(2H)-yl)-4-methylpentanamido)-3-(4'-cyano-4-fluoro-2',5,6'-trimethylbiphenyl-3-yl)propanoic acid (diastereomeric compounds DO-P1 and DO-P2)

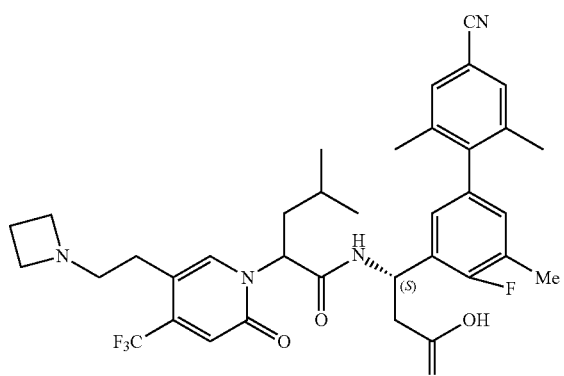

DO-P1 ESI 669.2 (M+H)⁺. 1H NMR (400 MHz, MeOD) δ 7.84 (s, 1H), 7.47 (d, J=10.3 Hz, 2H), 6.91 (d, J=6.7 Hz, 2H), 6.75 (s, 1H), 5.59 (d, J=7.7 Hz, 2H), 4.06 (t, J=8.1 Hz, 4H), 3.31-3.27 (m, 2H), 2.98-2.85 (m, 2H), 2.79-2.64 (m, 2H), 2.58-2.39 (m, 2H), 2.31 (s, 3H), 2.14-1.88 (m, 8H), 1.54-1.27 (m, 1H), 1.10-0.80 (m, 6H).

DO-P2 ESI 669.2 (M+H)⁺. 1H NMR (400 MHz, MeOD) δ 7.74 (s, 1H), 7.50 (s, 2H), 7.06-6.84 (m, 3H), 5.90-5.71 (m, 1H), 5.61 (t, J=7.6 Hz, 1H), 4.10 (s, 4H), 3.36 (s, 2H), 3.09-2.74 (m, 2H), 2.74-2.60 (m, 1H), 2.55-2.39 (m, 3H), 2.35 (s, 3H), 2.13-1.89 (m, 7H), 1.75-1.62 (m, 1H), 1.50-1.35 (m, 1H), 0.98-0.81 (m, 6H).

4-69. (3S)-3-(2'-cyano-4-fluoro-5,6'-dimethylbiphenyl-3-yl)-3-(2-(5-(2-(dimethylamino)ethyl)-2-oxo-4-(trifluoromethyl)pyridin-1(2H)-yl)-4-methylpentanamido)propanoic acid (Diastereomeric Compounds DP-P1 and DP-P2)

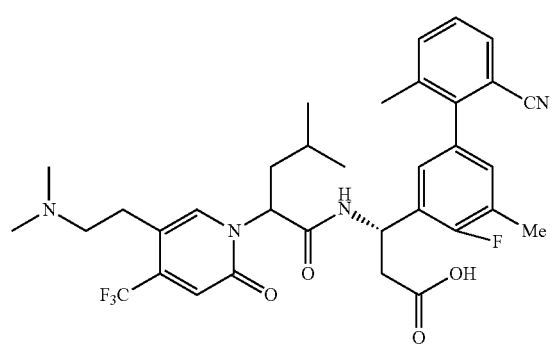 [SMILES: Cc1cc(-c2c(C)cccc2C#N)cc([C@H](CC(=O)O)NC(=O)C(CC(C)C)n2cc(CCN(C)C)c(C(F)(F)F)cc2=O)c1F]

DP-P1 ESI 643.2 (M+H)⁺. ¹H NMR (400 MHz, MeOD) δ 7.89 (s, 1H), 7.59 (s, 2H), 7.43 (t, J=7.7 Hz, 1H), 7.06 (s, 2H), 6.71 (d, J=26.7 Hz, 1H), 5.73 (s, 1H), 5.60 (d, J=7.3 Hz, 1H), 3.10 (s, 2H), 2.93 (d, J=8.3 Hz, 2H), 2.80-2.69 (m, 8H), 2.32 (s, 3H), 2.19 (s, 2H), 2.00 (s, 3H), 1.49-1.42 (m, 1H), 1.00-0.92 (m, 6H).

DP-P1 ESI 643.2 (M+H)⁺. ¹H NMR (400 MHz, MeOD) δ 7.81 (s, 1H), 7.66-7.52 (m, 2H), 7.45 (t, J=7.7 Hz, 1H), 7.13 (d, J=6.4 Hz, 2H), 6.90 (s, 1H), 5.77-5.59 (m, 2H), 3.23 (s, 2H), 3.01 (s, 2H), 2.83 (s, 6H), 2.69-2.53 (m, 1H), 2.58-2.49 (m, 1H), 2.37 (d, J=1.6 Hz, 3H), 2.19 (s, 3H), 2.05-1.96 (m, 1H), 1.81 (s, 1H), 1.42-1.36 (m, 1H), 0.99-0.91 (m, 6H).

4-70. (3S)-3-(2-(5-(2-(azetidin-1-yl)ethyl)-2-oxo-4-(trifluoromethyl)pyridin-1(2H)-yl)-4-methylpentanamido)-3-(4-fluoro-2'-methoxy-5,6'-dimethylbiphenyl-3-yl)propanoic acid (diastereomeric compounds DQ-P1 and DQ-P2)

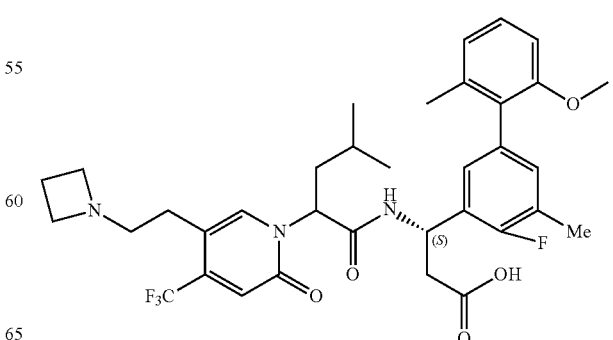

DQ-P1 ESI 660.2 (M+H)⁺. 1H NMR (400 MHz, MeOD) δ 7.82 (s, 1H), 7.21 (t, J=8.0 Hz, 1H), 6.99-6.82 (m, 5H), 5.70-5.62 (m, 2H), 4.01-3.96 (m, 4H), 3.66 (s, 3H), 3.30-3.27 (m, 2H), 2.88-2.85 (m, 2H), 2.71 (d, J=7.4 Hz, 2H), 2.45-2.39 (m, 2H), 2.29 (s, 3H), 2.02-1.93 (m, 5H), 1.45-1.38 (m, 1H), 0.97-0.93 (m, 6H).

DQ-P2 ESI 660.2 (M+H)⁺. 1H NMR (400 MHz, MeOD) δ 7.73 (s, 1H), 7.22 (t, J=8.0 Hz, 1H), 7.00-6.87 (m, 5H), 5.79-5.75 (m, 1H), 5.62 (t, J=7.6 Hz, 1H), 4.13 (t, J=7.9 Hz, 4H), 3.68 (s, 3H), 3.49-3.35 (m, 2H), 2.97-2.91 (d, J=16.1 Hz, 1H), 2.85-2.77 (m, 1H), 2.66-2.62 (m, 1H), 2.56-2.42 (m, 3H), 2.32 (d, J=1.7 Hz, 3H), 2.04 (s, 3H), 2.02-1.97 (m, 1H), 1.72-1.60 (m, 1H), 1.49-1.36 (m, 1H), 0.91 (d, J=6.5 Hz, 6H).

4-71. (3S)-3-(2'-cyclopropyl-4-fluoro-4',5,6'-trimethyl-[1,1'-biphenyl]-3-yl)-3-(2-(5-(2-(dimethylamino)ethyl)-4-methyl-2-oxopyridin-1(2H)-yl)-4-methylpentanamido)propanoic acid (diastereomeric compounds DR-P1 and DR-P2)

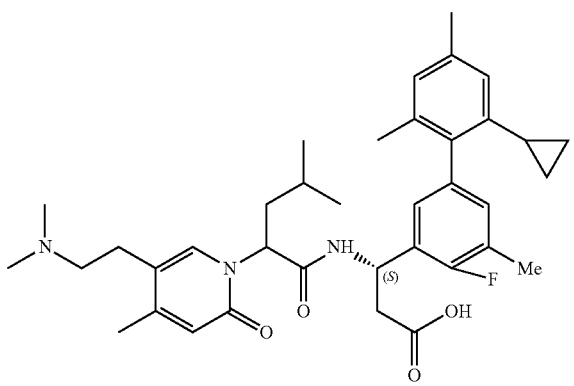

DR-P1 ESI 618.3 (M+H)⁺. ¹H NMR (400 MHz, MeOD) δ7.57 (d, J=1.8 Hz, 1), 6.91-6.84 (m, 3H), 6.57 (d, J=11.0 Hz, 1H), 6.38 (d, J=8.9 Hz, 1H), 5.59 (d, J=5.8 Hz, 1H), 5.46 (t, J=5.9 Hz, 1H), 3.22-3.06 (m, 2H), 2.87 (t, J=7.1 Hz, 2H), 2.74 (s, 6H), 2.71-2.56 (m, 2H), 2.27 (d, J=13.3 Hz, 9H), 2.04-1.87 (m, 5H), 1.48-1.38 (m, 2H), 0.95-0.89 (m, 6H), 0.72-0.67 (m, 1H), 0.63-0.55 (m, 1H), 0.53-0.48 (m, 2H).

DR-P2 ESI 618.3 (M+H)⁺. ¹H NMR (400 MHz, MeOD) δ 7.54 (d, J=10.5 Hz, 1H), 6.98-6.89 (m, 2H), 6.89 (s, 1H), 6.59 (s, 1H), 6.44 (d, J=5.1 Hz, 1H), 5.65-5.56 (m, 2H), 3.34-3.26 (m, 2H), 3.20-3.13 (m, 2H), 2.94-2.88 (m, 2H), 2.81 (d, J=2.0 Hz, 6H), 2.64-2.57 (m, 1H), 2.48-2.41 (m, 1H), 2.32-2.246 (m, 9H), 1.99-1.92 (m, 4H), 1.81-1.74 (m, 1H), 1.49-1.33 (m, 1H), 0.92-0.85 (m, 6H), 0.68-0.63 (m, 2H), 0.58-0.51 (m, 2H).

4-72. (3S)-3-(4'-cyclopropyl-4-fluoro-2',5,6'-trimethyl-[1,1'-biphenyl]-3-yl)-3-(2-(5-(2-(dimethylamino)ethyl)-4-methyl-2-oxopyridin-1(2H)-yl)-4-methylpentanamido)propanoic acid (diastereomeric compounds DS-P1 and DS-P2)

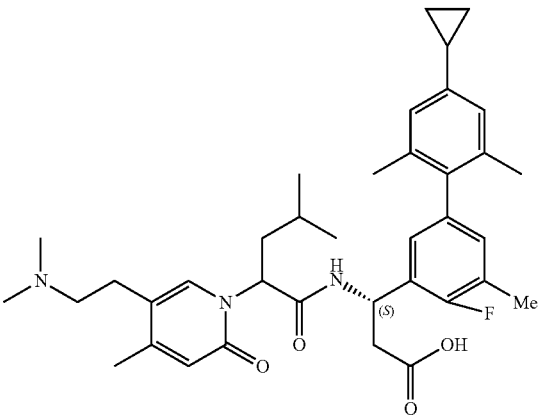

DS-P1 ESI 618.3 (M+H)⁺. ¹H NMR (400 MHz, MeOD) δ 7.46 (s, 1H), 6.84-6.65 (m, 3H), 6.45 (d, J=11.2 Hz, 1H), 6.27 (d, J=8.7 Hz, 1H), 5.48-5.46 (m, 1H), 5.33 (d, J=5.6 Hz, 1H), 3.15-2.95 (m, 2H), 2.78-2.74 (m, 3H), 2.60 (d, J=25.4 Hz, 6H), 2.58-2.40 (m, 2H), 2.17 (s, 6H), 2.13 (s, 3H), 1.95-1.73 (m, 5H), 1.34-1.28 (m, 2H), 0.86-0.73 (m, 6H), 0.62-0.32 (m, 4H).

DS-P2 ESI 618.3 (M+H)⁺. ¹H NMR (400 MHz, MeOD) δ 7.43 (s, 1H), 7.40 (s, 1H), 6.84 (t, J=6.2 Hz, 2H), 6.77 (s, 1H), 6.47 (s, 1H), 6.32 (d, J=5.5 Hz, 1H), 5.52-5.44 (m, 2H), 3.09-3.06 (m, 1H), 2.88-2.67 (m, 8H), 2.51-2.45 (m, 1H), 2.37-2.29 (m, 1H), 2.24-2.09 (m, 9H), 1.85-1.81 (m, 4H), 1.70-1.59 (m, 1H), 1.39-1.16 (m, 2H), 0.78-0.76 (m, 6H), 0.54 (t, J=7.6 Hz, 2H), 0.45 (d, J=4.5 Hz, 2H).

4-73. (3S)-3-(2'-chloro-4,4'-difluoro-5,6'-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid (diastereomeric compounds DT-P1 and DT-P2)

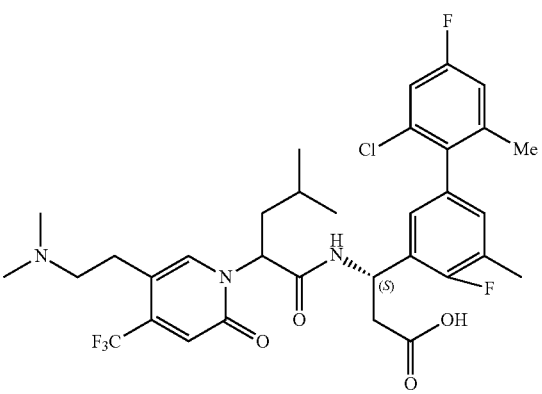

DT-P1 ESI 670.2 (M+H)⁺. 1H NMR (400 MHz, MeOD) δ 7.90 (d, J=3.1 Hz, 1H), 7.14-6.92 (m, 4H), 6.76 (d, J=5.6 Hz, 1H), 5.72-5.65 (m, 1H), 5.60-5.56 (m, 1H), 3.10-2.87

(m, 4H), 2.76-2.66 (m, 8H), 2.30 (s, 3H), 2.09-1.91 (m, 5H), 1.47-1.41 (m, 1H), 1.00-0.92 (m, 6H).

DT-P2 ESI 670.2 (M+H)⁺. ¹H NMR (400 MHz, MeOD) δ 7.84 (s, 1H), 7.16-7.12 (m, 1H), 7.07-6.95 (m, 3H), 6.91 (d, J=2.7 Hz, 1H), 5.74-5.59 (m, 2H), 3.32-3.21 (m, 2H), 3.03-2.99 (m, 2H), 2.84 (d, J=2.9 Hz, 6H), 2.67-2.49 (m, 2H), 2.34 (d, J=1.6 Hz, 3H), 2.03-1.90 (m, 1H), 1.76-1.67 (m, 1H), 1.46-1.37 (m, 1H), 0.92-0.89 (m, 6H).

4-74. (3S)-3-(2',6'-dichloro-4-fluoro-4',5-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid (diastereomeric compounds DU-P1 and DU-P2)

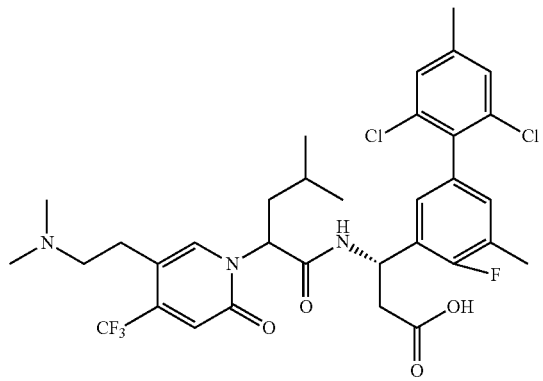

DU-P1 ESI 686.1 (M+H)⁺. ¹H NMR (400 MHz, MeOD) δ 7.90 (s, 1H), 7.31 (s, 1H), 7.23 (s, 1H), 7.02-6.91 (m, 2H), 6.76 (s, 1H), 5.76-5.66 (m, 1H), 5.63-5.53 (m, 1H), 3.15-3.04 (m, 2H), 2.94 (t, J=11.0 Hz, 2H), 2.80-2.66 (m, 8H), 2.38 (s, 3H), 2.29 (d, J=1.3 Hz, 3H), 2.04-1.92 (m, 2H), 1.51-1.42 (m, 1H), 1.01-0.90 (m, 6H).

DU-P2 ESI 686.1 (M+H)⁺. ¹H NMR (400 MHz, MeOD) δ 7.88 (s, 1H), 7.32 (s, 2H), 7.09-6.99 (m, 2H), 6.91 (s, 1H), 5.79-5.71 (m, 1H), 5.65 (t, J=7.7 Hz, 1H), 3.30-3.15 (m, 2H), 3.00 (t, J=6.8 Hz, 2H), 2.81 (s, 6H), 2.67-2.50 (m, 2H), 2.39 (s, 3H), 2.33 (d, J=1.5 Hz, 3H), 2.02-1.92 (m, 1H), 1.73-1.65 (m, 1H), 1.44-1.36 (m, 1H), 0.91-0.85 (m, 6H).

4-75. (3S)-3-(2-(5-(2-(dimethylamino)ethyl)-4-methyl-2-oxopyridin-1(2H)-yl)-4-methylpentanamido)-3-(4-fluoro-2',5',6'-trimethyl-4'-(trifluoromethyl)biphenyl-3-yl)propanoic acid (diastereomeric compounds DV-P1 and DV-P2)

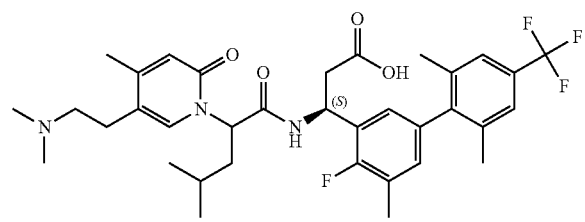

DV-P1 ESI 646.3 (M+H)⁺. ¹H NMR (400 MHz, MeOD) δ: 7.59 (s, 1H), 7.40 (s, 1H), 7.38 (s, 1H), 6.89 (d, J=6.8 Hz, 1H), 6.84 (d, J=6.4 Hz, 1H), 6.28 (s, 1H), 5.55 (t, J=5.6 Hz, 1H), 5.49 (t, J=6.0 Hz, 1H), 3.16-3.08 (m, 2H), 2.87 (t, J=7.2 Hz, 2H), 2.78 (s, 6H), 2.73-2.68 (m, 1H), 2.65-2.60 (m, 1H), 2.31 (s, 3H), 2.25 (s, 3H), 2.08 (s, 3H), 2.01-1.90 (m, 5H), 1.45-1.38 (m, 1H), 0.94 (d, J=6.4 Hz, 3H), 0.91 (d, J=6.8 Hz, 3H).

DV-P2 ESI 646.3 (M+H)⁺. ¹H NMR (400 MHz, MeOD) δ: 7.55 (s, 1H), 7.41 (s, 2H), 6.95-6.93 (m, 1H), 6.90 (d, J=6.4 Hz, 1H), 6.41 (s, 1H), 5.63-5.60 (m, 1H), 5.58-5.56 (m, 1H), 3.38-3.36 (m, 1H), 3.25-3.19 (m, 1H), 2.95-2.90 (m, 2H), 2.85 (s, 6H), 2.64-2.59 (m, 1H), 2.50-2.44 (m, 1H), 2.34 (d, J=1.6 Hz, 3H), 2.26 (s, 3H), 2.08 (s, 6H), 2.00-1.93 (m, 1H), 1.83-1.76 (m, 1H), 1.42-1.35 (m, 1H), 0.89 (t, J=6.4 Hz, 6H).

4.76. (3S)-3-(4'-cyclopropyl-4-fluoro-2',5,6'-trimethyl-[1,1'-biphenyl]-3-yl)-3-(2-(5-(2-(dimethylamino)ethyl)-3-fluoro-4-methyl-2-oxopyridin-1(2H)-yl)-4-methylpentanamido)propanoic acid (diastereomeric compounds DW-P1 and DW-P2)

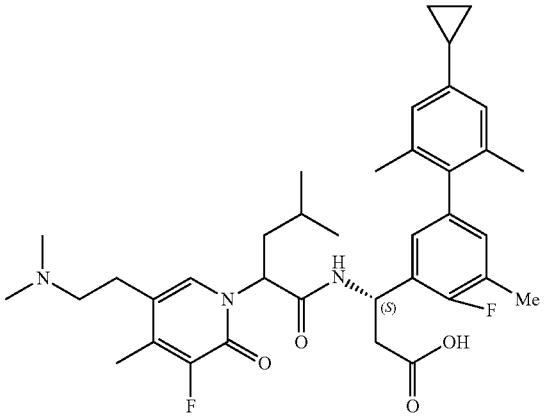

DW-P1 ESI 636.3 (M+H)⁺. ¹H NMR (400 MHz, MeOD) δ 7.47 (s, 1H), 6.94-6.78 (m, 3H), 6.57 (d, J=12.7 Hz, 1H), 5.74-5.57 (m, 1H), 5.46 (t, J=5.9 Hz, 1H), 3.25-3.10 (m, 2H), 2.92 (t, J=6.9 Hz, 2H), 2.75 (s, 6H), 2.70-2.52 (m, 2H), 2.30-2.25 (m, 9H), 1.99-1.88 (m, 5H), 1.46-1.39 (m, 2H), 0.97-0.86 (m, 6H), 0.72-0.43 (m, 4H).

DW-P2 ESI 636.3 (M+H)⁺. ¹H NMR (400 MHz, MeOD) δ 7.42 (d, J=11.3 Hz, 1H), 6.97 (t, J=8.2 Hz, 2H), 6.89 (s, 1H), 6.59 (s, 1H), 5.72-5.52 (m, 2H), 3.32-3.22 (m, 2H), 2.98-2.90 (m, 2H), 2.85 (s, 6H), 2.67-2.38 (m, 2H), 2.32-2.25 (m, 9H), 2.00-1.98 (m, 4H), 1.83-1.67 (m, 1H), 1.51-1.26 (m, 2H), 0.90 (d, J=6.6 Hz, 6H), 0.70-0.48 (m, 4H).

4-77. (3S)-3-(4-fluoro-2',4',5,6'-tetramethyl-[1,1'-biphenyl]-3-yl)-3-(2-(3-fluoro-5-(2-(3-methoxyazetidin-1-yl)ethyl)-4-methyl-2-oxopyridin-1(2H)-yl)-4-methylpentanamido)propanoic acid (diastereomeric compounds DX-P1 and DX-P2)

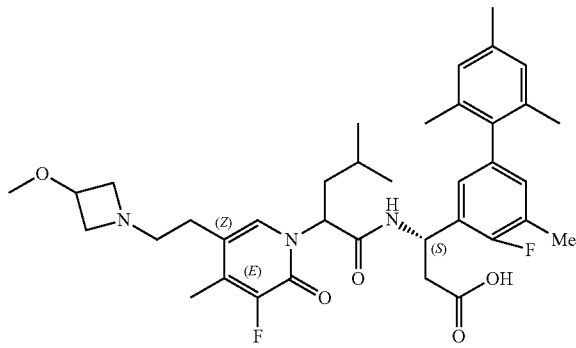

DX-P1 ESI 652.3 (M+H)⁺. ¹H NMR (400 MHz, MeOD) δ 7.26 (s, 1H), 6.84-6.68 (m, 4H), 5.54-5.45 (m, 1H), 5.41 (t, J=6.3 Hz, 1H), 4.14-3.93 (m, 3H), 3.64-3.54 (m, 1H), 3.52-3.50 (m, 1H), 3.25-3.16 (m, 5H), 2.74-2.55 (m, 4H), 2.18 (s, 6H), 2.12 (d, J=4.0 Hz, 3H), 1.88-1.74 (m, 8H), 1.29-1.25 (m, 1H), 0.83-0.78 (m, 6H).

DX-P2 ESI 652.3 (M+H)⁺. ¹H NMR (400 MHz, MeOD) δ 7.20 (s, 1H), 6.85-6.72 (m, 4H), 5.61-5.43 (m, 2H), 4.36-4.08 (m, 3H), 3.84-3.61 (m, 2H), 3.32-3.22 (m, 5H), 2.82-2.78 (m, 1H), 2.64-2.56 (m, 1H), 2.51-2.47 (m, 1H), 2.39-2.32 (m, 1H), 2.23-2.13 (m, 6H), 2.10 (d, J=2.7 Hz, 3H), 1.90-1.73 (m, 8H), 1.68-1.51 (m, 1H), 1.32-1.20 (m, 1H), 0.79-0.74 (m, 6H).

4-78. (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',5,5'-trimethylbiphenyl-3-yl)propanoic acid (Diastereomeric Compounds DY-P1 and DY-P2)

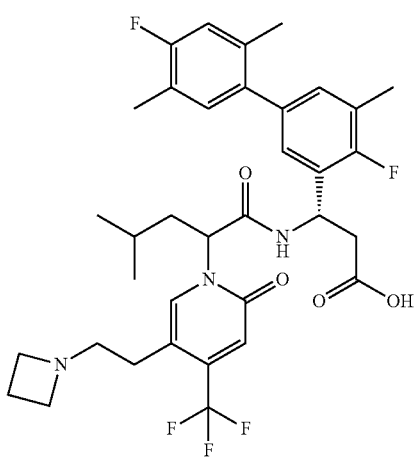 [SMILES: Cc1cc(-c2cc(C)c(F)c([C@H](CC(=O)O)NC(=O)C(CC(C)C)n3cc(CCN4CCC4)c(C(F)(F)F)cc3=O)c2)c(C)cc1F]

DY-P1 ESI 662.2 (M+H)⁺. 1H NMR (400 MHz, MeOD) δ 7.84 (s, 1H), 7.03-7.00 (m, 3H), 6.93 (d, J=10.6 Hz, 1H), 6.81 (s, 1H), 5.70-5.63 (m, 1H), 5.59 (t, J=6.7 Hz, 1H), 4.02 (t, J=8.2 Hz, 4H), 3.30 (s, 2H), 2.86 (t, J=6.9 Hz, 2H), 2.71 (d, J=6.8 Hz, 2H), 2.42-2.39 (m, 2H), 2.30 (d, J=1.4 Hz, 3H), 2.25 (s, 3H), 2.15 (s, 3H), 2.02-2.19 (m, 2H), 1.48-1.39 (m, 1H), 0.96-0.90 (m, 6H).

DY-P2 ESI 662.2 (M+H)⁺. 1H NMR (400 MHz, MeOD) δ 7.73 (s, 1H), 7.09-7.06 (m, 2H), 7.04 (d, J=8.1 Hz, 1H), 6.99-6.88 (m, 2H), 5.75-5.70 (m, 1H), 5.64 (t, J=7.7 Hz, 1H), 4.15 (t, J=8.0 Hz, 4H), 3.42-3.40 (m, 2H), 2.95 (d, J=16.2 Hz, 1H), 2.82-2.80 (m, 1H), 2.64-2.60 (m, 1H), 2.55-2.43 (m, 3H), 2.34 (s, 3H), 2.26 (s, 3H), 2.20 (s, 3H), 2.04-1.97 (m, 1H), 1.71-1.68 (m, 1H), 1.43-1.38 (m, 1H), 0.92 (t, J=6.3 Hz, 6H).

4-79. (3S)-3-(2-(5-(2-(azetidin-1-yl)ethyl)-2-oxo-4-(trifluoromethyl)pyridin-1(2H)-yl)-4-methylpentanamido)-3-(4-fluoro-4'-methoxy-2',5,5'-trimethyl-[1,1'-biphenyl]-3-yl)propanoic acid (diastereomeric compounds DZ-P1 and DZ-P2)

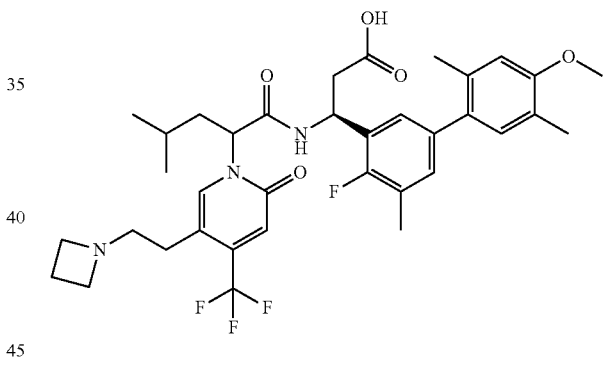

DZ-P1 ESI 674.3 (M+H)⁺. ¹H NMR (400 MHz, MeOD) δ 7.83 (s, 1H), 7.03 (t, J=7.3 Hz, 2H), 6.90 (s, 1H), 6.83 (s, 1H), 6.78 (s, 1H), 5.67 (t, J=8.0 Hz, 1H), 5.59 (t, J=6.7 Hz, 1H), 3.99 (t, J=8.2 Hz, 4H), 3.86 (s, 3H), 3.29 (d, J=3.5 Hz, 2H), 2.85 (t, J=6.7 Hz, 2H), 2.71 (d, J=6.7 Hz, 2H), 2.44-2.34 (m, 2H), 2.29 (d, J=1.6 Hz, 3H), 2.18 (s, 6H), 2.02 (t, J=7.5 Hz, 2H), 1.46-1.39 (m, 1H), 0.96 (t, J=6.2 Hz, 6H).

DZ-P2 ESI 674.3 (M+H)⁺. ¹H NMR (400 MHz, MeOD) δ 7.74 (s, 1H), 7.14-7.03 (m, 2H), 6.93 (s, 2H), 6.80 (s, 1H), 5.80-5.71 (m, 1H), 5.64 (t, J=7.6 Hz, 1H), 4.14 (t, J=8.0 Hz, 4H), 3.86 (s, 3H), 3.50-3.36 (m, 2H), 2.95 (d, J=15.7 Hz, 1H), 2.87-2.78 (m, 1H), 2.67-2.60 (m, 1H), 2.57-2.42 (m, 3H), 2.33 (d, J=1.6 Hz, 3H), 2.20 (d, J=19.2 Hz, 6H), 2.05-1.96 (m, 1H), 1.73-1.65 (m, 1H), 1.47-1.37 (m, 1H), 0.92 (t, J=6.7 Hz, 6H).

399

4-80. (3S)-3-(2-(5-(2-(azetidin-1-yl)ethyl)-2-oxo-4-(trifluoromethyl)pyridin-1(2H)-yl)-4-methylpentanamido)-3-(4'-cyano-4,5'-difluoro-2',5-dimethylbiphenyl-3-yl)propanoic acid (diastereomeric compounds EA-P1 and EA-P2)

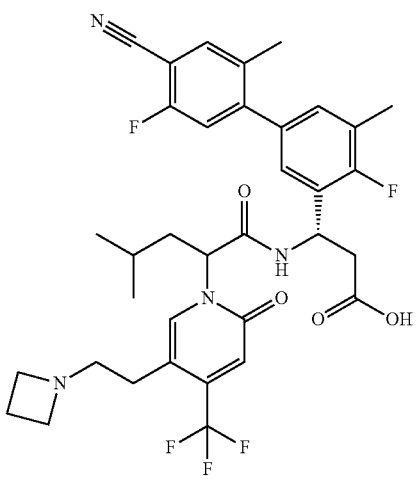 [SMILES: Cc1cc(C#N)c(F)cc1-c1cc(C)c(F)c([C@H](CC(=O)O)NC(=O)C(CC(C)C)n2cc(CCN3CCC3)c(C(F)(F)F)cc2=O)c1]

EA-P1 ESI 673.3 (M+H)+. $^1$H NMR (500 MHz, MeOD) δ 7.86 (s, 1H), 7.67 (d, J=6.6 Hz, 1H), 7.24-7.07 (m, 3H), 6.79 (d, J=7.4 Hz, 1H), 5.78-5.50 (m, 2H), 4.10 (t, J=8.1 Hz, 4H), 3.41-3.34 (m, 2H), 2.92-2.65 (m, 4H), 2.61-2.40 (m, 2H), 2.32 (s, 3H), 2.23 (s, 3H), 2.15-1.86 (m, 2H), 1.54-1.38 (m, 1H), 0.97 (t, J=6.6 Hz, 6H).

EA-P2 ESI 673.3 (M+H)+. $^1$H NMR (500 MHz, MeOD) δ 7.75-7.59 (m, 2H), 7.25-7.16 (m, 3H), 6.93 (s, 1H), 5.80-5.55 (m, 2H), 4.16 (t, J=7.9 Hz, 4H), 3.50-3.37 (m, 2H), 3.04-2.77 (m, 2H), 2.72-2.43 (m, 4H), 2.36 (s, 3H), 2.28 (s, 3H), 2.06-1.96 (m, 1H), 1.83-1.64 (m, 1H), 1.53-1.29 (m, 1H), 0.97-0.89 (m, 6H).

4-81. (3S)-3-(2-(5-(2-(azetidin-1-yl)ethyl)-2-oxo-4-(trifluoromethyl)pyridin-1(2H)-yl)-4-methylpentanamido)-3-(5'-cyano-4,4'-difluoro-2',5-dimethyl-[1,1'-biphenyl]-3-yl)propanoic acid (diastereomeric compounds EB-P1 and EB-P2)

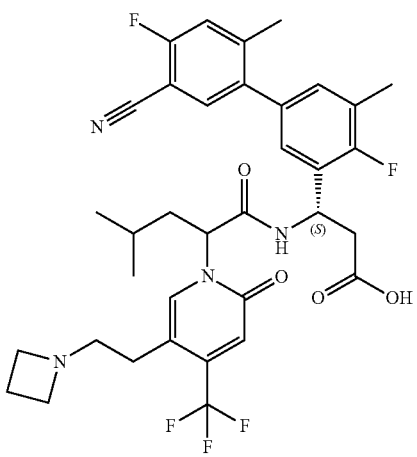

EB-P1 ESI 673.3 (M+H)+. $^1$H NMR (400 MHz, MeOD) δ 7.85 (s, 1H), 7.55 (d, J=6.7 Hz, 1H), 7.32 (d, J=10.3 Hz, 1H), 7.10 (d, J=6.4 Hz, 2H), 6.81 (s, 1H), 5.65-5.55 (m, 2H), 4.03 (t, J=8.0 Hz, 4H), 3.32-3.26 (m, 2H), 2.84 (t, J=7.0 Hz, 2H), 2.78-2.67 (m, 2H), 2.51-2.36 (m, 2H), 2.36-2.25 (m, 6H), 2.14-1.92 (m, 2H), 1.52-1.36 (m, 1H), 0.97 (t, J=6.1 Hz, 6H).

EB-P2 ESI 673.3 (M+H)+. $^1$H NMR (400 MHz, MeOD) δ 7.74 (s, 1H), 7.57 (d, J=6.7 Hz, 1H), 7.34 (d, J=10.2 Hz, 1H), 7.14 (d, J=6.7 Hz, 2H), 6.93 (s, 1H), 5.76-5.71 (m, 1H), 5.63 (t, J=7.7 Hz, 1H), 4.13 (t, J=7.9 Hz, 4H), 3.49-3.35 (m, 2H), 3.00-2.87 (m, 1H), 2.88-2.75 (m, 1H), 2.68-2.60 (m, 1H), 2.57-2.42 (m, 3H), 2.39-2.28 (m, 6H), 2.05-1.95 (m, 1H), 1.79-1.63 (m, 1H), 1.48-1.37 (m, 1H), 0.92 (t, J=6.6 Hz, 6H).

4-82. (3S)-3-(2-(5-(2-(dimethylamino)ethyl)-3-fluoro-2-oxo-4-(trifluoromethyl)pyridin-1(2H)-yl)-4-methylpentanamido)-3-(4-fluoro-2',5,6'-trimethylbiphenyl-3-yl)propanoic acid (Diastereomeric Compounds EC-P1 and EC-P2)

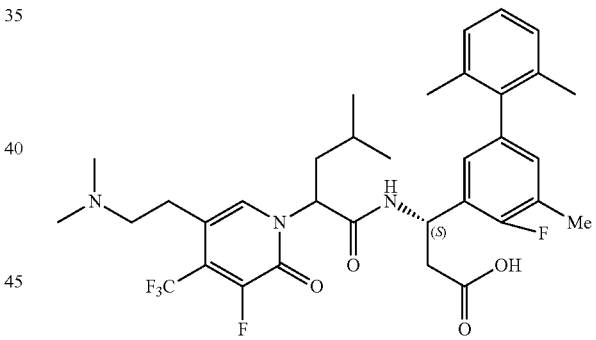

EC-P1 ESI 650.2 (M+H)+. 1H NMR (500 MHz, MeOD) δ 7.70 (s, 1H), 7.12 (t, J=7.5 Hz, 1H), 7.08-7.02 (m, 2H), 6.89-6.85 (m, 2H), 5.69 (t, J=8.0 Hz, 1H), 5.61-5.54 (m, 1H), 3.09-3.02 (m, 2H), 2.99 (d, J=7.3 Hz, 2H), 2.74-2.70 (m, 8H), 2.30 (s, 3H), 2.05-1.94 (m, 5H), 1.86 (s, 3H), 1.44 (m, 1H), 0.94-0.90 (m, 6H).

EC-P2 ESI 650.2 (M+H)+. 1H NMR (500 MHz, MeOD) δ 7.62 (s, 1H), 7.18-7.07 (m, 3H), 6.94 (t, J=6.8 Hz, 2H), 5.73-5.70 (m, 1H), 5.61 (t, J=7.6 Hz, 1H), 3.31-3.18 (m, 2H), 3.11-2.95 (m, 2H), 2.84 (s, 6H), 2.65-2.60 (m, 1H), 2.52-2.48 (m, 1H), 2.35-2.32 (m, 3H), 2.08-1.94 (m, 7H), 1.74-1.64 (m, 1H), 1.42-1.39 (m, 1H), 0.90 (d, J=6.6 Hz, 6H).

4-83. (3S)-3-(2-(5-(2-(dimethylamino)ethyl)-3-fluoro-2-oxo-4-(trifluoromethyl)pyridin-1(2H)-yl)-4-methylpentanamido)-3-(4-fluoro-2',4',5,6'-tetramethylbiphenyl-3-yl)propanoic acid (diastereomeric compounds ED-P1 and ED-P2)

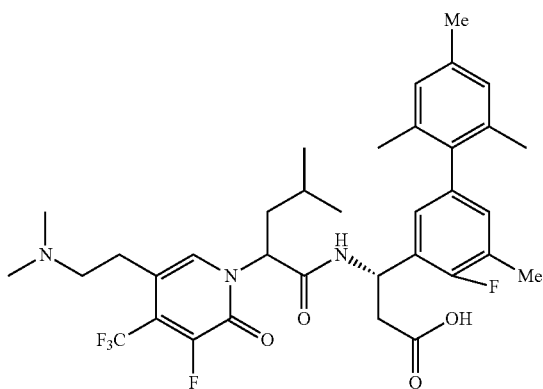 [SMILES: Cc1cc(C)c(-c2cc(C)c(F)c([C@H](CC(=O)O)NC(=O)C(CC(C)C)n3cc(CCN(C)C)c(C(F)(F)F)c(F)c3=O)c2)c(C)c1]

ED-P1 ESI 664.2 (M+H)⁺. 1H NMR (400 MHz, MeOD) δ 7.69 (s, 1H), 6.96-6.77 (m, 4H), 5.72-5.66 (m, 1H), 5.56 (s, 1H), 3.09-2.90 (m, 4H), 2.71 (d, J=4.8 Hz, 8H), 2.29 (s, 6H), 2.08-1.91 (m, 5H), 1.82 (s, 3H), 1.44 (s, 1H), 0.95-0.90 (m, 6H).

ED-P2 ESI 664.2 (M+H)⁺. 1H NMR (400 MHz, MeOD) δ 7.62 (d, J=12.1 Hz, 1H), 6.97-6.85 (m, 4H), 5.72-5.69 (m, 1H), 5.62 (t, J=7.6 Hz, 1H), 3.22 (qd, J=13.0, 6.1 Hz, 2H), 3.13-2.89 (m, 2H), 2.82 (s, 6H), 2.64-2.60 (m, 1H), 2.49-2.45 (m, 1H), 2.36-2.23 (m, 6H), 2.04-1.90 (m, 7H), 1.74-1.64 (m, 1H), 1.41-1.38 (m, 1H), 0.90-0.86 (m, 6H).

4-84. (3S)-3-(4,4'-difluoro-2',5,6'-trimethylbiphenyl-3-yl)-3-(2-(5-(2-(3-methoxyazetidin-1-yl)ethyl)-2-oxo-4-(trifluoromethyl)pyridin-1(2H)-yl)-4-methyl-pentanamido)propanoic acid (diastereomeric compounds EE-P1 and EE-P2)

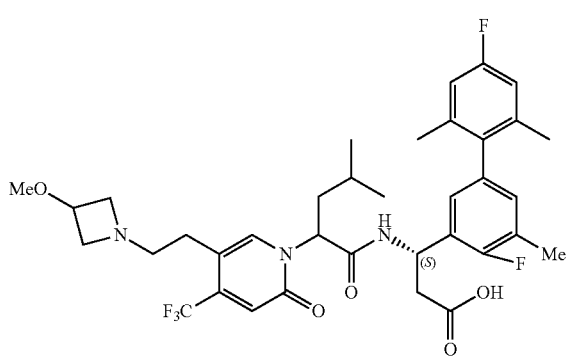

EE-P1 ESI 692.2 (M+H)⁺. 1H NMR (400 MHz, MeOD) δ 7.84 (s, 1H), 6.96-6.68 (m, 5H), 5.75-5.48 (m, 2H), 4.26-4.01 (m, 3H), 3.74-3.52 (m, 2H), 3.31 (s, 3H), 3.14 (t, J=6.8 Hz, 2H), 2.87-2.63 (m, 4H), 2.30 (s, 3H), 2.05-1.92 (m, 5H), 1.85 (s, 3H), 1.54-1.36 (m, 1H), 1.07-0.87 (m, 6H).

EE-P2 ESI 692.2 (M+H)⁺. 1H NMR (400 MHz, MeOD) δ 7.74 (s, 1H), 7.04-6.78 (m, 5H), 5.80-5.70 (m, 1H), 5.62 (t, J=7.7 Hz, 1H), 4.49-4.21 (m, 3H), 4.01-3.74 (m, 2H), 3.46-3.35 (m, 5H), 3.03-2.77 (m, 2H), 2.68-2.44 (m, 2H), 2.34 (d, J=1.7 Hz, 3H), 2.12-1.90 (m, 7H), 1.74-1.57 (m, 1H), 1.53-1.32 (m, 1H), 0.99-0.83 (m, 6H).

4-85. (3S)-3-(2-(5-(2-(dimethylamino)ethyl)-2-oxo-4-(trifluoromethyl)pyridin-1(2H)-yl)pentanamido)-3-(4-fluoro-2',4',5,6'-tetramethyl-[1,1'-biphenyl]-3-yl)propanoic acid (diastereomeric compounds EF-P1 and EF-P2)

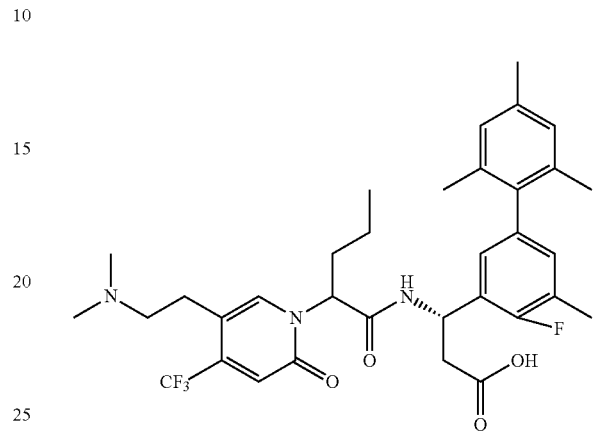

EF-P1 ESI 632.2 (M+H)⁺. ¹H NMR (500 MHz, MeOD) δ 7.88 (s, 1H), 6.92-6.79 (m, 4H), 6.74 (s, 1H), 5.66-5.45 (m, 2H), 3.11-2.85 (m, 5H), 2.78-2.68 (m, 7H), 2.32-2.22 (m, 6H), 2.18-2.08 (m, 1H), 2.06-1.92 (m, 4H), 1.78 (s, 3H), 1.41-1.24 (m, 2H), 0.97 (t, J=7.4 Hz, 3H).

EF-P2 ESI 632.2 (M+H)⁺. 1H NMR (500 MHz, MeOD) δ 7.82 (s, 1H), 6.90 (d, J=7.1 Hz, 5H), 5.79-5.64 (m, 1H), 5.52 (t, J=7.6 Hz, 1H), 3.30-3.15 (m, 2H), 3.00 (t, J=6.6 Hz, 2H), 2.83 (s, 6H), 2.69-2.59 (m, 1H), 2.58-2.44 (m, 1H), 2.31 (d, J=9.7 Hz, 6H), 2.13-2.01 (m, 1H), 1.97 (s, 6H), 1.91-1.73 (m, 1H), 1.39-1.02 (m, 2H), 0.91 (t, J=7.4 Hz, 3H).

4-86. (3S)-3-(2-(5-(2-(dimethylamino)ethyl)-4-methyl-2-oxopyridin-1(2H)-yl)-5-methylhexanamido)-3-(4-fluoro-2',4',5,6'-tetramethylbiphenyl-3-yl)propanoic acid (Diastereomeric Compounds EF2-P1 and EF2-P2)

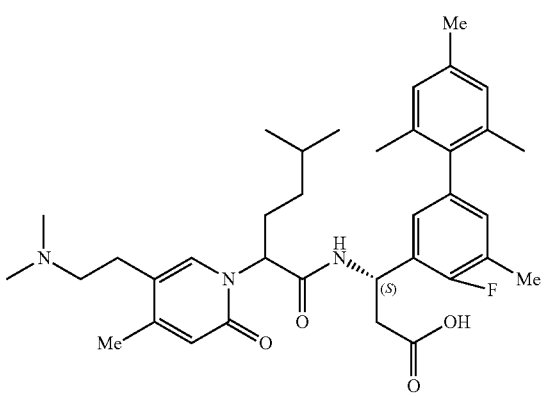

EF2-P1 ESI 606.3 (M+H)+. 1H NMR (400 MHz, MeOD) δ 7.57 (s, 1H), 6.90 (s, 2H), 6.85-6.80 (m, 2H), 6.34 (s, 1H), 5.48 (t, J=6.0 Hz, 1H), 5.42-5.37 (s, 1H), 3.24-3.02 (m, 2H), 2.89-2.85 (m, 2H), 2.76 (s, 6H), 2.71-2.60 (m, 2H), 2.30 (d, J=4.9 Hz, 6H), 2.25 (s, 3H), 2.22-2.14 (m, 1H), 1.95 (s, 4H), 1.87 (s, 3H), 1.60-1.53 (m, 1H), 1.25-1.14 (m, 1H), 1.12-1.00 (m, 1H), 0.89-0.87 (m, 6H).

EF2-P2 ESI 606.3 (M+H)+. 1H NMR (400 MHz, MeOD) δ 7.54 (s, 1H), 6.98-6.78 (m, 4H), 6.44 (s, 1H), 5.66-5.63 (m, 1H), 5.42 (t, J=7.7 Hz, 1H), 3.31-3.28 (m, 1H), 3.26-3.14 (m, 1H), 2.99-2.88 (m, 2H), 2.84 (s, 6H), 2.64-2.59 (m, 1H), 2.50-2.43 (m, 1H), 2.39-2.28 (m, 6H), 2.27 (s, 3H), 2.16-2.07 (m, 1H), 1.96 (s, 6H), 1.89-1.74 (m, 1H), 1.57-1.50 (m, 1H), 1.15-1.11 (m, 1H), 1.08-0.97 (m, 1H), 0.85 (t, J=6.5 Hz, 6H).

4-87. (3S)-3-(4,4'-difluoro-2',5,6'-trimethylbiphenyl-3-yl)-3-(2-(5-(2-(dimethylamino)ethyl)-4-methyl-2-oxopyridin-1(2H)-yl)-5-methylhexanamido)propanoic acid (diastereomeric compounds EG-P1 and EG-P2)

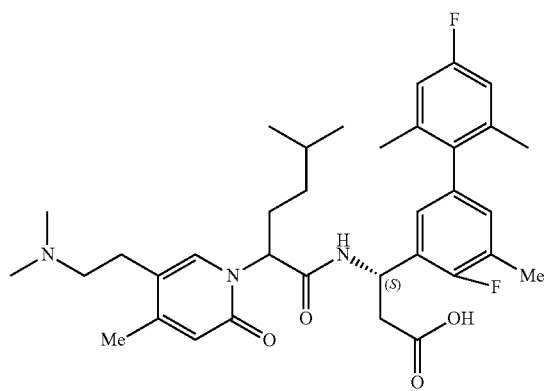

EG-P1 ESI 610.3 (M+H)+. 1H NMR (400 MHz, MeOD) δ 7.58 (s, 1H), 6.84 (t, J=9.1 Hz, 4H), 6.32 (s, 1H), 5.50 (t, J=6.2 Hz, 1H), 5.44-5.33 (m, 1H), 3.24-3.06 (m, 2H), 2.90-2.84 (m, 2H), 2.78 (s, 6H), 2.73-2.62 (m, 2H), 2.28 (d, J=14.1 Hz, 6H), 2.22-2.11 (m, 1H), 2.00-1.96 (m, 4H), 1.89 (s, 3H), 1.60-1.54 (m, 1H), 1.29-1.15 (m, 1H), 1.10-1.03 (m, 1H), 0.89-0.87 (m, 6H).

EG-P2 ESI 610.3 (M+H)+. 1H NMR (400 MHz, MeOD) δ 7.54 (s, 1H), 6.90 (d, J=6.9 Hz, 2H), 6.84 (d, J=9.6 Hz, 2H), 6.44 (s, 1H), 5.66-5.62 (m, 1H), 5.43 (t, J=7.6 Hz, 1H), 3.38-3.35 (m, 1H), 3.24-3.20 (m, 1H), 3.00-2.89 (m, 2H), 2.85 (s, 6H), 2.64-2.59 (m, 1H), 2.50-2.44 (m, 1H), 2.33 (d, J=4 Hz, 3H), 2.28 (s, 3H), 2.17-2.07 (m, 1H), 2.01 (s, 6H), 1.87-1.77 (m, 1H), 1.57-1.51 (m, 1H), 1.20-1.09 (m, 1H), 1.08-0.97 (m, 1H), 0.85 (t, J=6.4 Hz, 6H).

4-88. (3S)-3-(4,4'-difluoro-2',5,6'-trimethyl-[1,1'-biphenyl]-3-yl)-3-(2-(3-fluoro-5-(2-(3-methoxyazetidin-1-yl)ethyl)-4-methyl-2-oxopyridin-1(2H)-yl)-4-methylpentanamido)propanoic acid (diastereomeric compounds EH-P1 and EH-P2)

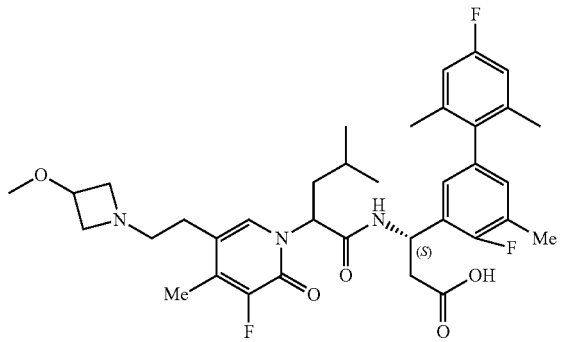

EH-P1 ESI 656.3 (M+H)+. 1H NMR (400 MHz, MeOD) δ 7.40 (s, 1H), 6.95-6.72 (m, 4H), 5.71-5.47 (m, 2H), 4.27-4.16 (m, 2H), 4.16-4.07 (m, 1H), 3.81-3.69 (m, 1H), 3.70-3.58 (m, 1H), 3.30 (s, 3H), 3.25 (t, J=6.8 Hz, 2H), 2.88-2.63 (m, 4H), 2.37-2.16 (m, 6H), 2.06-1.82 (m, 8H), 1.49-1.28 (m, 1H), 0.97-0.90 (m, 6H).

EH-P2 ESI 656.3 (M+H)+. 1H NMR (400 MHz, MeOD) δ 7.33 (s, 1H), 6.96-6.89 (m, 2H), 6.84 (d, J=9.7 Hz, 2H), 5.72-5.58 (m, 2H), 4.39-4.14 (m, 3H), 3.85-3.65 (m, 2H), 3.31-3.20 (m, 5H), 2.93-2.78 (m, 1H), 2.77-2.55 (m, 2H), 2.54-2.45 (m, 1H), 2.33 (d, J=1.7 Hz, 3H), 2.22 (d, J=2.7 Hz, 3H), 2.06-1.86 (m, 7H), 1.81-1.66 (m, 1H), 1.344-1.32 (m, 1H), 0.90 (d, J=6.6 Hz, 6H).

4-89. (3S)-3-(5-chloro-4-fluoro-2',4',6'-trimethylbiphenyl-3-yl)-3-(2-(5-(2-(dimethylamino)ethyl)-3-fluoro-2-oxo-4-(trifluoromethyl)pyridin-1(2H)-yl)-4-methylpentanamido)propanoic acid (diastereomeric compounds EI-P1 and EI-P2)

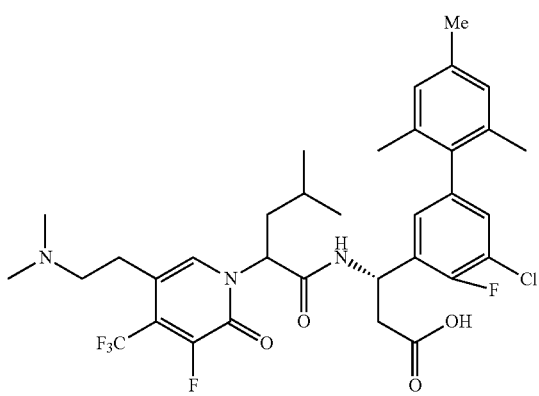 [SMILES: Cc1cc(C)c(-c2cc(Cl)c(F)c([C@H](CC(=O)O)NC(=O)C(CC(C)C)n3cc(CCN(C)C)c(C(F)(F)F)c(F)c3=O)c2)c(C)c1]

EI-P1 ESI 684.2 (M+H)⁺. 1H NMR (500 MHz, MeOD) δ 7.65 (s, 1H), 7.13 (d, J=6.3 Hz, 1H), 7.08 (d, J=6.1 Hz, 1H), 6.93 (s, 2H), 5.66 (d, J=5.4 Hz, 2H), 3.13-2.89 (m, 4H), 2.70 (s, 6H), 2.67-2.62 (m, 1H), 2.62-2.53 (m, 1H), 2.30 (s, 3H), 1.98 (d, J=6.9 Hz, 7H), 1.74-1.70 (m, 1H), 1.40-1.33 (m, 1H), 0.89 (d, J=5.6 Hz, 6H).

EI-P2 ESI 684.2 (M+H)⁺.

1H NMR (500 MHz, MeOD) δ 7.67 (s, 1H), 7.10 (d, J=6.9 Hz, 1H), 7.02 (d, J=6.1 Hz, 1H), 6.91 (d, J=13.0 Hz, 2H), 5.68 (t, J=8.1 Hz, 1H), 5.55 (t, J=7.0 Hz, 1H), 3.08 (s, 2H), 2.98 (d, J=7.7 Hz, 2H), 2.73 (d, J=9.7 Hz, 8H), 2.30 (s, 3H), 2.04-1.93 (m, 5H), 1.83 (s, 3H), 1.44-1.40 (m, 1H), 0.96-0.92 (m, 6H).

4-90. (3S)-3-(2-(5-(2-(azetidin-1-yl)ethyl)-2-oxo-4-(trifluoromethyl)pyridin-1(2H)-yl)-4-methylpentanamido)-3-(4'-cyano-4-fluoro-2',5,5'-trimethyl-[1,1'-biphenyl]-3-yl)propanoic acid (diastereomeric compounds EJ-P1 and EJ-P2)

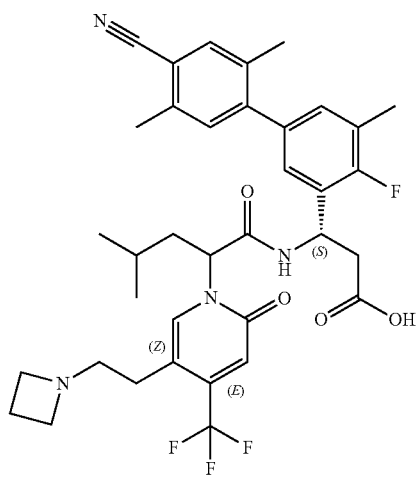

EJ-P1 ESI 669.3 (M+H)⁺. ¹H NMR (400 MHz, MeOD) δ 7.72 (s, 1H), 7.45 (s, 1H), 7.10 (s, 1H), 7.06-6.92 (m, 2H), 6.65 (s, 1H), 5.57-5.40 (m, 2H), 3.92 (t, J=8.1 Hz, 4H), 2.73-2.70 (m, 2H), 2.60 (d, J=7.6 Hz, 2H), 2.40 (s, 3H), 23.0-2.33 (m, 2H), 2.36-2.30 (m, 2H), 2.19 (s, 3H), 2.09 (s, 3H), 1.94-1.88 (m, 2H), 1.35-1.21 (m, 1H), 0.86-0.83 (m, 6H).

EJ-P2 ESI 669.3 (M+H)⁺. ¹H NMR (400 MHz, MeOD) δ 7.61 (s, 1H), 7.47 (s, 1H), 7.13 (s, 1H), 7.10-6.98 (m, 2H), 6.80 (s, 1H), 5.65-5.62 (m, 1H), 5.52 (t, J=7.7 Hz, 1H), 4.04 (t, J=8.1 Hz, 4H), 3.40-3.25 (m, 2H), 2.86-2.64 (m, 2H), 2.54-2.49 (m, 1H), 2.45-2.30 (m, 6H), 2.23 (d, J=1.5 Hz, 3H), 2.14 (s, 3H), 1.95-1.81 (m, 1H), 1.63-1.52 (m, 1H), 1.31-1.26 (m, 1H), 0.84-0.78 (m, 6H).

4-91. (3S)-3-(4-fluoro-4'-methoxy-2',5,6'-trimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid (diastereomeric compounds EK-P1 and EK-P2)

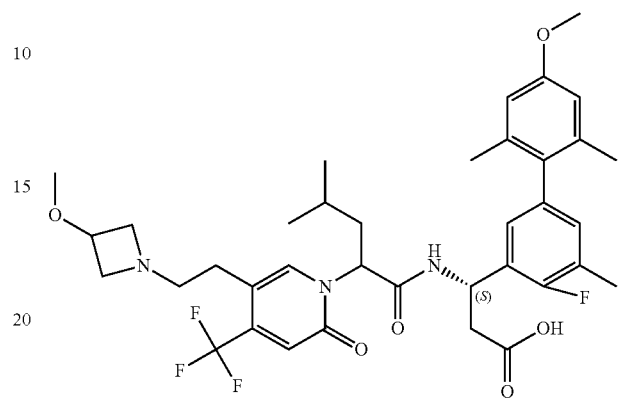

EK-P1 ESI 704.4 (M+H)⁺. ¹H NMR (400 MHz, MeOD) δ 7.85 (s, 1H), 6.86 (t, J=6.2 Hz, 2H), 6.77 (s, 1H), 6.65 (s, 1H), 6.62 (s, 1H), 5.67 (t, J=8.0 Hz, 1H), 5.61-5.56 (m, 1H), 4.25-4.09 (m, 3H), 3.79 (s, 3H), 3.71-3.61 (m, 2H), 3.31 (s, 3H), 3.17 (t, J=6.8 Hz, 2H), 2.81 (t, J=6.9 Hz, 2H), 2.76-2.69 (m, 2H), 2.28 (s, 3H), 2.04-1.97 (m, 5H), 1.82 (s, 3H), 1.48-1.41 (m, 1H), 0.98-0.93 (m, 6H).

EK-P2 ESI 704.4 (M+H)⁺. ¹H NMR (400 MHz, MeOD) δ 7.75 (s, 1H), 6.96-6.90 (m, 3H), 6.67 (s, 2H), 5.76-5.72 (m, 1H), 5.63 (t, J=7.7 Hz, 1H), 4.44-4.26 (m, 3H), 3.98-3.92 (m, 1H), 3.88-3.83 (m, 1H), 3.80 (s, 3H), 3.42-3.35 (m, 5H), 2.97-2.80 (m, 2H), 2.67-2.62 (m, 1H), 2.56-2.50 (m, 1H), 2.33 (d, J=1.6 Hz, 3H), 2.04-1.94 (m, 7H), 1.73-1.64 (m, 1H), 1.47-1.39 (m, 1H), 0.92-0.89 (m, 6H).

4-92. (3S)-3-(4'-cyano-4-fluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid (diastereomeric compounds EL-P1 and EL-P2)

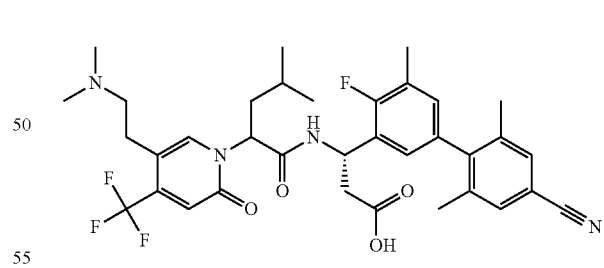

EL-P1 ESI 657.4 (M+H)⁺. ¹H NMR (400 MHz, MeOD) δ 7.88 (s, 1H), 7.45 (d, J=21.6 Hz, 2H), 6.88 (d, J=5.6 Hz, 2H), 6.71 (s, 1H), 5.72-5.47 (m, 2H), 3.08-2.85 (m, 4H), 2.79-2.57 (m, 8H), 2.30 (d, J=1.4 Hz, 3H), 2.11-1.93 (m, 5H), 1.88 (s, 3H), 1.50-1.37 (m, 1H), 1.06-0.86 (m, 6H).

EL-P2 ESI 657.4 (M+H)⁺. ¹H NMR (400 MHz, MeOD) δ 7.84 (s, 1H), 7.49 (s, 2H), 7.02-6.74 (m, 3H), 5.75-5.53 (m, 2H), 3.25-3.06 (m, 2H), 2.98 (t, J=6.9 Hz, 2H), 2.78 (s, 6H), 2.70-2.48 (m, 2H), 2.34 (d, J=1.4 Hz, 3H), 2.14-1.86 (m, 7H), 1.79-1.62 (m, 1H), 1.46-1.31 (m, 1H), 0.95-0.82 (m, 6H).

4-93. (3S)-3-(4'-chloro-4-fluoro-2',5,6'-trimethylbi-
phenyl-3-yl)-3-(2-(5-(2-(dimethylamino)ethyl)-2-
oxo-4-(trifluoromethyl)pyridin-1(2H)-yl)-4-methyl-
pentanamido)propanoic acid (Diastereomeric
Compounds EM-P1 and EM-P2)

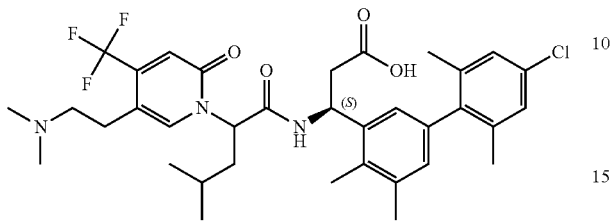

EM-P1 ESI 666.3 (M+H)+. 1H NMR (400 MHz, MeOD) δ 7.91 (s, 1H), 7.08 (d, J=24.1 Hz, 2H), 6.91-6.80 (m, 2H), 6.72 (s, 1H), 5.68 (t, J=8.0 Hz, 1H), 5.59-5.48 (m, 1H), 3.18-3.02 (m, 2H), 2.95 (t, J=7.0 Hz, 2H), 2.82-2.63 (m, 8H), 2.29 (s, 3H), 2.04-1.91 (m, 5H), 1.79 (s, 3H), 1.58-1.30 (m, 1H), 1.04-0.86 (m, 6H).

EM-P2 ESI 666.3 (M+H)+. 1H NMR (400 MHz, MeOD) δ 7.88 (s, 1H), 7.13 (s, 2H), 6.94-6.83 (m, 3H), 5.81-5.68 (m, 1H), 5.62 (t, J=7.7 Hz, 1H), 3.30-3.16 (m, 2H), 3.01 (t, J=6.8 Hz, 2H), 2.83 (s, 6H), 2.72-2.45 (m, 2H), 2.33 (d, J=1.1 Hz, 3H), 1.98 (d, 7H), 1.75-1.63 (m, 1H), 1.51-1.33 (m, 1H), 0.87 (d, J=6.6 Hz, 6H).

4-94. ((3S)-3-(4-fluoro-2',5,6'-trimethylbiphenyl-3-
yl)-3-(2-(5-(2-((R)-3-fluoropyrrolidin-1-yl)ethyl)-4-
methyl-2-oxopyridin-1(2H)-yl)-4-methylpentana-
mido)propanoic acid (Diastereomeric Compounds
EN-P1 and EN-P2)

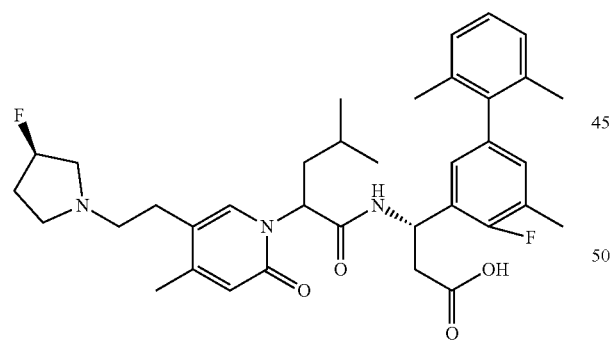

EN-P1 ESI 622.2 (M+H)+. 1H NMR (500 MHz, MeOD) δ 7.54 (s, 1H), 7.16-7.02 (m, 3H), 6.87-6.78 (m, 2H), 6.27 (s, 1H), 5.73-5.50 (m, 2H), 5.34-5.15 (m, 1H), 3.31-3.23 (m, 1H), 3.22-3.00 (m, 2H), 2.94-2.80 (m, 3H), 2.78-2.59 (m, 4H), 2.36-2.09 (m, 8H), 2.01-1.91 (m, 5H), 1.83 (s, 3H), 1.50-1.37 (m, 1H), 0.97-0.89 (m, 6H).

EN-P2 ESI 622.2 (M+H)+. 1H NMR (500 MHz, MeOD) δ 7.56 (s, 1H), 7.22-7.02 (m, 3H), 6.91 (d, J=6.8 Hz, 2H), 6.42 (s, 1H), 5.65-5.57 (m, 2H), 5.41-5.24 (m, 1H), 3.62-3.35 (m, 3H), 3.31-3.09 (m, 3H), 2.94-2.74 (m, 2H), 2.68-2.49 (m, 2H), 2.39-2.22 (m, 8H), 2.10-1.89 (m, 7H), 1.82-1.70 (m, 1H), 1.49-1.31 (m, 1H), 0.95-0.85 (m, 6H).

4-95. (3S)-3-(4-fluoro-2',4',5,6'-tetramethyl-[1,1'-
biphenyl]-3-yl)-3-(2-(5-(2-(3-fluoroazetidin- 1-yl)
ethyl)-2-oxopyridin-1(2H)-yl)-4-methylpentana-
mido)propanoic acid (diastereomeric compounds
EO-P1 and EO-P2)

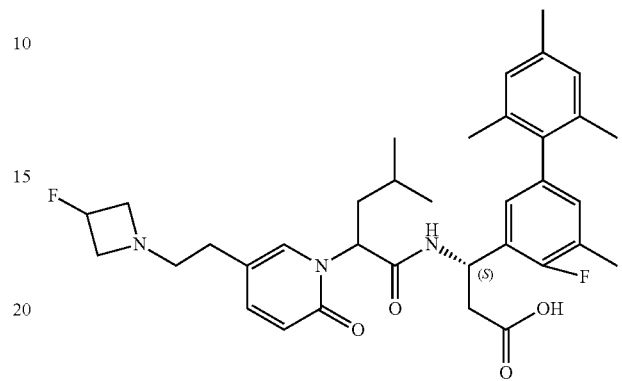

EO-P1 ESI 608.3 (M+H)+. 1H NMR (400 MHz, MeOD) δ 7.52 (s, 1H), 7.39 (d, J=9.0 Hz, 1H), 6.96-6.79 (m, 3H), 6.73 (s, 1H), 6.43 (d, J=9.5 Hz, 1H), 5.74-5.46 (m, 2H), 5.14 (d, J=57.6 Hz, 1H), 3.77 (s, 2H), 3.50 (s, 2H), 2.88 (s, 2H), 2.79-2.60 (m, 2H), 2.51 (s, 2H), 2.29 (d, J=14.1 Hz, 6H), 1.96 (d, J=12.7 Hz, 5H), 1.80 (s, 3H), 1.42 (s, 1H), 1.03-0.79 (m, 6H).

EO-P2 ESI 608.3 (M+H)+. 1H NMR (400 MHz, MeOD) δ 7.60-7.40 (m, 2H), 6.90 (d, J=7.8 Hz, 4H), 6.57 (d, J=9.2 Hz, 1H), 5.70-5.57 (m, 2H), 5.32 (d, J=57.4 Hz, 1H), 4.51-4.26 (m, 2H), 4.14-3.87 (m, 2H), 3.39 (d, J=5.3 Hz, 2H), 2.85-2.44 (m, 4H), 2.35-2.17 (m, 6H), 2.04-1.86 (m, 7H), 1.86-1.73 (m, 1H), 1.48-1.33 (m, 1H), 0.90 (t, J=6.3 Hz, 6H).

4-96. (3S)-3-(4,4'-difluoro-2',5,6'-trimethyl-[1,1'-
biphenyl]-3-yl)-3-(2-(5-(2-(3-fluoroazetidin- 1-yl)
ethyl)-2-oxopyridin-1(2H)-yl)-4-methylpentana-
mido)propanoic acid (diastereomeric compounds
EP-P1 and EP-P2)

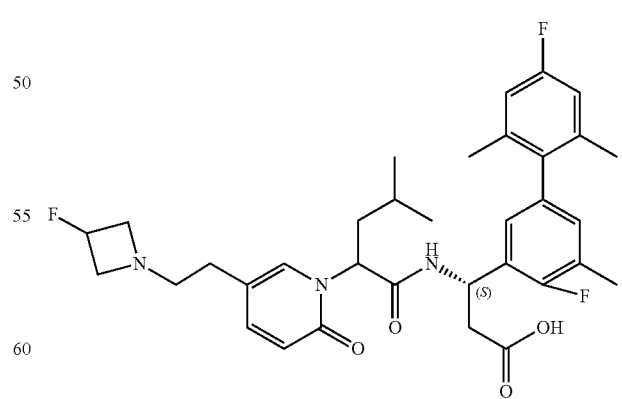

EP-P1 ESI 612.2 (M+H)+. 1H NMR (400 MHz, MeOD) δ 7.54 (s, 1H), 7.43 (dd, J=9.2, 2.3 Hz, 1H), 6.87-6.82 (m, 3H), 6.76 (d, J=6.7 Hz, 1H), 6.46 (d, J=9.3 Hz, 1H), 5.63 (d, J=7.9 Hz, 1H), 5.54-5.43 (m, 1H), 5.20 (d, J=57.2 Hz, 1H), 4.09-3.88 (m, 2H), 3.71-3.55 (m, 2H), 3.10-3.02 (m, 2H), 2.80-2.53 (m, 4H), 2.29 (s, 3H), 2.03-1.92 (m, 5H), 1.87 (s, 3H), 1.50-1.36 (m, 1H), 0.97-0.92 (m, 6H).

EP-P2 ESI 612.2 (M+H)$^+$. $^1$H NMR (400 MHz, MeOD) δ 7.41 (s, 1H), 7.38-7.35 (m, 1H), 6.79 (t, J=6.1 Hz, 2H), 6.73 (d, J=9.7 Hz, 2H), 6.45 (d, J=9.3 Hz, 1H), 5.53-5.48 (m, 2H), 5.20 (d, J=57.2 Hz, 1H), 4.39-4.14 (m, 2H), 3.99-3.87 (m, 2H), 3.32-3.25 (m, 2H), 2.67-2.48 (m, 3H), 2.40-2.34 (m, 1H), 2.21 (d, J=1.7 Hz, 3H), 1.90-1.81 (m, 7H), 1.72-1.64 (m, 1H), 1.33-1.22 (m, 1H), 0.79 (t, J=6.6 Hz, 6H).

4-97. (3S)-3-(4,4'-difluoro-2',5,6'-trimethyl-[1,1'-biphenyl]-3-yl)-3-(2-(3-fluoro-5-(2-(3-fluoroazetidin-1-yl)ethyl)-2-oxopyridin-1(2H)-yl)-4-methylpentanamido)propanoic acid (diastereomeric compounds EQ-P1 and EQ-P2)

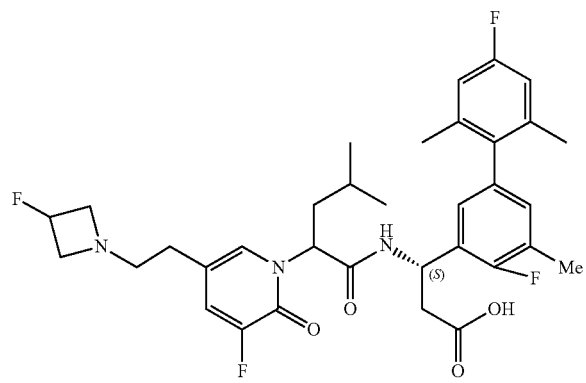

EQ-P1 ESI 630.2 (M+H)$^+$. $^1$H NMR (400 MHz, MeOD) δ 7.30 (s, 1H), 7.25-7.22 (m, 1H), 6.77-6.75 (m, 1H), 6.72-6.69 (m, 3H), 5.55 (t, J=8.0 Hz, 1H), 5.40-5.37 (m, 1H), 5.18-5.01 (m, 1H), 3.99-3.82 (m, 2H), 3.66-3.48 (m, 2H), 3.06-2.99 (m, 2H), 2.66-2.50 (m, 4H), 2.18 (d, J=1.5 Hz, 3H), 1.89-1.81 (m, 5H), 1.78 (s, 3H), 1.34-1.27 (m, 1H), 0.85-0.78 (m, 6H).

EQ-P2 ESI 630.2 (M+H)$^+$. $^1$H NMR (400 MHz, MeOD) δ 7.27-7.23 (m, 2H), 6.80 (d, J=6.9 Hz, 2H), 6.73 (d, J=9.6 Hz, 2H), 5.56-5.49 (m, 2H), 5.28-5.11 (m, 1H), 4.33-4.18 (m, 2H), 3.97-3.83 (m, 2H), 3.27-3.22 (m, 2H), 2.64-2.35 (m, 4H), 2.21 (d, J=1.9 Hz, 3H), 1.89-1.82 (m, 7H), 1.69-1.62 (m, 1H), 1.31-1.21 (m, 1H), 0.83-0.78 (m, 6H).

Introduction to the In Vitro Assays Described in Examples 5-7

Three in vitro assays were used to examine the $\alpha_4\beta_7$ mechanistic process used by cells: 1) ligand:receptor affinity, 2) the avidity of those interactions on a cell's surface, and 3) how those interactions fare under an imposing force. In Example 5, a Fluorescence Polarization (FP) assay is used to measure compound activity through binding competition with the fluorescein-labeled peptide. In Example 6, the potency of compounds against $\alpha_4\beta_7$ is measured in the cell-based ligand binding assay (LBA), using RPMI 8866 cells incubated with the compound samples in competition with soluble MAdCAM-1 ligand. In Example 7, activity of compounds is evaluated in a cell adhesion assay that mechanistically tests what occurs in vivo when trafficking cells utilize $\alpha_4\beta_7$ to adhere to MAdCAM-1 expressing HEVs of the gut during the extravasation process. In the cell adhesion assay of Example 7, a MAdCAMI1-(Fc) is coated on plastic, and $\alpha_4\beta_7$ expressing cells (RPMI-8866) are allowed to adhere to the coated surface in the presence of the test compounds. Next, the force of washing with buffer is applied to cells thereby testing the strength of that adhesion. Unattached cells are removed and the remaining adherent cells are quantified.

Example 5: Fluorescence Polarization Assays of Compounds for $\alpha_4\beta_7$ Binding Fluorescence Polarization (FP) assays were used to measure compound activity through binding competition with the fluorescein-labeled peptide CRSDTLCGE{Lys(FITC)}. In the assay, 6.5 nM of integrin $\alpha_4\beta_7$ was incubated with the test compound in 2 mM manganese chloride, 0.1 mM calcium chloride, 20 mM HEPES buffer at pH 7.3, 150 mM sodium chloride, 0.01% Triton X-100, 2% DMSO, and 3 nM of the fluorescein-labeled peptide. Running the assays in 384-well plates, the integrin protein was pre-incubated with the test compounds for 15 minutes at 22° C. before the fluorescein-labeled peptide was added. After the fluorescein-labeled peptide was added, the assay was incubated at 22° C. for 1 hour and fluorescence polarization was measured. IC$_{50}$ values were determined by nonlinear regression, four-parameter curve fitting.

An $\alpha_4\beta_7$ inhibition potency measurement for compounds including certain compounds in Table 1 of FIG. 1 was made using the FP assay of Example 5, and is provided in FIG. 1 (Table 1) as a numerical range of the resulting IC$_{50}$ value (A: <5.55 nM; B: 5.55-500 nM; C: >500 nM in FIG. 1).

An $\alpha_4\beta_7$ inhibition potency measurement was also performed using the FP assay of Example 5 for compounds in Table 3A, Table 3B and (comparative) Table 4 below, with results provided as a numerical range of the resulting IC$_{50}$ value (A: ≤10 nM; B: >10-500 nM; C: >500 nM in Table 3 and Table 4).

Example 6: Ligand Binding Assays

To measure the potency of compounds against $\alpha_4\beta_7$ in the cell-based ligand binding assay (LBA), RPMI 8866 cells were incubated with the compound samples in a volume of 10 μl at room temperature for 15 minutes in buffer containing 50 mM HEPES pH 7.3, 150 mM sodium chloride, 1% bovine serum albumin, 3 mM manganese chloride, 0.15 mM calcium chloride, 15 mM glucose, 1.5% dimethyl sulfoxide, and 0.025% e780 fixable viability dye. 5 ul of 33 nM MAdCAM-1-Fc fluorescently labeled with Dylight 650 in 50 mM HEPES pH 7.3, 150 mM sodium chloride, and 1% bovine serum albumin was added to the cells. The samples were incubated for 45 minutes at room temperature, fixed with 0.8% formaldehyde for 30 minutes at room temperature, and washed with 50 mM Tris pH 7.5, 150 mM NaCl, 1 mM EDTA, and 1% bovine serum albumin. Fluorescence intensity for each cell was measured via flow cytometry. Dead cells were excluded from further analysis based on staining with the 780 fixable viability dye. Median fluorescence intensity for Dylight 650 was determined for each sample and concentration-response curves were analyzed for IC50 values using 4-parameter non-linear regression analysis.

The $\alpha_4\beta_7$ ligand binding measurement from the assay of Example 6 was obtained from certain compounds in Table 1 of FIG. 1, and is provided for compounds in FIG. 1 (Table 1) by numerical range of the resulting IC$_{50}$ value (A: <5 nM; B: 5-500 nM; C: >500 nM in FIG. 1).

An $\alpha_4\beta_7$ ligand binding assay measurement was also performed using the ligand binding assay of Example 6 for compounds in Table 3 and (comparative) Table 4 below, with the resulting IC$_{50}$ value provided as a numerical range (A: <10 nM; B: >10-500 nM; C: >500 nM in Table 3 and Table 4).

Example 7: Cell Adhesion Assay

Example 7 describes a cell adhesion assay. The $\alpha_4\beta_7$ cell adhesion measurement from the assay of Example 7 was obtained from compounds in Table 3 below and comparative compounds in Table 4, and is provided by numerical range of the resulting IC$_{50}$ value (A: <5 nM; B: 5 to <10 nM; C10-50 nM; D: >50 nM; E:>100 nM and F>500 nM in Table 3 and Table 4).

To each well of a 96 well plate, 100 ug of recombinant human MAdCAM in 100 ul PBS is added and incubated overnight at 4° C. After incubation MAdCAM is removed by aspiration and 200 ul of PBS+1% BSA is added to block the plate for 2 hours at 37° C. and 5% CO$_2$. During this incubation dilution curves of compound are made in 100% DMSO in 96 well V bottom plates. 1.75 ul of diluted compounds are then transferred to a new 96 well U bottom plate containing 20 ul of assay media (phosphate free DMEM+25 mM HEPES+1% BSA). To this an additional 155 ul of assay media is added with mixing by pipetting up and down. This mixture is allowed to incubate for 15 minutes at 37° C. and 5% CO$_2$. After incubation 175 ul of assay media containing 2e6/mL RPMI8866 cells is added to compound containing wells without mixing and plate is allowed to incubate for another 15 minutes at 37° C. and 5% CO$_2$. During this incubation MAdCAM coated plates are removed from incubator and washed twice with 200 ul PBS+0.1% BSA. After cells have incubated with compound for 15 minutes they are mixed by pipetting up and down and 100 ul of mixture is transferred to the washed MAdCAM coated plates in triplicate. This plate is then incubated at 37° C. and 5% CO$_2$ for 1 hour. After incubation plates are washed twice with 200 ul and once with 50 ul of phenol free RPMI+1% BSA. A final 50 ul of phenol free RPMI+1% BSA is added to wells after last wash. Next 50 ul of Promega cell titer glow is added to the wells. Plate is incubated on shaker for 2 minutes at 200 RPM followed by another 8 minutes off shaker before having the luminescence read on a Biotek Citation 5 plate reader. Raw data is converted to % inhibition compared to bottom of curve and analyzed using a 4-parameter non linear curve in Prism to determine IC$_{50}$ and IC$_{90}$.

TABLE 3

Selected Exemplary Compounds.

| Compound | Example | FP Assay (Example 5) | LB Assay (Example 6) | CA Assay (Example 7) |
|---|---|---|---|---|
| | 3-1 (D-P2) | A | A | A |
| | 3-4 (G-P2) | A | A | A |

TABLE 3-continued

Selected Exemplary Compounds.

| Compound | Example | FP Assay (Example 5) | LB Assay (Example 6) | CA Assay (Example 7) |
|---|---|---|---|---|
| | 3-27 (AF-P2) | A | A | A |
| | 3-28 (AG-P2) | A | A | A |
| | 3-32 (AK-P2) | A | A | A |

TABLE 3-continued
Selected Exemplary Compounds.
| Compound | Example | FP Assay (Example 5) | LB Assay (Example 6) | CA Assay (Example 7) |
|---|---|---|---|---|
| 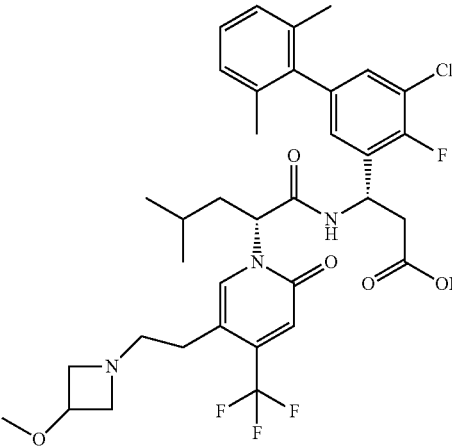 | 3-18 (W-P2) | A | A | A |
| 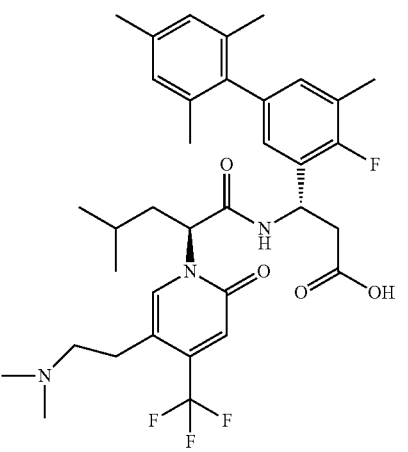 [SMILES: Cc1cc(C)c(-c2cc(C)c(F)c([C@H](CC(=O)O)NC(=O)[C@H](CC(C)C)n3cc(CCN(C)C)c(C(F)(F)F)cc3=O)c2)c(C)c1] | 3-24 (AC-P2) | A | A | A |
| 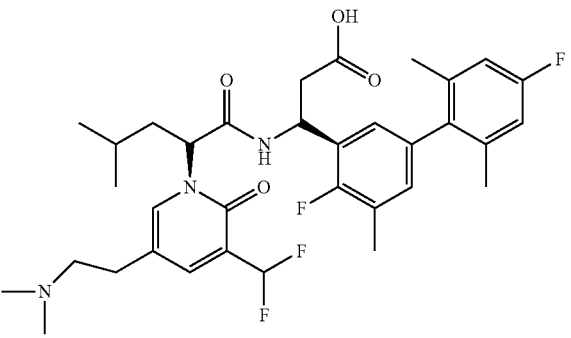 | 3-6 (I-P2) | A | A | A |

TABLE 3-continued
Selected Exemplary Compounds.
| Compound | Example | FP Assay (Example 5) | LB Assay (Example 6) | CA Assay (Example 7) |
|---|---|---|---|---|
| 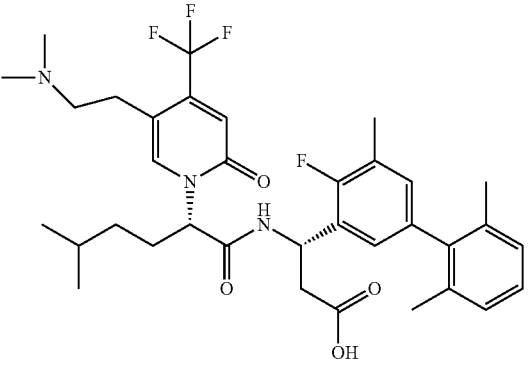 [SMILES: Cc1cc(-c2c(C)cccc2C)cc([C@H](CC(=O)O)NC(=O)[C@H](CCC(C)C)n2cc(CCN(C)C)c(C(F)(F)F)cc2=O)c1F] | 3-7 (J-P2) | A | A | A |
| 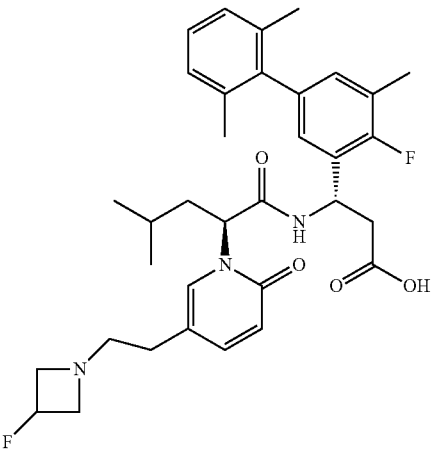 [SMILES: Cc1cc(-c2c(C)cccc2C)cc([C@H](CC(=O)O)NC(=O)[C@H](CC(C)C)n2cc(CCN3CC(F)C3)ccc2=O)c1F] | 3-43 (AV-P2) | A | A | A |
| 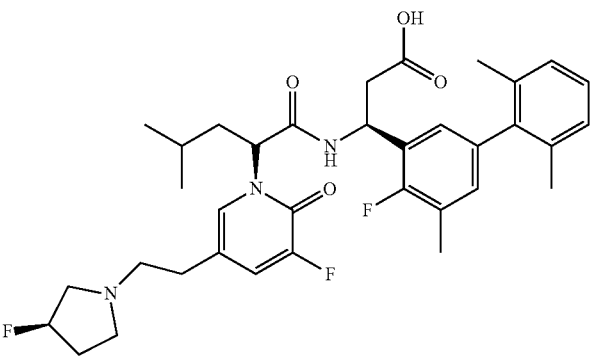 | 3-42 (AU-P2) | A | A | A |

TABLE 4

| Comparator Compound | FP Assay (Example 5) | LB Assay (Example 6) | CA Assay (Example 7) |
|---|---|---|---|
| *(structure)* | A | A | D |
| *(structure)* | A | A | B |
| *(structure)* | A | A | C |
| *(structure)* | A | B | E |

TABLE 4-continued

| Comparator Compound | FP Assay (Example 5) | LB Assay (Example 6) | CA Assay (Example 7) |
|---|---|---|---|
| [structure] | A | A | C |
| [structure] | A | A | D |
| [structure] | A | A | C |
| [structure] | A | A | C |

TABLE 4-continued
Comparative Compounds
| Comparator Compound | FP Assay (Example 5) | LB Assay (Example 6) | CA Assay (Example 7) |
|---|---|---|---|
| 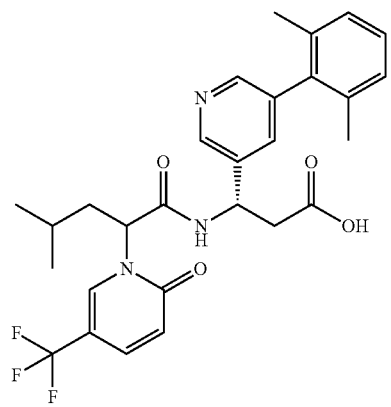 [SMILES: Cc1cccc(C)c1-c1cncc([C@H](CC(=O)O)NC(=O)C(CC(C)C)n2cc(C(F)(F)F)ccc2=O)c1] | A | | D |
| 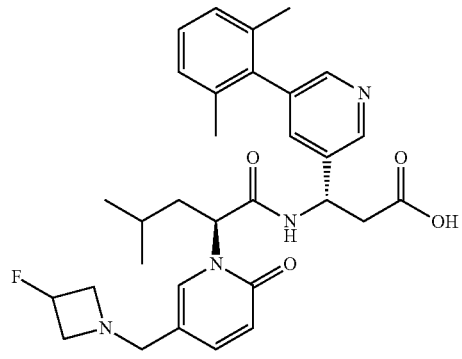 [SMILES: Cc1cccc(C)c1-c1cncc([C@H](CC(=O)O)NC(=O)[C@H](CC(C)C)n2cc(CN3CC(F)C3)ccc2=O)c1] | A | A | D |
| 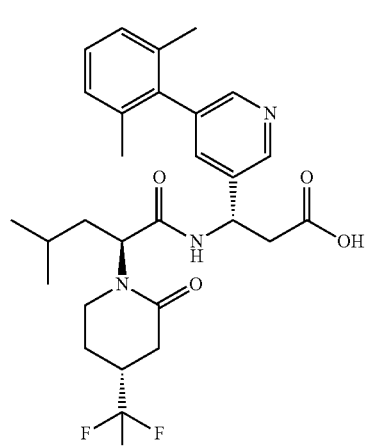 | A | B | D |

TABLE 4-continued

| Comparator Compound | FP Assay (Example 5) | LB Assay (Example 6) | CA Assay (Example 7) |
|---|---|---|---|
| [structure] | | B | E |
| [structure] | A | B | F |
| [structure] | A | A | D |

TABLE 4-continued
| | Comparative Compounds | | |
|---|---|---|---|
| Comparator Compound | FP Assay (Example 5) | LB Assay (Example 6) | CA Assay (Example 7) |
| 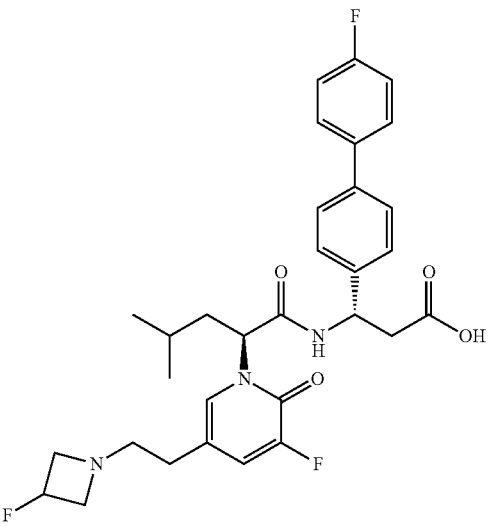 [SMILES: CC(C)C[C@@H](C(=O)N[C@@H](CC(=O)O)c1ccc(-c2ccc(F)cc2)cc1)n1cc(CCN2CC(F)C2)cc(F)c1=O] | A | B | F |
| 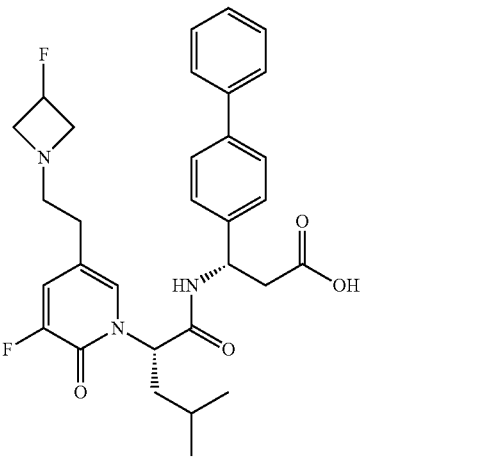 [SMILES: CC(C)C[C@@H](C(=O)N[C@@H](CC(=O)O)c1ccc(-c2ccccc2)cc1)n1cc(CCN2CC(F)C2)cc(F)c1=O] | A | B | F |
| 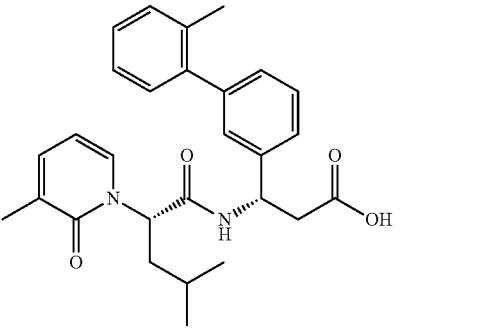 [SMILES: Cc1ccccc1-c1cccc([C@H](CC(=O)O)NC(=O)[C@H](CC(C)C)n2cccc(C)c2=O)c1] | A | B | F |

TABLE 4-continued

Comparative Compounds

| Comparator Compound | FP Assay (Example 5) | LB Assay (Example 6) | CA Assay (Example 7) |
|---|---|---|---|
| [structure] | A | A | D |
| [structure] | B | B | F |
| [structure] | B | | F |
| [structure] | B | | F |

TABLE 4-continued

| | | | |
|---|---|---|---|
| | Comparative Compounds | | |
| Comparator Compound | FP Assay (Example 5) | LB Assay (Example 6) | CA Assay (Example 7) |
| *(structure)* | B | | F |
| *(structure)* | A | A | D |
| *(structure)* | B | | F |
| *(structure)* | B | | F |

TABLE 4-continued
Comparative Compounds
| Comparator Compound | FP Assay (Example 5) | LB Assay (Example 6) | CA Assay (Example 7) |
|---|---|---|---|
| 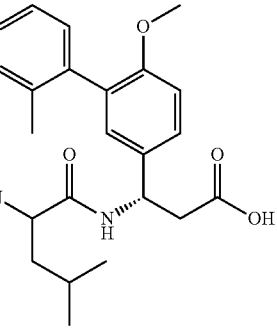 | | B | F |
| 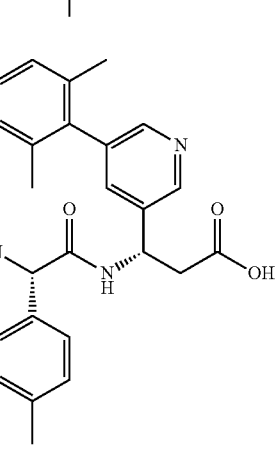 | A | B | F |
| 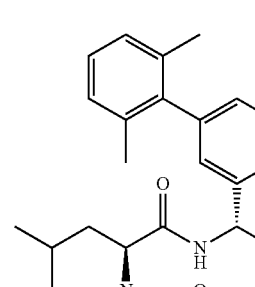 | A | A | A |
| 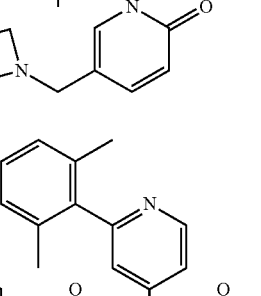 | | B | F |

TABLE 4-continued

Comparative Compounds

| Comparator Compound | FP Assay (Example 5) | LB Assay (Example 6) | CA Assay (Example 7) |
|---|---|---|---|
| [structure] | A | | F |
| [structure] | B | B | F |
| [structure] | B | | |
| [structure] | A | A | D |

TABLE 4-continued

Comparative Compounds

| Comparator Compound | FP Assay (Example 5) | LB Assay (Example 6) | CA Assay (Example 7) |
|---|---|---|---|
| 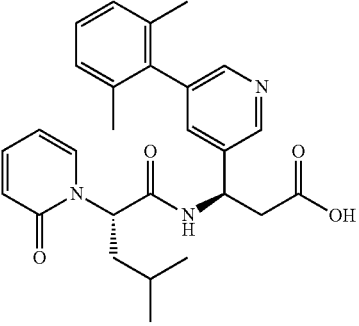 [SMILES: Cc1cccc(C)c1-c1cncc([C@@H](CC(=O)O)NC(=O)[C@H](CC(C)C)n2ccccc2=O)c1] | C | | |
| 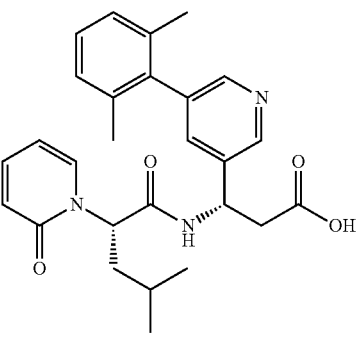 [SMILES: Cc1cccc(C)c1-c1cncc([C@H](CC(=O)O)NC(=O)[C@H](CC(C)C)n2ccccc2=O)c1] | A | | E |
| 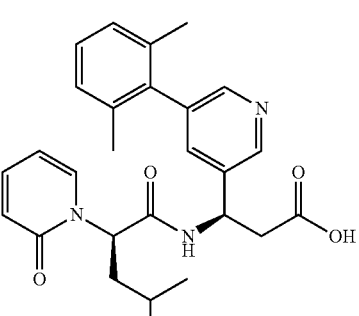 | C | | |

INCORPORATION BY REFERENCE

All of the U.S. patents and U.S. and PCT patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A compound selected from the group consisting of:
   a. (S)-3-(4,5-difluoro-2',6'-dimethyl-[1,1'-biphenyl]-3-yl)-3-((S)-2-(5-(2-(3-fluoroazetidin-1-yl)ethyl)-4-methyl-2-oxopyridin-1(2H)-yl)-4-methylpentanamido)propanoic acid;
   b. (S)-3-((S)-2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoic acid;
   c. (S)-3-((S)-2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic acid;
   d. (S)-3-((S)-2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic acid;
   e. (S)-3-(4,4'-difluoro-2',5,6'-trimethyl-[1,1'-biphenyl]-3-yl)-3-((S)-2-(5-(2-(dimethylamino)ethyl)-2-oxo-4-(trifluoromethyl)pyridin-1(2H)-yl)-4-methylpentanamido)propanoic acid;
   f. (S)-3-(5-chloro-4-fluoro-2',6'-dimethyl-[1,1'-biphenyl]-3-yl)-3-((S)-2-(5-(2-(3-methoxyazetidin-1-yl)ethyl)-2-oxo-4-(trifluoromethyl)pyridin-1(2H)-yl)-4-methylpentanamido)propanoic acid;

439 g. (S)-3-((S)-2-(5-(2-(dimethylamino)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoic acid;

h. (S)-3-(4,4'-difluoro-2',5,6'-trimethyl-[1,1'-biphenyl]-3-yl)-3-((S)-2-(3-(difluoromethyl)-5-(2-(dimethylamino)ethyl)-2-oxopyridin-1(2H)-yl)-4-methylpentanamido)propanoic acid;

i. (S)-3-((S)-2-(5-(2-(dimethylamino)ethyl)-4-methyl-2-oxopyridin-1(2H)-yl)-5-methylhexanamido)-3-(4-fluoro-2',5,6'-trimethyl-[1,1'-biphenyl]-3-yl)propanoic acid;

j. (S)-3-(4-fluoro-2',5,6'-trimethyl-[1,1'-biphenyl]-3-yl)-3-((S)-2-(3-fluoro-5-(2-(3-fluoroazetidin-1-yl)ethyl)-2-oxopyridin-1(2H)-yl)-4-methylpentanamido)propanoic acid; and k. (S)-3-(4-fluoro-2',5,6'-trimethyl-[1,1'-biphenyl]-3-yl)-3-((S)-2-(3-fluoro-5-(2-((R)-3-fluoropyrrolidin-1-yl)ethyl)-2-oxopyridin-1(2H)-yl)-4-methylpentanamido)propanoic acid;

or a pharmaceutically acceptable salt thereof.

2. The compound of claim 1, wherein the compound is (S)-3-(4,5-difluoro-2',6'-dimethyl-[1,1'-biphenyl]-3-yl)-3-((S)-2-(5-(2-(3-fluoroazetidin-1-yl)ethyl)-4-methyl-2-oxopyridin-1(2H)-yl)-4-methylpentanamido)propanoic acid, or a pharmaceutically acceptable salt thereof.

3. The compound of claim 1, wherein the compound is (S)-3-((S)-2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoic acid, or a pharmaceutically acceptable salt thereof.

4. The compound of claim 1, wherein the compound is (S)-3-((S)-2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic acid, or a pharmaceutically acceptable salt thereof.

5. The compound of claim 1, wherein the compound is (S)-3-((S)-2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic acid, or a pharmaceutically acceptable salt thereof.

6. The compound of claim 1, wherein the compound is (S)-3-(4,4'-difluoro-2',5,6'-trimethyl-[1,1'-biphenyl]-3-yl)-3-((S)-2-(5-(2-(dimethylamino)ethyl)-2-oxo-4-(trifluoromethyl)pyridin-1(2H)-yl)-4-methylpentanamido)propanoic acid, or a pharmaceutically acceptable salt thereof.

7. The compound of claim 1, wherein the compound is (S)-3-(5-chloro-4-fluoro-2',6'-dimethyl-[1,1'-biphenyl]-3-yl)-3-((S)-2-(5-(2-(3-methoxyazetidin-1-yl)ethyl)-2-oxo-4-(trifluoromethyl)pyridin-1(2H)-yl)-4-methylpentanamido)propanoic acid, or a pharmaceutically acceptable salt thereof.

8. The compound of claim 1, wherein the compound is (S)-3-((S)-2-(5-(2-(dimethylamino)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoic acid, or a pharmaceutically acceptable salt thereof.

9. The compound of claim 1, wherein the compound is (S)-3-(4,4'-difluoro-2',5,6'-trimethyl-[1,1'-biphenyl]-3-yl)-3-((S)-2-(3-(difluoromethyl)-5-(2-(dimethylamino)ethyl)-2-oxopyridin-1(2H)-yl)-4-methylpentanamido)propanoic acid, or a pharmaceutically acceptable salt thereof.

10. The compound of claim 1, wherein the compound is (S)-3-((S)-2-(5-(2-(dimethylamino)ethyl)-4-methyl-2-oxopyridin-1(2H)-yl)-5-methylhexanamido)-3-(4-fluoro-2',5,6'-trimethyl-[1,1'-biphenyl]-3-yl)propanoic acid, or a pharmaceutically acceptable salt thereof.

11. The compound of claim 1, wherein the compound is (S)-3-(4-fluoro-2',5,6'-trimethyl-[1,1'-biphenyl]-3-yl)-3-((S)-2-(3-fluoro-5-(2-(3-fluoroazetidin-1-yl)ethyl)-2-oxopyridin-1(2H)-yl)-4-methylpentanamido)propanoic acid, or a pharmaceutically acceptable salt thereof.

12. The compound of claim 1, wherein the compound is (S)-3-(4-fluoro-2',5,6'-trimethyl-[1,1'-biphenyl]-3-yl)-3-((S)-2-(3-fluoro-5-(2-((R)-3-fluoropyrrolidin-1-yl)ethyl)-2-oxopyridin-1(2H)-yl)-4-methylpentanamido)propanoic acid, or a pharmaceutically acceptable salt thereof.

13. A pharmaceutical composition comprising a compound selected from the group consisting of:

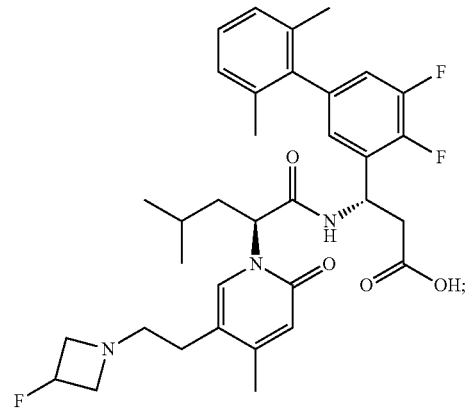

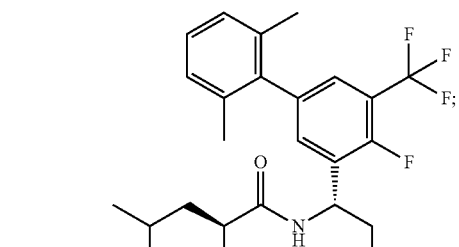

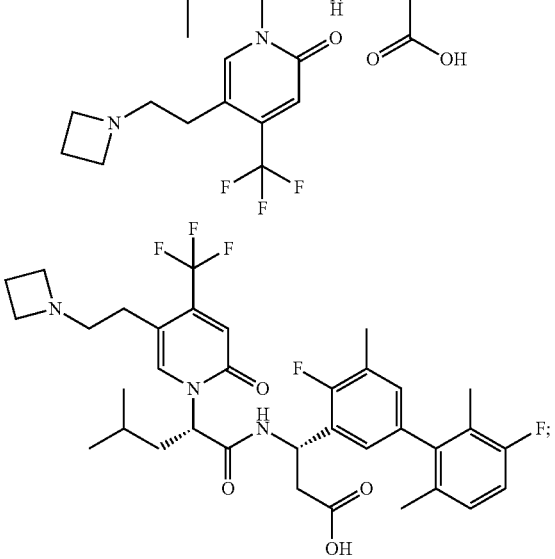

441
-continued
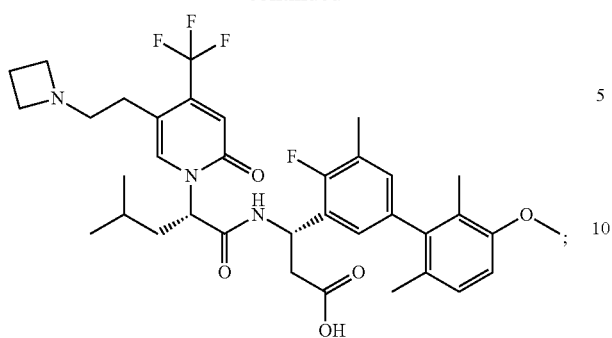
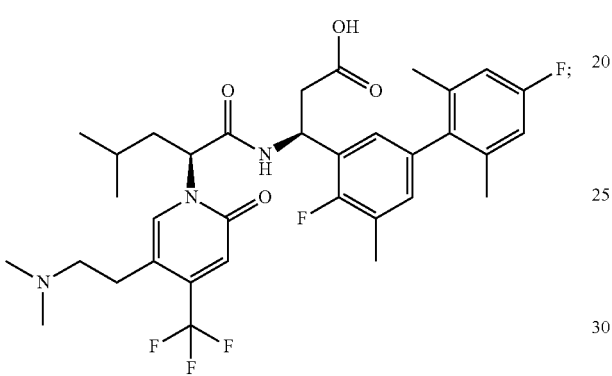
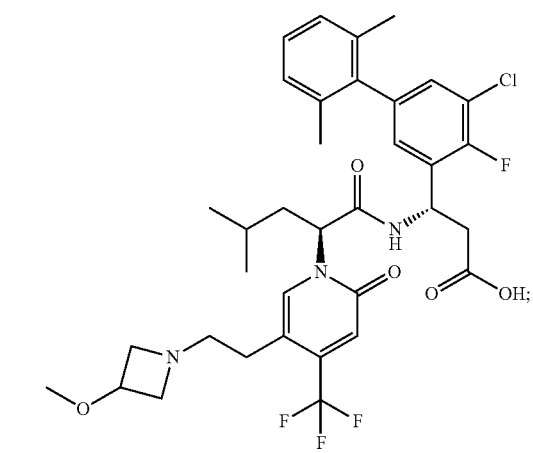
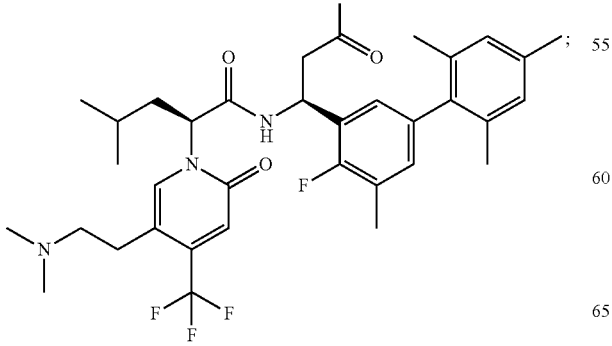
442
-continued
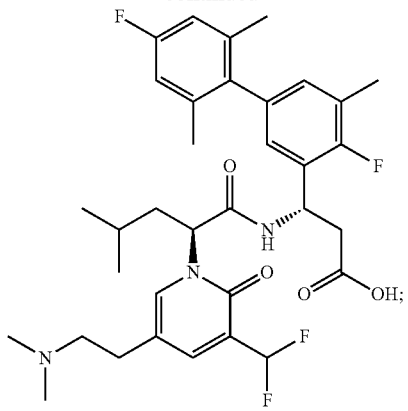
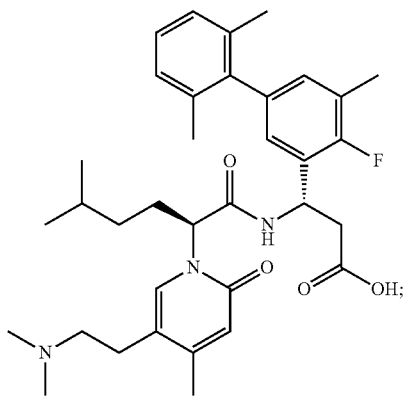
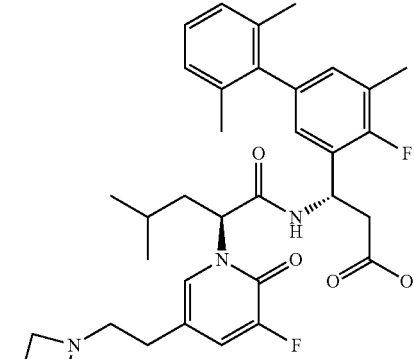
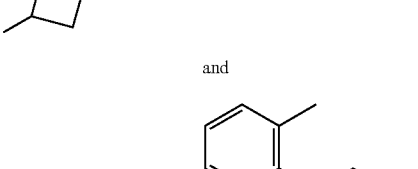
and
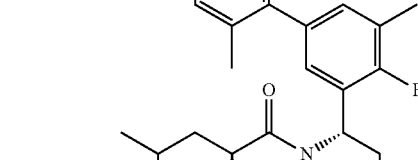
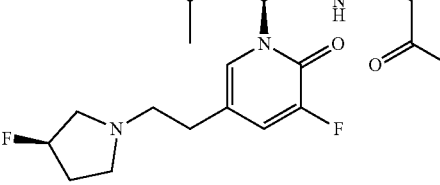
or a pharmaceutically acceptable salt thereof.

14. The composition of claim 13, wherein the compound is

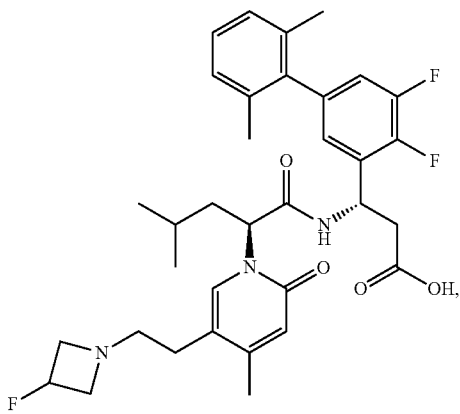 [SMILES: Cc1cc(=O)n([C@@H](CC(C)C)C(=O)N[C@@H](CC(=O)O)c2cc(-c3c(C)cccc3C)cc(F)c2F)cc1CCN1CC(F)C1]

or a pharmaceutically acceptable salt thereof.

15. The composition of claim 13, wherein the compound is

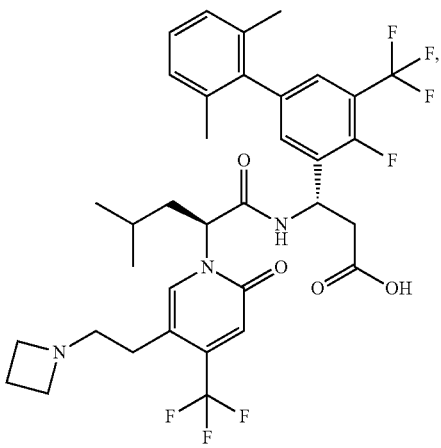 [SMILES: Cc1cccc(C)c1-c1cc([C@H](CC(=O)O)NC(=O)[C@H](CC(C)C)n2cc(CCN3CCC3)c(C(F)(F)F)cc2=O)c(F)c(C(F)(F)F)c1]

or a pharmaceutically acceptable salt thereof.

16. The composition of claim 13, wherein the compound is

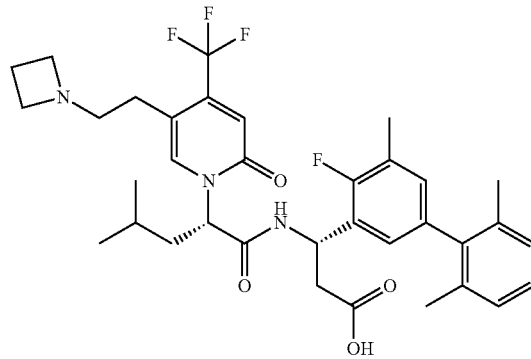

or a pharmaceutically acceptable salt thereof.

17. The composition of claim 13, wherein the compound is

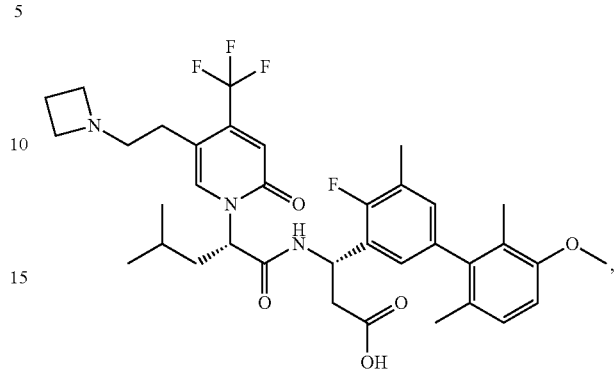

or a pharmaceutically acceptable salt thereof.

18. The composition of claim 13, wherein the compound is

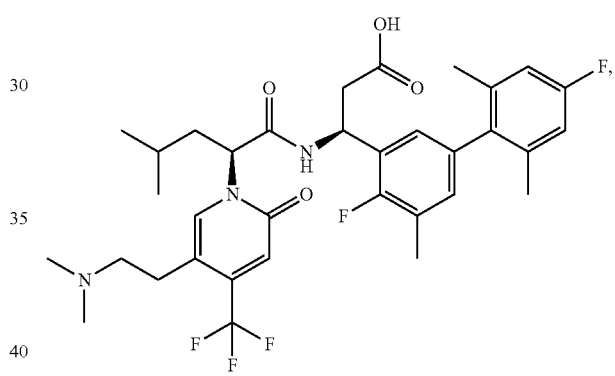

or a pharmaceutically acceptable salt thereof.

19. The composition of claim 13, wherein the compound is

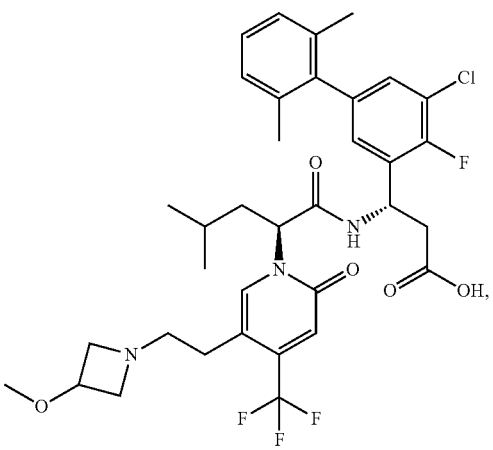 [SMILES: COC1CN(CCc2cn([C@@H](CC(C)C)C(=O)N[C@@H](CC(=O)O)c3cc(-c4c(C)cccc4C)cc(Cl)c3F)c(=O)cc2C(F)(F)F)C1]

or a pharmaceutically acceptable salt thereof.

20. The composition of claim 13, wherein the compound is

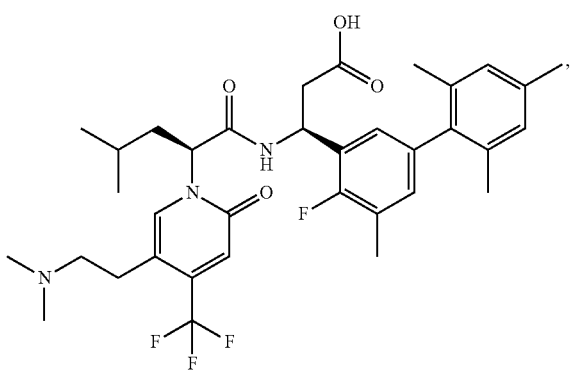

or a pharmaceutically acceptable salt thereof.

21. The composition of claim 13, wherein the compound is

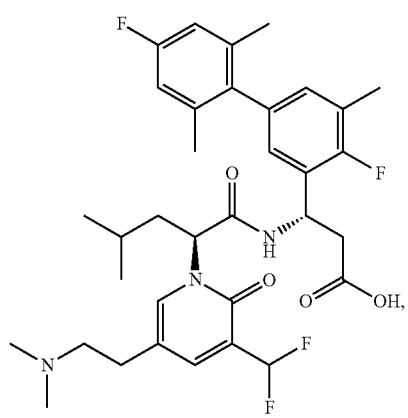

or a pharmaceutically acceptable salt thereof.

22. The composition of claim 13, wherein the compound is

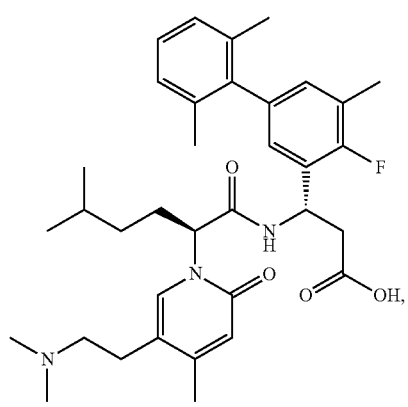

or a pharmaceutically acceptable salt thereof.

23. The composition of claim 13, wherein the compound is

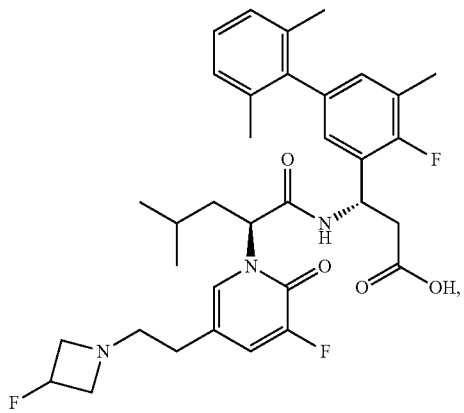 [SMILES: Cc1cc(-c2c(C)cccc2C)cc([C@H](CC(=O)O)NC(=O)[C@H](CC(C)C)n2cc(CCN3CC(F)C3)cc(F)c2=O)c1F]

or a pharmaceutically acceptable salt thereof.

24. The composition of claim 13, wherein the compound is

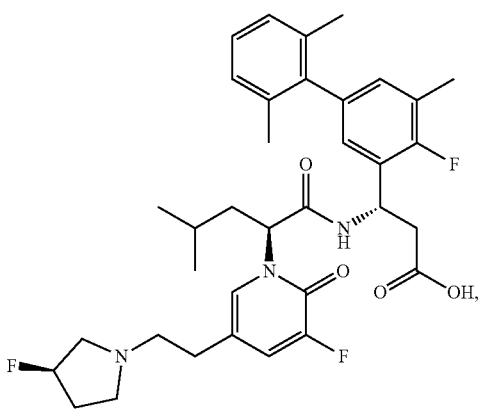 [SMILES: Cc1cc(-c2c(C)cccc2C)cc([C@H](CC(=O)O)NC(=O)[C@H](CC(C)C)n2cc(CCN3CC[C@@H](F)C3)cc(F)c2=O)c1F]

or a pharmaceutically acceptable salt thereof.

* * * * *